United States Patent
Jaganathan et al.

(10) Patent No.: US 11,436,429 B2
(45) Date of Patent: Sep. 6, 2022

(54) ARTIFICIAL INTELLIGENCE-BASED SEQUENCING

(71) Applicant: Illumina, Inc., San Diego, CA (US)

(72) Inventors: Kishore Jaganathan, San Francisco, CA (US); Anindita Dutta, Brisbane, CA (US); Dorna Kashefhaghighi, Menlo Park, CA (US); John Randall Gobbel, Brisbane, CA (US); Amirali Kia, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 16/826,168

(22) Filed: Mar. 21, 2020

(65) Prior Publication Data

US 2020/0302224 A1    Sep. 24, 2020

Related U.S. Application Data

(60) Provisional application No. 62/821,602, filed on Mar. 21, 2019, provisional application No. 62/821,618, (Continued)

(30) Foreign Application Priority Data

Jun. 14, 2019    (NL) .................................... 2023314

(51) Int. Cl.
*G06K 9/00*    (2022.01)
*G06K 9/62*    (2022.01)
(Continued)

(52) U.S. Cl.
CPC ......... *G06K 9/6218* (2013.01); *G06F 16/907* (2019.01); *G06K 9/628* (2013.01);
(Continued)

(58) Field of Classification Search
CPC ........ G06F 16/907; G16B 40/00; G06N 3/04; G06N 7/005
See application file for complete search history.

(56) References Cited

U.S. PATENT DOCUMENTS

| 8,182,993 B2 | 5/2012 | Tomaney et al. |
| 8,241,573 B2 | 8/2012 | Banerjee et al. |
| (Continued) | | |

FOREIGN PATENT DOCUMENTS

| CA | 2894317 A1 | 12/2016 |
| EP | 3130681 A1 | 2/2017 |
| (Continued) | | |

OTHER PUBLICATIONS

Wong, Sebastien C., et al. "Understanding data augmentation for classification—when to warp?." 2016 international conference on digital image computing—techniques and applications (DICTA). IEEE, 2016.

(Continued)

*Primary Examiner* — Oneal R Mistry
(74) *Attorney, Agent, or Firm* — Haynes Beffel & Wolfeld LLP; Ernest J. Beffel, Jr.; Sikander M. Khan

(57) ABSTRACT

The technology disclosed processes a first input through a first neural network and produces a first output. The first input comprises first image data derived from images of analytes and their surrounding background captured by a sequencing system for a sequencing run. The technology disclosed processes the first output through a post-processor and produces metadata about the analytes and their surrounding background. The technology disclosed processes a second input through a second neural network and produces a second output. The second input comprises third image data derived by modifying second image data based on the metadata. The second image data is derived from the images of the analytes and their surrounding background. The (Continued)

second output identifies base calls for one or more of the analytes at one or more sequencing cycles of the sequencing run.

22 Claims, 169 Drawing Sheets
(139 of 169 Drawing Sheet(s) Filed in Color)

Related U.S. Application Data filed on Mar. 21, 2019, provisional application No. 62/821,681, filed on Mar. 21, 2019, provisional application No. 62/821,724, filed on Mar. 21, 2019, provisional application No. 62/821,766, filed on Mar. 21, 2019.

(51) Int. Cl.

| | | |
|---|---|---|
| *G06N 3/08* | (2006.01) | |
| *G16B 40/00* | (2019.01) | |
| *G06N 3/04* | (2006.01) | |
| *G06F 16/907* | (2019.01) | |
| *G06N 7/00* | (2006.01) | |
| *G06V 10/75* | (2022.01) | |
| *G06N 5/04* | (2006.01) | |

(52) U.S. Cl.
CPC ......... *G06K 9/6222* (2013.01); *G06K 9/6232* (2013.01); *G06K 9/6256* (2013.01); *G06K 9/6262* (2013.01); *G06K 9/6267* (2013.01); *G06K 9/6277* (2013.01); *G06N 3/04* (2013.01); *G06N 3/08* (2013.01); *G06N 3/084* (2013.01); *G06N 7/005* (2013.01); *G06V 10/751* (2022.01); *G16B 40/00* (2019.02); *G06N 5/046* (2013.01)

(56) References Cited

U.S. PATENT DOCUMENTS

| 3,401,258 | A1 | 3/2013 | Hargrove et al. | |
|---|---|---|---|---|
| 8,392,126 | B2 | 3/2013 | Mann | |
| 8,407,012 | B2* | 3/2013 | Erlich ............... | G16B 30/00 |
| | | | | 702/20 |
| 3,594,439 | A1 | 11/2013 | Staelin et al. | |
| 8,725,425 | B2 | 5/2014 | Heiner et al. | |
| 8,795,971 | B2 | 8/2014 | Kersey et al. | |
| 8,965,076 | B2 | 2/2015 | Garcia et al. | |
| 9,708,656 | B2 | 7/2017 | Turner et al. | |
| 10,023,911 | B2 | 7/2018 | Tomaney et al. | |
| 10,068,054 | B2 | 9/2018 | Van Rooyen et al. | |
| 10,168,438 | B2 | 1/2019 | Dennis et al. | |
| 10,241,075 | B2 | 3/2019 | Davey et al. | |
| 10,354,747 | B1* | 7/2019 | DePristo ............ | G06N 3/0454 |
| 10,423,861 | B2 | 9/2019 | Gao et al. | |
| 10,527,549 | B2 | 1/2020 | Rebetez et al. | |
| 10,540,591 | B2 | 1/2020 | Gao et al. | |
| 10,648,027 | B2 | 5/2020 | Mannion et al. | |
| 10,711,299 | B2 | 7/2020 | Rothberg et al. | |
| 10,740,883 | B2 | 8/2020 | Zerfass et al. | |
| 10,963,673 | B2 | 3/2021 | Schaumberg et al. | |
| 11,138,496 | B2* | 10/2021 | Seth .................... | G06N 3/0472 |
| 2003/0062485 | A1 | 4/2003 | Fernandez et al. | |
| 2006/0014151 | A1* | 1/2006 | Ogura ................ | G01N 21/6454 |
| | | | | 435/6.11 |
| 2006/0040297 | A1 | 2/2006 | Leamon et al. | |
| 2006/0064248 | A1 | 3/2006 | Saidi et al. | |
| 2006/0269130 | A1 | 11/2006 | Maroy et al. | |
| 2009/0081775 | A1 | 3/2009 | Hodneland et al. | |
| 2010/0046830 | A1 | 2/2010 | Wang et al. | |
| 2010/0111370 | A1 | 5/2010 | Black et al. | |
| 2010/0157086 | A1 | 6/2010 | Segale et al. | |
| 2011/0065607 | A1* | 3/2011 | Kersey ................ | C12Q 1/6874 |
| | | | | 506/30 |
| 2011/0286628 | A1 | 11/2011 | Goncalves et al. | |
| 2012/0015825 | A1 | 1/2012 | Zhong et al. | |
| 2012/0020537 | A1 | 1/2012 | Garcia et al. | |
| 2013/0079232 | A1 | 3/2013 | Kain et al. | |
| 2013/0124100 | A1 | 5/2013 | Drmanac et al. | |
| 2013/0188866 | A1 | 7/2013 | Obrador et al. | |
| 2013/0250407 | A1 | 9/2013 | Schaffer et al. | |
| 2014/0152801 | A1 | 6/2014 | Fine et al. | |
| 2015/0079596 | A1 | 3/2015 | Eltoukhy et al. | |
| 2015/0117784 | A1 | 4/2015 | Lin et al. | |
| 2015/0169824 | A1 | 6/2015 | Kermani et al. | |
| 2016/0042511 | A1 | 2/2016 | Chukka et al. | |
| 2016/0078272 | A1 | 3/2016 | Hammoud | |
| 2016/0110498 | A1 | 4/2016 | Bruand et al. | |
| 2016/0196479 | A1 | 7/2016 | Chertok et al. | |
| 2016/0356715 | A1 | 12/2016 | Zhong et al. | |
| 2016/0357903 | A1 | 12/2016 | Shendure et al. | |
| 2016/0371431 | A1 | 12/2016 | Haque et al. | |
| 2017/0044601 | A1 | 2/2017 | Crnogorac et al. | |
| 2017/0116520 | A1 | 4/2017 | Min et al. | |
| 2017/0169313 | A1 | 6/2017 | Choi et al. | |
| 2017/0249421 | A1 | 8/2017 | Eberle et al. | |
| 2017/0249744 | A1 | 8/2017 | Wang et al. | |
| 2017/0362634 | A1* | 12/2017 | Ota .................... | G01N 21/6428 |
| 2018/0075279 | A1 | 3/2018 | Gertych et al. | |
| 2018/0107927 | A1 | 4/2018 | Frey | |
| 2018/0114337 | A1 | 4/2018 | Li et al. | |
| 2018/0189613 | A1 | 7/2018 | Wolf et al. | |
| 2018/0195953 | A1 | 7/2018 | Langlois et al. | |
| 2018/0201992 | A1 | 7/2018 | Wu et al. | |
| 2018/0211001 | A1 | 7/2018 | Gopalan et al. | |
| 2018/0274023 | A1 | 9/2018 | Belitz et al. | |
| 2018/0305751 | A1 | 10/2018 | Vermaas et al. | |
| 2018/0322327 | A1 | 11/2018 | Smith et al. | |
| 2018/0330824 | A1 | 11/2018 | Athey | |
| 2018/0334711 | A1 | 11/2018 | Kelley et al. | |
| 2018/0334712 | A1 | 11/2018 | Singer et al. | |
| 2018/0340234 | A1 | 11/2018 | Scafe et al. | |
| 2019/0034586 | A1* | 1/2019 | Pirrotte ................ | G16B 40/10 |
| 2019/0080450 | A1 | 3/2019 | Arar et al. | |
| 2019/0107642 | A1 | 4/2019 | Farhadi Nia et al. | |
| 2019/0114544 | A1 | 4/2019 | Sundaram et al. | |
| 2019/0156915 | A1 | 5/2019 | Zhang et al. | |
| 2019/0164010 | A1 | 5/2019 | Ma et al. | |
| 2019/0170680 | A1 | 6/2019 | Sikora et al. | |
| 2019/0213473 | A1 | 7/2019 | Dutta et al. | |
| 2019/0237160 | A1 | 8/2019 | Rothberg et al. | |
| 2019/0237163 | A1 | 8/2019 | Wang et al. | |
| 2019/0272638 | A1 | 9/2019 | Mouton et al. | |
| 2019/0332118 | A1 | 10/2019 | Wang et al. | |
| 2019/0392578 | A1 | 12/2019 | Chukka et al. | |
| 2020/0027002 | A1 | 1/2020 | Hickson et al. | |
| 2020/0054306 | A1* | 2/2020 | Mehanian ............ | G06T 7/70 |
| 2020/0057838 | A1 | 2/2020 | Yekhanin et al. | |
| 2020/0065675 | A1 | 2/2020 | Sundaram et al. | |
| 2020/0076082 | A1 | 6/2020 | Massingham | |
| 2020/0193597 | A1* | 6/2020 | Fan .................... | G16H 30/40 |
| 2020/0302603 | A1 | 9/2020 | Barnes et al. | |
| 2020/0320294 | A1 | 10/2020 | Mangal et al. | |
| 2020/0388029 | A1 | 12/2020 | Saltz et al. | |
| 2021/0027462 | A1 | 1/2021 | Bredno et al. | |
| 2021/0056287 | A1 | 2/2021 | Schaumburg et al. | |
| 2021/0072391 | A1 | 3/2021 | Li et al. | |
| 2021/0089827 | A1 | 3/2021 | Kumagai et al. | |
| 2021/0115490 | A1* | 4/2021 | Embree ................ | G16B 5/20 |

FOREIGN PATENT DOCUMENTS

| EP | 3373238 | A1 | 9/2018 |
|---|---|---|---|
| JP | 2007199397 | A | 8/2007 |
| WO | 2008154317 | A1 | 12/2008 |
| WO | 2014142921 | A1 | 9/2014 |
| WO | 2015084985 | A2 | 6/2015 |
| WO | 2016145516 | A1 | 9/2016 |
| WO | 2016201564 | A1 | 12/2016 |
| WO | 2017184997 | A1 | 10/2017 |
| WO | 2018129314 | A1 | 7/2018 |

(56) References Cited

FOREIGN PATENT DOCUMENTS

| | | |
|---|---|---|
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |

OTHER PUBLICATIONS

Chang, Chia-Yun, et al. "Oversampling to overcome overfitting—exploring the relationship between data set composition, molecular descriptors, and predictive modeling methods." Journal of chemical information and modeling 53.4 (2013) 958-971.
Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.
Martin-Navarro, Antonio, et al. "Machine learning classifier for identification of damaging missense mutations exclusive to human mitochondrial DNA-encoded polypeptides." BMC bioinformatics 18.1 (2017) p. 158.
Krizhevsky, Alex, et al., ImageNet Classification with Deep Convolutional Neural Networks, 2012, 9 Pages.
Geeks for Geeks, "Underfitting and Overfilling in Machine Learning", [retrieved on Aug. 26, 2019]. Retrieved from the Internet <www.geeksforgeeks.org/underfitting-and-overfitting-in-machine-learning/>, 2 pages.
Despois, Julien, "Memorizing is not learning!—6 tricks to prevent overfitting in machine learning", Mar. 20, 2018, 17 pages.
Bhande, Anup What is underfitting and overfitting in machine learning and how to deal with it, Mar. 11, 2018, 10pages.
PCT/US2019031621—International Search Report and Written Opinion dated Aug. 7, 2019, 17 pages.
Carter et al., "Cancer-specific high-throughput annotation of somatic mutations—computational prediction of driver missense mutations," Cancer research 69, No. 16 (2009) pp. 6660-6667.
Min, et al., "Deep Learning in Bioinformatics", Jun. 19, 2016, 46pgs.
Jiminez et al., DeepSite—protein binding site predictor using 3D CNNs, dated Oct. 1, 2017, 7 pages.
Pu et al., "DeepDrug3D: Classification of ligand-binding pockets in proteins with a convolutional neural network", dated Feb. 4, 2019, 23 pages.
Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et al., "Predicting changes in protein thermostability upon mutation with deep 3D convolutional neural networks", dated Feb. 28, 2020, 21 pages.
Raschka et al., "Machine Learning and AI-based approaches for bioactive ligand discovery and GPCR-ligand recognition", dated Jun. 6, 2020, 33 pages.
Torng et al., "3D deep convolutional neural networks for amino acid environment similarity analysis", dated 2017, 23 pages.
Morrone et al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Anonymous, "Transferrable end-to-end learning for protein interface prediction", dated 2019, 12 pages.
Eraslan et. al., "Deep Learning: New computational modelling techniques for genomics", dated Jul. 2019, 15 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.
Li et. al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Illumina, Low-diversity sequencing on the Illumina HiSeq Platform, 2014, 2 pages.
Hedegaard, An introduction to "Next Generation" DNA Sequencing, dated Nov. 26, 2017, 63 pages.
Jordan, An overview of semantic image segmentation, dated May 21, 2018, 28 pages retrieved on Jul. 21, 2021. Retrieved from the internet [URL: https://www jeremyjordan.me/semantic-segmentation/ ].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa ].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing—Assessing sequencing accuracy using Phred quality scoring, 2011, 2 pages.
Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Semantic Segmentation Examples—MATLAB and Simulink, 22 pages, retrieved from [URL: https://www.mathworks.com/help/vision/ug/semantic-segmentation-examples.html ].
Illumina, An Introduction to Next-Generation Sequencing Technology, 2017, 16 pages.

(56) References Cited

OTHER PUBLICATIONS

Supplementary Information, Nature, 55 pages, retrieved from [URL: https://media.nature.com/original/nature-assets/nature/journal/v456/n7218/extref/nature07517-s1.pdf].
Belanovic, Library of Parameterized Hardware Modules for Floating-Point Arithmetic with an Example Application, Northeastern University, Boston, MA, May 2002, 83 pages.
PCT/US2020/024090 Article 34 Amendment, dated Mar. 18, 2021, 3 pages.
Albrecht et. al., Deep learning for single-molecule science, Nanotechnology (28), dated 2017, 423001, 11 pages.
MiSEQ: Imaging and Base Calling: Illumina, Inc. Online Training Course, dated Jan. 1, 2013 [retrieved on Jul. 13, 2020], Retrieved from <URL: https://support.illumina.com/training.html >, 13 pages.
MiSEQ: Imaging and Base Calling Script, retrieved on [Jun. 14, 2021], Retrieved from the internet <URL: https://support.Illumina.com/content/dam/illumina-support/courses/MiSeq_Imaging_and_Base_Calling/story_content/external_files/MiSeq%20Imaging%20and%20Base%20Calling%20Script.pdf >.
PCT/US2020/024087 PCT Direct Letter, dated Mar. 21, 2020, 5 pages.
PCT/US2020/024087 International Search Report and Written Opinion, dated Aug. 28, 2020, 24 pages.
PCT/US2020/024087 Article 34 Amendment, filed Mar. 21, 2020, 7 pages.
PCT/US2020/024087 Second Written Opinion, dated Apr. 7, 2021, 12 pages.
PCT/US2020/024087 Article 34 Letter Response to Second Written Opinion, dated May 7, 2021, 7 pages.
Zhao et al., Object detection with Deep Learning: A Review, dated Jul. 15, 2018, 22 pages.
Lee et al., Fast Object Localization Using a CNN Feature Map Based Multi-Scale Search, dated Apr. 12, 2016, 16 pages.
PCT/US2020/24088 PCT Direct Letter, filed Mar. 21, 2020, 4 pages.
PCT/US2020/024088 Article 34 Letter in response to Second Written Opinion, dated May 28, 2021, 9 pages.
PCT/US2020/024088 Second Written Opinion, dated Apr. 20, 2021, 17 pages.
PCT/US2020/024088 International Search Report and Written Opinion, dated Sep. 7, 2020, 29 pages.
PCT/US2020/024088 Article 34 Letter in Response to Written Opinion, dated Mar. 9, 2021, 11 pages.
PCT/US2020/024088 Partial Search Report and Invitation to Pay Fees, dated Jul. 8, 2020, 22 pages.
Misiunas et al., QuipuNet: convolutional neural network for single-molecule nanopore sensing, dated May 30, 2018, 7 pages.
Boza et al., Deep Recurrent Neural Networks for Base Calling in MinION Nanopore Reads, dated Mar. 30, 2016, 12 pages.
Kao et al., BayesCall: A model-based base-calling algorithm for high-throughput short-read sequencing, Genome Research (19), pp. 1884-1895, dated 2009.
Rang et al., From squiggle to basepair: computational approaches for improving nanopore sequencing read accuracy, Genome Biology 2018, (19), 30.
Wang et al., An adaptive decorrelation method removes Illumina DNA base-calling errors caused by crosstalk between adjacent clusters, Scientific Reports, published Feb. 20, 2017, 11 pages.
Cacho et al., A comparison of Base Calling Algorithms for Illumina Sequencing Technology, dated Oct. 5, 2015, Briefings in Bioinformatics 2016 (17), 786-795.
PCT/US2020/024091 PCT Direct Letter, dated Mar. 21, 2020, 5 pages.
PCT/US2020/024091 Partial Search Report and Invitation to Pay Fee, dated Jul. 3, 2020, 17 pages.
PCT/US2020/024091 International Search Report and Written Opinion, dated Oct. 23, 2020, 24 pages.
PCT/US2020/024091 Article 34 Letter in Reponse to International Search Report and Written Opinion, filed Mar. 8, 2021, 10 pages.
PCT/US2020/024091 Second Article 34 Amendment Letter, dated Mar. 22, 2021, 10 pages.
PCT/US2020/024091 Written Opinion of the International Preliminary Examining Authority (Second Written Opinon), dated Apr. 20, 2021, 14 pages.
PCT/US2020/024091 Second Article 34 Amendment in response to Second Written Opinion, dated May 30, 2021, 9 pages.
Luo et. al., G-softmax: Improving Intra-class Compactness and Inter-class Separability of Features, dated Apr. 8, 2019, 15 pages.
Luo et. al., A multi-task convolutional deep neural network for variant calling in single molecule sequencing, Nature Communications (10), No. 1, dated Mar. 1, 2019.
Kingma et. al., Adam: A method for Stochastic Optimization, ICLR 2015, dated Jul. 23, 2015.
Luo et. al., Skyhawk: An Artificial Neural Network-based discriminator for reviewing clinically significant genomic Variants, dated Jan. 28, 2019, 8 pages.
Anonymous, Calculating Percent Passing Filter for Patterned and Nonpatterned Flow Cells, Illumina, 2 pages.
MiSEQ: Imaging and Base Calling: Illumina, Inc. Online Training Course, colored version, [retrieved on Oct. 11, 2020], Retrieved from <URL: https://support.illumina.com/training.html >, 9 pages.
PCT/US2020/024092 PCT Direct Letter, dated Mar. 21, 2020, 5 pages.
PCT/US2020/024092 Partial Search Report and Invitation to Pay Fees, dated Sep. 11, 2020, 22 pages.
PCT/US2020/024092 International Search Report and Written Opinion, dated Nov. 2, 2020, 24 pages.
PCT/US2020/024092 Article 34 Amendment in Response to International Search Report and Written Opinion, dated Mar. 4, 20221, 7 pages.
PCT/US2020/024092 Second Written Opinion dated Apr. 7, 2021, 13 pages.
PCT/US2020/024092 Article 34 Amendment Response to Second Written Opinion, dated May 7, 2021, 10 pages.
PCT/US2021/018910—Partial Search Report and Invitation to Pay Fees dated May 31, 2021, 14 pgs.
Arpali et. al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et. al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.
Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.

(56) References Cited

OTHER PUBLICATIONS

Huang et. al., Speed/accuracy trade-offs for modern convolutional detectors, 2016.
Oord, Dieleman et. al., WAVENET: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et. al., Highway Networks, 2015.
Huang et. al., Densely Connected Convolutional Networks, 2017.
Szegedy et. al., Going Deeper with Convolutions, 2014.
Ioffe et. al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.
Piqueras, Autoregressive Model Based on a Deep Convolutional Neural Network for Audio Generation, Tampere University of Technology, 2016.
Wu, Introduction to Convolutional Neural Networks, Nanjing University, 2017.
Ilumina CMOS Chip and One-Channel SBS Chemistry, Illumina Inc, 2018, 2 pgs.
Scikit-image/peak.py at master, Github, retrieved on Jun. 8, 2021, 10 pages, Retrieved from the internet <URL: https://github.com/scikit-image/scikit-image/blob/main/skimage/feature/peak.py>.
3.3.9.11.Watershed and random walker for segmentation, Scipy lecture notes, 2 pages. [retrieved on Jun. 8, 2021] Retrieved from the internet <URL: http:scipy-lectures.org/packages/scikit-image/auto_examples/plot_segmentations.html>.
Mordvintsev et al., Image Segmentation with Watershed Algorithm, Revision 43532856, 2013, 6 pages, [retrieved on Jun. 8, 2021] Retrieved from the Internet <URL: https://opencv-python-tutroals.readthedocs.io/en/latest/py_tutorials/by_imgproc/py_watershed/py_watershed.html>.
Mzur, Watershed.py, Github, 3 pages, [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.
Assem, Predicting periodic and chaotic signals using Wavenets, Master of Science thesis, Delft University of Technology, Aug. 18, 2017, pp. 3-38.
Goodfellow et. al., Convolutional Networks, Deep Learning, MIT Press, 2016.
Gu et. al., Recent Advances in Convolutional Neural Networks, 2017.
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
U.S. Appl. No. 16/825,991—Notice of Allowance dated Apr. 19, 2021, 12 pages.
PCT/US2020/024090 International Preliminary Report on Patentability, dated Apr. 13, 2021, 20 pages.
PCT/US2020/024090 Written Opinion of the International Preliminary Examining Authority, dated Dec. 22, 2020, 11 pages.
PCT/US2020/024090 PCT Direct Letter, filed Mar. 21, 2020, 5 pages.
PCT/US2020/024090 International Search Report, dated Aug. 31, 2020, 8 pages.
PCT/US2020/024090 Article 34 Amendment, dated Dec. 4, 2020, 6 pages.
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations—application to cancer genomics. Nucleic Acids Res 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Hefferman, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.
Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Nakamura, K. et al. Clinical spectrum of SCN2A mutations expanding to Ohtahara syndrome. Neurology 81, 992-998 (2013).

(56) References Cited

OTHER PUBLICATIONS

Ioannidis, Nilah M., et al., "REVEL—An Ensemble Method for Predicting the Pathogenicity of Rare Missense Variants", Oct. 5, 2016, 9 pages.
Quang Daniel, et. al., "DANN—a deep learning approach for annotating the pathogenicity of genetic variants", Oct. 22, 2014, 3 pages.
Sundaram, et. al., "Predicting the clinical impact of human mutation with deep neural networks", Aug. 2018, 15pgs.
Xiong, et. al., "The human splicing code reveals new insights into the genetic determinants of disease", Jan. 9, 2015, 20pgs.
Yue, et. al., "Deep Learning for Genomics—A Concise Overview from internet", May 8, 2018, 40pgs.
Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et. al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et. al., "Selene—a PyTorch based deep learning library for sequence level data", Oct. 10, 2018, 15pages.
Grob, C., et. al., "Predicting variant deleteriousness in non human species Applying the CADD approach in mouse", 2018, 11 pages.
Li, et. al., "FoldingZero—Protein Folding from Scratch in Hydrophobic Polar Model", Dec. 3, 2018, 10 pages.
Rentzsch, et. al.,_"CADD—predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
PCT/US2018/055840—International Search Report and Written Opinion dated Jan. 25, 2019, 18 pages.
Wei etal_The Role of Balanced Training and Testing Data Sets for Binary Classifiers in Bioinformatics dated Jul. 9, 2013 12 pages.
PCT/US2018/055878—International Search Report and Written Opinion dated Jan. 22, 2019, 20 pages.
PCT/US2018/055881—International Search Report and Written Opinion dated Jan. 25, 2019, 17 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.
Bahar, Protein Actions Principles and Modeling, Chapter 7, 2017 pp. 165-166.
Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.
DbSNP rs2241788 [Retrieved on Mar. 13, 2019], Retrieved from the Internet<www.ncbi.nlm.nih.gov/snp/rs2241788>, 5 pages.
Wei, et. al., "Prediction of phenotypes of missense mutations in human proteins from biological assemblies", Feb. 2013, 28 pages.
Zhang, Jun, and Bin Liu. "PSFM-DBT—identifying DNA-binding proteins by combing position specific frequency matrix and distance-bigram transformation." International journal of molecular sciences 18.9 (2017) 1856.
Gao, Tingting, et al. "Identifying translation initiation sites in prokaryotes using support vector machine." Journal of theoretical biology 262.4 (2010) 644-649. (Year 2010).
Bi, Yingtao, et al. "Tree-based position weight matrix approach to model transcription factor binding site profiles." PloS one6.9 (2011) e24210.
Korhonen, Janne H., et al. "Fast motif matching revisited—high-order PWMs, SNPs and indels." Bioinformatics 33.4 (2016) 514-521.

De Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability—an exome sequencing study. Lancet 380, 1674-1682 (2012).
Epi, K. C. et al. De novo mutations in epileptic encephalopathies. Nature 501, 217-221 (2013).
EuroEPINOMICS-RES Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Gilissen, C. et al. Genome sequencing identifies major causes of severe intellectual disability. Nature 511, 344-347 (2014).
Lelieveld, S. H. et al. Meta-analysis of 2,104 trios provides support for 10 new genes for intellectual disability. Nat. Neurosci. 19, 1194-1196 (2016).
Famiglietti, M. L. et al. Genetic variations and diseases in UniProtKB Swiss-Prot—the ins and outs of expert manual curation Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39,425 (2007).
Stenson, P. D. et al. The Human Gene Mutation Database—building a comprehensive mutation repository for clinical and molecular genetics, diagnostic testing and personalized genomic medicine. Hum. Genet 133, 1-9 (2014).
Alipanahi, et. al., "Predicting the Sequence Specificities of DNA and RNA Binding Proteins by Deep Learning", Aug. 2015, 9pgs.
Angermueller, et al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Gu, et. al., "Recent Advances in Convolutional Neural Networks", Jan. 5, 2017, 37pgs.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755(2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium. et al. A global reference for human genetic variation. Nature 526, 68-74 (2015).
Liu, X., Jian, X. & Boerwinkle, E. dbNSFP—a lightweight database of human nonsynonymous SNPs and their functional predictions. Human. Mutat. 32, 894-899 (2011).

(56) References Cited

OTHER PUBLICATIONS

Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
De Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).
Schrago, C. G., & Russo, C. A. Timing the origin of New World monkeys. Mol. Biol. Evol. 20, 1620-1625 (2003).
Landrum, M. J. et al. ClinVar—public archive of interpretations of clinically relevant variants. Nucleic Acids Res. 44, D862-868 (2016).
Brandon, E. P., Idzerda, R. L. & McKnight, G. S. Targeting the mouse genome—a compendium of knockouts (Part II). Curr. Biol. 5, 758-765 (1995).
Lieschke, J. G. & Currie, P. D. Animal models of human disease—zebrafish swim into view. Nat. Rev. Genet. 8, 353-367 (2007).
Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Dash et. al., Artificial Intelligence and Evolutionary Computations in Engineering Systems, Advances in Intelligent Systems and Computing, vol. 1056, Springer 2020, 781 pages.
Ahmed, SIGNET: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Baek et. al., LncRNAnet: long non-coding RNA identification using deep learning, Bioinformatics, vol. 34 (22), 2018, pp. 3889-3897, 9 pages.
Evans et. al.. Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Wang et al., DeepDNA: a hybrid convolutional and recurrent neural network for compressing human mitochondrial genomes, IEEE International Conference on Bioinformatics and Biomedicine, 2018, 5 pages.
PCT/US2020/024092, International Preliminary Reporton Patentability (IPRP), dated Jun. 30, 2021, 30 pages.
PCT/US2020/024091 International Preliminary Report and Patentability (IPRP), dated Jun. 30, 2021, 32 pages.
PCT/US2020/024088 International Preliminary Report on Patentability (IPRP), dated Jun. 30, 2021, 35 pages.
PCT/US2020/024087 International Preliminary Report on Patentability (IPRP), dated Jun. 30, 2021, 26 pages.
PCT/US2021/018917 Internation Search Report and Written Opinion, dated Jul. 1, 2021, 15 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].
PCT/US2020/033281, Second Article 34 Amendment Letter in response to Second Written Opinion, dated Jul. 10, 2021, 4 pages.
NL 2023310 NL Search Report, dated Mar. 5, 2020, 17 pages.
NL 2023311 NL Search Report, dated Mar. 24, 2020, 15 pages.
NL 2023312, NL Search Report, dated Mar. 24, 2020, 22 pages.
NL 2023317, NL Search Report, dated Mar. 24, 2020, 16 pages.
NL 2023316, NL Search Report, dated Mar. 23, 2020, 15 pages.
MX/a/2020/014288 First Office Action, dated Mar. 10, 2021, 2 pages.
MX/a/2020/014288 Response to First Office Action, dated May 5, 2021, 390 pages.
PCT/US2021/018917—Second Written Opinion, dated Feb. 4, 2022, 7 pages.
PCT/US2021/018917—Article 34 Amendment, filed Dec. 19, 2021, 6 pages.
U.S. Appl. No. 17/468,411—Office Action, dated Feb. 24, 2022, 36 pages.
Gao et al., Deep Learning in Protein Structural Modeling and Design, Patterns—CelPress, dated Dec. 11, 2020, 23 pages.
Pejaver et al., Inferring the molecular and phenotypic impact of amino acid variants with MutPred2—with Supplementary Information, Nature Communications, dated 2020, 59 pages.
Pakhrin et al., Deep learning based advances in protein structure prediction, International Journal of Molecular sciences, published May 24, 2021, 30 pages.
Wang et al. Predicting the impacts of mutations on protein-ligand binding affinity based on molecular dynamics simulations and machine learning methods, Computational and Structural Biotechnology Journal 18, dated Feb. 20, 2022, pp. 439-454, 16 pages.
Iqbal et al., Comprehensive characterization of amino acid positions in protein structures reveals molecular effects of missense variants, and supplemental information, PNAS, vol. 117, No. 45, dated Nov. 10, 2020, 35 pages.
Forghani et al., Convolutional Neural Network Based Approach to In Silica Non-Anticipating Prediction of Antigenic Distance for Influenza Virus, Viruses, published Sep. 12, 2020, vol. 12, 20 pages.
Jing et al., Learning from protein structure with geometric vector perceptrons, Arxiv: 2009: 01411v2, dated Dec. 31, 2020, 18 pages.
Massingham, Base Calling: methods, problems and alternatives, EMBL Advanced Course in Analysis of Short Read Sequencing Data, Jun. 8, 2009-Jun. 10, 2009, 84 pages.
Thoma, A Survey of Semantic Segmentation, dated May 11, 2016, 16 pages.

(56) References Cited

OTHER PUBLICATIONS

Rodriguez-Ezpeleta, Bioinformatics for High Throughput Sequencing, Springer, 2012, 266 pages.
Illumina, Optimizing Cluster Density on Illumina Sequencing Systems, 2016, 12 pages.
Boza et. al., DeepNano: Deep recurrent neural networks for base calling in MinION nanopore reads, PLOS ONE, dated Jun. 5, 2017, 13 pages.
Kircher, Understanding and Improving high-throughput sequencing data production and analysis, Leipzig University, 2011, 216 pages.
Lutteropp, Error-Profile-Aware Correction of Next Generation Sequencing Reads, Karlsruhe Institute of Technology, dated Mar. 31, 2017, 96 pages.
Illumina, GA Bootcamp, Sequencing Module 3: Overview, Broad Institute, 73 pages.
Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.
Zhou et. al., Incorporating Side-Channel Information into Convolutional Neural Networks for Robotic Tasks, 2017, 7 pages.
Linder, Modeling the intronic regulation of Alternative Splicing using Deep Convolutional Neural Nets, KTH Institute of Technology, dated Jun. 14, 2015, 53 pages.
Grange, NGS: the basics, Institut Jacques Monod, 59 pages.
Bentley et. al., Accurate Whole Human Genome Sequencing using Reversible Terminator Chemistry, Nature, Nov. 2008, 21 pages.
Illumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Python Implementation of the color map function for the PASCAL VOC data set, Github, 4 pages, retrieved on Jul. 23, 2021. Retrieved from [URL: https://gist.github.com/wllhf/a4533e0adebe57e3ed06d4b50c8419ae].
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23, 2021. Retrieved from [URL: https://boofcv.org/index.php?title=Tutorial_Image_Segmentation ].
Illumina, Understanding Illumina Quality Scores, dated Apr. 23, 2014, 2 pages.
Yue et al., Deep Learning for Genomics: A Concise Overview, dated May 8, 2018, 40 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].
Teng et al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et al., Chiron: translating nanopore raw signal directly into nucleotide sequence using deep learning, dated Aug. 23, 2017, 10 pages.
Stoiber et al., BasecRAWller: Streaming Nanopore Basecalling Directly from Raw Signal, dated May 1, 2017, 15 pages.
Li et al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, pp. 489-497, dated Jan. 18, 2011, 9 pages.
Sheikh et al., Chapter 5 Base-Calling for Bioinformaticians, 2012, 17 pages.
Kriseman et al., BING: Biomedical informatics pipeline for Next Generation Sequencing, Journal of Biomedical Informatics, vol. 43, 2010, pp. 428-434, 7 pages.
Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Ye et. al., BlindCall: ultra-fast base-calling of high-throughput sequencing data by blind deconvolution, Bioinformatics, vol. 30, No. 9, 2014, pp. 1214-1219, 6 pages.
Wolowski, High-quality, high-throughput measurement of protein-DNA binding using HiTS-FLIP, Ludwig Maxmilian University, 2016, 251 pages.
Bravo et. al., Model-Based Quality Assessment and Base-Calling for Second-Generation Sequencing Data, Biometrics, 2009, 10 pages.
Massignham et. al., All Your Base: a fast and accurate probabilistic approach to base calling, European Bioinformatics Institute, 22 pages.
Illumina, RTA Theory of Operation, 2009, 8 pages.
PCT/US2021/018422 Second Written Opinion, dated Feb. 4, 2022, 8 pages.
Adriana Romero et. al., FitNets: Hints for Thin Deep Nets, published Mar. 27, 2015, 13 pages.
U.S. Appl. No. 16/874,599—Notice of Allowance dated Dec. 3, 2021, 12 pages.
U.S. Appl. No. 16/825,987—Response to Office Action (Quayle) dated Oct. 19, 2021, filed Jan. 13, 2022, 11 pages.
U.S. Appl. No. 16/825,987—Notice of Allowance, dated Jan. 28, 2022, 12 pages.
U.S. Appl. No. 16/825,987—Supplemental Notice of Allowance, dated Feb. 7, 2022, 8 pages.
CN 2020800036223—Voluntary Amendments, filed May 20, 2021, 26 pages.
EP 20719053.9—Rules 161(2) and 162 Communication, dated Oct. 28, 2021, 3 pages.
IL 279522—Notice Before Acceptance (in Hebrew), dated Aug. 1, 2021, 2 pages.

(56) References Cited

OTHER PUBLICATIONS

IL 279522—Response to Notice Before Acceptance dated Aug. 1, 2021, filed Nov. 28, 2021, 3 pages.
KR 10-2020-7037712—Voluntary Amendments with translation, dated Nov. 9, 2021, 7 pages.
EP 20719052.1—Rules 161(1) and 162 Communication, dated Oct. 28, 2021. 3 pages.
IL 279525—Notice Before Acceptance (in Hebrew), dated Aug. 1, 2021, 2 pages.
IL 279525—Response to Notice Before Acceptance dated Aug. 1, 2021, filed Nov. 28, 2021, 4 pages.
KR 10-2020-7037713—Voluntary Amendments with translation, dated Nov. 9, 2021, 26 pages.
ZA 2020/07998—Notice of Allowance, dated Aug. 12, 2021, 2 pages.
EP 20718112.4—Rules 161(2) and 162 Communication, dated Oct. 28, 2021, 3 pages.
IL 279527—Notice Before Examination (in Hebrew), dated Aug. 1, 2021, 2 pages.
IL 279527—Response to Notice Before Examination dated Aug. 1, 2021, filed Nov. 28, 2021, 3 pages.
KR 10-2021-7003269—Voluntary Amendments with translation, dated Nov. 9, 2021, 7 pages.
ZA 2020/07999—Notice of Allowance, dated Aug. 12, 2021, 2 pages.
EP 20719294.9—Rules 161(1) and 162 Communication, dated Oct. 28, 2021, 3 pages.
IL 281668—Notice Before Examination, dated Oct. 10, 2021, 2 pages.
IL 281668—Response to Notice Before Examination dated Oct. 10, 2021, filed Feb. 8, 2022, 4 pages.
KR 10-2021-7009877—Voluntary Amendments with translation, dated Nov. 9, 2021, 21 pages.
EP 20757979.8—Rules 161(2) and 162 Communication, dated Oct. 28, 2021, 3 pages.
IL 279533—Notice Before Examination, dated Aug. 1, 2021, 2 pages.
IL 279533—Response to Notice Before Examination dated Aug. 1, 2021, filed Nov. 29, 2021, 3 pages.
KR 10-2021-7003270—Voluntary Amendments with translation, dated Nov. 9, 2021, 29 pages.
ZA 2020/08000—Notice of Acceptance, dated Aug. 12, 2021, 2 pages.
Robinson et al., Computational Exome and Genome Analysis—Chapter 3 Illumina Technology, dated 2018, 25 pages.
Wang et al., An adaptive decorrelation method removes Illumina DNA base-calling errors caused by crosstalk between adjacent clusters—with Supplemental Materials, Scientific Reports, published Feb. 20, 2017, 17 pages.
PCT/US2020/033280—International Preliminary Reporton Patentability, dated Jul. 23, 2021, 11 pages.
Pfeiffer et. al., Systematic evaluation of error rates and causes in short samples in next-generation sequencing, Scientific Reports, published Jul. 19, 2018, 14 pages.
PCT/US2020/033281—International Preliminary Reporton Patentability, dated Aug. 31, 2021, 10 pages.
PCT/US2021/018258—Second Written Opinion, dated Jan. 25, 2022, 11 pages.
PCT/US2021/018910—International Search Report and Written Opinion, dated Aug. 25, 2021, 24 pages.
Puckelwartz et al., Supercomputing for the parallelization of whole genome analysis, Bioinformatics, dated Feb. 12, 2014, pp. 1508-1513, 6 pages.
Kelly et al., Churchill: an ultra-fast, deterministic, highly scalable and balanced parallelization strategy for the discovery of human genetic variation in clinical and population-scale genomics, Genome Biology, Bio-Med Central Ltd, vol. 16, No. 1, dated Jan. 20, 2015, 14 pages.
PCT/US2021/018910—Article 34 Amendment, filed Dec. 19, 2021, 9 pages.
PCT/US2021/018910—Second Written Opinion, dated Feb. 21, 2022, 17 pages.
PCT/US2021/018422—Article 34 Amendment, dated Dec. 20, 2021, 7 pages.
PCT/US/2021/018427—Second Written Opinion, dated Feb. 4, 2022, 9 pages.
PCT/US/2021/018427—Article 34 Amendment, filed Dec. 19, 2021, 7 pages.
PCT/US2021/018913—Second Written Opinion, dated Feb. 4, 2022, 8 pages.
Ye et al., BlindCall: ultra-fast base-calling of high-throughput sequencing data by blind deconvolution, Bioinformatics, vol. 30, No. 9, dated Jan. 9, 2014, pp. 1214-1219, 6 pages.
Wang et al., Achieving Accurate and Fast Base-calling by a Block model of the Illumina Sequencing Data, Science Direct, vol. 48, No. 28, dated Jan. 1, 2015, pp. 1462-1465, 4 pages.
PCT/US2021/018913—Article 34 Amendment, filed Dec. 19, 2021, 18 pages.
PCT/US2021/018915—Second Written Opinion, dated Feb. 4, 2022, 9 pages.
PCT/US2021/018915—Article 34 Amendment, filed Dec. 19, 2021, 7 pages.
PCT/US2020/033280 International Search Report and Written Opinion, dated Jul. 22, 2020, 18 pages.
PCT/US2020/033280 Article 34 Amendment, dated Apr. 19, 2021, 10 pages.
PCT/US2020/033281 International Search Report and Written Opinion, dated Aug. 14, 2020, 15 pages.
Kircher et. al., Improved base-calling for the Illumina Genome Analyzer using Machine Learning Strategies, Genome Biology, published Aug. 14, 2009, 9 pages.
PCT/US2020/033281 Article 34 Amendment, dated Apr. 19, 2021, 8 pages.
PCT/US2020/033281 Second Written Opinion, dated May 10, 2021, 8 pages.
Angermueller, Christof, et al., "Deep learning for computational biology", Jun. 6, 2016, 16 pages.
PCT/US2021/018258 International Search Report and Written Opinion, dated May 26, 2021, 17 pages.
Smith et.al., Barcoding and demultiplexing Oxford nanopore native RNA sequencing reads with deep residual learning, bioRxiv, dated Dec. 5, 2019, 18 pages.
PCT/US2021/018910 Partial Search Report and Invitation to pay fee, dated May 31, 2021, 14 pages.
PCT/US2021/018422 International Search Report and Written Opinion, dated Jun. 10, 2021, 12 pages.
Aggarwal, Neural Networks and Deep Learning: A Textbook, Springer, dated Aug. 26, 2018, 512 pages.
Wang et. al., Deep Neural Netwotk Approximation for Custom Hardware: Where We've Been, Where We're Going, Cornell University, dated Jan. 21, 2019, 37 pages.
Lavin et. al., Fast Algorithms for Convolutional Neural Networks, dated Nov. 10, 2015, 9 pages.
Liu et. al., A Uniform Architecture Design for Accelerating 2D and 3D CNNs on FPGAs, published Jan. 7, 2019, 19 pages.
PCT/US2021/018427 International Search Report and Written Opinion, dated Jun. 1, 2021, 15 pages.
PCT/US2021/018913 International Search Report and Written Opinion, dated Jun. 10, 2021, 11 pages.
Zeng et al., Causalcall: Nanopore Basecalling Using a Temporal Convolutional Network, dated Jan. 20, 2020, 11 pages.
PCT/US2021/018915 International Search Report and Written Opinion, dated Jun. 15, 2021, 13 pages.
Kwon et al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et al., Efficient Processing of Deep Neural Networks: A Tutorial and Survey, Cornell University Library, dated Mar. 27, 2017, 21 pages.
Sundaram, L. et. al., "Predicitng the clinical impact of human mutation with deep neural networks", Nat. Genet. 50, 1161-1170 (2018).

(56) References Cited

OTHER PUBLICATIONS

Jaganathan, K. et. al., "Predicting splicing from primary sequence with deep learning", Cell 176, 535-548, (2019).

Kircher, Martin, et al. "A general framework for estimating the relative pathogenicity of human genetic variants." Nature genetics 46.3 (2014): 310. (Year:2014).

Henikoff, S. & Henikoff, J. G. Amino acid substitution matrices from protein blocks. Proc. Natl. Acad. Sci. USA 89, 10915-10919 (1992).

Li, W. H., Wu, C. I. & Luo, C. C. Nonrandomness of point mutation as reflected in nucleotide substitutions in pseudogenes and its evolutionary implications. J. Molec. Evol. 21, 58-71 (1984).

Grantham, R. Amino acid difference formula to help explain protein evolution. Science 185, 862-864 (1974).

LeCun, Y., Botlou, L., Bengio, Y., & Haffner, P. Gradient based learning applied to document recognition. Proc. IEEE 86, 2278-2324 (1998).

Vissers, L. E., Gilissen, C., & Veltman, J. A. Genetic studies in intellectual disability and related disorders. Nat. Rev. Genet. 17, 9-18 (2016).

Neale, B. M. et al. Patterns and rates of exonicde novo mutations in autism spectrum disorders. Nature 485, 242-245 (2012).

Sanders, S. J. et al. De novo mutations revealed by whole-exome sequencing are strongly associated with autism. Nature 485, 237-241 (2012).

De Rubeis, S. et al. Synaptic, transcriptional and chromatin genes disrupted in autism. Nature 515, 209-215 (2014).

Deciphering Developmental Disorders Study. Large-scale discovery of novel genetic causes of developmental disorders. Nature 519, 223-228 (2015).

Deciphering Developmental Disorders Study. Prevalence and architecture of de novo mutations in developmental disorders. Nature 542, 433-438 (2017).

Iossifov, I. et al. The contribution of de novo coding mutations to autism spectrum disorder. Nature 515, 216-221 (2014).

Zhu, X. Need, A. C., Petrovski, S. & Goldstein, D. B. One gene, many neuropsychiatric disorders: lessons from Mendelian diseases. Nat. Neurosci. 17, 773-781, (2014).

Leffler, E. M. et al. Revisiting an old riddle: what determines genetic diversity levels within species? PLoS Biol. 10, e1001388 (2012), 9pages.

Estrada, A. et al. Impending extinction crisis of the worid's primates—why primates matter. Sc. Adv. 3, e1600946 (2017), 17 pages.

Kent, W. J. et al. The human genome browser at UCSC. Genome Res. 12, 996-1006 (2002).

Tyner, C. et al. The UCSC Genome Browser database—2017 update. Nucleic Acids Res. 45, D626-D634 (2017).

Kabsch, W., & Sander, C. Dictionary of protein secondary structure—pattern recognition of hydrogen-bonded and geometrical features. Biopolymers 22, 2577-2637 (1983).

Joosten, R. P. et al. A series of PDB related databases for everyday needs. Nucleic Acids Res. 39, 411-419 (2011).

He, K, Zhang, X., Ren, S., & Sun, J. Identity mappings in deep residual networks, in 14th European Conference on Computer Vision—ECCV 2016. ECCV 2016. Lecture Notes in Computer Science, vol. 9908; 630 6,15 (Springer, Cham, Switzerland; 2016).

Ionita-Laza, I., McCallum, K., Xu, B., & Buxbaum, J. D. A spectral approach integrating functional genomic annotations for coding and noncoding variants. Nat. Genet. 48, 214-220 (2016).

Li, B. et al. Automated inference of molecular mechanisms of disease from amino acid substitutions. Bioinformatics 25, 2744-2750 (2009).

Lu, Q. et al. A statistical framework to predict functional non-coding regions in the human genome through integrated analysis of annotation data Sci. Rep. 5, 10576 (2015), 13pgs.

Shihab, H. A. et al. Predicting the functional, molecular, and phenotypic consequences of amino acid substitutions using hidden Markov models. Human. Mutat. 34, 57-65 (2013).

Davydov, E. V. et al. Identifying a high fraction of the human genome to be under selective constraint using GERP++. PLoS Comput. Biol. 6, Dec. 2, 2010, 13 pages.

Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).

Jain, S., White, M., Radivojac, P. Recovering true classifier performance in positive-unlabeled learning, in Proceedings Thirty-First AAAI Conference on Artificial Intelligence. 2066-2072 (AAAI Press, San Francisco; 2017).

U.S. Appl. No. 16/825,991—Notice of Allowance dated Aug. 5, 2021, 10 pages.

Krishnakumar et. al., Systematic and stochastic influences on the performance of the MinION nanopore sequencer across a range of nucleotide bias, Scientific Reports, published Feb. 16, 2018, 13 pages.

Tegfalk, Application of Machine Learning techniques to perform base-calling in next-generation DNA sequencing, KTH Royal Institue of Technology, dated 2020, 53 pages.

Kircher et al, "Improved base-calling for the lllumina Genome Analyzer using Machine Learning Strategies", Genome Biology 2009, 10:R83, Aug. 14, 2009, 10 pages.

Albrecht etal, "Deep Learning for single-molecule science", Nanotechnology 28, IOP Publishuigm Sep. 18, 2017 11 pages.

U.S. Appl. No. 16/825,987—Office Action (Quayle) dated Oct. 19, 2021, 85 pages.

PCT/US2021047763—International Search Report and Written Opinion, dated Dec. 20, 2021, 11 pages.

\* cited by examiner

Cluster Centers (RTA) and Origin Subpixels

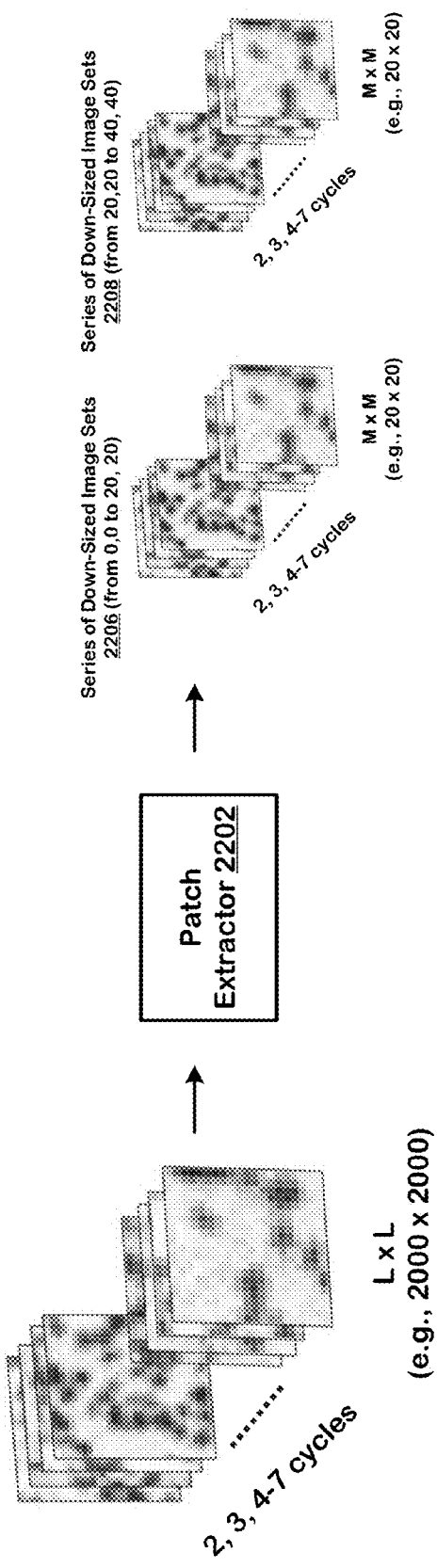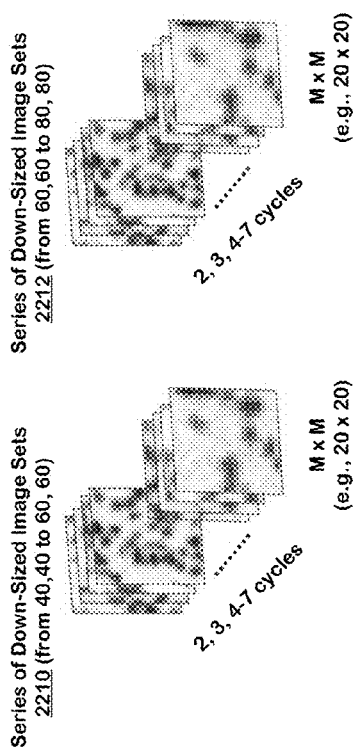
Figure 22

Regression Model 2600

| Layer (type) | Output Shape | Param # | Connected to |
|---|---|---|---|
| input_1 (InputLayer) | (None, None, None, 28) | 0 | |
| batch_normalization_1 (BatchNormali | (None, None, None, 28) | 112 | input_1[0][0] |
| conv2d_1 (Conv2D) | (None, None, None, 32) | 8064 | batch_normalization_1[0][0] |
| batch_normalization_2 (BatchNormali | (None, None, None, 32) | 128 | conv2d_1[0][0] |
| conv2d_2 (Conv2D) | (None, None, None, 32) | 9216 | batch_normalization_2[0][0] |
| batch_normalization_3 (BatchNormali | (None, None, None, 32) | 128 | conv2d_2[0][0] |
| max_pooling2d_1 (MaxPooling2D) | (None, None, None, 32) | 0 | batch_normalization_3[0][0] |
| conv2d_3 (Conv2D) | (None, None, None, 64) | 18432 | max_pooling2d_1[0][0] |
| batch_normalization_4 (BatchNormali | (None, None, None, 64) | 256 | conv2d_3[0][0] |
| conv2d_4 (Conv2D) | (None, None, None, 64) | 36864 | batch_normalization_4[0][0] |
| batch_normalization_5 (BatchNormali | (None, None, None, 64) | 256 | conv2d_4[0][0] |
| max_pooling2d_2 (MaxPooling2D) | (None, None, None, 64) | 0 | batch_normalization_5[0][0] |
| conv2d_5 (Conv2D) | (None, None, None, 128) | 73728 | max_pooling2d_2[0][0] |
| batch_normalization_6 (BatchNormali | (None, None, None, 128) | 512 | conv2d_5[0][0] |
| conv2d_6 (Conv2D) | (None, None, None, 128) | 147456 | batch_normalization_6[0][0] |
| batch_normalization_7 (BatchNormali | (None, None, None, 128) | 512 | conv2d_6[0][0] |
| dropout_1 (Dropout) | (None, None, None, 128) | 0 | batch_normalization_7[0][0] |
| max_pooling2d_3 (MaxPooling2D) | (None, None, None, 128) | 0 | dropout_1[0][0] |
| conv2d_7 (Conv2D) | (None, None, None, 256) | 294912 | max_pooling2d_3[0][0] |
| batch_normalization_8 (BatchNormali | (None, None, None, 256) | 1024 | conv2d_7[0][0] |
| conv2d_8 (Conv2D) | (None, None, None, 256) | 589824 | batch_normalization_8[0][0] |
| batch_normalization_9 (BatchNormali | (None, None, None, 256) | 1024 | conv2d_8[0][0] |
| dropout_2 (Dropout) | (None, None, None, 256) | 0 | batch_normalization_9[0][0] |
| up_sampling2d_1 (UpSampling2D) | (None, None, None, 256) | 0 | dropout_2[0][0] |
| concatenate_1 (Concatenate) | (None, None, None, 384) | 0 | up_sampling2d_1[0][0]<br>batch_normalization_7[0][0] |
| conv2d_9 (Conv2D) | (None, None, None, 128) | 442368 | concatenate_1[0][0] |
| batch_normalization_10 (BatchNormal | (None, None, None, 128) | 512 | conv2d_9[0][0] |
| conv2d_10 (Conv2D) | (None, None, None, 128) | 147456 | batch_normalization_10[0][0] |
| batch_normalization_11 (BatchNormal | (None, None, None, 128) | 512 | conv2d_10[0][0] |
| dropout_3 (Dropout) | (None, None, None, 128) | 0 | batch_normalization_11[0][0] |
| up_sampling2d_2 (UpSampling2D) | (None, None, None, 128) | 0 | dropout_3[0][0] |
| concatenate_2 (Concatenate) | (None, None, None, 192) | 0 | up_sampling2d_2[0][0]<br>batch_normalization_5[0][0] |
| conv2d_11 (Conv2D) | (None, None, None, 64) | 110592 | concatenate_2[0][0] |
| batch_normalization_12 (BatchNormal | (None, None, None, 64) | 256 | conv2d_11[0][0] |
| conv2d_12 (Conv2D) | (None, None, None, 64) | 36864 | batch_normalization_12[0][0] |
| batch_normalization_13 (BatchNormal | (None, None, None, 64) | 256 | conv2d_12[0][0] |
| up_sampling2d_3 (UpSampling2D) | (None, None, None, 64) | 0 | batch_normalization_13[0][0] |
| concatenate_3 (Concatenate) | (None, None, None, 96) | 0 | up_sampling2d_3[0][0]<br>batch_normalization_3[0][0] |
| conv2d_13 (Conv2D) | (None, None, None, 32) | 27648 | concatenate_3[0][0] |
| batch_normalization_14 (BatchNormal | (None, None, None, 32) | 128 | conv2d_13[0][0] |
| conv2d_14 (Conv2D) | (None, None, None, 32) | 9216 | batch_normalization_14[0][0] |
| batch_normalization_15 (BatchNormal | (None, None, None, 32) | 128 | conv2d_14[0][0] |
| pred (Conv2D) | (None, None, None, 1) | 32 | batch_normalization_15[0][0] |

Total params: 1,958,816
Trainable params: 1,955,944
Non-trainable params: 2,872

Figure 32

Centers of Mass vs. RTA centers

Centers of Mass

956048 + 0 in total (QC-passed reads + QC-failed reads)
158 + 0 secondary
0 + 0 supplementary
841 + 0 duplicates
936609 + 0 mapped (97.97% : N/A)
955890 + 0 paired in sequencing
477945 + 0 read1
477945 + 0 read2
928926 + 0 properly paired (97.18% : N/A)
930732 + 0 with itself and mate mapped
5719 + 0 singletons (0.60% : N/A)
0 + 0 with mate mapped to a different chr
0 + 0 with mate mapped to a different chr (mapQ>=5)

bases mapped: 141404101    # ignores clipping
bases mapped (cigar): 140673703
bases trimmed: 0
bases duplicated:    126991
mismatches:    498799  # from NM fields
error rate: 3.545787e-03    # mismatches / bases mapped (cigar)

RTA centers

956054 + 0 in total (QC-passed reads + QC-failed reads)
164 + 0 secondary
0 + 0 supplementary
1045 + 0 duplicates
932910 + 0 mapped (97.58% : N/A)
955890 + 0 paired in sequencing
477945 + 0 read1
477945 + 0 read2
923322 + 0 properly paired (96.59% : N/A)
925276 + 0 with itself and mate mapped
7470 + 0 singletons (0.78% : N/A)
0 + 0 with mate mapped to a different chr
0 + 0 with mate mapped to a different chr (mapQ>=5)

bases mapped: 140844646    # ignores clipping
bases mapped (cigar): 139683478
bases trimmed: 0
bases duplicated: 157795
mismatches: 821045  # from NM fields
error rate: 5.877897e-03    # mismatches / bases mapped (cigar)

Figure 35

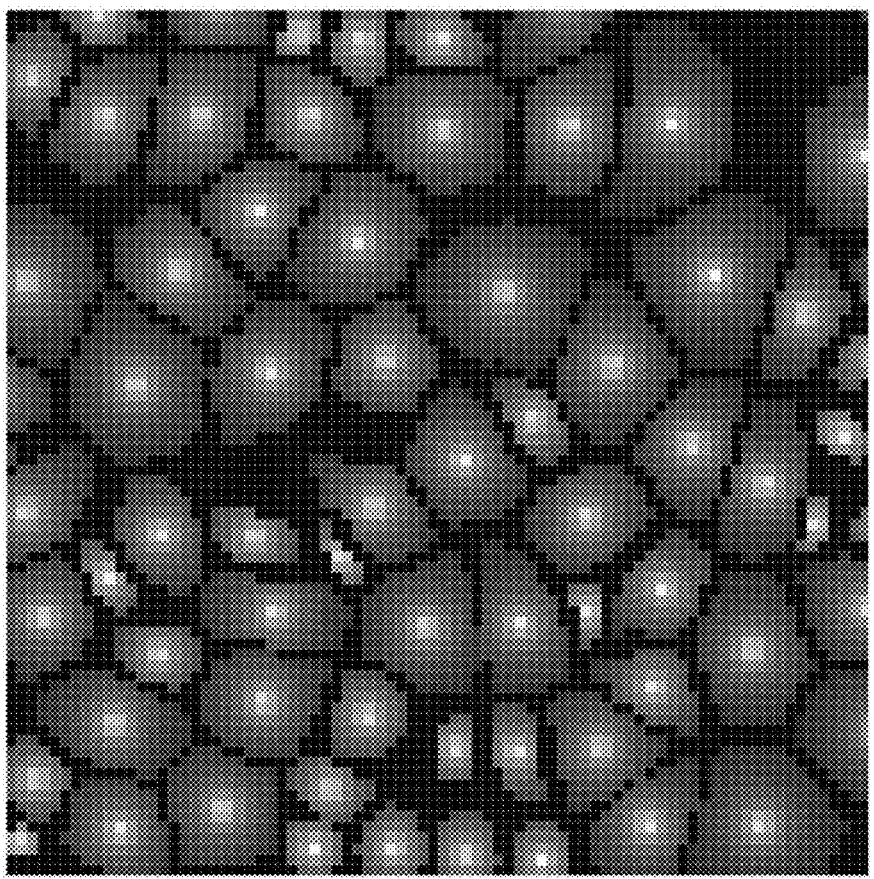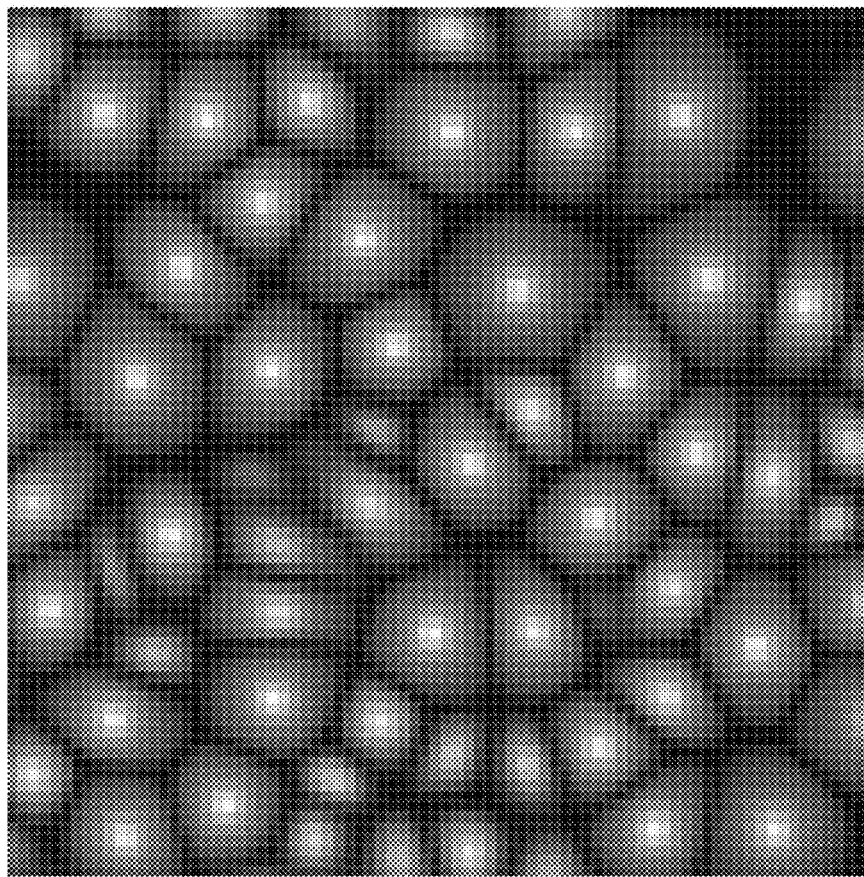
Figure 36

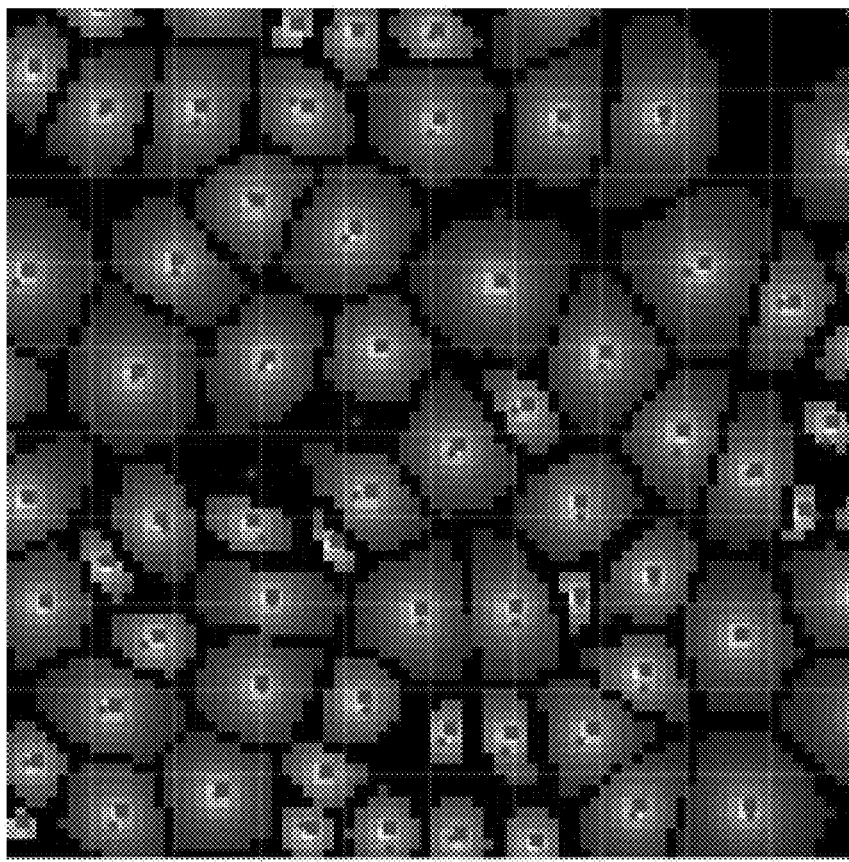
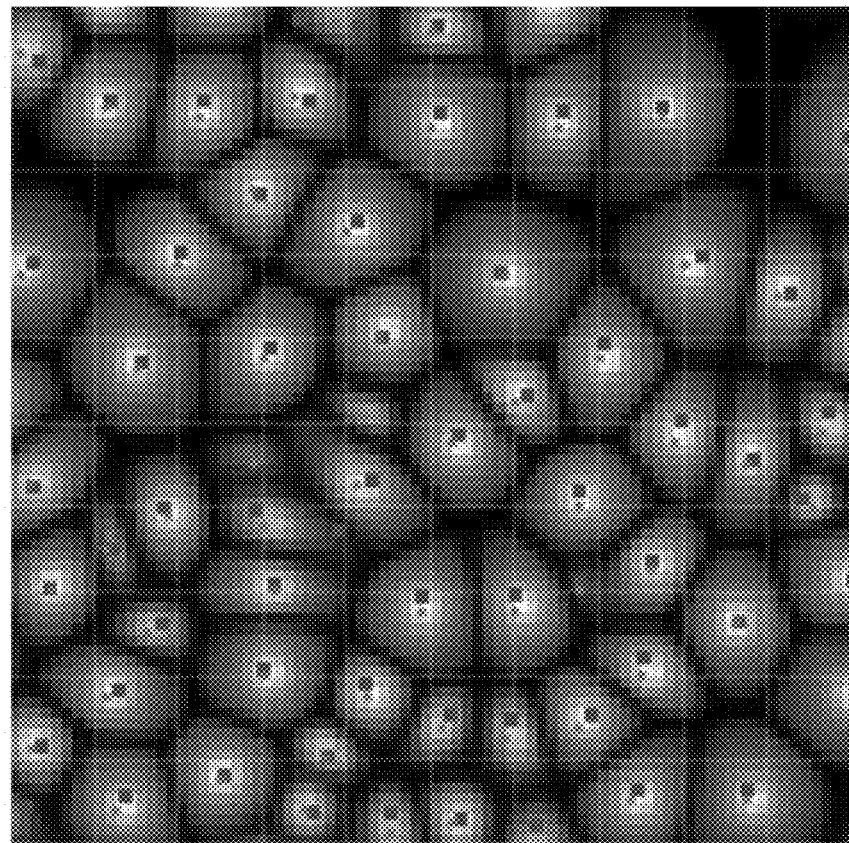
Figure 38

NORMAL RUN 20pM Tile: 1102 (7 cycles)

| | RTA | Within Boundary +/- 10 (Unet) |
|---|---|---|
| # clusters | 903,040 | 988,884 |
| % PF | 88.55% (799,684) | 84.54% (836,197) |
| % Aligned | 97.50% | 97.47% |
| % Duplicate | 0.05% | 0.12% |
| % Mismatch | 0.37% | 0.34% |
| % soft clipped | 2.07% | 2.05% |
| % Q30 bases | 90.59% | 91.42% |
| Non-duplicate proper read pairs | 769,150 | 803,473 (4.46%, 34,323) |

Figure 40

DENSE RUN 30pM Tile: 2103 (7 cycles)

| | RTA | Within Boundary +/- 10 (Unet) |
|---|---|---|
| # clusters | 1,157,285 | 1,351,588 |
| % PF | 78.58% (909,340) | 71.62% (968,066) |
| % Aligned | 97.69% | 97.62% |
| % Duplicate | 0.05% | 0.07% |
| % Mismatch | 0.65% | 0.63% |
| % soft clipped | 2.60% | 2.57% |
| % Q30 bases | 83.45% | 83.88% |
| Non-duplicate proper read pairs | 874,000 | 928,787 (6.27%) |

Figure 41

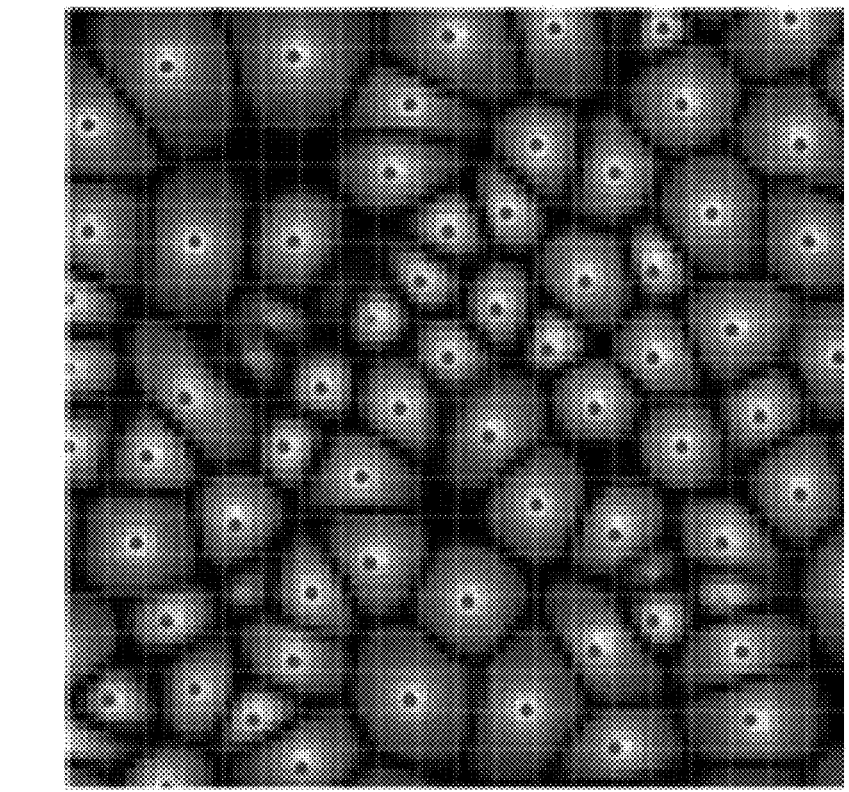
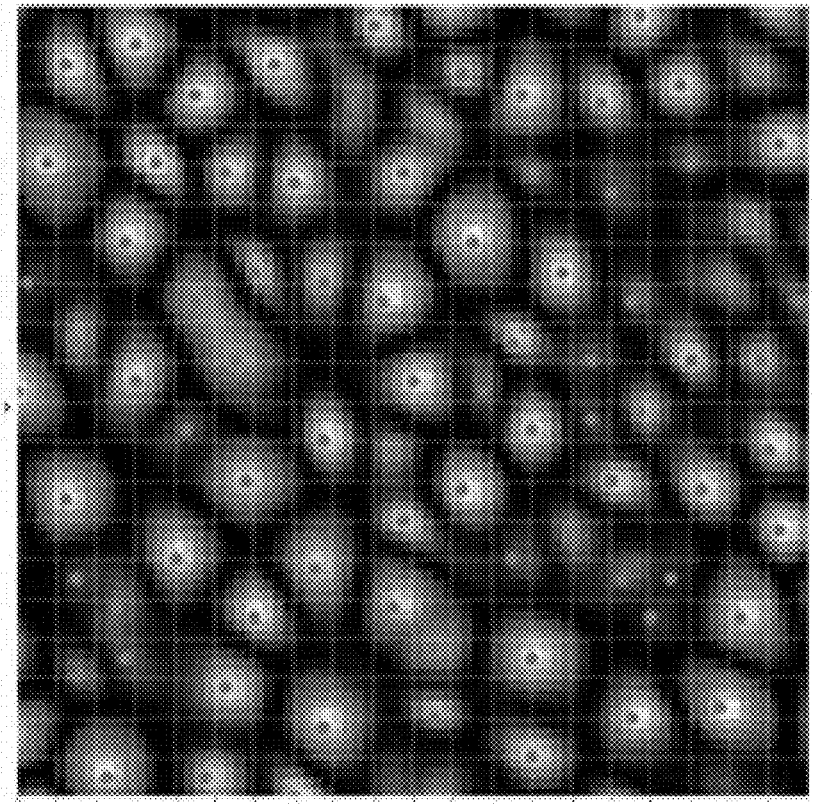
Figure 43

DENSE RUN 40pM Tile: 1101 (7 cycles)

| | RTA | Within Boundary +/- 10 (Unet) |
|---|---|---|
| # clusters | 1,089,460 | 1,509,395 |
| % PF | 42.60% (464,095) | 54.00% (815,168) |
| % Aligned | 93.00% | 96.58% |
| % Duplicate | 0.25% | 0.04% |
| % Mismatch | 2.93% | 2.02% |
| % soft clipped | 4.79% | 11.83% |
| % Q30 bases | 60.10% | 65.33% |
| Non-duplicate proper read pairs | 415,877 | 771,851 (85.6%) |
| Total aligned bases | 117,893,944 | 207,335,632 |

Figure 44

| Layer (type) | Output Shape | Param # |
|---|---|---|
| input_1 (InputLayer) | (None, 80, 80, 28) | 0 |
| conv2d_1 (Conv2D) | (None, 80, 80, 32) | 8064 |
| batch_normalization_1 (Batch | (None, 80, 80, 32) | 128 |
| conv2d_2 (Conv2D) | (None, 80, 80, 32) | 9216 |
| batch_normalization_2 (Batch | (None, 80, 80, 32) | 128 |
| max_pooling2d_1 (MaxPooling2 | (None, 40, 40, 32) | 0 |
| conv2d_3 (Conv2D) | (None, 40, 40, 64) | 18432 |
| batch_normalization_3 (Batch | (None, 40, 40, 64) | 256 |
| conv2d_4 (Conv2D) | (None, 40, 40, 64) | 36864 |
| batch_normalization_4 (Batch | (None, 40, 40, 64) | 256 |
| max_pooling2d_2 (MaxPooling2 | (None, 20, 20, 64) | 0 |
| conv2d_5 (Conv2D) | (None, 20, 20, 128) | 73728 |
| batch_normalization_5 (Batch | (None, 20, 20, 128) | 512 |
| conv2d_6 (Conv2D) | (None, 20, 20, 128) | 147456 |
| batch_normalization_6 (Batch | (None, 20, 20, 128) | 512 |
| dropout_1 (Dropout) | (None, 20, 20, 128) | 0 |
| max_pooling2d_3 (MaxPooling2 | (None, 10, 10, 128) | 0 |
| conv2d_7 (Conv2D) | (None, 10, 10, 512) | 589824 |
| batch_normalization_7 (Batch | (None, 10, 10, 512) | 2048 |
| dropout_2 (Dropout) | (None, 10, 10, 512) | 0 |
| up_sampling2d_1 (UpSampling2 | (None, 20, 20, 512) | 0 |
| conv2d_8 (Conv2D) | (None, 20, 20, 128) | 589824 |
| batch_normalization_8 (Batch | (None, 20, 20, 128) | 512 |
| conv2d_9 (Conv2D) | (None, 20, 20, 128) | 147456 |
| batch_normalization_9 (Batch | (None, 20, 20, 128) | 512 |
| dropout_3 (Dropout) | (None, 20, 20, 128) | 0 |
| up_sampling2d_2 (UpSampling2 | (None, 40, 40, 128) | 0 |
| conv2d_10 (Conv2D) | (None, 40, 40, 64) | 73728 |
| batch_normalization_10 (Batc | (None, 40, 40, 64) | 256 |
| conv2d_11 (Conv2D) | (None, 40, 40, 64) | 36864 |
| batch_normalization_11 (Batc | (None, 40, 40, 64) | 256 |
| up_sampling2d_3 (UpSampling2 | (None, 80, 80, 64) | 0 |
| conv2d_12 (Conv2D) | (None, 80, 80, 32) | 18432 |
| batch_normalization_12 (Batc | (None, 80, 80, 32) | 128 |
| conv2d_13 (Conv2D) | (None, 80, 80, 32) | 9216 |
| batch_normalization_13 (Batc | (None, 80, 80, 32) | 128 |
| pred (Conv2D) | (None, 80, 80, 2) | 64 |

Total params: 1,764,800
Trainable params: 1,761,984
Non-trainable params: 2,816

Figure 53

Ternary Classification Model 5400

Figure 57

Three-Category Classification: Predictions
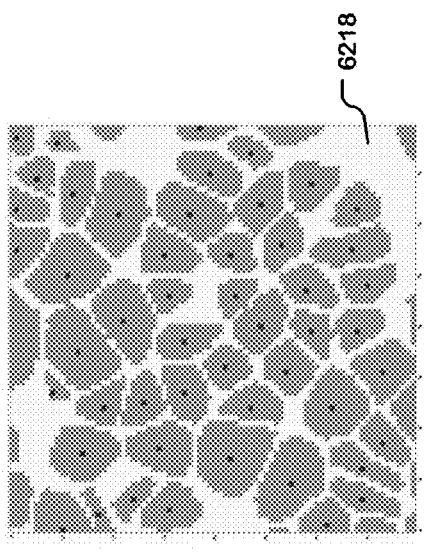
Truth map
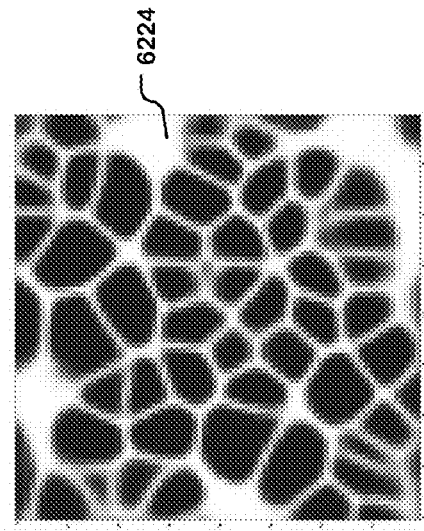
Background
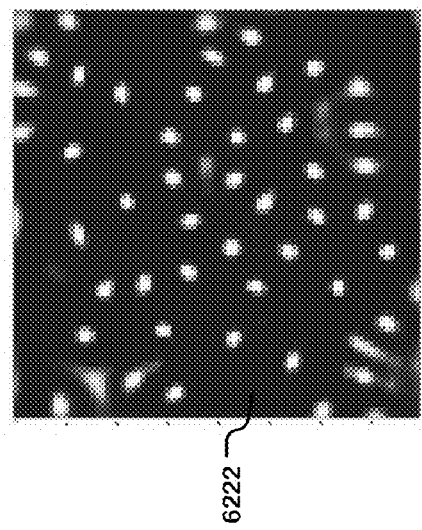
Cluster centers
Figure 62c
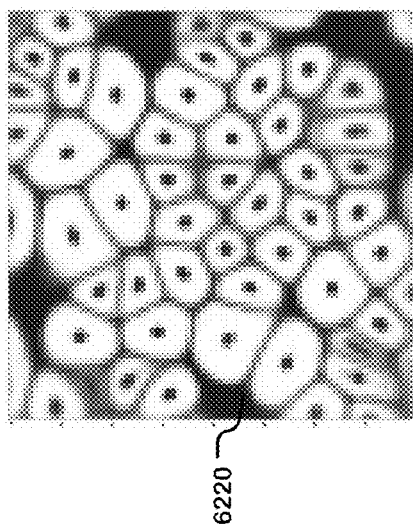
Cluster interiors
Model predictions

Basecall comparisons (using RTA 1.18)

| | RTA | DL binary classification | DL regression |
|---|---|---|---|
| # clusters | 493,944 | 519,100 | 543,348 |
| % PF | 88.8% | 86.99% | 85.86% |
| % Aligned | 97.63% | 97.68% | 97.67% |
| % Duplicate | 0.02% | 0.2% | 0.14% |
| % Mismatch | 0.34% | 0.29% | 0.29% |
| % soft clipped | 2.02% | 1.97% | 1.97% |
| % Q30 bases | 91.94% | 92.76% | 92.81% |
| Total proper read pairs | 422,907 | 435,737 | 449,993 |
| Non-duplicate proper read pairs | 424,665 | 434,869 | 449,344 |

Figure 64

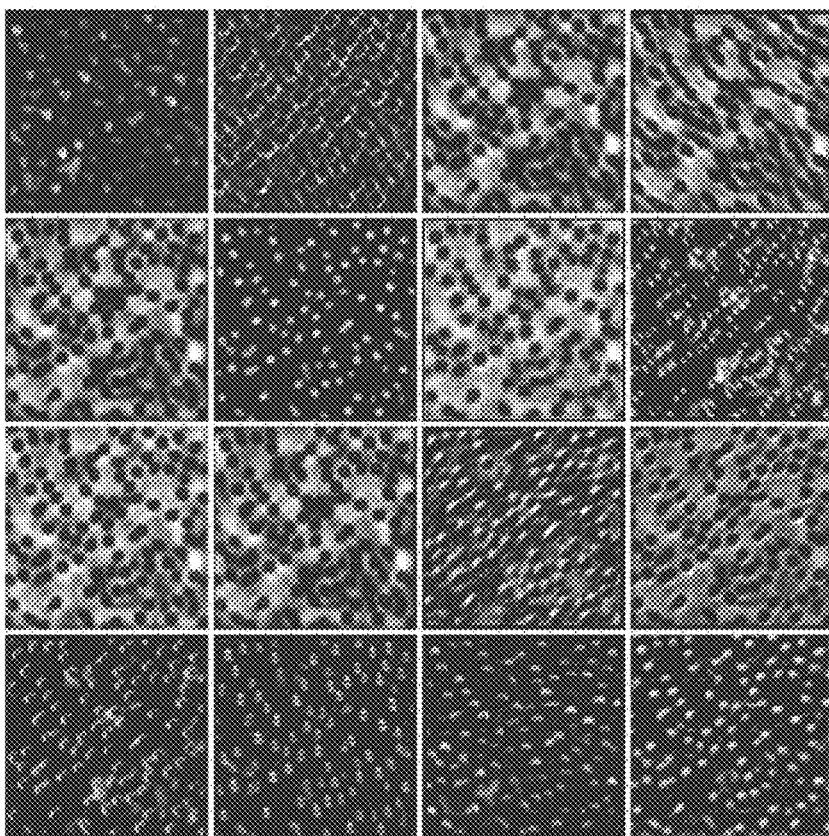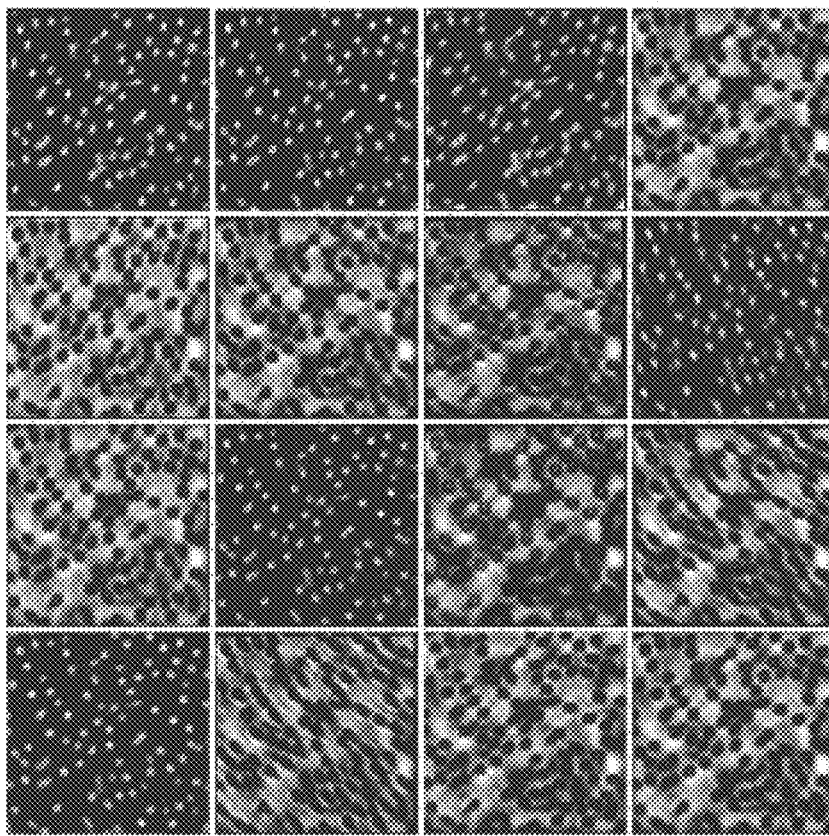
Figure 70

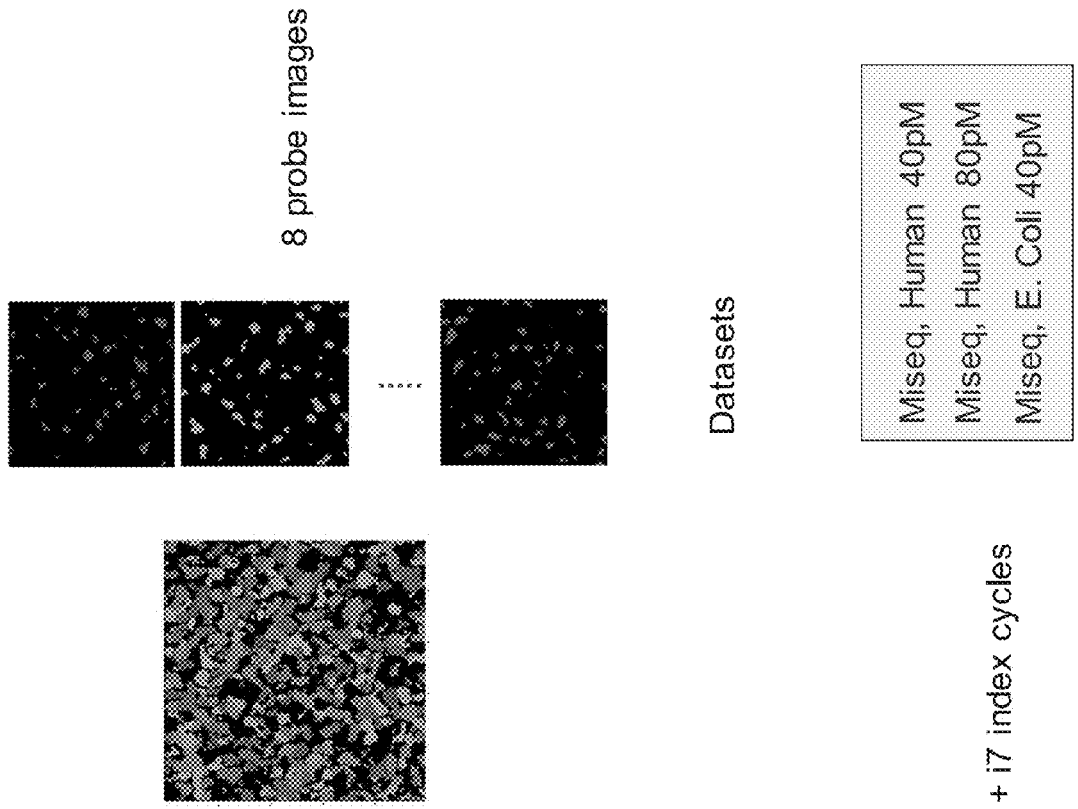
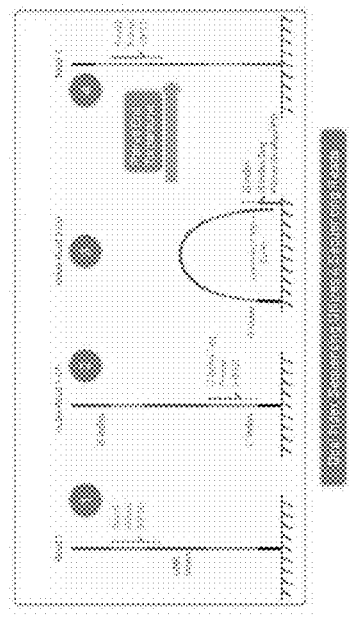
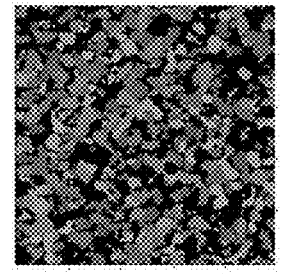
Figure 71

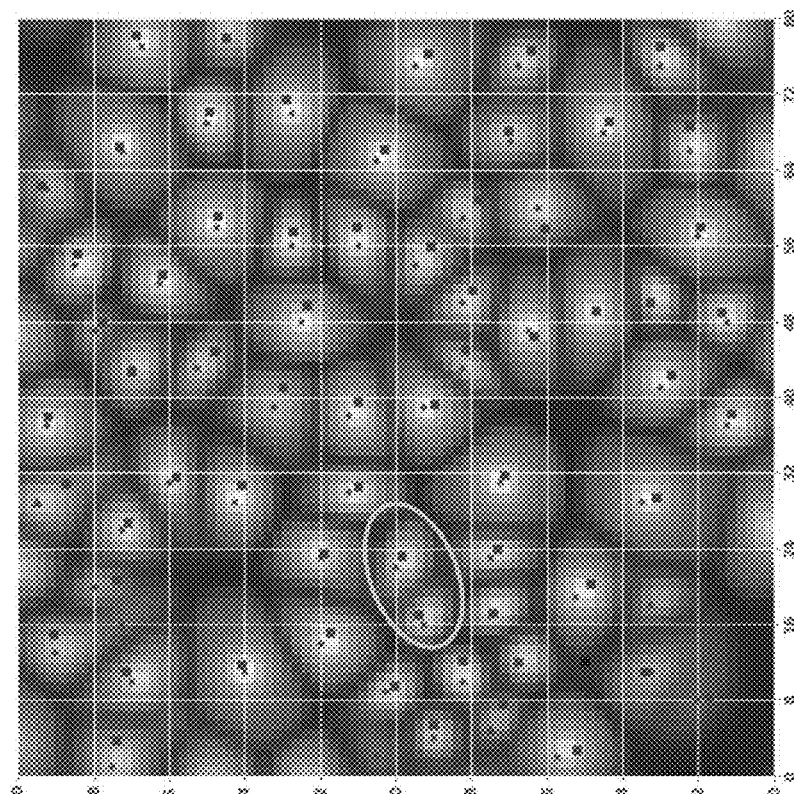
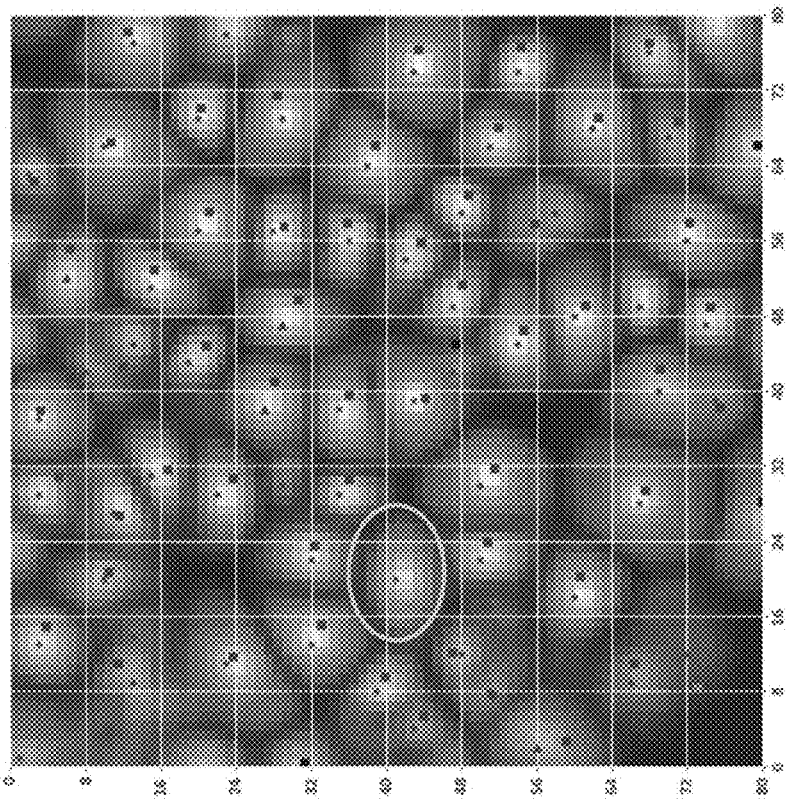
Figure 74

RTA centers vs. mass centers

Mass centers

```
956048 + 0 in total (QC-passed reads + QC-
failed reads)
158 + 0 secondary
0 + 0 supplementary
841 + 0 duplicates
936609 + 0 mapped (97.97% : N/A)
955890 + 0 paired in sequencing
477945 + 0 read1
477945 + 0 read2
928926 + 0 properly paired (97.18% : N/A)
930732 + 0 with itself and mate mapped
5719 + 0 singletons (0.60% : N/A)
0 + 0 with mate mapped to a different chr
0 + 0 with mate mapped to a different chr
(mapQ>=5)
```

```
bases mapped: 141404101 # ignores clipping
bases mapped (cigar): 140673703
bases trimmed: 0
bases duplicated:   126991
mismatches:   498799 # from NM fields
error rate: 3.545787e-03  # mismatches /
bases mapped (cigar)
```

RTA centers

```
956054 + 0 in total (QC-passed reads + QC-
failed reads)
164 + 0 secondary
0 + 0 supplementary
1045 + 0 duplicates
932910 + 0 mapped (97.58% : N/A)
955890 + 0 paired in sequencing
477945 + 0 read1
477945 + 0 read2
923322 + 0 properly paired (96.59% : N/A)
925276 + 0 with itself and mate mapped
7470 + 0 singletons (0.78% : N/A)
0 + 0 with mate mapped to a different chr
0 + 0 with mate mapped to a different chr
(mapQ>=5)
```

```
bases mapped: 140844646  # ignores clipping
bases mapped (cigar): 139683478
bases trimmed: 0
bases duplicated: 157795
mismatches: 821045 # from NM fields
error rate: 5.877897e-03   # mismatches /
bases mapped (cigar)
```

Figure 75

Extra grown clusters

```
102777 + 0 in total (QC-passed reads + QC-failed reads)
27 + 0 secondary
0 + 0 supplementary
129 + 0 duplicates
99134 + 0 mapped (96.46% : N/A)
102750 + 0 paired in sequencing
51375 + 0 read1
51375 + 0 read2
96742 + 0 properly paired (94.15% : N/A)
97296 + 0 with itself and mate mapped
1811 + 0 singletons (1.76% : N/A)
0 + 0 with mate mapped to a different chr
0 + 0 with mate mapped to a different chr (mapQ>=5)
```

```
bases mapped: 14965157    # ignores clipping
bases mapped (cigar): 14637927
bases trimmed: 0
bases duplicated: 19479
mismatches: 285579 # from NM fields
error rate: 1.950952e-02    # mismatches / bases mapped (cigar)
```

Figure 76

Data sets

Miseq

| Library | Density | RTA PF% |
|---|---|---|
| 20pM | 1254 K/mm2 | 85% |
| 30pM | 1524 K/mm2 | 72% |
| 40pM | 1529 K/mm2 | 31% |

Nextseq

| Library | RTA PF% |
|---|---|
| 1.3pM | 61% |
| 1.3pM | 42% |
| 3pM | 14% |

Figure 77

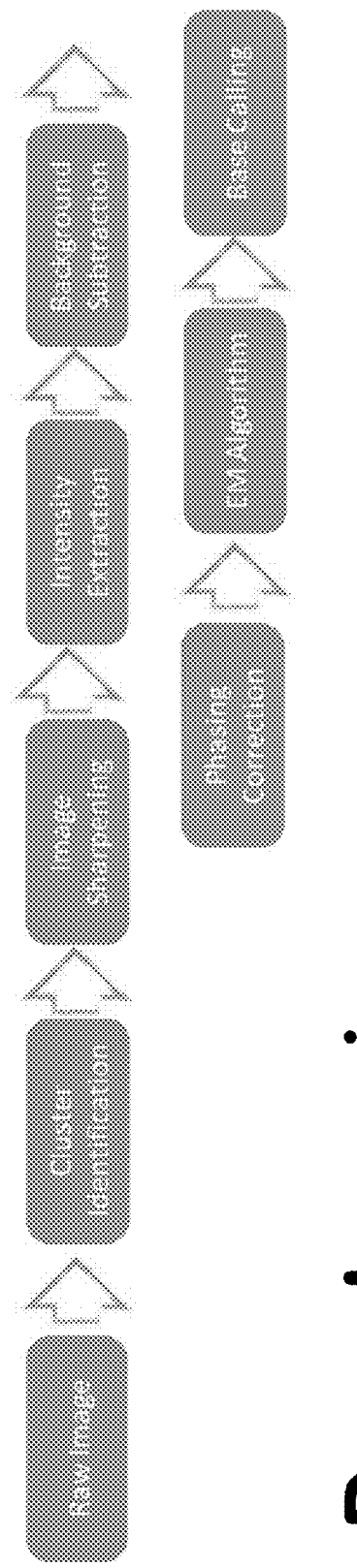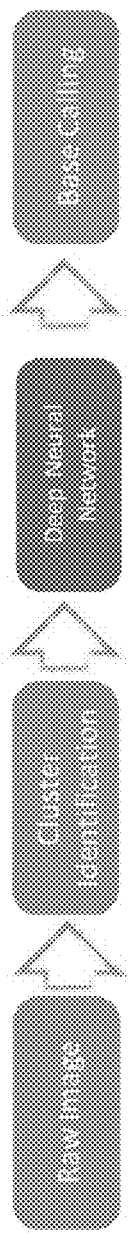
Figure 78

Multiple Clusters Distance Channel n x n
(e.g., 15 x 15)

| d1 | d2 | d3 |  |  |  |  |
|---|---|---|---|---|---|---|
| d8 | d9 | d10 |  |  | d13 | d14 |
|  |  |  |  |  | d20 | d21 |
|  |  |  | dc | d26 | d27 |  |
|  |  |  | d32 | d33 |  |  |
| d29 | d30 | d31 |  |  |  |  |
| d36 | d37 | d38 |  |  |  | dn | pixel 1 → (lower-left); center pixel → dc; pixel n → dn

Pixel-Wise Encoding of Distances 8602

Figure 86

Pixel Centers-to-Assigned Cluster Center Distances 8802

Multiple Clusters, Shape-Based Distance Channel
n x n
(e.g., 15 x 15)

| d2 | d3 | | d5 | d6 | d7 | | |
|----|----|----|----|----|----|----|----|
| d9 | d10 | | d12 | d13 | d14 | | |
| | d17 | d18 | d19 | d20 | d21 | | |
| d22 | d23 | d24 | d25 | d26 | d27 | d28 | |
| d29 | d30 | d31 | d32 | d33 | d34 | d35 | |
| d36 | d37 | d38 | d39 | | | | |
| | | | | | | | |
| | | | | | | | | center pixel → d25 pixel n (top-right area)

pixel 1 (bottom-left area)

Pixel-Wise Encoding of Distances 8902

Figure 89

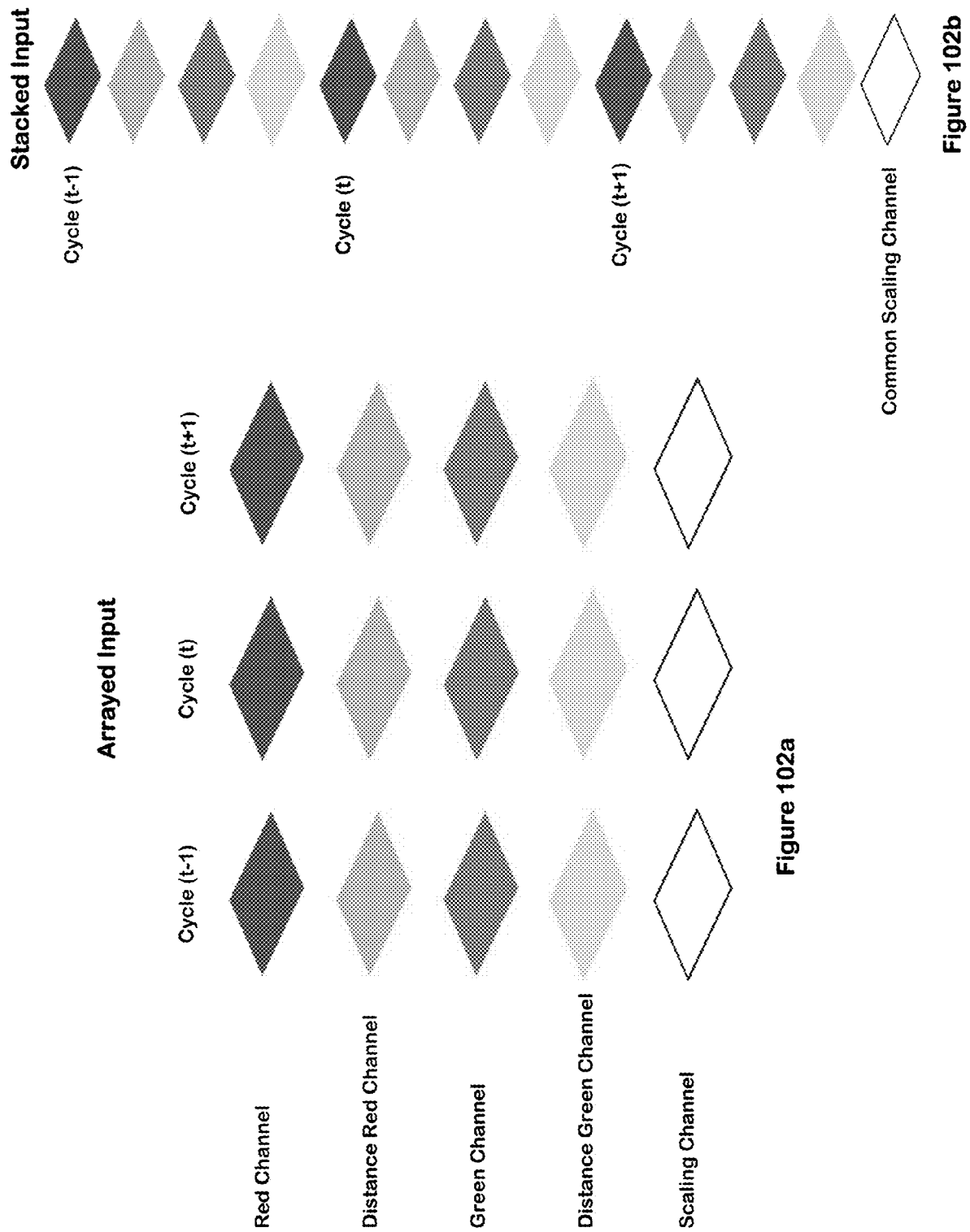

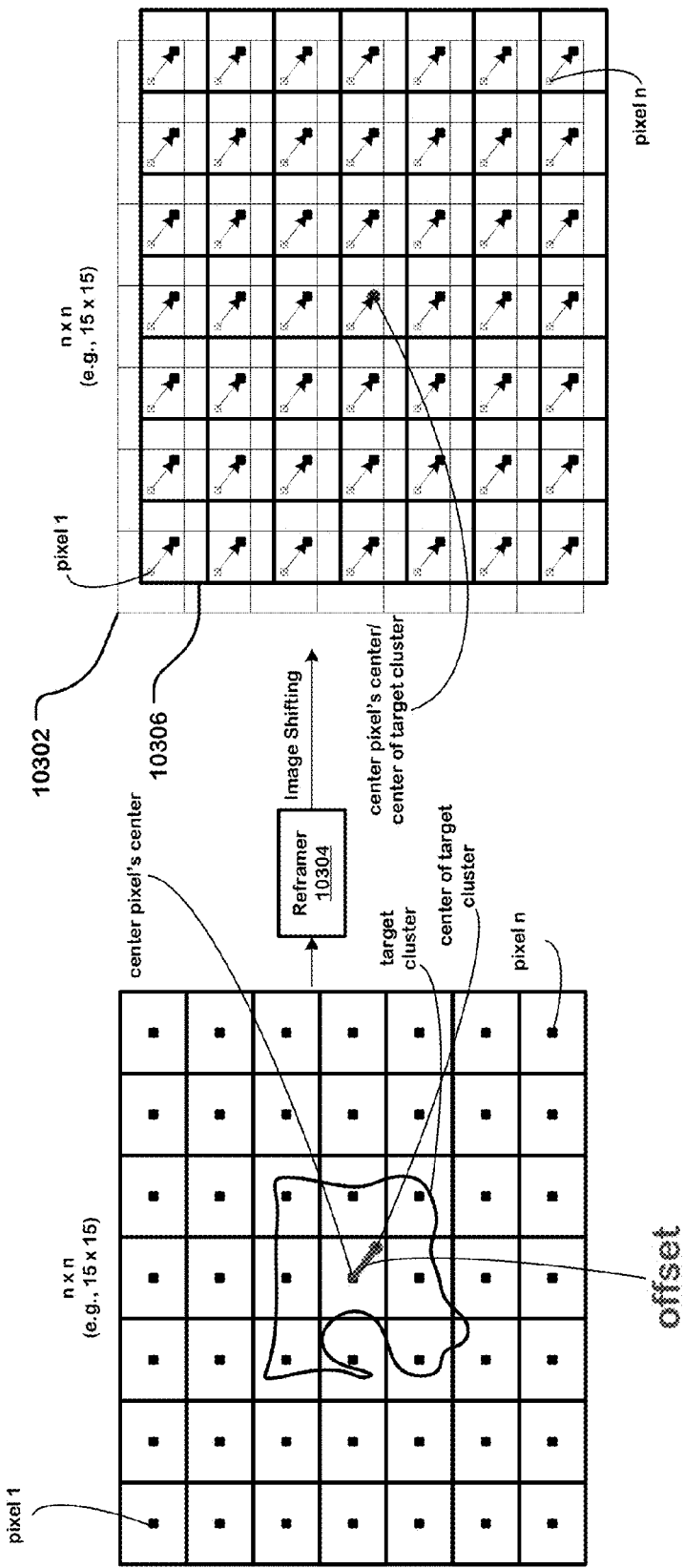

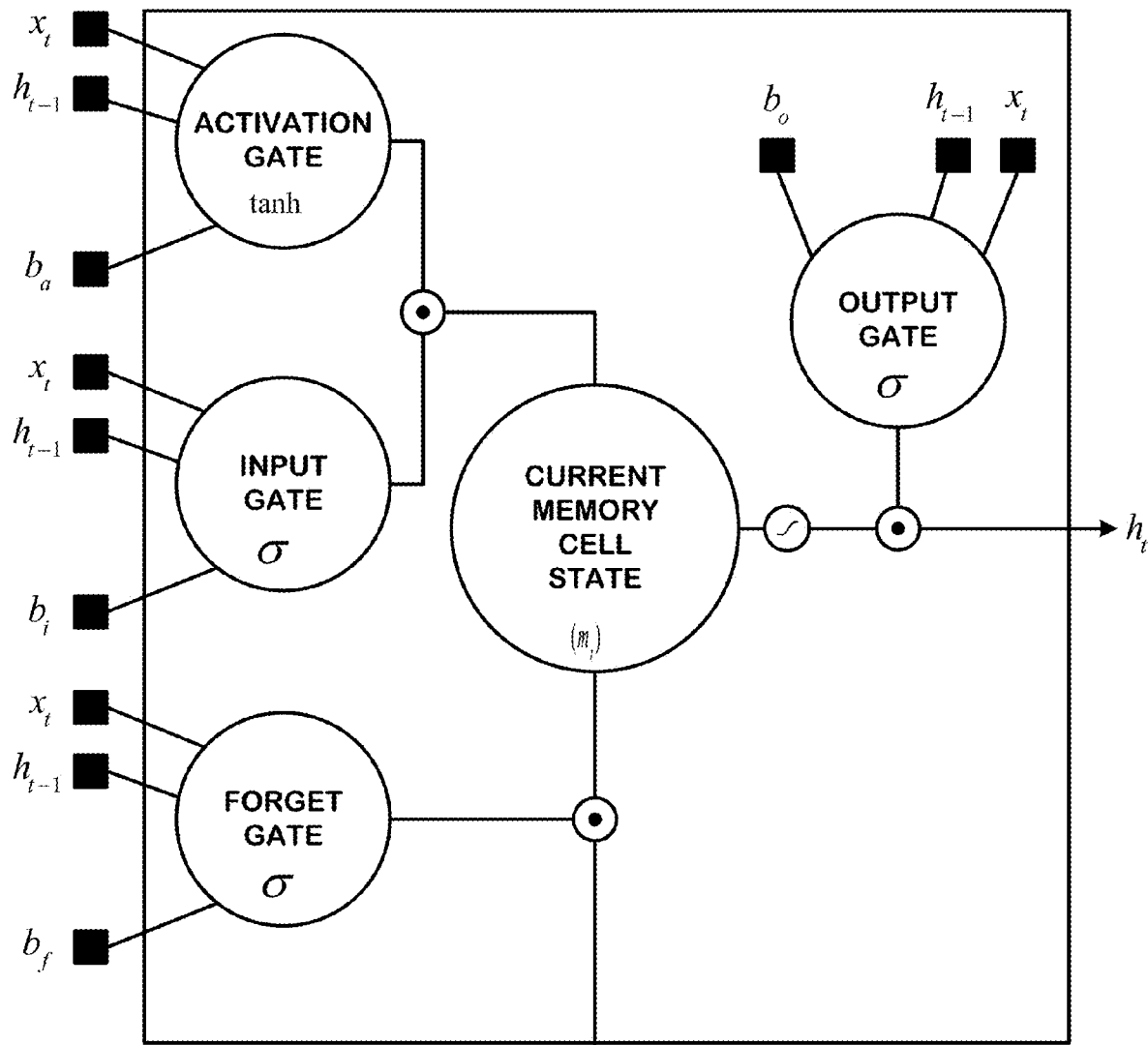
h_t = current hidden state
x_t = current input
h_{t-1} = previous hidden state
b_a = activation bias
b_i = input bias
b_f = forget bias
b_o = output bias
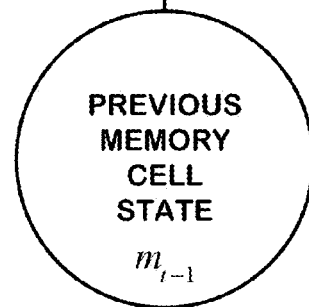
LSTM with 3D CONV 11200b
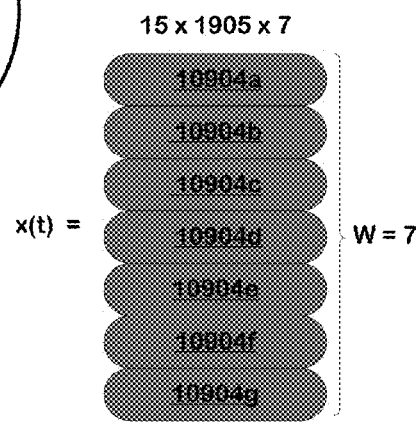
Figure 112b

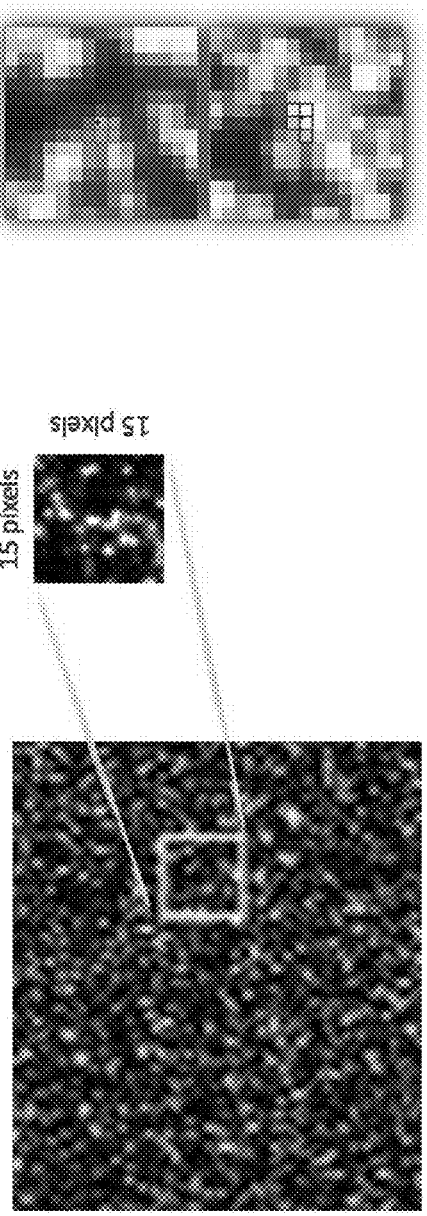
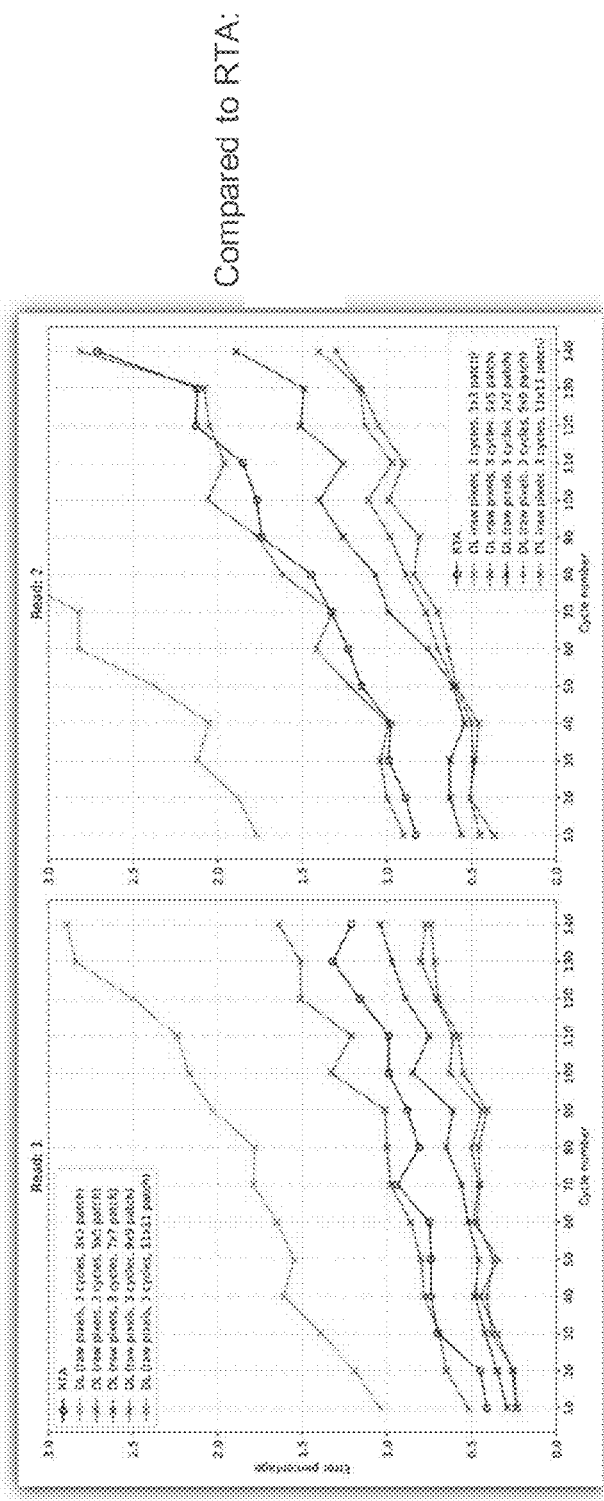
Figure 118

Training the Model

- Lane to Lane Generalization
- Cross organism check
  - Multiple organisms - multiplexed

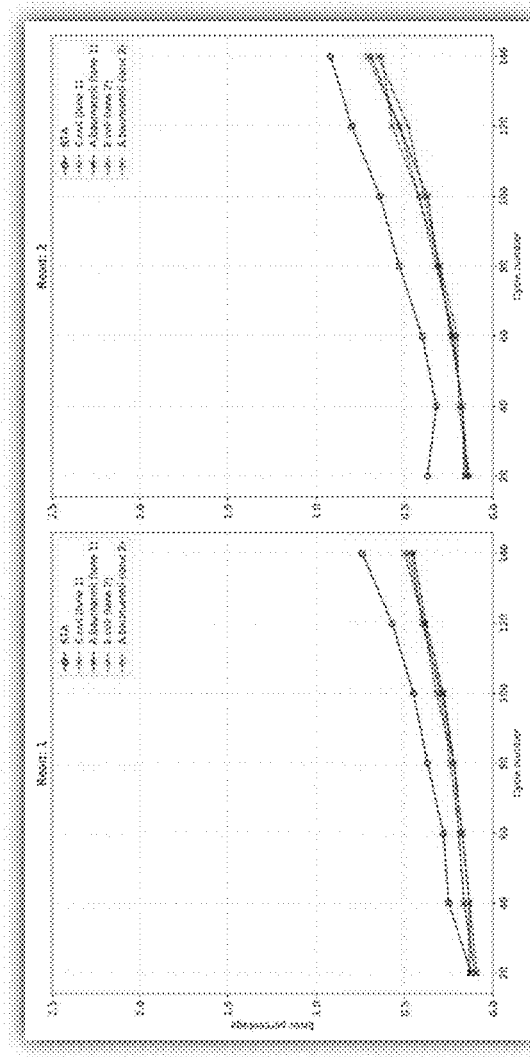
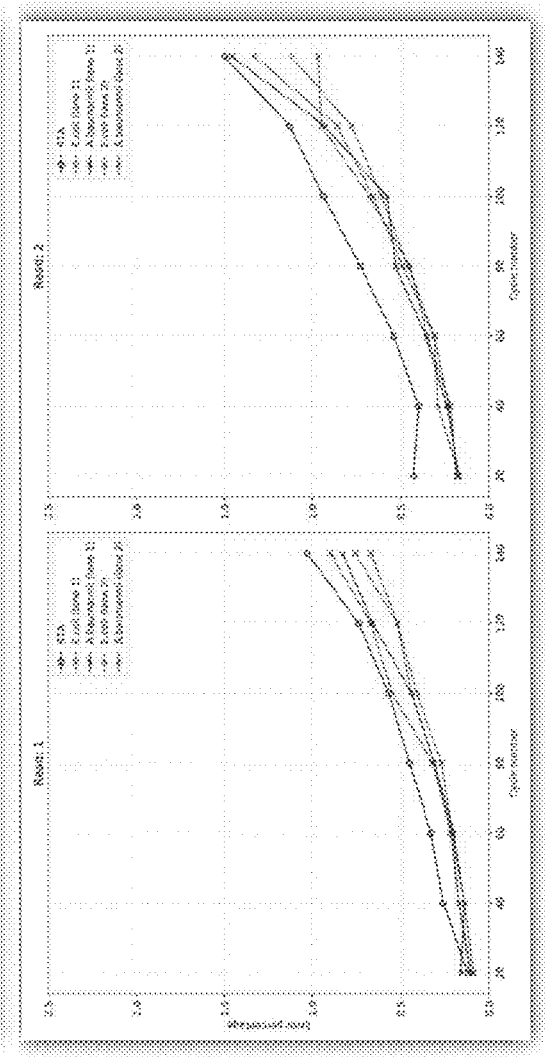
Figure 120

Test: *A. baumannii* (lane 1)
Test: *E. coli* (lane 1)
Between 50-80% error reduction
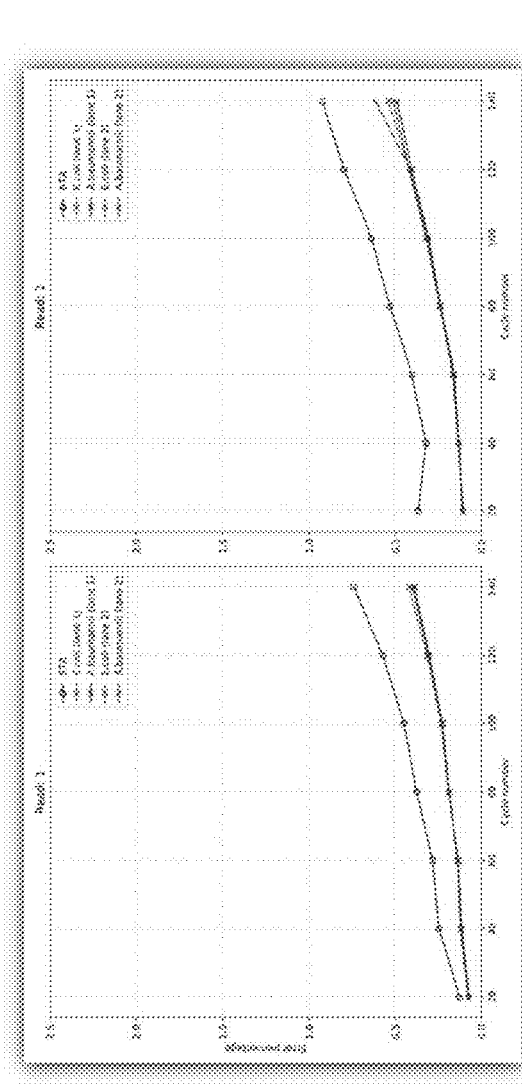
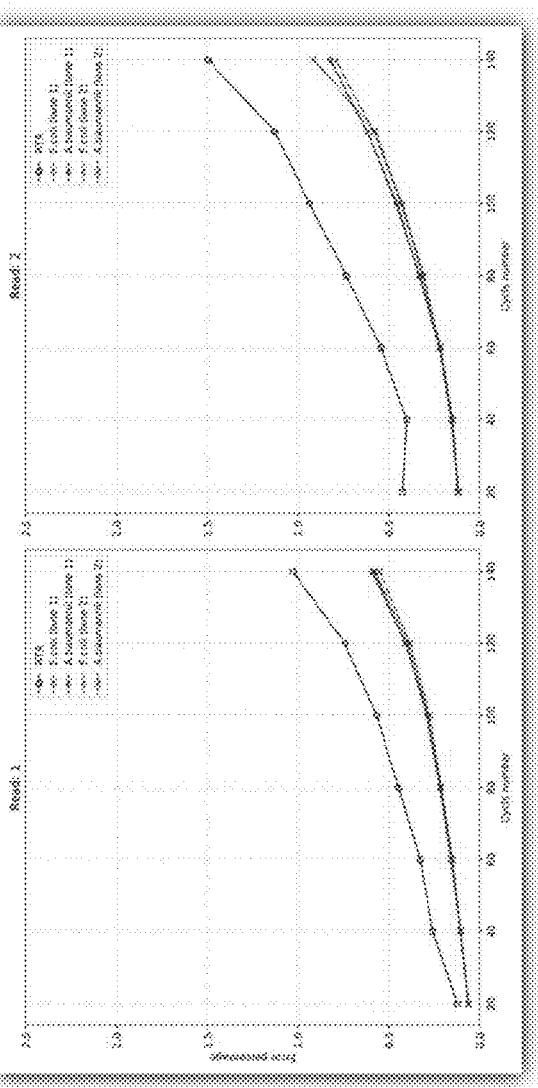
Figure 121

Test: *A. baumannii* (lane 2)
Test: *E. coli* (lane 2)
Between 50-80% error reduction
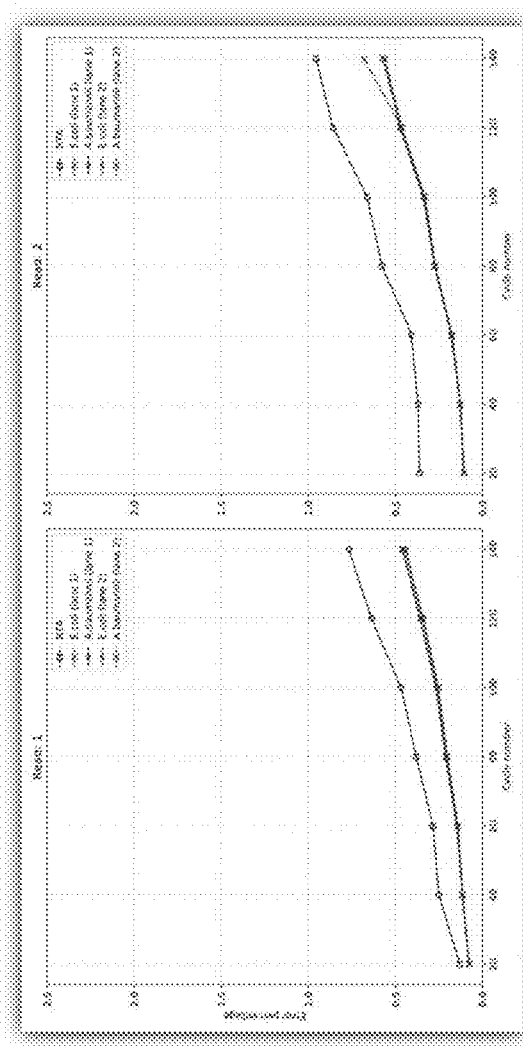
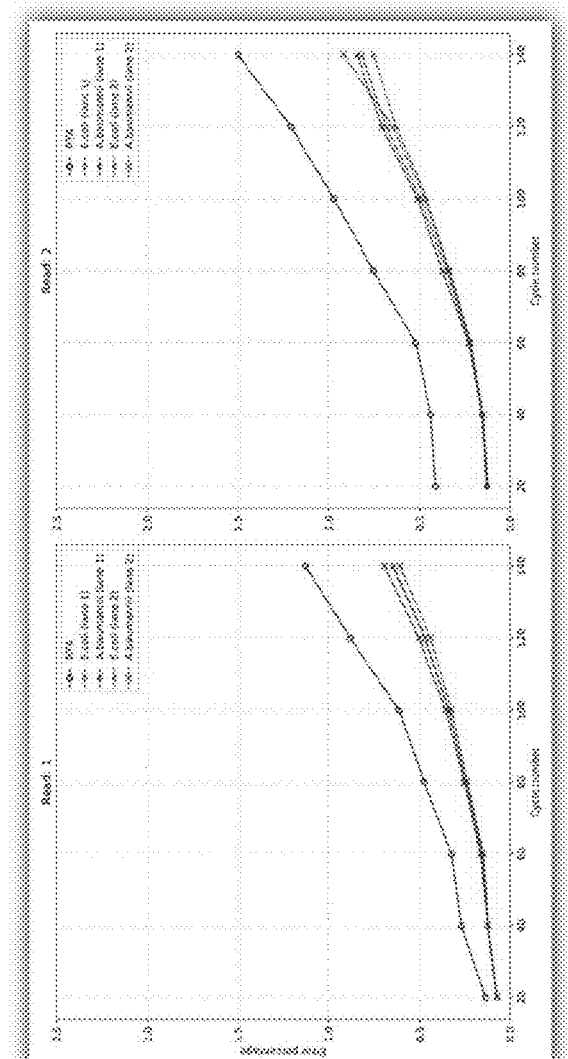
Figure 122

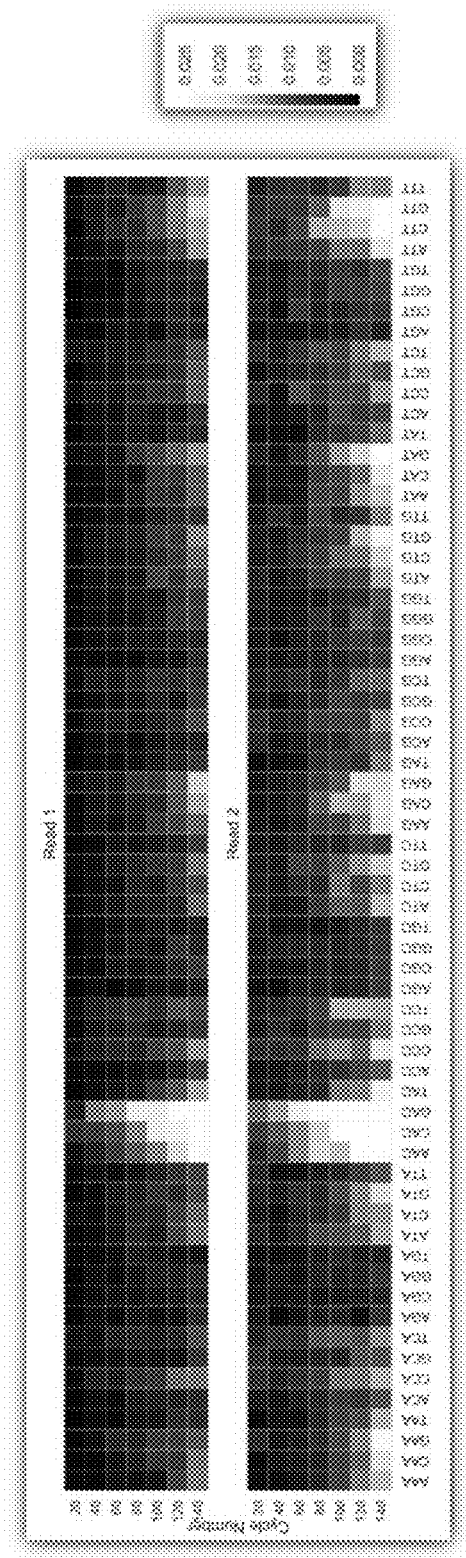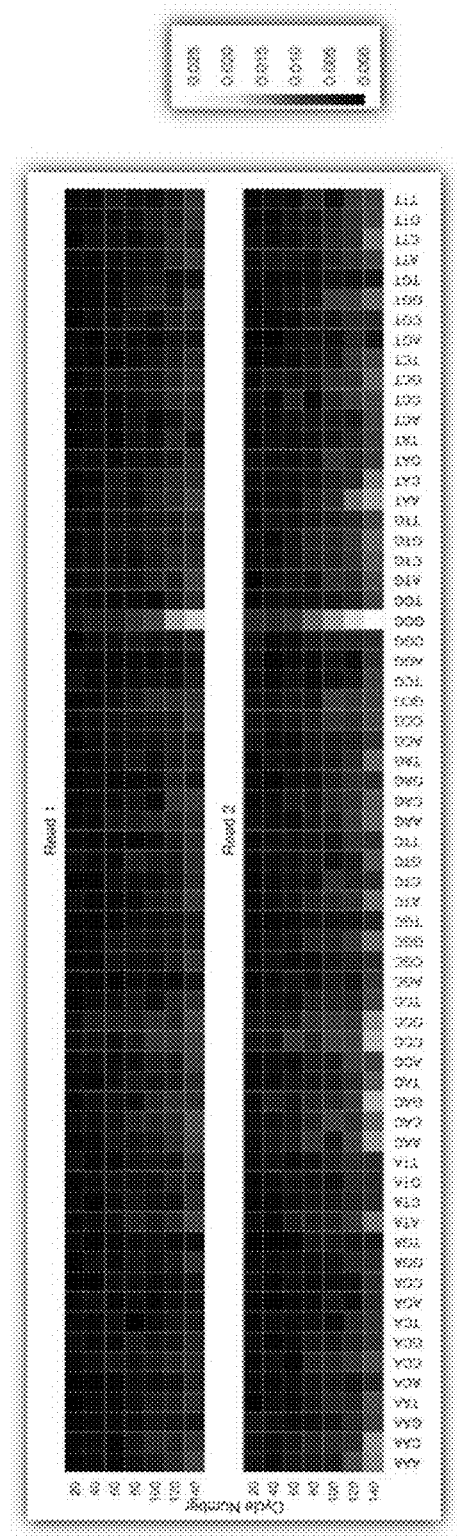
Figure 125

Quality Score Correspondence 13600

Quality Score Correspondence Scheme 13600a

| Quality Score | Softmax Score |
|---|---|
| Q10 | 0.90 |
| Q20 | 0.99 |
| Q30 | 0.999 |
| Q40 | 0.9999 |
| Q50 | 0.99999 |
| Q60 | 0.999999 |

Figure 136a

Quality Score Correspondence Scheme 13600b

| Binned Quality Score | Softmax Score |
|---|---|
| Q2-Q9 -> Q06 | 0.80 |
| Q10-Q19 -> Q15 | 0.95 |
| Q20-Q24 -> Q22 | 0.993 |
| Q25-Q29 -> Q27 | 0.997 |
| Q30-Q34 -> Q33 | 0.9991 |
| Q35-Q39 -> Q37 | 0.9995 |
| Q40 or > Q40 -> Q40 | 0.9999 |

Figure 136b

Upsampling & Background Masking 14500

ARTIFICIAL INTELLIGENCE-BASED SEQUENCING

PRIORITY APPLICATIONS

This application claims priority to or the benefit of the following applications:

U.S. Provisional Patent Application No. 62/821,602, entitled "Training Data Generation for Artificial Intelligence-Based Sequencing," filed 21 Mar. 2019;

U.S. Provisional Patent Application No. 62/821,618, entitled "Artificial Intelligence-Based Generation of Sequencing Metadata," filed 21 Mar. 2019;

U.S. Provisional Patent Application No. 62/821,681, entitled "Artificial Intelligence-Based Base Calling," filed 21 Mar. 2019;

U.S. Provisional Patent Application No. 62/821,724, entitled "Artificial Intelligence-Based Quality Scoring," filed 21 Mar. 2019;

U.S. Provisional Patent Application No. 62/821,766, entitled "Artificial Intelligence-Based Sequencing," filed 21 Mar. 2019;

NL Application No. 2023310, entitled "Training Data Generation for Artificial Intelligence-Based Sequencing," filed 14 Jun. 2019;

NL Application No. 2023311, entitled "Artificial Intelligence-Based Generation of Sequencing Metadata," filed 14 Jun. 2019;

NL Application No. 2023312, entitled "Artificial Intelligence-Based Base Calling," filed 14 Jun. 2019;

NL Application No. 2023314, entitled "Artificial Intelligence-Based Quality Scoring," filed 14 Jun. 2019; and NL Application No. 2023316, entitled "Artificial Intelligence-Based Sequencing," filed 14 Jun. 2019.

US Non-Provisional Applications

U.S. patent application Ser. No. 16/825,987, entitled "Training Data Generation for Artificial Intelligence-Based Sequencing," filed Mar. 20, 2020;

U.S. patent application Ser. No. 16/825,991, entitled "Artificial Intelligence-Based Generation of Sequencing Metadata," filed Mar. 20, 2020;

U.S. patent application Ser. No. 16/826,126, entitled "Artificial Intelligence-Based Base Calling," filed Mar. 20, 2020; and U.S. patent application Ser. No. 16/826,134, entitled "Artificial Intelligence-Based Quality Scoring," filed Mar. 20, 2020.

PCT Patent Application No. PCT/US2020/024090, titled "Training Data Generation for Artificial Intelligence-Based Sequencing," filed Mar. 21, 2020, subsequently published as PCT Publication No. WO 2020/191389 A1;

PCT Patent Application No. PCT/US2020/024087, titled "Artificial Intelligence-Based Generation of Sequencing Metadata," filed Mar. 21, 2020, subsequently published as PCT Publication No. WO 2020/205296 A1;

PCT Patent Application No. PCT/US2020/024088, titled "Artificial Intelligence-Based Base Calling," filed Mar. 21, 2020, subsequently published as PCT Publication No. WO 2020/191387 A1;

PCT Patent Application No. PCT/US2020/024091, titled "Artificial Intelligence-Based Quality Scoring," filed Mar. 21, 2020, subsequently published as PCT Publication No. WO 2020/191390 A1;

PCT Patent Application No. PCT/US2020/024092, titled "Artificial Intelligence-Based Sequencing," filed Mar. 22, 2020, subsequently published as PCT Publication No. WO 2020/191391 A2;

The priority applications are hereby incorporated by reference for all purposes as if fully set forth herein.

INCORPORATIONS

The following are incorporated by reference for all purposes as if fully set forth herein:

U.S. Provisional Patent Application No. 62/849,091, entitled, "Systems and Devices for Characterization and Performance Analysis of Pixel-Based Sequencing," filed May 16, 2019;

U.S. Provisional Patent Application No. 62/849,132, entitled, "Base Calling Using Convolutions," filed May 16, 2019;

U.S. Provisional Patent Application No. 62/849,133, entitled, "Base Calling Using Compact Convolutions," filed May 16, 2019;

U.S. Provisional Patent Application No. 62/979,384, entitled, "Artificial Intelligence-Based Base Calling of Index Sequences," filed Feb. 20, 2020;

U.S. Provisional Patent Application No. 62/979,414, entitled, "Artificial Intelligence-Based Many-To-Many Base Calling," filed Feb. 20, 2020;

U.S. Provisional Patent Application No. 62/979,385, entitled, "Knowledge Distillation-Based Compression of Artificial Intelligence-Based Base Caller," filed Feb. 20, 2020;

U.S. Provisional Patent Application No. 62/979,412, entitled, "Multi-Cycle Cluster Based Real Time Analysis System," filed Feb. 20, 2020;

U.S. Provisional Patent Application No. 62/979,411, entitled, "Data Compression for Artificial Intelligence-Based Base Calling," filed Feb. 20, 2020;

U.S. Provisional Patent Application No. 62/979,399, entitled, "Squeezing Layer for Artificial Intelligence-Based Base Calling," filed Feb. 20, 2020;

Liu P, Hemani A, Paul K, Weis C, Jung M, Wehn N. 3D-Stacked Many-Core Architecture for Biological Sequence Analysis Problems. Int J Parallel Prog. 2017; 45(6):1420-60;

Z. Wu, K. Hammad, R. Mittmann, S. Magierowski, E. Ghafar-Zadeh, and X. Zhong, "FPGA-Based DNA Basecalling Hardware Acceleration," in Proc. IEEE 61st Int. Midwest Symp. Circuits Syst., August 2018, pp. 1098-1101;

Z. Wu, K. Hammad, E. Ghafar-Zadeh, and S. Magierowski, "FPGA-Accelerated 3rd Generation DNA Sequencing," in IEEE Transactions on Biomedical Circuits and Systems, Volume 14, Issue 1, February 2020, pp. 65-74;

Prabhakar et al., "Plasticine: A Reconfigurable Architecture for Parallel Patterns," ISCA '17, Jun. 24-28, 2017, Toronto, ON, Canada;

M. Lin, Q. Chen, and S. Yan, "Network in Network," in Proc. of ICLR, 2014;

L. Sifre, "Rigid-motion Scattering for Image Classification, Ph.D. thesis, 2014;

L. Sifre and S. Mallat, "Rotation, Scaling and Deformation Invariant Scattering for Texture Discrimination," in Proc. of CVPR, 2013;

F. Chollet, "Xception: Deep Learning with Depthwise Separable Convolutions," in Proc. of CVPR, 2017;

X. Zhang, X. Zhou, M. Lin, and J. Sun, "ShuffleNet: An Extremely Efficient Convolutional Neural Network for Mobile Devices," in arXiv:1707.01083, 2017;

K. He, X. Zhang, S. Ren, and J. Sun, "Deep Residual Learning for Image Recognition," in Proc. of CVPR, 2016;

S. Xie, R. Girshick, P. Dollar, Z. Tu, and K. He, "Aggregated Residual Transformations for Deep Neural Networks," in Proc. of CVPR, 2017;

A. G. Howard, M. Zhu, B. Chen, D. Kalenichenko, W. Wang, T. Weyand, M. Andreetto, and H. Adam, "Mobilenets: Efficient Convolutional Neural Networks for Mobile Vision Applications," in arXiv:1704.04861, 2017;

M. Sandler, A. Howard, M. Zhu, A. Zhmoginov, and L. Chen, "MobileNetV2: Inverted Residuals and Linear Bottlenecks," in arXiv:1801.04381v3, 2018;

Z. Qin, Z. Zhang, X. Chen, and Y. Peng, "FD-MobileNet: Improved MobileNet with a Fast Downsampling Strategy," in arXiv:1802.03750, 2018;

Liang-Chieh Chen, George Papandreou, Florian Schroff, and Hartwig Adam. Rethinking atrous convolution for semantic image segmentation. CoRR, abs/1706.05587, 2017;

J. Huang, V. Rathod, C. Sun, M. Zhu, A. Korattikara, A. Fathi, I. Fischer, Z. Wojna, Y. Song, S. Guadarrama, et al. Speed/accuracy trade-offs for modern convolutional object detectors, arXiv preprint arXiv:1611.10012, 2016;

S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

S. Ö. Arik, M. Chrzanowski, A. Coates, G. Diamos, A. Gibiansky, Y. Kang, X. Li, J. Miller, A. Ng, J. Raiman, S. Sengupta and M. Shoeybi, "DEEP VOICE: REAL-TIME NEURAL TEXT-TO-SPEECH," arXiv:1702.07825, 2017;

F. Yu and V. Koltun, "MULTI-SCALE CONTEXT AGGREGATION BY DILATED CONVOLUTIONS," arXiv: 1511.07122, 2016;

K. He, X. Zhang, S. Ren, and J. Sun, "DEEP RESIDUAL LEARNING FOR IMAGE RECOGNITION," arXiv: 1512.03385, 2015;

R. K. Srivastava, K. Greff, and J. Schmidhuber, "HIGHWAY NETWORKS," arXiv: 1505.00387, 2015;

G. Huang, Z. Liu, L. van der Maaten and K. Q. Weinberger, "DENSELY CONNECTED CONVOLUTIONAL NETWORKS," arXiv:1608.06993, 2017;

C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv: 1409.4842, 2014;

S. Ioffe and C. Szegedy, "BATCH NORMALIZATION: ACCELERATING DEEP NETWORK TRAINING BY REDUCING INTERNAL COVARIATE SHIFT," arXiv: 1502.03167, 2015;

J. M. Wolterink, T. Leiner, M. A. Viergever, and I. Išgum, "DILATED CONVOLUTIONAL NEURAL NETWORKS FOR CARDIOVASCULAR MR SEGMENTATION IN CONGENITAL HEART DISEASE," arXiv: 1704.03669, 2017;

L. C. Piqueras, "AUTOREGRESSIVE MODEL BASED ON A DEEP CONVOLUTIONAL NEURAL NETWORK FOR AUDIO GENERATION," Tampere University of Technology, 2016;

J. Wu, "Introduction to Convolutional Neural Networks," Nanjing University, 2017;

"Illumina CMOS Chip and One-Channel SBS Chemistry", Illumina, Inc. 2018, 2 pages;

"skikit-image/peak.py at master", GitHub, 5 pages, [retrieved on 2018 Nov. 16]. Retrieved from the Internet <URL: https://github.com/scikit-image/scikit-image/blob/master/skimage/feature/peak.py#L25>;

"3.3.9.11. Watershed and random walker for segmentation", Scipy lecture notes, 2 pages, [retrieved on 2018 Nov. 13]. Retrieved from the Internet <URL: http://scipy-lectures.org/packages/scikit-image/auto_examples/plot_segmentations.html>;

Mordvintsev, Alexander and Revision, Abid K., "Image Segmentation with Watershed Algorithm", Revision 43532856, 2013, 6 pages [retrieved on 2018 Nov. 13]. Retrieved from the Internet <URL: https://opencv-python-tutroals.readthedocs.io/en/latest/py_tutorials/py_imgproc/py_watershed/py_watershed.html>;

Mzur, "Watershed.py", 25 Oct. 2017, 3 pages, [retrieved on 2018 Nov. 13]. Retrieved from the Internet <URL: https://github.com/mzur/watershed/blob/master/Watershed.py>;

Thakur, Pratibha, et. al. "A Survey of Image Segmentation Techniques", International Journal of Research in Computer Applications and Robotics, Vol. 2, Issue. 4, April 2014, Pg.: 158-165;

Long, Jonathan, et. al., "Fully Convolutional Networks for Semantic Segmentation", IEEE Transactions on Pattern Analysis and Machine Intelligence, Vol 39, Issue 4, 1 Apr. 2017, 10 pages;

Ronneberger, Olaf, et. al., "U-net: Convolutional networks for biomedical image segmentation." In *International Conference on Medical image computing and computer-assisted intervention,* 18 May 2015, 8 pages;

Xie, W., et. al., "Microscopy cell counting and detection with fully convolutional regression networks", *Computer methods in biomechanics and biomedical engineering: Imaging & Visualization,* 6 (3), pp. 283-292, 2018;

Xie, Yuanpu, et al., "Beyond classification: structured regression for robust cell detection using convolutional neural network", *International Conference on Medical Image Computing and Computer-Assisted Intervention.* October 2015, 12 pages;

Snuverink, I. A. F., "Deep Learning for Pixelwise Classification of Hyperspectral Images", Master of Science Thesis, Delft University of Technology, 23 Nov. 2017, 19 pages;

Shevchenko, A., "Keras weighted categorical_crossentropy", 1 page, [retrieved on 2019 Jan. 15]. Retrieved from the Internet <URL: https://gist.github.com/skeeet/cad06d584548fb45eece1d4e28cfa98b>;

van den Assem, D. C. F., "Predicting periodic and chaotic signals using Wavenets", Master of Science Thesis, Delft University of Technology, 18 Aug. 2017, pages 3-38;

I. J. Goodfellow, D. Warde-Farley, M. Mirza, A. Courville, and Y. Bengio, "CONVOLUTIONAL NETWORKS", Deep Learning, MIT Press, 2016; and J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv: 1512.07108, 2017.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters.

Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, an opportunity arises to use a principled deep learning-based framework for template generation and base calling.

In the era of high-throughput technology, amassing the highest yield of interpretable data at the lowest cost per effort remains a significant challenge. Cluster-based methods of nucleic acid sequencing, such as those that utilize bridge amplification for cluster formation, have made a valuable contribution toward the goal of increasing the throughput of nucleic acid sequencing. These cluster-based methods rely on sequencing a dense population of nucleic acids immobilized on a solid support, and typically involve the use of image analysis software to deconvolve optical signals generated in the course of simultaneously sequencing multiple clusters situated at distinct locations on a solid support.

However, such solid-phase nucleic acid cluster-based sequencing technologies still face considerable obstacles that limit the amount of throughput that can be achieved. For example, in cluster-based sequencing methods, determining the nucleic acid sequences of two or more clusters that are physically too close to one another to be resolved spatially, or that in fact physically overlap on the solid support, can pose an obstacle. For example, current image analysis software can require valuable time and computational resources for determining from which of two overlapping clusters an optical signal has emanated. As a consequence, compromises are inevitable for a variety of detection platforms with respect to the quantity and/or quality of nucleic acid sequence information that can be obtained.

High density nucleic acid cluster-based genomics methods extend to other areas of genome analysis as well. For example, nucleic acid cluster-based genomics can be used in sequencing applications, diagnostics and screening, gene expression analysis, epigenetic analysis, genetic analysis of polymorphisms, and the like. Each of these nucleic acid cluster-based genomics technologies, too, is limited when there is an inability to resolve data generated from closely proximate or spatially overlapping nucleic acid clusters.

Clearly there remains a need for increasing the quality and quantity of nucleic acid sequencing data that can be obtained rapidly and cost-effectively for a wide variety of uses, including for genomics (e.g., for genome characterization of any and all animal, plant, microbial or other biological species or populations), pharmacogenomics, transcriptomics, diagnostics, prognostics, biomedical risk assessment, clinical and research genetics, personalized medicine, drug efficacy and drug interactions assessments, veterinary medicine, agriculture, evolutionary and biodiversity studies, aquaculture, forestry, oceanography, ecological and environmental management, and other purposes.

The technology disclosed provides neural network-based methods and systems that address these and similar needs, including increasing the level of throughput in high-throughput nucleic acid sequencing technologies, and offers other related advantages.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 22 shows one implementation of extracting patches from the series of image sets in FIG. 21b to produce a series of "down-sized" image sets that form the input image data.

FIG. 32 is a table that shows an example U-Net architecture of the regression model.

FIG. 35 illustrates the difference in base calling performance when the RTA base caller uses ground truth center of mass (COM) location as the cluster center, as opposed to using a non-COM location as the cluster center. The results show that using COM improves base calling.

FIG. 36 shows, on the left, an example decay map produced the regression model. On the right, FIG. 36 also shows an example ground truth decay map that the regression model approximates during the training.

FIG. 38 compares peaks detected by the peak locator in a decay map produced by the regression model with peaks in a corresponding ground truth decay map.

FIG. 40 compares performance of the regression model with the RTA base caller for 20 pM library concentration (normal run).

FIG. 41 compares performance of the regression model with the RTA base caller for 30 pM library concentration (dense run).

FIG. 43 shows, on the right, a first decay map produced by the regression model. On the left, FIG. 43 shows a second decay map produced by the regression model.

FIG. 44 compares performance of the regression model with the RTA base caller for 40 pM library concentration (highly dense run).

FIG. 45 shows the results of the thresholding, the peak locating, and the watershed segmentation technique applied to the first decay map.

FIG. 53 is a table that shows an example architecture of the binary classification model.

FIG. 57 is a table that shows an example architecture of the ternary classification model.

FIG. 62c shows yet other example predictions of the ternary classification model.

FIG. 63 depicts one implementation of deriving the cluster centers and cluster shapes from the output of the ternary classification model in FIG. 62a.

FIG. 64 compares base calling performance of the binary classification model, the regression model, and the RTA base caller.

FIG. 70 overlays cluster center predictions made by the RTA base caller (in pink) onto visualization of the trained convolution filters of the penultimate layer of the binary classification model.

FIG. 71 illustrates one implementation of training data used to train the neural network-based template generator.

FIG. 74 shows how the neural network-based template generator's ability to distinguish between adjacent clusters improves when the number of initial sequencing cycles for which the input image data is used increases from five to seven.

FIG. 75 illustrates the difference in base calling performance when a RTA base caller uses ground truth center of mass (COM) location as the cluster center, as opposed to when a non-COM location is used as the cluster center.

FIG. 76 portrays the performance of the neural network-based template generator on extra detected clusters.

FIG. 77 shows different datasets used for training the neural network-based template generator.

FIG. 78 shows the processing stages used by the RTA base caller for base calling, according to one implementation.

FIG. 86 shows one implementation of pixel-wise encoding the minimum distance values that are calculated between the pixels and the nearest one of the clusters.

FIG. 89 shows one implementation of pixel-wise encoding the distance values that are calculated between the pixels and the assigned clusters.

FIG. 102a depicts an example arrayed input configuration the multi-cycle input data.

FIG. 102b shows an example stacked input configuration the multi-cycle input data.

FIG. 103a depicts one implementation of reframing pixels of an image patch to center a center of a target cluster being base called in a center pixel.

FIG. 108a depicts one implementation of a hybrid neural network that is used as the neural network-based base caller.

FIG. 108b shows one implementation of 3D convolutions used by the recurrent module of the hybrid neural network to produce the current hidden state representations.

FIG. 109 illustrates one implementation of processing, through a cascade of convolution layers of the convolution module, per-cycle input data for a single sequencing cycle among the series of t sequencing cycles to be base called.

FIG. 110 depicts one implementation of mixing the single sequencing cycle's per-cycle input data with its corresponding convolved representations produced by the cascade of convolution layers of the convolution module.

FIG. 111 shows one implementation of arranging flattened mixed representations of successive sequencing cycles as a stack.

FIG. 112a illustrates one implementation of subjecting the stack of FIG. 111 to recurrent application of 3D convolutions in forward and backward directions and producing base calls for each of the clusters at each of the t sequencing cycles in the series.

FIG. 112b shows one implementation of processing a 3D input volume x(t), which comprises groups of flattened mixed representations, through an input gate, an activation gate, a forget gate, and an output gate of a long short-term memory (LSTM) network that applies the 3D convolutions. The LSTM network is part of the recurrent module of the hybrid neural network.

FIG. 113 shows one implementation of balancing trinucleotides (3-mers) in the training data used to train the neural network-based base caller.

Figure 114:
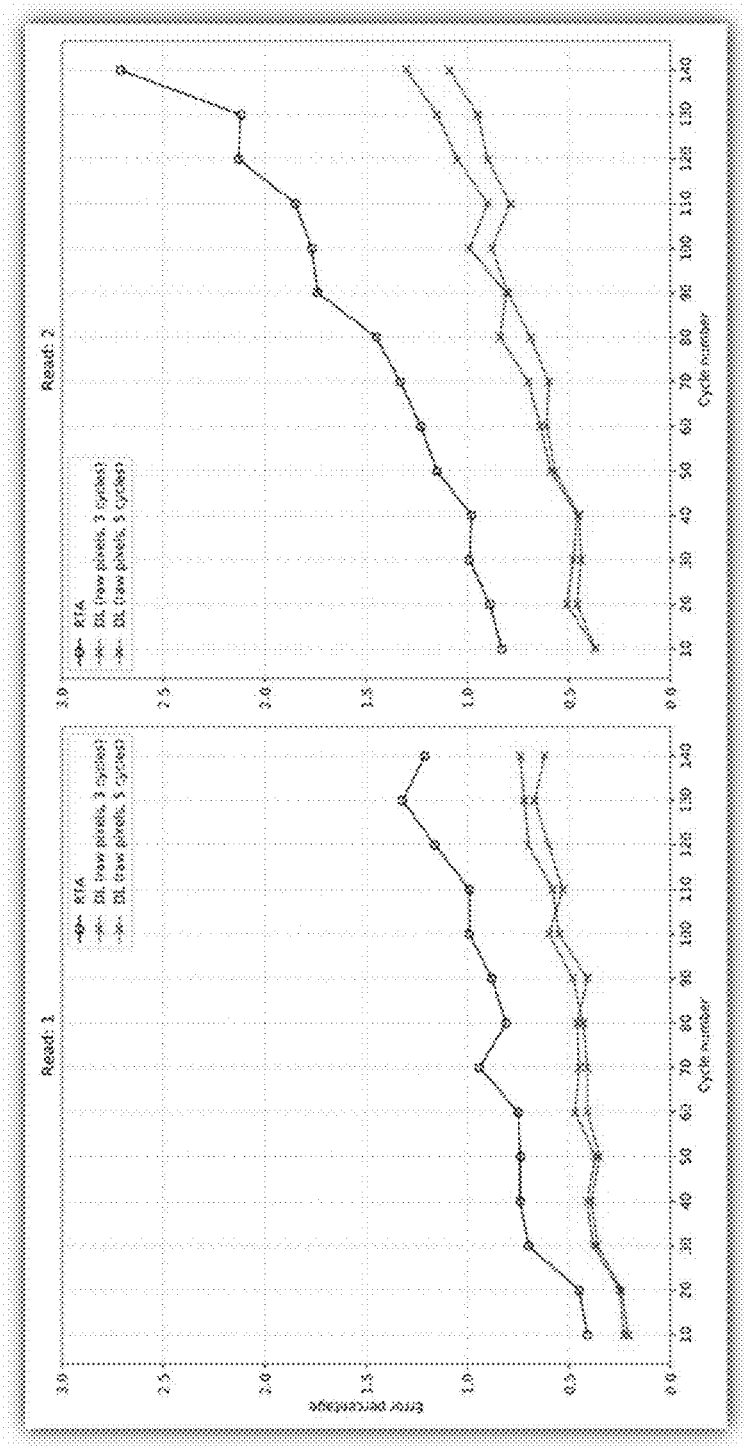

FIG. 114 compares base calling accuracy of the RTA base caller against the neural network-based base caller.

Figure 115:
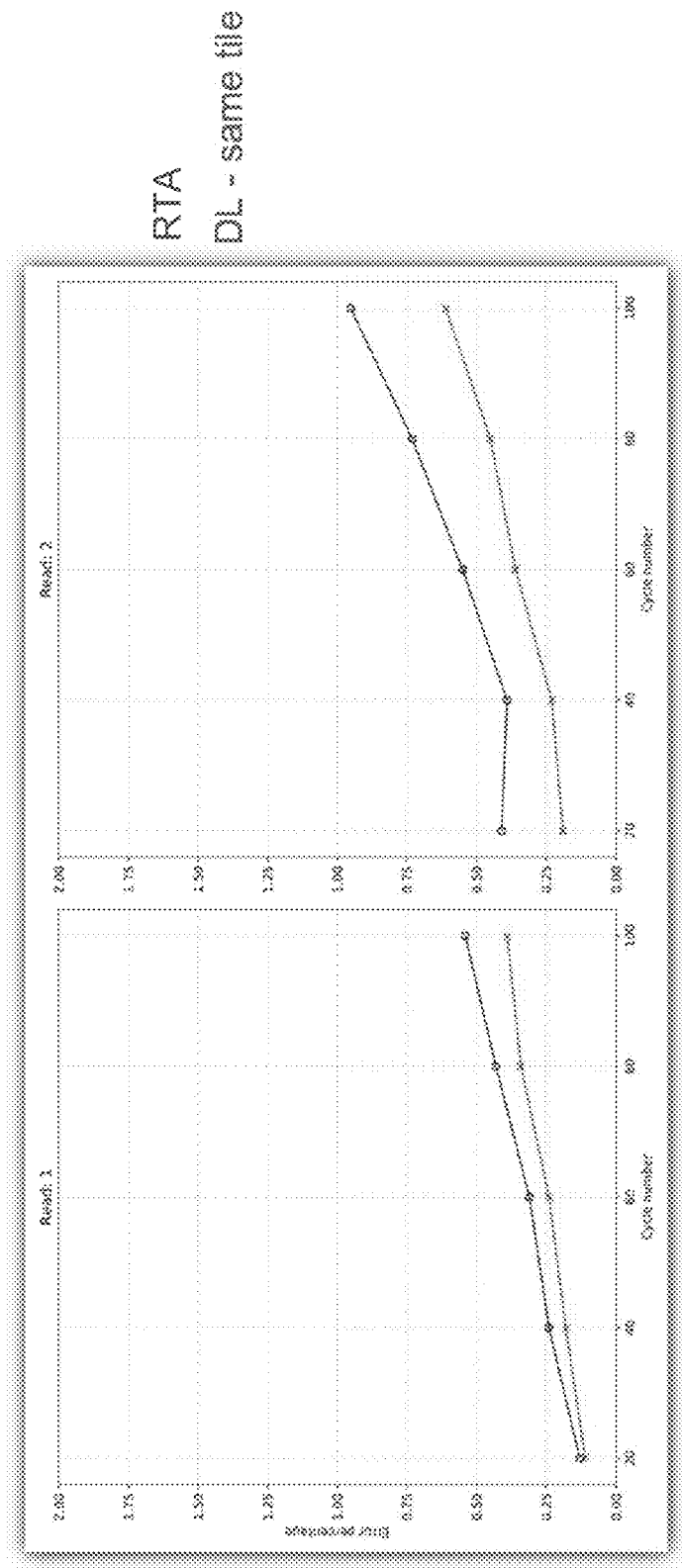

FIG. 115 compares tile-to-tile generalization of the RTA base caller with that of the neural network-based base caller on a same tile.

Figure 116:
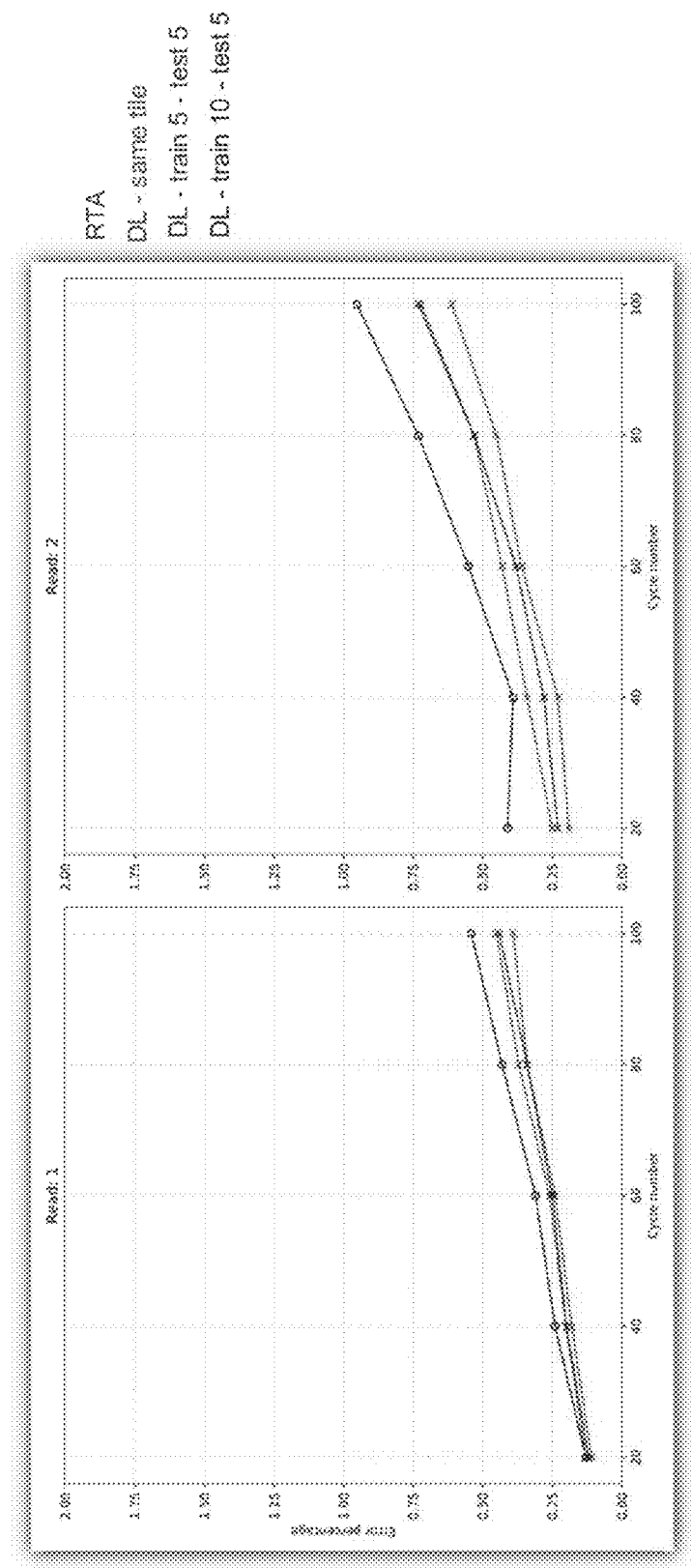

FIG. 116 compares tile-to-tile generalization of the RTA base caller with that of the neural network-based base caller on a same tile and on different tiles.

Figure 117:
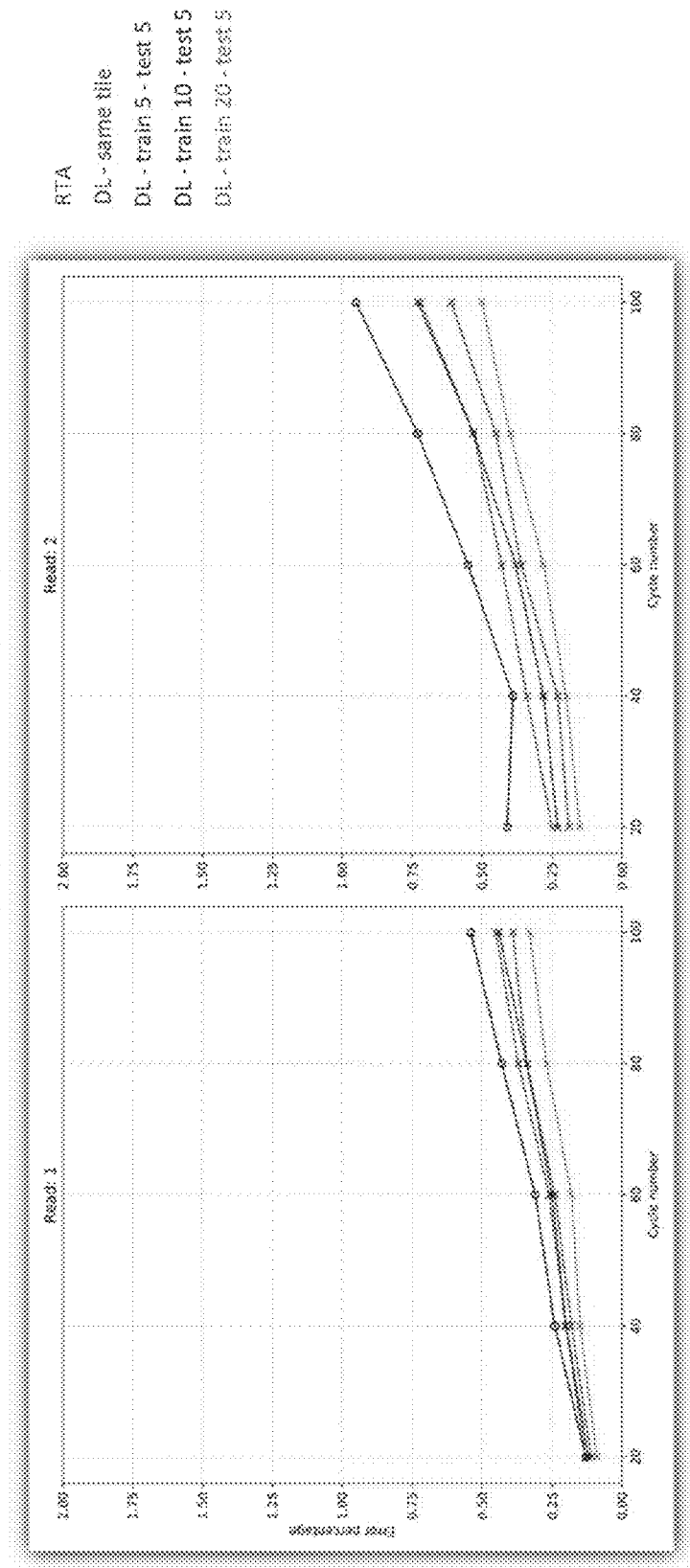
Figure 119:
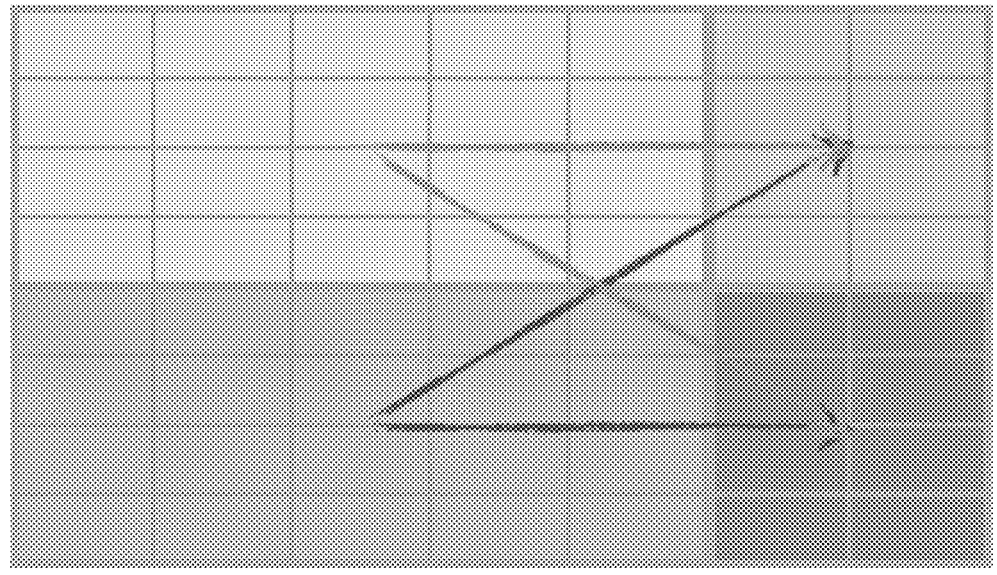

FIG. 117 also compares tile-to-tile generalization of the RTA base caller with that of the neural network-based base caller on different tiles.

FIG. 118 shows how different sizes of the image patches fed as input to the neural network-based base caller effect the base calling accuracy.

FIGS. 119, 120, 121, and 122 show lane-to-lane generalization of the neural network-based base caller on training data from *A. baumanni* and *E. coli*.

Figure 123:
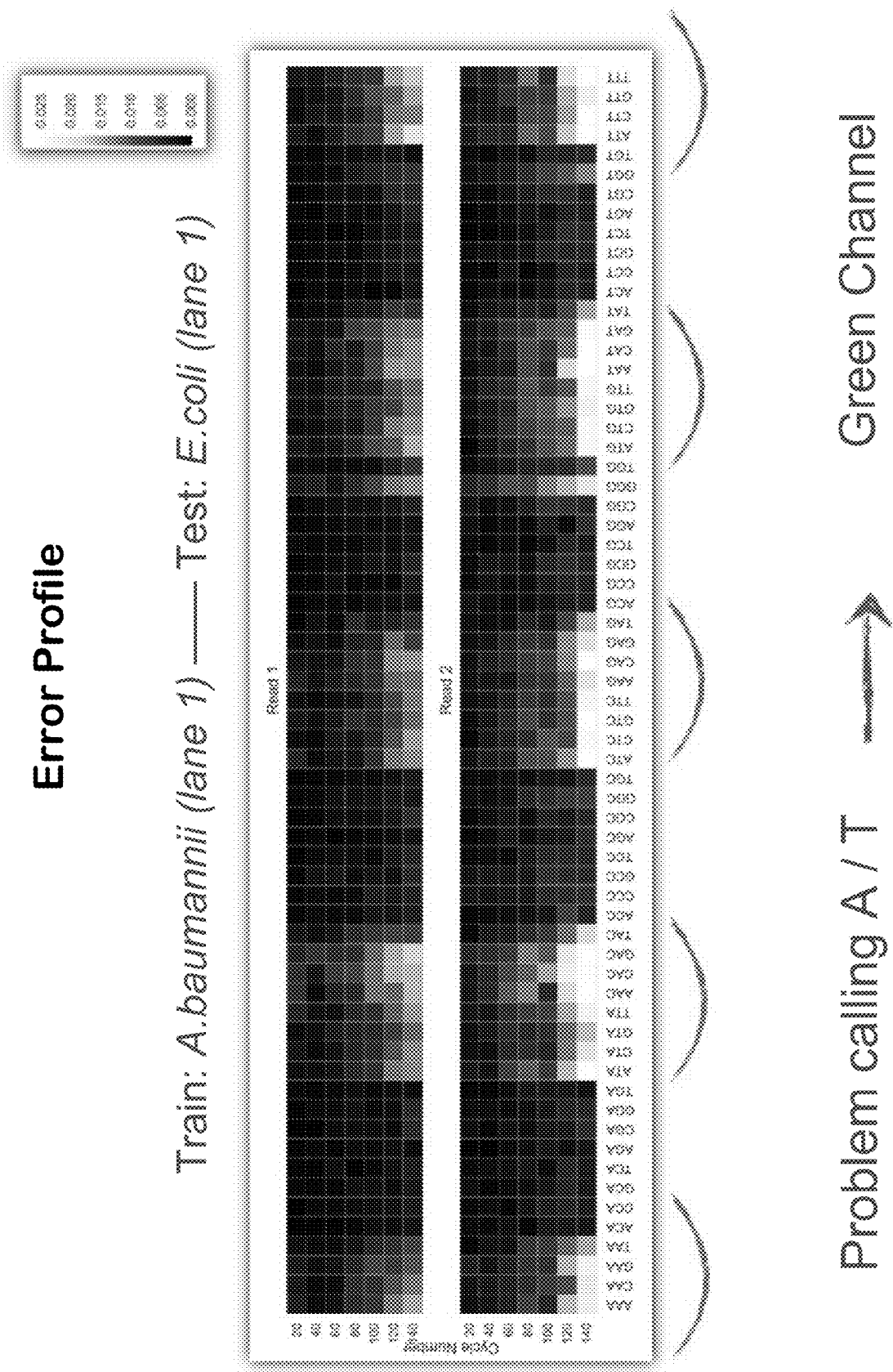

FIG. 123 depicts an error profile for the lane-to-lane generalization discussed above with respect to FIGS. 119, 120, 121, and 122.

Figure 124:
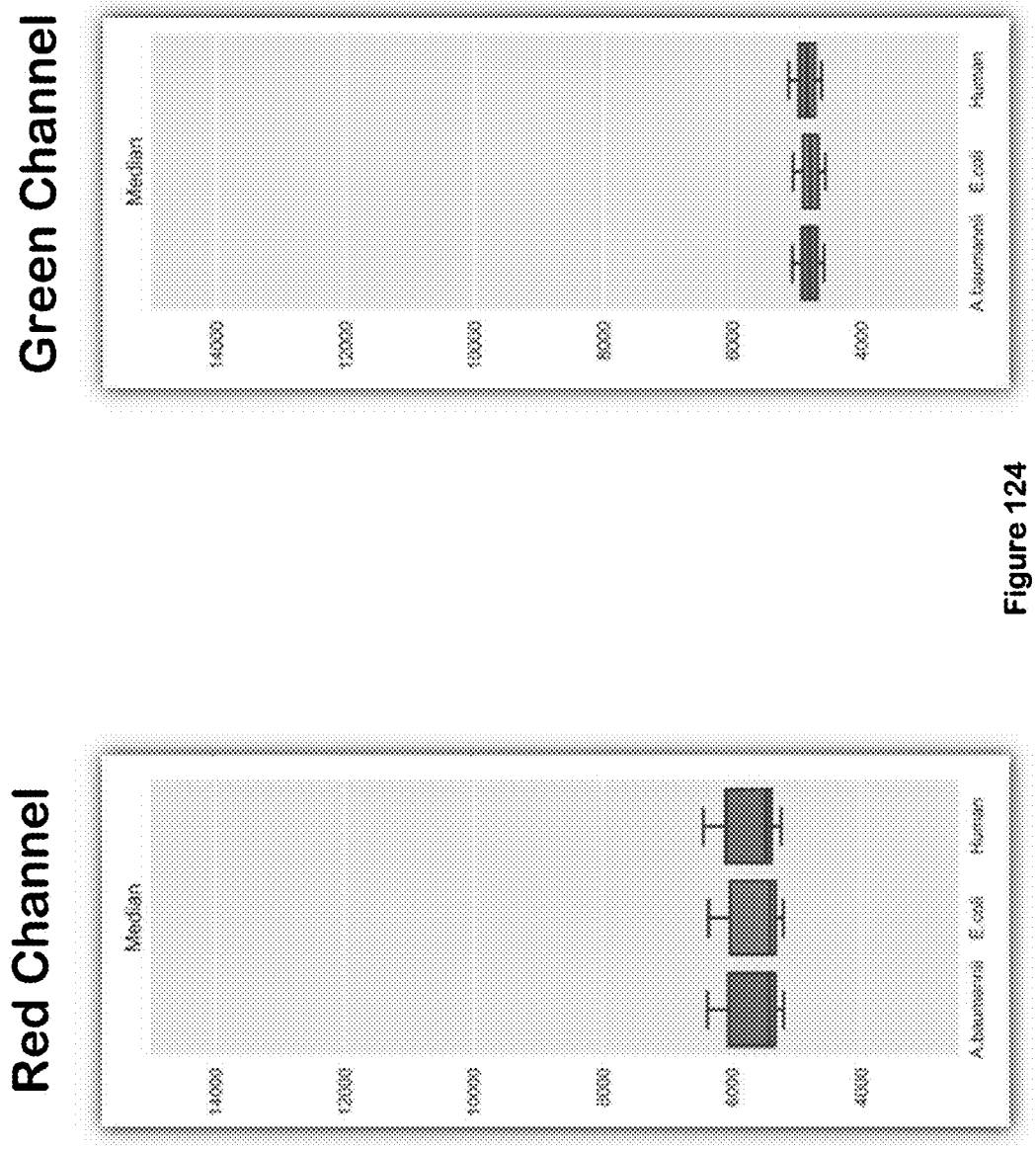

FIG. 124 attributes the source of the error detected by the error profile of FIG. 123 to low cluster intensity in the green channel.

FIG. 125 compares error profiles of the RTA base caller and the neural network-based base caller for two sequencing runs (Read 1 and Read 2).

Figure 126A:
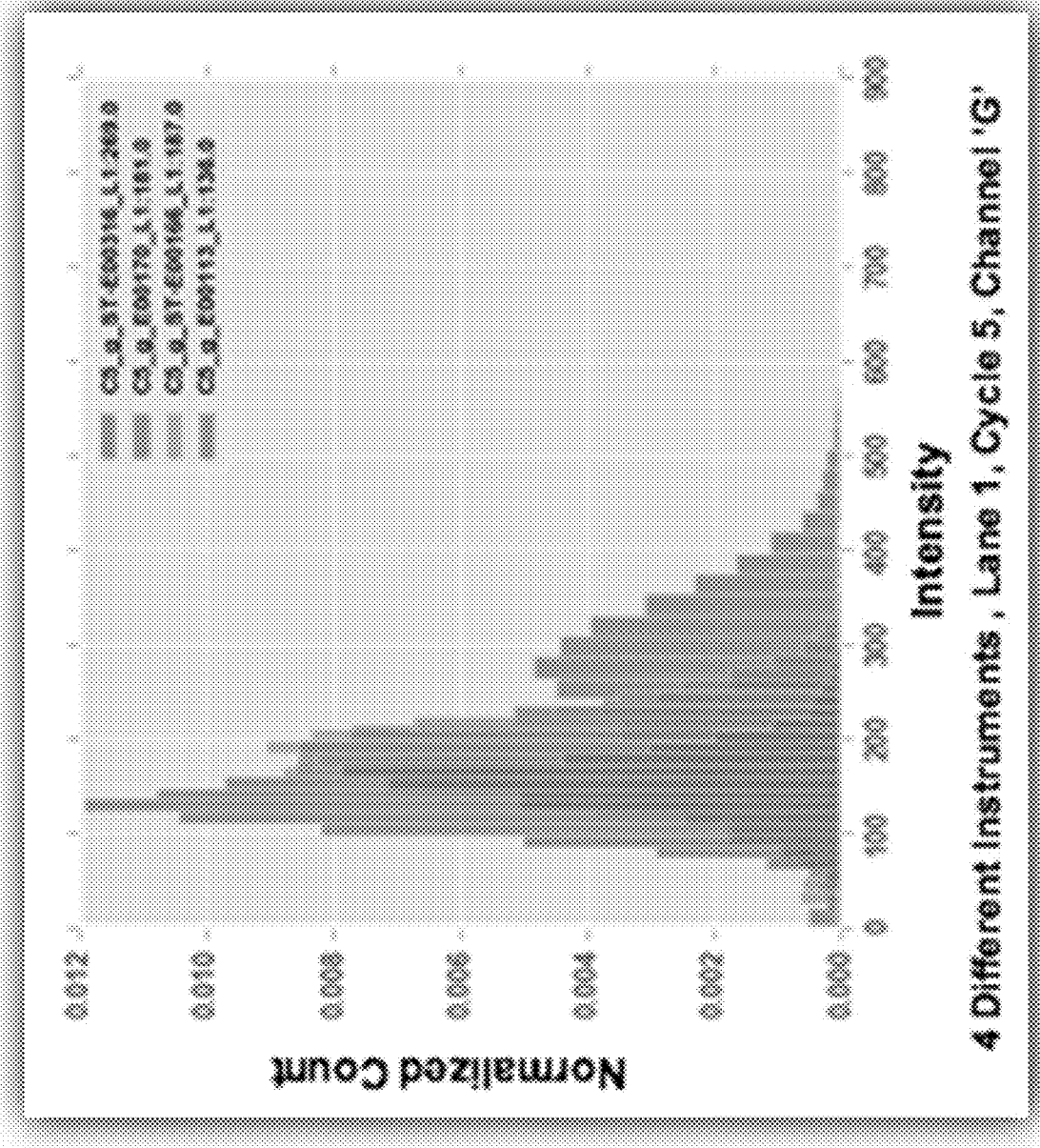

FIG. 126a shows run-to-run generalization of the neural network-based base caller on four different instruments.

Figure 126B:
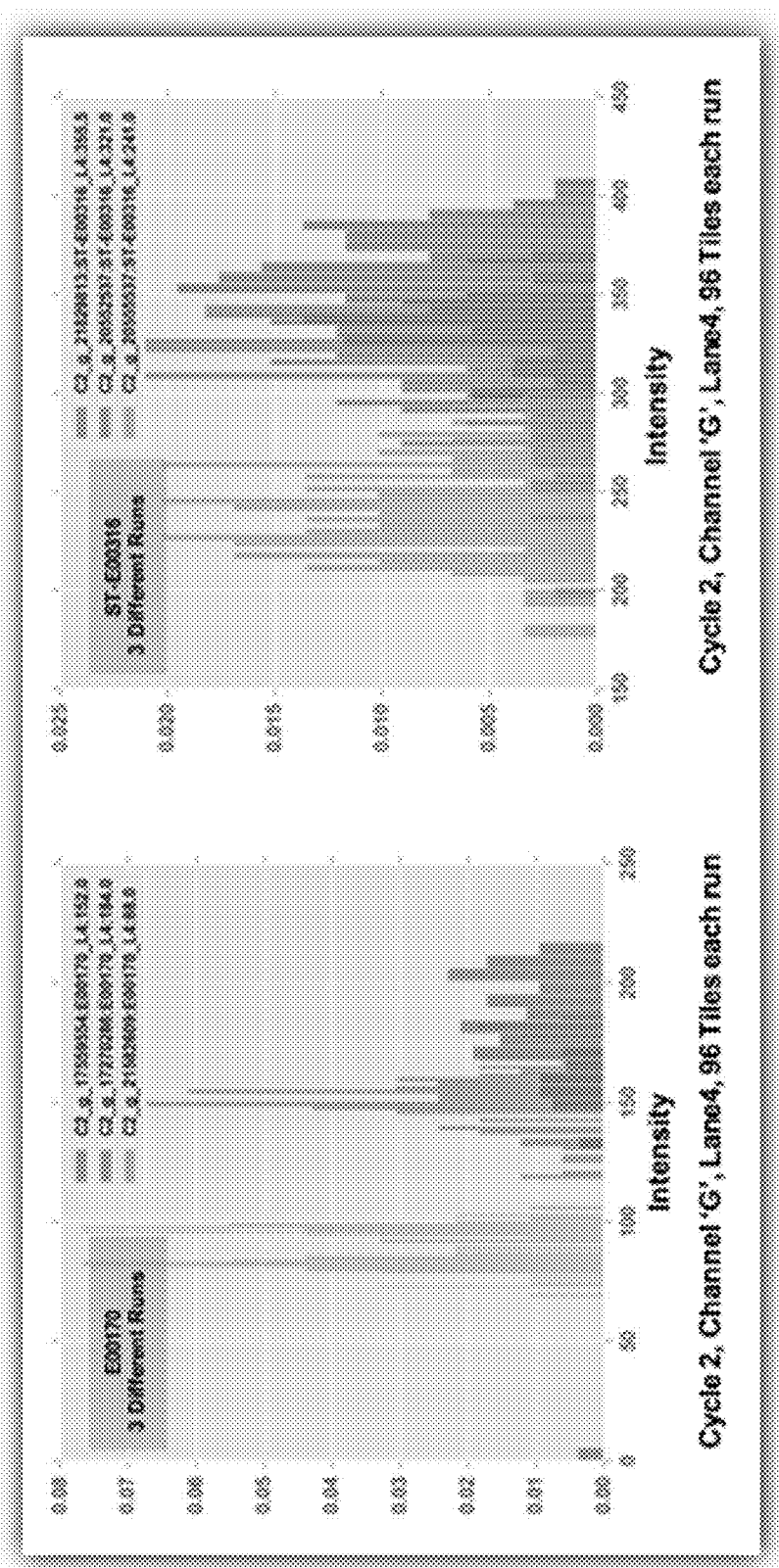

FIG. 126b shows run-to-run generalization of the neural network-based base caller on four different runs executed on a same instrument.

Figure 127:
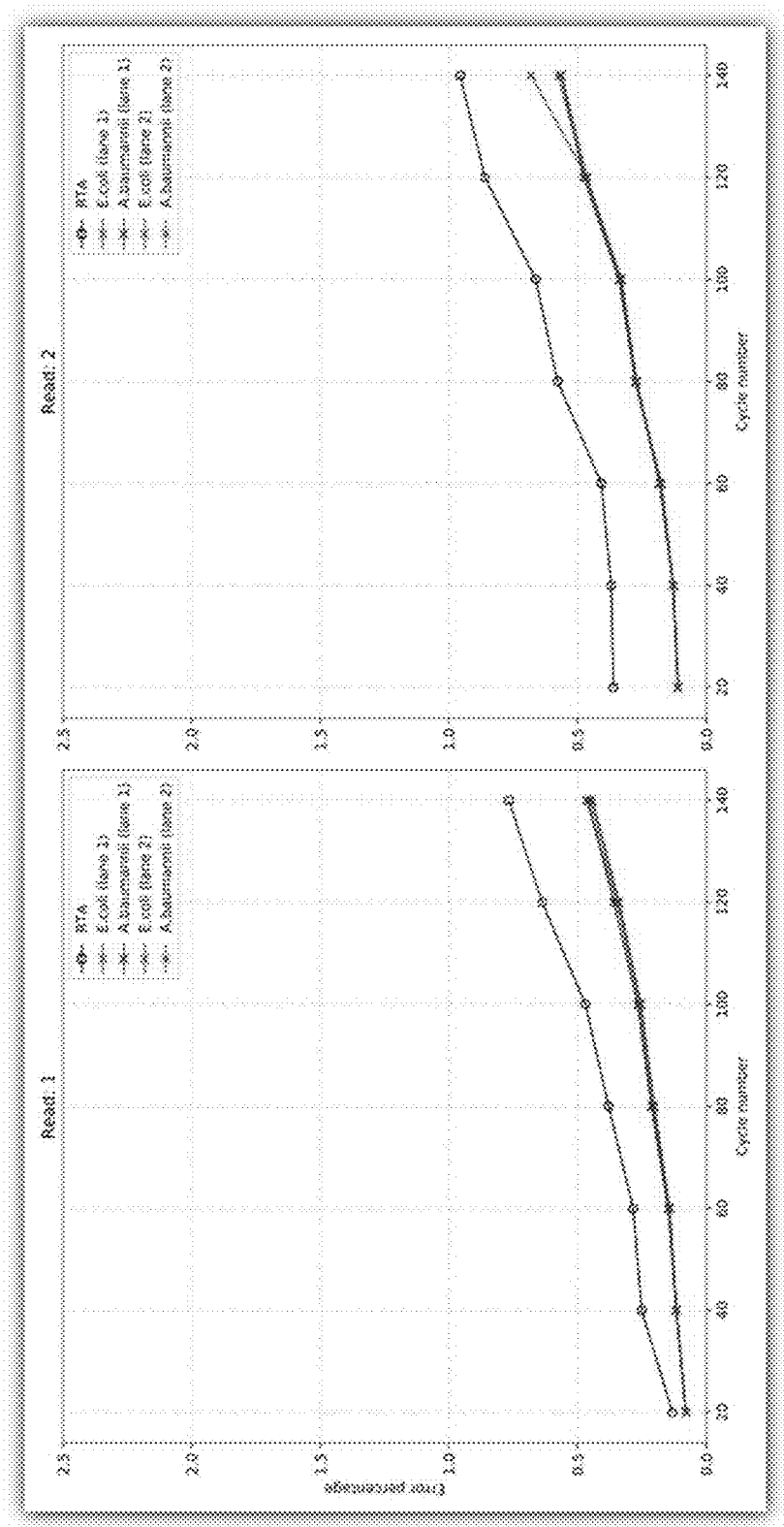

FIG. 127 shows the genome statistics of the training data used to train the neural network-based base caller.

Figure 128:
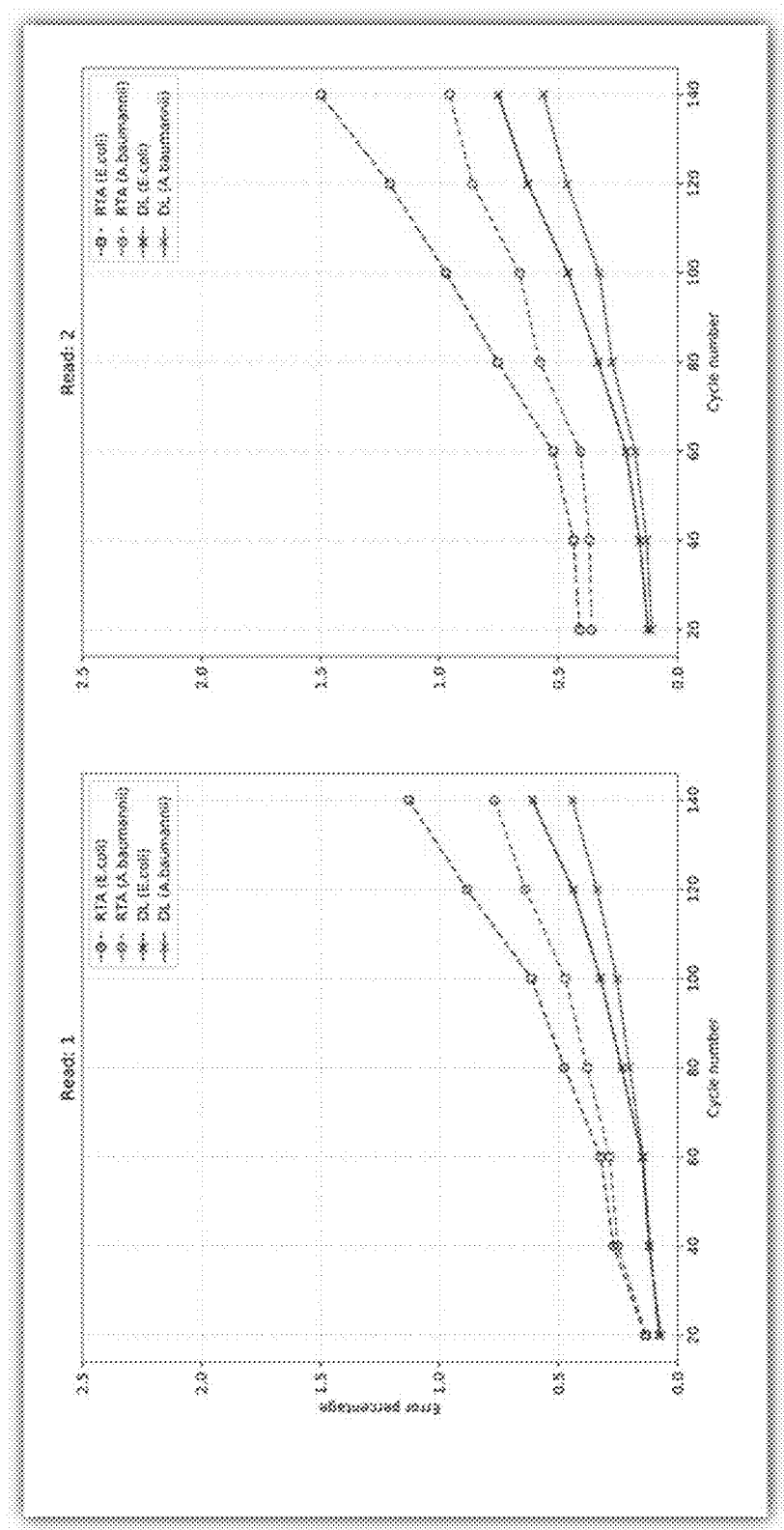

FIG. 128 shows the genome context of the training data used to train the neural network-based base caller.

Figure 129:
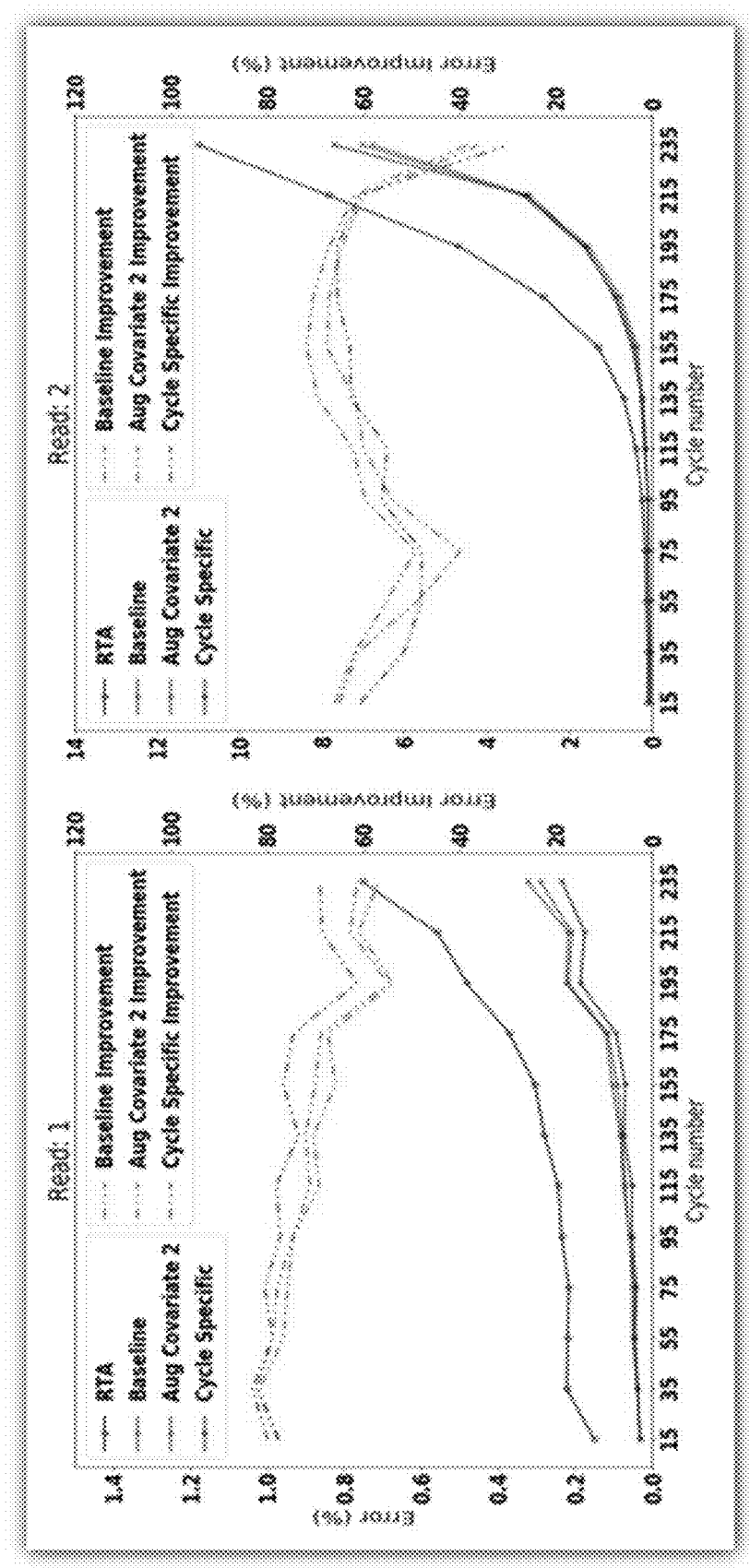

FIG. 129 shows the base calling accuracy of the neural network-based base caller in base calling long reads (e.g., 2×250).

Figure 130:
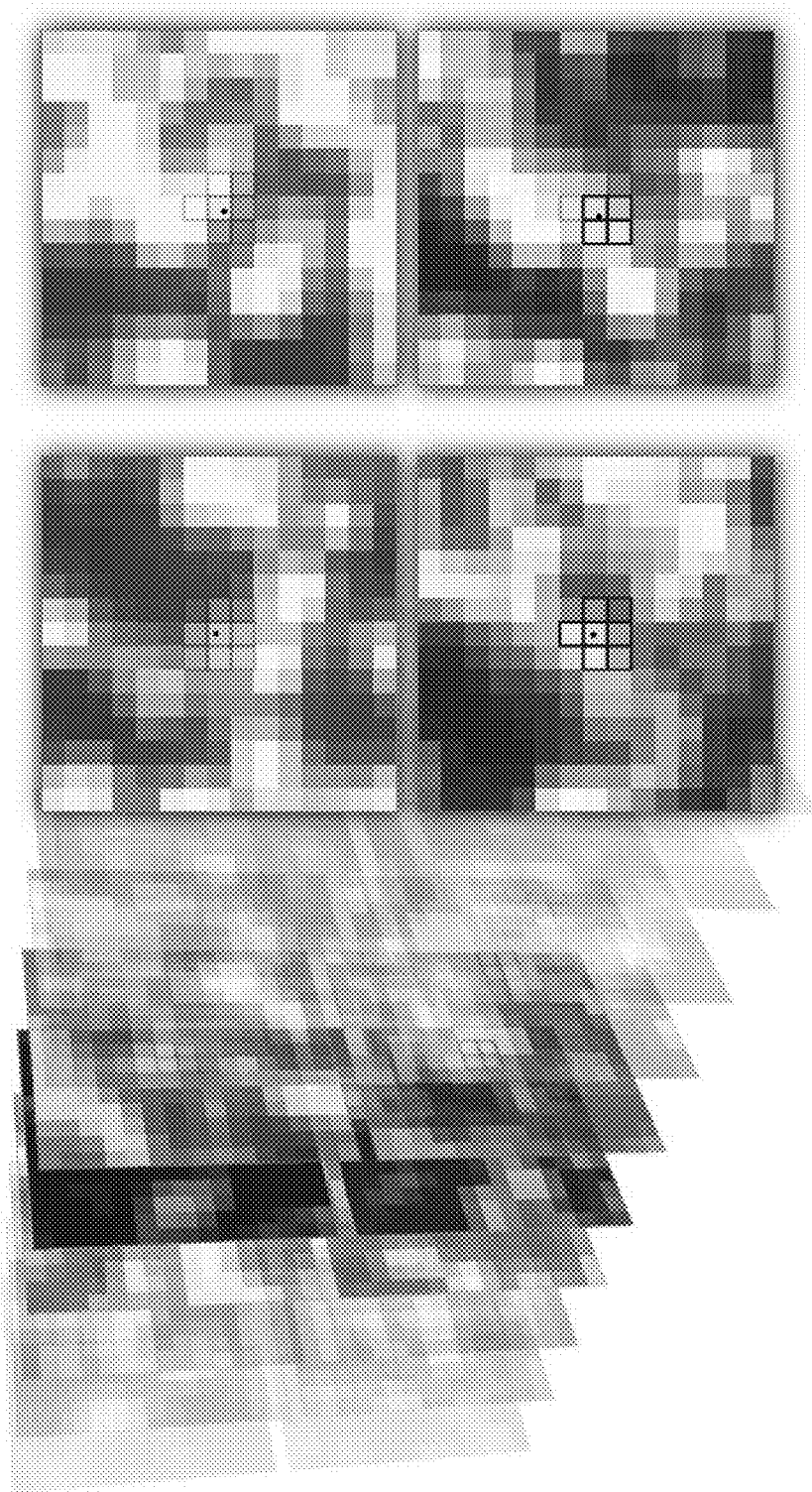

FIG. 130 illustrates one implementation of how the neural network-based base caller attends to the central cluster pixel(s) and its neighboring pixels across image patches.

Figure 131:
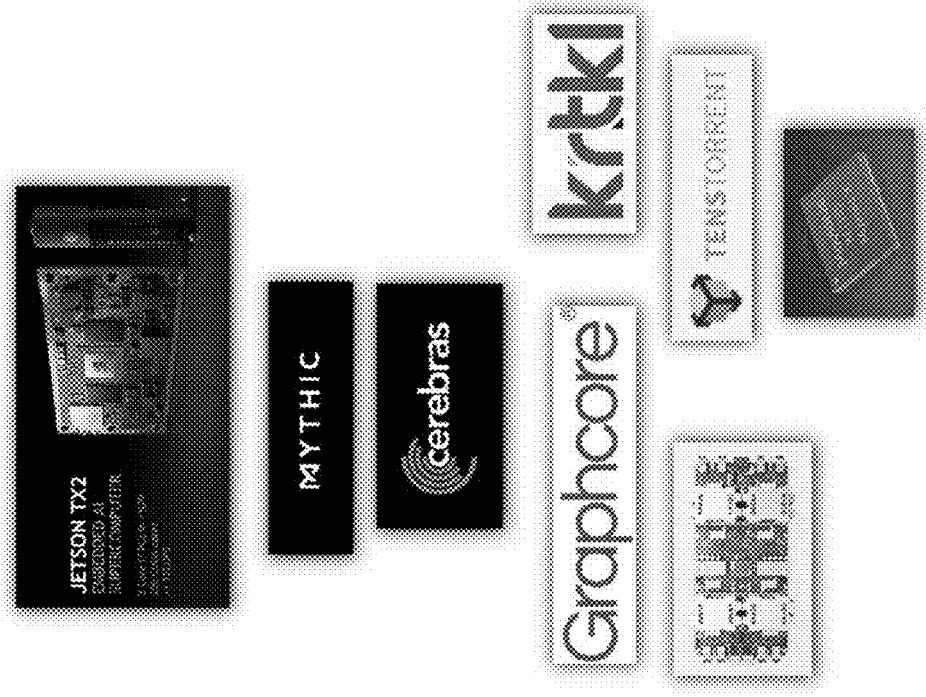

FIG. 131 shows various hardware components and configurations used to train and run the neural network-based base caller, according to one implementation. In other implementations, different hardware components and configurations are used.

Figure 132:
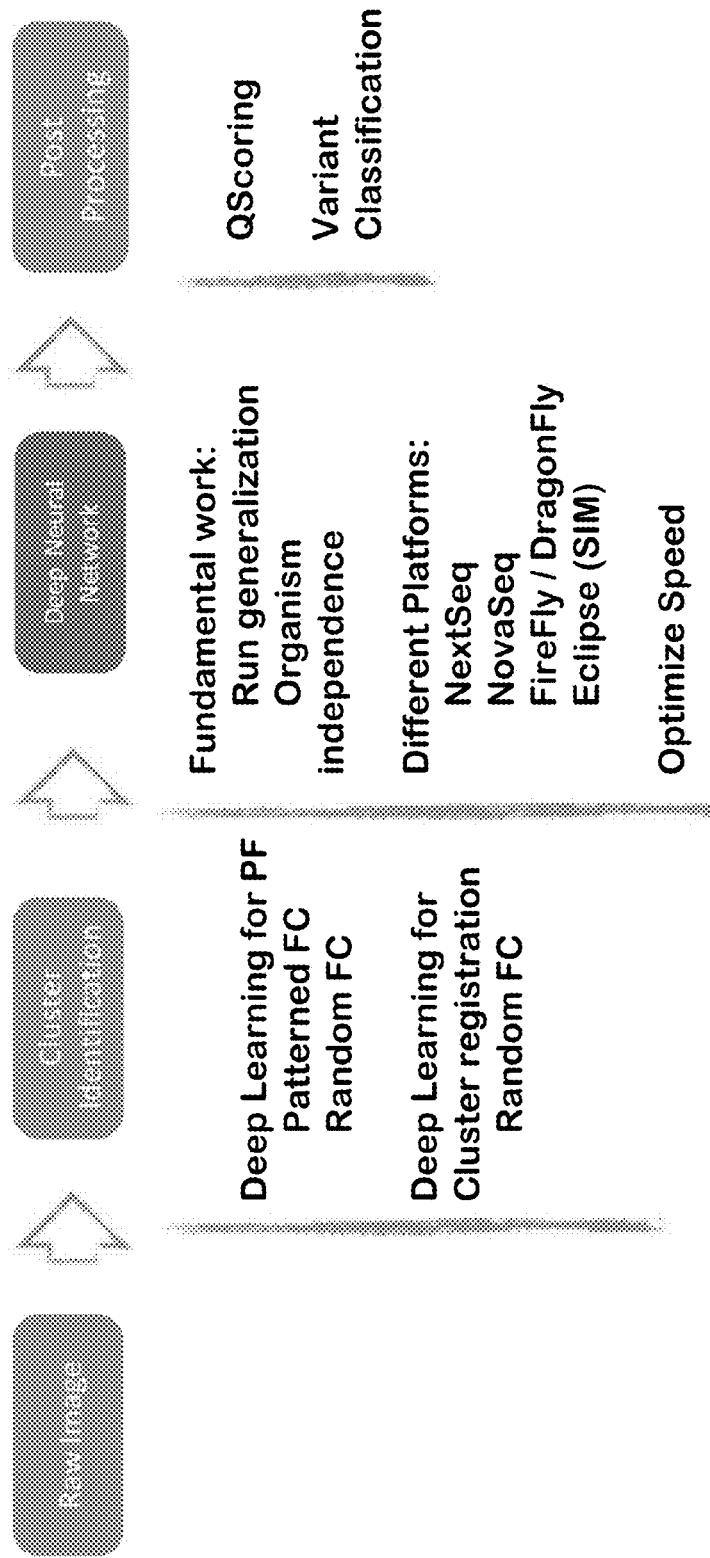

FIG. 132 shows various sequencing tasks that can be performed using the neural network-based base caller.

Figure 133:
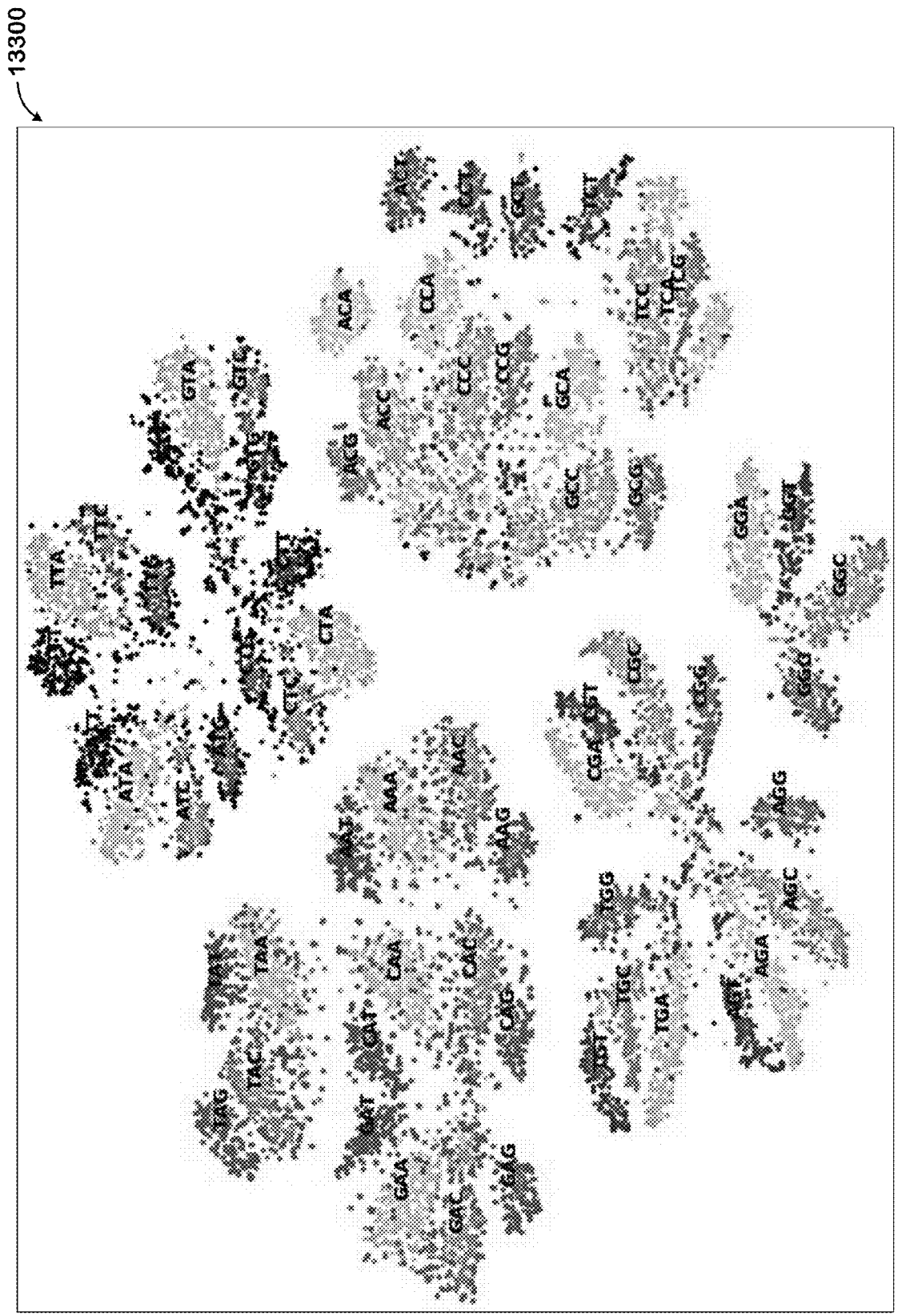

FIG. 133 is a scatter plot visualized by t-Distributed Stochastic Neighbor Embedding (t-SNE) and portrays base calling results of the neural network-based base caller.

Figure 134:
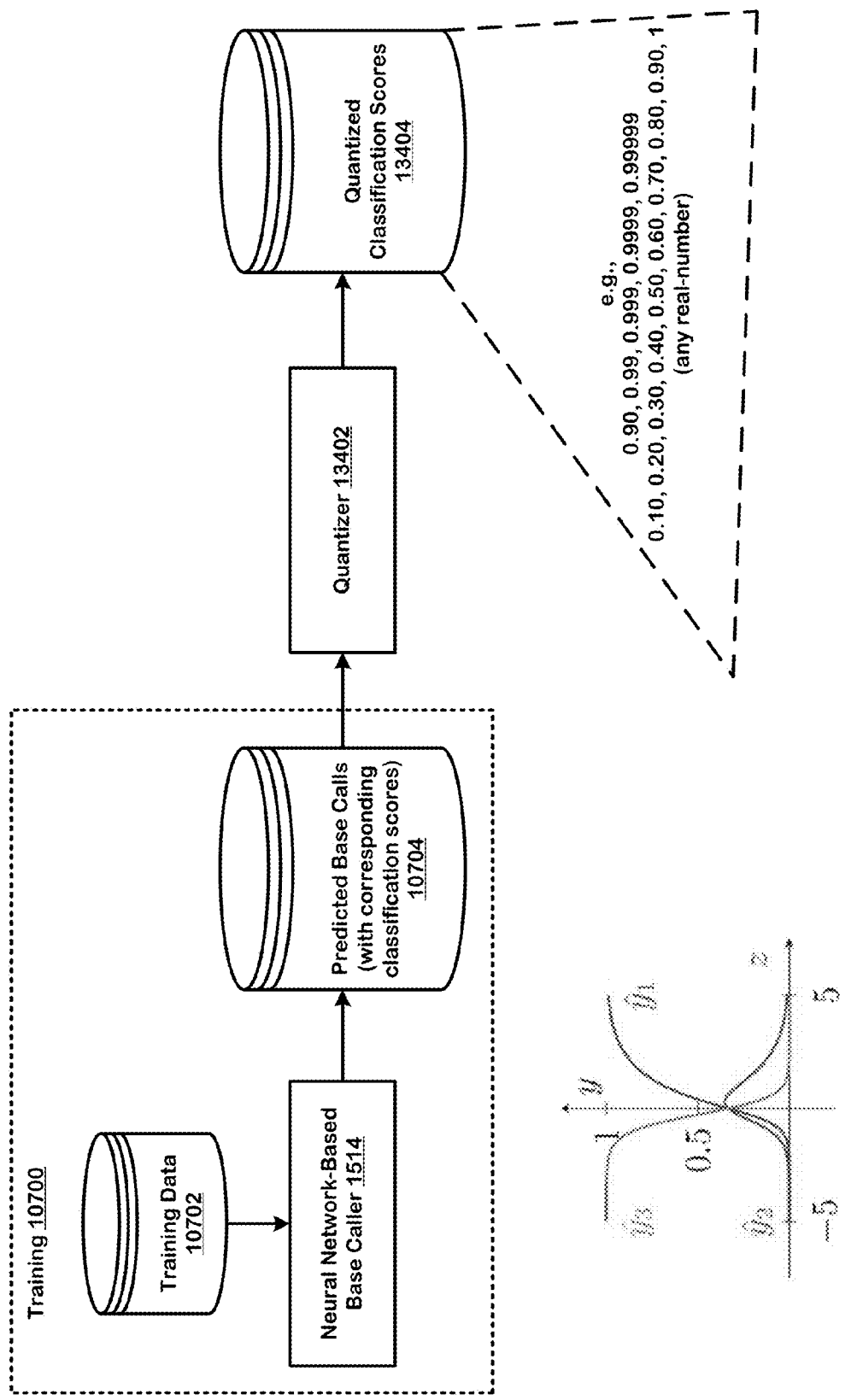

FIG. 134 illustrates one implementation of selecting the base call confidence probabilities made by the neural network-based base caller for quality scoring.

Figure 135:
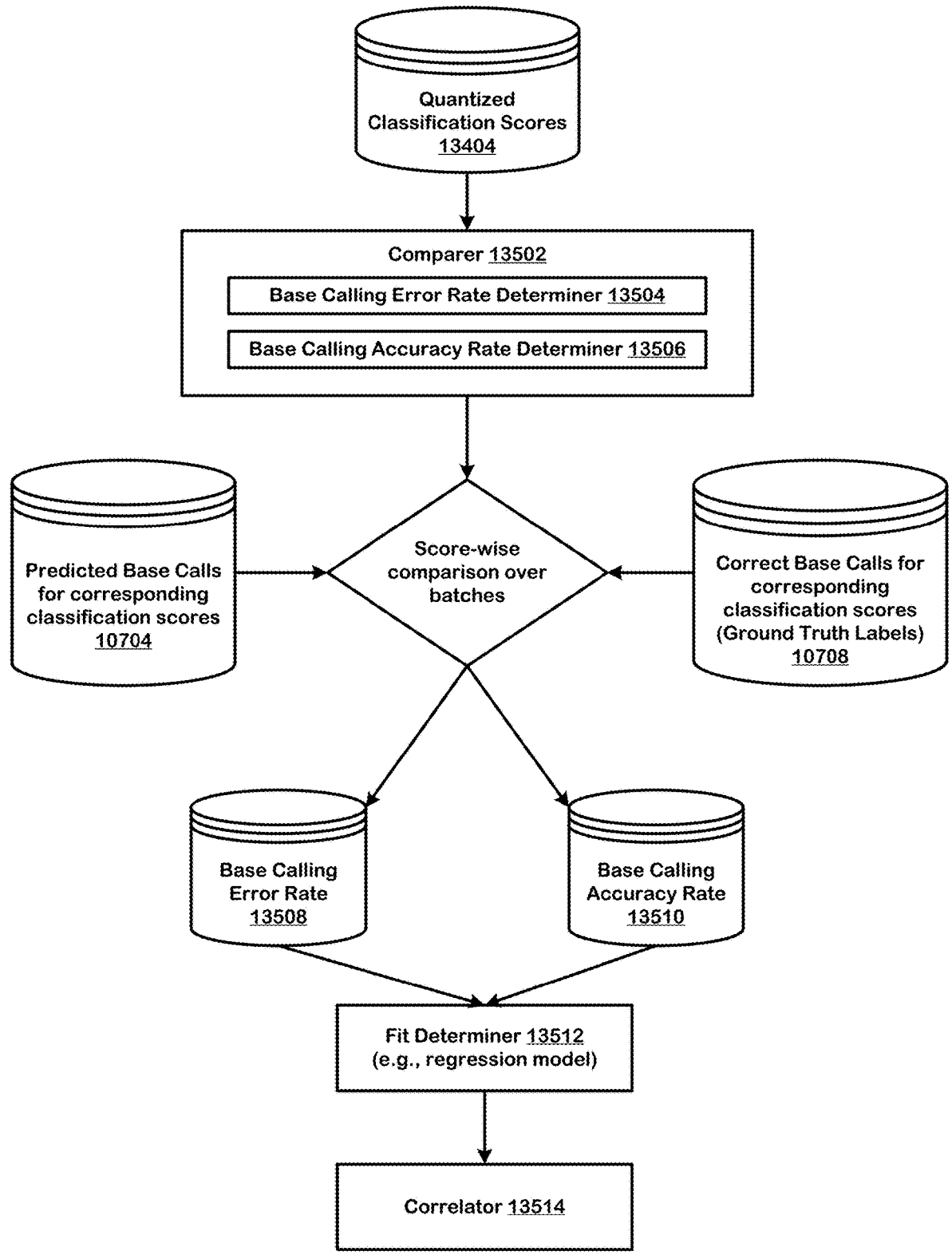

FIG. 135 shows one implementation of the neural network-based quality scoring.

FIGS. 136a-136b depict one implementation of correspondence between the quality scores and the base call confidence predictions made by the neural network-based base caller.

Figure 137:
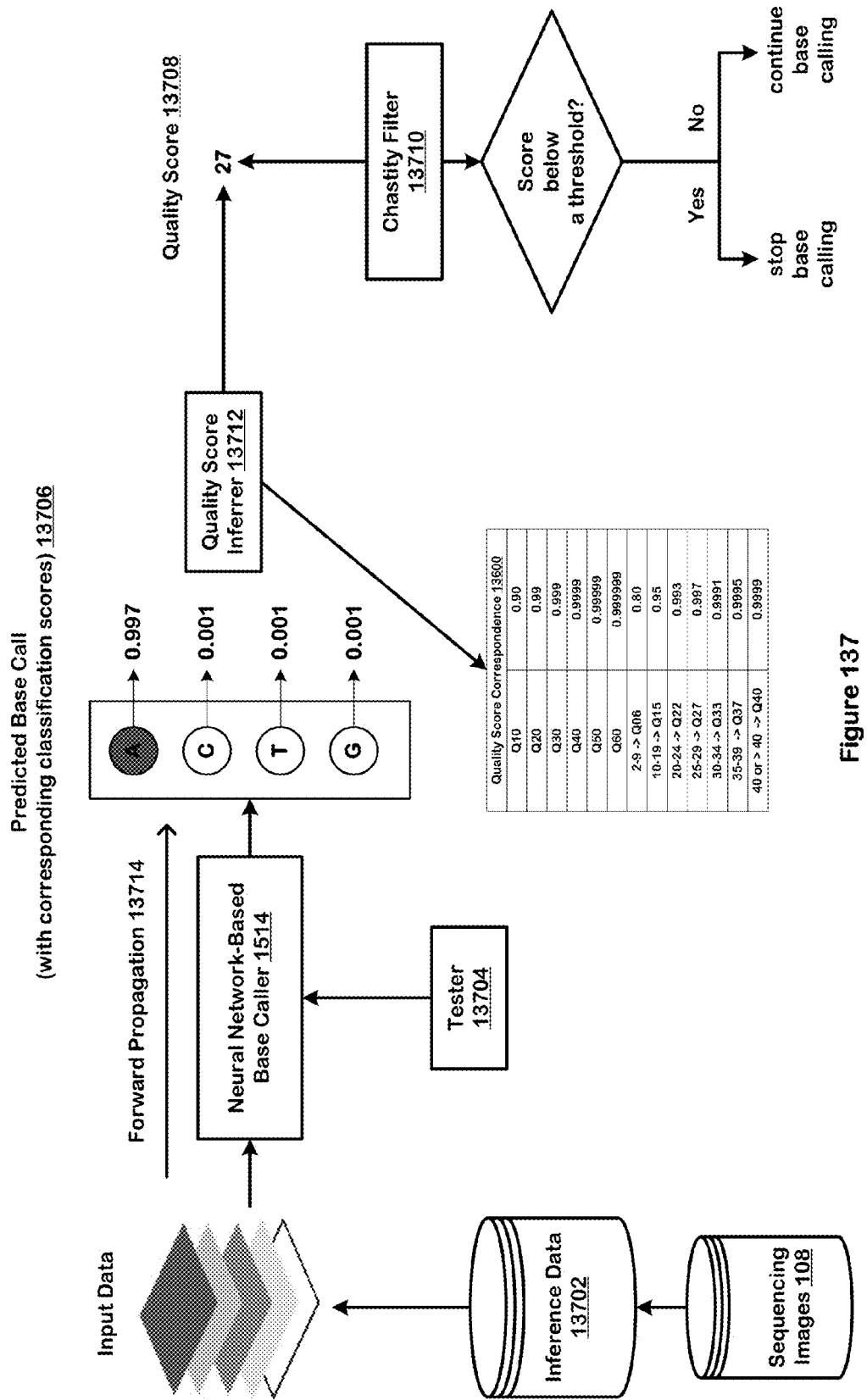

FIG. 137 shows one implementation of inferring quality scores from base call confidence predictions made by the neural network-based base caller during inference.

Figure 138:
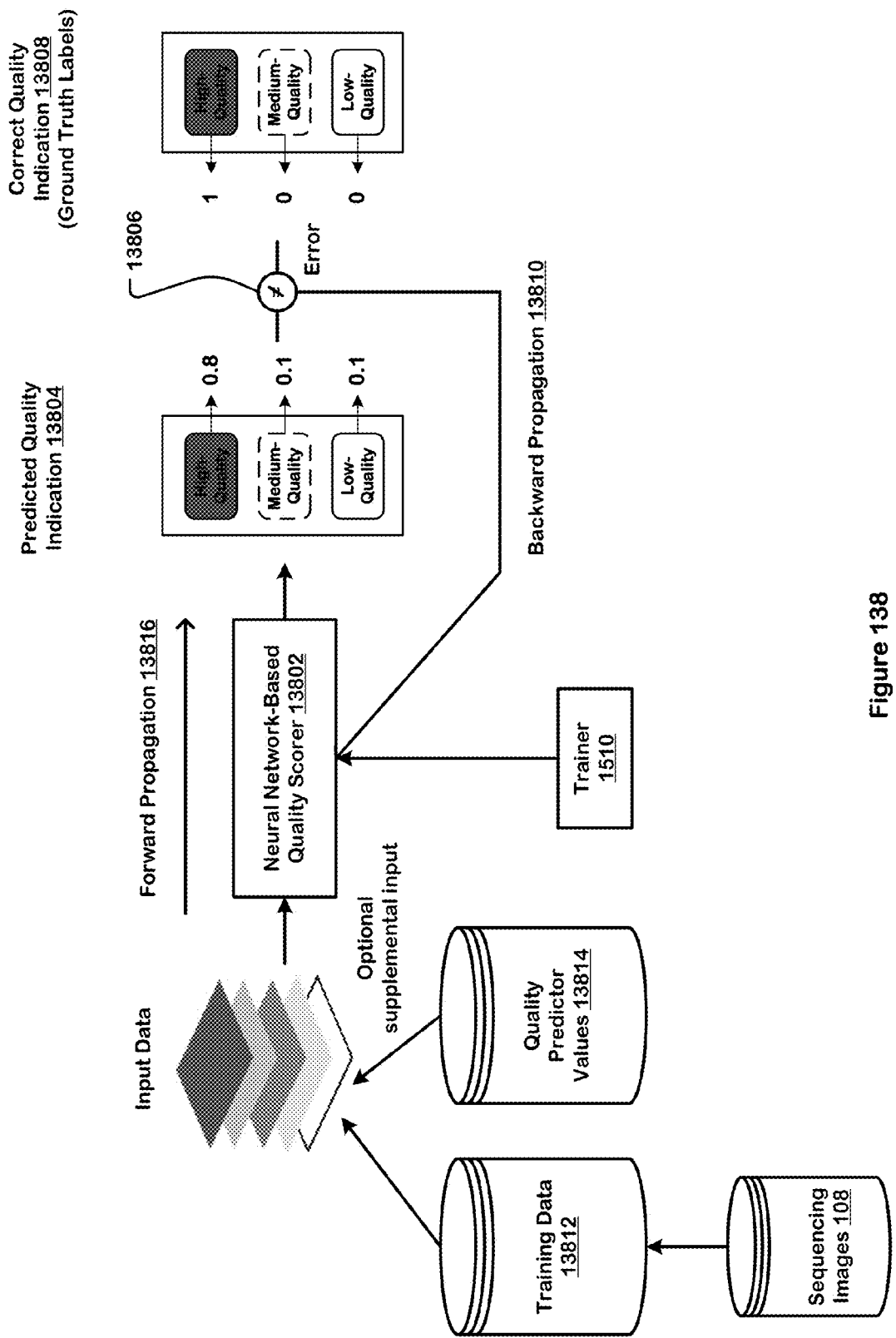

FIG. 138 shows one implementation of training the neural network-based quality scorer to process input data derived from the sequencing images and directly produce quality indications.

Figure 139:
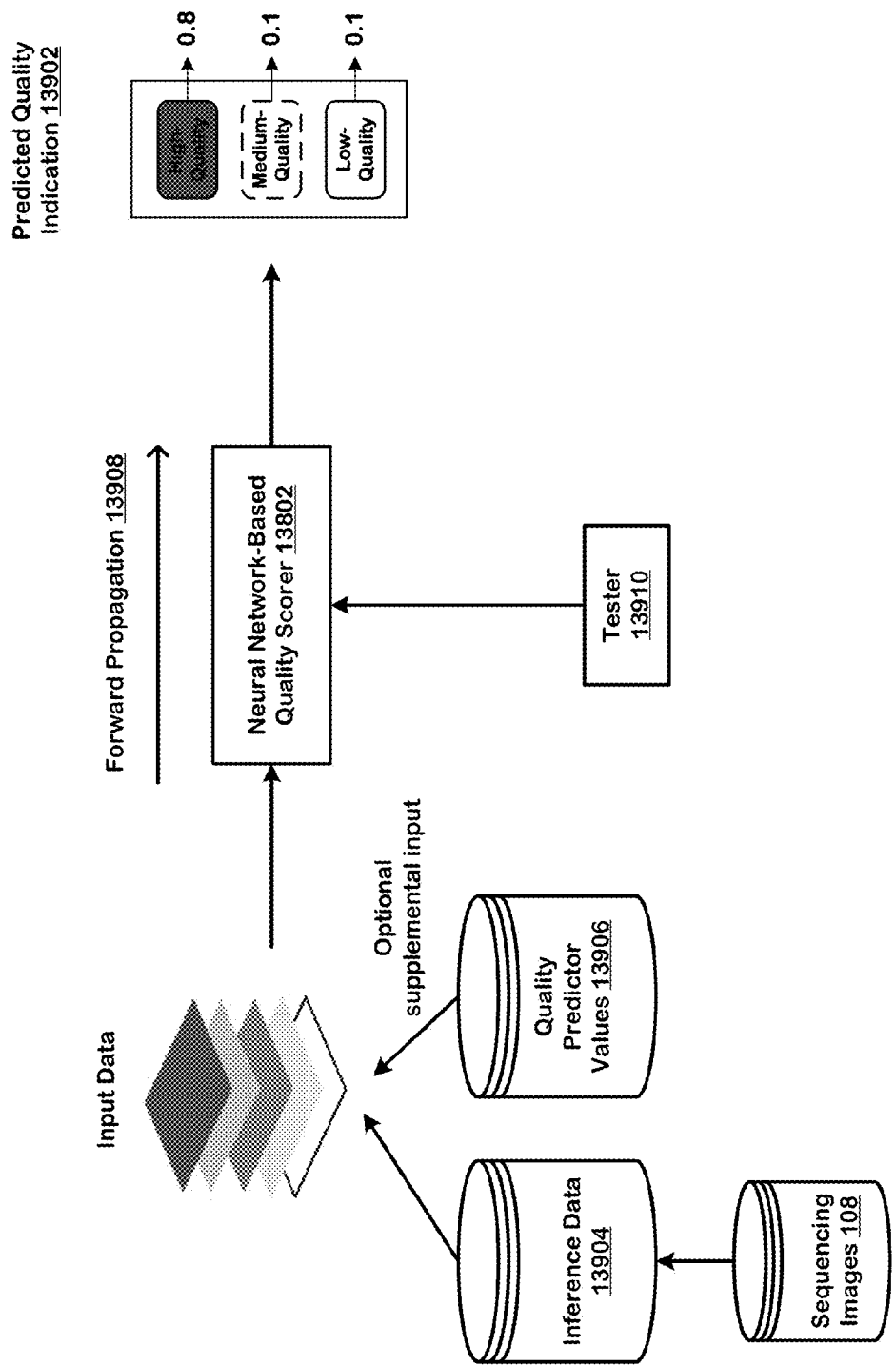

FIG. 139 shows one implementation of directly producing quality indications as outputs of the neural network-based quality scorer during inference.

Figure 140:
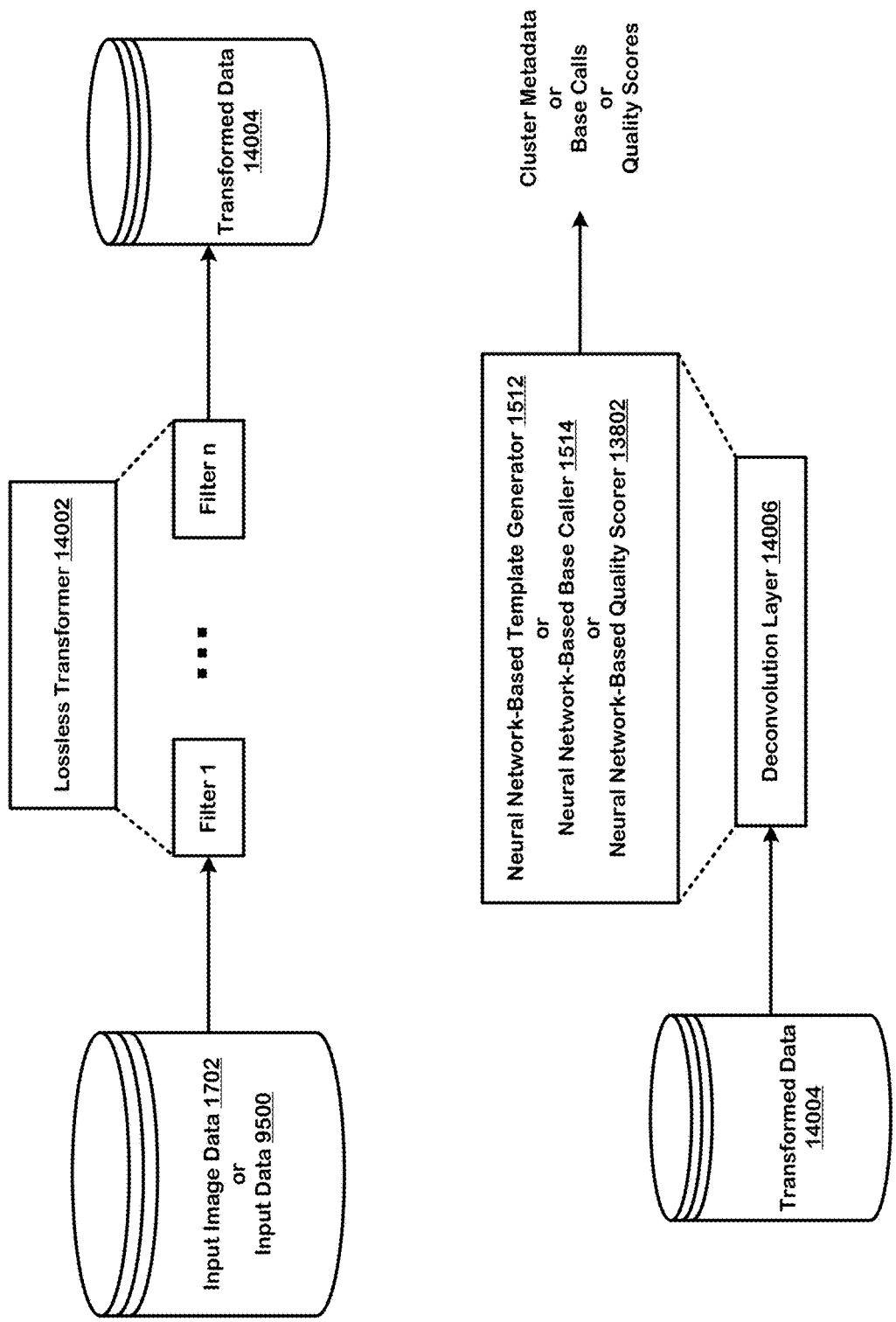

FIG. 140 depicts one implementation of using lossless transformation to generate transformed data that can be fed as input to the neural network-based template generator, the neural network-based base caller, and the neural network-based quality scorer.

Figure 141:
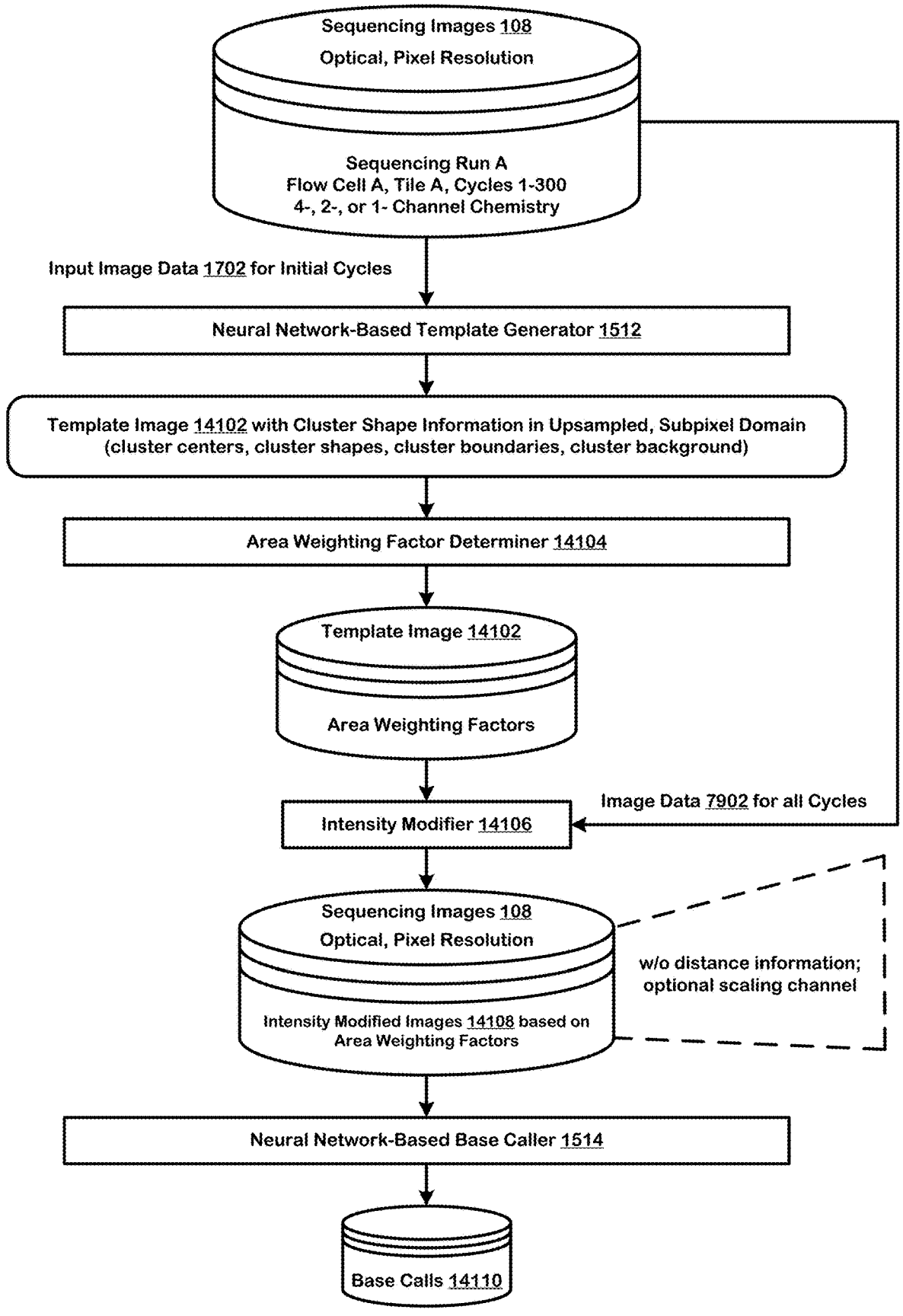

FIG. 141 illustrates one implementation of integrating the neural network-based template generator with the neural network-based base caller using area weighting factoring.

Figure 142:
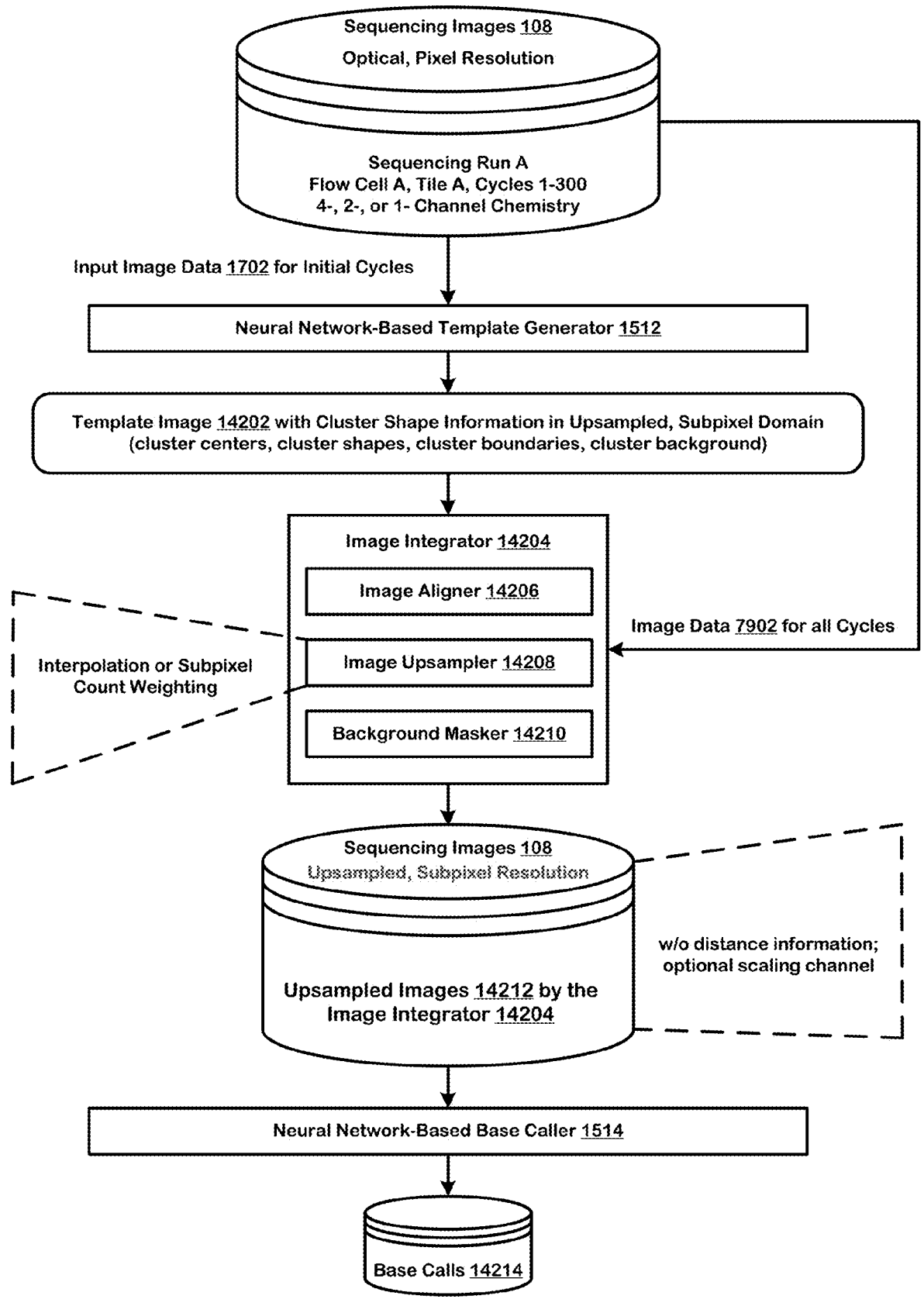

FIG. 142 illustrates another implementation of integrating the neural network-based template generator with the neural network-based base caller using upsampling and background masking.

Figure 143:
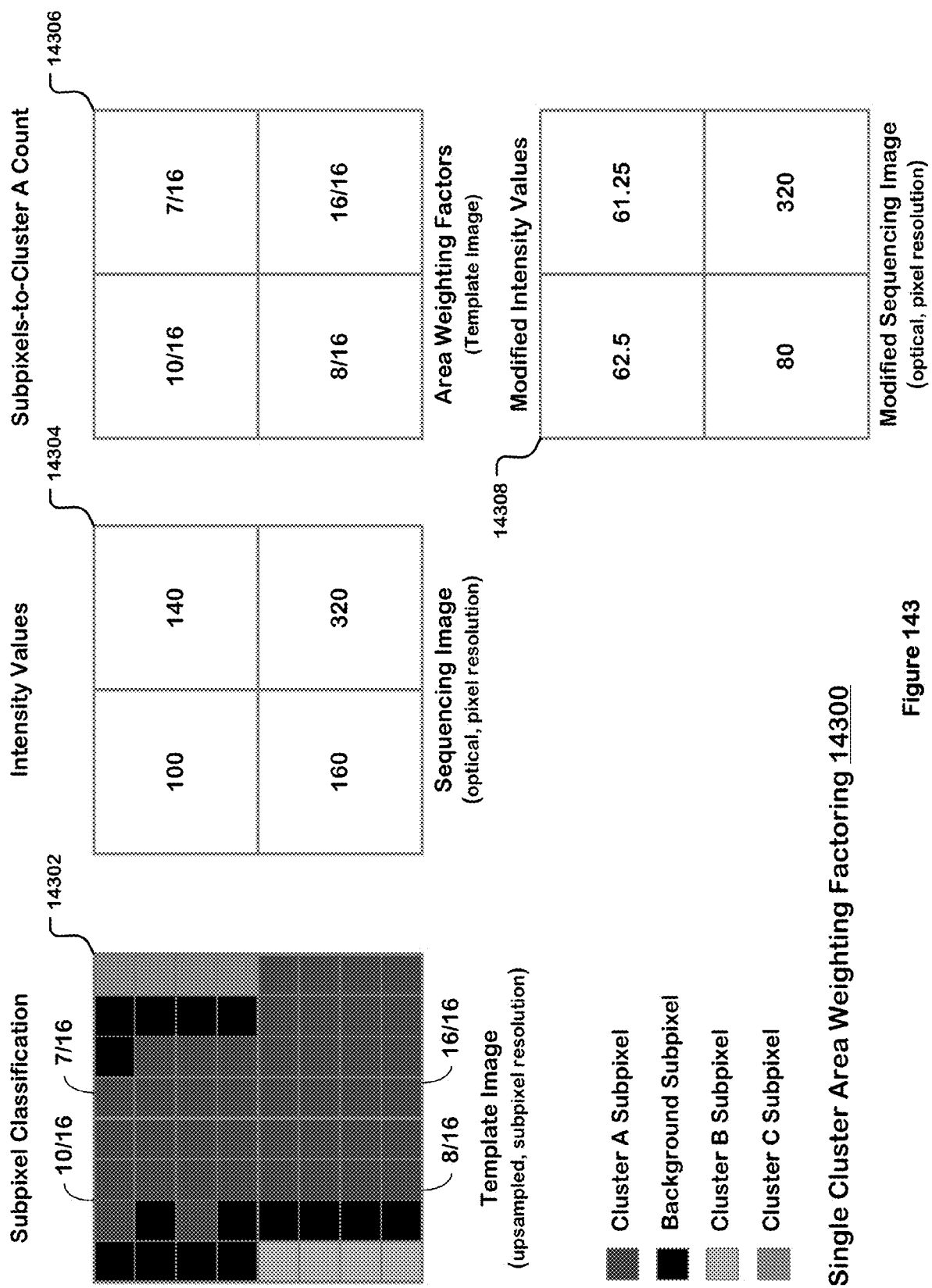

FIG. 143 depicts one example of area weighting factoring 14300 for contribution from only a single cluster per pixel.

Figure 144:
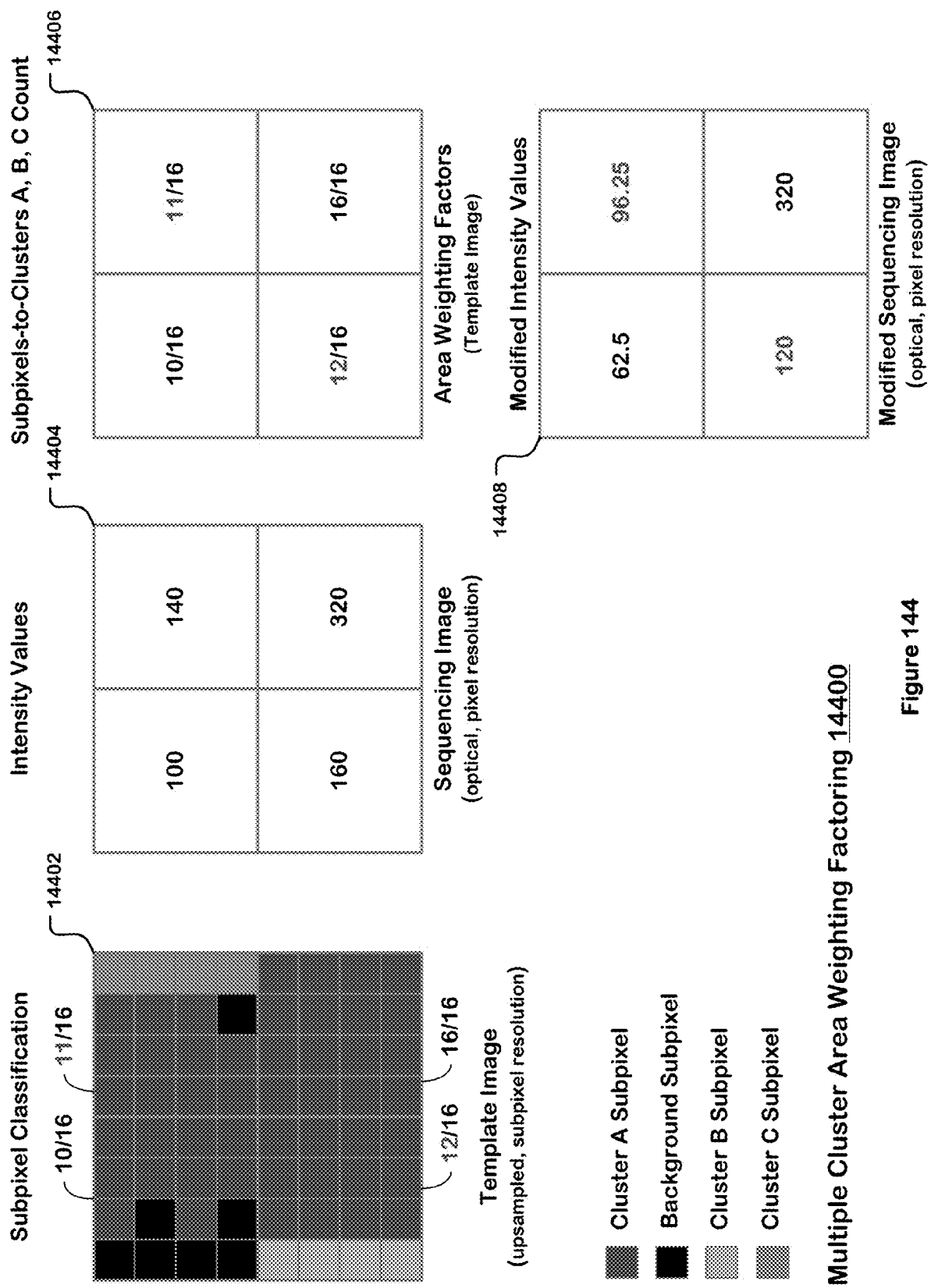

FIG. 144 depicts one example of area weighting factoring for contributions from multiple clusters per pixel.

Figure 145:
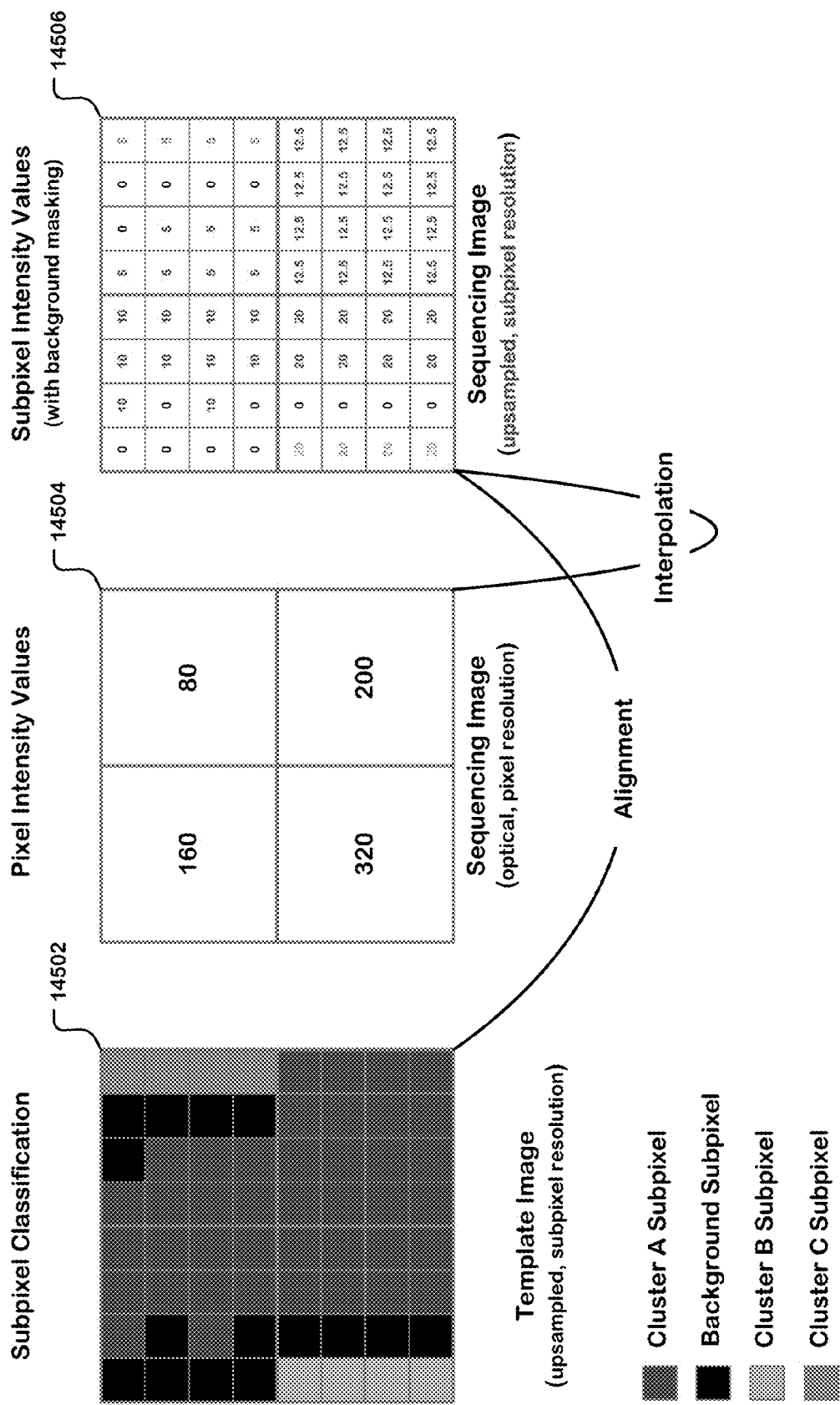

FIG. 145 depicts one example of using interpolation for upsampling and background masking.

Figure 146:
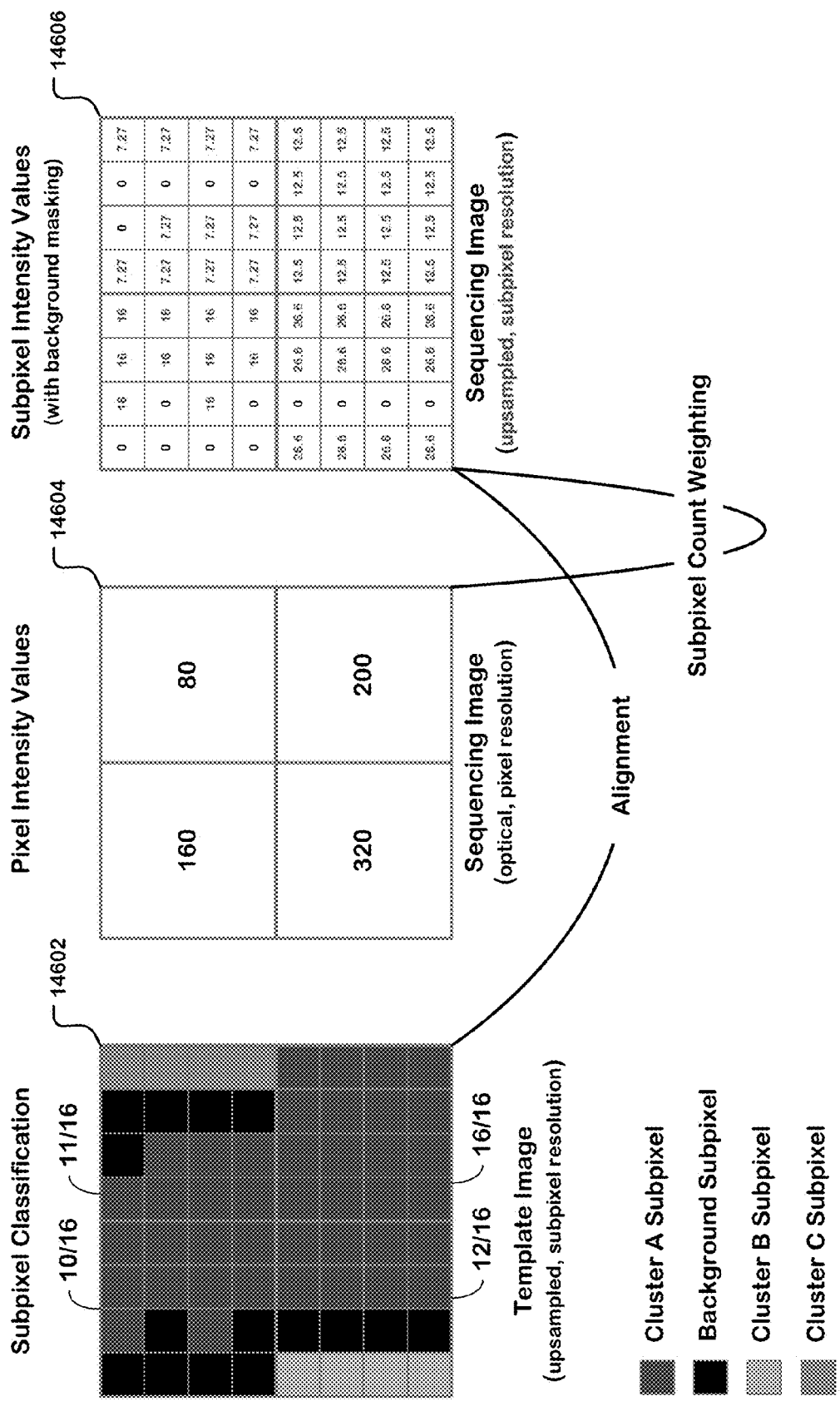

FIG. 146 depicts one example of using subpixel count weighting for upsampling and background masking.

Figure 147A:
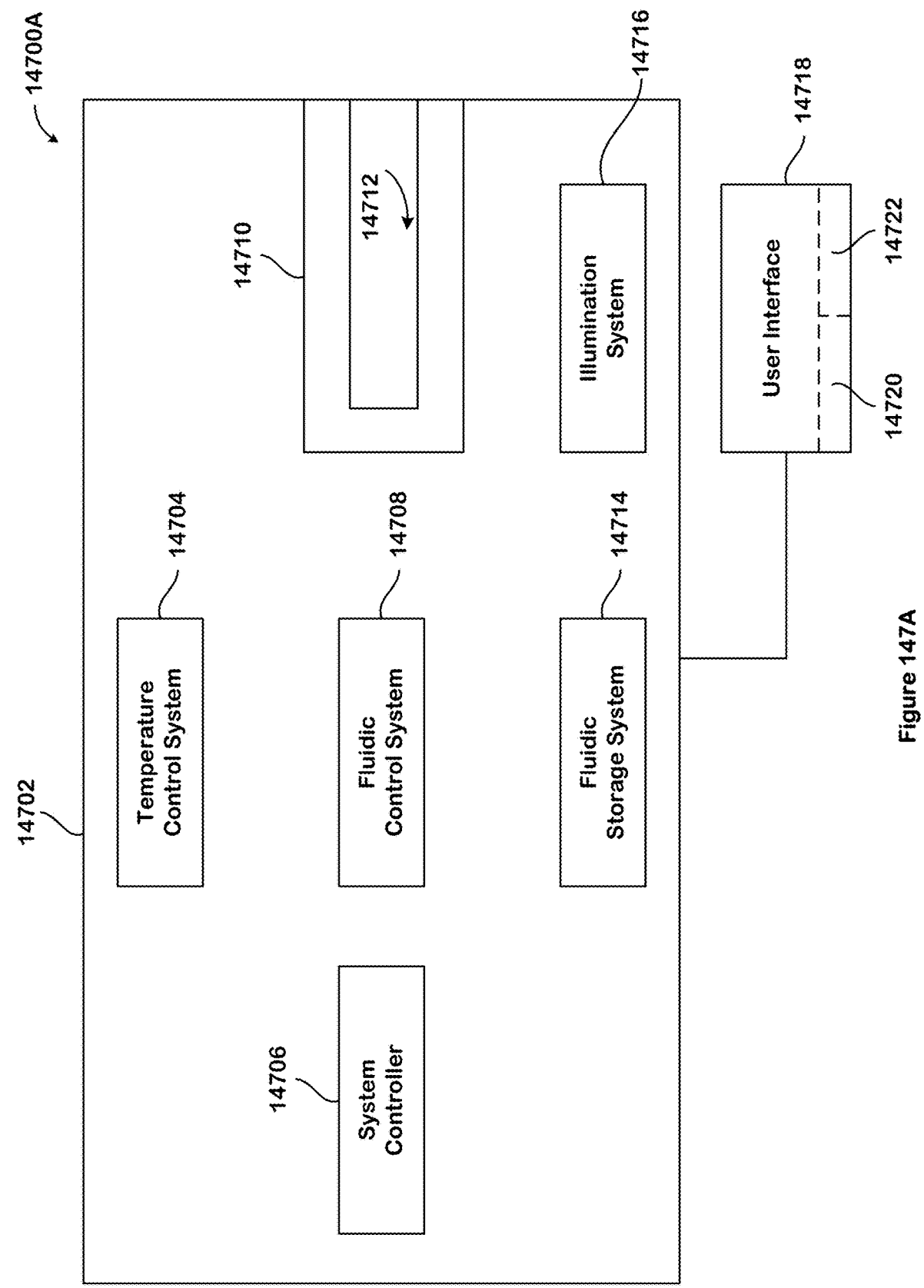
Figure 147B:
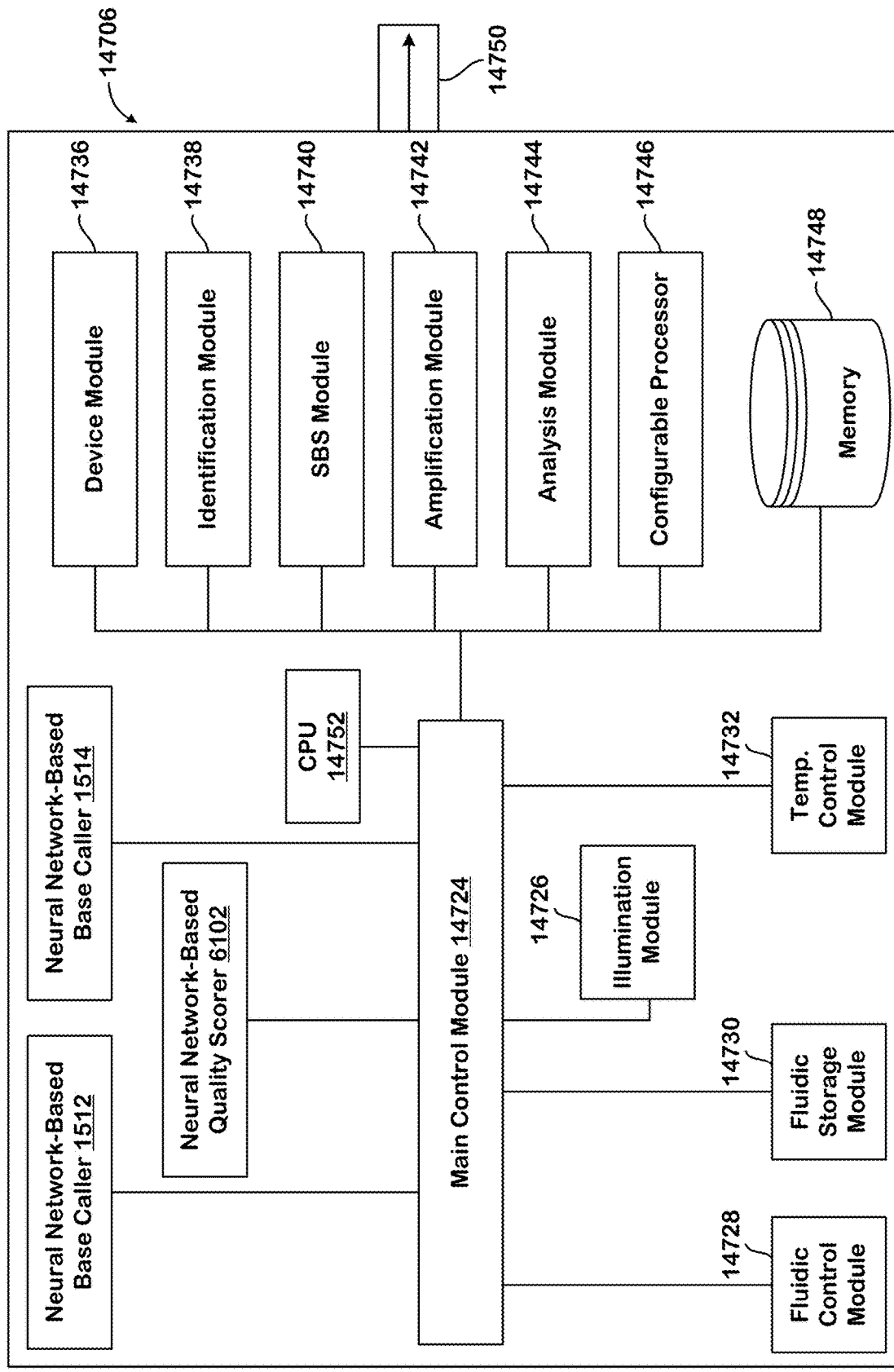

FIGS. 147A and 147B depict one implementation of a sequencing system. The sequencing system comprises a configurable processor.

Figure 147C:
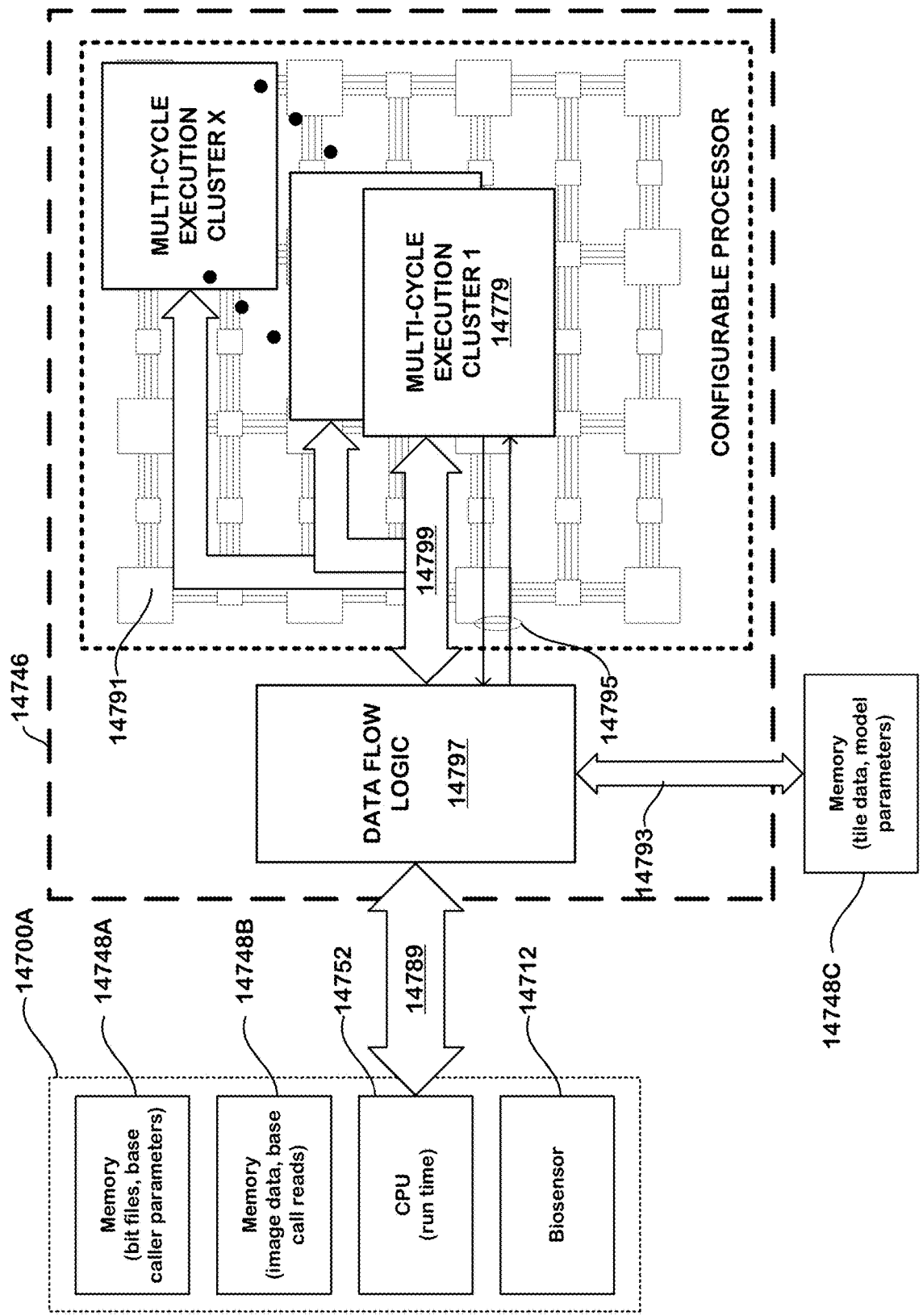

FIG. 147C is a simplified block diagram of a system for analysis of sensor data from the sequencing system, such as base call sensor outputs.

Figure 148A:
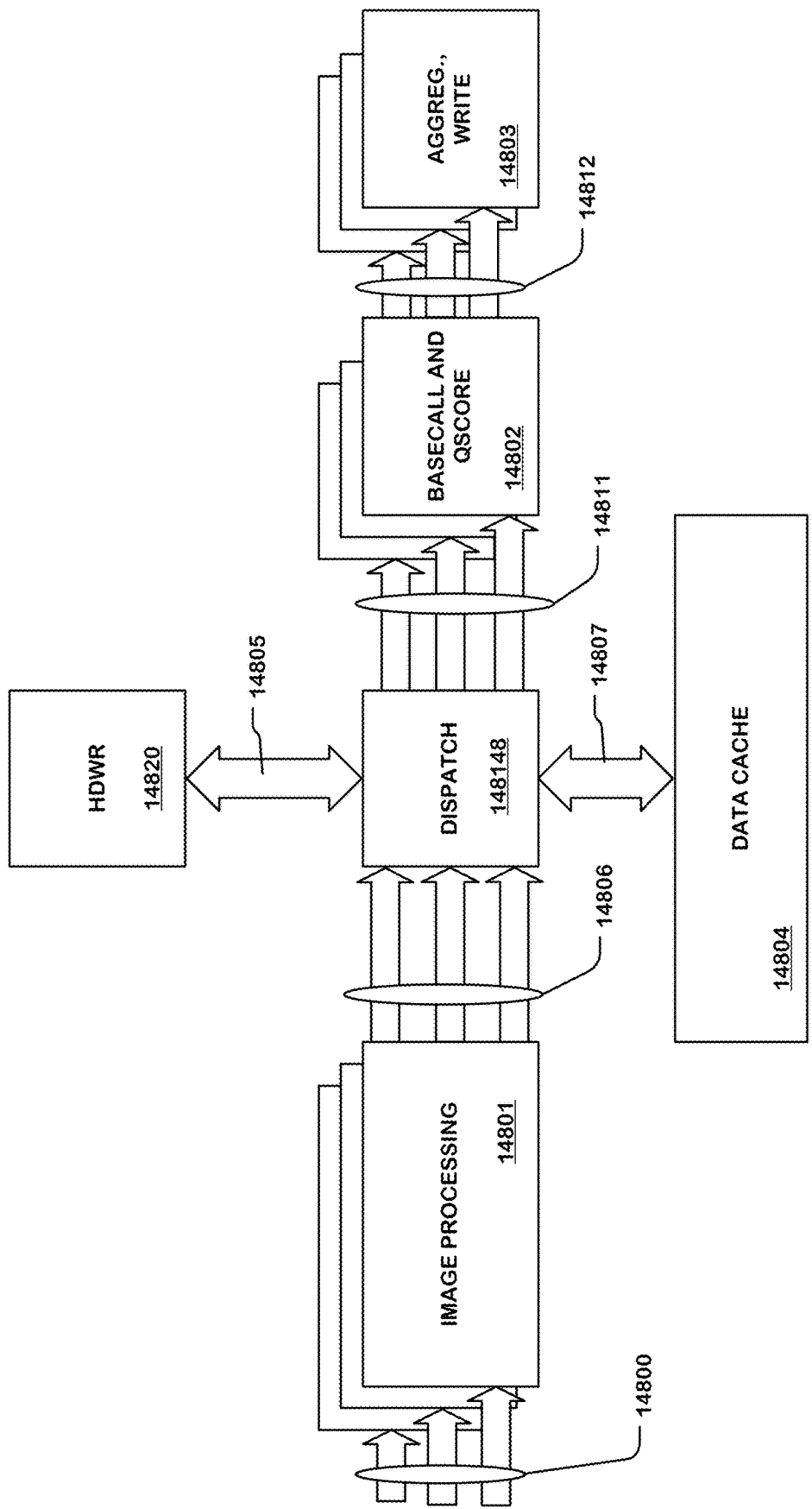

FIG. 148A is a simplified diagram showing aspects of the base calling operation, including functions of a runtime program executed by a host processor.

Figure 148B:
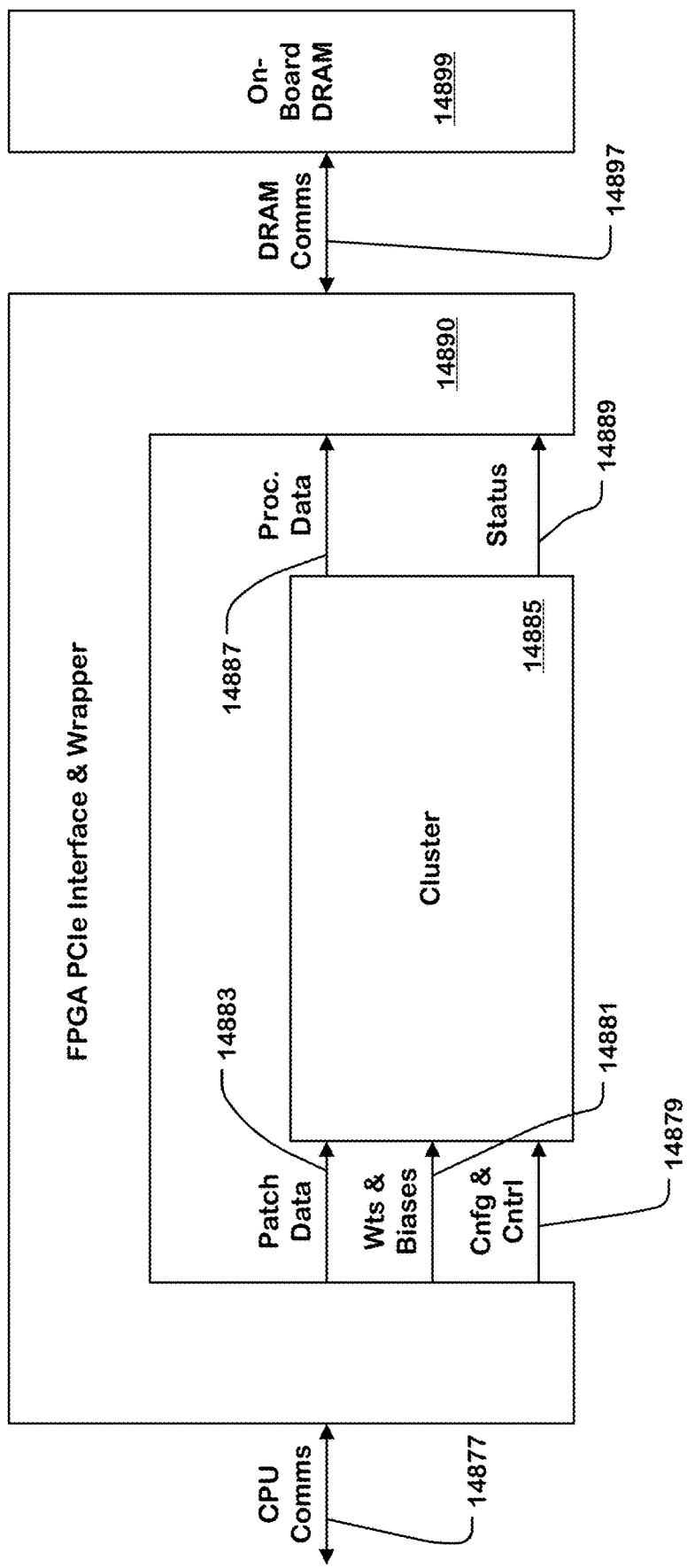

FIG. 148B is a simplified diagram of a configuration of a configurable processor such as the one depicted in FIG. 147C.

Figure 149:
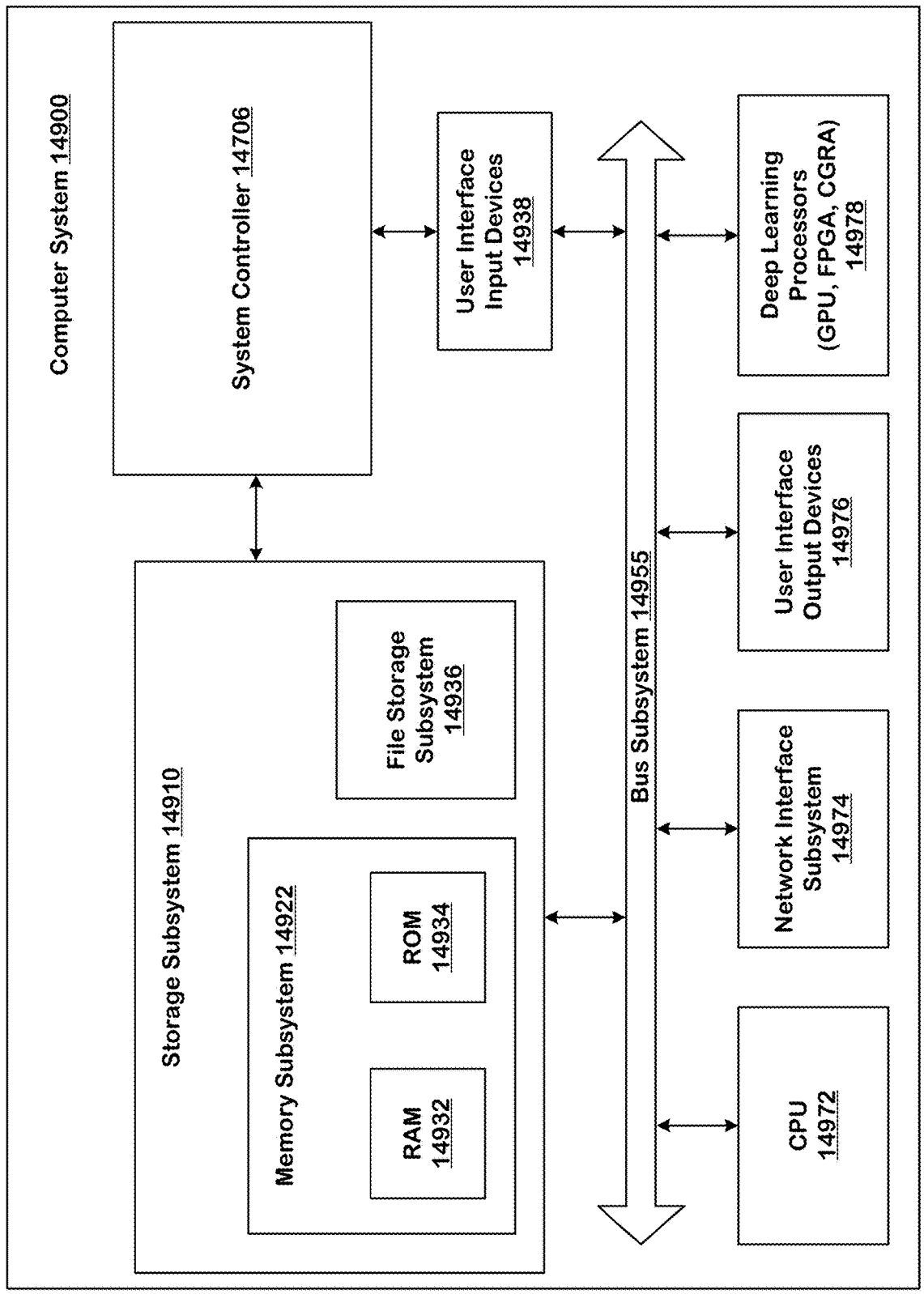

FIG. 149 is a computer system that can be used by the sequencing system of FIG. 147A to implement the technology disclosed herein.

Figure 150:
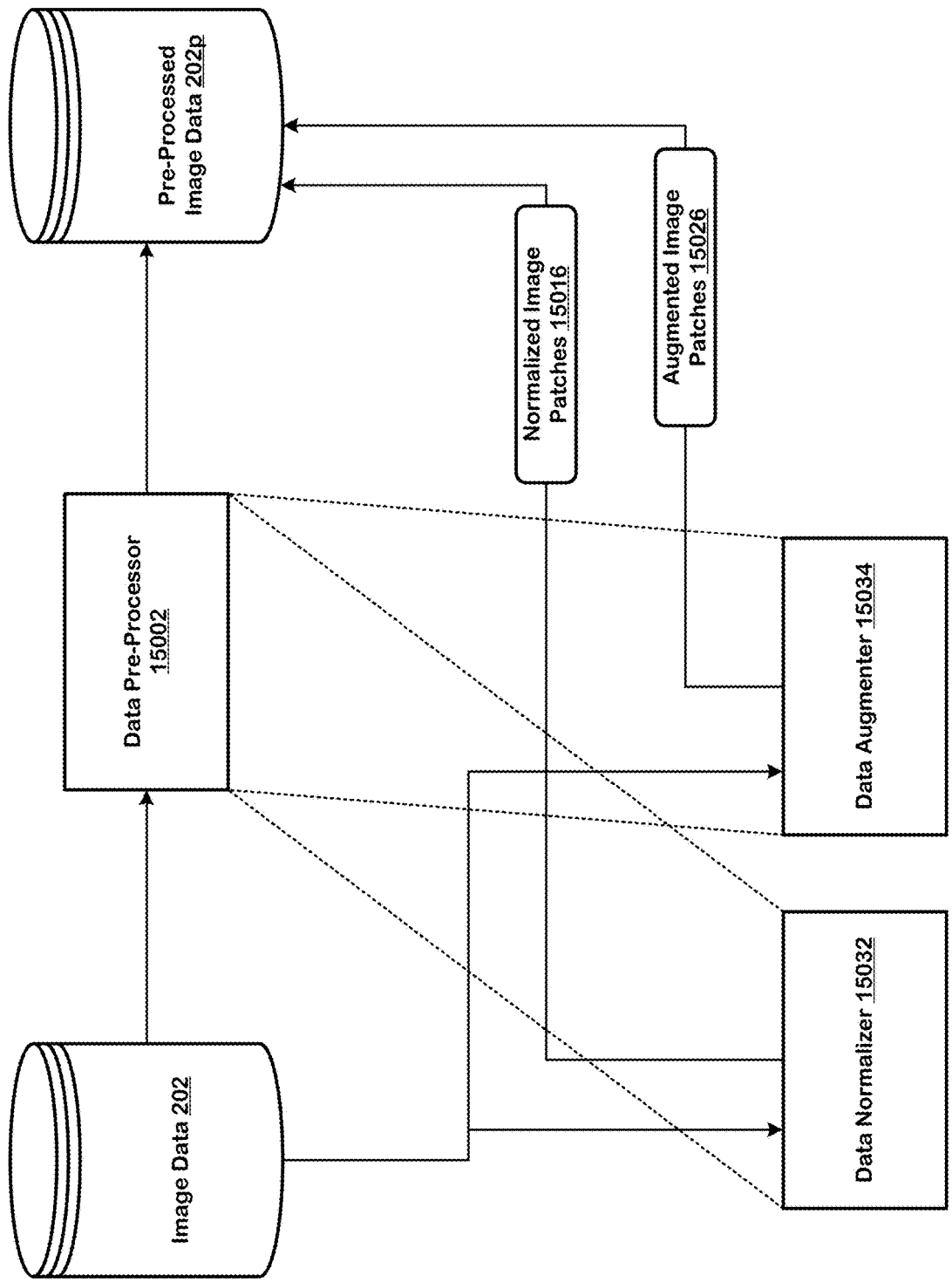

FIG. 150 shows different implementations of data preprocessing, which can include data normalization and data augmentation.

Figure 151:
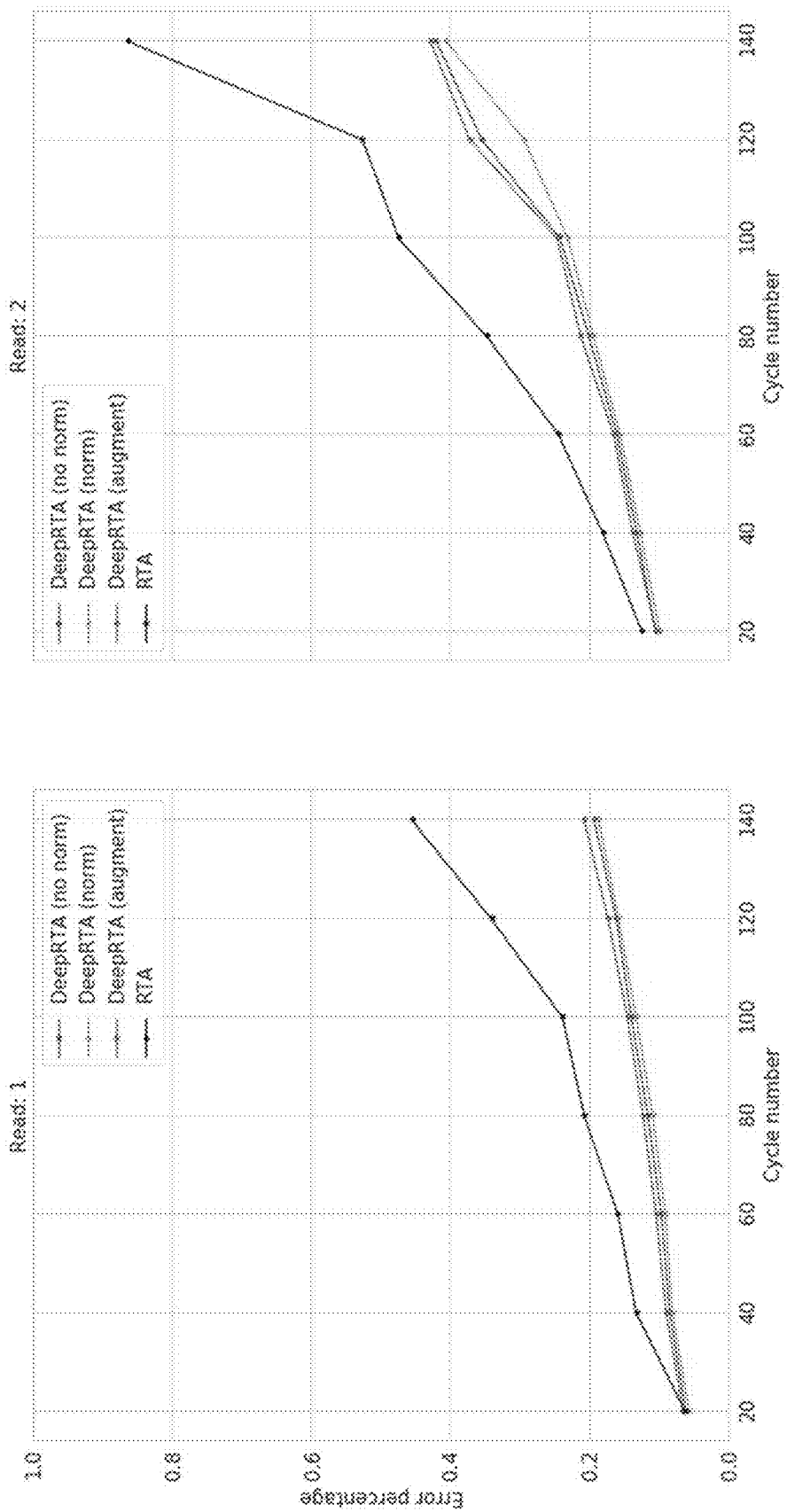

FIG. 151 shows that the data normalization technique (DeepRTA (norm)) and the data augmentation technique (DeepRTA (augment)) of FIG. 150 reduce the base calling error percentage when the neural network-based base caller is trained on bacterial data and tested on human data, where the bacterial data and the human data share the same assay (e.g., both contain intronic data).

Figure 152:
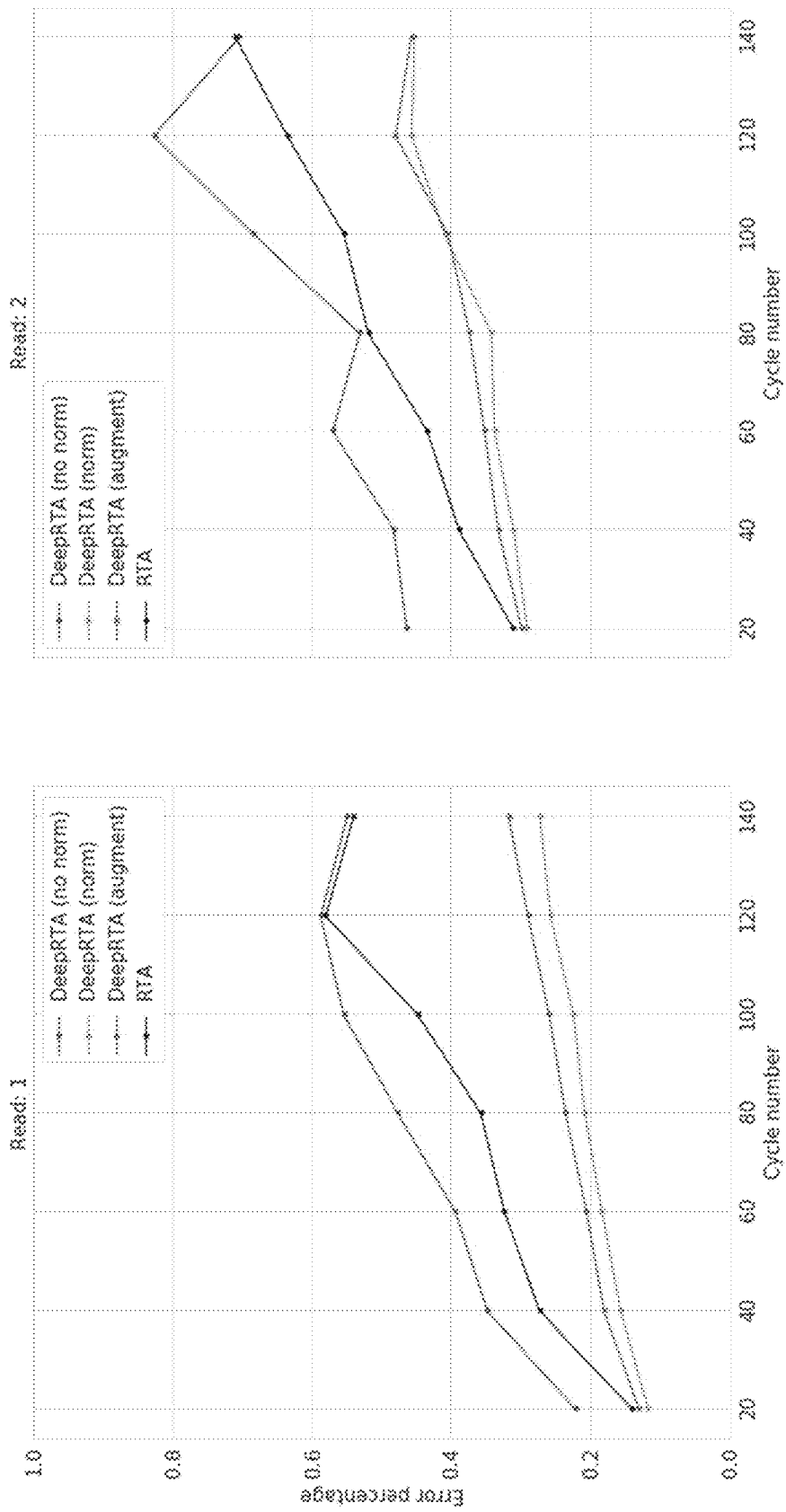

FIG. 152 shows that the data normalization technique (DeepRTA (norm)) and the data augmentation technique (DeepRTA (augment)) of FIG. 151 reduce the base calling error percentage when the neural network-based base caller is trained on non-exonic data (e.g., intronic data) and tested on exonic data.

DETAILED DESCRIPTION

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

Base calling from digital images is massively parallel and computationally intensive. This presents numerous technical challenges that we identify before introducing our new technology.

The signal from an image set being evaluated is increasingly faint as classification of bases proceeds in cycles, especially over increasingly long strands of bases. The signal-to-noise ratio decreases as base classification extends over the length of a strand, so reliability decreases. Updated estimates of reliability are expected as the estimated reliability of base classification changes.

Digital images are captured from amplified clusters of sample strands. Samples are amplified by duplicating strands using a variety of physical structures and chemistries. During sequencing by synthesis, tags are chemically attached in cycles and stimulated to glow. Digital sensors collect photons from the tags that are read out of pixels to produce images.

Interpreting digital images to classify bases requires resolving positional uncertainty, handicapped by limited image resolution. At a greater resolution than collected during base calling, it is apparent imaged clusters have irregular shapes and indeterminate center positions. Cluster positions are not mechanically regulated, so cluster centers are not aligned with pixel centers. A pixel center can be the integer coordinate assigned to a pixel. In other implementations, it can be the top-left corner of the pixel. In yet other implementations, it can be the centroid or center-of-mass of the pixel. Amplification does not produce uniform cluster shapes. Distribution of cluster signals in the digital image is, therefore, a statistical distribution rather than a regular pattern. We call this positional uncertainty.

One of the signal classes may produce no detectable signal and be classified at a particular position based on a "dark" signal. Thus, templates are necessary for classification during dark cycles. Production of templates resolves initial positional uncertainty using multiple imaging cycles to avoid missing dark signals.

Trade-offs in image sensor size, magnification, and stepper design lead to pixel sizes that are relatively large, that are too large to treat cluster centers as coincident with sensor pixel centers. This disclosure uses pixel in two senses. The physical, sensor pixel is a region of an optical sensor that reports detected photons. A logical pixel, simply referred to as a pixel, is data corresponding to at least one physical pixel, data read from the sensor pixel. The pixel can be subdivided or "up sampled" into sub pixels, such as 4×4 sub pixels. To take into account the possibility that all the photons are hitting one side of the physical pixel and not the opposite side, values can be assigned to sub pixels by interpolation, such as bilinear interpolation or area weighting. Interpolation or bilinear interpolation also is applied when pixels are re-framed by applying an affine transformation to data from physical pixels.

Larger physical pixels are more sensitive to faint signals than smaller pixels. While digital sensors improve with time, the physical limitation of collector surface area is unavoidable Taking design trade-offs into consideration, legacy systems have been designed to collect and analyze image data from a three-by-three patch of sensor pixels, with the center of the cluster somewhere in the center pixel of the patch.

High resolution sensors capture only part of an imaged media at a time. The sensor is stepped over the imaged media to cover the whole field. Thousands of digital images can be collected during one processing cycle.

Sensor and illumination design are combined to distinguish among at least four illumination response values that are used to classify bases. If a traditional RGB camera with a Bayer color filter array were used, four sensor pixels would be combined into a single RGB value. This would reduce the effective sensor resolution by four-fold. Alternatively, multiple images can be collected at a single position using different illumination wavelengths and/or different filters rotated into position between the imaged media and the sensor. The number of images required to distinguish among four base classifications varies between systems. Some systems use one image with four intensity levels for different classes of bases. Other systems use two images with different illumination wavelengths (red and green, for instance) and/or filters with a sort of truth table to classify bases. Systems also can use four images with different illumination wavelengths and/or filters tuned to specific base classes.

Massively parallel processing of digital images is practically necessary to align and combine relatively short strands, on the order of 30 to 2000 base pairs, into longer sequences, potentially millions or even billions of bases in length. Redundant samples are desirable over an imaged media, so a part of a sequence may be covered by dozens of sample reads. Millions or at least hundreds of thousands of sample clusters are imaged from a single imaged media. Massively parallel processing of so many clusters has increased in sequencing capacity while decreasing cost.

The capacity for sequencing has increased at a pace that rivals Moore's law. While the first sequencing cost billions of dollars, in 2018 services such as Illumina™ are delivering results for hundred(s) of dollars. As sequencing goes mainstream and unit prices drop, less computing power is available for classification, which increases the challenge of near real time classification. With these technical challenges in mind, we turn to the technology disclosed.

The technology disclosed improves processing during both template generation to resolve positional uncertainty and during base classification of clusters at resolved positions. Applying the technology disclosed, less expensive hardware can be used to reduce the cost of machines. Near real time analysis can become cost effective, reducing the lag between image collection and base classification.

The technology disclosed can use upsampled images produced by interpolating sensor pixels into subpixels and then producing templates that resolve positional uncertainty. A resulting subpixel is submitted to a base caller for classification that treats the subpixel as if it were at the center of a cluster. Clusters are determined from groups of adjoining subpixels that repeatedly receive the same base classification. This aspect of the technology leverages existing base calling technology to determine shapes of clusters and to hyper-locate cluster centers with a subpixel resolution.

Another aspect of the technology disclosed is to create ground truth, training data sets that pair images with confidently determined cluster centers and/or cluster shapes. Deep learning systems and other machine learning approaches require substantial training sets. Human curated data is expensive to compile. The technology disclosed can be used to leverage existing classifiers, in a non-standard mode of operation, to generate large sets of confidently classified training data without intervention or the expense of a human curator. The training data correlates raw images with cluster centers and/or cluster shapes available from existing classifiers, in a non-standard mode of operation, such as CNN-based deep learning systems, which can then directly process image sequences. One training image can be rotated and reflected to produce additional, equally valid examples. Training examples can focus on regions of a predetermined size within an overall image. The context evaluated during base calling determines the size of example training regions, rather than the size of an image from or overall imaged media.

The technology disclosed can produce different types of maps, usable as training data or as templates for base classification, which correlate cluster centers and/or cluster shapes with digital images. First, a subpixel can be classified as a cluster center, thereby localizing a cluster center within a physical sensor pixel. Second, a cluster center can be calculated as the centroid of a cluster shape. This location can be reported with a selected numeric precision. Third, a cluster center can be reported with surrounding subpixels in a decay map, either at subpixel or pixel resolution. A decay map reduces weight given to photons detected in regions as separation of the regions from the cluster center increase, attenuating signals from more distant positions. Fourth, binary or ternary classifications can be applied to subpixels or pixels in clusters of adjoining regions. In binary classification, a region is classified as belonging to a cluster center or as background. In ternary classification, the third class type is assigned to the region that contains the cluster interior, but not the cluster center. Subpixel classification of cluster center locations could be substituted for real valued cluster center coordinates within a larger optical pixel.

The alternative styles of maps can initially be produced as ground truth data sets, or, with training, they can be produced using a neural network. For instance, clusters can be depicted as disjoint regions of adjoining subpixels with appropriate classifications. Intensity mapped clusters from a neural network can be post-processed by a peak detector filter, to calculate cluster centers, if the centers have not already been determined. Applying a so-called watershed analysis, abutting regions can be assigned to separate clusters. When produced by a neural network inference engine, the maps can be used as templates for evaluating a sequence of digital images and classifying bases over cycles of base calling.

When bases are classified in sequences of digital images, the neural network processes multiple image channels in a current cycle together with image channels of past and future cycles. In a cluster, some of the strands may run ahead or behind the main course of synthesis, which out-of-phase tagging is known as pre-phasing or phasing. Given the low rates of pre-phasing and post-phasing observed empirically, nearly all of the noise in the signal resulting from pre-phasing and post-phasing can be handled by a neural network that processes digital images in current, past and future cycles, in just three cycles.

Among digital image channels in the current cycle, careful registration to align images within a cycle contributes strongly to accurate base classification. A combination of wavelengths and non-coincident illumination sources, among other sources of error, produces a small, correctable difference in measured cluster center locations. A general affine transformation, with translation, rotation and scaling, can be used to bring the cluster centers across an image tile into precise alignment. An affine transformation can be used to reframe image data and to resolve offsets for cluster centers.

Reframing image data means interpolating image data, typically by applying an affine transformation. Reframing can put a cluster center of interest in the middle of the center pixel of a pixel patch. Or, it can align an image with a template, to overcome jitter and other discrepancies during image collection. Reframing involves adjusting intensity values of all pixels in the pixel patch. Bi-linear and bi-cubic interpolation and weighted area adjustments are alternative strategies.

In some implementations, cluster center coordinates can be fed to a neural network as an additional image channel.

Distance signals also can contribute to base classification. Several types of distance signals reflect separation of regions from cluster centers. The strongest optical signal is deemed to coincide with the cluster center. The optical signal along the cluster perimeter sometimes includes a stray signal from a nearby cluster. Classification has been observed to be more accurate when contribution of signal component is attenuated according to its separation from the cluster center. Distance signals that work include a single cluster distance channel, a multi-cluster distance channel, and a multi-cluster shape-based distance channel. A single cluster distance channel applies to a patch with a cluster center in the center pixel. Then, distance of all regions in the patch is a distance from the cluster center in the center pixel. Pixels that do not belong to same cluster as the center pixel can be flagged as background, instead of given a calculated distance. A multi-cluster distance channel pre-calculates distance of each region to the closest cluster center. This has the potential of connecting a region to the wrong cluster center, but that potential is low. A multi-cluster shape-based distance channel associates regions (sub-pixels or pixels) through adjoining regions to a pixel center that produces a same base classification. At some computational expense, this avoids the possibility of measuring a distance to the wrong pixel. The multi-cluster and multi-cluster shape-based approaches to distance signals have the advantage of being subject to pre-calculation and use with multiple clusters in an image.

Shape information can be used by a neural network to separate signal from noise, to improve the signal-to-noise ratio. In the discussion above, several approaches to region classification and to supplying distance channel information were identified. In any of the approaches, regions can be marked as background, as not being part of a cluster, to define cluster edges. A neural network can be trained to take advantage of the resulting information about irregular cluster shapes. Distance information and background classification can be combined or used separately. Separating signals from abutting clusters will be increasingly important as cluster density increases.

One direction for increasing the scale of parallel processing is to increase cluster density on the imaged media. Increasing density has the downside of increasing background noise when reading a cluster that has an adjacent neighbor. Using shape data, instead of an arbitrary patch (e.g., of 3×3 pixels), for instance, helps maintain signal separation as cluster density increases.

Applying one aspect of the technology disclosed, base classification scores also can be leveraged to predict quality. The technology disclosed includes correlating classification scores, directly or through a prediction model, with traditional Sanger or Phred quality Q-scores. Scores such as Q20, Q30 or Q40 are logarithmically related to base classification error probabilities, by $Q=-10 \log_{10} P$. Correlation of class scores with Q scores can be performed using a multi-output neural network or multi-variate regression analysis. An advantage of real time calculation of quality scores, during base classification, is that a flawed sequencing run can be terminated early. Applicant has found that occasional (rare) decisions to terminate runs can be made one-eighth to one-quarter of the way through the analysis sequence. A decision to terminate can be made after 50 cycles or after 25 to 75 cycles. In a sequential process that would otherwise run 300 to 1000 cycles, early termination results in substantial resource savings.

Specialized convolutional neural network (CNN) architectures can be used to classify bases over multiple cycles. One specialization involves segregation among digital image channels during initial layers of processing. Convolution filters stacks can be structured to segregate processing among cycles, preventing cross-talk between digital image sets from different cycles. The motivation for segregating processing among cycles is that images taken at different cycles have residual registration error and are thus misaligned and have random translational offsets with respect to each other. This occurs due to the finite accuracy of the movements of the sensor's motion stage and also because images taken in different frequency channels have different optical paths and wavelengths.

The motivation for using image sets from successive cycles is that the contribution of pre-phasing and post-phasing to signals in a particular cycle is a second order contribution. It follows that it can be helpful for the convolutional neural network to structurally segregate lower layer convolution of digital image sets among image collection cycles.

The convolutional neural network structure also can be specialized in handling information about clustering. Templates for cluster centers and/or shapes provide additional information, which the convolutional neural network combines with the digital image data. The cluster center classification and distance data can be applied repeatedly across cycles.

The convolutional neural network can be structured to classify multiple clusters in an image field. When multiple clusters are classified, the distance channel for a pixel or subpixel can more compactly contain distance information relative to either the closest cluster center or to the adjoining cluster center, to which a pixel or subpixel belongs. Alternatively, a large distance vector could be supplied for each pixel or subpixel, or at least for each one that contains a cluster center, which gives complete distance information from a cluster center to all other pixels that are context for the given pixel.

Some combinations of template generation with base calling can use variations on area weighting to supplant a distance channel. The discussion now turns to how output of the template generator can be used directly, in lieu of a distance channel.

We discuss three considerations that impact direct application of template images to pixel value modification: whether image sets are processed in the pixel or subpixel domain; in either domain, how area weights are calculated; and in the subpixel domain, applying a template image as mask to modify interpolated intensity values.

Performing base classification in the pixel domain has the advantage of not calling for an increase in calculations, such as 16 fold, which results from upsampling. In the pixel domain, even the top layer of convolutions may have sufficient cluster density to justify performing calculations that would not be harvested, instead of adding logic to cancel unneeded calculations. We begin with examples in the pixel domain of directly using template image data without a distance channel.

In some implementations, classification focuses on a particular cluster. In these instances, pixels on the perimeter of a cluster may have different modified intensity values, depending on which adjoining cluster is the focus of classification. The template image in the subpixel domain can indicate that an overlap pixel contributes intensity value to two different clusters. We refer to optical pixel as an "overlap pixel" when two or more adjacent or abutting clusters both overlap the pixel; both contribute to the intensity reading from the optical pixel. Watershed analysis, named after separating rain flows into different watersheds at a ridge line, can be applied to separate even abutting clusters. When data is received for classification on a cluster-by-cluster basis, the template image can be used to modify intensity data for overlap pixels along the perimeter of clusters. The overlap pixels can have different modified intensities, depending on which cluster is the focus of classification.

The modified intensity of a pixel can be reduced based on subpixel contribution in the overlap pixel to a home cluster (i.e., the cluster to which the pixel belongs or the cluster whose intensity emissions the pixel primarily depicts), as opposed to an away cluster (i.e., the non-home cluster whose intensity emissions the pixel depicts). Suppose that 5 subpixels are part of the home cluster and 2 subpixels are part of the away cluster. Then, 7 subpixels contribute intensity to the home or away cluster. During focus on the home cluster, in one implementation the overlap pixel is reduced in intensity by $7/16$, because 7 of the 16 subpixels contribute intensity to the home or away cluster. In another implementation, intensity is reduced by $5/16$, based on the area of subpixels contributing to the home cluster divided by the total number of subpixels. In a third implementation, intensity is reduced by $5/7$, based on the area of subpixels contributing to the home cluster divided by the total area of contributing subpixels. The latter two calculations change when the focus turns to the away cluster, producing fractions with "2" in the numerator.

Of course, further reduction in intensity can be applied if a distance channel is being considered along with a subpixel map of cluster shapes.

Once the pixel intensities for a cluster that is the focus of classification have been modified using the template image, the modified pixel values are convolved through layers of a neural network-based classifier to produce modified images. The modified images are used to classify bases in successive sequencing cycles.

Alternatively, classification in the pixel domain can proceed in parallel for all pixels or all clusters in a chunk of an image. Only one modification of a pixel value can be applied in this scenario to assure reusability of intermediate calculations. Any of the fractions given above can be used to modify pixel intensity, depending on whether a smaller or larger attenuation of intensity is desired.

Once the pixel intensities for the image chunk have been modified using the template image, pixels and surrounding context can be convolved through layers of a neural network-based classifier to produce modified images. Performing convolutions on an image chunk allows reuse of intermediate calculations among pixels that have shared context. The modified images are used to classify bases in successive sequencing cycles.

This description can be paralleled for application of area weights in the subpixel domain. The parallel is that weights can be calculated for individual subpixels. The weights can, but do not need to, be the same for different subpixel parts of an optical pixel. Repeating the scenario above of home and away clusters, with 5 and 2 subpixels of the overlap pixel, respectively, the assignment of intensity to a subpixel belonging to the home cluster can be $7/16$, $5/16$ or $5/7$ of the pixel intensity. Again, further reduction in intensity can be applied if a distance channel is being considered along with a subpixel map of cluster shapes.

Once the pixel intensities for the image chunk have been modified using the template image, subpixels and surrounding context can be convolved through layers of a neural network-based classifier to produce modified images. Performing convolutions on an image chunk allows reuse of intermediate calculations among subpixels that have shared context. The modified images are used to classify bases in successive sequencing cycles.

Another alternative is to apply the template image as a binary mask, in the subpixel domain, to image data interpolated into the subpixel domain. The template image can either be arranged to require a background pixel between clusters or to allow subpixels from different clusters to abut. The template image can be applied as a mask. The mask determines whether an interpolated pixel keeps the value assigned by interpolation or receives a background value (e.g., zero), if it is classified in the template image as background.

Again, once the pixel intensities for the image chunk have been masked using the template image, subpixels and surrounding context can be convolved through layers of a neural network-based classifier to produce modified images. Performing convolutions on an image chunk allows reuse of intermediate calculations among subpixels that have shared context. The modified images are used to classify bases in successive sequencing cycles.

Features of the technology disclosed are combinable to classify an arbitrary number of clusters within a shared context, reusing intermediate calculations. At optical pixel resolution, in one implementation, about ten percent of pixels hold cluster centers to be classified. In legacy systems, three by three optical pixels were grouped for analysis as potential signal contributors for a cluster center, given observation of irregularly shaped clusters. Even one 3-by-3 filter away from the top convolution layer, cluster densities are likely to roll up into pixels at cluster centers optical signals from substantially more than half of the optical pixels. Only at super sampled resolution does cluster center density for the top convolution layer drop below one percent.

Shared context is substantial in some implementations. For instance, 15-by-15 optical pixel context may contribute to accurate base classification. An equivalent 4× up sampled context would be 60-by-60 sub pixels. This extent of context helps the neural network recognize impacts of non-uniform illumination and background during imaging.

The technology disclosed uses small filters at a lower convolution layer to combine cluster boundaries in template input with boundaries detected in digital image input. Cluster boundaries help the neural network separate signal from background conditions and normalize image processing against the background.

The technology disclosed substantially reuses intermediate calculations. Suppose that 20 to 25 cluster centers appear within a context area of 15-by-15 optical pixels. Then, first layer convolutions stand to be reused 20 to 25 times in blockwise convolution roll-ups. The reuse factor is reduced layer-by-layer until the penultimate layer, which is the first time that the reuse factor at optical resolution drops below 1×.

Blockwise roll-up training and inference from multiple convolution layers applies successive roll-ups to a block of pixels or sub pixels. Around a block perimeter, there is an overlap zone in which data used during roll-up of a first data block overlaps with and can be reused for a second block of roll-ups. Within the block, in a center area surrounded by the overlap zone, are pixel values and intermediate calculations that can be rolled up and that can be reused. With an overlap zone, convolution results that progressively reduce the size of a context field, for instance from 15-by-15 to 13-by-13 by application of a 3-by-3 filter, can be written into the same memory block that holds the values convolved, conserving memory without impairing reuse of underlying calculations within the block. With larger blocks, sharing intermediate calculations in the overlap zone, requires less resources. With smaller blocks, it can be possible to calculate multiple blocks in parallel, to share the intermediate calculations in the overlap zones.

Larger filters and dilations would reduce the number of convolution layers, which may be speed calculation without impairing classification, after lower convolution layers have reacted to cluster boundaries in the template and/or digital image data.

The input channels for template data can be chosen to make the template structure consistent with classifying multiple cluster centers in a digital image field. Two alternatives described above do not satisfy this consistency criteria: reframing and distance mapping over an entire context. Reframing places the center of just one cluster in the center of an optical pixel. Better for classifying multiple clusters is supplying center offsets for pixels classified as holding cluster centers.

Distance mapping, if provided, is difficult to perform across a whole context area unless every pixel has its own distance map over a whole context. Simpler distance maps provide the useful consistency for classifying multiple clusters from a digital image input block.

A neural network can learn from classification in a template of pixels or sub pixels at the boundary of a cluster, so a distance channel can be supplanted by a template that supplies binary or ternary classification, accompanied by a cluster center offset channel. When used, a distance map can give a distance of a pixel from a cluster center to which the pixel (or subpixel) belongs. Or the distance map can give a distance to the closest cluster center. The distance map can encode binary classification with a flag value assigned to background pixels or it can be a separate channel from pixel classification. Combined with cluster center offsets, the distance map can encode ternary classification. In some implementations, particularly ones that encode pixel classifications with one or two bits, it may be desirable, at least during development, to use separate channels for pixel classification and for distance.

The technology disclosed can include reduction of calculations to save some calculation resources in upper layers. The cluster center offset channel or a ternary classification map can be used to identify centers of pixel convolutions that do not contribute to an ultimate classification of a pixel center. In many hardware/software implementations, performing a lookup during inference and skipping a convolution roll up can be more efficient in upper layer(s) than performing even nine multiplies and eight adds to apply a 3-by-3 filter. In custom hardware that pipelines calculations for parallel execution, every pixel can be classified within the pipeline. Then, the cluster center map can be used after the final convolution to harvest results for only pixels that coincide with cluster centers, because an ultimate classification is only desired for those pixels. Again, in the optical pixel domain, at currently observed cluster densities, rolled up calculations for about ten percent of the pixels would be harvested. In a 4× up sampled domain, more layers could benefit from skipped convolutions, on some hardware, because less than one percent of the sub pixel classifications in the top layer would be harvested.

Neural Network-Based Template Generation

The first step of template generation is determining cluster metadata. Cluster metadata identifies spatial distribution of clusters, including their centers, shapes, sizes, background, and/or boundaries.

Determining Cluster Metadata

Figure 1:
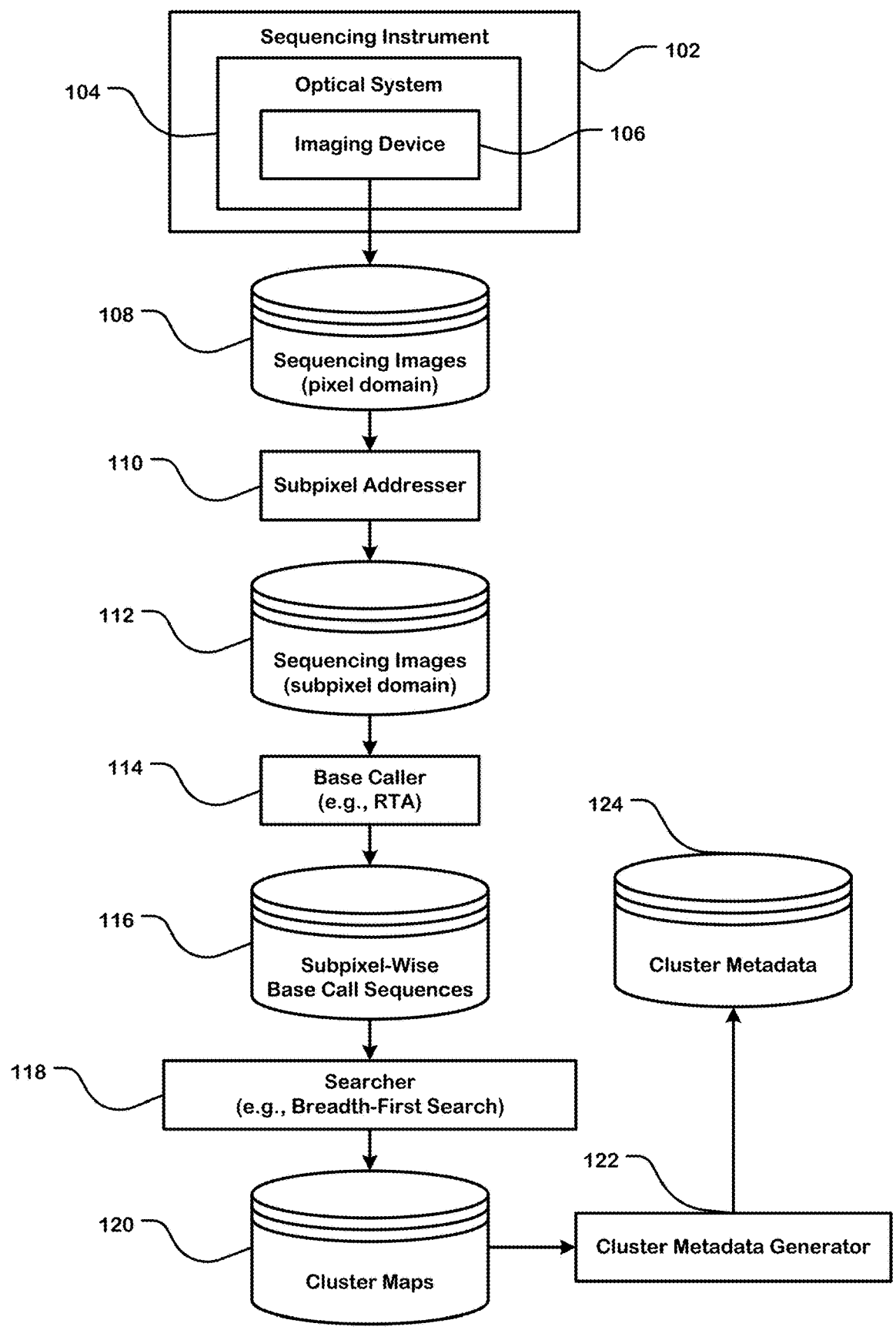
FIG. 1 shows one implementation of a processing pipeline that determines cluster metadata using subpixel base calling.

FIG. 1 shows one implementation of a processing pipeline that determines cluster metadata using subpixel base calling.

Figure 2:
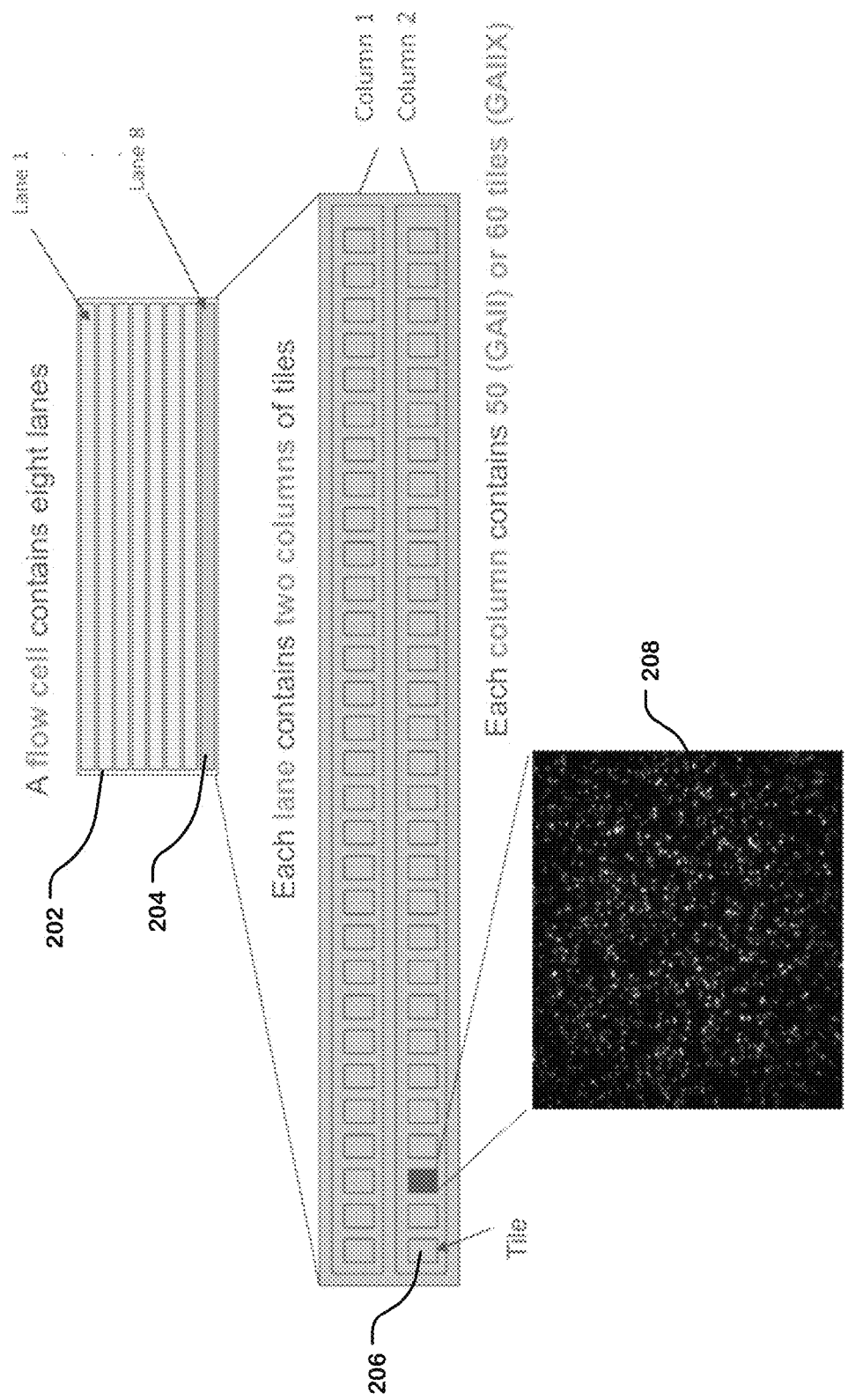
FIG. 2 depicts one implementation of a flow cell that contains clusters in its tiles.

FIG. 2 depicts one implementation of a flow cell that contains clusters in its tiles. The flow cell is partitioned into lanes. The lanes are further partitioned into non-overlapping regions called "tiles". During the sequencing procedure, the clusters and their surrounding background on the tiles are imaged.

Figure 3:
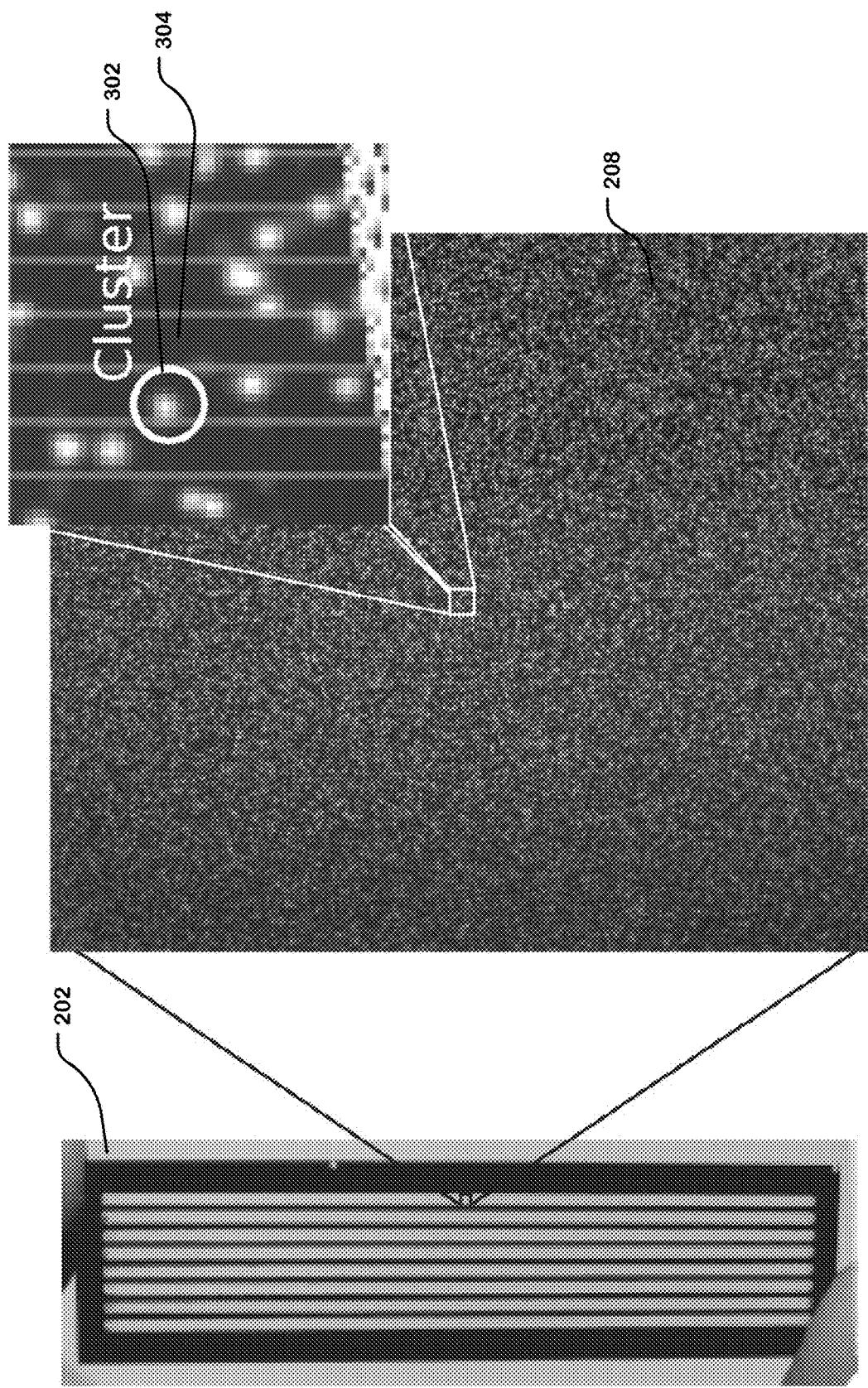
FIG. 3 illustrates one example of the Illumina GA-IIx flow cell with eight lanes.

FIG. 3 illustrates an example Illumina GA-IIx™ flow cell with eight lanes. FIG. 3 also shows a zoom-in on one tile and its clusters and their surrounding background.

Figure 4:
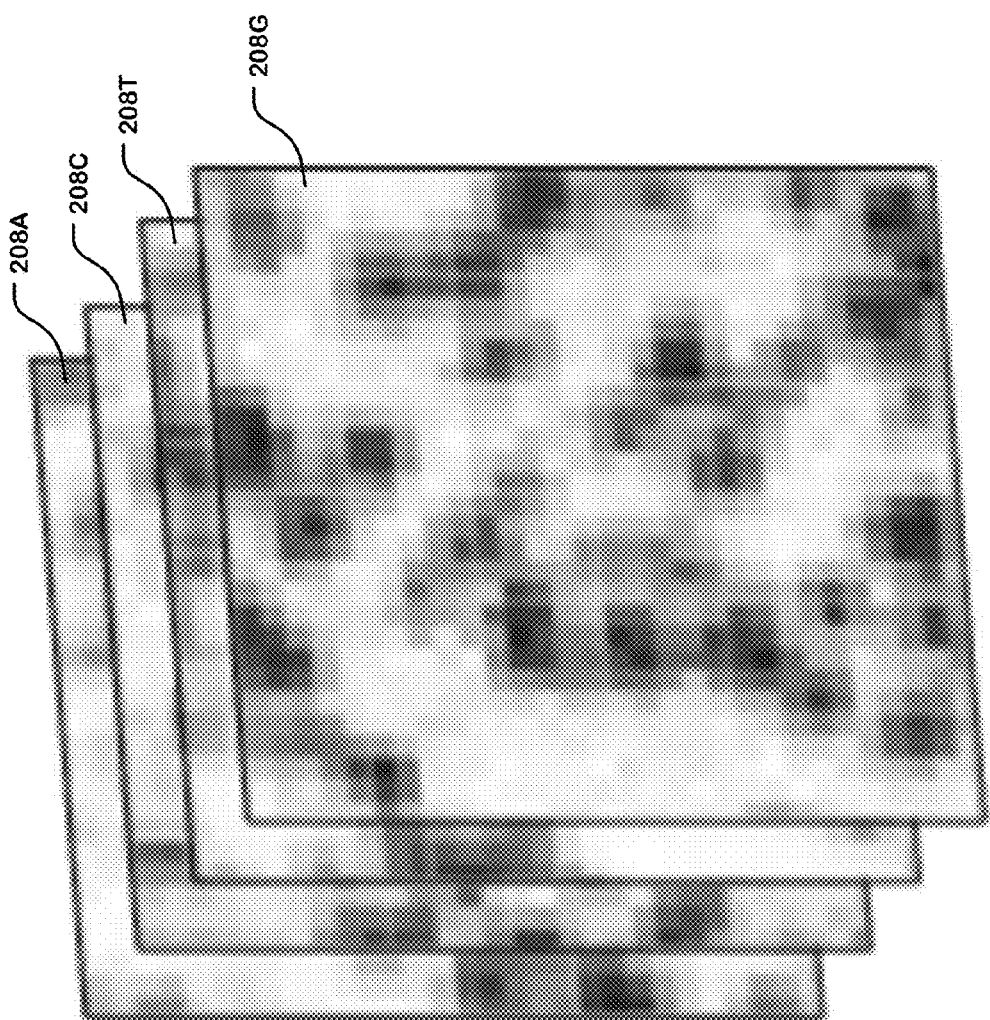
FIG. 4 depicts an image set of sequencing images for four-channel chemistry, i.e., the image set has four sequencing images, captured using four different wavelength bands (image/imaging channel) in the pixel domain.

FIG. 4 depicts an image set of sequencing images for four-channel chemistry, i.e., the image set has four sequencing images, captured using four different wavelength bands (image/imaging channel) in the pixel domain. Each image in the image set covers a tile of a flow cell and depicts intensity emissions of clusters on the tile and their surrounding background captured for a particular image channel at a particular one of a plurality of sequencing cycles of a sequencing run performed on the flow cell. In one implementation, each imaged channel corresponds to one of a plurality of filter wavelength bands. In another implementation, each imaged channel corresponds to one of a plurality of imaging events at a sequencing cycle. In yet another implementation, each imaged channel corresponds to a combination of illumination with a specific laser and imaging through a specific optical filter. The intensity emissions of a cluster comprise signals detected from an analyte that can be used to classify a base associated with the analyte. For example, the intensity emissions may be signals indicative of photons emitted by tags that are chemically attached to an analyte during a cycle when the tags are stimulated and that may be detected by one or more digital sensors, as described above.

Figure 5:
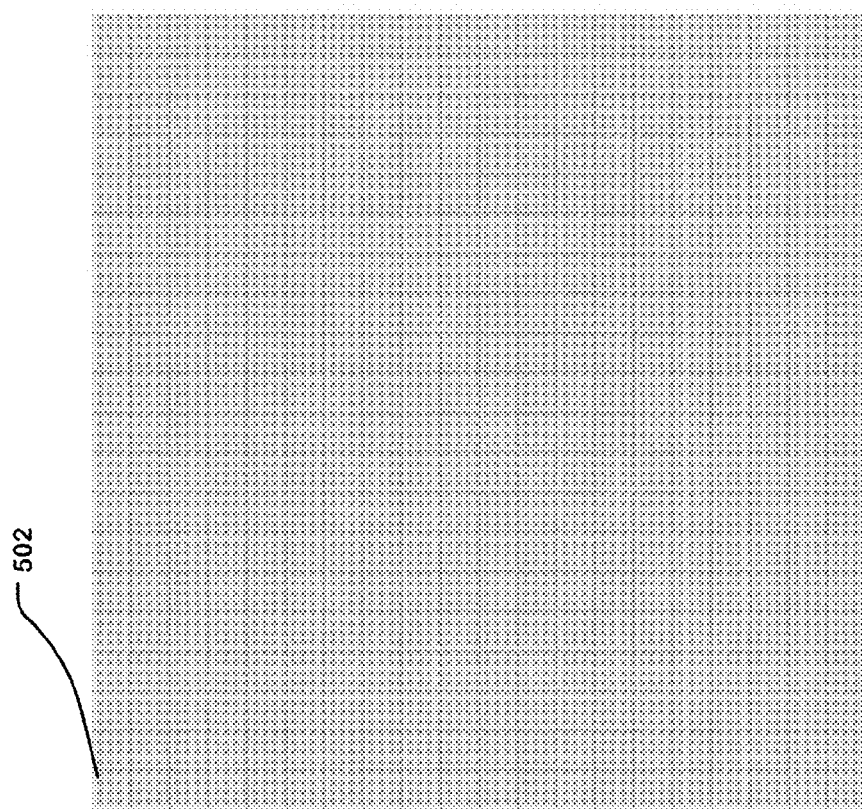
FIG. 5 is one implementation of dividing a sequencing image into subpixels (or subpixel regions).

FIG. 5 is one implementation of dividing a sequencing image into subpixels (or subpixel regions). In the illustrated implementation, quarter (0.25) subpixels are used, which results in each pixel in the sequencing image being divided into sixteen subpixels. Given that the illustrated sequencing image has a resolution of 20×20 pixels, i.e., 400 pixels, the division produces 6400 subpixels. Each of the subpixels is treated by a base caller as a region center for subpixel base calling. In some implementations, this base caller does not use neural network-based processing. In other implementations, this base caller is a neural network-based base caller.

For a given sequencing cycle and a particular subpixel, the base caller is configured with logic to produce a base call for the given sequencing cycle particular subpixel by performing image processing steps and extracting intensity data for the subpixel from the corresponding image set of the sequencing cycle. This is done for each of the subpixels and for each of a plurality of sequencing cycles. Experiments have also been carried out with quarter subpixel division of 1800×1800 pixel resolution tile images of the Illumina MiSeq sequencer. Subpixel base calling was performed for fifty sequencing cycles and for ten tiles of a lane.

Figure 6:
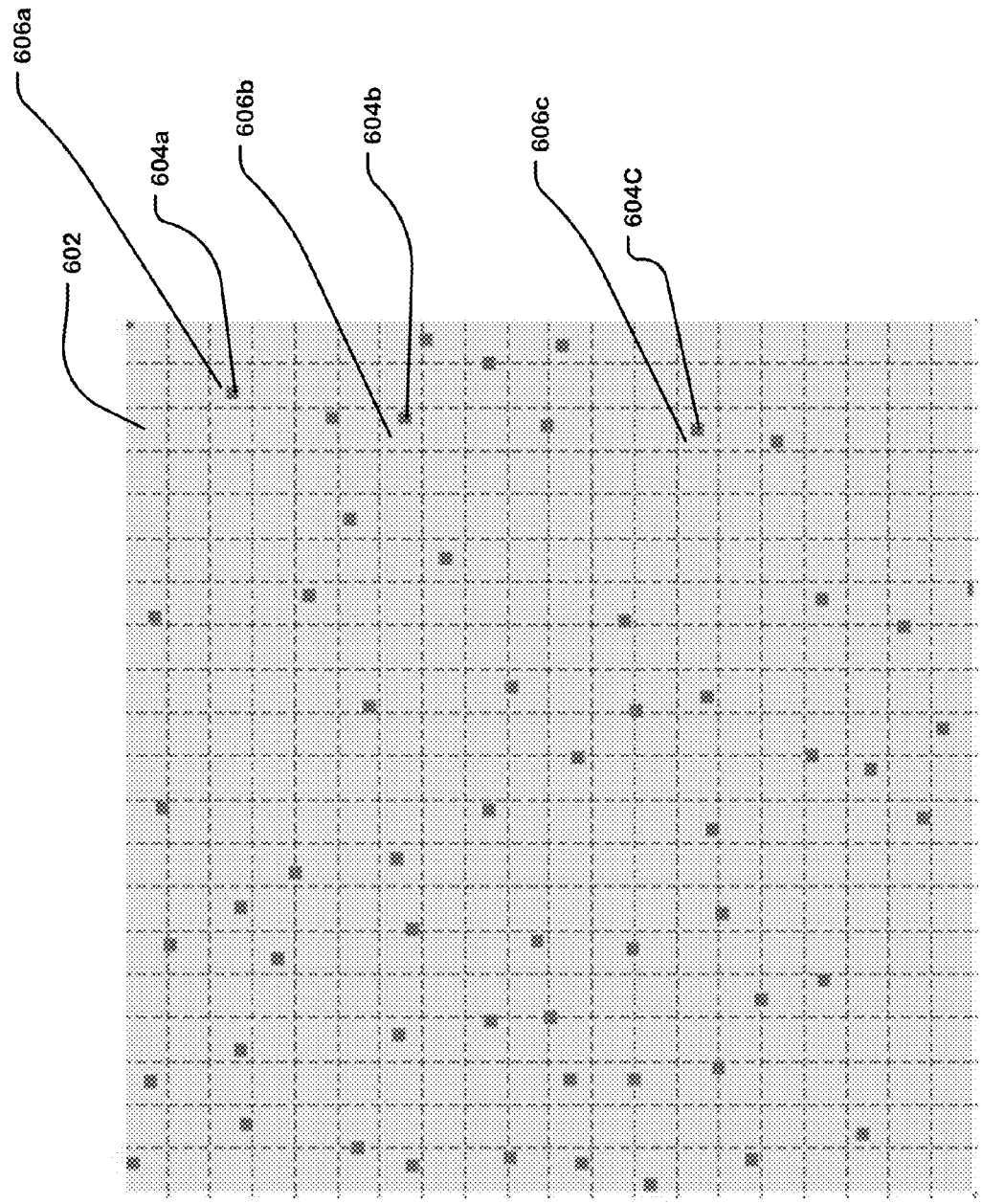
FIG. 6 shows preliminary center coordinates of the clusters identified by the base caller during the subpixel base calling.

FIG. 6 shows preliminary center coordinates of the clusters identified by the base caller during the subpixel base calling. FIG. 6 also shows "origin subpixels" or "center subpixels" that contain the preliminary center coordinates.

Figure 7:
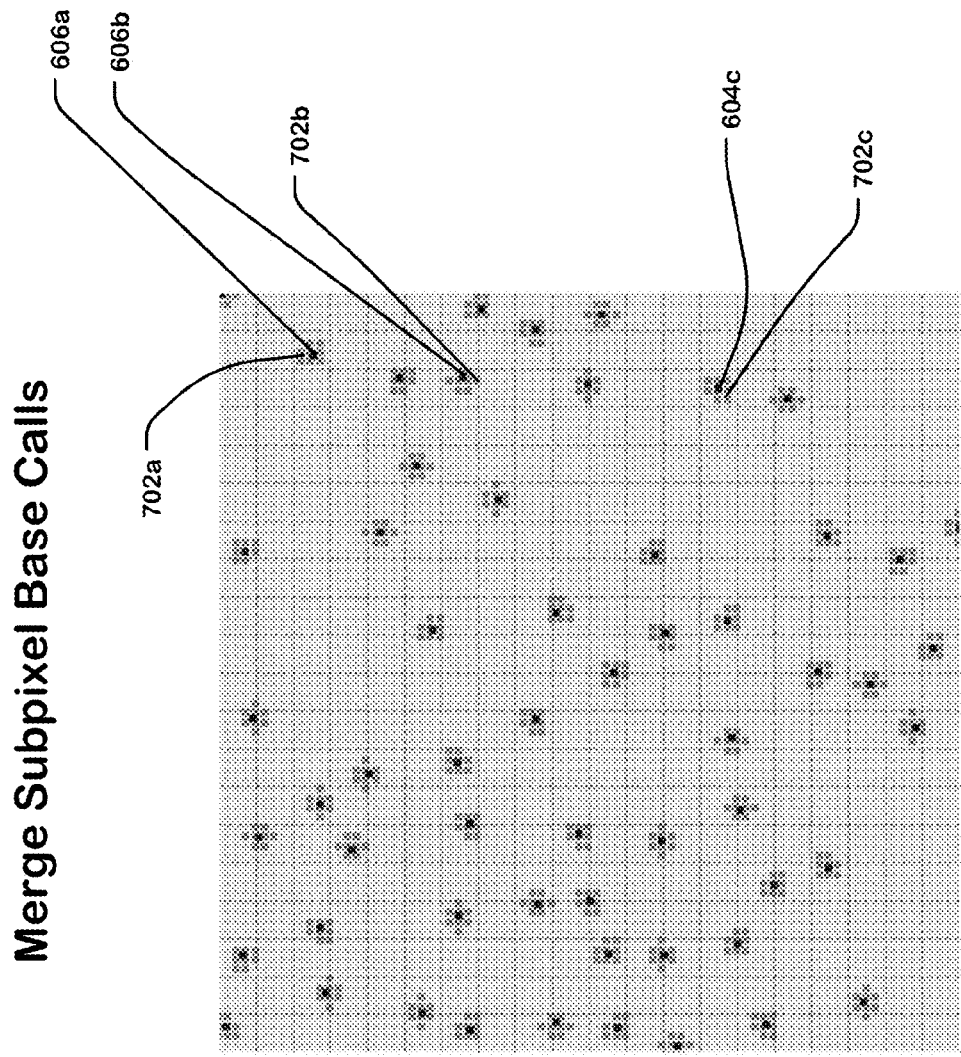
FIG. 7 depicts one implementation of merging subpixel base calls produced over the plurality of sequencing cycles to generate the so-called "cluster maps" that contain the cluster metadata.

FIG. 7 depicts one example of merging subpixel base calls produced over the plurality of sequencing cycles to generate the so-called "cluster maps" that contain the cluster metadata. In the illustrated implementation, the subpixel base calls are merged using a breadth-first search approach.

Figure 8A:
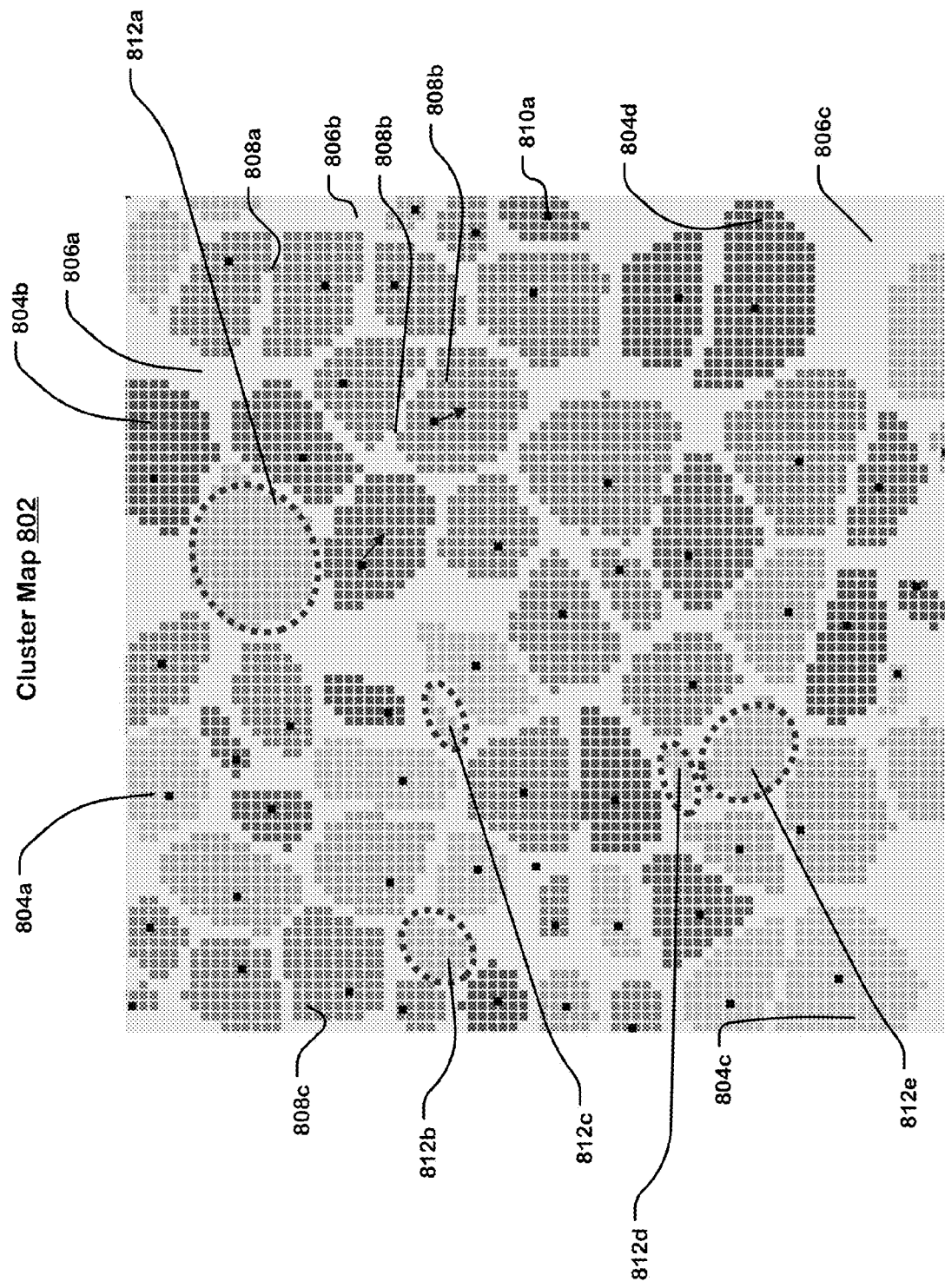
FIG. 8a illustrates one example of a cluster map generated by the merging of the subpixel base calls.
Figure 8B:
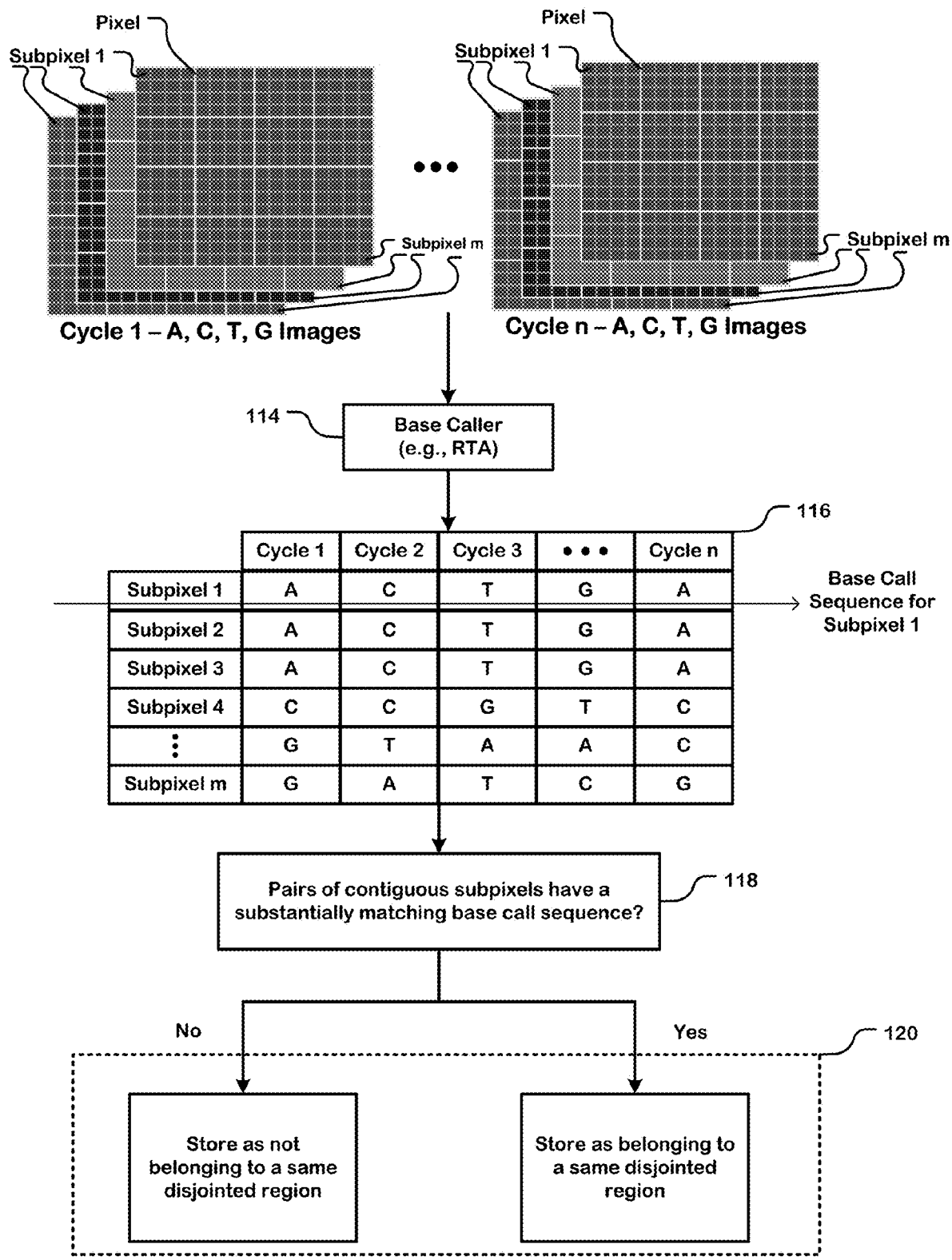
FIG. 8b depicts one implementation of subpixel base calling.

FIG. 8*a* illustrates one example of a cluster map generated by the merging of the subpixel base calls. FIG. 8*b* depicts one example of subpixel base calling. FIG. 8*b* also shows one implementation of analyzing subpixel-wise base call sequences produced from the subpixel base calling to generate a cluster map.

Sequencing Images

Cluster metadata determination involves analyzing image data produced by a sequencing instrument 102 (e.g., Illumina's iSeq, HiSeqX, HiSeq3000, HiSeq4000, HiSeq2500, NovaSeq 6000, NextSeq, NextSeqDx, MiSeq and MiSeqDx). The following discussion outlines how the image data is generated and what it depicts, in accordance with one implementation.

Base calling is the process in which the raw signal of the sequencing instrument 102, i.e., intensity data extracted from images, is decoded into DNA sequences and quality scores. In one implementation, the Illumina platforms employ cyclic reversible termination (CRT) chemistry for base calling. The process relies on growing nascent DNA strands complementary to template DNA strands with modified nucleotides, while tracking the emitted signal of each newly added nucleotide. The modified nucleotides have a 3' removable block that anchors a fluorophore signal of the nucleotide type.

Sequencing occurs in repetitive cycles, each comprising three steps: (a) extension of a nascent strand by adding a modified nucleotide; (b) excitation of the fluorophores using one or more lasers of the optical system 104 and imaging through different filters of the optical system 104, yielding sequencing images 108; and (c) cleavage of the fluorophores and removal of the 3' block in preparation for the next sequencing cycle. Incorporation and imaging cycles are repeated up to a designated number of sequencing cycles, defining the read length of all clusters. Using this approach, each cycle interrogates a new position along the template strands.

The tremendous power of the Illumina platforms stems from their ability to simultaneously execute and sense millions or even billions clusters undergoing CRT reactions. The sequencing process occurs in a flow cell 202—a small glass slide that holds the input DNA fragments during the sequencing process. The flow cell 202 is connected to the high-throughput optical system 104, which comprises microscopic imaging, excitation lasers, and fluorescence filters. The flow cell 202 comprises multiple chambers called lanes 204. The lanes 204 are physically separated from each other and may contain different tagged sequencing libraries, distinguishable without sample cross contamination. The imaging device 106 (e.g., a solid-state imager such as a charge-coupled device (CCD) or a complementary metal-oxide-semiconductor (CMOS) sensor) takes snapshots at multiple locations along the lanes 204 in a series of non-overlapping regions called tiles 206.

For example, there are a hundred tiles per lane in Illumina Genome Analyzer II and sixty-eight tiles per lane in Illumina HiSeq2000. A tile 206 holds hundreds of thousands to millions of clusters. An image generated from a tile with clusters shown as bright spots is shown at 208. A cluster 302 comprises approximately one thousand identical copies of a template molecule, though clusters vary in size and shape. The clusters are grown from the template molecule, prior to the sequencing run, by bridge amplification of the input library. The purpose of the amplification and cluster growth is to increase the intensity of the emitted signal since the imaging device 106 cannot reliably sense a single fluorophore. However, the physical distance of the DNA fragments within a cluster 302 is small, so the imaging device 106 perceives the cluster of fragments as a single spot 302.

The output of a sequencing run is the sequencing images 108, each depicting intensity emissions of clusters on the tile in the pixel domain for a specific combination of lane, tile, sequencing cycle, and fluorophore (208A, 208C, 208T, 208G).

In one implementation, a biosensor comprises an array of light sensors. A light sensor is configured to sense information from a corresponding pixel area (e.g., a reaction site/well/nanowell) on the detection surface of the biosensor. An analyte disposed in a pixel area is said to be associated with the pixel area, i.e., the associated analyte. At a sequencing cycle, the light sensor corresponding to the pixel area is configured to detect/capture/sense emissions/photons from the associated analyte and, in response, generate a pixel signal for each imaged channel. In one implementation, each imaged channel corresponds to one of a plurality of filter wavelength bands. In another implementation, each imaged channel corresponds to one of a plurality of imaging events at a sequencing cycle. In yet another implementation, each imaged channel corresponds to a combination of illumination with a specific laser and imaging through a specific optical filter.

Pixel signals from the light sensors are communicated to a signal processor coupled to the biosensor (e.g., via a communication port). For each sequencing cycle and each imaged channel, the signal processor produces an image whose pixels respectively depict/contain/denote/represent/characterize pixel signals obtained from the corresponding light sensors. This way, a pixel in the image corresponds to: (i) a light sensor of the biosensor that generated the pixel signal depicted by the pixel, (ii) an associated analyte whose emissions were detected by the corresponding light sensor and converted into the pixel signal, and (iii) a pixel area on the detection surface of the biosensor that holds the associated analyte.

Consider, for example, that a sequencing run uses two different imaged channels: a red channel and a green channel. Then, at each sequencing cycle, the signal processor produces a red image and a green image. This way, for a series of k sequencing cycles of the sequencing run, a sequence with k pairs of red and green images is produced as output.

Pixels in the red and green images (i.e., different imaged channels) have one-to-one correspondence within a sequencing cycle. This means that corresponding pixels in a pair of the red and green images depict intensity data for the same associated analyte, albeit in different imaged channels. Similarly, pixels across the pairs of red and green images have one-to-one correspondence between the sequencing cycles. This means that corresponding pixels in different pairs of the red and green images depict intensity data for the same associated analyte, albeit for different acquisition events/timesteps (sequencing cycles) of the sequencing run.

Corresponding pixels in the red and green images (i.e., different imaged channels) can be considered a pixel of a "per-cycle image" that expresses intensity data in a first red channel and a second green channel. A per-cycle image whose pixels depict pixel signals for a subset of the pixel areas, i.e., a region (tile) of the detection surface of the biosensor, is called a "per-cycle tile image." A patch extracted from a per-cycle tile image is called a "per-cycle image patch." In one implementation, the patch extraction is performed by an input preparer.

The image data comprises a sequence of per-cycle image patches generated for a series of k sequencing cycles of a sequencing run. The pixels in the per-cycle image patches contain intensity data for associated analytes and the intensity data is obtained for one or more imaged channels (e.g., a red channel and a green channel) by corresponding light sensors configured to detect emissions from the associated analytes. In one implementation, when a single target cluster is to be base called, the per-cycle image patches are centered at a center pixel that contains intensity data for a target associated analyte and non-center pixels in the per-cycle image patches contain intensity data for associated analytes adjacent to the target associated analyte. In one implementation, the image data is prepared by an input preparer.

Subpixel Base Calling

The technology disclosed accesses a series of image sets generated during a sequencing run. The image sets comprise the sequencing images 108. Each image set in the series is captured during a respective sequencing cycle of the sequencing run. Each image (or sequencing image) in the series captures clusters on a tile of a flow cell and their surrounding background.

In one implementation, the sequencing run utilizes four-channel chemistry and each image set has four images. In another implementation, the sequencing run utilizes two-channel chemistry and each image set has two images. In yet another implementation, the sequencing run utilizes one-channel chemistry and each image set has two images. In yet other implementations, each image set has only one image.

The sequencing images 108 in the pixel domain are first converted into the subpixel domain by a subpixel addresser 110 to produce sequencing images 112 in the subpixel domain. In one implementation, each pixel in the sequencing images 108 is divided into sixteen subpixels 502. Thus, in one implementation, the subpixels 502 are quarter subpixels. In another implementation, the subpixels 502 are half subpixels. As a result, each of the sequencing images 112 in the subpixel domain has a plurality of subpixels 502.

The subpixels are then separately fed as input to a base caller 114 to obtain, from the base caller 114, a base call classifying each of the subpixels as one of four bases (A, C, T, and G). This produces a base call sequence 116 for each of the subpixels across a plurality of sequencing cycles of the sequencing run. In one implementation, the subpixels 502 are identified to the base caller 114 based on their integer or non-integer coordinates. By tracking the emission signal from the subpixels 502 across image sets generated during the plurality of sequencing cycles, the base caller 114 recovers the underlying DNA sequence for each subpixel. An example of this is illustrated in FIG. 8b.

In other implementations, the technology disclosed obtains, from the base caller 114, the base call classifying each of the subpixels as one of five bases (A, C, T, G, and N). In such implementations, N base call denotes an undecided base call, usually due to low levels of extracted intensity.

Some examples of the base caller 114 include non-neural network-based Illumina offerings such as the RTA (Real Time Analysis), the Firecrest program of the Genome Analyzer Analysis Pipeline, the IPAR (Integrated Primary Analysis and Reporting) machine, and the OLB (Off-Line Basecaller). For example, the base caller 114 produces the base call sequences by interpolating intensity of the subpixels, including at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. These techniques are described in detail in Appendix entitled "Intensity Extraction Methods".

In other implementations, the base caller 114 can be a neural network-based base caller, such as the neural network-based base caller 1514 disclosed herein.

The subpixel-wise base call sequences 116 are then fed as input to a searcher 118. The searcher 118 searches for substantially matching base call sequences of contiguous subpixels. Base call sequences of contiguous subpixels are "substantially matching" when a predetermined portion of base calls match on an ordinal position-wise basis (e.g., >=41 matches in 45 cycles, <=4 mismatches in 45 cycles, <=4 mismatches in 50 cycles, or <=2 mismatches in 34 cycles).

The searcher 118 then generates a cluster map 802 that identifies clusters as disjointed regions, e.g., 804a-d, of contiguous subpixels that share a substantially matching base call sequence. This application uses "disjointed", "disjoint", and "non-overlapping" interchangeably. The search involves base calling the subpixels that contain parts of clusters to allow linking the called subpixels to contiguous subpixels with which they share a substantially matching base call sequence. In some implementations, the searcher 118 requires that at least some of the disjointed regions have a predetermined minimum number of subpixels (e.g., more than 4, 6, or 10 subpixels) to be processed as a cluster.

In some implementations, the base caller 114 also identifies preliminary center coordinates of the clusters. Subpixels that contain the preliminary center coordinates are referred to as origin subpixels. Some example preliminary center coordinates (604a-c) identified by the base caller 114 and corresponding origin subpixels (606a-c) are shown in FIG. 6. However, identification of the origin subpixels (preliminary center coordinates of the clusters) is not needed, as explained below. In some implementations, the searcher 118 uses breadth-first search for identifying substantially matching base call sequences of the subpixels by beginning with the origin subpixels 606a-c and continuing with successively contiguous non-origin subpixels 702a-c. This again is optional, as explained below.

Cluster Man

FIG. 8a illustrates one example of a cluster map 802 generated by the merging of the subpixel base calls. The cluster map identifies a plurality of disjointed regions (depicted in various colors in FIG. 8a). Each disjointed region comprises a non-overlapping group of contiguous subpixels that represents a respective cluster on a tile (from whose sequencing images and for which the cluster map is generated via the subpixel base calling). The region between the disjointed regions represents the background on the tile. The subpixels in the background region are called "background subpixels". The subpixels in the disjointed regions are called "cluster subpixels" or "cluster interior subpixels". In this discussion, origin subpixels are those subpixels in which preliminary center cluster coordinates determined by the RTA or another base caller, are located.

The origin subpixels contain the preliminary center cluster coordinates. This means that the area covered by an origin subpixel includes a coordinate location that coincides with a preliminary center cluster coordinate location. Since the cluster map 802 is an image of logical subpixels, the origin subpixels are some of the subpixels in the cluster map.

The search to identify clusters with substantially matching base call sequences of the subpixels does not need to begin with identification of the origin subpixels (preliminary center coordinates of the clusters) because the search can be done for all the subpixels and can start from any subpixel (e.g., 0,0 subpixel or any random subpixel). Thus, since each subpixel is evaluated to determine whether it shares a substantially matching base call sequence with another contiguous subpixel, the search does not depend on origin subpixels; the search can start with any subpixel.

Irrespective of whether origin subpixels are used or not, certain clusters are identified that do not contain the origin subpixels (preliminary center coordinates of the clusters) predicted by the base caller 114. Some examples of clusters identified by the merging of the subpixel base calls and not containing an origin subpixel are clusters 812a, 812b, 812c, 812d, and 812e in FIG. 8a. Thus, the technology disclosed identifies additional or extra clusters for which the centers may not have been identified by the base caller 114. Therefore, use of the base caller 114 for identification of origin subpixels (preliminary center coordinates of the clusters) is optional and not essential for the search of substantially matching base call sequences of contiguous subpixels.

In one implementation, first, the origin subpixels (preliminary center coordinates of the clusters) identified by the base caller 114 are used to identify a first set of clusters (by identification of substantially matching base call sequences of contiguous subpixels). Then, subpixels that are not part of the first set of clusters are used to identify a second set of clusters (by identification of substantially matching base call sequences of contiguous subpixels). This allows the technology disclosed to identify additional or extra clusters for which the centers are not identified by the base caller 114. Finally, subpixels that are not part of the first and second sets of clusters are identified as background subpixels.

FIG. 8b depicts one example of subpixel base calling. In FIG. 8b, each sequencing cycle has an image set with four distinct images (i.e., A, C, T, G images) captured using four different wavelength bands (image/imaging channel) and four different fluorescent dyes (one for each base).

In this example, pixels in images are divided into sixteen subpixels. Subpixels are then separately base called at each sequencing cycle by the base caller 114. To base call a given subpixel at a particular sequencing cycle, the base caller 114 uses intensities of the given subpixel in each of the four A, C, T, G images. For example, intensities in image regions covered by subpixel 1 in each of the each of the four A, C, T, G images of cycle 1 are used to base call subpixel 1 at cycle 1. For subpixel 1, these image regions include top-left one-sixteenth area of the respective top-left pixels in each of the four A, C, T, G images of cycle 1. Similarly, intensities in image regions covered by subpixel m in each of the each of the four A, C, T, G images of cycle n are used to base call subpixel m at cycle n. For subpixel m, these image regions include bottom-right one-sixteenth area of the respective bottom-right pixels in each of the four A, C, T, G images of cycle 1.

This process produces subpixel-wise base call sequences 116 across the plurality of sequencing cycles. Then, the searcher 118 evaluates pairs of contiguous subpixels to determine whether they have a substantially matching base call sequence. If yes, then the pair of subpixels is stored in the cluster map 802 as belonging to a same cluster in a disjointed region. If no, then the pair of subpixels is stored in the cluster map 802 as not belonging to a same disjointed region. The cluster map 802 therefore identifies contiguous sets of sub-pixels for which the base calls for the sub-pixels substantially match across a plurality of cycles. Cluster map 802 therefore uses information from multiple cycles to provide a plurality of clusters with a high confidence that each cluster of the plurality of clusters provides sequence data for a single DNA strand.

Figure 9:
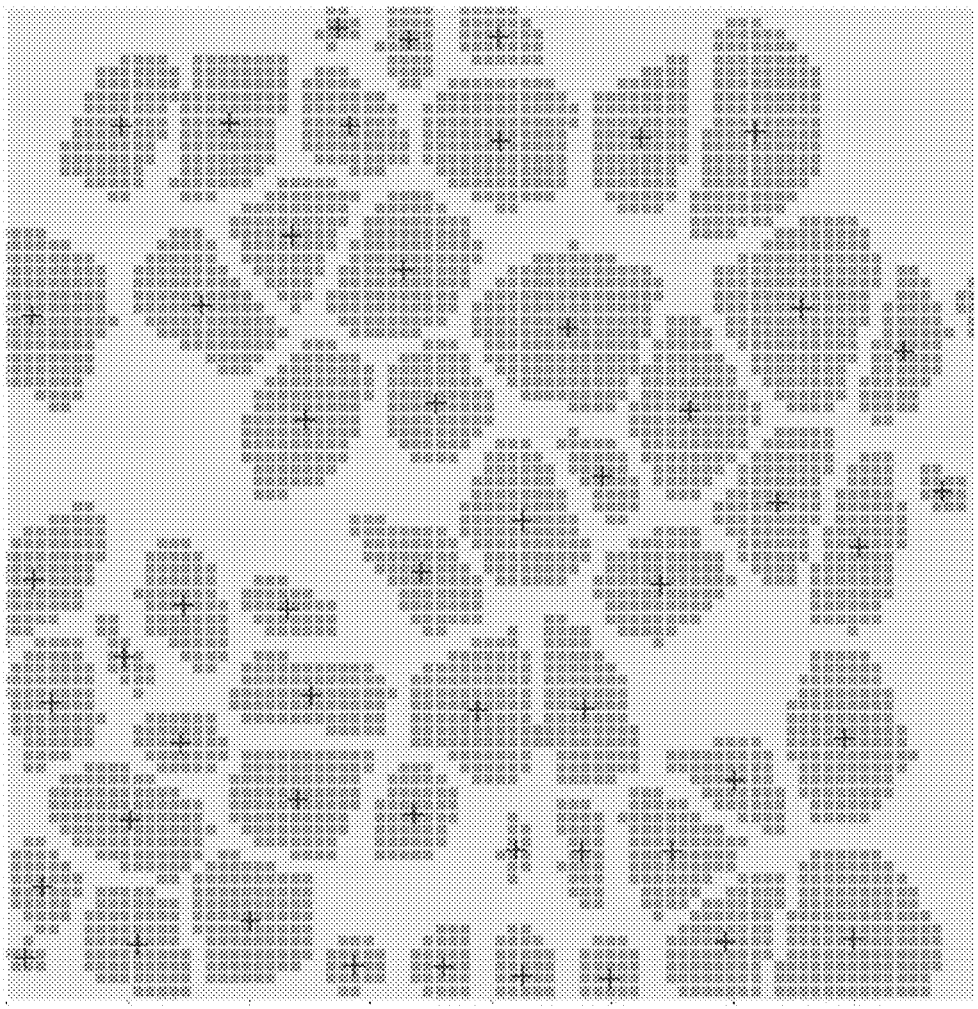
FIG. 9 shows another example of a cluster map that identifies cluster metadata.

A cluster metadata generator 122 then processes the cluster map 802 to determine cluster metadata, including determining spatial distribution of clusters, including their centers (810*a*), shapes, sizes, background, and/or boundaries based on the disjointed regions (FIG. 9).

In some implementations, the cluster metadata generator 122 identifies as background those subpixels in the cluster map 802 that do not belong to any of the disjointed regions and therefore do not contribute to any clusters. Such subpixels are referred to as background subpixels 806*a-c*.

In some implementations, the cluster map 802 identifies cluster boundary portions 808*a-c* between two contiguous subpixels whose base call sequences do not substantially match.

The cluster map is stored in memory (e.g., cluster maps data store 120) for use as ground truth for training a classifier such as the neural network-based template generator 1512 and the neural network-based base caller 1514. The cluster metadata can also be stored in memory (e.g., cluster metadata data store 124).

FIG. 9 shows another example of a cluster map that identifies cluster metadata, including spatial distribution of the clusters, along with cluster centers, cluster shapes, cluster sizes, cluster background, and/or cluster boundaries.

Center of Mass (COM)

Figure 10:
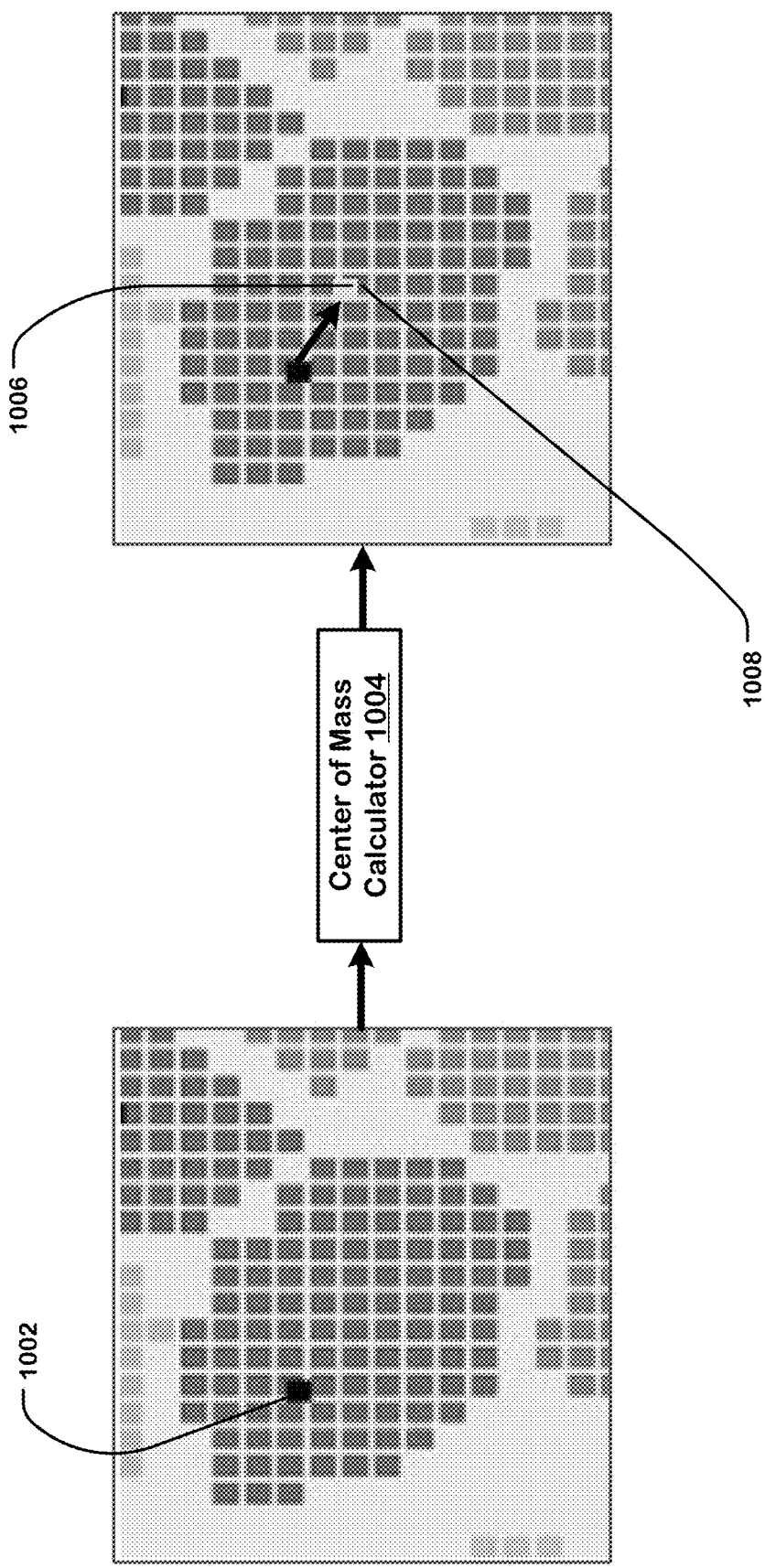
FIG. 10 shows how a center of mass (COM) of a disjointed region in a cluster map is calculated.

FIG. 10 shows how a center of mass (COM) of a disjointed region in a cluster map is calculated. The COM can be used as the "revised" or "improved" center of the corresponding cluster in downstream processing.

In some implementations, a center of mass generator 1004, on a cluster-by-cluster basis, determines hyperlocated center coordinates 1006 of the clusters by calculating centers of mass of the disjointed regions of the cluster map as an average of coordinates of respective contiguous subpixels forming the disjointed regions. It then stores the hyperlocated center coordinates of the clusters in the memory on the cluster-by-cluster basis for use as ground truth for training the classifier.

In some implementations, a subpixel categorizer, on the cluster-by-cluster basis, identifies centers of mass subpixels 1008 in the disjointed regions 804*a-d* of the cluster map 802 at the hyperlocated center coordinates 1006 of the clusters.

In other implementations, the cluster map is upsampled using interpolation. The upsampled cluster map is stored in the memory for use as ground truth for training the classifier.

Decay Factor & Decay Man

Figure 11:
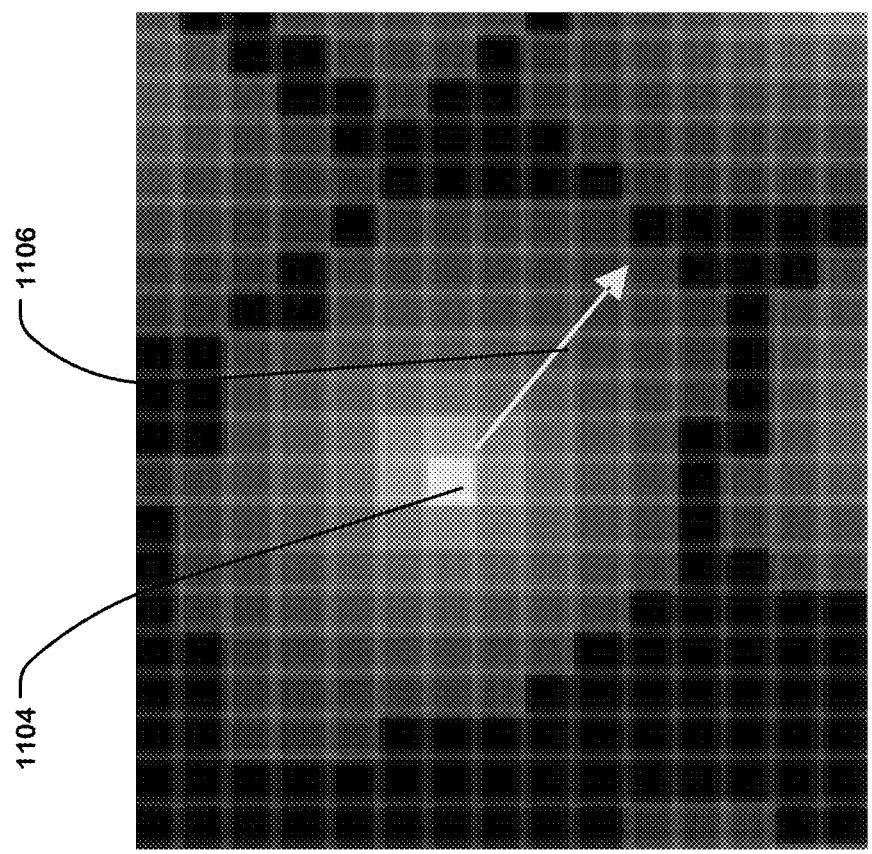
FIG. 11 depicts one implementation of calculation of a weighted decay factor based on the Euclidean distance from a subpixel in a disjointed region to the COM of the disjointed region.

FIG. 11 depicts one implementation of calculation of a weighted decay factor for a subpixel based on the Euclidean distance from the subpixel to the center of mass (COM) of the disjointed region to which the subpixel belongs. In the illustrated implementation, the weighted decay factor gives the highest value to the subpixel containing the COM and decreases for subpixels further away from the COM. The weighted decay factor is used to derive a ground truth decay map 1204 from a cluster map generated from the subpixel base calling discussed above. The ground truth decay map 1204 contains an array of units and assigns at least one output value to each unit in the array. In some implementations, the units are subpixels and each subpixel is assigned an output value based on the weighted decay factor. The ground truth decay map 1204 is then used as ground truth for training the disclosed neural network-based template generator 1512. In some implementations, information from the ground truth decay map 1204 is also used to prepare input for the disclosed neural network-based base caller 1514.

Figure 12:
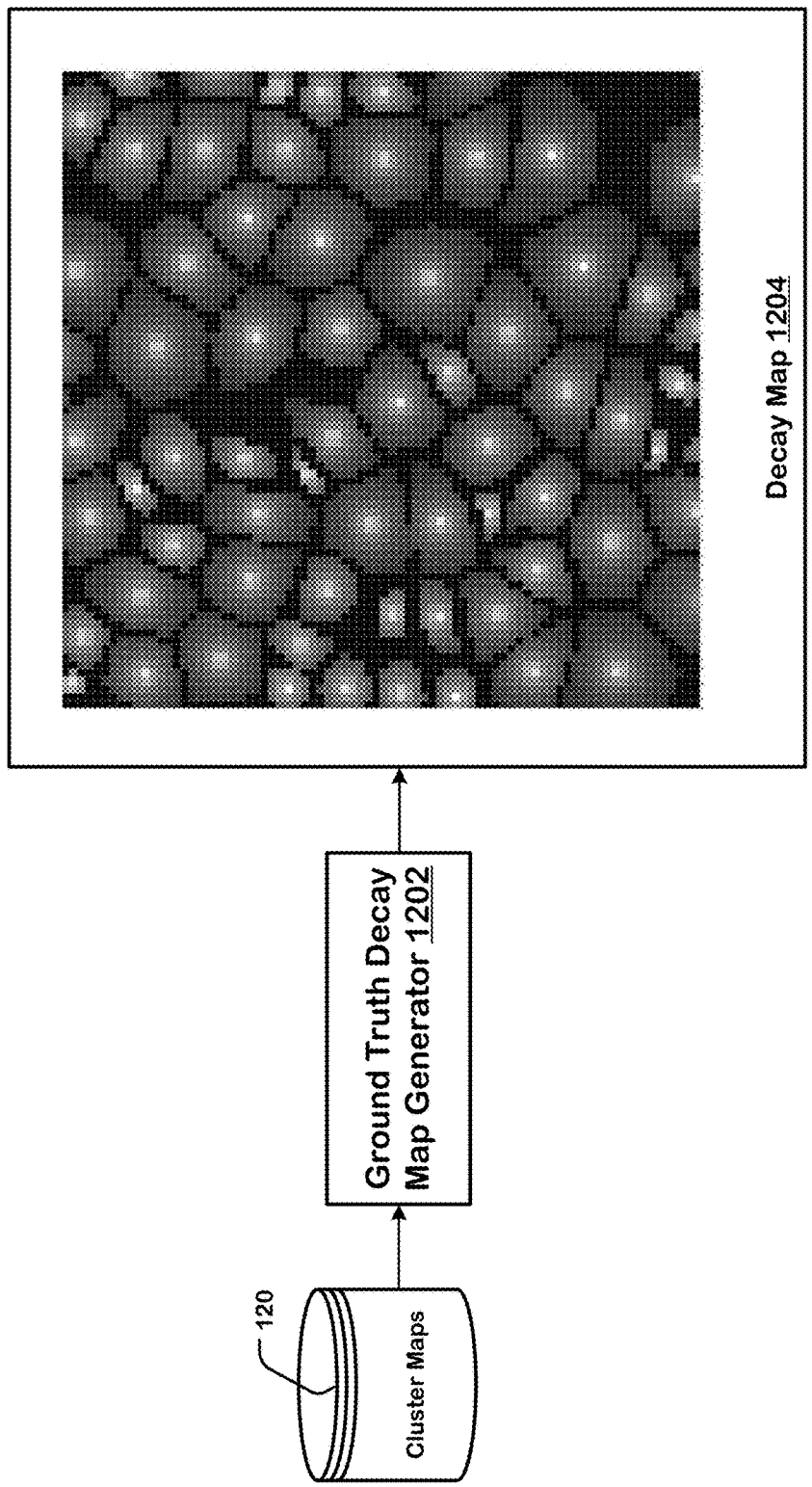
FIG. 12 illustrates one implementation of an example ground truth decay map derived from an example cluster map produced by the subpixel base calling.

FIG. 12 illustrates one implementation of an example ground truth decay map 1204 derived from an example cluster map produced by the subpixel base calling as discussed above. In some implementations, in the upsampled cluster map, on the cluster-by-cluster basis, a value is assigned to each contiguous subpixel in the disjointed regions based on a decay factor 1102 that is proportional to distance 1106 of an contiguous subpixel from a center of mass subpixel 1104 in a disjointed region to which the contiguous subpixel belongs.

FIG. 12 depicts a ground truth decay map 1204. In one implementation, the subpixel value is an intensity value normalized between zero and one. In another implementation, in the upsampled cluster map, a same predetermined value is assigned to all the subpixels identified as the background. In some implementations, the predetermined value is a zero intensity value.

In some implementations, the ground truth decay map 1204 is generated by a ground truth decay map generator 1202 from the upsampled cluster map that expresses the contiguous subpixels in the disjointed regions and the subpixels identified as the background based on their assigned values. The ground truth decay map 1204 is stored in the memory for use as ground truth for training the classifier. In one implementation, each subpixel in the ground truth decay map 1204 has a value normalized between zero and one.

Ternary (Three Class) Man

Figure 13:
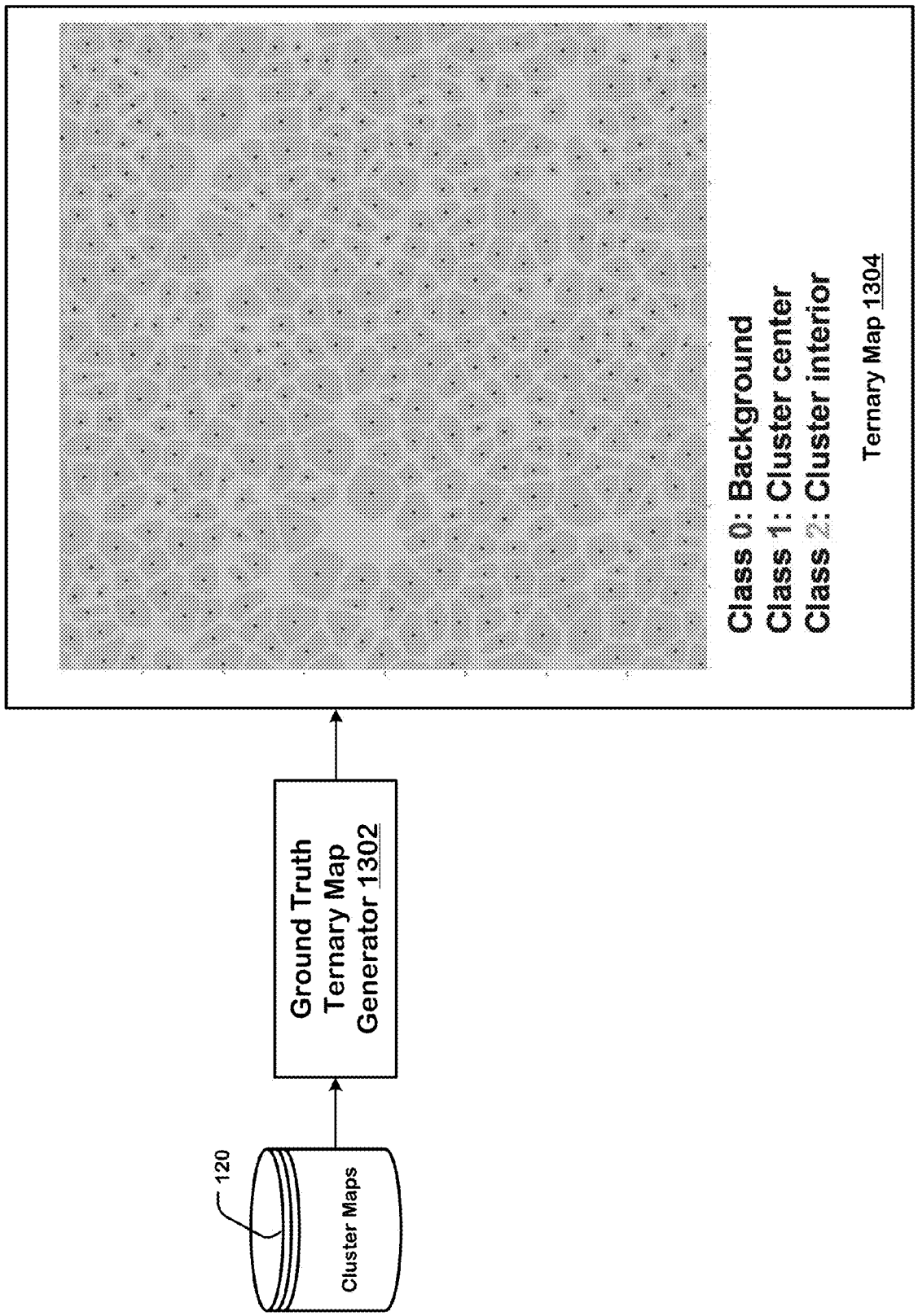
FIG. 13 illustrates one implementation of deriving a ternary map from a cluster map.

FIG. 13 illustrates one implementation of deriving a ground truth ternary map 1304 from a cluster map. The ground truth ternary map 1304 contains an array of units and assigns at least one output value to each unit in the array. By name, ternary map implementations of the ground truth ternary map 1304 assign three output values to each unit in the array, such that, for each unit, a first output value corresponds to a classification label or score for a background class, a second output value corresponds to a classification label or score for a cluster center class, and a third output value corresponds to a classification label or score for a cluster/cluster interior class. The ground truth ternary map 1304 is used as ground truth data for training the neural network-based template generator 1512. In some implementations, information from the ground truth ternary map 1304 is also used to prepare input for the neural network-based base caller 1514.

FIG. 13 depicts an example ground truth ternary map 1304. In another implementation, in the upsampled cluster map, the contiguous subpixels in the disjointed regions are categorized on the cluster-by-cluster basis by a ground truth ternary map generator 1302, as cluster interior subpixels belonging to a same cluster, the centers of mass subpixels as cluster center subpixels, and as background subpixels the subpixels not belonging to any cluster. In some implementations, the categorizations are stored in the ground truth ternary map 1304. These categorizations and the ground truth ternary map 1304 are stored in the memory for use as ground truth for training the classifier.

In other implementations, on the cluster-by-cluster basis, coordinates of the cluster interior subpixels, the cluster center subpixels, and the background subpixels are stored in the memory for use as ground truth for training the classifier. Then, the coordinates are downscaled by a factor used to upsample the cluster map. Then, on the cluster-by-cluster basis, the downscaled coordinates are stored in the memory for use as ground truth for training the classifier.

In yet other implementations, the ground truth ternary map generator 1302 uses the cluster maps to generate the ternary ground truth data 1304 from the upsampled cluster map. The ternary ground truth data 1304 labels the background subpixels as belonging to a background class, the cluster center subpixels as belonging to a cluster center class, and the cluster interior subpixels as belonging to a cluster interior class. In some visualization implementations, color coding can be used to depict and distinguish the different class labels. The ternary ground truth data 1304 is stored in the memory for use as ground truth for training the classifier.

Binary (Two Class) Man

Figure 14:
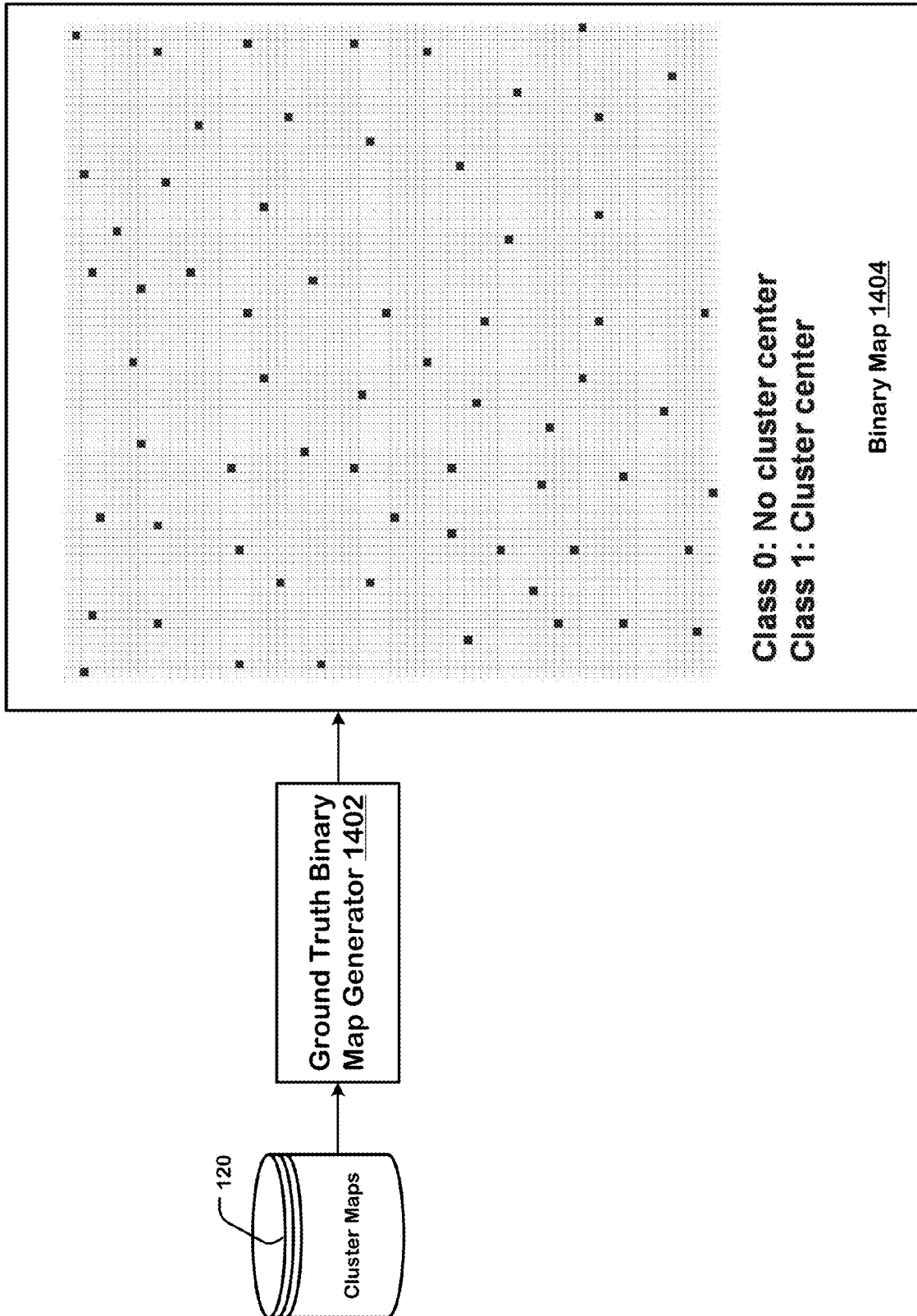
FIG. 14 illustrates one implementation of deriving a binary map from a cluster map.

FIG. 14 illustrates one implementation of deriving a ground truth binary map 1404 from a cluster map. The binary map 1404 contains an array of units and assigns at least one output value to each unit in the array. By name, the binary map assigns two output values to each unit in the array, such that, for each unit, a first output value corresponds to a classification label or score for a cluster center class and a second output value corresponds to a classification label or score for a non-center class. The binary map is used as ground truth data for training the neural network-based template generator 1512. In some implementations, information from the binary map is also used to prepare input for the neural network-based base caller 1514.

FIG. 14 depicts a ground truth binary map 1404. The ground truth binary map generator 1402 uses the cluster maps 120 to generate the binary ground truth data 1404 from the upsampled cluster maps. The binary ground truth data 1404 labels the cluster center subpixels as belonging to a cluster center class and labels all other subpixels as belonging to a non-center class. The binary ground truth data 1404 is stored in the memory for use as ground truth for training the classifier.

In some implementations, the technology disclosed generates cluster maps 120 for a plurality of tiles of the flow cell, stores the cluster maps in memory, and determines spatial distribution of clusters in the tiles based on the cluster maps 120, including their shapes and sizes. Then, the technology disclosed, in the upsampled cluster maps 120 of the clusters in the tiles, categorizes, on a cluster-by-cluster basis, subpixels as cluster interior subpixels belonging to a same cluster, cluster center subpixels, and background subpixels. The technology disclosed then stores the categorizations in the memory for use as ground truth for training the classifier, and stores, on the cluster-by-cluster basis across the tiles, coordinates of the cluster interior subpixels, the cluster center subpixels, and the background subpixels in the memory for use as ground truth for training the classifier. The technology disclosed then downscales the coordinates by the factor used to upsample the cluster map and stores, on the cluster-by-cluster basis across the tiles, the downscaled coordinates in the memory for use as ground truth for training the classifier.

In some implementations, the flow cell has at least one patterned surface with an array of wells that occupy the clusters. In such implementations, based on the determined shapes and sizes of the clusters, the technology disclosed determines: (1) which ones of the wells are substantially occupied by at least one cluster, (2) which ones of the wells are minimally occupied, and (3) which ones of the wells are co-occupied by multiple clusters. This allows for determining respective metadata of multiple clusters that co-occupy a same well, i.e., centers, shapes, and sizes of two or more clusters that share a same well.

In some implementations, the solid support on which samples are amplified into clusters comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some implementations, the pattern can be an x-y format of features that are in rows and columns. In some implementations, the pattern can be a repeating arrangement of features and/or interstitial regions. In some implementations, the pattern can be a random arrangement of features and/or interstitial regions. Exemplary patterned surfaces that can be used in the methods and compositions set forth herein are described in U.S. Pat. Nos. 8,778,849, 9,079,148, 8,778,848, and US Pub. No. 2014/0243224, each of which is incorporated herein by reference.

In some implementations, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015-002813, each of which is incorporated herein by reference in its entirety). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many implementations, the gel need not be covalently linked to the wells. For example, in some conditions silane free acrylamide (SFA, see, for example, U.S. Pat. No. 8,563,477, which is incorporated herein by reference in its entirety) which is not covalently attached to any part of the structured substrate, can be used as the gel material.

In particular implementations, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing micro- or nano-fabrication methods.

The term "flow cell" as used herein refers to a chamber comprising a solid surface across which one or more fluid reagents can be flowed. Examples of flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Throughout this disclosure, the terms "P5" and "P7" are used when referring to amplification primers. It will be understood that any suitable amplification primers can be used in the methods presented herein, and that the use of P5 and P7 are exemplary implementations only. Uses of amplification primers such as P5 and P7 on flow cells is known in the art, as exemplified by the disclosures of WO 2007/010251, WO 2006/064199, WO 2005/065814, WO 2015/106941, WO 1998/044151, and WO 2000/018957, each of which is incorporated by reference in its entirety. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture, and amplification of nucleic acids as presented herein.

In some implementations, the flow cell has at least one nonpatterned surface and the clusters are unevenly scattered over the nonpatterned surface.

In some implementations, density of the clusters ranges from about 100,000 clusters/mm$^2$ to about 1,000,000 clusters/mm$^2$. In other implementations, density of the clusters ranges from about 1,000,000 clusters/mm$^2$ to about 10,000,000 clusters/mm$^2$.

In one implementation, the preliminary center coordinates of the clusters determined by the base caller are defined in a template image of the tile. In some implementations, a pixel resolution, an image coordinate system, and measurement scales of the image coordinate system are same for the template image and the images.

In another implementation, the technology disclosed relates to determining metadata about clusters on a tile of a flow cell. First, the technology disclosed accesses (1) a set of images of the tile captured during a sequencing run and (2) preliminary center coordinates of the clusters determined by a base caller.

Then, for each image set, the technology disclosed obtains a base call classifying, as one of four bases, (1) origin subpixels that contain the preliminary center coordinates and (2) a predetermined neighborhood of contiguous subpixels that are successively contiguous to respective ones of the origin subpixels. This produces a base call sequence for each of the origin subpixels and for each of the predetermined neighborhood of contiguous subpixels. The predetermined neighborhood of contiguous subpixels can be a m×n subpixel patch centered at subpixels containing the origin subpixels. In one implementation, the subpixel patch is 3×3 subpixels. In other implementations, it the image patch can be of any size, such as 5×5, 15×15, 20×20, and so on. In other implementations, the predetermined neighborhood of contiguous subpixels can be a re-connected subpixel neighborhood centered at subpixels containing the origin subpixels.

In one implementation, the technology disclosed identifies as background those subpixels in the cluster map that do not belong to any of the disjointed regions.

Then, the technology disclosed generates a cluster map that identifies the clusters as disjointed regions of contiguous subpixels that: (a) are successively contiguous to at least some of the respective ones of the origin subpixels and (b) share a substantially matching base call sequence of the one of four bases with the at least some of the respective ones of the origin subpixels.

The technology disclosed then stores the cluster map in memory and determines the shapes and the sizes of the clusters based on the disjointed regions in the cluster map. In other implementations, centers of the clusters are also determined.

Generating Training Data for Template Generator

Figure 15:
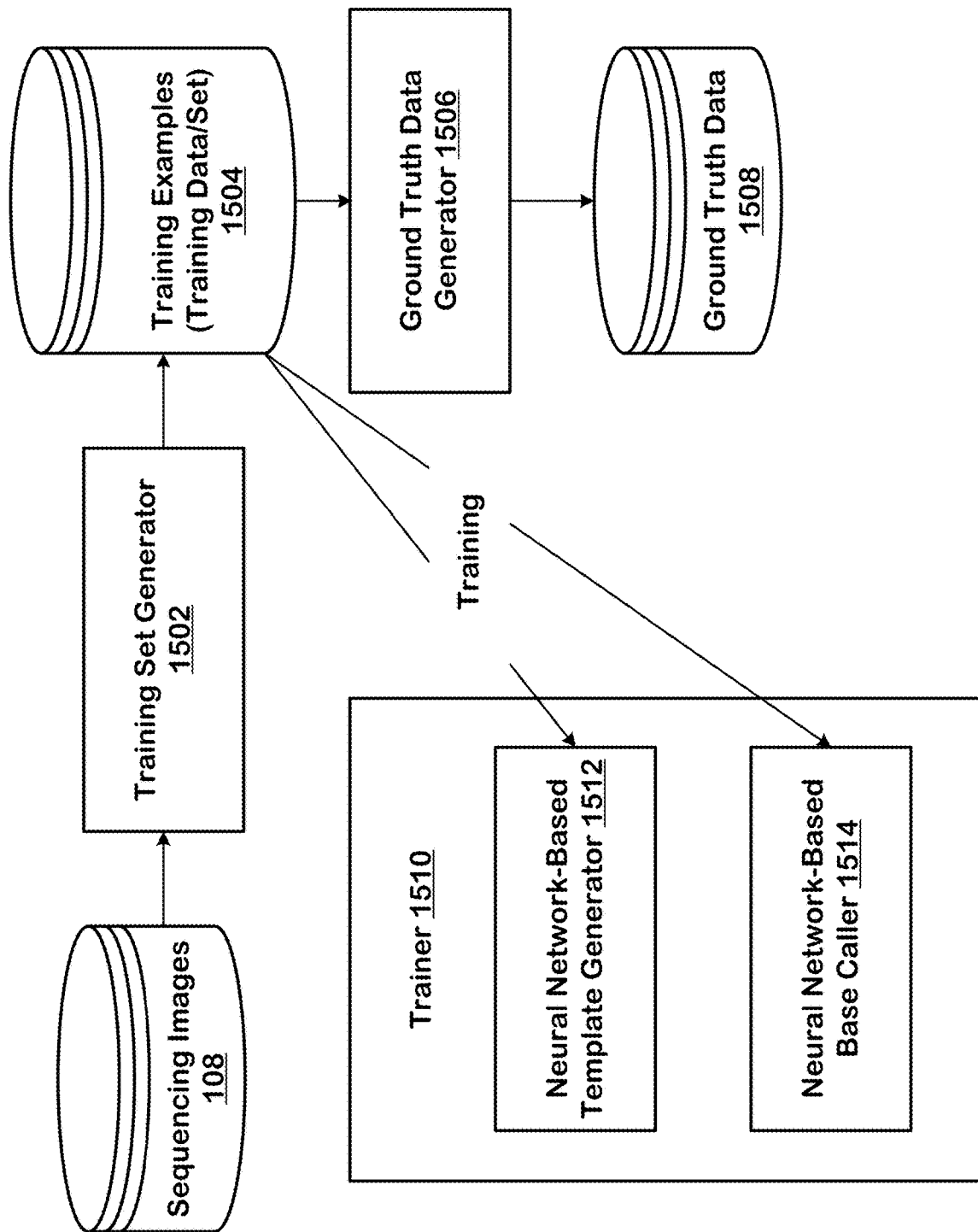
FIG. 15 is a block diagram that shows one implementation of generating training data that is used to train the neural network-based template generator and the neural network-based base caller.

FIG. 15 is a block diagram that shows one implementation of generating training data that is used to train the neural network-based template generator 1512 and the neural network-based base caller 1514.

Figure 16:
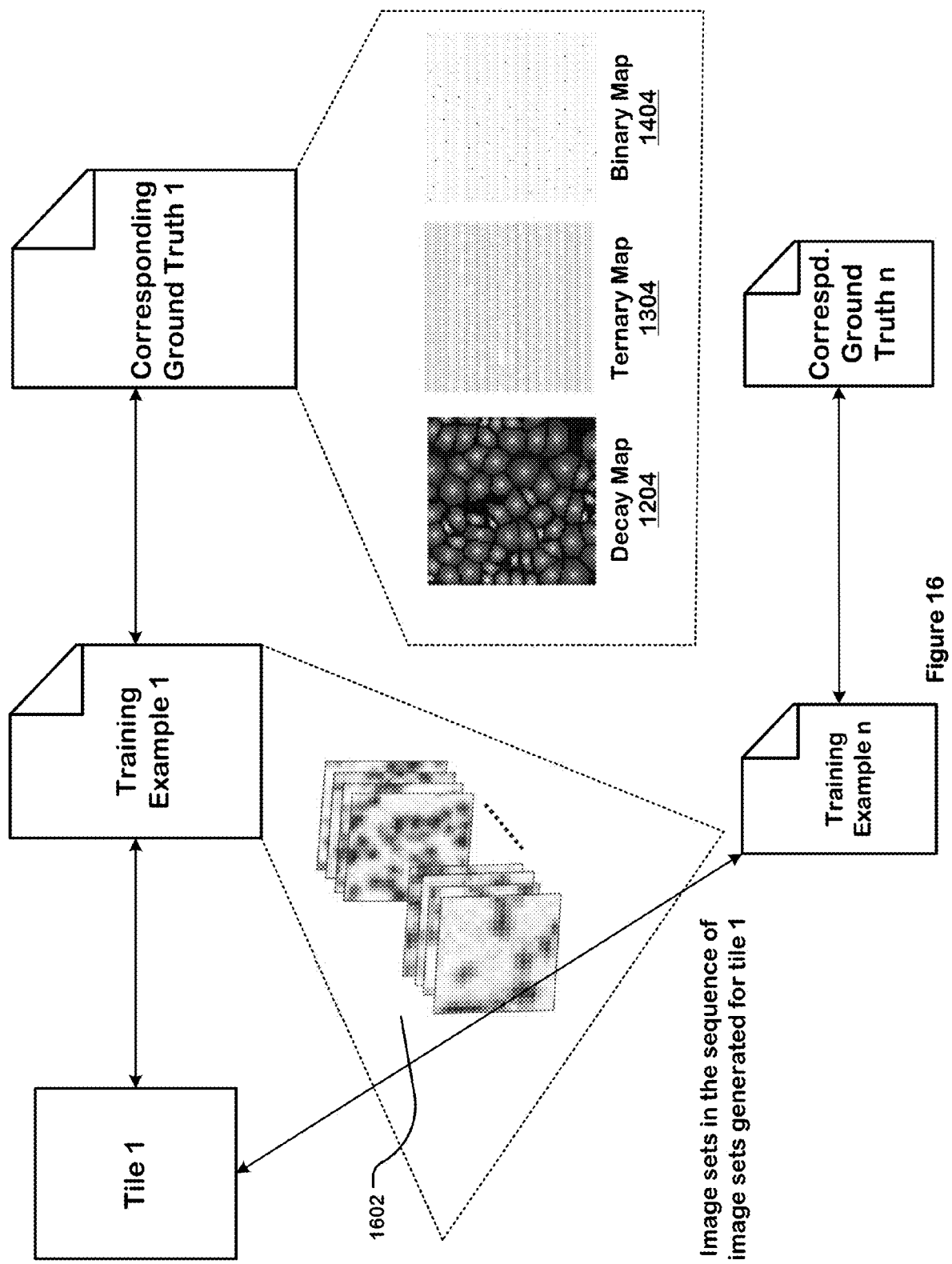
FIG. 16 shows characteristics of the disclosed training examples used to train the neural network-based template generator and the neural network-based base caller.

FIG. 16 shows characteristics of the disclosed training examples used to train the neural network-based template generator 1512 and the neural network-based base caller 1514. Each training example corresponds to a tile and is labelled with a corresponding ground truth data representation. In some implementations, the ground truth data representation is a ground truth mask or a ground truth map that identifies the ground truth cluster metadata in the form of the ground truth decay map 1204, the ground truth ternary map 1304, or the ground truth binary map 1404. In some implementation, multiple training examples correspond to a same tile.

In one implementation, the technology disclosed relates to generating training data 1504 for neural network-based template generation and base calling. First, the technology disclosed accesses a multitude of images 108 of a flow cell 202 captured over a plurality of cycles of a sequencing run. The flow cell 202 has a plurality of tiles. In the multitude of images 108, each of the tiles has a sequence of image sets generated over the plurality of cycles. Each image in the sequence of image sets 108 depicts intensity emissions of clusters 302 and their surrounding background 304 on a particular one of the tiles at a particular one the cycles.

Then, a training set constructor 1502 constructs a training set 1504 that has a plurality of training examples. As shown in FIG. 16, each training example corresponds to a particular one of the tiles and includes image data from at least some image sets in the sequence of image sets 1602 of the particular one of the tiles. In one implementation, the image data includes images in at least some image sets in the sequence of image sets 1602 of the particular one of the tiles. For example, the images can have a resolution of 1800× 1800. In other implementations, it can be any resolution such as 100×100, 3000×3000, 10000×10000, and so on. In yet other implementations, the image data includes at least one image patch from each of the images. In one implementation, the image patch covers a portion of the particular one of the tiles. In one example, the image patch can have a resolution of 20×20. In other implementations, the image patch can have any resolution, such as 50×50, 70×70, 90×90, 100×100, 3000×3000, 10000×10000, and so on.

In some implementations, the image data includes an upsampled representation of the image patch. The upsampled representation can have a resolution of 80×80, for example. In other implementations, the upsampled representation can have any resolution, such as 50×50, 70×70, 90×90, 100×100, 3000×3000, 10000×10000, and so on.

In some implementations, multiple training examples correspond to a same particular one of the tiles and respectively include as image data different image patches from each image in each of at least some image sets in a sequence of image sets 1602 of the same particular one of the tiles. In such implementations, at least some of the different image patches overlap with each other.

Then, a ground truth generator 1506 generates at least one ground truth data representation for each of the training examples. The ground truth data representation identifies at least one of spatial distribution of clusters and their surrounding background on the particular one of the tiles whose intensity emissions are depicted by the image data, including at least one of cluster shapes, cluster sizes, and/or cluster boundaries, and/or centers of the clusters.

In one implementation, the ground truth data representation identifies the clusters as disjointed regions of contiguous subpixels, the centers of the clusters as centers of mass subpixels within respective ones of the disjointed regions, and their surrounding background as subpixels that do not belong to any of the disjointed regions.

In one implementation, the ground truth data representation has an upsampled resolution of 80×80. In other implementations, the ground truth data representation can have any resolution, such as 50×50, 70×70, 90×90, 100×100, 3000×3000, 10000×10000, and so on.

In one implementation, the ground truth data representation identifies each subpixel as either being a cluster center or a non-center. In another implementation, the ground truth data representation identifies each subpixel as either being cluster interior, cluster center, or surrounding background.

In some implementations, the technology disclosed stores, in memory, the training examples in the training set 1504 and associated ground truth data 1508 as the training data 1504 for training the neural network-based template generator 1512 and the neural network-based base caller 1514. The training is operationalized by trainer 1510.

In some implementations, the technology disclosed generates the training data for a variety of flow cells, sequencing instruments, sequencing protocols, sequencing chemistries, sequencing reagents, and cluster densities.

Neural Network-Based Template Generator

In an inference or production implementation, the technology disclosed uses peak detection and segmentation to determine cluster metadata. The technology disclosed processes input image data 1702 derived from a series of image sets 1602 through a neural network 1706 to generate an alternative representation 1708 of the input image data 1702. For example, an image set can be for a particular sequencing cycle and include four images, one for each image channel A, C, T, and G. Then, for a sequencing run with fifty sequencing cycles, there will be fifty such image sets, i.e., a total of 200 images. When arranged temporally, fifty image sets with four images-per image set would form the series of image sets 1602. In some implementations, image patches of a certain size are extracted from each image in the fifty image sets, forming fifty image patch sets with four image patches-per image patch set and, in one implementation, this is the input image data 1702. In other implementations, the input image data 1702 comprises image patch sets with four image patches-per image patch set for fewer than the fifty sequencing cycles, i.e., just one, two, three, fifteen, twenty sequencing cycles.

Figure 17:
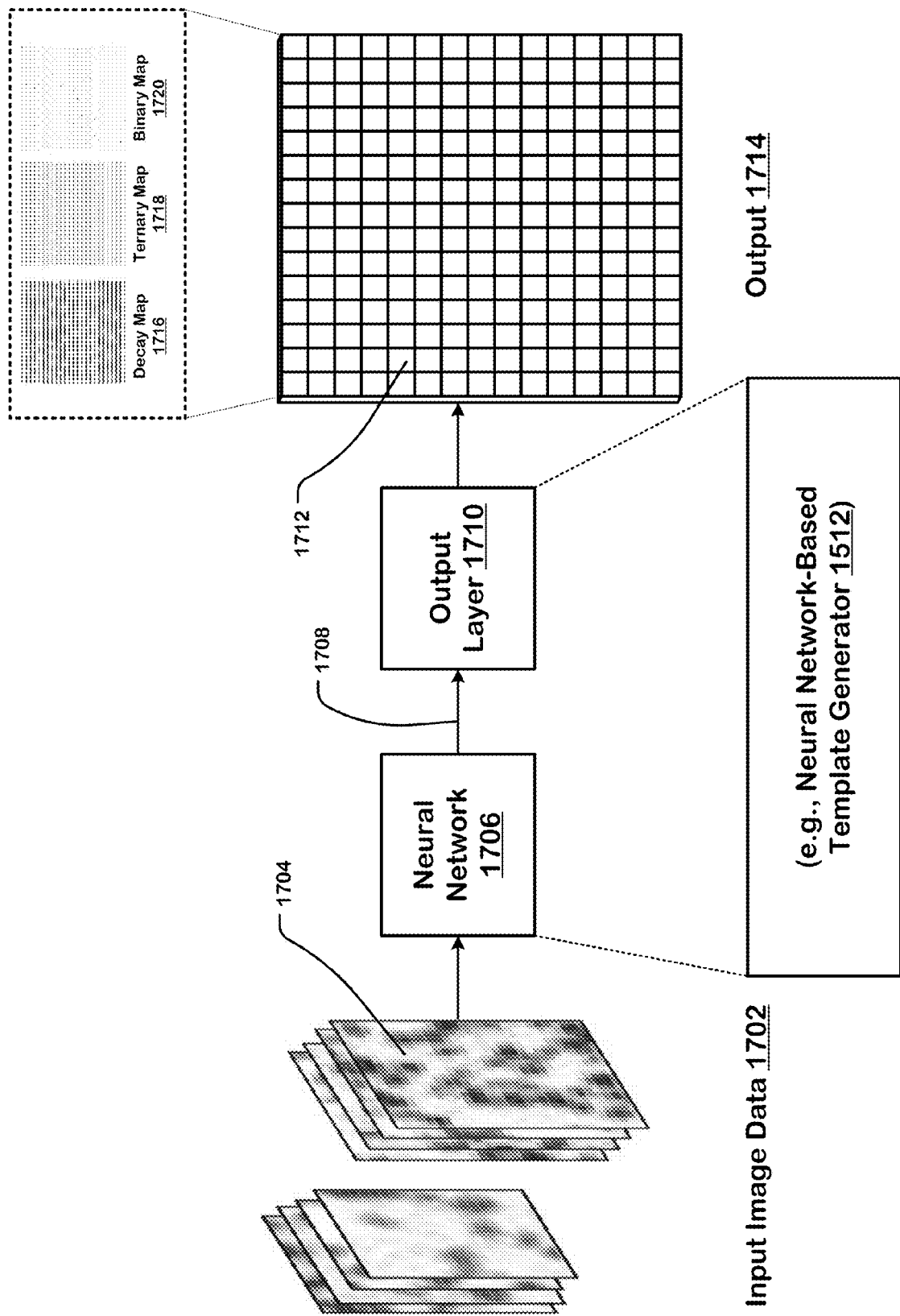
FIG. 17 illustrates one implementation of processing input image data through the disclosed neural network-based template generator and generating an output value for each unit in an array. In one implementation, the array is a decay map. In another implementation, the array is a ternary map. In yet another implementation, the array is a binary map.

FIG. 17 illustrates one implementation of processing input image data 1702 through the neural network-based template generator 1512 and generating an output value for each unit in an array. In one implementation, the array is a decay map 1716. In another implementation, the array is a ternary map 1718. In yet another implementation, the array is a binary map 1720. The array may therefore represent one or more properties of each of a plurality of locations represented in the input image data 1702.

Different than training the template generator using structures in earlier figures, including the ground truth decay map 1204, the ground truth ternary map 1304, and the ground truth binary 1404, the decay map 1716, the ternary map 1718, and/or the binary map 1720 are generated by forward propagation of the trained neural network-based template generator 1512. The forward propagation can be during training or during inference. During the training, due to the backward propagation-based gradient update, the decay map 1716, the ternary map 1718, and the binary map 1720 (i.e., cumulatively the output 1714) progressively match or approach the ground truth decay map 1204, the ground truth ternary map 1304, and the ground truth binary map 1404, respectively.

The size of the image array analyzed during inference depends on the size of the input image data 1702 (e.g., be the same or an upscaled or downscaled version), according to one implementation. Each unit can represent a pixel, a subpixel, or a superpixel. The unit-wise output values of an array can characterize/represent/denote the decay map 1716, the ternary map 1718, or the binary map 1720. In some implementations, the input image data 1702 is also an array of units in the pixel, subpixel, or superpixel resolution. In such an implementation, the neural network-based template generator 1512 uses semantic segmentation techniques to produce an output value for each unit in the input array. Additional details about the input image data 1702 can be found in FIGS. 21b, 22, 23, and 24 and their discussion.

In some implementations, the neural network-based template generator 1512 is a fully convolutional network, such as the one described in J. Long, E. Shelhamer, and T. Darrell, "Fully convolutional networks for semantic segmentation," in CVPR, (2015), which is incorporated herein by reference. In other implementations, the neural network-based template generator 1512 is a U-Net network with skip connections between the decoder and the encoder between the decoder and the encoder, such as the one described in Ronneberger O, Fischer P, Brox T., "U-net: Convolutional networks for biomedical image segmentation," Med. Image Comput. Comput. Assist. Interv. (2015), available at: http://link.springer.com/chapter/10.1007/978-3-319-24574-4_28, which is incorporated herein by reference. The U-Net architecture resembles an autoencoder with two main sub-structures: 1) an encoder, which takes an input image and reduces its spatial resolution through multiple convolutional layers to create a representation encoding. 2) A decoder, which takes the representation encoding and increases spatial resolution back to produce a reconstructed image as output. The U-Net introduces two innovations to this architecture: First, the objective function is set to reconstruct a segmentation mask using a loss function; and second, the convolutional layers of the encoder are connected to the corresponding layers of the same resolution in the decoder using skip connections. In yet further implementations, the neural network-based template generator 1512 is a deep fully convolutional segmentation neural network with an encoder subnetwork and a corresponding decoder network. In such an implementation, the encoder subnetwork includes a hierarchy of encoders and the decoder subnetwork includes a hierarchy of decoders that map low resolution encoder feature maps to full input resolution feature maps. Additional details about segmentation networks can be found in Appendix entitled "Segmentation Networks".

In one implementation, the neural network-based template generator 1512 is a convolutional neural network. In another implementation, the neural network-based template generator 1512 is a recurrent neural network. In yet another implementation, the neural network-based template generator 1512 is a residual neural network with residual bocks and residual connections. In a further implementation, the neural network-based template generator 1512 is a combination of a convolutional neural network and a recurrent neural network.

One skilled in the art will appreciate that the neural network-based template generator 1512 (i.e., the neural network 1706 and/or the output layer 1710) can use various padding and striding configurations. It can use different output functions (e.g., classification or regression) and may or may not include one or more fully-connected layers. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

In some implementations, each image in the sequence of image sets 1602 covers a tile and depicts intensity emissions of clusters on a tile and their surrounding background captured for a particular imaging channel at a particular one of a plurality of sequencing cycles of a sequencing run performed on a flow cell. In one implementation, the input image data 1702 includes at least one image patch from each of the images in the sequence of image sets 1602. In such an implementation, the image patch covers a portion of the tile. In one example, the image patch has a resolution of 20×20. In other cases, the resolution of the image patch can range from 20×20 to 10000×10000. In another implementation, the input image data 1702 includes an upsampled, subpixel resolution representation of the image patch from each of the images in the sequence of image sets 1602. In one example, the upsampled, subpixel representation has a resolution of 80×80. In other cases, the resolution of the upsampled, subpixel representation can range from 80×80 to 10000× 10000.

The input image data 1702 has an array of units 1704 that depicts clusters and their surrounding background. For example, an image set can be for a particular sequencing cycle and include four images, one for each image channel A, C, T, and G. Then, for a sequencing run with fifty sequencing cycles, there will be fifty such image sets, i.e., a total of 200 images. When arranged temporally, fifty image sets with four images-per image set would form the series of image sets 1602. In some implementations, image patches of a certain size are extracted from each image in the fifty image sets, forming fifty image patch sets with four image patches-per image patch set and, in one implementation, this is the input image data 1702. In other implementations, the input image data 1702 comprises image patch sets with four image patches-per image patch set for fewer than the fifty sequencing cycles, i.e., just one, two, three, fifteen, twenty sequencing cycles. The alternative representation is a feature map. The feature map can be a convolved feature or convolved representation when the neural network is a convolutional neural network. The feature map can be a hidden state feature or hidden state representation when the neural network is a recurrent neural network.

Then, the technology disclosed processes the alternative representation 1708 through an output layer 1710 to generate an output 1714 that has an output value 1712 for each unit in the array 1704. The output layer can be a classification layer such as softmax or sigmoid that produces unit-wise output values. In one implementation, the output layer is a ReLU layer or any other activation function layer that produces unit-wise output values.

In one implementation, the units in the input image data 1702 are pixels and therefore pixel-wise output values 1712 are produced in the output 1714. In another implementation, the units in the input image data 1702 are subpixels and therefore subpixel-wise output values 1712 are produced in the output 1714. In yet another implementation, the units in the input image data 1702 are superpixels and therefore superpixel-wise output values 1712 are produced in the output 1714.

Deriving Cluster Metadata from Decay Map, Ternary Map, and/or Binary Man

Figure 18:
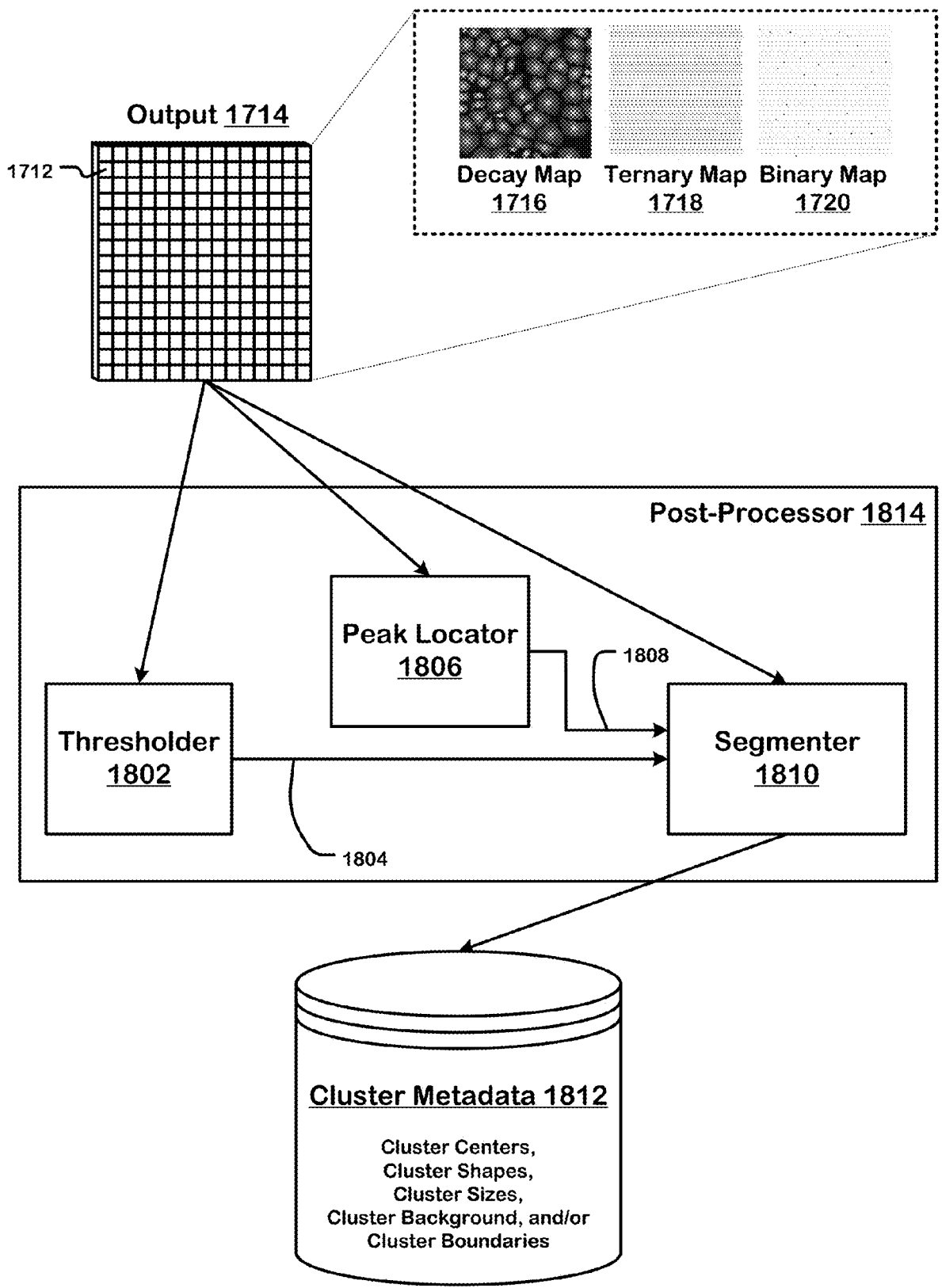
FIG. 18 shows one implementation of post-processing techniques that are applied to the decay map, the ternary map, or the binary map produced by the neural network-based template generator to derive cluster metadata, including cluster centers, cluster shapes, cluster sizes, cluster background, and/or cluster boundaries.

FIG. 18 shows one implementation of post-processing techniques that are applied to the decay map 1716, the ternary map 1718, or the binary map 1720 produced by the neural network-based template generator 1512 to derive cluster metadata, including cluster centers, cluster shapes, cluster sizes, cluster background, and/or cluster boundaries. In some implementations, the post-processing techniques are applied by a post-processor 1814 that further comprises a thresholder 1802, a peak locator 1806, and a segmenter 1810.

The input to the thresholder 1802 is the decay map 1716, the ternary map 1718, or the binary map 1720 produced by template generator 1512, such as the disclosed neural network-based template generator. In one implementation, the thresholder 1802 applies thresholding on the values in the decay map, the ternary map, or the binary map to identify background units 1804 (i.e., subpixels characterizing non-cluster background).) and non-background units. Said differently, once the output 1714 is produced, the thresholder 1802 thresholds output values of the units 1712 and classifies, or can reclassify a first subset of the units 1712 as "background units" 1804 depicting the surrounding background of the clusters and "non-background units" depicting units that potentially belong to clusters. The threshold value applied by the thresholder 1802 can be preset.

The input to the peak locator 1806 is also the decay map 1716, the ternary map 1718, or the binary map 1720 produced by the neural network-based template generator 1512. In one implementation, the peak locator 1806 applies peak detection on the values in the decay map 1716, the ternary map 1718, or the binary map 1720 to identify center units 1808 (i.e., center subpixels characterizing cluster centers). Said differently, the peak locator 1806 processes the output values of the units 1712 in the output 1714 and classifies a second subset of the units 1712 as "center units" 1808 containing centers of the clusters. In some implementations, the centers of the clusters detected by the peak locator 1806 are also the centers of mass of the clusters. The center units 1808 are then provided to the segmenter 1810. Additional details about the peak locator 1806 can be found in the Appendix entitled "Peak Detection".

The thresholding and the peak detection can be done in parallel or one after the other. That is, they are not dependent on each other.

The input to the segmenter 1810 is also the decay map 1716, the ternary map 1718, or the binary map 1720 produced by the neural network-based template generator 1512. Additional supplemental input to the segmenter 1810 comprises the thresholded units (background, non-background) 1804 identified by the thresholder 1802 and the center units 1808 identified by the peak locator 1806. The segmenter 1810 uses the background, non-background 1804 and the center units 1808 to identify disjointed regions 1812 (i.e., non-overlapping groups of contiguous cluster/cluster interior subpixels characterizing clusters). Said differently, the segmenter 1810 processes the output values of the units 1712 in the output 1714 and uses the background, non-background units 1804 and the center units 1808 to determine shapes 1812 of the clusters as non-overlapping regions of contiguous units separated by the background units 1804 and centered at the center units 1808. The output of the segmenter 1810 is cluster metadata 1812. The cluster metadata 1812 identifies cluster centers, cluster shapes, cluster sizes, cluster background, and/or cluster boundaries.

In one implementation, the segmenter 1810 begins with the center units 1808 and determines, for each center unit, a group of successively contiguous units that depict a same cluster whose center of mass is contained in the center unit. In one implementation, the segmenter 1810 uses a so-called "watershed" segmentation technique to subdivide contiguous clusters into multiple adjoining clusters at a valley in intensity. Additional details about the watershed segmentation technique and other segmentation techniques can be found in Appendix entitled "Watershed Segmentation".

In one implementation, the output values of the units 1712 in the output 1714 are continuous values, such as the one encoded in the ground truth decay map 1204. In another implementation, the output values are softmax scores, such as the one encoded in the ground truth ternary map 1304 and the ground truth binary map 1404. In the ground truth decay map 1204, according to one implementation, the contiguous units in the respective ones of the non-overlapping regions have output values weighted according to distance of a contiguous unit from a center unit in a non-overlapping region to which the contiguous unit belongs. In such an implementation, the center units have highest output values within the respective ones of the non-overlapping regions. As discussed above, during the training, due to the backward propagation-based gradient update, the decay map 1716, the ternary map 1718, and the binary map 1720 (i.e., cumulatively the output 1714) progressively match or approach the ground truth decay map 1204, the ground truth ternary map 1304, and the ground truth binary map 1404, respectively.

Pixel Domain—Intensity Extraction from Irregular Cluster Shapes

The discussion now turns to how cluster shapes determined by the technology disclosed can be used to extract intensity of the clusters. Since clusters typically have irregular shapes and contours, the technology disclosed can be used to identify which subpixels contribute to the irregularly shaped disjointed/non-overlapping regions that represent the cluster shapes.

Figure 19:
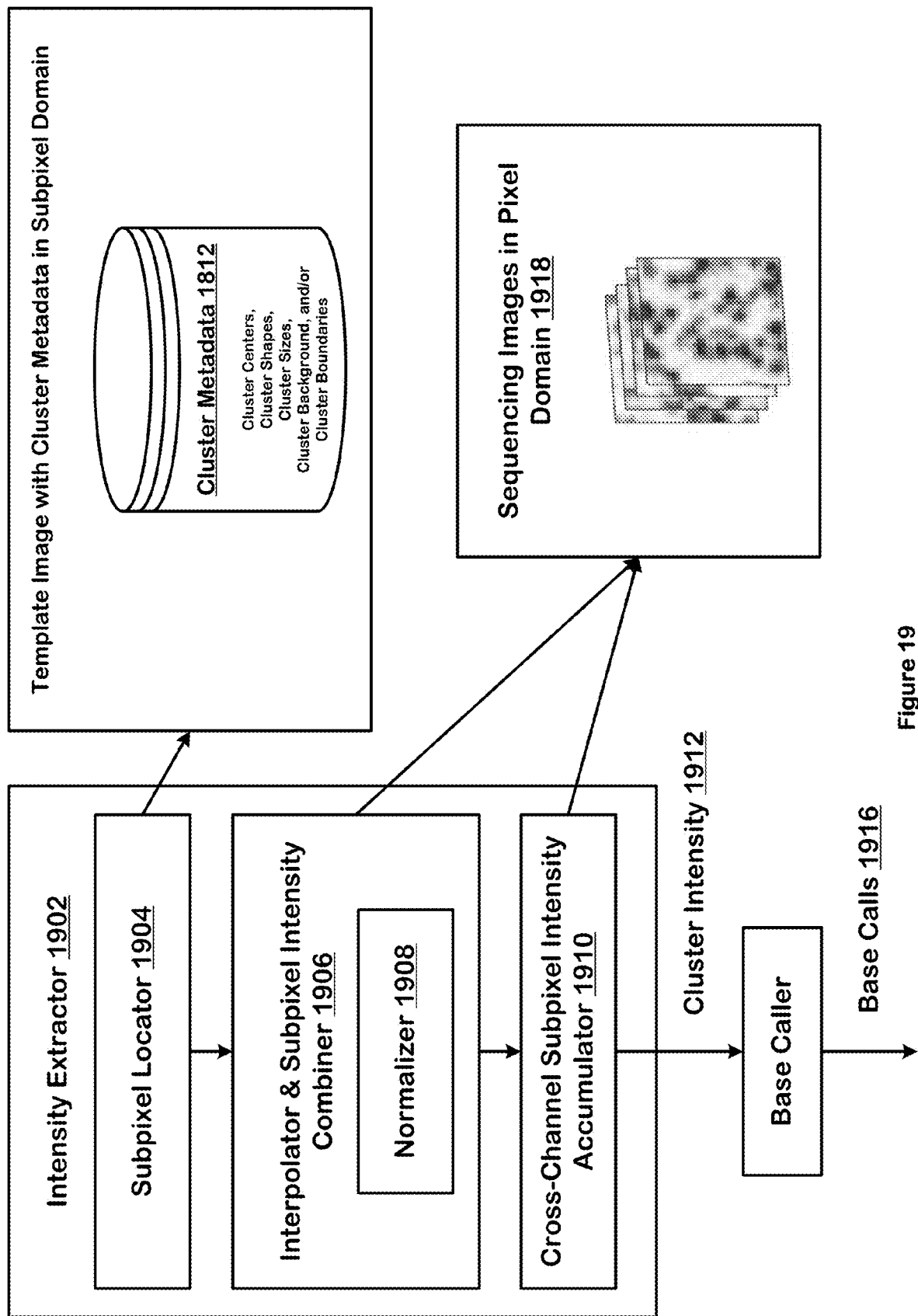
FIG. 19 depicts one implementation of extracting cluster intensity in the pixel domain.

FIG. 19 depicts one implementation of extracting cluster intensity in the pixel domain. "Template image" or "template" can refer to a data structure that contains or identifies the cluster metadata 1812 derived from the decay map 1716, the ternary map 1718, and/or the binary map 1718. The cluster metadata 1812 identifies cluster centers, cluster shapes, cluster sizes, cluster background, and/or cluster boundaries.

In some implementations, the template image is in the upsampled, subpixel domain to distinguish the cluster boundaries at a fine-grained level. However, the sequencing images 108, which contain the cluster and background intensity data, are typically in the pixel domain. Thus, the technology disclosed proposes two approaches to use the cluster shape information encoded in the template image in the upsampled, subpixel resolution to extract intensities of the irregularly shaped clusters from the optical, pixel-resolution sequencing images. In the first approach, depicted in FIG. 19, the non-overlapping groups of contiguous subpixels identified in the template image are located in the pixel resolution sequencing images and their intensities extracted via interpolation. Additional details about this intensity extraction technique can be found in FIG. 33 and its discussion.

In one implementation, when the non-overlapping regions have irregular contours and the units are subpixels, the cluster intensity 1912 of a given cluster is determined by an intensity extractor 1902 as follows.

First, a subpixel locator 1904 identifies subpixels that contribute to the cluster intensity of the given cluster based on a corresponding non-overlapping region of contiguous subpixels that identifies a shape of the given cluster.

Then, the subpixel locator 1904 locates the identified subpixels in one or more optical, pixel-resolution images 1918 generated for one or more imaging channels at a current sequencing cycle. In one implementation, integer or non-integer coordinates (e.g., floating points) are located in the optical, pixel-resolution images, after a downscaling based on a downscaling factor that matches an upsampling factor used to create the subpixel domain.

Then, an interpolator and subpixel intensity combiner 1906, intensities of the identified subpixels in the images processed, combines the interpolated intensities, and normalizes the combined interpolated intensities to produce a per-image cluster intensity for the given cluster in each of the images. The normalization is performed by a normalizer 1908 and is based on a normalization factor. In one implementation, the normalization factor is a number of the identified subpixels. This is done to normalize/account for different cluster sizes and uneven illuminations that clusters receive depending on their location on the flow cell.

Finally, a cross-channel subpixel intensity accumulator 1910 combines the per-image cluster intensity for each of the images to determine the cluster intensity 1912 of the given cluster at the current sequencing cycle.

Then, the given cluster is base called based on the cluster intensity 1912 at the current sequencing cycle by any one of the base callers discussed in this application, yielding base calls 1916.

In some implementations though, when the cluster sizes are large enough, the output of the neural network-based base caller 1514, i.e., the decay map 1716, the ternary map 1718, and the binary map 1720 are in the optical, pixel domain. Accordingly, in such implementations, the template image is also in the optical, pixel domain.

Subpixel Domain—Intensity Extraction from Irregular Cluster Shapes

Figure 20:
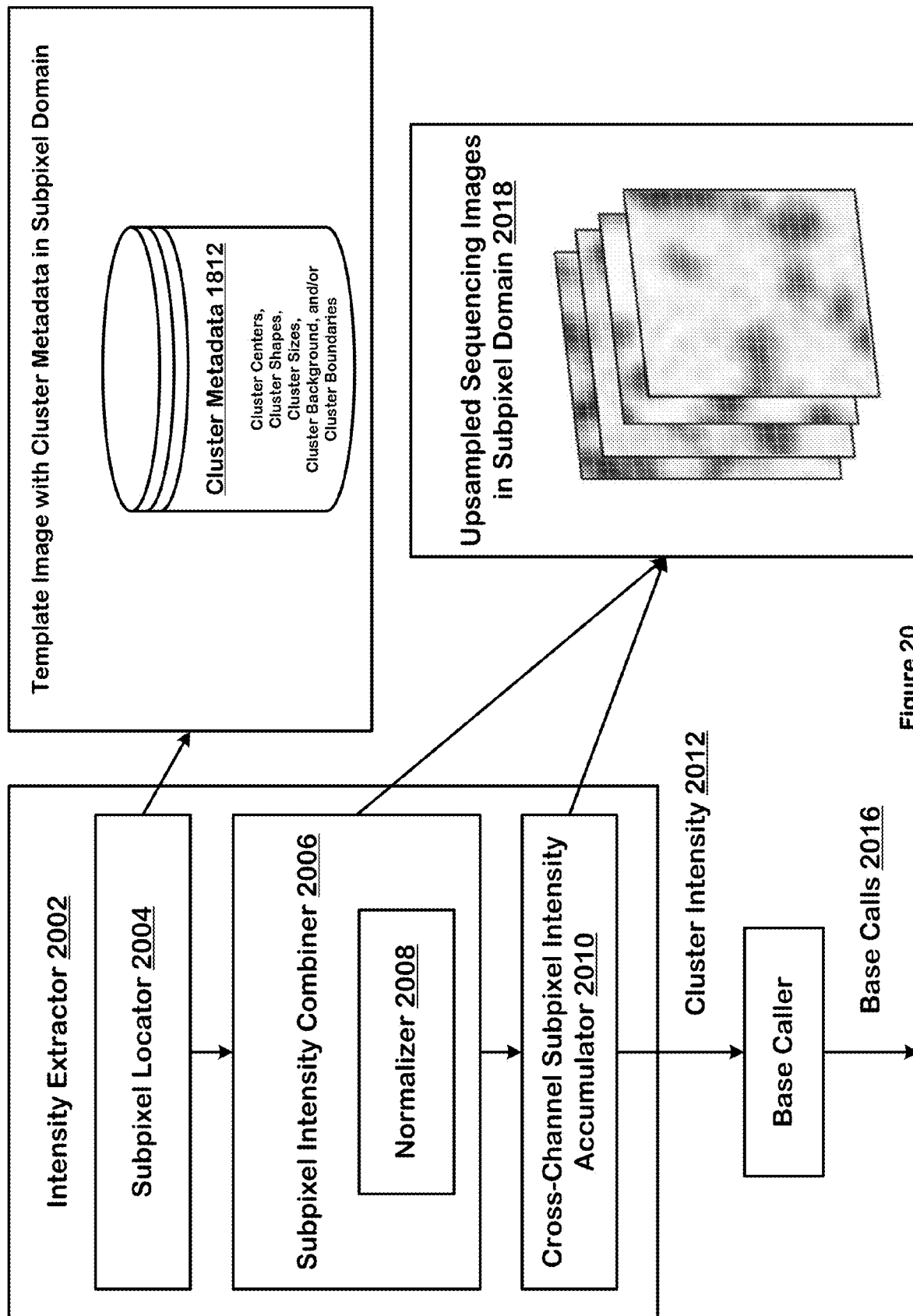
FIG. 20 illustrates one implementation of extracting cluster intensity in the subpixel domain.

FIG. 20 depicts the second approach of extracting cluster intensity in the subpixel domain. In this second approach, the sequencing images in the optical, pixel-resolution are upsampled into the subpixel resolution. This results in correspondence between the "cluster shape depicting subpixels" in the template image and the "cluster intensity depicting subpixels" in the upsampled sequencing images. The cluster intensity is then extracted based on the correspondence. Additional details about this intensity extraction technique can be found in FIG. 33 and its discussion.

In one implementation, when the non-overlapping regions have irregular contours and the units are subpixels, the cluster intensity 2012 of a given cluster is determined by an intensity extractor 2002 as follows.

First, a subpixel locator 2004 identifies subpixels that contribute to the cluster intensity of the given cluster based on a corresponding non-overlapping region of contiguous subpixels that identifies a shape of the given cluster.

Then, the subpixel locator 2004 locates the identified subpixels in one or more subpixel resolution images 2018 upsampled from corresponding optical, pixel-resolution images 1918 generated for one or more imaging channels at a current sequencing cycle. The upsampling can be performed by nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. These techniques are described in detail in Appendix entitled "Intensity Extraction Methods". The template image can, in some implementations, serve as a mask for intensity extraction.

Then, a subpixel intensity combiner 2006, in each of the upsampled images, combines intensities of the identified subpixels and normalizes the combined intensities to produce a per-image cluster intensity for the given cluster in each of the upsampled images. The normalization is performed by a normalizer 2008 and is based on a normalization factor. In one implementation, the normalization factor is a number of the identified subpixels. This is done to normalize/account for different cluster sizes and uneven illuminations that clusters receive depending on their location on the flow cell.

Finally, a cross-channel, subpixel-intensity accumulator 2010 combines the per-image cluster intensity for each of the upsampled images to determine the cluster intensity 2012 of the given cluster at the current sequencing cycle.

Then, the given cluster is base called based on the cluster intensity 2012 at the current sequencing cycle by any one of the base callers discussed in this application, yielding base calls 2016.

Types of Neural Network-Based Template Generators

Figure 21A:
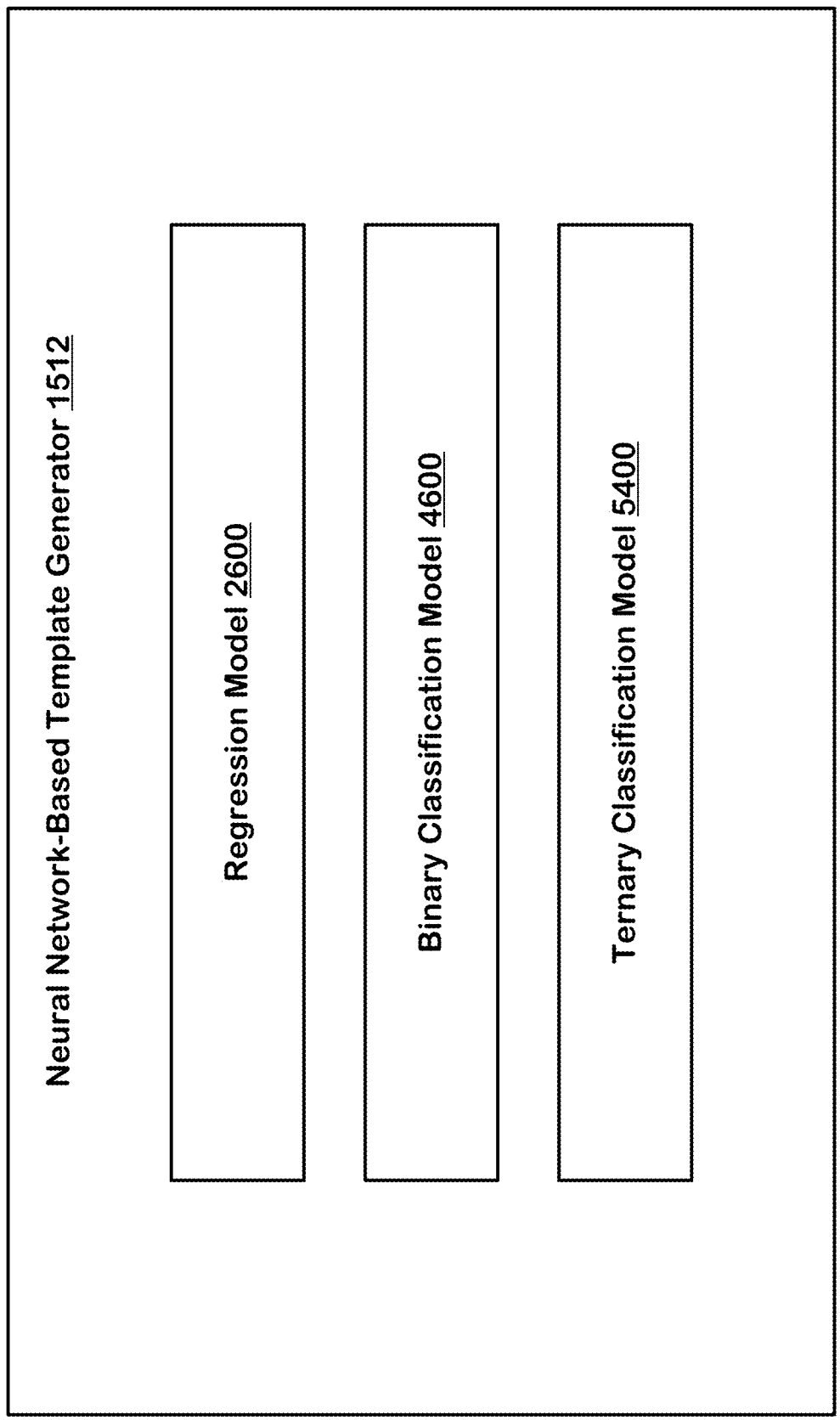
FIG. 21a shows three different implementations of the neural network-based template generator.

The discussion now turns to details of three different implementations of the neural network-based template generator 1512. There are shown in FIG. 21*a* and include: (1) the decay map-based template generator 2600 (also called the regression model), (2) the binary map-based template generator 4600 (also called the binary classification model), and (3) the ternary map-based template generator 5400 (also called the ternary classification model).

In one implementation, the regression model 2600 is a fully convolutional network. In another implementation, the regression model 2600 is a U-Net network with skip connections between the decoder and the encoder. In one implementation, the binary classification model 4600 is a fully convolutional network. In another implementation, the binary classification model 4600 is a U-Net network with skip connections between the decoder and the encoder. In one implementation, the ternary classification model 5400 is a fully convolutional network. In another implementation, the ternary classification model 5400 is a U-Net network with skip connections between the decoder and the encoder.

Input Image Data

Figure 21B:
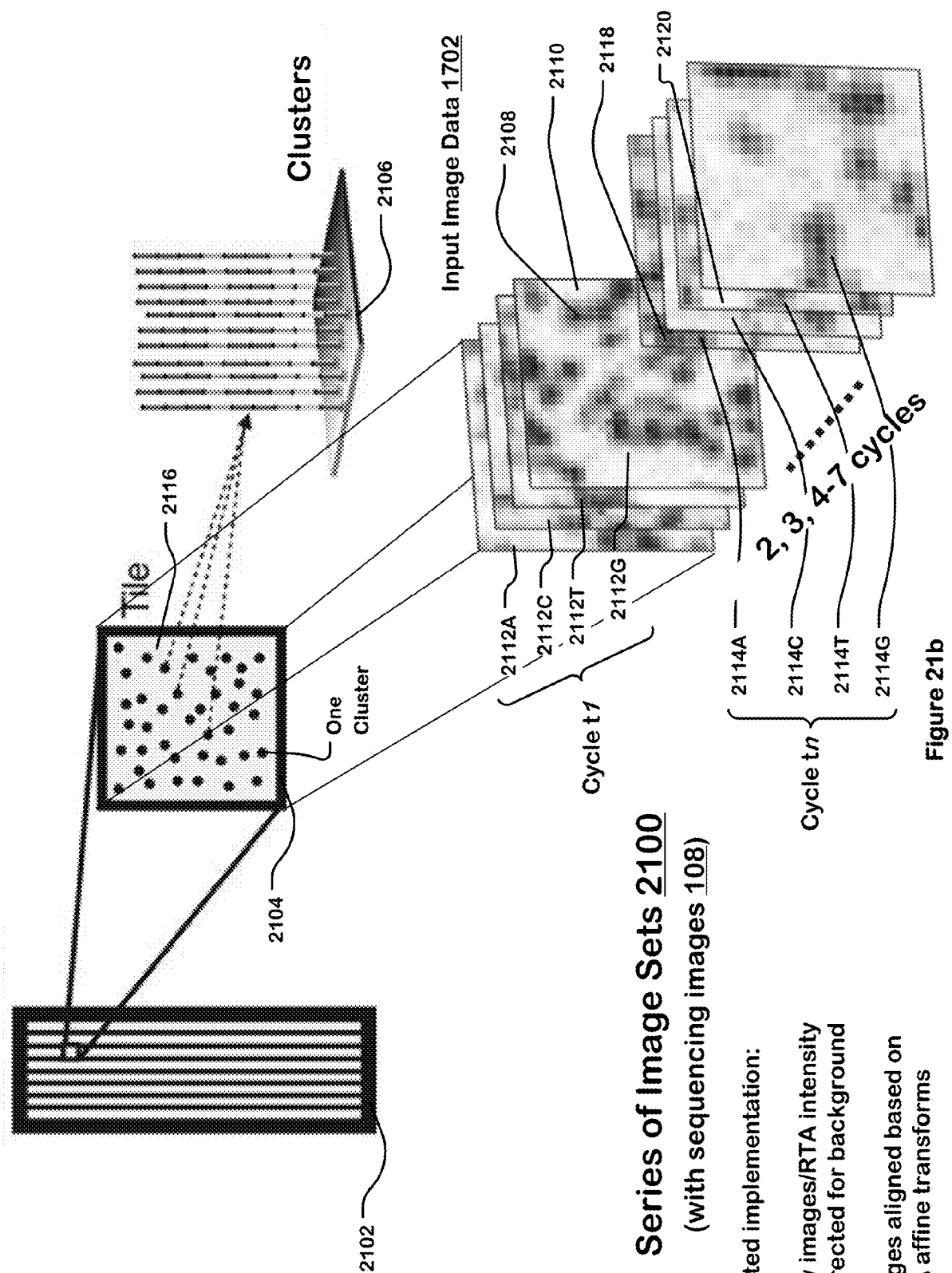
FIG. 21b depicts one implementation of the input image data that is fed as input to the neural network-based template generator 1512. The input image data comprises a series of image sets with sequencing images that are generated during a certain number of initial sequences cycles of a sequencing run.

FIG. 21*b* depicts one implementation of the input image data 1702 that is fed as input to the neural network-based template generator 1512. The input image data 1702 comprises a series of image sets 2100 with the sequencing images 108 that are generated during a certain number of initial sequences cycles of a sequencing run (e.g., the first 2 to 7 sequencing cycles).

In some implementations, intensities of the sequencing images 108 are corrected for background and/or aligned with each other using affine transformation. In one implementation, the sequencing run utilizes four-channel chemistry and each image set has four images. In another implementation, the sequencing run utilizes two-channel chemistry and each image set has two images. In yet another implementation, the sequencing run utilizes one-channel chemistry and each image set has two images. In yet other implementations, each image set has only one image. These and other different implementations are described in Appendices 6 and 9.

Each image 2116 in the series of image sets 2100 covers a tile 2104 of a flow cell 2102 and depicts intensity emissions of clusters 2106 on the tile 2104 and their surrounding background captured for a particular image channel at a particular one of a plurality of sequencing cycles of the sequencing run. In one example, for cycle t1, the image set includes four images 2112A, 2112C, 2112T, and 2112G: one image for each base A, C, T, and G labeled with a corresponding fluorescent dye and imaged in a corresponding wavelength band (image/imaging channel).

For illustration purposes, in image 2112G, FIG. 21b depicts cluster intensity emissions as 2108 and background intensity emissions as 2110. In another example, for cycle tn, the image set also includes four images 2114A, 2114C, 2114T, and 2114G: one image for each base A, C, T, and G labeled with a corresponding fluorescent dye and imaged in a corresponding wavelength band (image/imaging channel). Also for illustration purposes, in image 2114A, FIG. 21b depicts cluster intensity emissions as 2118 and, in image 2114T, depicts background intensity emissions as 2120.

Non-Image Data

The input image data 1702 is encoded using intensity channels (also called imaged channels). For each of the c images obtained from the sequencer for a particular sequencing cycle, a separate imaged channel is used to encode its intensity signal data. Consider, for example, that the sequencing run uses the 2-channel chemistry which produces a red image and a green image at each sequencing cycle. In such a case, the input data 2632 comprises (i) a first red imaged channel with w×h pixels that depict intensity emissions of the one or more clusters and their surrounding background captured in the red image and (ii) a second green imaged channel with w×h pixels that depict intensity emissions of the one or more clusters and their surrounding background captured in the green image.

In another implementation, image data is not used as input to the neural network-based template generator 1512 or the neural network-based base caller 1514. Instead, the input to the neural network-based template generator 1512 and the neural network-based base caller 1514 is based on pH changes induced by the release of hydrogen ions during molecule extension. The pH changes are detected and converted to a voltage change that is proportional to the number of bases incorporated (e.g., in the case of Ion Torrent).

In yet another implementation, the input to the neural network-based template generator 1512 and the neural network-based base caller 1514 is constructed from nanopore sensing that uses biosensors to measure the disruption in current as an analyte passes through a nanopore or near its aperture while determining the identity of the base. For example, the Oxford Nanopore Technologies (ONT) sequencing is based on the following concept: pass a single strand of DNA (or RNA) through a membrane via a nanopore and apply a voltage difference across the membrane. The nucleotides present in the pore will affect the pore's electrical resistance, so current measurements over time can indicate the sequence of DNA bases passing through the pore. This electrical current signal (the 'squiggle' due to its appearance when plotted) is the raw data gathered by an ONT sequencer. These measurements are stored as 16-bit integer data acquisition (DAC) values, taken at 4 kHz frequency (for example). With a DNA strand velocity of ~450 base pairs per second, this gives approximately nine raw observations per base on average. This signal is then processed to identify breaks in the open pore signal corresponding to individual reads. These stretches of raw signal are base called—the process of converting DAC values into a sequence of DNA bases. In some implementations, the input data 2632 comprises normalized or scaled DAC values.

Patch Extraction

FIG. 22 shows one implementation of extracting patches from the series of image sets 2100 in FIG. 21b to produce a series of "down-sized" image sets that form the input image data 1702. In the illustrated implementation, the sequencing images 108 in the series of image sets 2100 are of size L×L (e.g., 2000×2000). In other implementations, L is any number ranging from 1 and 10,000.

In one implementation, a patch extractor 2202 extracts patches from the sequencing images 108 in the series of image sets 2100 and produces a series of down-sized image sets 2206, 2208, 2210, and 2212. Each image in the series of down-sized image sets is a patch of size M×M (e.g., 20×20) that is extracted from a corresponding sequencing image in the series of image sets 2100. The size of the patches can be preset. In other implementations, M is any number ranging from 1 and 1000.

In FIG. 22, four example series of down-sized image sets are shown. The first example series of down-sized image sets 2206 is extracted from coordinates 0,0 to 20,20 in the sequencing images 108 in the series of image sets 2100. The second example series of down-sized image sets 2208 is extracted from coordinates 20,20 to 40,40 in the sequencing images 108 in the series of image sets 2100. The third example series of down-sized image sets 2210 is extracted from coordinates 40,40 to 60,60 in the sequencing images 108 in the series of image sets 2100. The fourth example series of down-sized image sets 2212 is extracted from coordinates 60,60 to 80,80 in the sequencing images 108 in the series of image sets 2100.

In some implementations, the series of down-sized image sets form the input image data 1702 that is fed as input to the neural network-based template generator 1512. Multiple series of down-sized image sets can be simultaneously fed as an input batch and a separate output can be produced for each series in the input batch.

Upsampling

Figure 23:
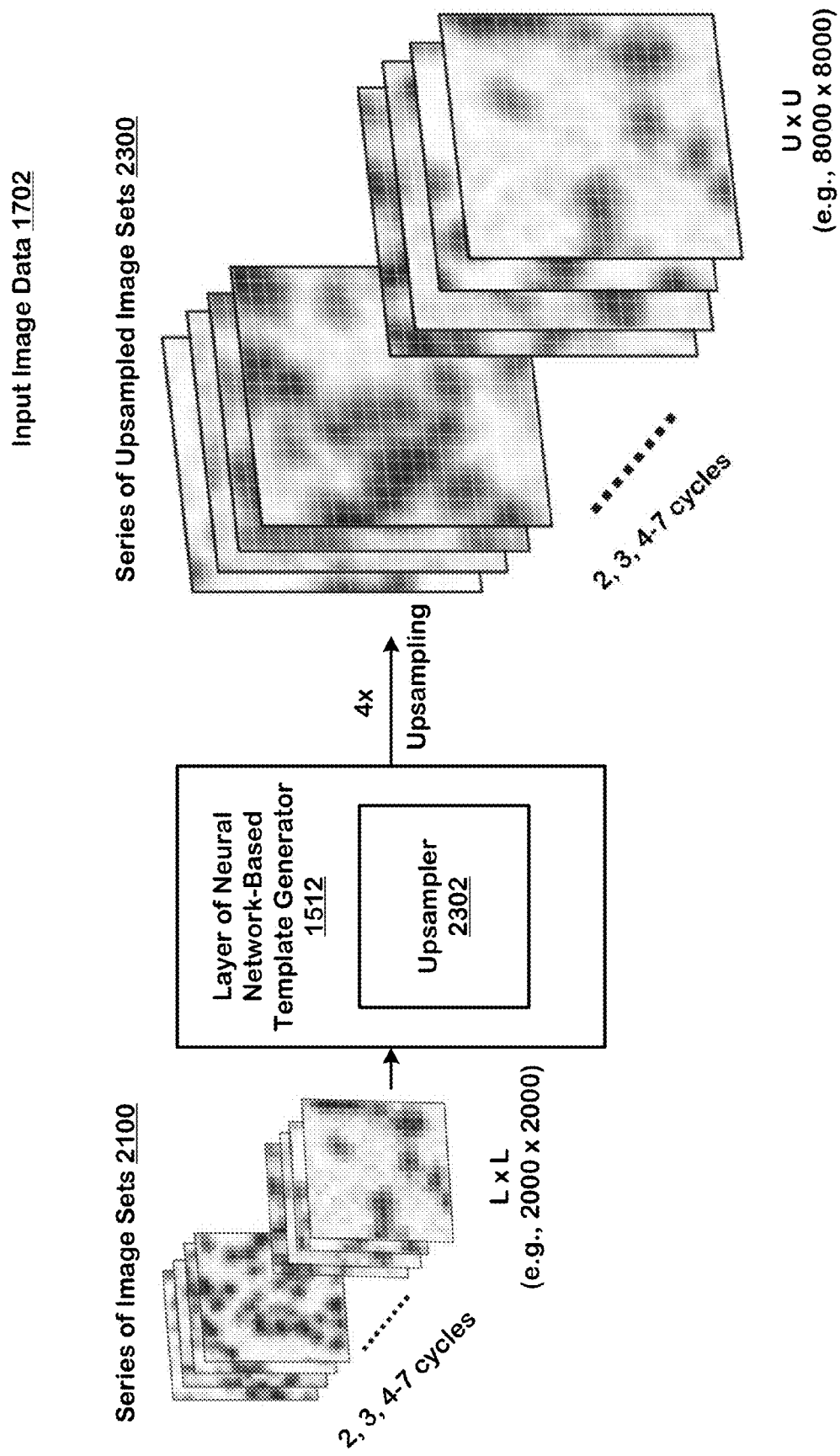
FIG. 23 depicts one implementation of upsampling the series of image sets in FIG. 21b to produce a series of "upsampled" image sets that forms the input image data.

FIG. 23 depicts one implementation of upsampling the series of image sets 2100 in FIG. 21b to produce a series of "upsampled" image sets 2300 that forms the input image data 1702.

In one implementation, an upsampler 2302 uses interpolation (e.g., bicubic interpolation) to upsample the sequencing images 108 in the series of image sets 2100 by an upsampling factor (e.g., 4×) and the series of upsampled image sets 2300.

In the illustrated implementation, the sequencing images 108 in the series of image sets 2100 are of size L×L (e.g., 2000×2000) and are upsampled by an upsampling factor of four to produce upsampled images of size U×U (e.g., 8000×8000) in the series of upsampled image sets 2300.

In one implementation, the sequencing images 108 in the series of image sets 2100 are fed directly to the neural network-based template generator 1512 and the upsampling is performed by an initial layer of the neural network-based template generator 1512. That is, the upsampler 2302 is part of the neural network-based template generator 1512 and operates as its first layer that upsamples the sequencing images 108 in the series of image sets 2100 and produces the series of upsampled image sets 2300.

In some implementations, the series of upsampled image sets 2300 forms the input image data 1702 that is fed as input to the neural network-based template generator 1512.

Figure 24:
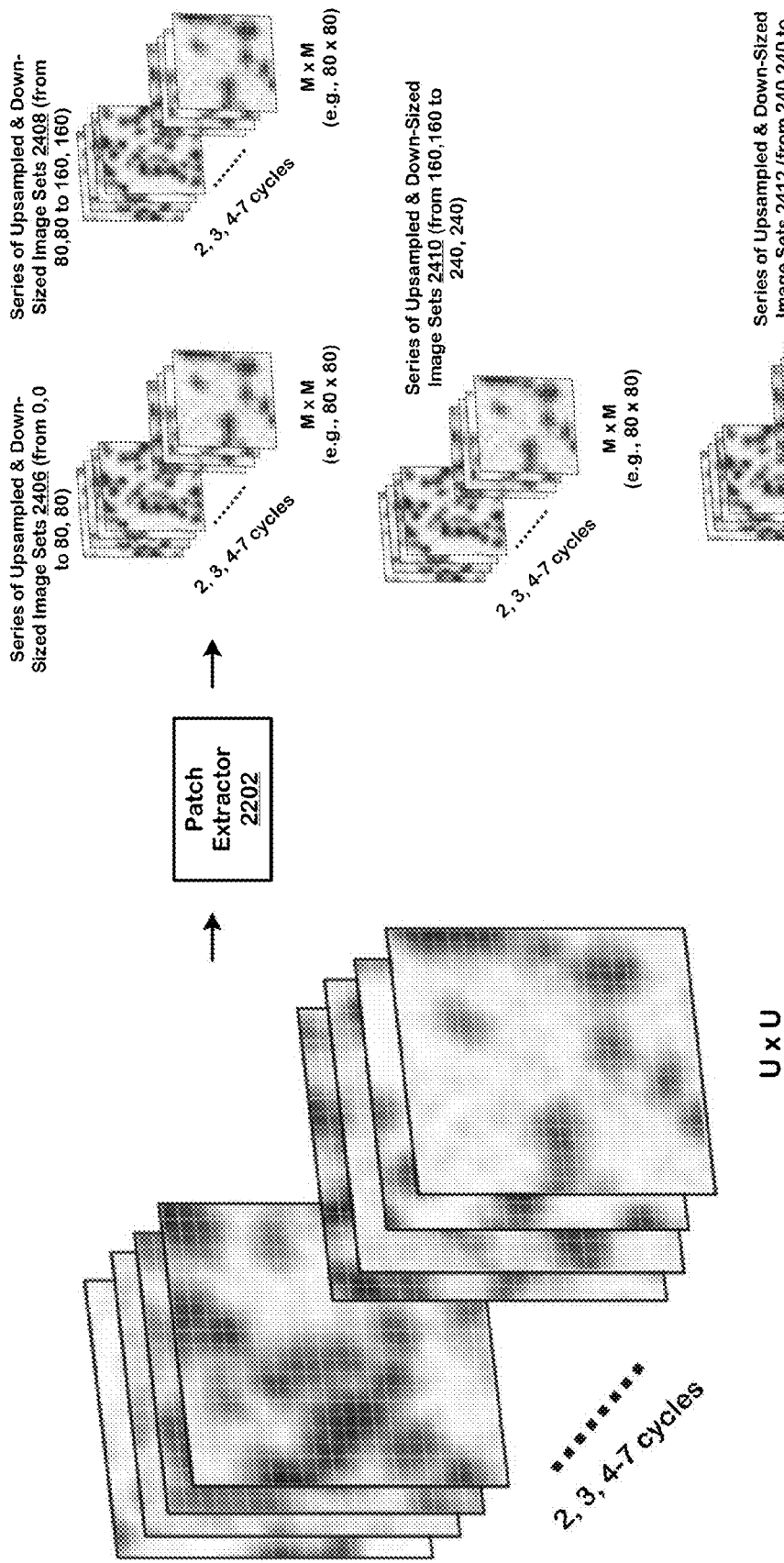
FIG. 24 shows one implementation of extracting patches from the series of upsampled image sets in FIG. 23 to produce a series of "upsampled and down-sized" image sets that form the input image data.

FIG. 24 shows one implementation of extracting patches from the series of upsampled image sets 2300 in FIG. 23 to produce a series of "upsampled and down-sized" image sets 2406, 2408, 2410, and 2412 that form the input image data 1702.

In one implementation, the patch extractor 2202 extracts patches from the upsampled images in the series of upsampled image sets 2300 and produces series of upsampled and down-sized image sets 2406, 2408, 2410, and 2412. Each upsampled image in the series of upsampled and down-sized image sets is a patch of size M×M (e.g., 80×80) that is extracted from a corresponding upsampled image in the series of upsampled image sets 2300. The size of the patches can be preset. In other implementations, M is any number ranging from 1 and 1000.

In FIG. 24, four example series of upsampled and down-sized image sets are shown. The first example series of upsampled and down-sized image sets 2406 is extracted from coordinates 0,0 to 80,80 in the upsampled images in the series of upsampled image sets 2300. The second example series of upsampled and down-sized image sets 2408 is extracted from coordinates 80,80 to 160,160 in the upsampled images in the series of upsampled image sets 2300. The third example series of upsampled and down-sized image sets 2410 is extracted from coordinates 160,160 to 240,240 in the upsampled images in the series of upsampled image sets 2300. The fourth example series of upsampled and down-sized image sets 2412 is extracted from coordinates 240,240 to 320,320 in the upsampled images in the series of upsampled image sets 2300.

In some implementations, the series of upsampled and down-sized image sets form the input image data 1702 that is fed as input to the neural network-based template generator 1512. Multiple series of upsampled and down-sized image sets can be simultaneously fed as an input batch and a separate output can be produced for each series in the input batch.

Output

The three models are trained to produce different outputs. This is achieved by using different types of ground truth data representations as training labels. The regression model 2600 is trained to produce output that characterizes/represents/denotes a so-called "decay map" 1716. The binary classification model 4600 is trained to produce output that characterizes/represents/denotes a so-called "binary map" 1720. The ternary classification model 5400 is trained to produce output that characterizes/represents/denotes a so-called "ternary map" 1718.

The output 1714 of each type of model comprises an array of units 1712. The units 1712 can be pixels, subpixels, or superpixels. The output of each type of model includes unit-wise output values, such that the output values of an array of units together characterize/represent/denote the decay map 1716 in the case of the regression model 2600, the binary map 1720 in the case of the binary classification model 4600, and the ternary map 1718 in the case of the ternary classification model 5400. More details follow.

Ground Truth Data Generation

Figure 25:
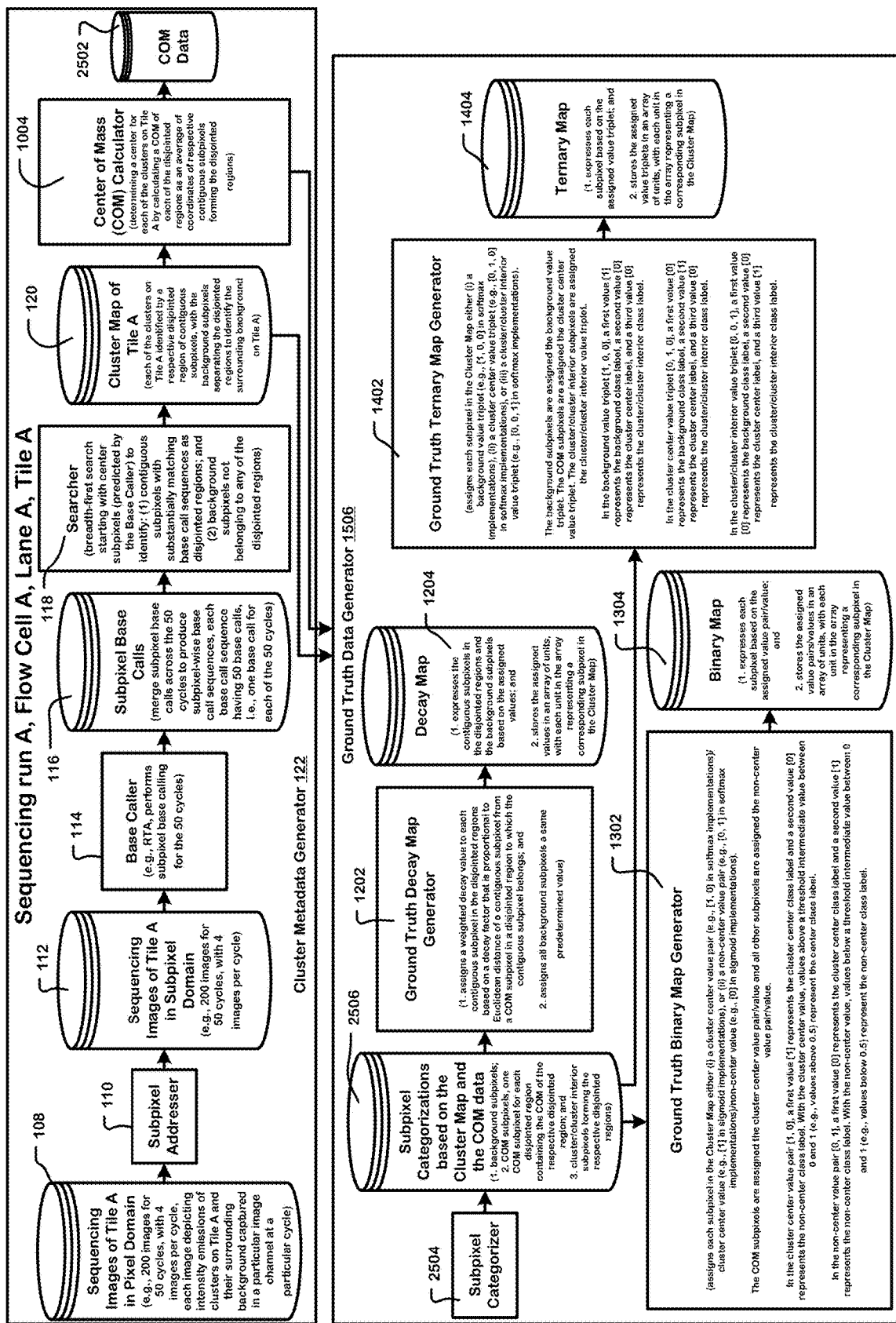
FIG. 25 illustrates one implementation of an overall example process of generating ground truth data for training the neural network-based template generator.

FIG. 25 illustrates one implementation of an overall example process of generating ground truth data for training the neural network-based template generator 1512. For the regression model 2600, the ground truth data can be the decay map 1204. For the binary classification model 4600, the ground truth data can be the binary map 1404. For the ternary classification model 5400, the ground truth data can be the ternary map 1304. The ground truth data is generated from the cluster metadata. The cluster metadata is generated by the cluster metadata generator 122. The ground truth data is generated by the ground truth data generator 1506.

In the illustrated implementation, the ground truth data is generated for tile A that is on lane A of flow cell A. The ground truth data is generated from the sequencing images 108 of tile A captured during sequencing run A. The sequencing images 108 of tile A are in the pixel domain. In one example involving 4-channel chemistry that generates four sequencing images per sequencing cycle, two hundred sequencing images 108 for fifty sequencing cycles are accessed. Each of the two hundred sequencing images 108 depicts intensity emissions of clusters on tile A and their surrounding background captured in a particular image channel at a particular sequencing cycle.

The subpixel addresser 110 converts the sequencing images 108 into the subpixel domain (e.g., by dividing each pixel into a plurality of subpixels) and produces sequencing images 112 in the subpixel domain.

The base caller 114 (e.g., RTA) then processes the sequencing images 112 in the subpixel domain and produces a base call for each subpixel and for each of the fifty sequencing cycles. This is referred to herein as "subpixel base calling".

The subpixel base calls 116 are then merged to produce, for each subpixel, a base call sequence across the fifty sequencing cycles. Each subpixel's base call sequence has fifty base calls, i.e., one base call for each of the fifty sequencing cycles.

The searcher 118 evaluates base call sequences of contiguous subpixels on a pair-wise basis. The search involves evaluating each subpixel to determine with which of its contiguous subpixels it shares a substantially matching base call sequence. Base call sequences of contiguous subpixels are "substantially matching" when a predetermined portion of base calls match on an ordinal position-wise basis (e.g., >=41 matches in 45 cycles, <=4 mismatches in 45 cycles, <=4 mismatches in 50 cycles, or <=2 mismatches in 34 cycles).

In some implementations, the base caller 114 also identifies preliminary center coordinates of the clusters. Subpixels that contain the preliminary center coordinates are referred to as center or origin subpixels. Some example preliminary center coordinates (604*a-c*) identified by the base caller 114 and corresponding origin subpixels (606*a-c*) are shown in FIG. 6. However, identification of the origin subpixels (preliminary center coordinates of the clusters) is not needed, as explained below. In some implementations, the searcher 118 uses a breadth-first search for identifying substantially matching base call sequences of the subpixels by beginning with the origin subpixels 606*a-c* and continuing with successively contiguous non-origin subpixels 702*a-c*. This again is optional, as explained below.

The search for substantially matching base call sequences of the subpixels does not need identification of the origin subpixels (preliminary center coordinates of the clusters) because the search can be done for all the subpixels and the search does not have to start from the origin subpixels and instead can start from any subpixel (e.g., 0,0 subpixel or any random subpixel). Thus, since each subpixel is evaluated to determine whether it shares a substantially matching base call sequence with another contiguous subpixel, the search does not have to utilize the origin subpixels and can start with any subpixel.

Irrespective of whether origin subpixels are used or not, certain clusters are identified that do not contain the origin subpixels (preliminary center coordinates of the clusters) predicted by the base caller 114. Some examples of clusters identified by the merging of the subpixel base calls and not containing an origin subpixel are clusters 812*a*, 812*b*, 812*c*, 812*d*, and 812*e* in FIG. 8*a*. Therefore, use of the base caller 114 for identification of origin subpixels (preliminary center coordinates of the clusters) is optional and not essential for the search of substantially matching base call sequences of the subpixels.

The searcher 118: (1) identifies contiguous subpixels with substantially matching base call sequences as so-called "disjointed regions", (2) further evaluates base call sequences of those subpixels that do not belong to any of the disjointed regions already identified at (1) to yield additional disjointed regions, and (3) then identifies background subpixels as those subpixels that do not belong to any of the disjointed regions already identified at (1) and (2). Action (2) allows the technology disclosed to identify additional or extra clusters for which the centers are not identified by the base caller 114.

The results of the searcher 118 are encoded in a so-called "cluster map" of tile A and stored in the cluster map data store 120. In the cluster map, each of the clusters on tile A are identified by a respective disjointed region of contiguous subpixels, with background subpixels separating the disjointed regions to identify the surrounding background on tile A.

The center of mass (COM) calculator 1004 determines a center for each of the clusters on tile A by calculating a COM of each of the disjointed regions as an average of coordinates of respective contiguous subpixels forming the disjointed regions. The centers of mass of the clusters are stored as COM data 2502.

A subpixel categorizer 2504 uses the cluster map and the COM data 2502 to produce subpixel categorizations 2506. The subpixel categorizations 2506 classify subpixels in the cluster map as (1) backgrounds subpixels, (2) COM subpixels (one COM subpixel for each disjointed region containing the COM of the respective disjointed region), and (3) cluster/cluster interior subpixels forming the respective disjointed regions. That is, each subpixel in the cluster map is assigned one of the three categories.

Based on the subpixel categorizations 2506, in some implementations, (i) the ground truth decay map 1204 is produced by the ground truth decay map generator 1202, (ii) the ground truth binary map 1304 is produced by the ground truth binary map generator 1302, and (iii) the ground truth ternary map 1404 is produced by the ground truth ternary map generator 1402.

1. Regression Model

Figure 26:
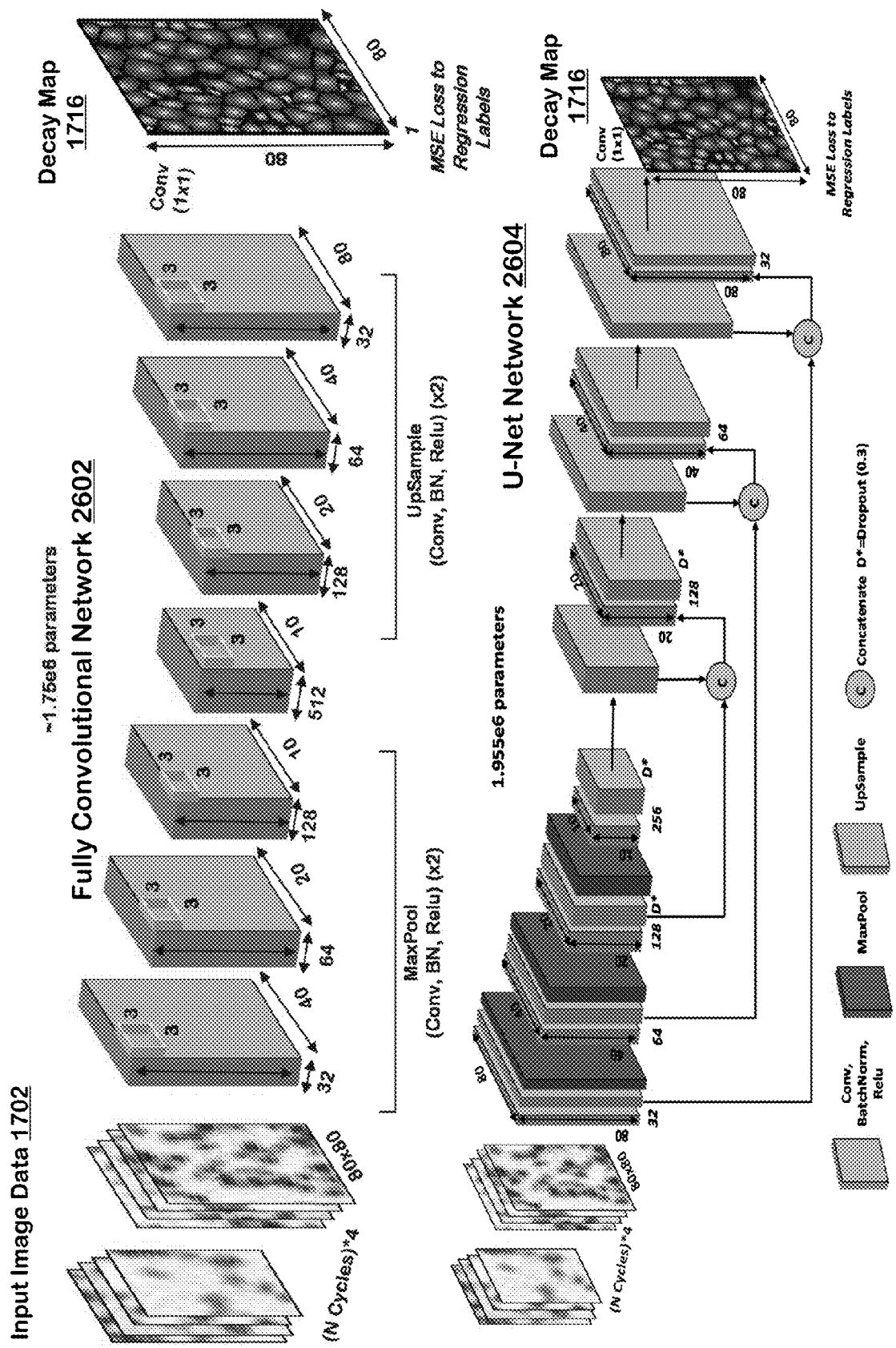
FIG. 26 illustrates one implementation of the regression model.

FIG. 26 illustrates one implementation of the regression model 2600. In the illustrated implementation, the regression model 2600 is a fully convolutional network 2602 that processes the input image data 1702 through an encoder subnetwork and a corresponding decoder subnetwork. The encoder subnetwork includes a hierarchy of encoders. The decoder subnetwork includes a hierarchy of decoders that map low resolution encoder feature maps to a full input resolution decay map 1716. In another implementation, the regression model 2600 is a U-Net network 2604 with skip connections between the decoder and the encoder. Additional details about the segmentation networks can be found in the Appendix entitled "Segmentation Networks".

Decay Man

Figure 27:
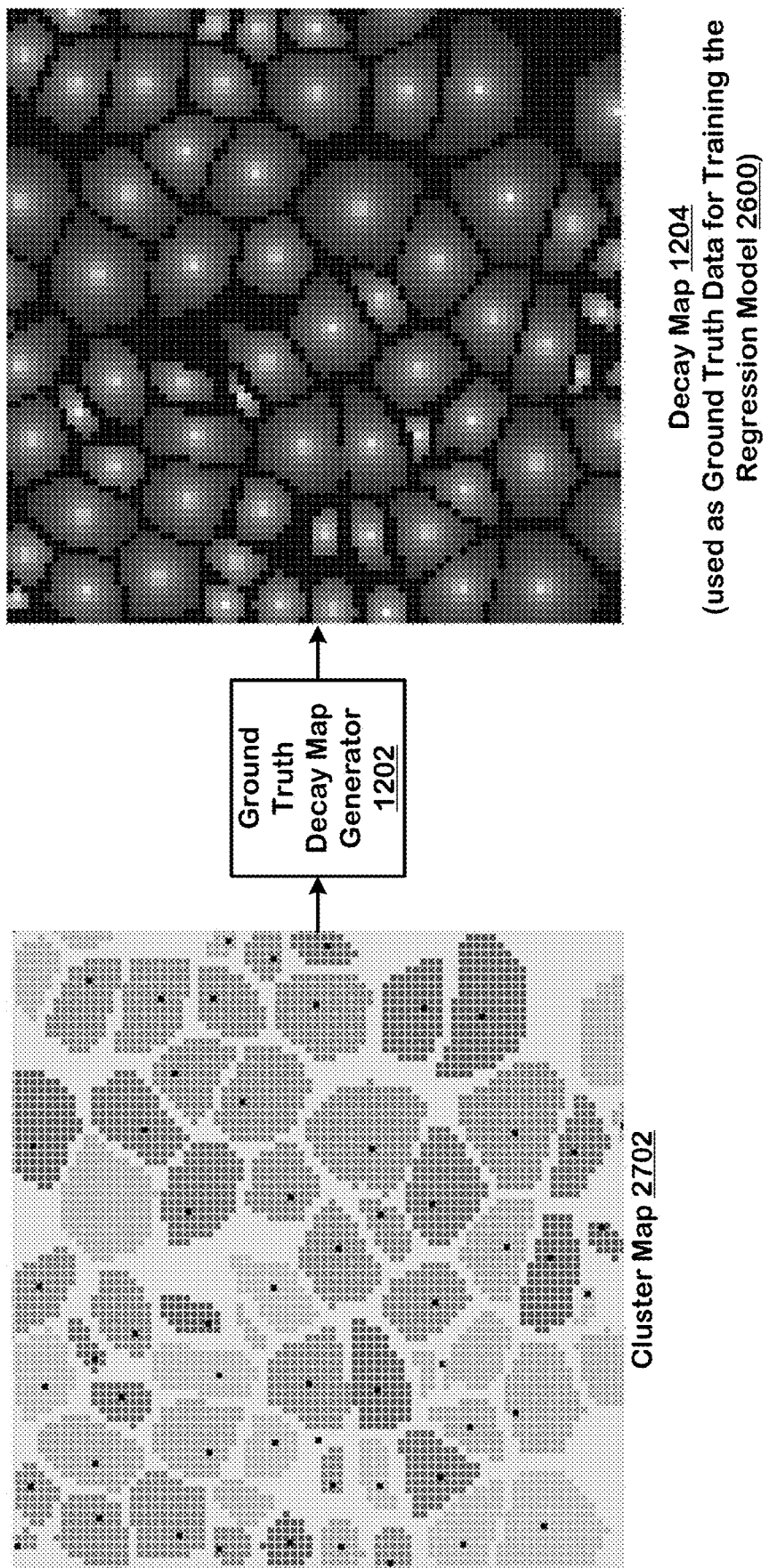
FIG. 27 depicts one implementation of generating a ground truth decay map from a cluster map. The ground truth decay map is used as ground truth data for training the regression model.

FIG. 27 depicts one implementation of generating a ground truth decay map 1204 from a cluster map 2702. The ground truth decay map 1204 is used as ground truth data for training the regression model 2600. In the ground truth decay map 1204, the ground truth decay map generator 1202 assigns a weighted decay value to each contiguous subpixel in the disjointed regions based on a weighted decay factor. The weighted decay value is proportional to Euclidean distance of a contiguous subpixel from a center of mass (COM) subpixel in a disjointed region to which the contiguous subpixel belongs, such that the weighted decay value is highest (e.g., 1 or 100) for the COM subpixel and decreases for subpixels further away from the COM subpixel. In some implementations, the weighted decay value is multiplied by a preset factor, such as 100.

Further, the ground truth decay map generator 1202 assigns all background subpixels a same predetermine value (e.g., a minimalist background value).

The ground truth decay map 1204 expresses the contiguous subpixels in the disjointed regions and the background subpixels based on the assigned values. The ground truth decay map 1204 also stores the assigned values in an array of units, with each unit in the array representing a corresponding subpixel in the input.

Training

Figure 28:
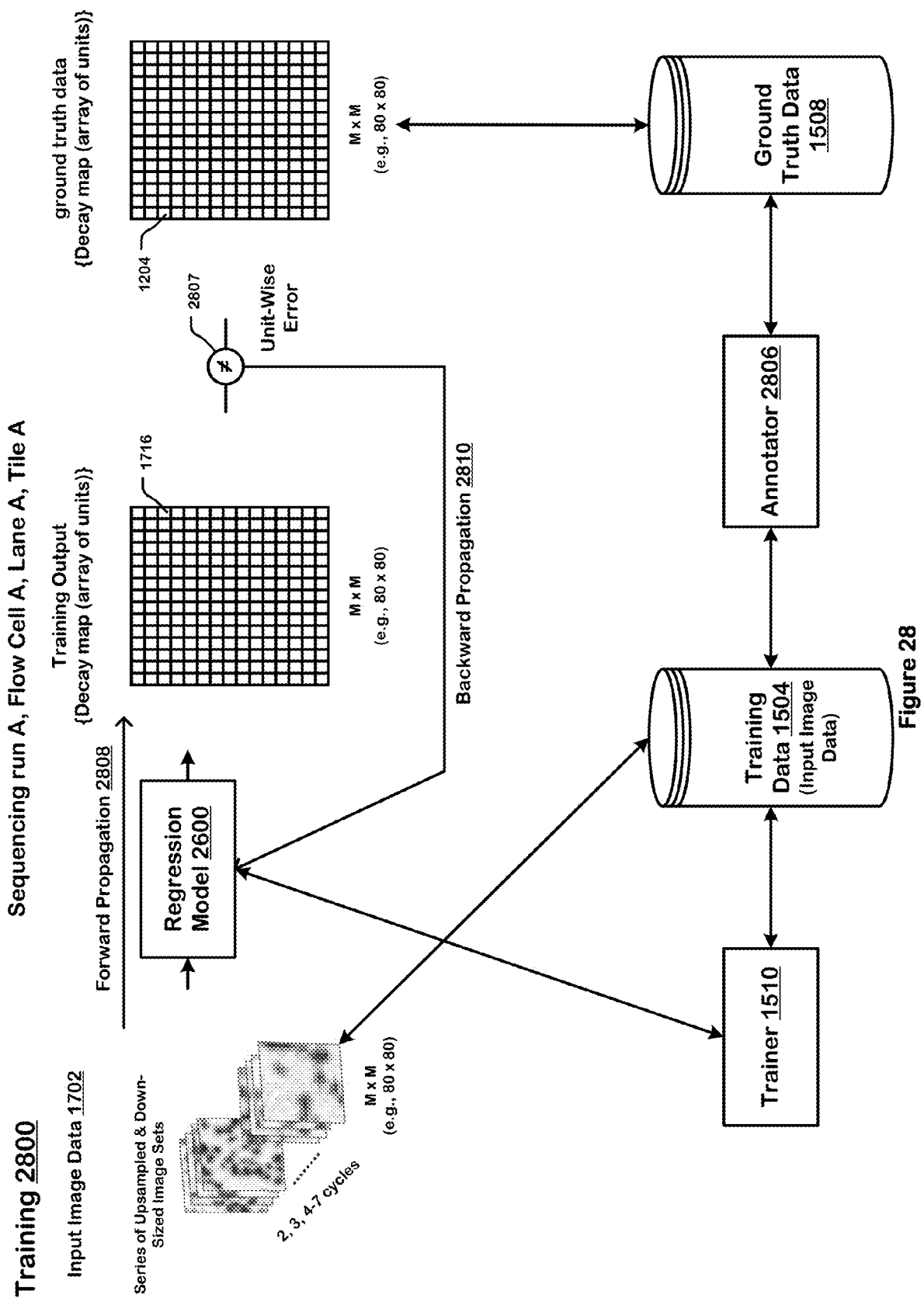
FIG. 28 is one implementation of training the regression model using a backpropagation-based gradient update technique.

FIG. 28 is one implementation of training 2800 the regression model 2600 using a backpropagation-based gradient update technique that modifies parameters of the regression model 2600 until the decay map 1716 produced by the regression model 2600 as training output during the training 2800 progressively approaches or matches the ground truth decay map 1204.

The training 2800 includes iteratively optimizing a loss function that minimizes error 2807 between the decay map 1716 and the ground truth decay map 1204, and updating parameters of the regression model 2600 based on the error 2807. In one implementation, the loss function is mean squared error and the error is minimized on a subpixel-by-subpixel basis between weighted decay values of corresponding subpixels in the decay map 1716 and the ground truth decay map 1204.

The training 2800 includes hundreds, thousands, and/or millions of iterations of forward propagation 2808 and backward propagation 2810, including parallelization techniques such as batching. The training data 1504 includes, as the input image data 1702, a series of upsampled and down-sized image sets. The training data 1504 is annotated with ground truth labels by an annotator 2806. The training 2800 is operationalized by the trainer 1510 using a stochastic gradient update algorithm such as ADAM.

Inference

Figure 29:
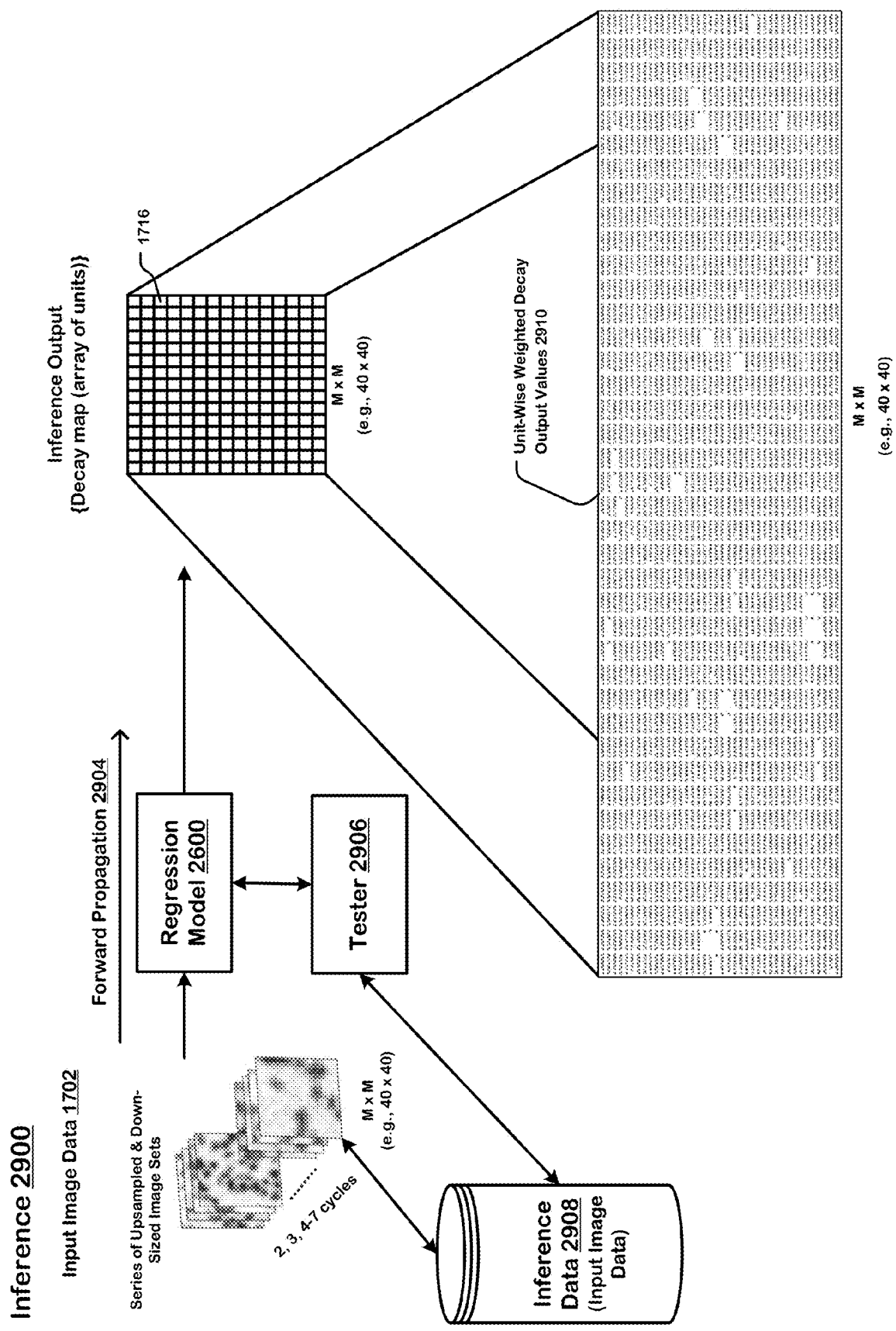
FIG. 29 is one implementation of template generation by the regression model during inference.

FIG. 29 is one implementation of template generation by the regression model 2600 during inference 2900 in which the decay map 1716 is produced by the regression model 2600 as the inference output during the inference 2900. One example of the decay map 1716 is disclosed in the Appendix titled "Regression Model Sample Ouput". The Appendix includes unit-wise weighted decay output values 2910 that together represent the decay map 1716.

The inference 2900 includes hundreds, thousands, and/or millions of iterations of forward propagation 2904, including parallelization techniques such as batching. The inference 2900 is performed on inference data 2908 that includes, as the input image data 1702, a series of upsampled and down-sized image sets. The inference 2900 is operationalized by a tester 2906.

Watershed Segmentation

Figure 30:
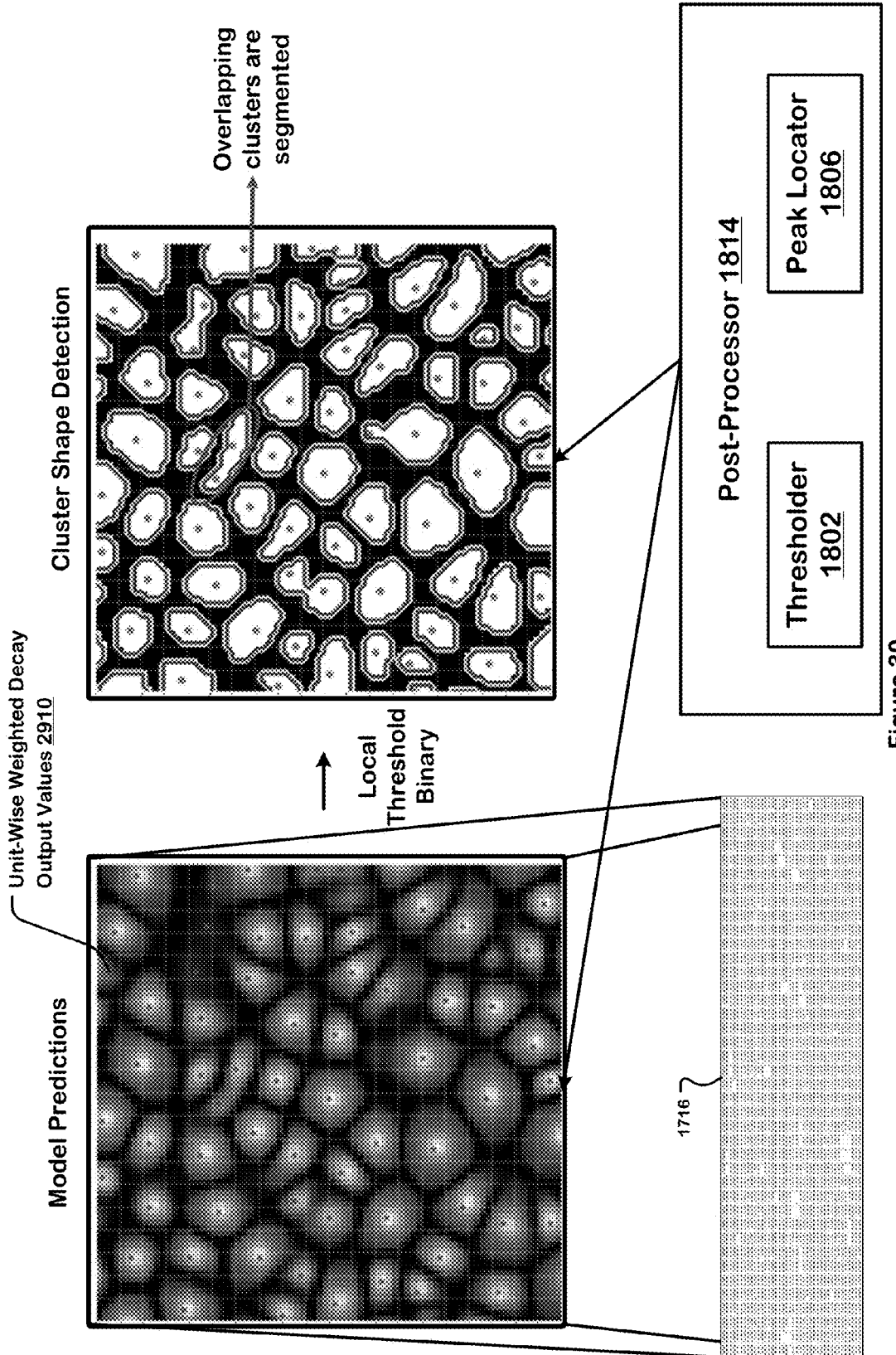
FIG. 30 illustrates one implementation of subjecting the decay map to post-processing to identify cluster metadata.

FIG. 30 illustrates one implementation of subjecting the decay map 1716 to (i) thresholding to identify background subpixels characterizing cluster background and to (ii) peak detection to identify center subpixels characterizing cluster centers. The thresholding is performed by the thresholder 1802 that uses a local threshold binary to produce binarized output. The peak detection is performed by the peak locator 1806 to identify the cluster centers. Additional details about the peak locator can be found in the Appendix entitled "Peak Detection".

Figure 31:
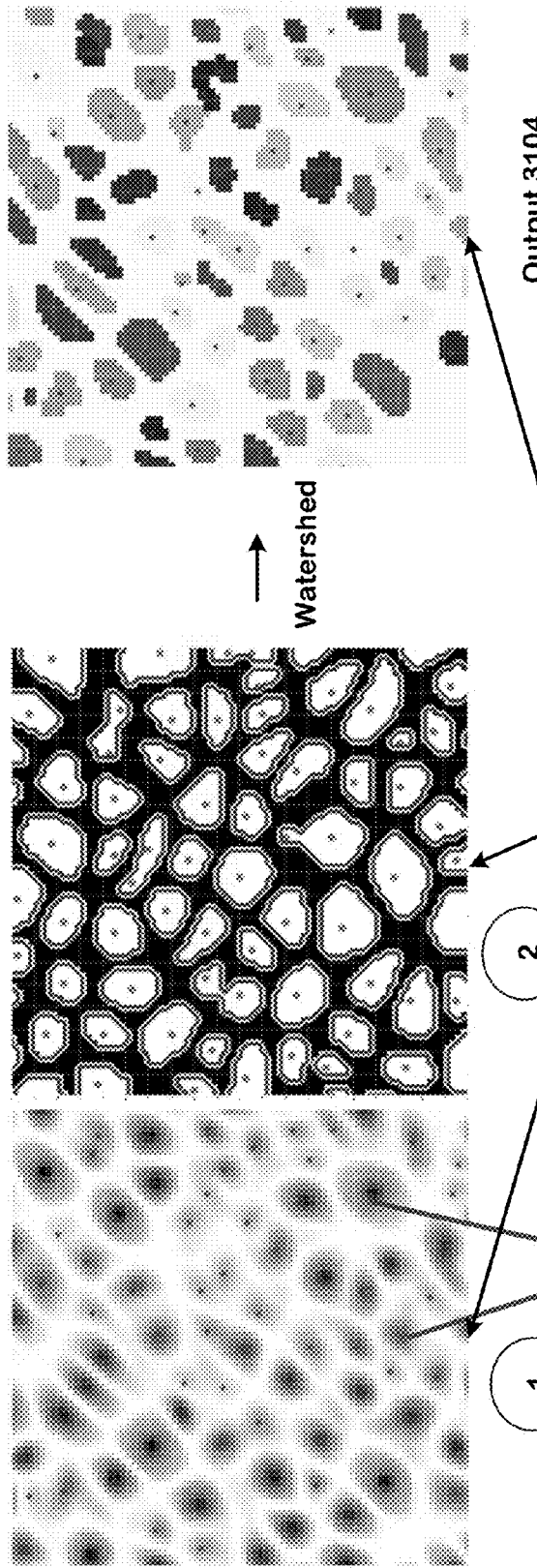
FIG. 31 depicts one implementation of a watershed segmentation technique identifying non-overlapping groups of contiguous cluster/cluster interior subpixels that characterize the clusters.

FIG. 31 depicts one implementation of a watershed segmentation technique that takes as input the background subpixels and the center subpixels respectively identified by the thresholder 1802 and the peak locator 1806, finds valleys in intensity between adjoining clusters, and outputs non-overlapping groups of contiguous cluster/cluster interior subpixels characterizing the clusters. Additional details about the watershed segmentation technique can be found in the Appendix entitled "Watershed Segmentation".

In one implementation, a watershed segmenter 3102 takes as input (1) negativized output values 2910 in the decay map 1716, (2) binarized output of the thresholder 1802, and (3) cluster centers identified by the peak locator 1806. Then, based on the input, the watershed segmenter 3102 produces output 3104. In the output 3104, each cluster center is identified as a unique set/group of subpixels that belong to the cluster center (as long as the subpixels are "1" in the binary output, i.e., not background subpixels). Further, the clusters are filtered based on containing at least four subpixels. The watershed segmenter 3102 can be part of the segmenter 1810, which in turn is part of the post-processor 1814.

Network Architecture

FIG. 32 is a table that shows an example U-Net architecture of the regression model 2600, along with details of the layers of the regression model 2600, dimensionality of the output of the layers, magnitude of the model parameters, and interconnections between the layers. Similar details are disclosed in the file titled "Regression Model Example Architecture", which is submitted as an appendix to this application.

Cluster Intensity Extraction

Figure 33:
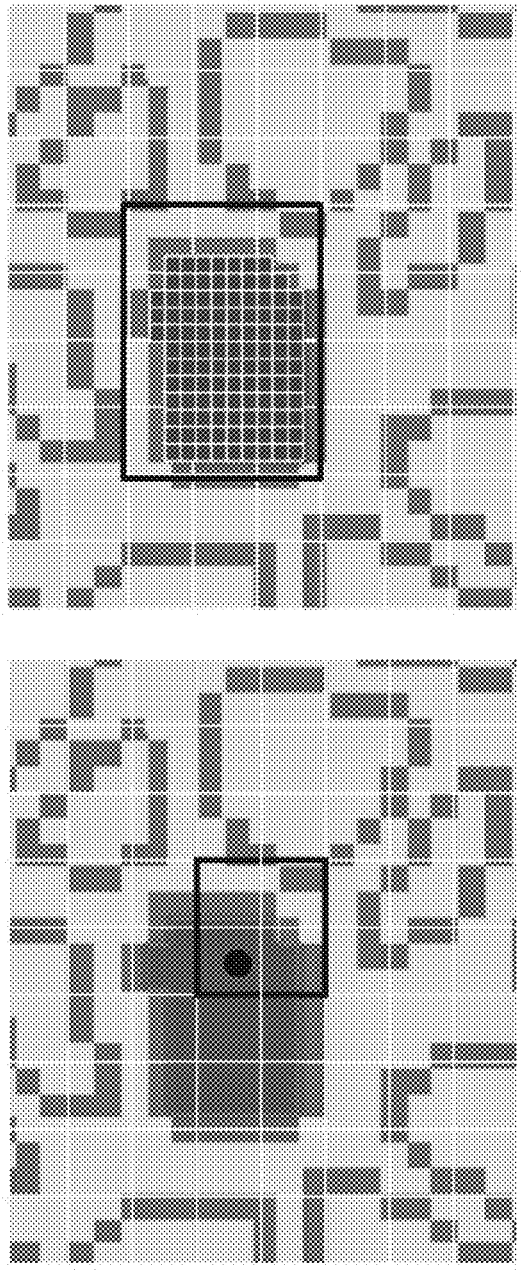
FIG. 33 illustrates different approaches of extracting cluster intensity using cluster shape information identified in a template image.

FIG. 33 illustrates different approaches of extracting cluster intensity using cluster shape information identified in a template image. As discussed above, the template image identifies the cluster shape information in the upsampled, subpixel resolution. However, the cluster intensity information is in the sequencing images 108, which are typically in the optical, pixel-resolution.

According to a first approach, coordinates of the subpixels are located in the sequencing images 108 and their respective intensities extracted using bilinear interpolation and normalized based on a count of the subpixels that contribute to a cluster.

The second approach uses a weighted area coverage technique to modulate the intensity of a pixel according to a number of subpixels that contribute to the pixel. Here too, the modulated pixel intensity is normalized by a subpixel count parameter.

The third approach upsamples the sequencing images into the subpixel domain using bicubic interpolation, sums the intensity of the upsampled pixels belonging to a cluster, and normalizes the summed intensity based on a count of the upsampled pixels that belong to the cluster.

Experimental Results and Observations

Figure 34:
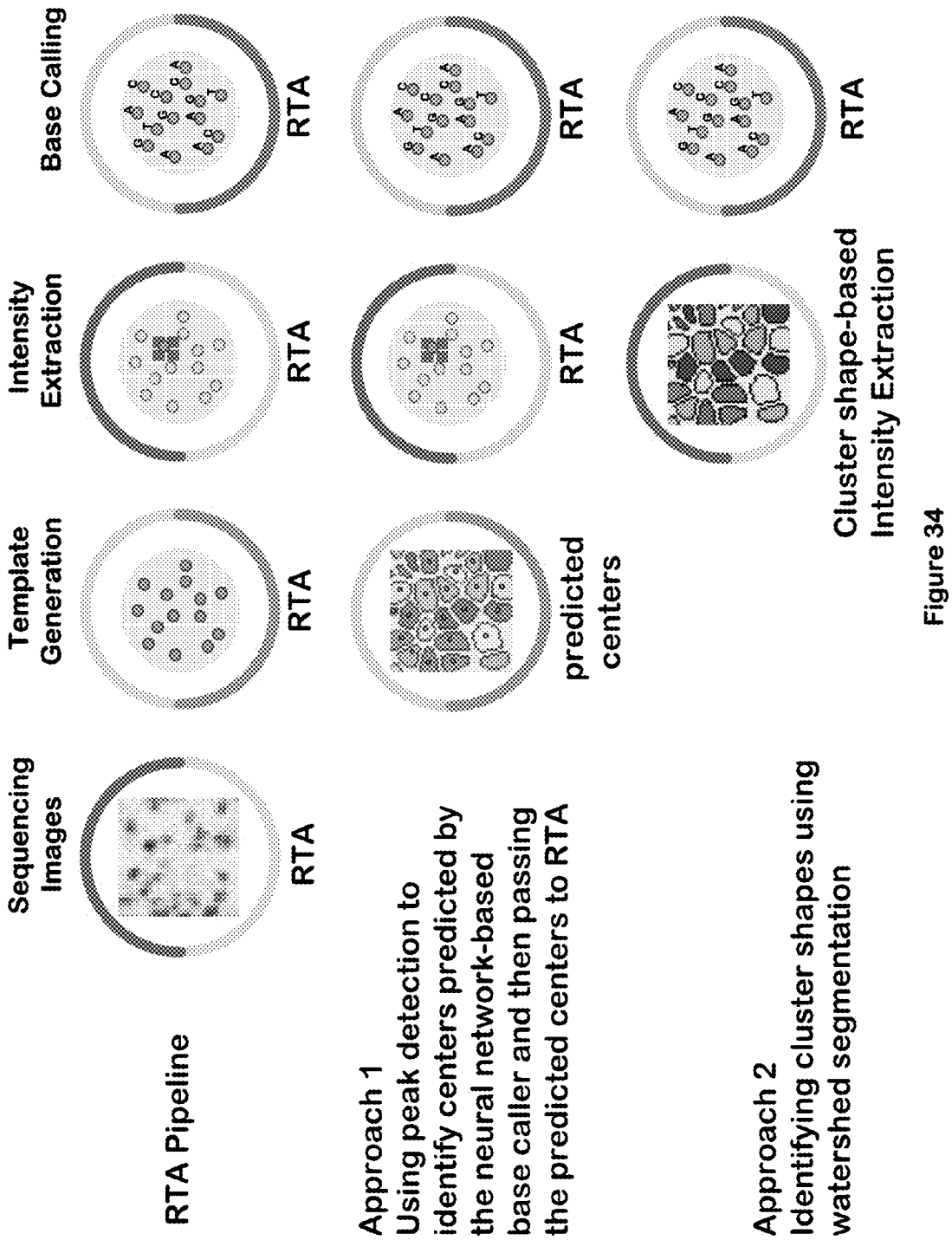
FIG. 34 shows different approaches of base calling using the outputs of the regression model.

FIG. 34 shows different approaches of base calling using the outputs of the regression model 2600. In the first approach, the cluster centers identified from the output of the neural network-based template generator 1512 in the template image are fed to a base caller (e.g., Illumina's Real-Time Analysis software, referred to herein as "RTA base caller") for base calling.

In the second approach, instead of the cluster centers, the cluster intensities extracted from the sequencing images based on the cluster shape information in the template image are fed to the RTA base caller for base calling.

FIG. 35 illustrates the difference in base calling performance when the RTA base caller uses ground truth center of mass (COM) location as the cluster center, as opposed to using a non-COM location as the cluster center. The results show that using COM improves base calling.

Example Model Outputs

FIG. 36 shows, on the left, an example decay map 1716 produced by the regression model 2600. On the right, FIG. 36 also shows an example ground truth decay map 1204 that the regression model 2600 approximates during the training.

Both the decay map 1716 and the ground truth decay map 1204 depict clusters as disjointed regions of contiguous subpixels, the centers of the clusters as center subpixels at centers of mass of the respective ones of the disjointed regions, and their surrounding background as background subpixels not belonging to any of the disjointed regions.

Also, the contiguous subpixels in the respective ones of the disjointed regions have values weighted according to distance of a contiguous subpixel from a center subpixel in a disjointed region to which the contiguous subpixel belongs. In one implementation, the center subpixels have the highest values within the respective ones of the disjointed regions. In one implementation, the background subpixels all have a same minimalist background value within a decay map.

Figure 37:
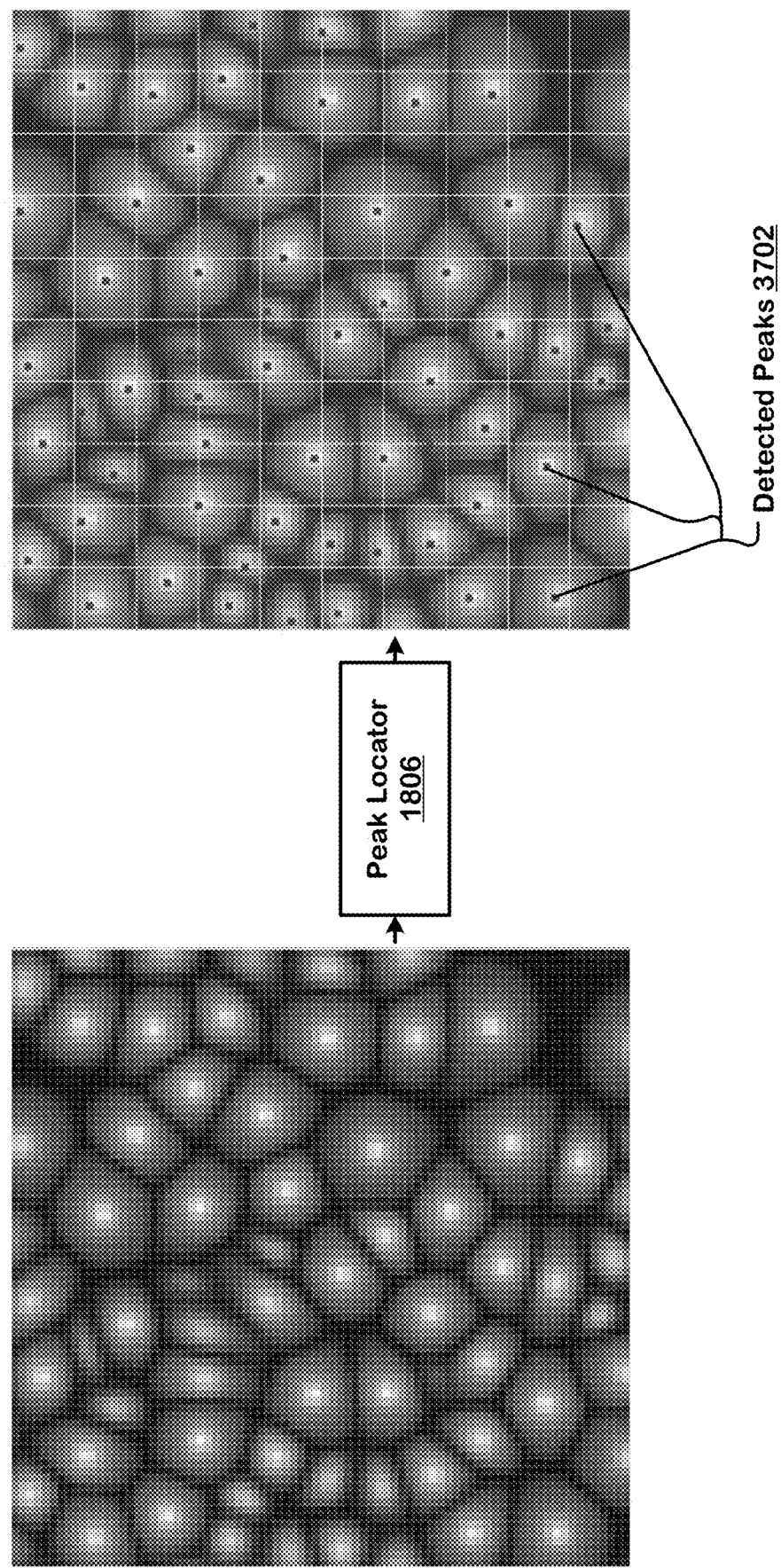
FIG. 37 portrays one implementation of the peak locator identifying cluster centers in the decay map by detecting peaks.

FIG. 37 portrays one implementation of the peak locator 1806 identifying cluster centers in a decay map by detecting peaks 3702. Additional details about the peak locator can be found in the Appendix entitled "Peak Detection".

FIG. 38 compares peaks detected by the peak locator 1806 in the decay map 1716 produced by the regression model 2600 with peaks in a corresponding ground truth decay map 1204. The red markers are peaks predicted by the regression model 2600 as cluster centers and the green markers are the ground truth centers of mass of the clusters.

More Experimental Results and Observations

Figure 39:
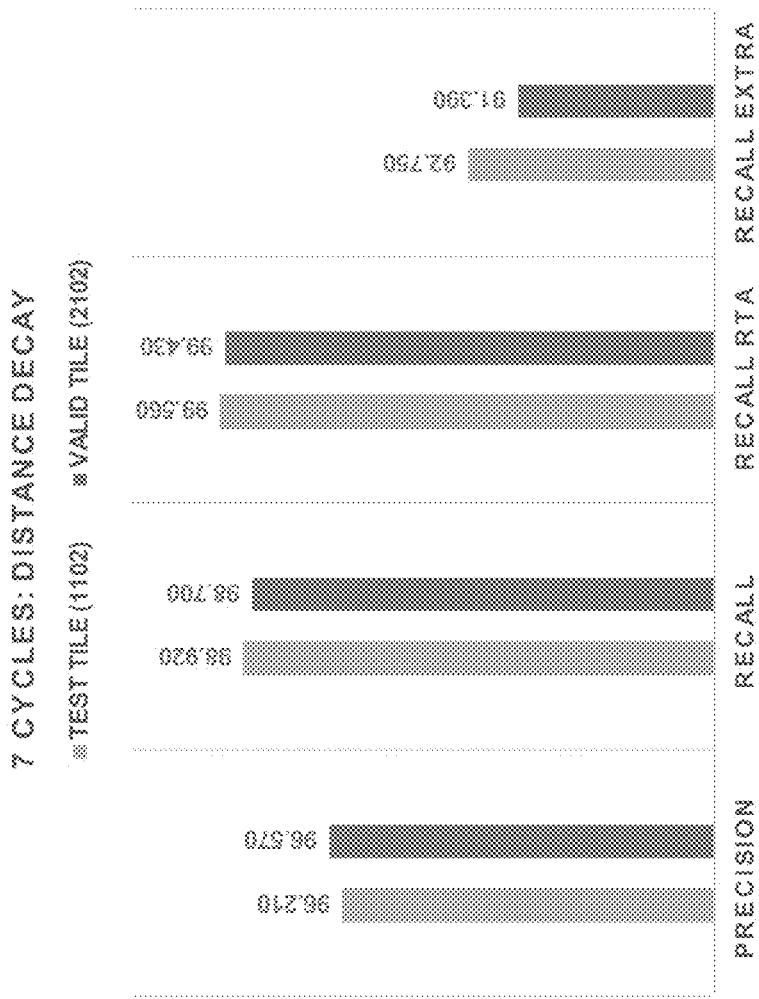
FIG. 39 illustrates performance of the regression model using precision and recall statistics.

FIG. 39 illustrates performance of the regression model 2600 using precision and recall statistics. The precision and recall statistics demonstrate that the regression model 2600 is good at recovering all identified cluster centers.

FIG. 40 compares performance of the regression model 2600 with the RTA base caller for 20 pM library concentration (normal run). Outperforming the RTA base caller, the regression model 2600 identifies 34,323 (4.46%) more clusters in a higher cluster density environment (i.e., 988,884 clusters).

FIG. 40 also shows results for other sequencing metrics such as number of clusters that pass the chastity filter ("% PF" (pass-filter)), number of aligned reads ("% Aligned"), number of duplicate reads ("% Duplicate"), number of reads mismatching the reference sequence for all reads aligned to the reference sequence ("% Mismatch"), bases called with quality score 30 and above ("% Q30 bases"), and so on.

FIG. 41 compares performance of the regression model 2600 with the RTA base caller for 30 pM library concentration (dense run). Outperforming the RTA base caller, the regression model 2600 identifies 34,323 (6.27%) more clusters in a much higher cluster density environment (i.e., 1,351,588 clusters).

FIG. 41 also shows results for other sequencing metrics such as number of clusters that pass the chastity filter ("% PF" (pass-filter)), number of aligned reads ("% Aligned"), number of duplicate reads ("% Duplicate"), number of reads mismatching the reference sequence for all reads aligned to the reference sequence ("% Mismatch"), bases called with quality score 30 and above ("% Q30 bases"), and so on.

Figure 42:
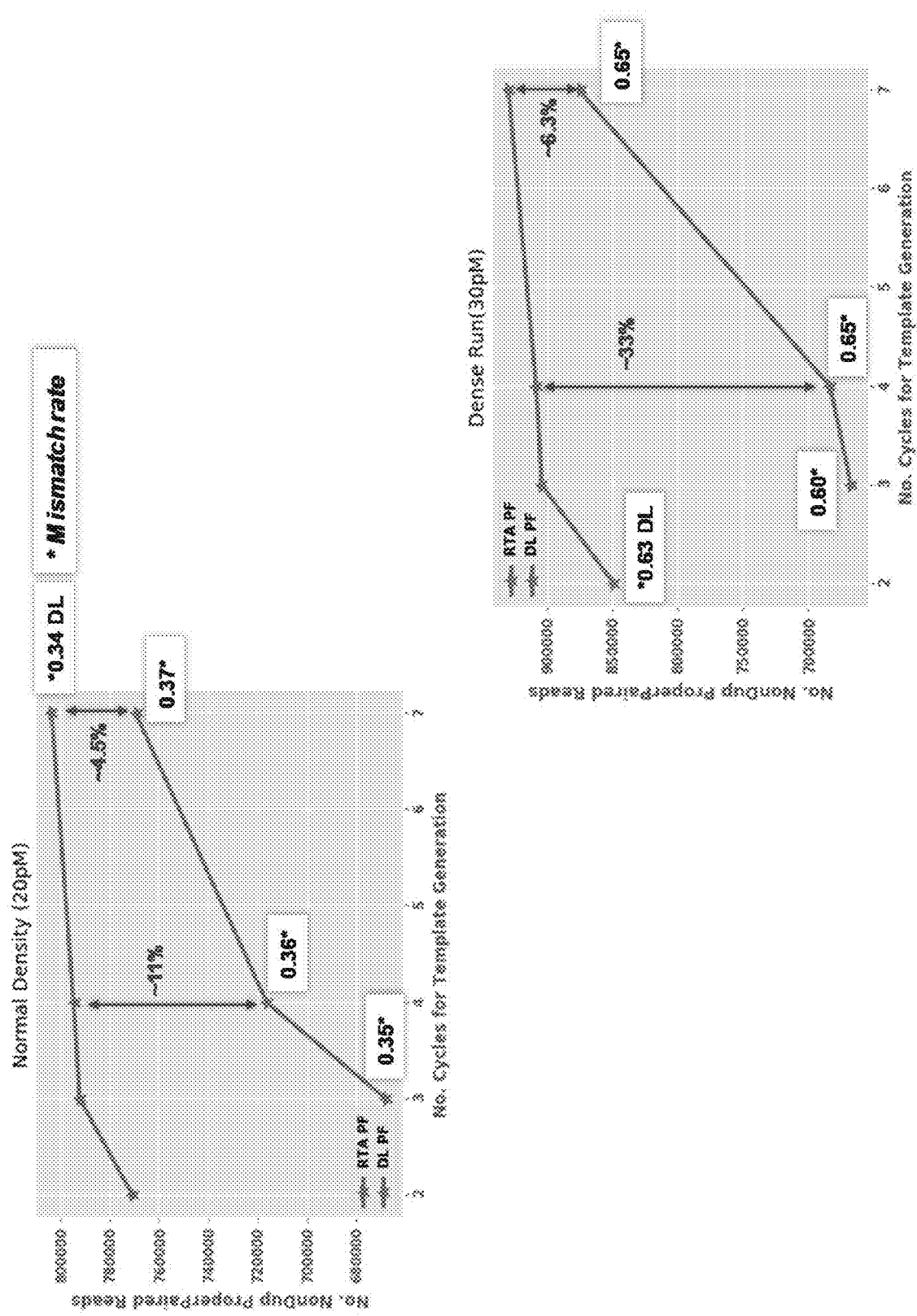
FIG. 42 compares number of non-duplicate proper read pairs, i.e., the number of paired reads that do not have both reads aligned inwards within a reasonable distance detected by the regression model versus the same detected by the RTA base caller.

FIG. 42 compares number of non-duplicate (unique or deduplicated) proper read pairs, i.e., the number of paired reads that have both reads aligned inwards within a reasonable distance detected by the regression model 2600 versus the same detected by the RTA base caller. The comparison is made both for the 20 pM normal run and the 30 pM dense run.

More importantly, FIG. 42 shows that the disclosed neural network-based template generators are able to detect more clusters in fewer sequencing cycles of input to template generation than the RTA base caller. In just four sequencing cycles, the regression model 2600 identifies 11% more non-duplicate proper read pairs than the RTA base caller during the 20 pM normal run and 33% more non-duplicate proper read pairs than the RTA base caller during the 30 pM dense run. In just seven sequencing cycles, the regression model 2600 identifies 4.5% more non-duplicate proper read pairs than the RTA base caller during the 20 pM normal run and 6.3% more non-duplicate proper read pairs than the RTA base caller during the 30 pM dense run.

FIG. 43 shows, on the right, a first decay map produced by the regression model 2600. The first decay map identifies clusters and their surrounding background imaged during the 20 pM normal run, along with their spatial distribution depicting cluster shapes, cluster sizes, and cluster centers.

On the left, FIG. 43 shows a second decay map produced by the regression model 2600. The second decay map identifies clusters and their surrounding background imaged during the 30 pM dense run, along with their spatial distribution depicting cluster shapes, cluster sizes, and cluster centers.

FIG. 44 compares performance of the regression model 2600 with the RTA base caller for 40 pM library concentration (highly dense run). The regression model 2600 produced 89,441,688 more aligned bases than the RTA base caller in a much higher cluster density environment (i.e., 1,509,395 clusters).

FIG. 44 also shows results for other sequencing metrics such as number of clusters that pass the chastity filter ("% PF" (pass-filter)), number of aligned reads ("% Aligned"), number of duplicate reads ("% Duplicate"), number of reads mismatching the reference sequence for all reads aligned to the reference sequence ("% Mismatch"), bases called with a quality score 30 and above ("% Q30 bases"), and so on.

More Example Model Outputs

Figure 45:
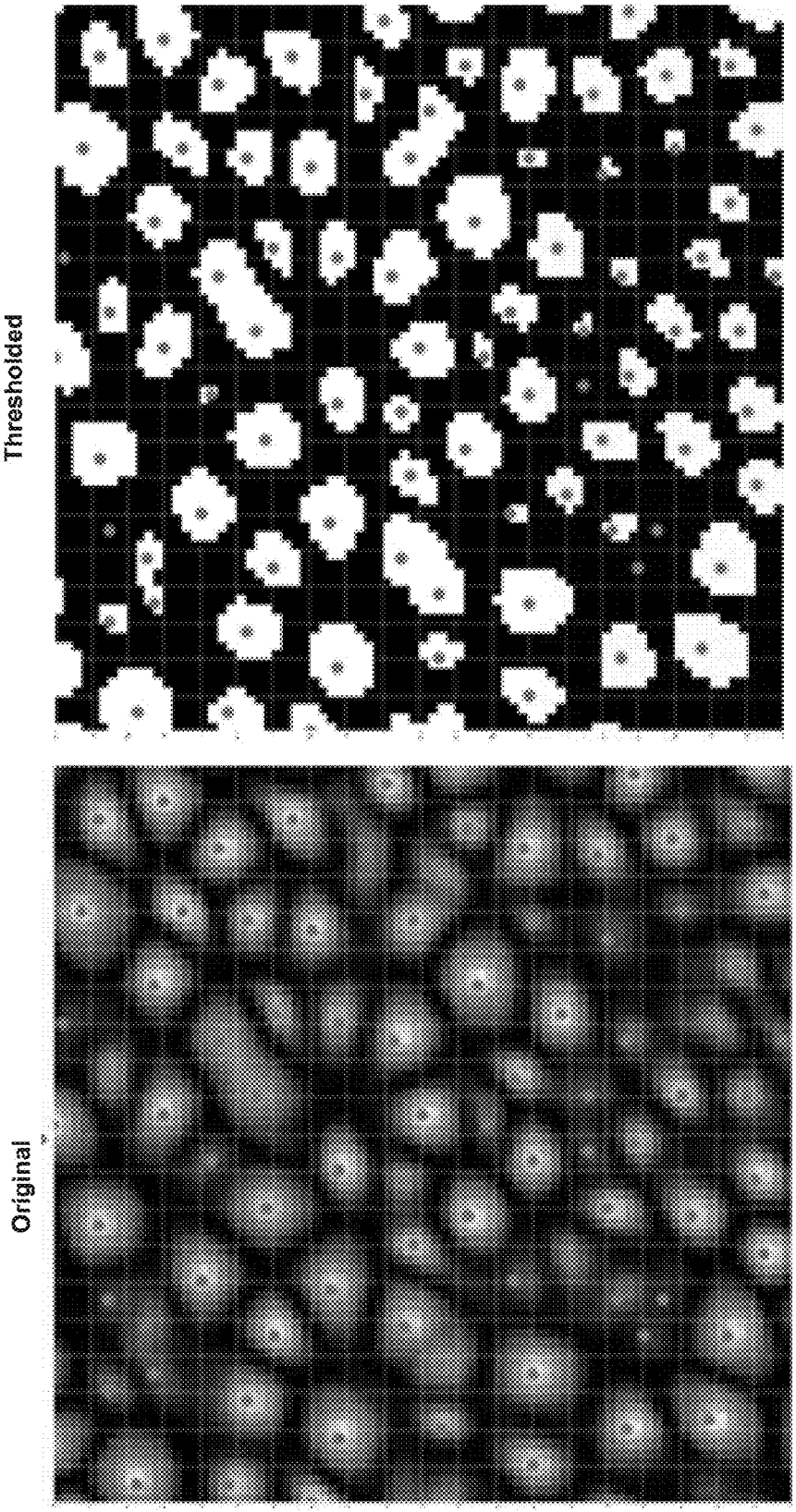
FIG. 45 shows, on the left, a first decay map produced by the regression model. On the right.

FIG. 45 shows, on the left, a first decay map produced by the regression model 2600. The first decay map identifies clusters and their surrounding background imaged during the 40 pM normal run, along with their spatial distribution depicting cluster shapes, cluster sizes, and cluster centers.

On the right, FIG. 45 shows the results of the thresholding and the peak locating applied to the first decay map to distinguish the respective clusters from each other and from the background and to identify their respective cluster centers. In some implementations, intensities of the respective clusters are identified and a chastity filter (or passing filter) applied to reduce the mismatch rate.

2. Binary Classification Model

Figure 46:
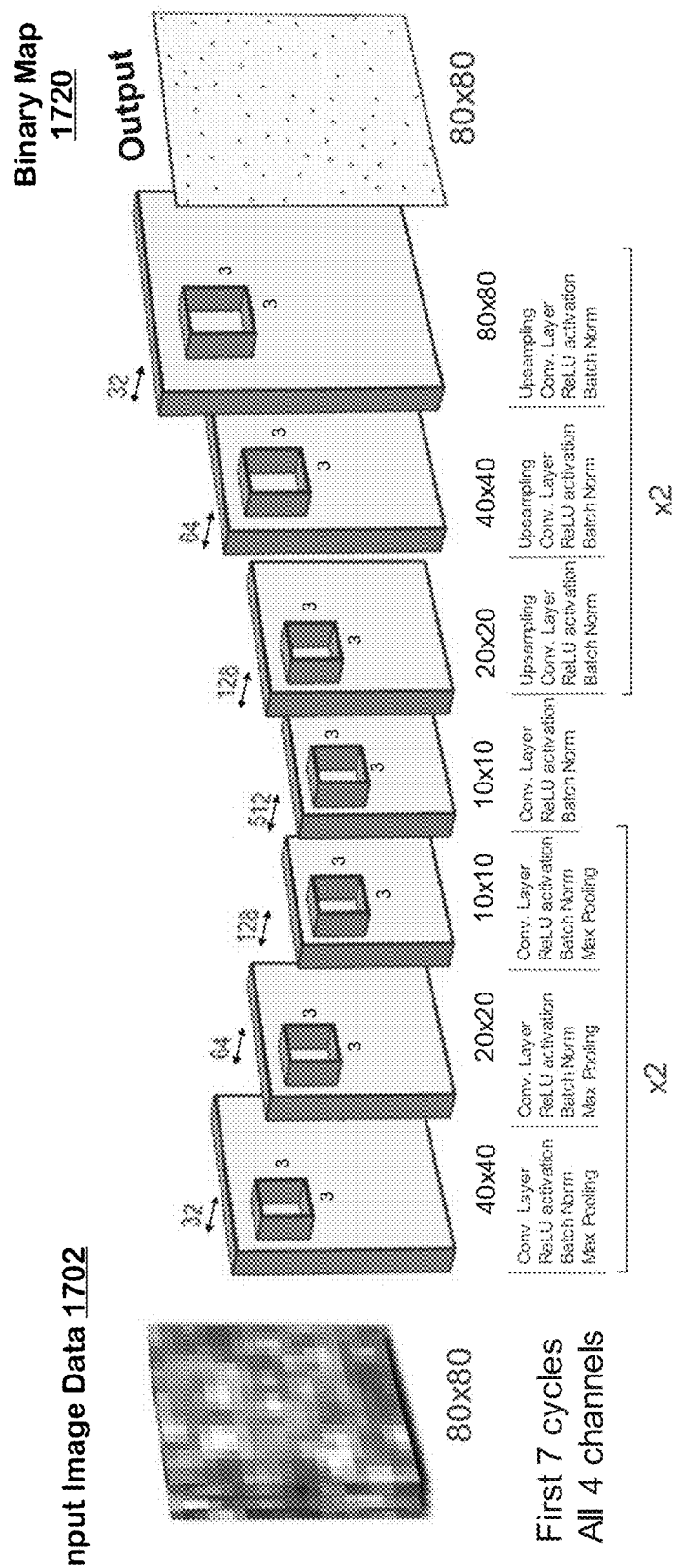
FIG. 46 illustrates one implementation of the binary classification model.

FIG. 46 illustrates one implementation of the binary classification model 4600. In the illustrated implementation, the binary classification model 4600 is a deep fully convolutional segmentation neural network that processes the input image data 1702 through an encoder subnetwork and a corresponding decoder subnetwork. The encoder subnetwork includes a hierarchy of encoders. The decoder subnetwork includes a hierarchy of decoders that map low resolution encoder feature maps to a full input resolution binary map 1720. In another implementation, the binary classification model 4600 is a U-Net network with skip connections between the decoder and the encoder. Additional details about the segmentation networks can be found in the Appendix entitled "Segmentation Networks".

Binary Map

The final output layer of the binary classification model 4600 is a unit-wise classification layer that produces a classification label for each unit in an output array. In some implementations, the unit-wise classification layer is a subpixel-wise classification layer that produces a softmax classification score distribution for each subpixel in the binary map 1720 across two classes, namely, a cluster center class and a non-cluster class, and the classification label for a given subpixel is determined from the corresponding softmax classification score distribution.

In other implementations, the unit-wise classification layer is a subpixel-wise classification layer that produces a sigmoid classification score for each subpixel in the binary map 1720, such that the activation of a unit is interpreted as the probability that the unit belongs to the first class and, conversely, one minus the activation gives the probability that it belongs to the second class.

The binary map 1720 expresses each subpixel based on the predicted classification scores. The binary map 1720 also stores the predicted value classification scores in an array of units, with each unit in the array representing a corresponding subpixel in the input.

Training

Figure 47:
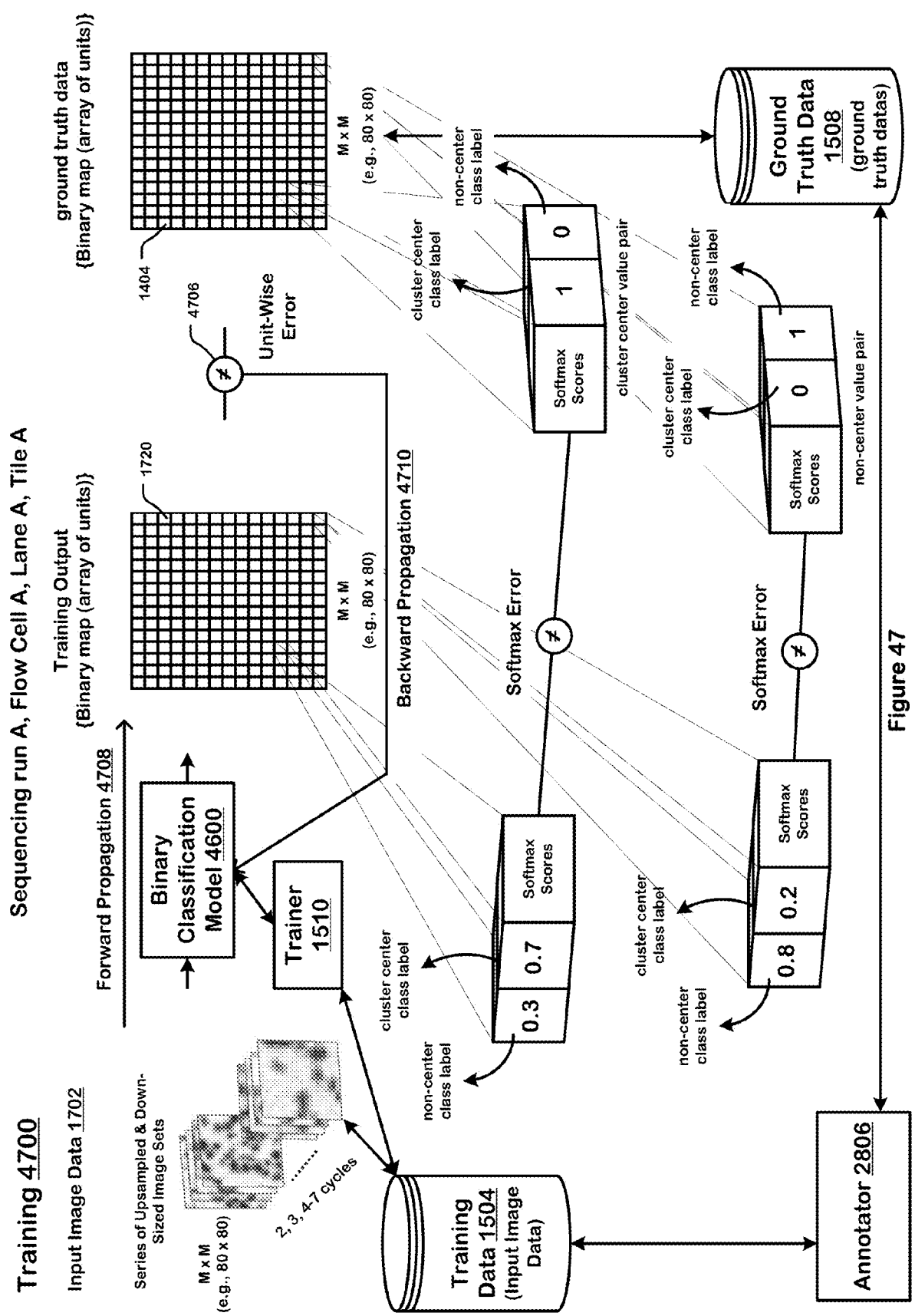
FIG. 47 is one implementation of training the binary classification model using a backpropagation-based gradient update technique that involves softmax scores.

FIG. 47 is one implementation of training 4700 the binary classification model 4600 using a backpropagation-based gradient update technique that modifies parameters of the binary classification model 4600 until the binary map 1720 of the binary classification model 4600 progressively approaches or matches the ground truth binary map 1404.

In the illustrated implementation, the final output layer of the binary classification model 4600 is a softmax-based subpixel-wise classification layer. In softmax implementations, the ground truth binary map generator 1402 assigns each ground truth subpixel either (i) a cluster center value pair (e.g., [1, 0]) or (ii) a non-center value pair (e.g., [0, 1]).

In the cluster center value pair [1, 0], a first value [1] represents the cluster center class label and a second value [0] represents the non-center class label. In the non-center value pair [0, 1], a first value [0] represents the cluster center class label and a second value [1] represents the non-center class label.

The ground truth binary map 1404 expresses each subpixel based on the assigned value pair/value. The ground truth binary map 1404 also stores the assigned value pairs/values in an array of units, with each unit in the array representing a corresponding subpixel in the input.

The training includes iteratively optimizing a loss function that minimizes error 4706 (e.g., softmax error) between the binary map 1720 and the ground truth binary map 1404, and updating parameters of the binary classification model 4600 based on the error 4706.

In one implementation, the loss function is a custom-weighted binary cross-entropy loss and the error 4706 is minimized on a subpixel-by-subpixel basis between predicted classification scores (e.g., softmax scores) and labelled class scores (e.g., softmax scores) of corresponding subpixels in the binary map 1720 and the ground truth binary map 1404, as shown in FIG. 47.

The custom-weighted loss function gives more weight to the COM subpixels, such that the cross-entropy loss is multiplied by a corresponding reward (or penalty) weight specified in a reward (or penalty) matrix whenever a COM subpixel is misclassified. Additional details about the custom-weighted loss function can be found in the Appendix entitled "Custom-Weighted Loss Function".

The training 4700 includes hundreds, thousands, and/or millions of iterations of forward propagation 4708 and backward propagation 4710, including parallelization techniques such as batching. The training data 1504 includes, as the input image data 1702, a series of upsampled and down-sized image sets. The training data 1504 is annotated with ground truth labels by the annotator 2806. The training 2800 is operationalized by the trainer 1510 using a stochastic gradient update algorithm such as ADAM.

Figure 48:
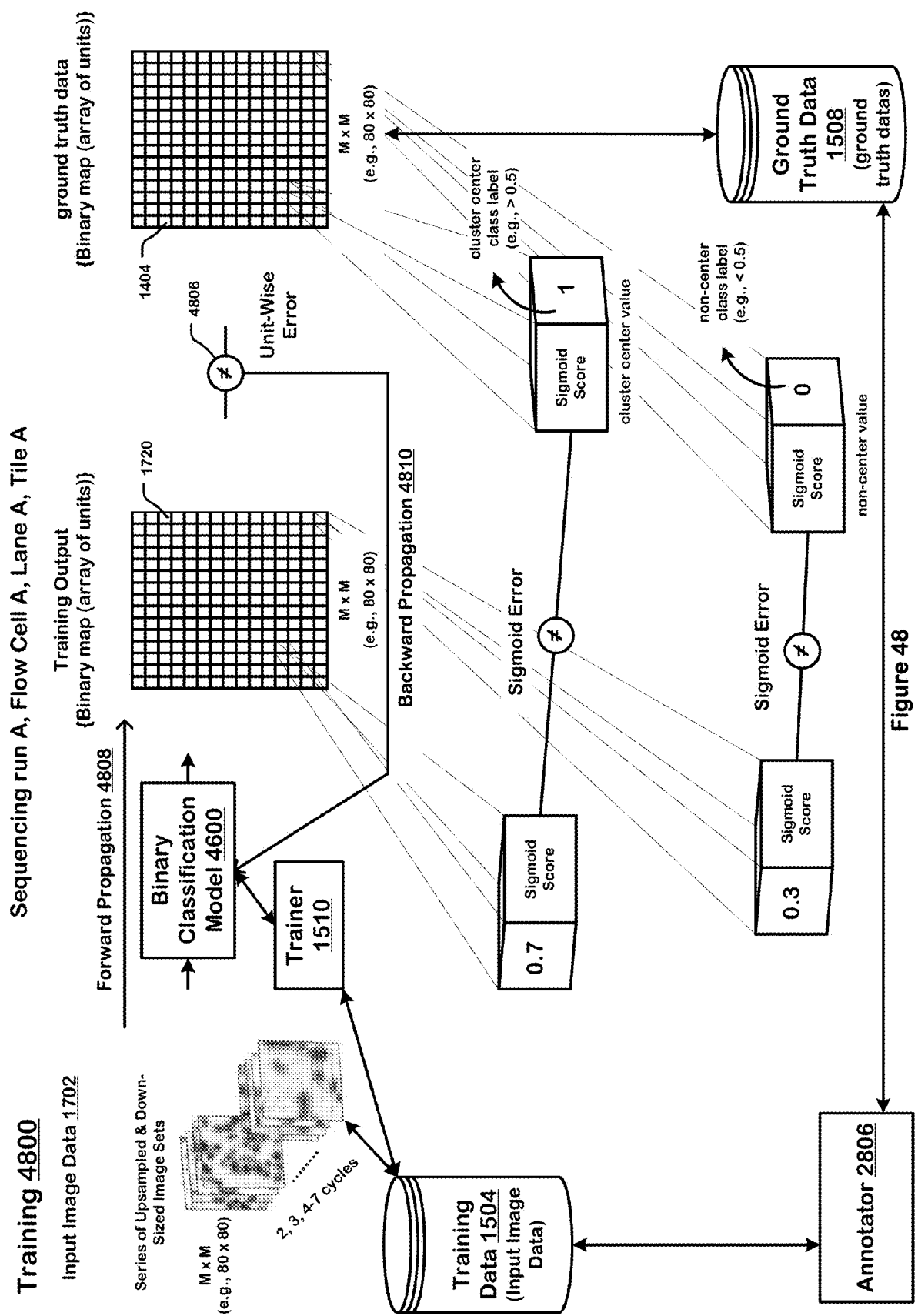
FIG. 48 is another implementation of training the binary classification model using a backpropagation-based gradient update technique that involves sigmoid scores.

FIG. 48 is another implementation of training 4800 the binary classification model 4600, in which the final output layer of the binary classification model 4600 is a sigmoid-based subpixel-wise classification layer.

In sigmoid implementations, the ground truth binary map generator 1302 assigns each ground truth subpixel either (i) a cluster center value (e.g., [1]) or (ii) a non-center value (e.g., [0]). The COM subpixels are assigned the cluster center value pair/value and all other subpixels are assigned the non-center value pair/value.

With the cluster center value, values above a threshold intermediate value between 0 and 1 (e.g., values above 0.5) represent the center class label. With the non-center value, values below a threshold intermediate value between 0 and 1 (e.g., values below 0.5) represent the non-center class label.

The ground truth binary map 1404 expresses each subpixel based on the assigned value pair/value. The ground truth binary map 1404 also stores the assigned value pairs/values in an array of units, with each unit in the array representing a corresponding subpixel in the input.

The training includes iteratively optimizing a loss function that minimizes error 4806 (e.g., sigmoid error) between the binary map 1720 and the ground truth binary map 1404, and updating parameters of the binary classification model 4600 based on the error 4806.

In one implementation, the loss function is a custom-weighted binary cross-entropy loss and the error 4806 is minimized on a subpixel-by-subpixel basis between predicted scores (e.g., sigmoid scores) and labelled scores (e.g., sigmoid scores) of corresponding subpixels in the binary map 1720 and the ground truth binary map 1404, as shown in FIG. 48.

The custom-weighted loss function gives more weight to the COM subpixels, such that the cross-entropy loss is multiplied by a corresponding reward (or penalty) weight specified in a reward (or penalty) matrix whenever a COM subpixel is misclassified. Additional details about the custom-weighted loss function can be found in the Appendix entitled "Custom-Weighted Loss Function".

The training 4800 includes hundreds, thousands, and/or millions of iterations of forward propagation 4808 and backward propagation 4810, including parallelization techniques such as batching. The training data 1504 includes, as the input image data 1702, a series of upsampled and down-sized image sets. The training data 1504 is annotated with ground truth labels by the annotator 2806. The training 2800 is operationalized by the trainer 1510 using a stochastic gradient update algorithm such as ADAM.

Figure 49:
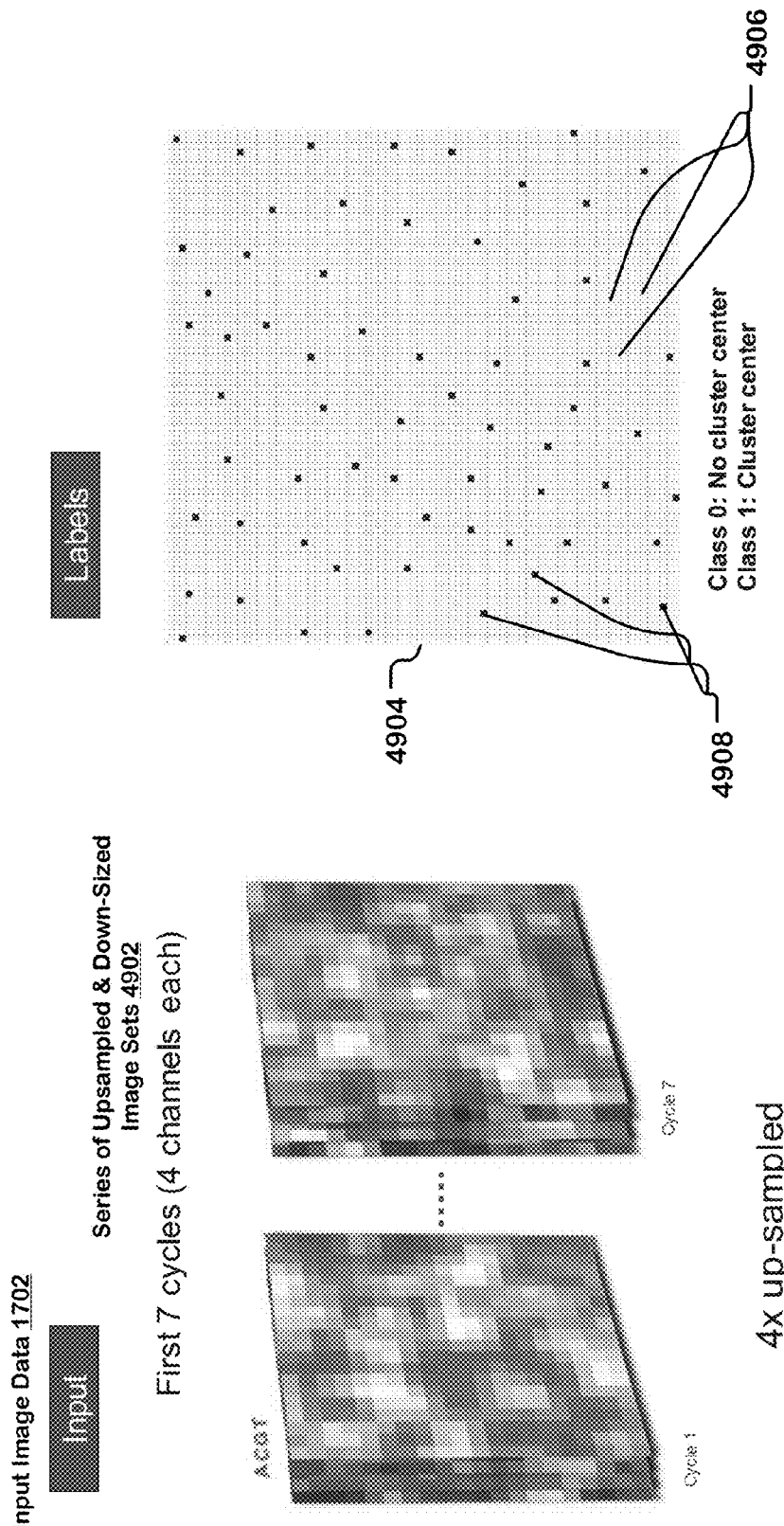
FIG. 49 illustrates another implementation of the input image data fed to the binary classification model and the corresponding class labels used to train the binary classification model.

FIG. 49 illustrates another implementation of the input image data 1702 fed to the binary classification model 4600 and the corresponding class labels 4904 used to train the binary classification model 4600.

In the illustrated implementation, the input image data 1702 comprises a series of upsampled and down-sized image sets 4902. The class labels 4904 comprise two classes: (1) "no cluster center" and (2) "cluster center", which are distinguished using different output values. That is, (1) the light green units/subpixels 4906 represent subpixels that are predicted by the binary classification model 4600 to not contain the cluster centers and (2) the dark green subpixels 4908 represent units/subpixels that are predicted by the binary classification model 4600 to contain the cluster centers.

Inference

Figure 50:
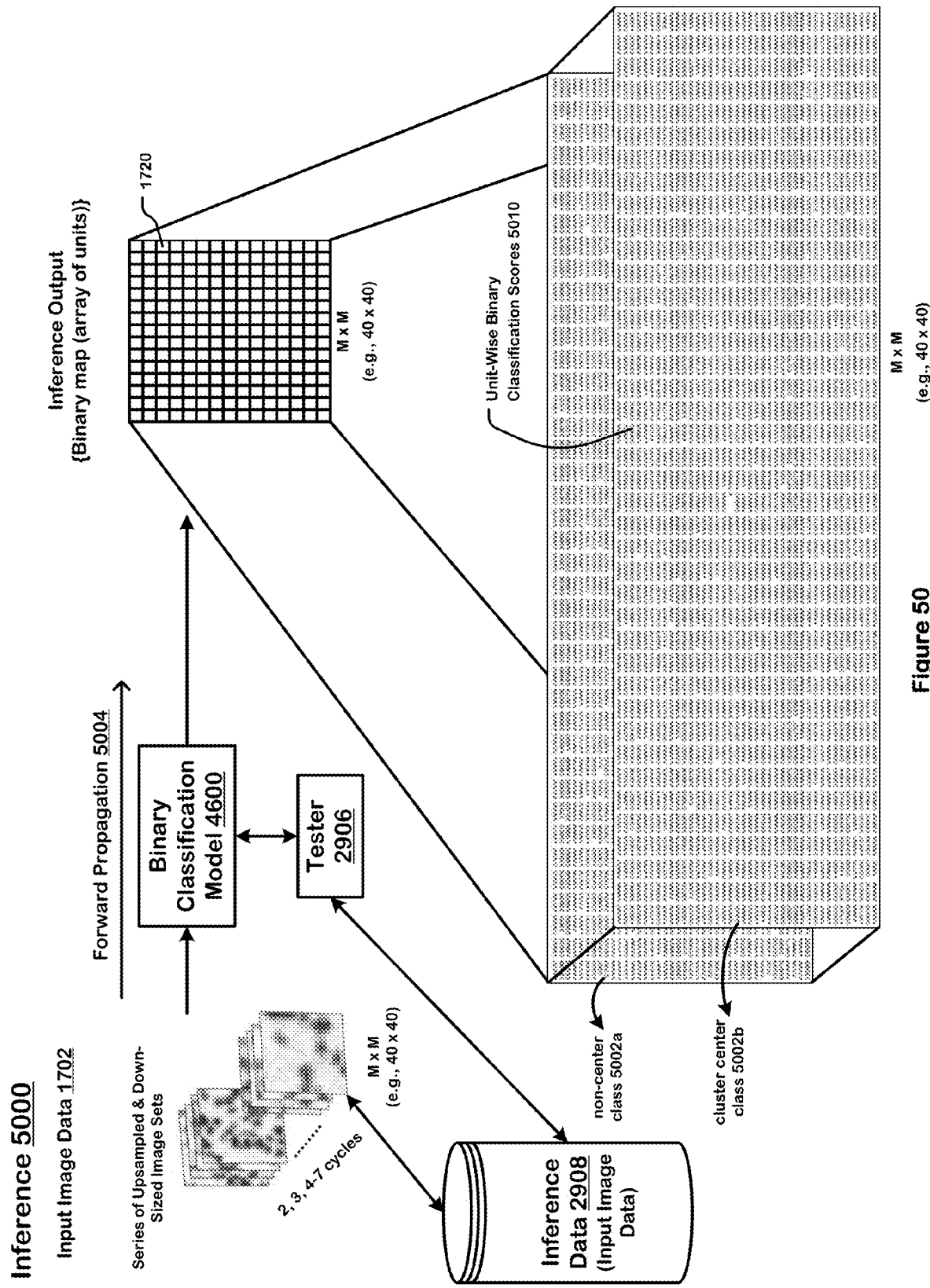
FIG. 50 is one implementation of template generation by the binary classification model during inference.

FIG. 50 is one implementation of template generation by the binary classification model 4600 during inference 5000 in which the binary map 1720 is produced by the binary classification model 4600 as the inference output during the inference 5000. One example of the binary map 1720 includes unit-wise binary classification scores 5010 that together represent the binary map 1720. In the softmax applications, the binary map 1720 has a first array 5002a of unit-wise classification scores for the non-center class and a second array 5002b of unit-wise classification scores for the cluster center class.

The inference 5000 includes hundreds, thousands, and/or millions of iterations of forward propagation 5004, including parallelization techniques such as batching. The inference 5000 is performed on inference data 2908 that includes, as the input image data 1702, a series of upsampled and down-sized image sets. The inference 5000 is operationalized by the tester 2906.

In some implementations, the binary map 1720 is subjected to post-processing techniques discussed above, such as thresholding, peak detection, and/or watershed segmentation to generate cluster metadata.

Peak Detection

Figure 51:
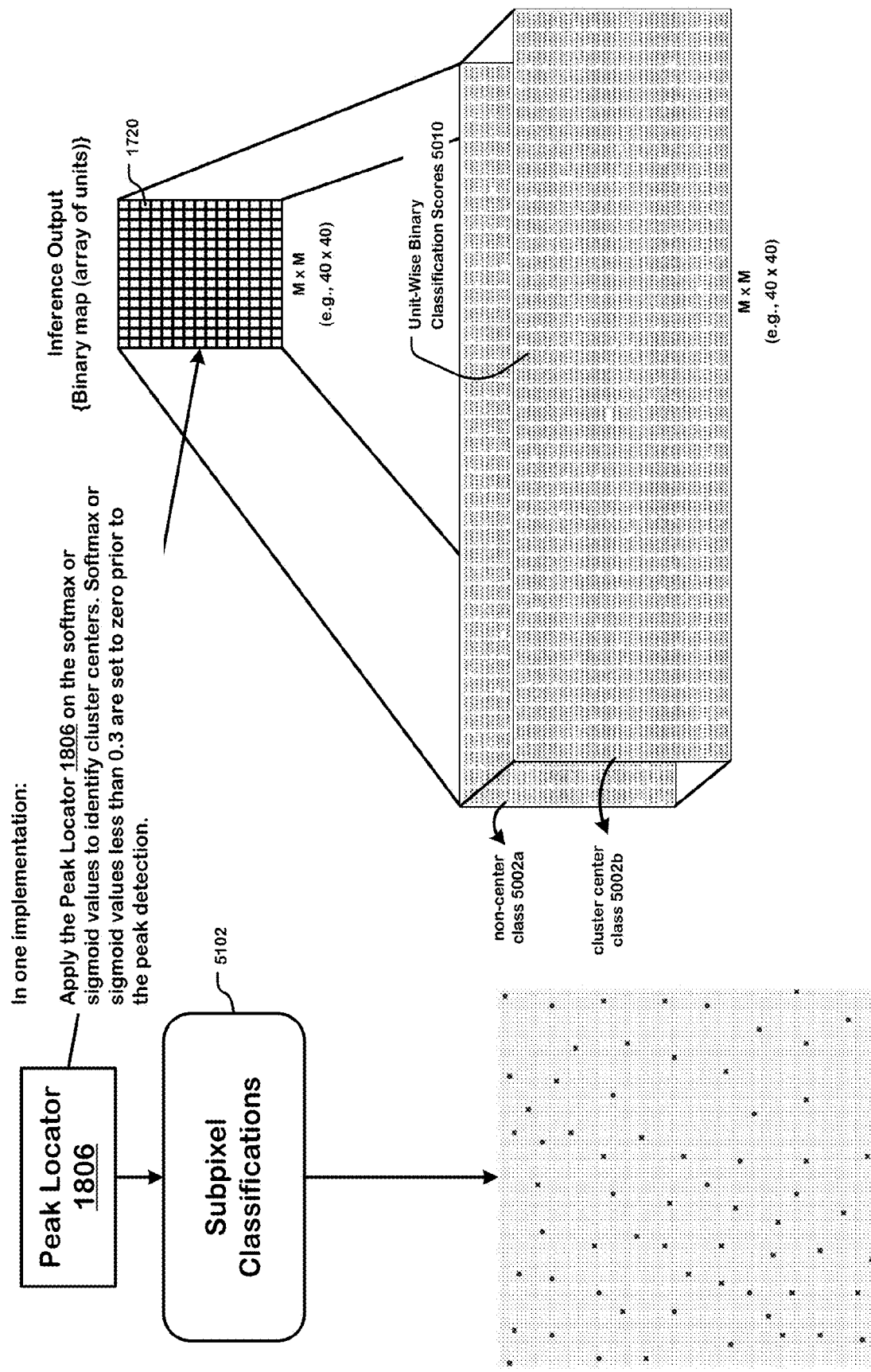
FIG. 51 illustrates one implementation of subjecting the binary map to peak detection to identify cluster centers.

FIG. 51 depicts one implementation of subjecting the binary map 1720 to peak detection to identify cluster centers. As discussed above, the binary map 1720 is an array of units that classifies each subpixel based on the predicted classification scores, with each unit in the array representing a corresponding subpixel in the input. The classification scores can be softmax scores or sigmoid scores.

In the softmax applications, the binary map 1720 includes two arrays: (1) a first array 5002a of unit-wise classification scores for the non-center class and (2) a second array 5002b of unit-wise classification scores for the cluster center class. In both the arrays, each unit represents a corresponding subpixel in the input.

To determine which subpixels in the input contain the cluster centers and which do not contain the cluster centers, the peak locator 1806 applies peak detection on the units in the binary map 1720. The peak detection identifies those units that have classification scores (e.g., softmax/sigmoid scores) above a preset threshold. The identified units are inferred as the cluster centers and their corresponding subpixels in the input are determined to contain the cluster centers and stored as cluster center subpixels in a subpixel classifications data store 5102. Additional details about the peak locator 1806 can be found in the Appendix entitled "Peak Detection".

The remaining units and their corresponding subpixels in the input are determined to not contain the cluster centers and stored as non-center subpixels in the subpixel classifications data store 5102.

In some implementations, prior to applying the peak detection, those units that have classification scores below a certain background threshold (e.g., 0.3) are set to zero. In some implementations, such units and their corresponding subpixels in the input are inferred to denote the background surrounding the clusters and stored as background subpixels in the subpixel classifications data store 5102. In other implementations, such units can be considered noise and ignored.

Example Model Outputs

Figure 52A:
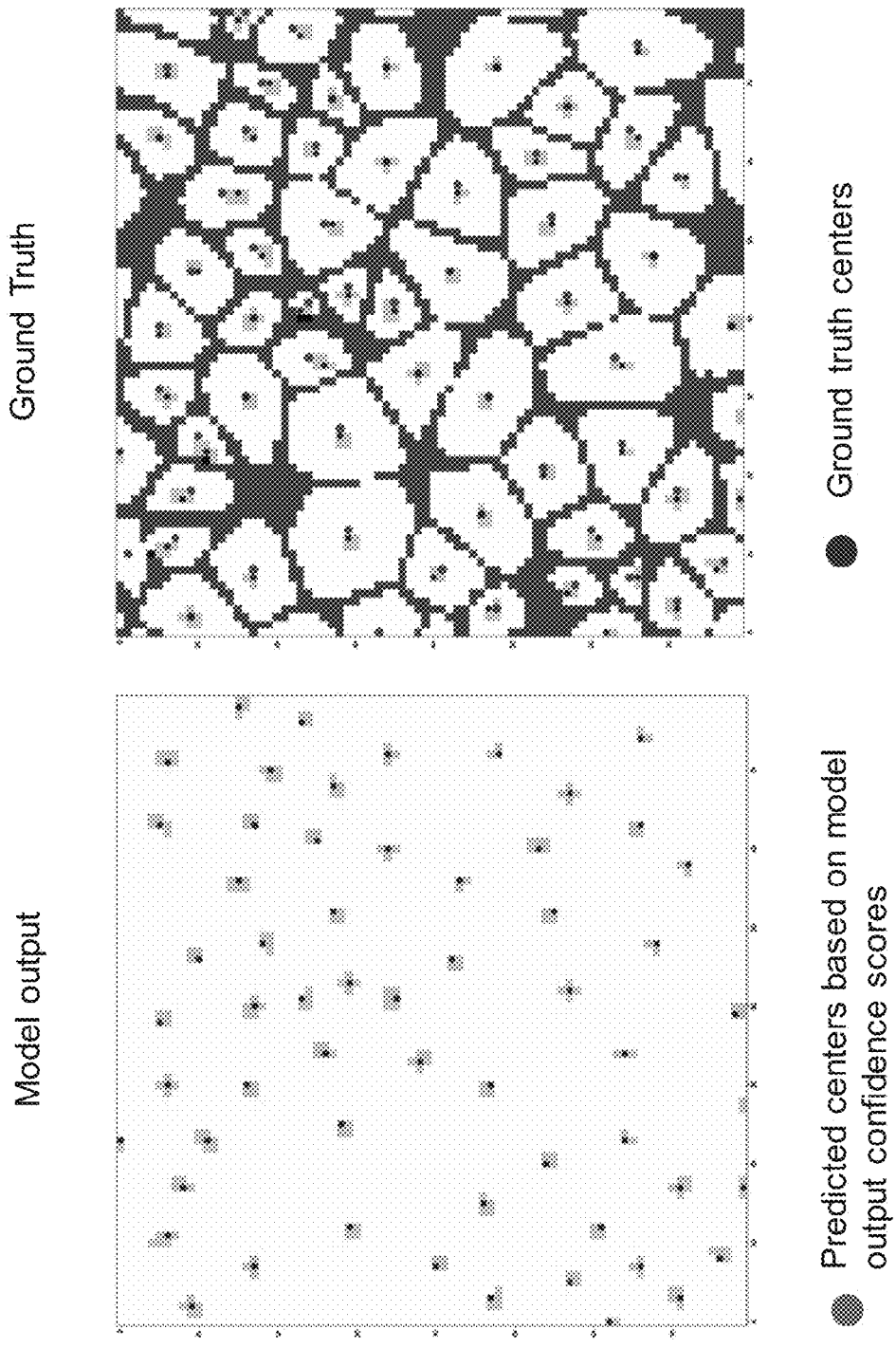
FIG. 52a shows, on the left, an example binary map produced by the binary classification model. On the right, FIG. 52a also shows an example ground truth binary map that the binary classification model approximates during the training.

FIG. 52a shows, on the left, an example binary map produced by the binary classification model 4600. On the right, FIG. 52a also shows an example ground truth binary map that the binary classification model 4600 approximates during the training. The binary map has a plurality of subpixels and classifies each subpixel as either a cluster center or a non-center. Similarly, the ground truth binary map has a plurality of subpixels and classifies each subpixel as either a cluster center or a non-center.

Experimental Results and Observations

Figure 52B:
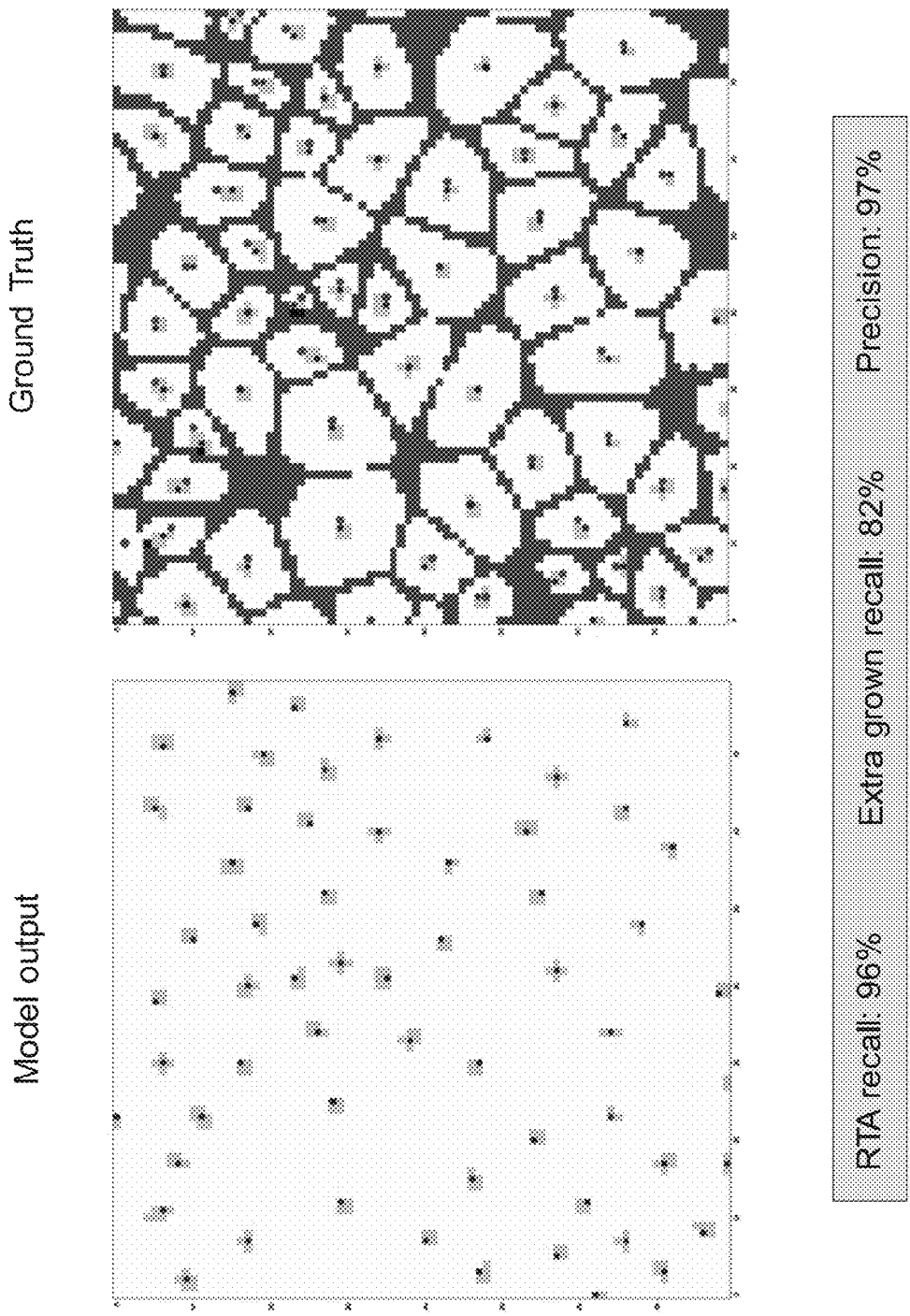
FIG. 52b illustrates performance of the binary classification model using a precision statistic.

FIG. 52b illustrates performance of the binary classification model 4600 using recall and precision statistics. Applying these statistics, the binary classification model 4600 outperforms the RTA base caller.

Network Architecture

FIG. 53 is a table that shows an example architecture of the binary classification model 4600, along with details of the layers of the binary classification model 4600, dimensionality of the output of the layers, magnitude of the model parameters, and interconnections between the layers. Similar details are disclosed in the Appendix titled "Binary Classification Model Example Architecture".

3. Ternary (Three Class) Classification Model

Figure 54:
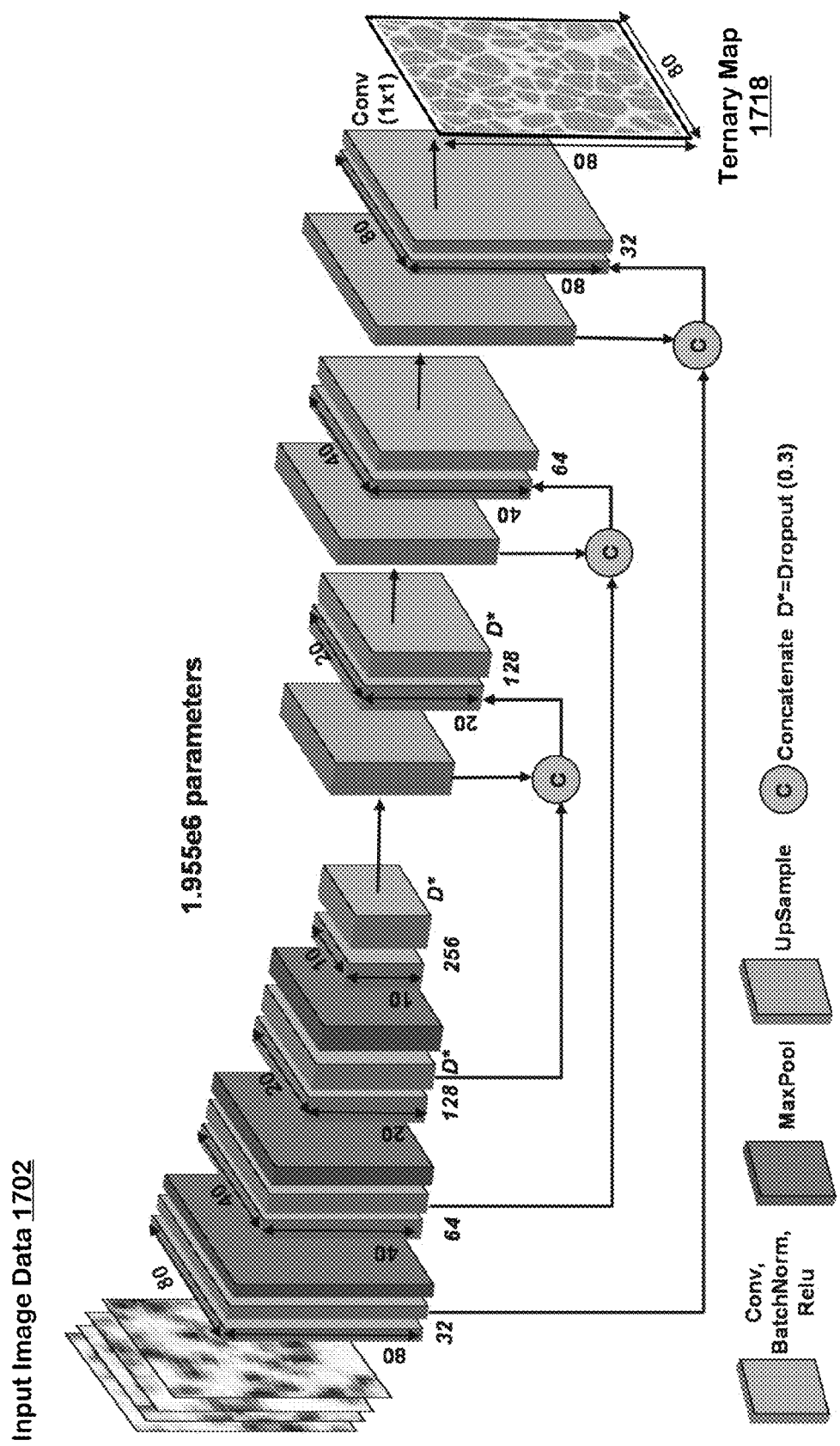
FIG. 54 illustrates one implementation of the ternary classification model.

FIG. 54 illustrates one implementation of the ternary classification model 5400. In the illustrated implementation, the ternary classification model 5400 is a deep fully convolutional segmentation neural network that processes the input image data 1702 through an encoder subnetwork and a corresponding decoder subnetwork. The encoder subnetwork includes a hierarchy of encoders. The decoder subnetwork includes a hierarchy of decoders that map low resolution encoder feature maps to a full input resolution ternary map 1718. In another implementation, the ternary classification model 5400 is a U-Net network with skip connections between the decoder and the encoder. Additional details about the segmentation networks can be found in the Appendix entitled "Segmentation Networks".

Ternary Map

The final output layer of the ternary classification model 5400 is a unit-wise classification layer that produces a classification label for each unit in an output array. In some implementations, the unit-wise classification layer is a subpixel-wise classification layer that produces a softmax classification score distribution for each subpixel in the ternary map 1718 across three classes, namely, a background class, a cluster center class, and a cluster/cluster interior class, and the classification label for a given subpixel is determined from the corresponding softmax classification score distribution.

The ternary map 1718 expresses each subpixel based on the predicted classification scores. The ternary map 1718 also stores the predicted value classification scores in an array of units, with each unit in the array representing a corresponding subpixel in the input.

Training

Figure 55:
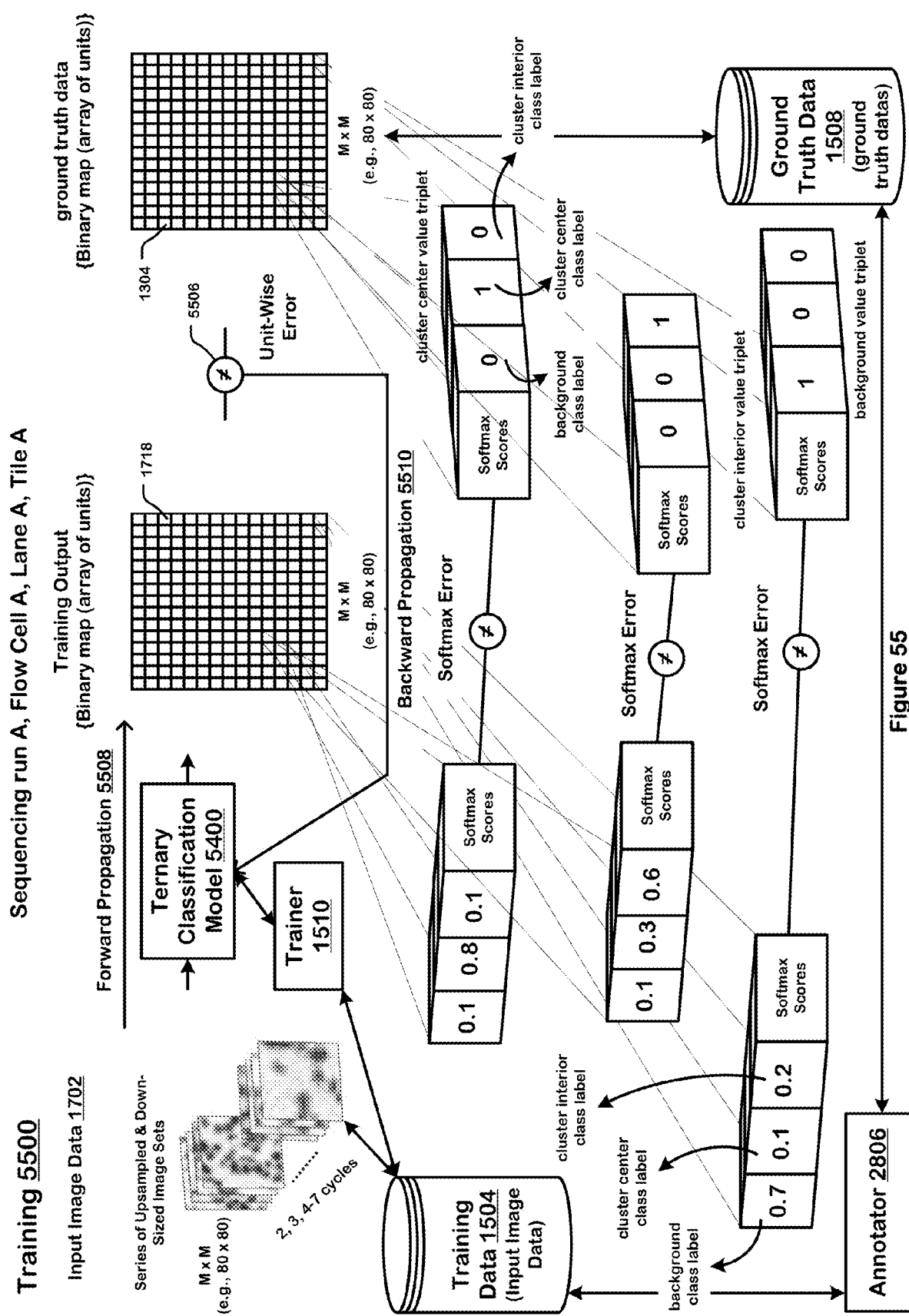
FIG. 55 is one implementation of training the ternary classification model using a backpropagation-based gradient update technique.

FIG. 55 is one implementation of training 5500 the ternary classification model 5400 using a backpropagation-based gradient update technique that modifies parameters of the ternary classification model 5400 until the ternary map 1718 of the ternary classification model 5400 progressively approaches or matches training ground truth ternary maps 1304.

In the illustrated implementation, the final output layer of the ternary classification model 5400 is a softmax-based subpixel-wise classification layer. In softmax implementations, the ground truth ternary map generator 1402 assigns each ground truth subpixel either (i) a background value triplet (e.g., [1, 0, 0]), (ii) a cluster center value triplet (e.g., [0, 1, 0]), or (iii) a cluster/cluster interior value triplet (e.g., [0, 0, 1]).

The background subpixels are assigned the background value triplet. The center of mass (COM) subpixels are assigned the cluster center value triplet. The cluster/cluster interior subpixels are assigned the cluster/cluster interior value triplet.

In the background value triplet [1, 0, 0], a first value [1] represents the background class label, a second value [0] represents the cluster center label, and a third value [0] represents the cluster/cluster interior class label.

In the cluster center value triplet [0, 1, 0], a first value [0] represents the background class label, a second value [1] represents the cluster center label, and a third value [0] represents the cluster/cluster interior class label.

In the cluster/cluster interior value triplet [0, 0, 1], a first value [0] represents the background class label, a second value [0] represents the cluster center label, and a third value [1] represents the cluster/cluster interior class label.

The ground truth ternary map 1304 expresses each subpixel based on the assigned value triplet. The ground truth ternary map 1304 also stores the assigned triplets in an array of units, with each unit in the array representing a corresponding subpixel in the input.

The training includes iteratively optimizing a loss function that minimizes error 5506 (e.g., softmax error) between the ternary map 1718 and the ground truth ternary map 1304, and updating parameters of the ternary classification model 5400 based on the error 5506.

In one implementation, the loss function is a custom-weighted categorical cross-entropy loss and the error 5506 is minimized on a subpixel-by-subpixel basis between predicted classification scores (e.g., softmax scores) and labelled class scores (e.g., softmax scores) of corresponding subpixels in the ternary map 1718 and the ground truth ternary map 1304, as shown in FIG. 54.

The custom-weighted loss function gives more weight to the COM subpixels, such that the cross-entropy loss is multiplied by a corresponding reward (or penalty) weight specified in a reward (or penalty) matrix whenever a COM subpixel is misclassified. Additional details about the custom-weighted loss function can be found in the Appendix entitled "Custom-Weighted Loss Function".

The training 5500 includes hundreds, thousands, and/or millions of iterations of forward propagation 5508 and backward propagation 5510, including parallelization techniques such as batching. The training data 1504 includes, as the input image data 1702, a series of upsampled and down-sized image sets. The training data 1504 is annotated with ground truth labels by the annotator 2806. The training 5500 is operationalized by the trainer 1510 using a stochastic gradient update algorithm such as ADAM.

Figure 56:
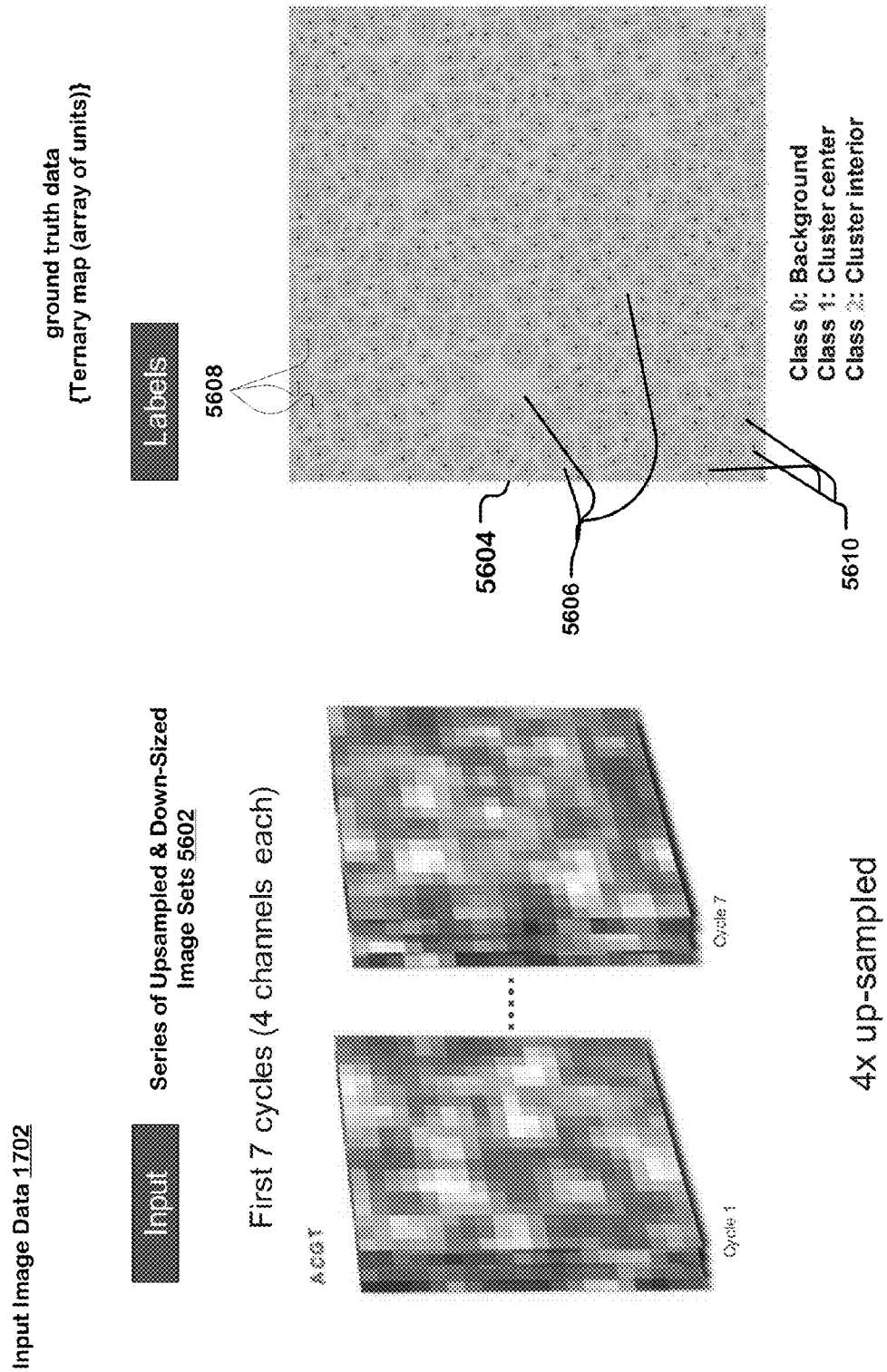
FIG. 56 illustrates another implementation of the input image data fed to the ternary classification model and the corresponding class labels used to train the ternary classification model.

FIG. 56 illustrates one implementation of input image data 1702 fed to the ternary classification model 5400 and the corresponding class labels used to train the ternary classification model 5400.

In the illustrated implementation, the input image data 1702 comprises a series of upsampled and down-sized image sets 5602. The class labels 5604 comprise three classes: (1) "background class", (2) "cluster center class", and (3) "cluster interior class", which are distinguished using different output values. For example, some of these different output values can be visually represented as follows: (1) the grey units/subpixels 5606 represent subpixels that are predicted by the ternary classification model 5400 to be the background, (2) the dark green units/subpixels 5608 represent subpixels that are predicted by the ternary classification model 5400 to contain the cluster centers, and (3) the light green subpixels 5610 represent subpixels that are predicted by the ternary classification model 5400 to contain the interior of the clusters.

Network Architecture

FIG. 57 is a table that shows an example architecture of the ternary classification model 5400, along with details of the layers of the ternary classification model 5400, dimensionality of the output of the layers, magnitude of the model parameters, and interconnections between the layers. Similar details are disclosed in the Appendix titled "Ternary Classification Model Example Architecture".

Inference

Figure 58:
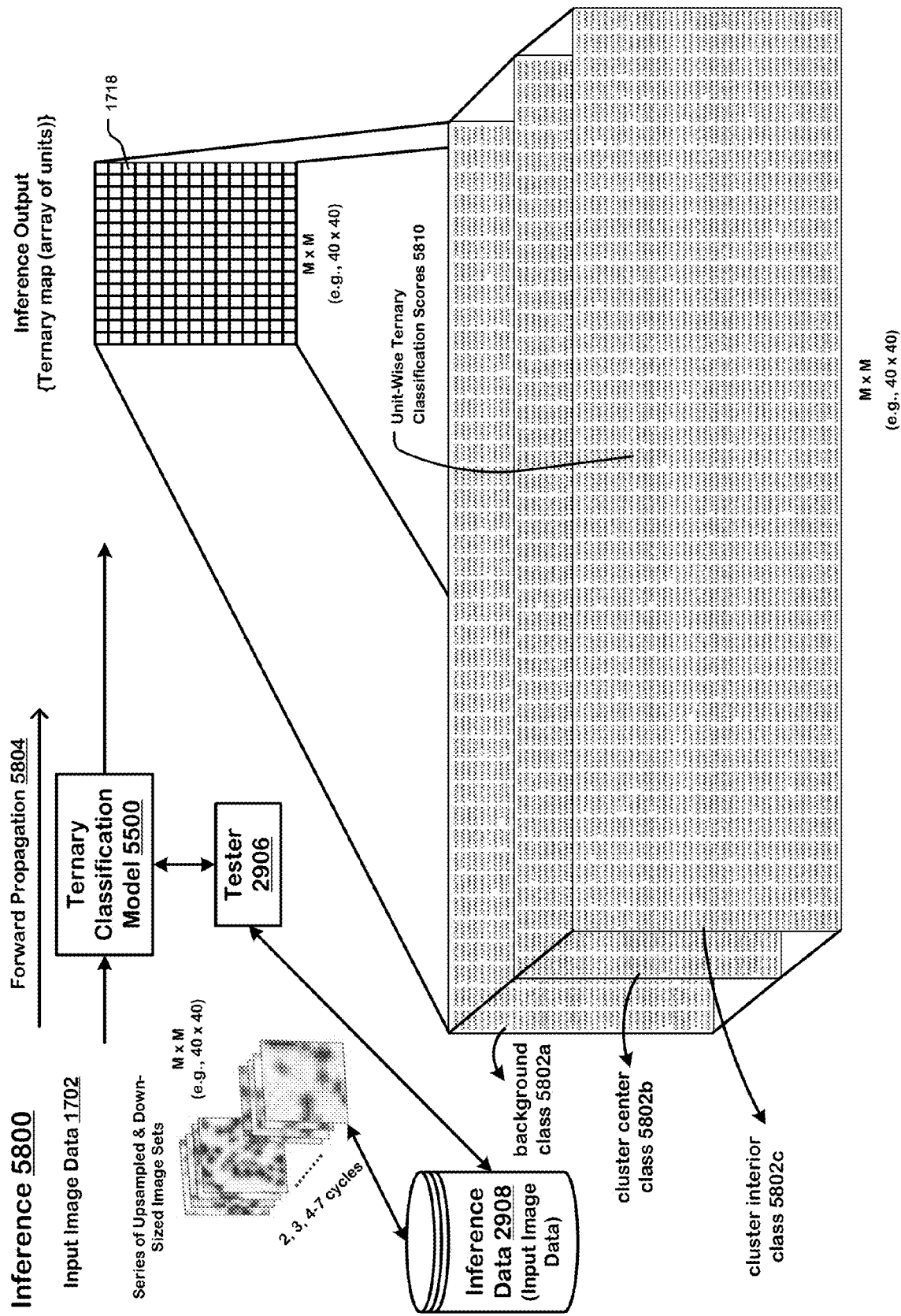
FIG. 58 is one implementation of template generation by the ternary classification model during inference.

FIG. 58 is one implementation of template generation by the ternary classification model 5400 during inference 5800 in which the ternary map 1718 is produced by the ternary classification model 5400 as the inference output during the inference 5800. One example of the ternary map 1718 is disclosed in the Appendix titled "Ternary Classification Model Sample Ouput". The Appendix includes unit-wise binary classification scores 5810 that together represent the ternary map 1718. In the softmax applications, the Appendix has a first array 5802a of unit-wise classification scores for the background class, a second array 5802b of unit-wise classification scores for the cluster center class, and a third array 5802c of unit-wise classification scores for the cluster/cluster interior class.

The inference 5800 includes hundreds, thousands, and/or millions of iterations of forward propagation 5804, including parallelization techniques such as batching. The inference 5800 is performed on inference data 2908 that includes, as the input image data 1702, a series of upsampled and down-sized image sets. The inference 5000 is operationalized by the tester 2906.

In some implementations, the ternary map 1718 is produced by the ternary classification model 5400 using post-processing techniques discussed above, such as thresholding, peak detection, and/or watershed segmentation.

Figure 59:
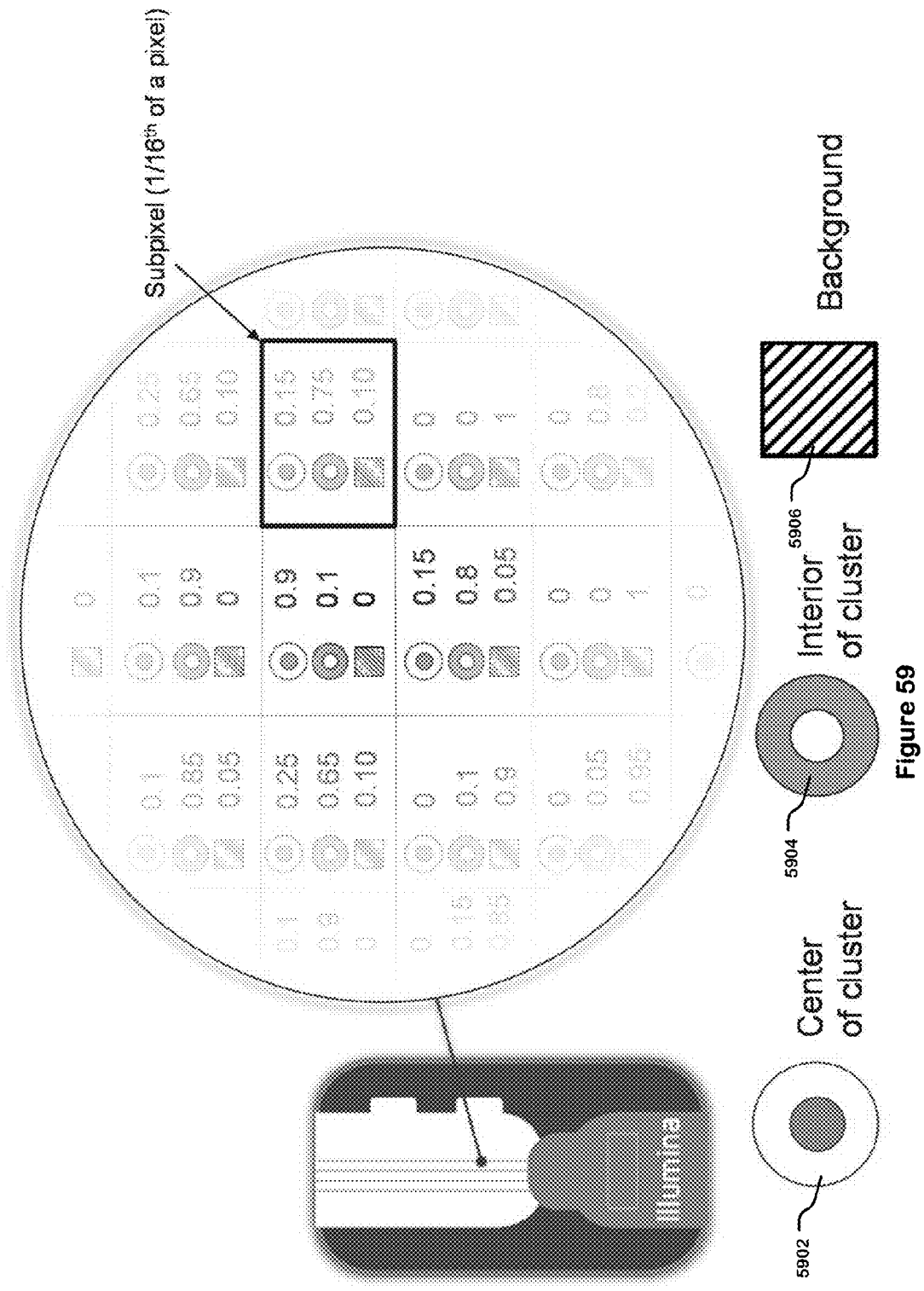
FIG. 59 shows a ternary map produced by the ternary classification model.

FIG. 59 graphically portrays the ternary map 1718 produced by the ternary classification model 5400 in which each subpixel has a three-way softmax classification score distribution for the three corresponding classes, namely, the background class 5906, the cluster center class 5902, and the cluster/cluster interior class 5904.

Figure 60:
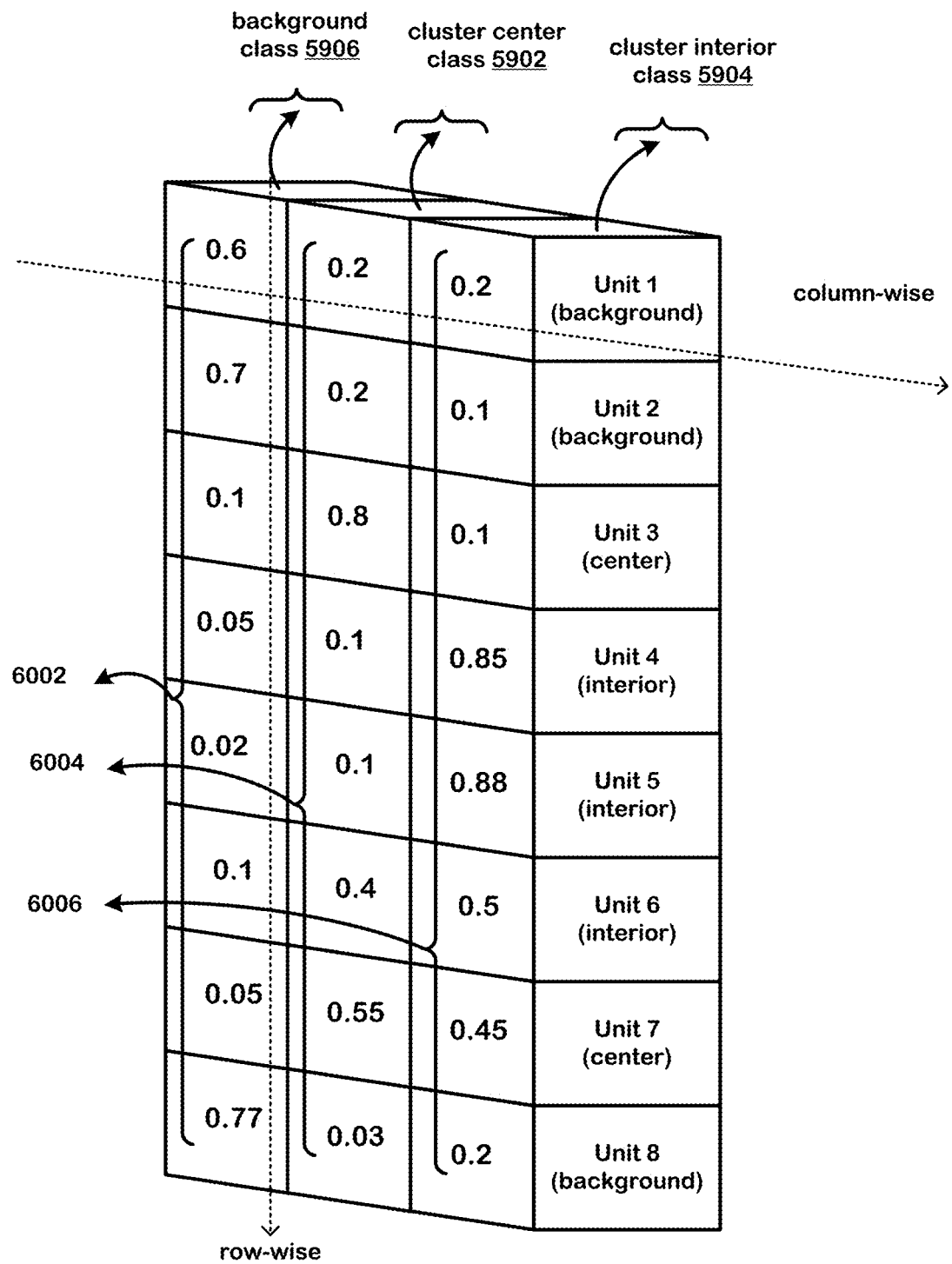
FIG. 60 depicts an array of units produced by the ternary classification model 5400, along with the unit-wise output values.

FIG. 60 depicts an array of units produced by the ternary classification model 5400, along with the unit-wise output values. As depicted, each unit has three output values for the three corresponding classes, namely, the background class 5906, the cluster center class 5902, and the cluster/cluster interior class 5904. For each classification (column-wise), each unit is assigned the class that has the highest output value, as indicated by the class in parenthesis under each unit. In some implementations, the output values 6002, 6004, and 6006 are analyzed for each of the respective classes 5906, 5902, and 5904 (row-wise).

Peak Detection & Watershed Segmentation

Figure 61:
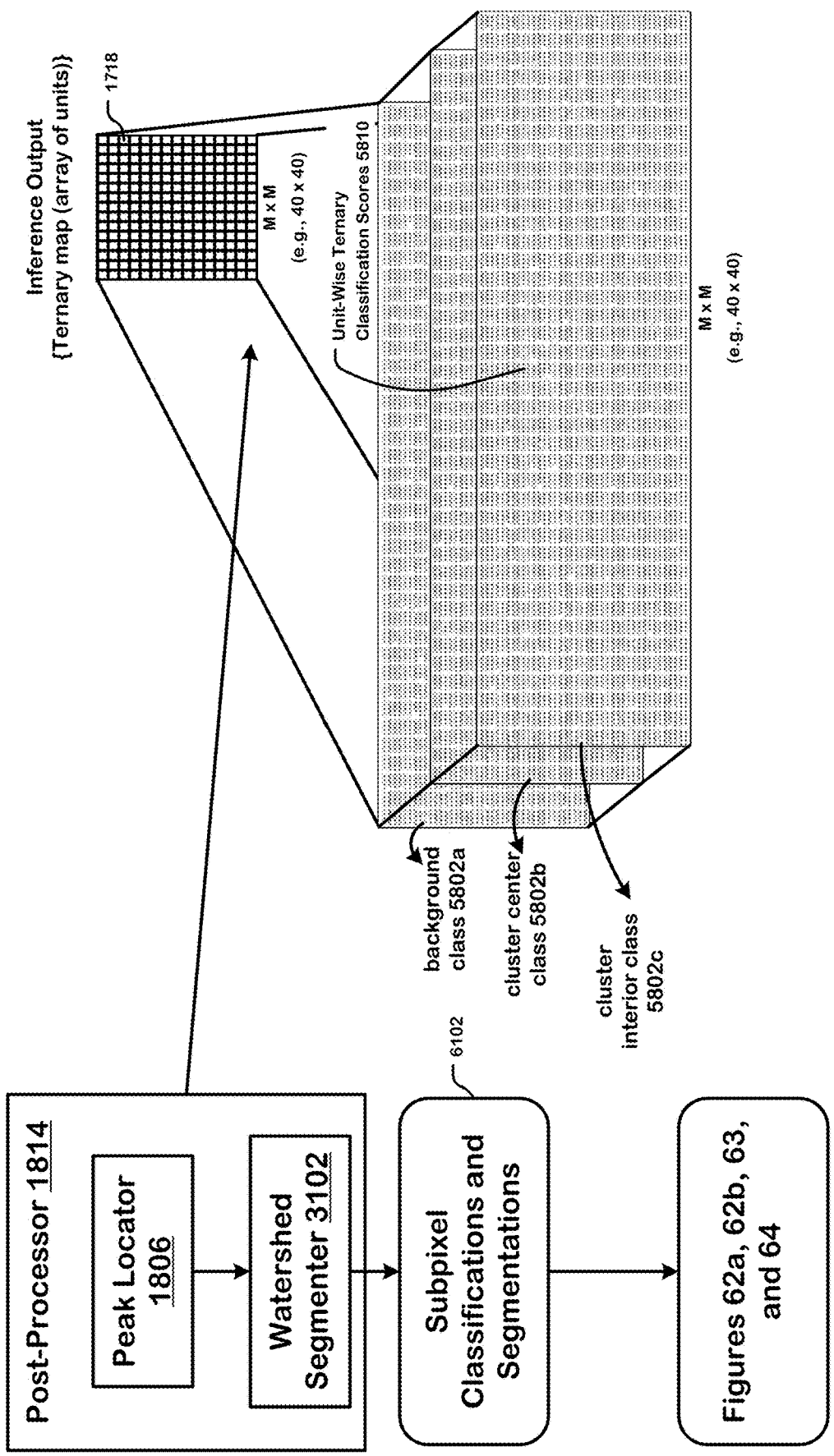
FIG. 61 shows one implementation of subjecting the ternary map to post-processing to identify cluster centers, cluster background, and cluster interior.

FIG. 61 shows one implementation of subjecting the ternary map 1718 to post-processing to identify cluster centers, cluster background, and cluster interior. As discussed above, the ternary map 1718 is an array of units that classifies each subpixel based on the predicted classification scores, with each unit in the array representing a corresponding subpixel in the input. The classification scores can be softmax scores.

In the softmax applications, the ternary map 1718 includes three arrays: (1) a first array 5802a of unit-wise classification scores for the background class, (2) a second array 5802b of unit-wise classification scores for the cluster center class, and (3) a third array 5802c of unit-wise classification scores for the cluster interior class. In all three arrays, each unit represents a corresponding subpixel in the input.

To determine which subpixels in the input contain the cluster centers, which contain the interior of the clusters, and which contain the background, the peak locator 1806 applies peak detection on softmax values in the ternary map 1718 for the cluster center class 5802b. The peak detection identifies those units that have classification scores (e.g., softmax scores) above a preset threshold. The identified units are inferred as the cluster centers and their corresponding subpixels in the input are determined to contain the cluster centers and stored as cluster center subpixels in a subpixel classifications and segmentations data store 6102. Additional details about the peak locator 1806 can be found in the Appendix entitled "Peak Detection".

In some implementations, prior to applying the peak detection, those units that have classification scores below a certain noise threshold (e.g., 0.3) are set to zero. Such units can be considered noise and ignored.

Also, units that have classification scores for the background class 5802a above a certain background threshold (e.g., equal to or greater than 0.5) and their corresponding subpixels in the input are inferred to denote the background surrounding the clusters and stored as background subpixels in the subpixel classifications and segmentations data store 6102.

Then, the watershed segmentation algorithm, operationalized by the watershed segmenter 3102, is used to determine the shapes of the clusters. In some implementations, the background units/subpixels are used as a mask by the watershed segmentation algorithm. Classification scores of the unit/subpixels inferred as the cluster centers and the cluster interior are summed to produce so-called "cluster labels". The cluster centers are used as watershed markers, for separation by intensity valleys by the watershed segmentation algorithm.

In one implementation, negativized cluster labels are provided as an input image to the watershed segmenter 3102 that performs segmentation and produces the cluster shapes as disjointed regions of contiguous cluster interior subpixels separated by the background subpixels. Furthermore, each disjointed region includes a corresponding cluster center subpixel. In some implementations, the corresponding cluster center subpixel is the center of the disjointed region to which it belongs. In other implementations, centers of mass (COM) of the disjointed regions are calculated based on the underlying location coordinates and stored as new centers of the clusters.

The outputs of the watershed segmenter 3102 are stored in the subpixel classifications and segmentations data store 6102. Additional details about the watershed segmentation algorithm and other segmentation algorithms can be found in Appendix entitled "Watershed Segmentation".

Example outputs of the peak locator 1806 and the watershed segmenter 3102 are shown in FIGS. 62a, 62b, 63, and 64.

Example Model Outputs

Figure 62A:
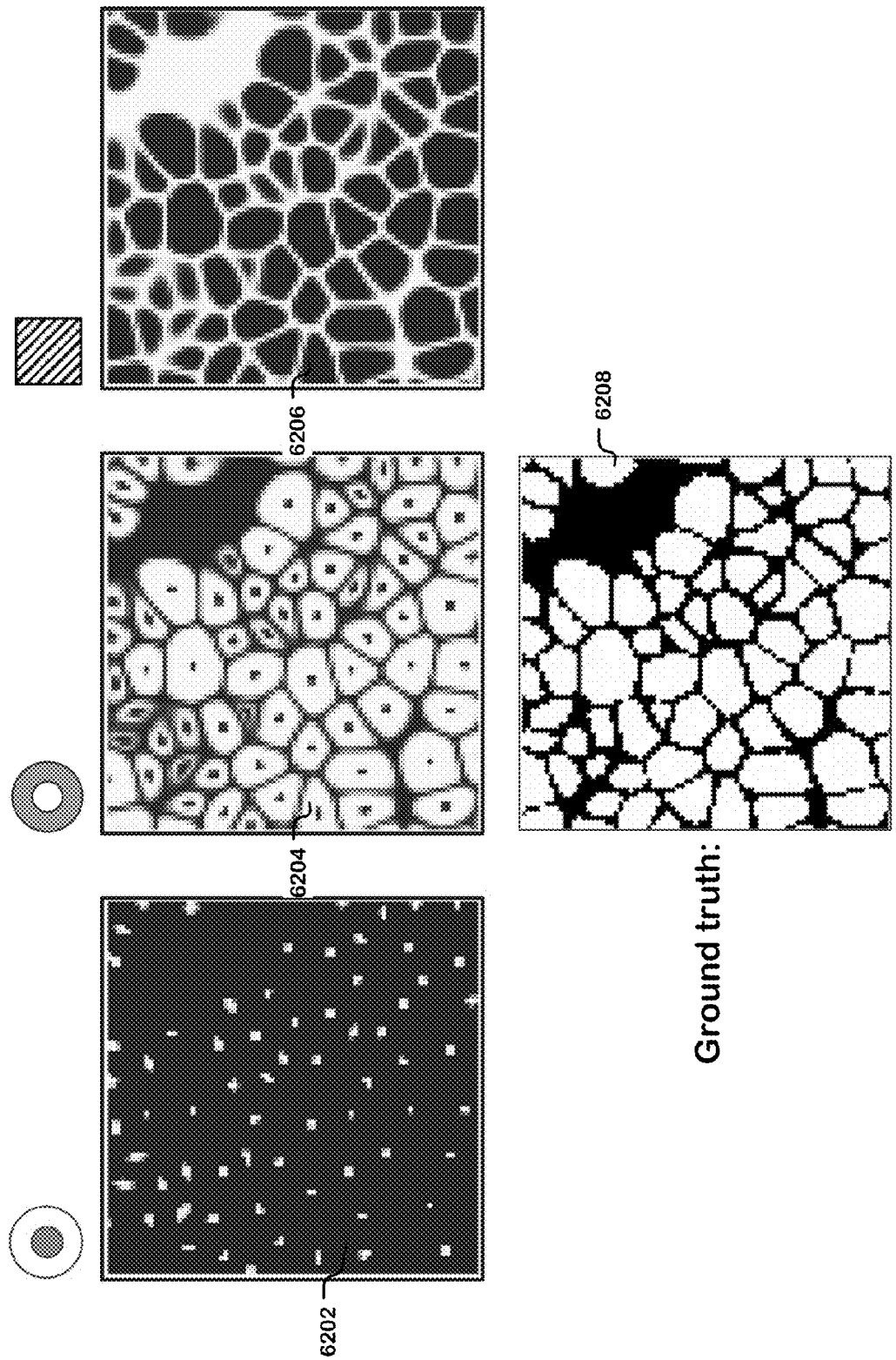
FIG. 62a shows example predictions of the ternary classification model.

FIG. 62a shows example predictions of the ternary classification model 5400. FIG. 62a shows four maps and each map has an array of units. The first map 6202 (left most) shows each unit's output values for the cluster center class

5802*b*. The second map 6204 shows each unit's output values for the cluster/cluster interior class 5802*c*. The third map 6206 (right most) shows each unit's output values for the background class 5802*a*. The fourth map 6208 (bottom) is a binary mask of ground truth ternary map 6008 that assigns each unit the class label that has the highest output value.

Figure 62B:
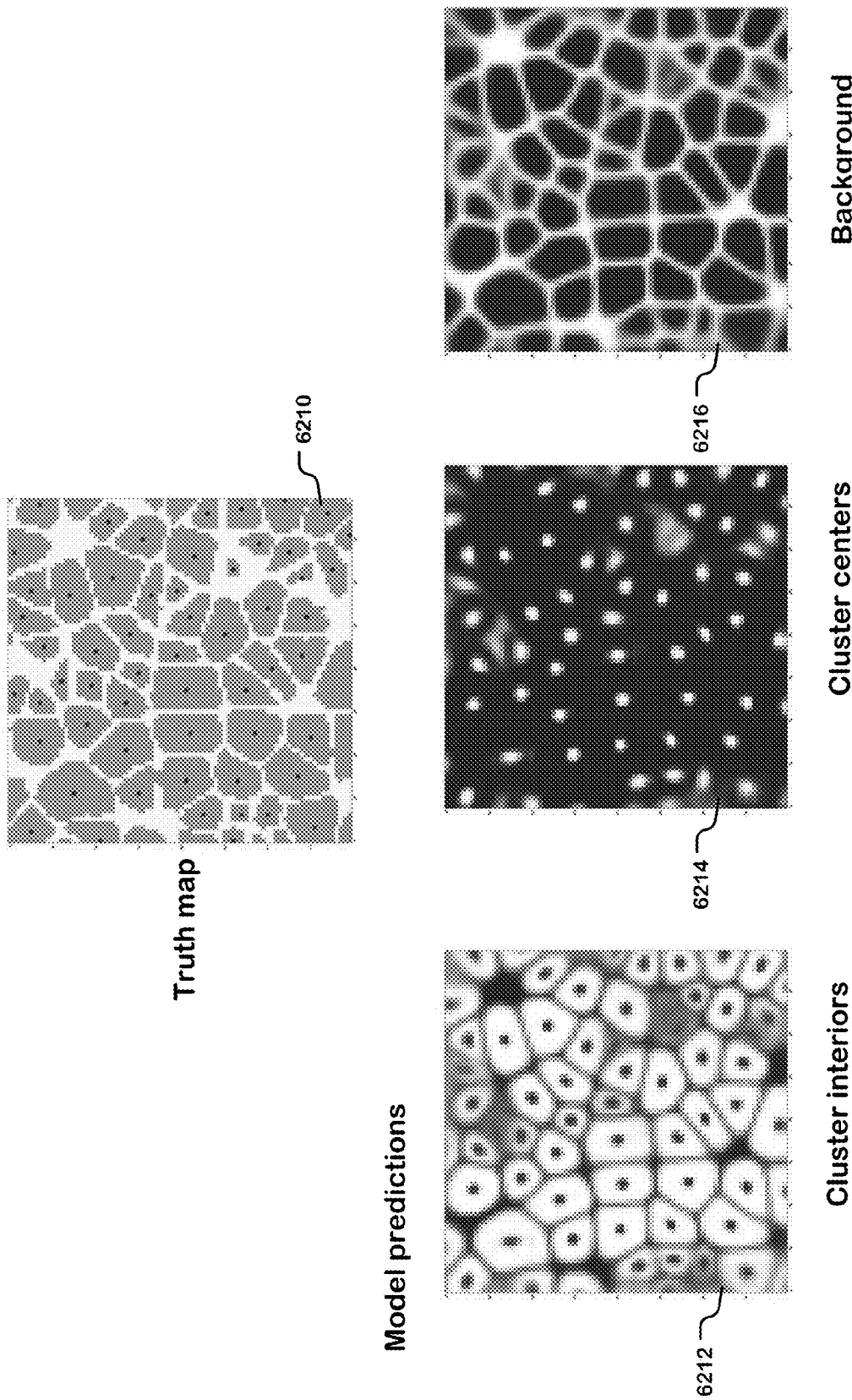
FIG. 62b illustrates other example predictions of the ternary classification model.

FIG. 62*b* illustrates other example predictions of the ternary classification model 5400. FIG. 62*b* shows four maps and each map has an array of units. The first map 6212 (bottom left most) shows each unit's output values for the cluster/cluster interior class. The second map 6214 shows each unit's output values for the cluster center class. The third map 6216 (bottom right most) shows each unit's output values for the background class. The fourth map (top) 6210 is the ground truth ternary map that assigns each unit the class label that has the highest output value.

FIG. 62*c* shows yet other example predictions of the ternary classification model 5400. FIG. 64 shows four maps and each map has an array of units. The first map 6220 (bottom left most) shows each unit's output values for the cluster/cluster interior class. The second map 6222 shows each unit's output values for the cluster center class. The third map 6224 (bottom right most) shows each unit's output values for the background class. The fourth map 6218 (*top*) is the ground truth ternary map that assigns each unit the class label that has the highest output value.

Figure 63:
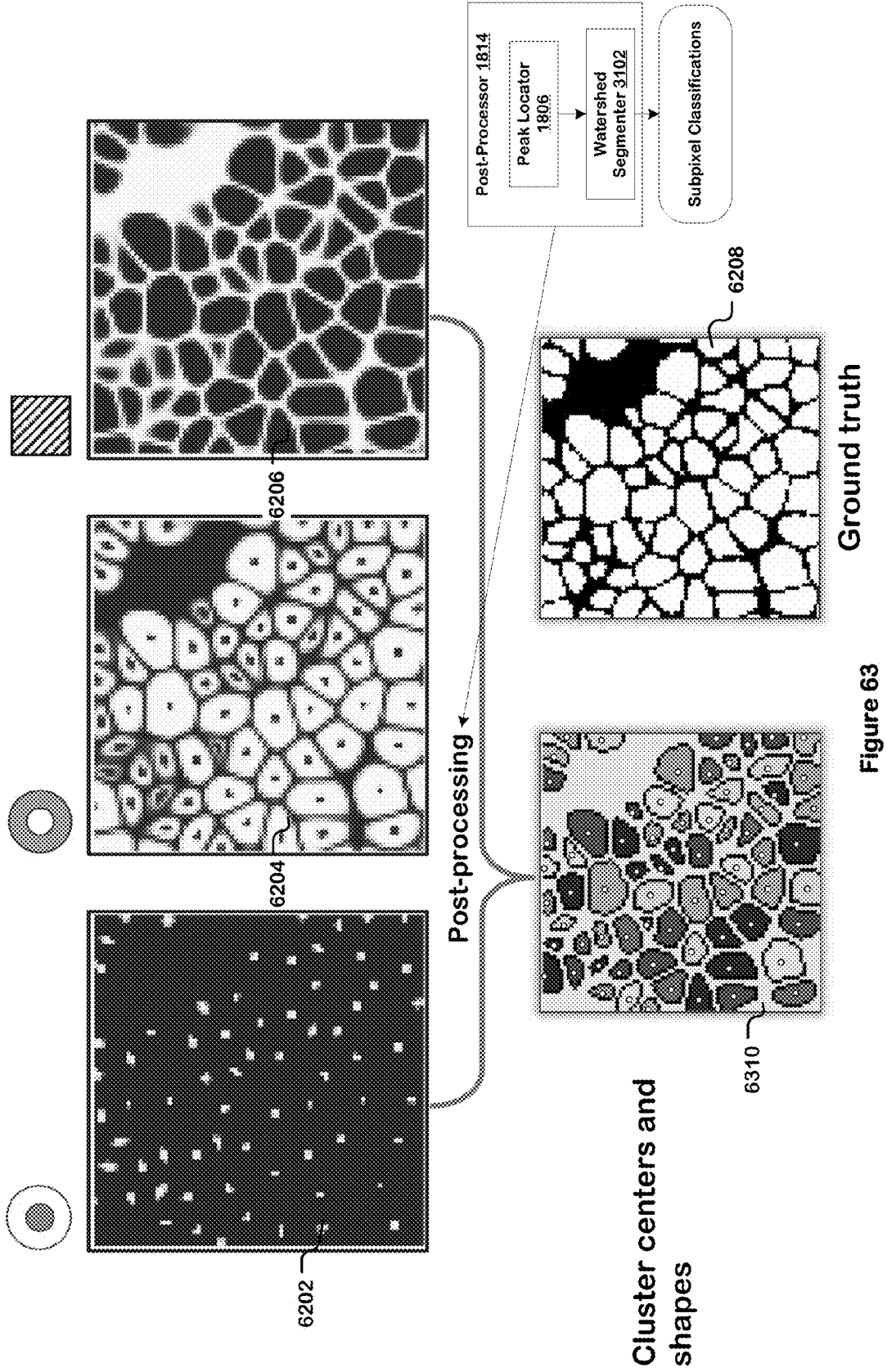

FIG. 63 depicts one implementation of deriving the cluster centers and cluster shapes from the output of the ternary classification model 5400 in FIG. 62*a* by subjecting the output to post-processing. The post-processing (e.g., peak locating, watershed segmentation) generates cluster shape data and other metadata, which is identified in the cluster map 6310.

Experimental Results and Observations

FIG. 64 compares performance of the binary classification model 4600, the regression model 2600, and the RTA base caller. The performance is evaluated using a variety of sequencing metrics. One metric is the total number of clusters detected ("# clusters"), which can be measured by the number of unique cluster centers that are detected. Another metric is the number of detected clusters that pass the chastity filter ("% PF" (pass-filter)). During cycles 1-25 of a sequencing run, the chastity filter removes the least reliable clusters from the image extraction results. Clusters "pass filter" if no more than one base call has a chastity value below 0.6 in the first 25 cycles. Chastity is defined as the ratio of the brightest base intensity divided by the sum of the brightest and the second brightest base intensities. This metric goes beyond the quantity of the detected clusters and also conveys their quality, i.e., how many of the detected clusters can be used for accurate base calling and downstream secondary and ternary analysis such as variant calling and variant pathogenicity annotation.

Other metrics that measure how good the detected clusters are for downstream analysis include the number of aligned reads produced from the detected clusters ("% Aligned"), the number of duplicate reads produced from the detected clusters ("% Duplicate"), the number of reads produced from the detected clusters mismatching the reference sequence for all reads aligned to the reference sequence ("% Mismatch"), the number of reads produced from the detected clusters whose portions do not match well to the reference sequence on either side and thus are ignored for the alignment ("% soft clipped"), the number of bases called for the detected clusters with quality score 30 and above ("% Q30 bases"), the number of paired reads produced from the detected clusters that have both reads aligned inwards within a reasonable distance ("total proper read pairs"), and the number of unique or deduplicated proper read pairs produced from the detected clusters ("non-duplicate proper read pairs").

As shown in FIG. 64, both the binary classification model 4600 and the regression model 2600 outperform the RTA base caller at template generation on most of the metrics.

Figure 65:
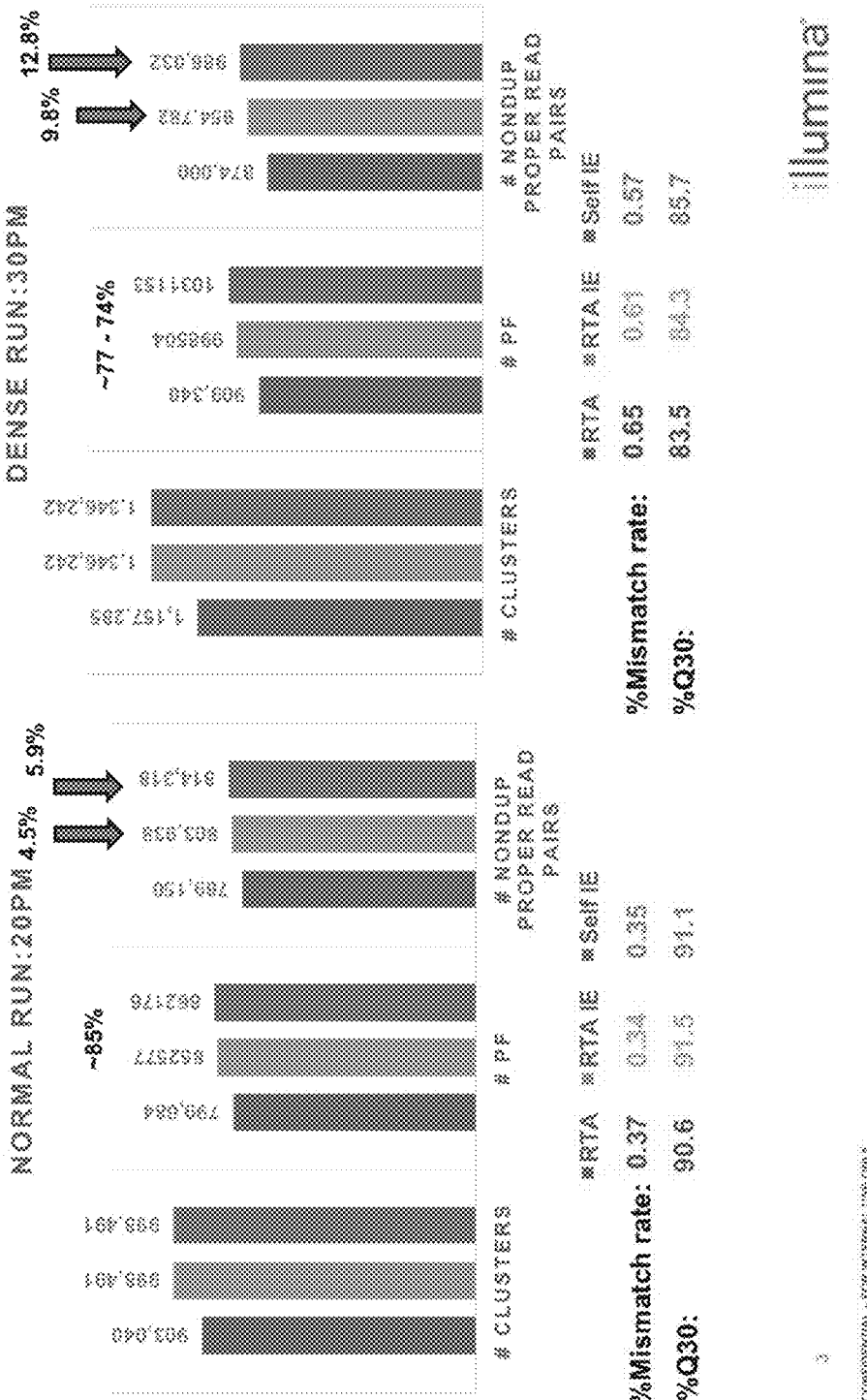
FIG. 65 compares the performance of the ternary classification model with that of the RTA base caller under three contexts, five sequencing metrics, and two run densities.

FIG. 65 compares the performance of the ternary classification model 5400 with that of the RTA base caller under three contexts, five sequencing metrics, and two run densities.

In the first context called "RTA", the cluster centers are detected by the RTA base caller, the intensity extraction from the clusters is done by the RTA base caller, and the clusters are also base called using the RTA base caller. In the second context called "RTA IE", the cluster centers are detected by the ternary classification model 5400; however, the intensity extraction from the clusters is done by the RTA base caller and the clusters are also base called using the RTA base caller. In the third context called "Self IE", the cluster centers are detected by the ternary classification model 5400 and the intensity extraction from the clusters is done using the cluster shape-based intensity extraction techniques disclosed herein (note that the cluster shape information is generated by the ternary classification model 5400); but the clusters are base called using the RTA base caller.

The performance is compared between the ternary classification model 5400 and the RTA base caller along five metrics: (1) the total number of clusters detected ("# clusters"), (2) the number of detected clusters that pass the chastity filter ("# PF"), (3) the number of unique or deduplicated proper read pairs produced from the detected clusters ("# nondup proper read pairs"), (4) the rate of mismatches between a sequence read produced from the detected clusters and a reference sequence after alignment ("% Mismatch rate"), and (5) bases called for the detected clusters with quality score 30 and above ("% Q30").

The performance is compared between the ternary classification model 5400 and the RTA base caller under the three contexts and the five metrics for two types of sequencing runs: (1) a normal run with 20 pM library concentration and (2) a dense run with 30 pM library concentration.

As shown in FIG. 65, the ternary classification model 5400 outperforms the RTA base caller on all the metrics.

Figure 66:
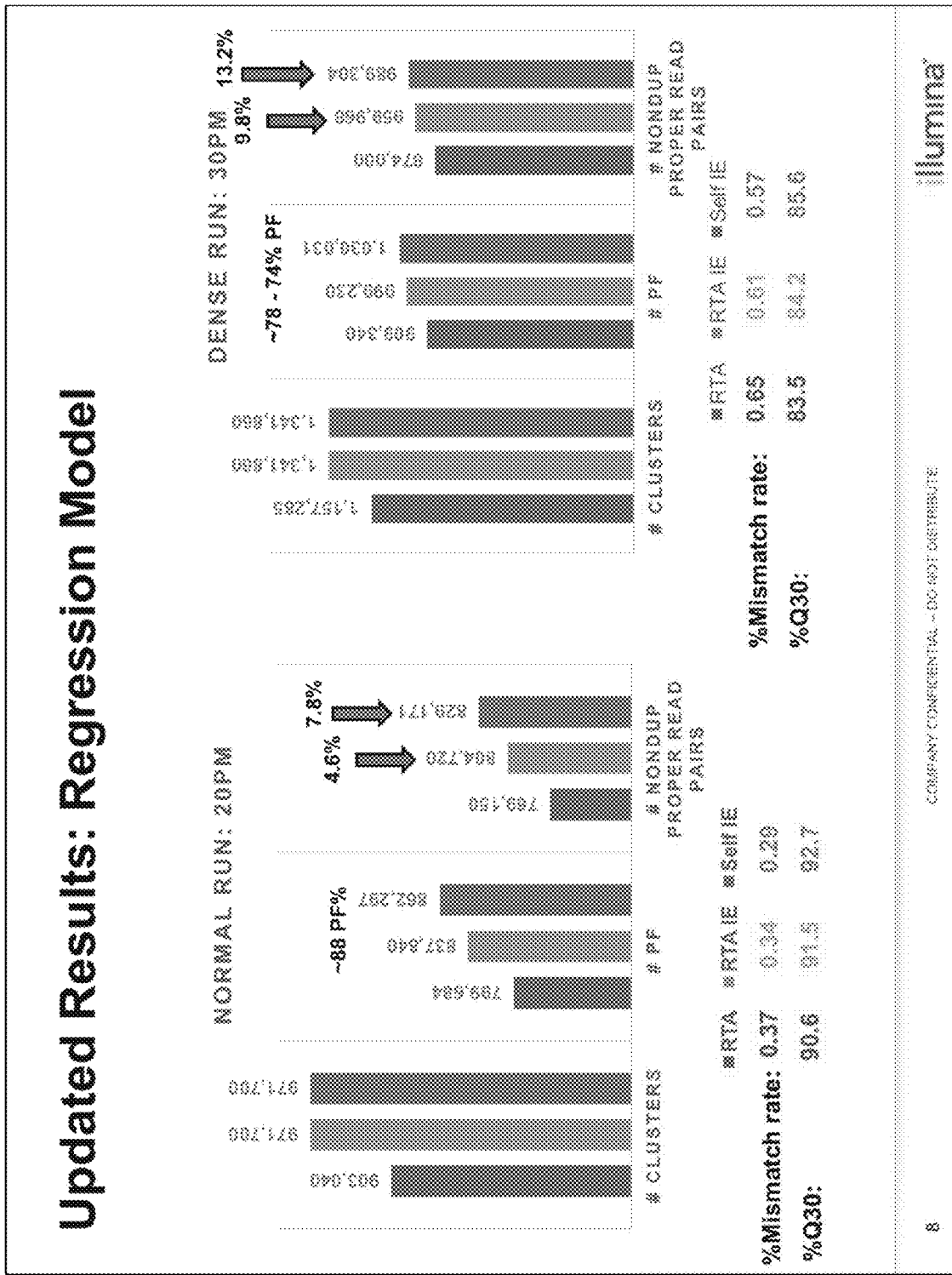
FIG. 66 compares the performance of the regression model with that of the RTA base caller under the three contexts, the five sequencing metrics, and the two run densities discussed in FIG. 65.

Under the same three contexts, five metrics, and two run densities, FIG. 66 shows that the regression model 2600 outperforms the RTA base caller on all the metrics.

Figure 67:
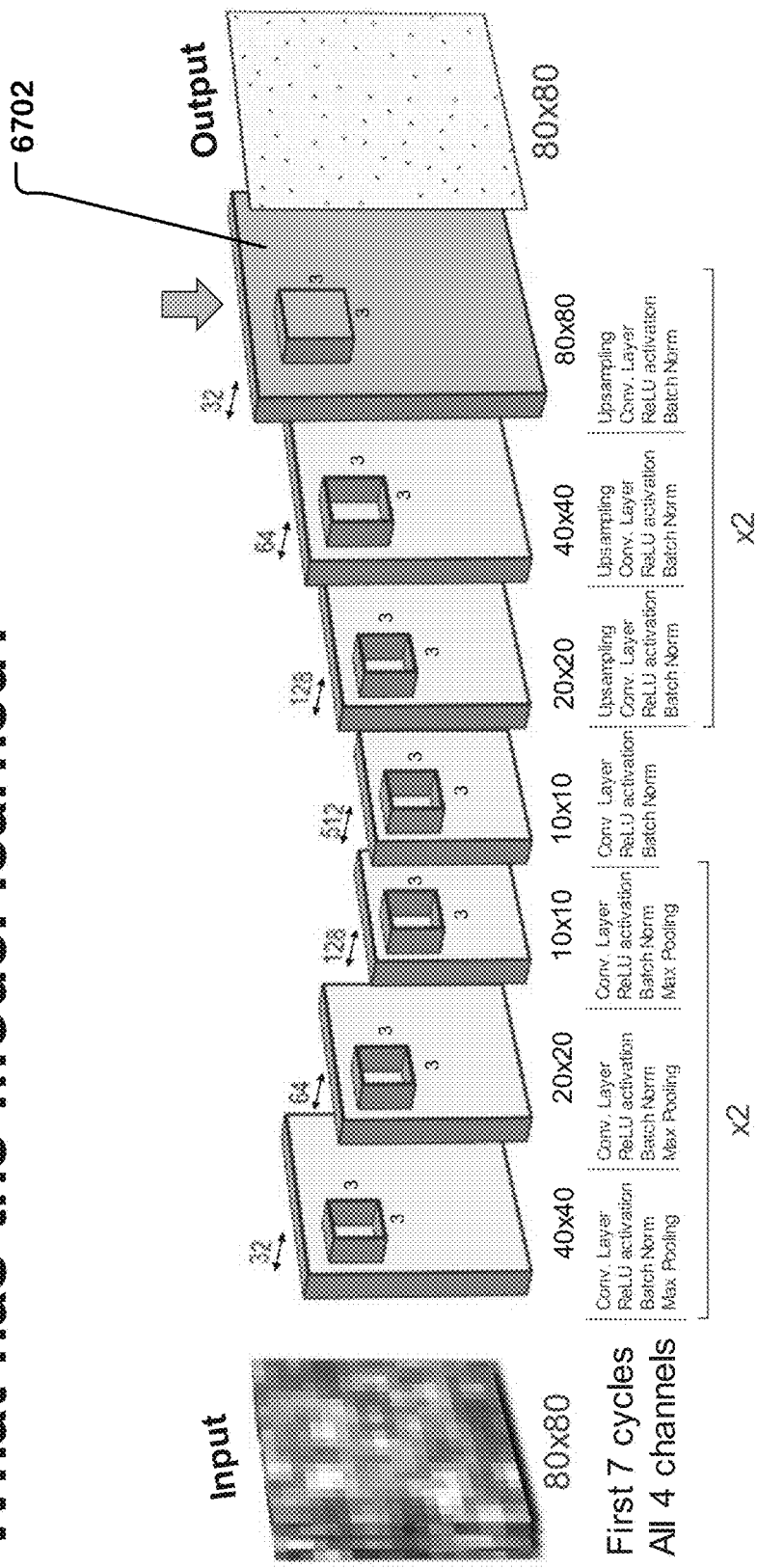
FIG. 67 focuses on the penultimate layer of the neural network-based template generator.

FIG. 67 focuses on the penultimate layer 6702 of the neural network-based template generator 1512.

Figure 68:
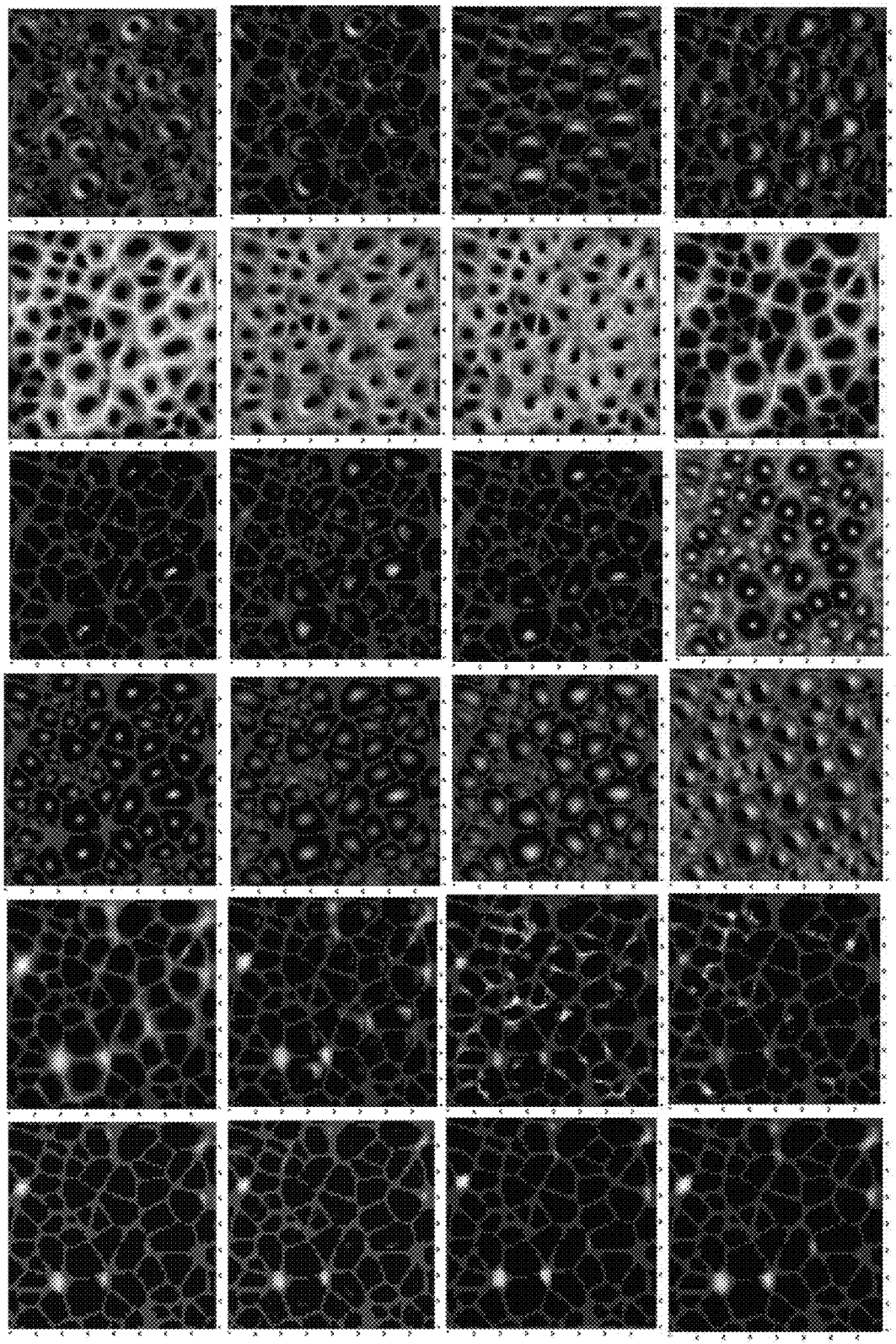
FIG. 68 visualizes what the penultimate layer of the neural network-based template generator has learned as a result of the backpropagation-based gradient update training. The illustrated implementation visualizes twenty-four out of the thirty-two trained convolution filters of the penultimate layer depicted in FIG. 67.

FIG. 68 visualizes what the penultimate layer 6702 of the neural network-based template generator 1512 has learned as a result of the backpropagation-based gradient update training. The illustrated implementation visualizes twenty-four out of the thirty-two convolution filters of the penultimate layer 6702 overlaid on the ground truth cluster shapes. As shown in FIG. 68, the penultimate layer 6702 has learned the cluster metadata, including spatial distribution of the clusters such as cluster centers, cluster shapes, cluster sizes, cluster background, and cluster boundaries.

Figure 69:
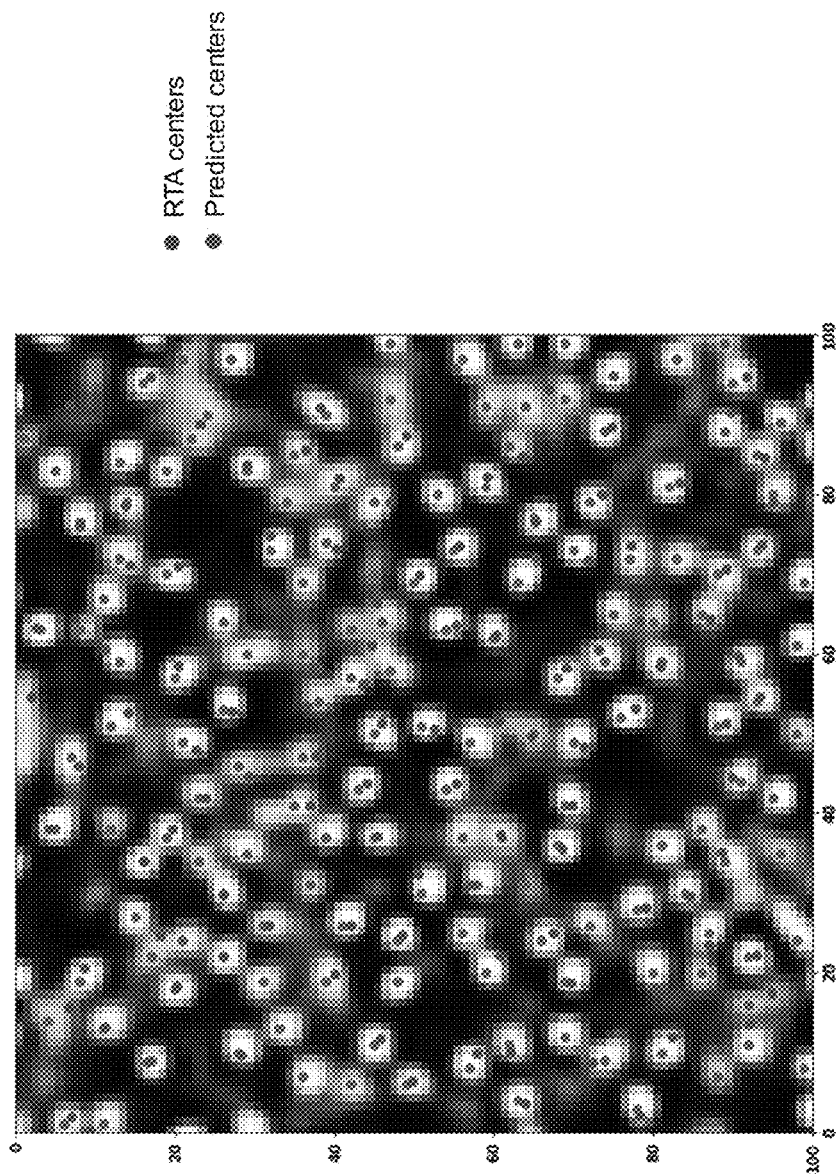
FIG. 69 overlays cluster center predictions of the binary classification model (in blue) onto those of the RTA base caller (in pink).

FIG. 69 overlays cluster center predictions of the binary classification model 4600 (in blue) onto those of the RTA base caller (in pink). The predictions are made on sequencing image data from the Illumina NextSeq sequencer.

FIG. 70 overlays cluster center predictions made by the RTA base caller (in pink) onto visualization of the trained convolution filters of the penultimate layer of the binary classification model 4600. These convolution filters are learned as a result of training on sequencing image data from the Illumina NextSeq sequencer.

FIG. 71 illustrates one implementation of training data used to train the neural network-based template generator 1512. In this implementation, the training data is obtained from dense flow cells that produce data with storm probe images. In another implementation, the training data is obtained from dense flow cells that produce data with fewer bridge amplification cycles.

Figure 72:
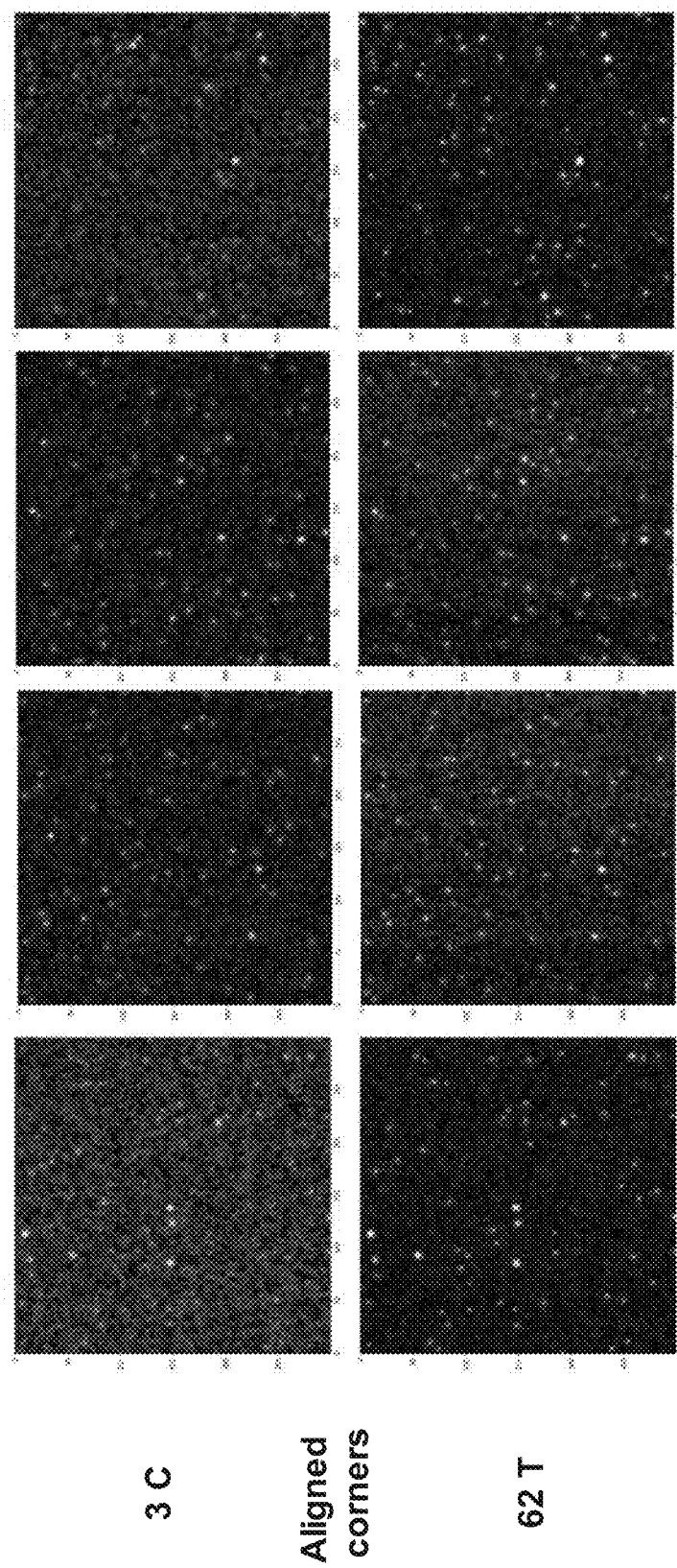
FIG. 72 is one implementation of using beads for image registration based on cluster center predictions of the neural network-based template generator.

FIG. 72 is one implementation of using beads for image registration based on cluster center predictions of the neural network-based template generator 1512.

Figure 73:
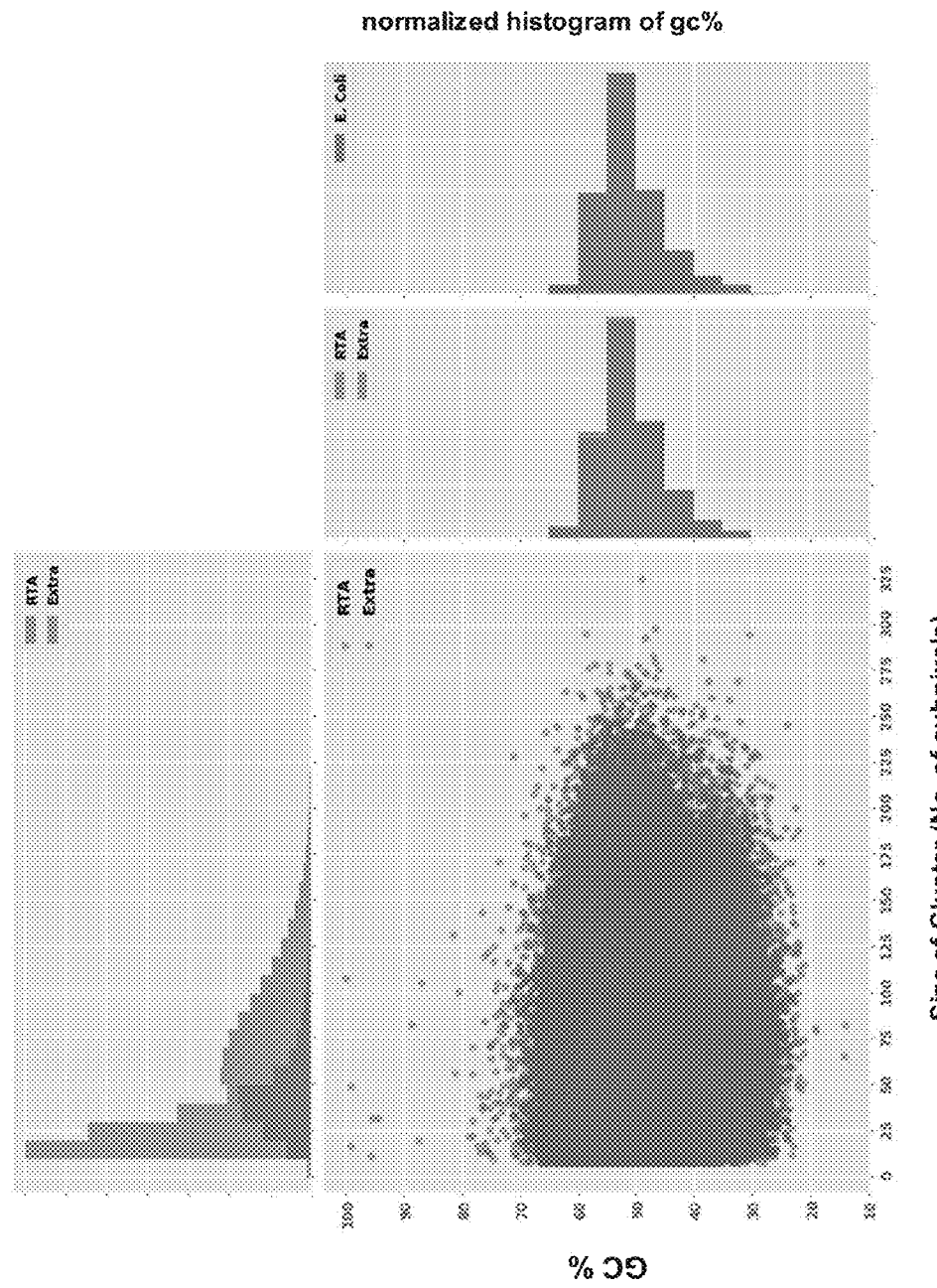
FIG. 73 illustrates one implementation of cluster statistics of clusters identified by the neural network-based template generator.

FIG. 73 illustrates one implementation of cluster statistics of clusters identified by the neural network-based template generator 1512. The cluster statistics include cluster size based on number of contributive subpixels and GC-content.

FIG. 74 shows how the neural network-based template generator 1512's ability to distinguish between adjacent clusters improves when the number of initial sequencing cycles for which the input image data 1702 is used increases from five to seven. For five sequencing cycles, a single cluster is identified by a single disjointed region of contiguous subpixels. For seven sequencing cycles, the single cluster is segmented into two adjacent clusters, each having their own disjointed regions of contiguous subpixels.

FIG. 75 illustrates the difference in base calling performance when a RTA base caller uses ground truth center of mass (COM) location as the cluster center, as opposed to when a non-COM location is used as the cluster center.

FIG. 76 portrays the performance of the neural network-based template generator 1512 on extra detected clusters.

FIG. 77 shows different datasets used for training the neural network-based template generator 1512.

FIG. 78 shows the processing stages used by the RTA base caller for base calling, according to one implementation. FIG. 78 also shows the processing stages used by the disclosed neural network-based base caller for base calling, according to two implementations. As shown in FIG. 78, the neural network-based base caller 1514 can streamline the base calling process by obviating many of the processing stages used by the RTA base caller. The streamlining improves base calling accuracy and scale. In a first implementation of the neural network-based base caller 1514, it performs base calling using location/position information of cluster centers identified from the output of the neural network-based template generator 1512. In a second implementation, the neural network-based base caller 1514 does not use the location/position information of the cluster centers for base calling. The second implementation is used when a patterned flow cell design is used for cluster generation. The patterned flow cell contains nanowells that are precisely positioned relative to known fiducial locations and provide prearranged cluster distribution on the patterned flow cell. In other implementations, the neural network-based base caller 1514 base calls clusters generated on random flow cells.

Neural Network-Based Base Calling

The discussion now turns to the neural network-based base calling in which a neural network is trained to map sequencing images to base calls. The discussion is organized as follows. First, the inputs to the neural network are described. Then, the structure and form of the neural network are described. Finally, the outputs of the neural network are described.

Input

Figure 79:
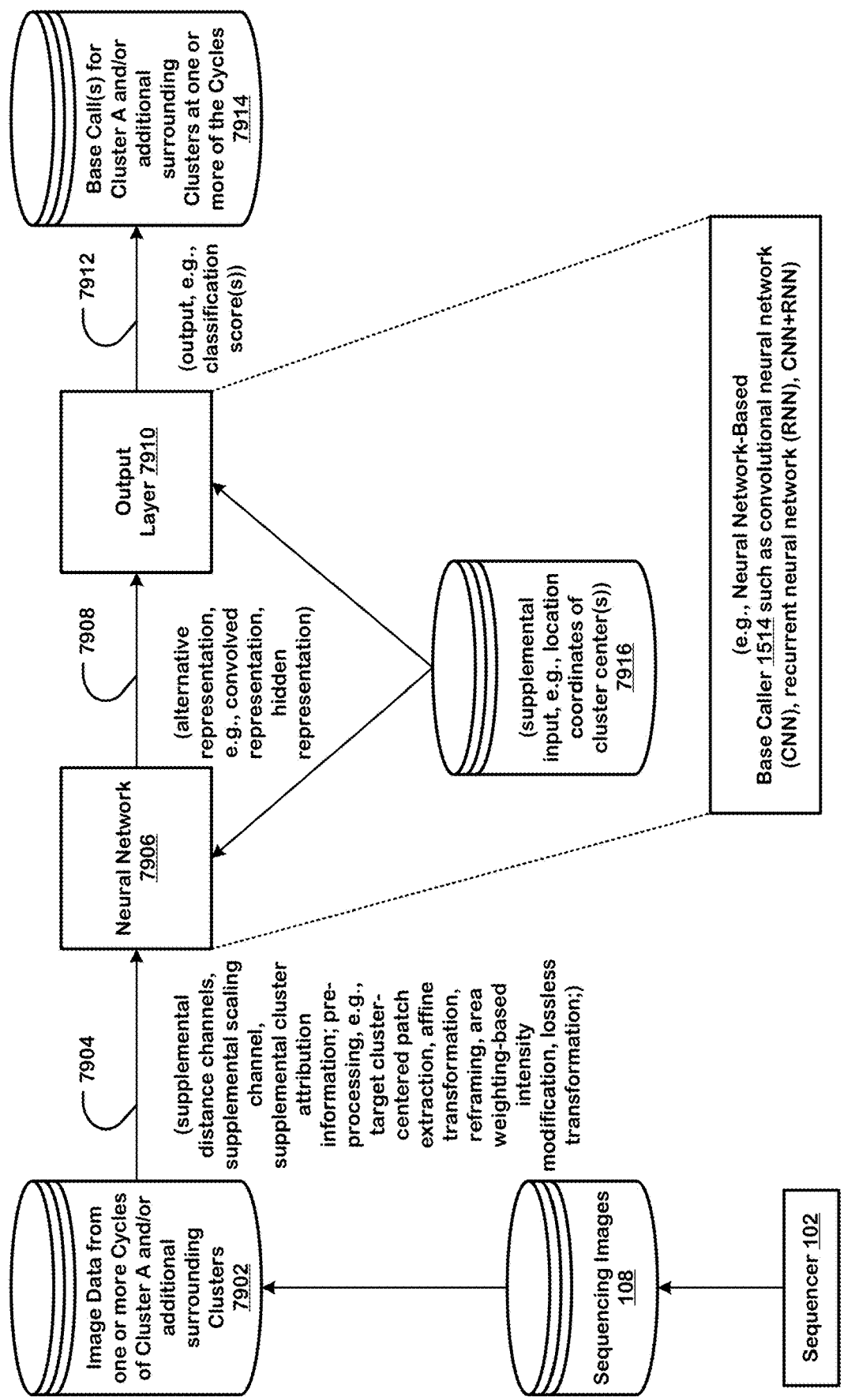
FIG. 79 illustrates one implementation of base calling using the disclosed neural network-based base caller.

FIG. 79 illustrates one implementation of base calling using the neural network 7906.

Main Input: Image Channels

The main input to the neural network 7906 is image data 7902. The image data 7902 is derived from the sequencing images 108 produced by the sequencer 102 during a sequencing run. In one implementation, the image data 7902 comprises n×n image patches extracted from the sequencing images 102, where n is any number ranging from 1 and 10,000. The sequencing run produces m image(s) per sequencing cycle for corresponding m image channels, and an image patch is extracted from each of the m image(s) to prepare the image data for a particular sequencing cycle. In different implementations such as 4-, 2-, and 1-channel chemistries, m is 4 or 2. In other implementations, m is 1, 3, or greater than 4. The image data 7902 is in the optical, pixel domain in some implementations, and in the upsampled, subpixel domain in other implementations.

The image data 7902 comprises data for multiple sequencing cycles (e.g., a current sequencing cycle, one or more preceding sequencing cycles, and one or more successive sequencing cycles). In one implementation, the image data 7902 comprises data for three sequencing cycles, such that data for a current (time t) sequencing cycle to be base called is accompanied with (i) data for a left flanking/context/previous/preceding/prior (time t−1) sequencing cycle and (ii) data for a right flanking/context/next/successive/subsequent (time t+1) sequencing cycle. In other implementations, the image data 7902 comprises data for a single sequencing cycle.

The image data 7902 depicts intensity emissions of one or more clusters and their surrounding background. In one implementation, when a single target cluster is to be base called, the image patches are extracted from the sequencing images 108 in such a way that each image patch contains the center of the target cluster in its center pixel, a concept referred to herein as the "target cluster-centered patch extraction".

The image data 7902 is encoded in the input data 7904 using intensity channels (also called image channels). For each of the m images obtained from the sequencer 102 for a particular sequencing cycle, a separate image channel is used to encode its intensity data. Consider, for example, that the sequencing run uses the 2-channel chemistry which produces a red image and a green image at each sequencing cycle, then the input data 7904 comprises (i) a first red image channel with n×n pixels that depict intensity emissions of the one or more clusters and their surrounding background captured in the red image and (ii) a second green image channel with n×n pixels that depict intensity emissions of the one or more clusters and their surrounding background captured in the green image.

Supplemental Input: Distance Channels

The image data 7902 is accompanied with supplemental distance data (also called distance channels). Distance channels supply additive bias that is incorporated in the feature maps generated from the image channels. This additive bias contributes to base calling accuracy because it is based on pixel center-to-cluster center(s) distances, which are pixel-wise encoded in the distance channels.

In a "single target cluster" base calling implementation, for each image channel (image patch) in the input data 7904, a supplemental distance channel identifies distances of its pixels' centers from the center of a target cluster containing its center pixel and to be base called. The distance channel thereby indicates respective distances of pixels of an image patch from a center pixel of the image patch.

In a "multi-cluster" base calling implementation, for each image channel (image patch) in the input data 7904, a supplemental distance channel identifies each pixel's center-to-center distance from a nearest one of the clusters selected based on center-to-center distances between the pixel and each of the clusters.

In a "multi-cluster shape-based" base calling implementation, for each image channel (image patch) in the input data 7904, a supplemental distance channel identifies each cluster pixel's center-to-center distance from an assigned cluster selected based on classifying each cluster pixel to only one cluster.

Supplemental Input: Scaling Channel

The image data 7902 is accompanied with supplemental scaling data (also called scaling channel) that accounts for different cluster sizes and uneven illumination conditions. Scaling channel also supplies additive bias that is incorporated in the feature maps generated from the image channels. This additive bias contributes to base calling accuracy because it is based on mean intensities of central cluster pixel(s), which are pixel-wise encoded in the scaling channel.

Supplemental Input: Cluster Center Coordinates

In some implementations, the location/position information 7916 (e.g., x-y coordinates) of cluster center(s) identified from the output of the neural network-based template generator 1512 is fed as supplemental input to the neural network 7906.

Supplemental Input: Cluster Attribution Information

In some implementations, the neural network 7906 receives, as supplemental input, cluster attribution information that classifies which pixels or subpixels are: background pixels or subpixels, cluster center pixels or subpixels, and cluster/cluster interior pixels or subpixels depicting/contributing to/belonging to a same cluster. In other implementations, the decay map, the binary map, and/or the ternary map or a variation of those is fed as supplemental input to the neural network 7906.

Pre-Processing: Intensity Modification

In some implementations, the input data 7904 does not contain the distance channels, but instead the neural network 7906 receives, as input, modified image data that is modified based on the output of the neural network-based template generator 1512, i.e., the decay map, the binary map, and/or the ternary map. In such implementations, the intensities of the image data 7902 are modified to account for the absence distance channels.

In other implementations, the image data 7902 is subjected to one or more lossless transformation operations (e.g., convolutions, deconvolutions, Fourier transforms) and the resulting modified image data is fed as input to the neural network 7906.

Network Structure and Form

The neural network 7906 is also referred to herein as the "neural network-based base caller" 1514. In one implementation, the neural network-based base caller 1514 is a multilayer perceptron (MLP). In another implementation, the neural network-based base caller 1514 is a feedforward neural network. In yet another implementation, the neural network-based base caller 1514 is a fully-connected neural network. In a further implementation, the neural network-based base caller 1514 is a fully convolutional neural network. In yet further implementation, the neural network-based base caller 1514 is a semantic segmentation neural network.

In one implementation, the neural network-based base caller 1514 is a convolutional neural network (CNN) with a plurality of convolution layers. In another implementation, it is a recurrent neural network (RNN) such as a long short-term memory network (LSTM), bi-directional LSTM (Bi-LSTM), or a gated recurrent unit (GRU). In yet another implementation, it includes both a CNN and a RNN.

In yet other implementations, the neural network-based base caller 1514 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

The neural network-based base caller 1514 processes the input data 7904 and produces an alternative representation 7908 of the input data 7904. The alternative representation 7908 is a convolved representation in some implementations and a hidden representation in other implementations. The alternative representation 7908 is then processed by an output layer 7910 to produce an output 7912. The output 7912 is used to produce the base call(s), as discussed below.

Output

In one implementation, the neural network-based base caller 1514 outputs a base call for a single target cluster for a particular sequencing cycle. In another implementation, it outputs a base call for each target cluster in a plurality of target clusters for the particular sequencing cycle. In yet another implementation, it outputs a base call for each target cluster in a plurality of target clusters for each sequencing cycle in a plurality of sequencing cycles, thereby producing a base call sequence for each target cluster.

Distance Channel Calculation

The discussion now turns to how appropriate location/position information (e.g., x-y coordinates) of cluster center(s) is obtained for use in calculating distance values of the distance channels.

Downscaling of Coordinates

Figure 80:
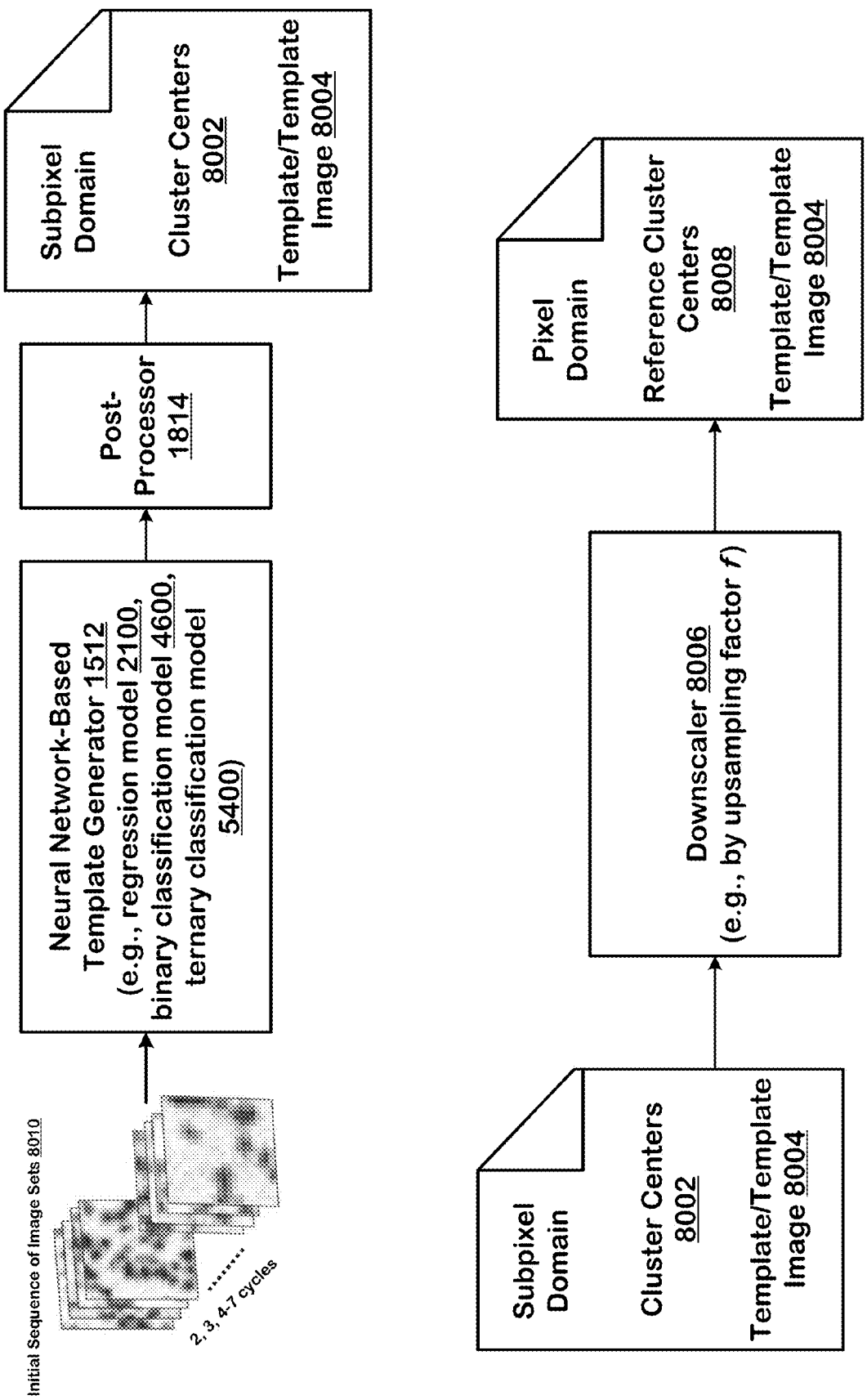
FIG. 80 is one implementation of transforming, from subpixel domain to pixel domain, location/position information of cluster centers identified from the output of the neural network-based template generator.

FIG. 80 is one implementation of transforming, from subpixel domain to pixel domain, location/position information of cluster centers identified from the output of the neural network-based template generator 1512.

Cluster center location/position information is used for the neural network-based base calling at least (i) to construct the input data by extracting image patches from the sequencing images 108 that contain the centers of target clusters to be base called in their center pixels, (ii) to construct the distance channel that identifies distances of an image patch's pixels' centers from the center of a target cluster contained its center pixel, and/or (iii) as supplemental input 7916 to the neural network-based base caller 1514.

In some implementations, the cluster center location/position information is identified from the output of the neural network-based template generator 1512 in the upsampled, subpixel resolution. However, in some implementations, the neural network-based base caller 1514 operates on image data that is in optical, pixel-resolution. Therefore, in one implementation, the cluster center location/position information is transformed into the pixel domain by downscaling coordinates of the cluster centers by the same upsampling factor used to upsample image data fed as input to the neural network-based template generator 1512.

Consider, for example, that the image patches data fed as input to the neural network-based template generator 1512 are derived by upsampling sequencing images 108 from some initial sequencing cycles by an upsampling factor f. Then, in one implementation, the coordinates of the cluster centers 8002, produced by the neural network-based template generator 1512 by the post-processor 1814 and stored in the template/template image 8004, are divided by f (the divisor). These downscaled cluster center coordinates are referred to herein as the "reference cluster centers" 8008 and stored in the template/template image 8004. In one implementation, the downscaling is performed by a downscaler 8006.

Transformation of Coordinates

Figure 81:
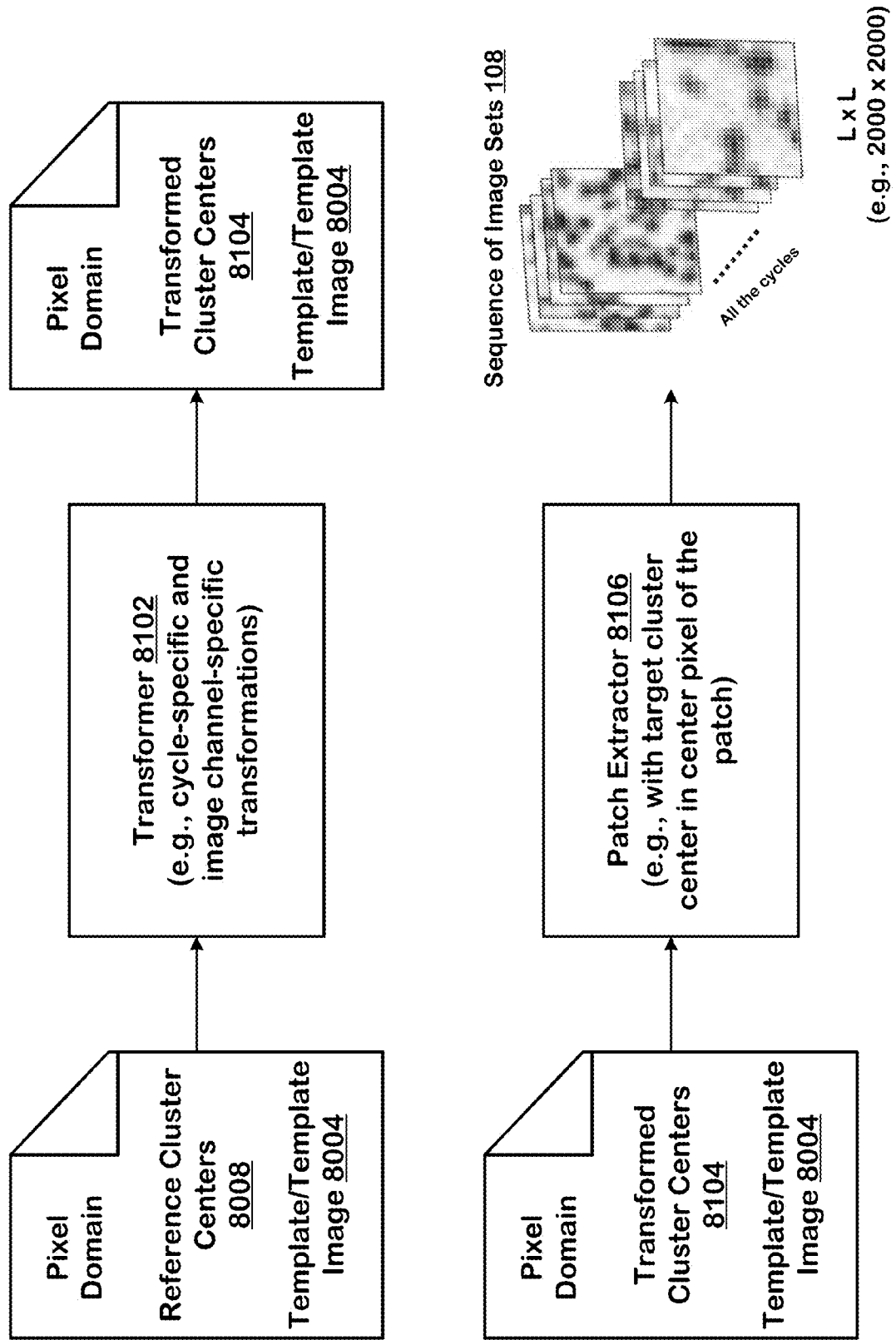
FIG. 81 is one implementation of using cycle-specific and image channel-specific transformations to derive the so-called "transformed cluster centers" from the reference cluster centers.

FIG. 81 is one implementation of using cycle-specific and image channel-specific transformations to derive the so-called "transformed cluster centers" 8104 from the reference cluster centers 8008. The motivation for doing so is discussed first.

Sequencing images taken at different sequencing cycles are misaligned and have random translational offsets with respect to each other. This occurs due to the finite accuracy of the movements of the sensor's motion stage and also because images taken in different image/frequency channels have different optical paths and wavelengths. Consequently, an offset exists between the reference cluster centers and locations/positions of the cluster centers in the sequencing images. This offset varies between images captured at different sequencing cycles and within images captured at a same sequencing cycle in different image channels.

To account for this offset, cycle-specific and image channel-specific transformations are applied to the reference cluster centers to produce respective transformed cluster centers for image patches of each sequencing cycle. The cycle-specific and image channel-specific transformations are derived by an image registration process that uses image correlation to determine a full six-parameter affine transformation (e.g., translation, rotation, scaling, shear, right reflection, left reflection) or a Procrustes transformation (e.g., translation, rotation, scaling, optionally extended to aspect ratio), additional details of which can be found in Appendices 1, 2, 3, and 4.

Consider, for example, that the reference cluster centers for four cluster centers are $(x_1,y_1); (x_2,y_2); (x_3,y_3); (x_4,y_4)$ and the sequencing run uses 2-channel chemistry in which a red image and a green image are produced at each sequencing cycle. Then, for example sequencing cycle 3, the cycle-specific and image channel-specific transformations are $\{\alpha_r^3, \beta_r^3, \chi_r^3, \delta_r^3, \varepsilon_r^3, \phi_r^3\}$ for the red image and $\{\alpha_g^3, \beta_g^3, \chi_g^3, \delta_g^3, \varepsilon_g^3, \phi_g^3\}$ for the green image.

Similarly, for example sequencing cycle 9, the cycle-specific and image channel-specific transformations are $\{\alpha_r^9, \beta_r^9, \chi_r^9, \delta_r^9, \varepsilon_r^9, \phi_r^9\}$ for the red image and $\{\alpha_g^9, \beta_g^9, \chi_g^9, \delta_g^9, \varepsilon_g^9, \phi_g^9\}$ for the green image.

Then, the transformed cluster centers for the red image of sequencing cycle 3 $(\hat{x}_1,\hat{y}_1); (\hat{x}_2,\hat{y}_2); (\hat{x}_3,\hat{y}_3); (\hat{x}_4,\hat{y}_4)$ are derived by applying the transformation $\{\alpha_r^3, \beta_r^3, \chi_r^3, \delta_r^3, \varepsilon_r^3, \phi_r^3\}$ to the reference cluster centers $(x_1,y_1); (x_2,y_2); (x_3,y_3); (x_4,y_4)$, and the transformed cluster centers for the green image of sequencing cycle 3 $(\tilde{x}_1, \tilde{y}_1); (\tilde{x}_2, \tilde{y}_2); (\tilde{x}_3, \tilde{y}_3); (\tilde{x}_4, \tilde{y}_4)$ are derived by applying the transformation $\{\alpha_g^3, \beta_g^3, \chi_g^3, \delta_g^3, \varepsilon_g^3, \phi_g^3\}$ to the reference cluster centers $(x_1,y_1); (x_2,y_2); (x_3,y_3); (x_4,y_4)$.

Similarly, the transformed cluster centers for the red image of sequencing cycle 9 $(\vec{x}_1, \vec{y}_1); (\vec{x}_2, \vec{y}_2); (\vec{x}_3, \vec{y}_3); (\vec{x}_2, \vec{y}_2)$ are derived by applying the transformation $\{\alpha_r^9, \beta_r^9, \chi_r^9, \delta_r^9, \varepsilon_r^9, \phi_r^9\}$ to the reference cluster centers $(x_1,y_1); (x_2,y_2); (x_3,y_3); (x_4,y_4)$, and the transformed cluster centers for the green image of sequencing cycle 9 $(\tilde{x}_1,\tilde{y}_1); (\tilde{x}_2,\tilde{y}_2); (\tilde{x}_3,\tilde{y}_3); (\tilde{x}_4,\tilde{y}_4)$ are derived by applying the transformation $\{\alpha_g^9, \beta_g^9, \chi_g^9, \delta_g^9, \varepsilon_g^9, \phi_g^9\}$ to the reference cluster centers $(x_1,y_1); (x_2,y_2); (x_3,y_3); (x_4,y_4)$.

In one implementation, the transformations are performed by a transformer 8102.

The transformed cluster centers 8104 are the stored in the template/template image 8004 and respectively used (i) to do the patch extraction from corresponding sequencing images 108 (e.g., by a patch extractor 8106), (ii) in the distance formula $d=(x_2-x_1)^2+(y_2-y_1)^2)$ to calculate the distance channels for corresponding image patches, and (iii) as supplemental input to the neural network-based base caller 1514 for the corresponding sequencing cycle being base called. In other implementations, a different distance formula can be used such as distance squared, e^-distance, and e^-distance squared.

Image Patch

Figure 82:
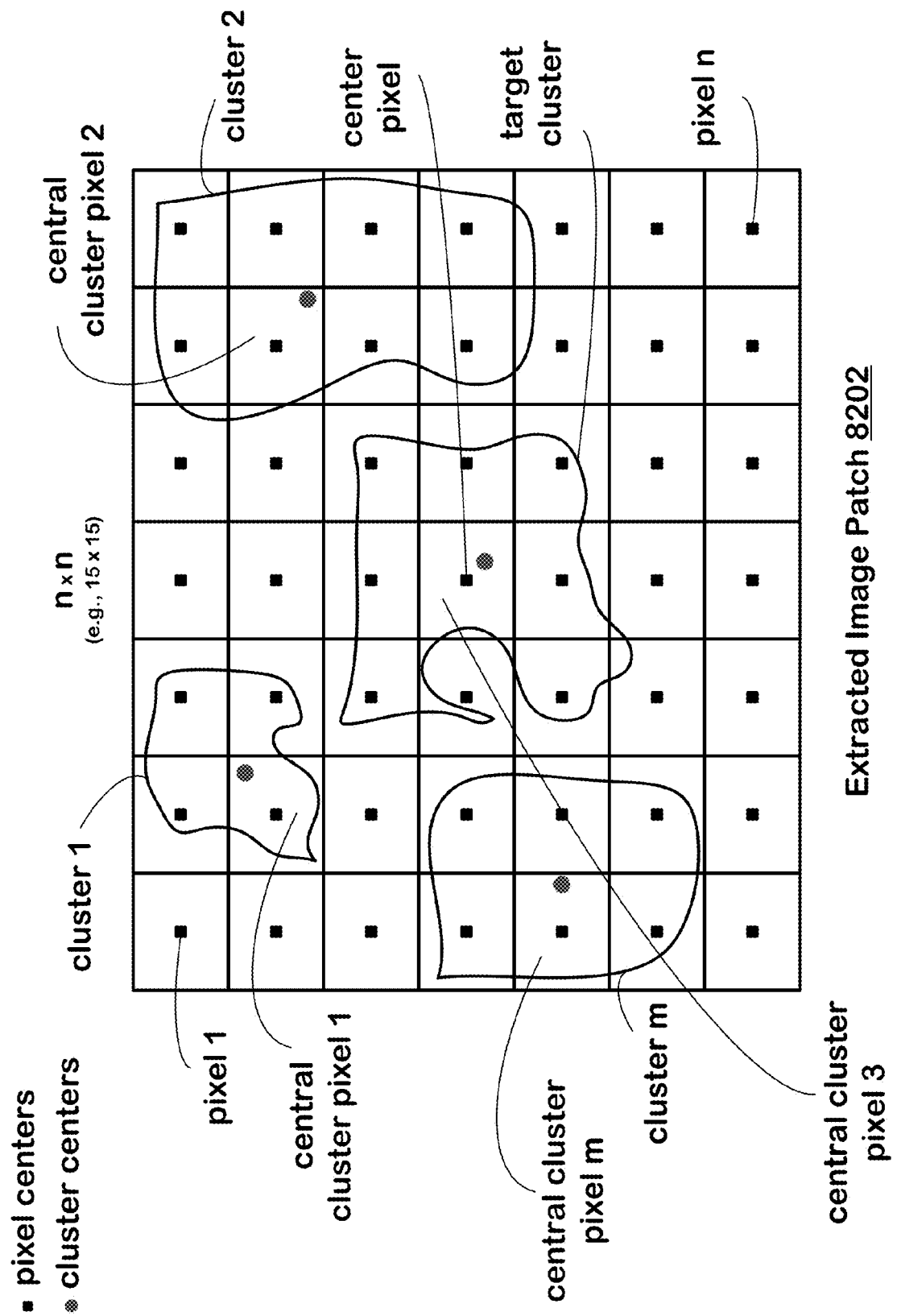
FIG. 82 illustrates an image patch that is part of the input data fed to the neural network-based base caller.

FIG. 82 illustrates an image patch 8202 that is part of the input data fed to the neural network-based base caller 1514. The input data includes a sequence of per-cycle image patch sets generated for a series of sequencing cycles of a sequencing run. Each per-cycle image patch set in the sequence has an image patch for a respective one of one or more image channels.

Consider, for example, that the sequencing run uses the 2-channel chemistry which produces a red image and a green image at each sequencing cycle, and the input data comprises data spanning a series of three sequencing cycles of the sequencing run: a current (time t) sequencing cycle to be base called, a previous (time t−1) sequencing cycle, and a next (time t+1) sequencing cycle.

Then, the input data comprises the following sequence of per-cycle image patch sets: a current cycle image patch set with a current red image patch and a current green image patch respectively extracted from the red and green sequencing images captured at the current sequencing cycle, a previous cycle image patch set with a previous red image patch and a previous green image patch respectively extracted from the red and green sequencing images captured at the previous sequencing cycle, and a next cycle image patch set with a next red image patch and a next green image patch respectively extracted from the red and green sequencing images captured at the next sequencing cycle.

The size of each image patch can be n×n, where n can be any number ranging from 1 and 10,000. Each image patch can be in the optical, pixel domain or in the upsampled, subpixel domain. In the implementation illustrated in FIG. 82, the extracted image page 8202 has pixel intensity data for pixels that cover/depict a plurality of clusters 1-m and their surrounding background. Also, in the illustrated implementation, the image patch 8202 is extracted in such a way that is contains in its center pixel the center of a target cluster being base called.

In FIG. 82, the pixel centers are depicted by a black rectangle and have integer location/position coordinates, and the cluster centers are depicted by a purple circle and have floating-point location/position coordinates.

Distance Calculation for a Single Target Cluster

Figure 83:
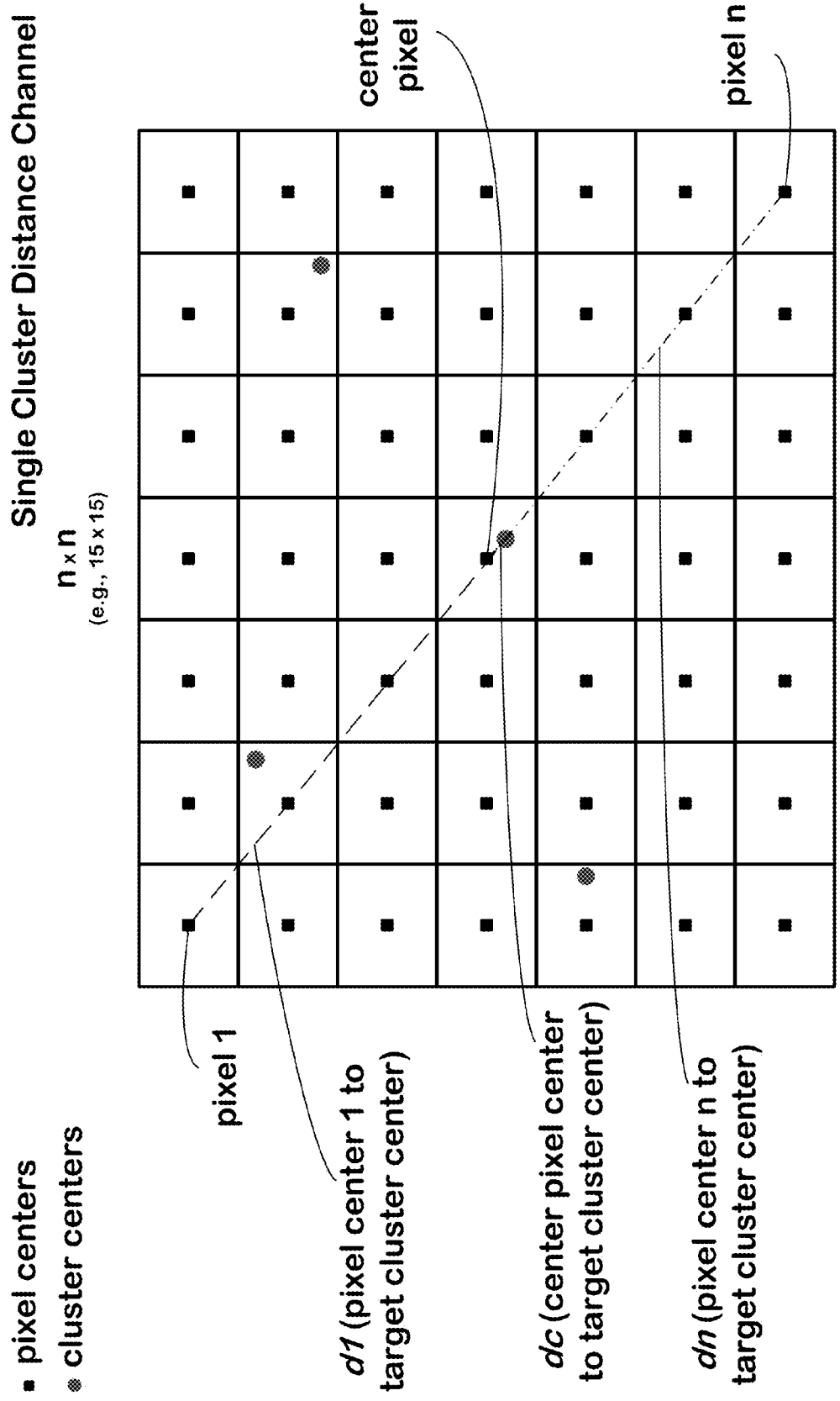
FIG. 83 depicts one implementation of determining distance values for a distance channel when a single target cluster is being base called by the neural network-based base caller.

FIG. 83 depicts one implementation of determining distance values 8302 for a distance channel when a single target cluster is being base called by the neural network-based base caller 1514. The center of the target cluster is contained in the center pixels of the image patches that are fed as input to the neural network-based base caller 1514. The distance values are calculated on a pixel-by-pixel basis, such that, for each pixel, the distance between its center and the center of the target cluster is determined. Accordingly, a distance value is calculated for each pixel in each of the image patches that are part of the input data.

FIG. 83 shows three distance values dl, dc, and dn for a particular image patch. In one implementation, the distance values 8302 are calculated using the following distance formula: $d=\sqrt{(x_2-x_1)^2+(y^2-y^1)^2}$, which operates on the transformed cluster centers 8104. In other implementations, a different distance formula can be used such as distance squared, $e^\wedge$-distance, and $e^\wedge$-distance squared.

In other implementations, when the image patches are in the upsampled, subpixel resolution, the distance values 8302 are calculated in the subpixel domain.

Thus, in the single target cluster base calling implementation, the distance channels are calculated only with respect to the target cluster being base called.

Figure 84:
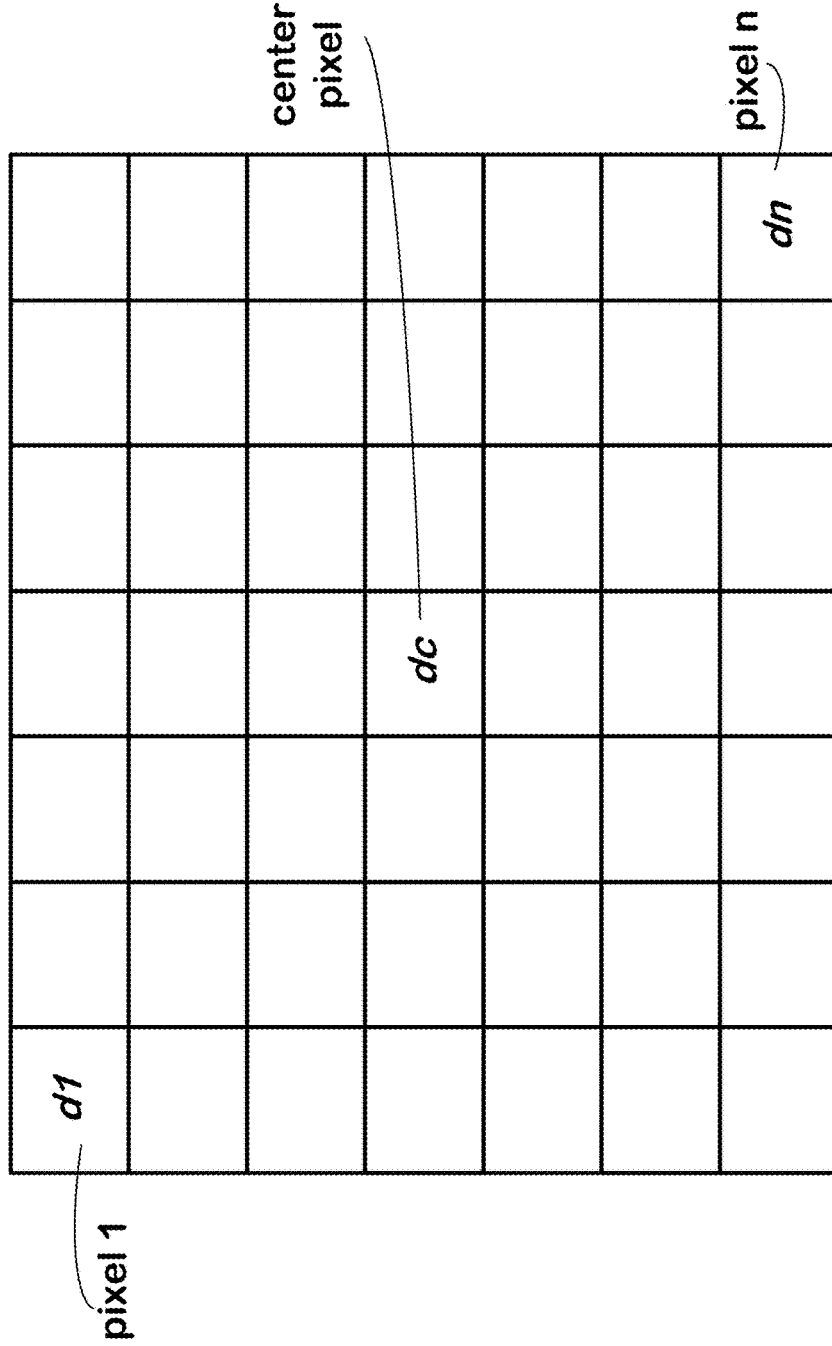
FIG. 84 shows one implementation of pixel-wise encoding the distance values that are calculated between the pixels and the target cluster.

FIG. 84 shows one implementation of pixel-wise encoding 8402 the distance values 8302 that are calculated between the pixels and the target cluster. In one implementation, in the input data, the distance values 8302, as part of the distance channel, supplement each corresponding image channel (image patch) as "pixel distance data". Returning to the example of a red image and a green image being generated per-sequencing cycle, the input data comprises a red distance channel and a green distance channel that supplement the red image channel and the green image channel as pixel distance data, respectively.

In other implementations, when the image patches are in the upsampled, subpixel resolution, the distance channels are encoded on a subpixel-by-subpixel basis.

Distance Calculation for Multiple Target Clusters

Figure 85A:
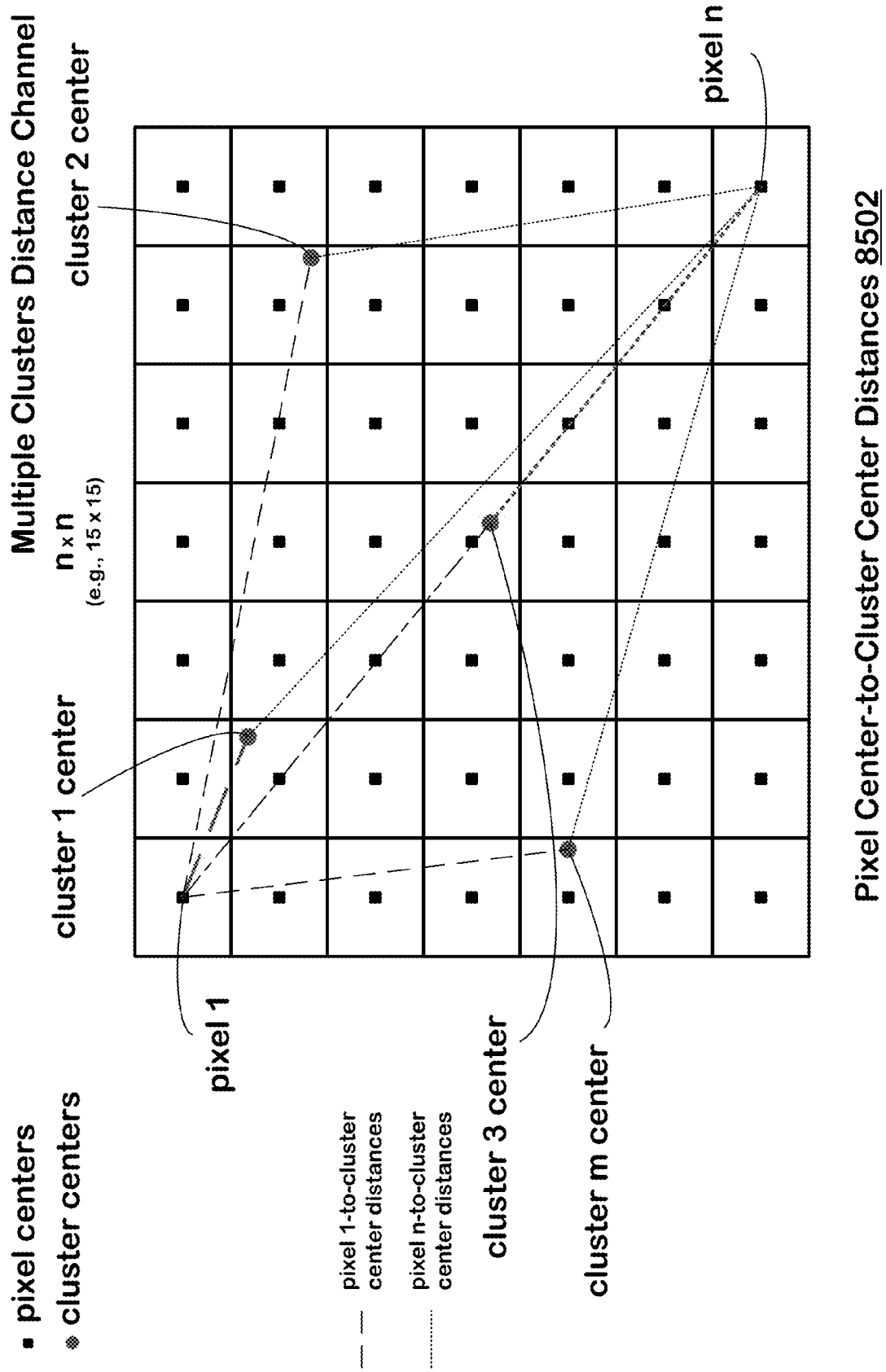
FIG. 85a depicts one implementation of determining distance values for a distance channel when multiple target clusters are being simultaneously base called by the neural network-based base caller.

FIG. 85*a* depicts one implementation of determining distance values 8502 for a distance channel when multiple target clusters 1-m are being simultaneously base called by the neural network-based base caller 1514. The distance values are calculated on a pixel-by-pixel basis, such that, for each pixel, the distance between its center and respective centers of each of the multiple clusters 1-m is determined and the minimum distance value (in red) is assigned to the pixel.

Accordingly, the distance channel identifies each pixel's center-to-center distance from a nearest one of the clusters selected based on center-to-center distances between the pixel and each of the clusters. In the illustrated implementation, FIG. 85*a* shows pixel center-to-cluster center distances for two pixels and four cluster centers. Pixel 1 is nearest to cluster 1 and pixel n is nearest to cluster 3.

In one implementation, the distance values 8502 are calculated using the following distance formula: $d=\sqrt{(x_2-x_1)^2+(y_2-y_1)^2}$, which operates on the transformed cluster centers 8104. In other implementations, a different distance formula can be used such as distance squared, $e^\wedge$-distance, and $e^\wedge$-distance squared.

In other implementations, when the image patches are in the upsampled, subpixel resolution, the distance values 8502 are calculated in the subpixel domain.

Thus, in the multi-cluster base calling implementation, the distance channels are calculated with respect to the nearest cluster from among a plurality of clusters.

Figure 85B:
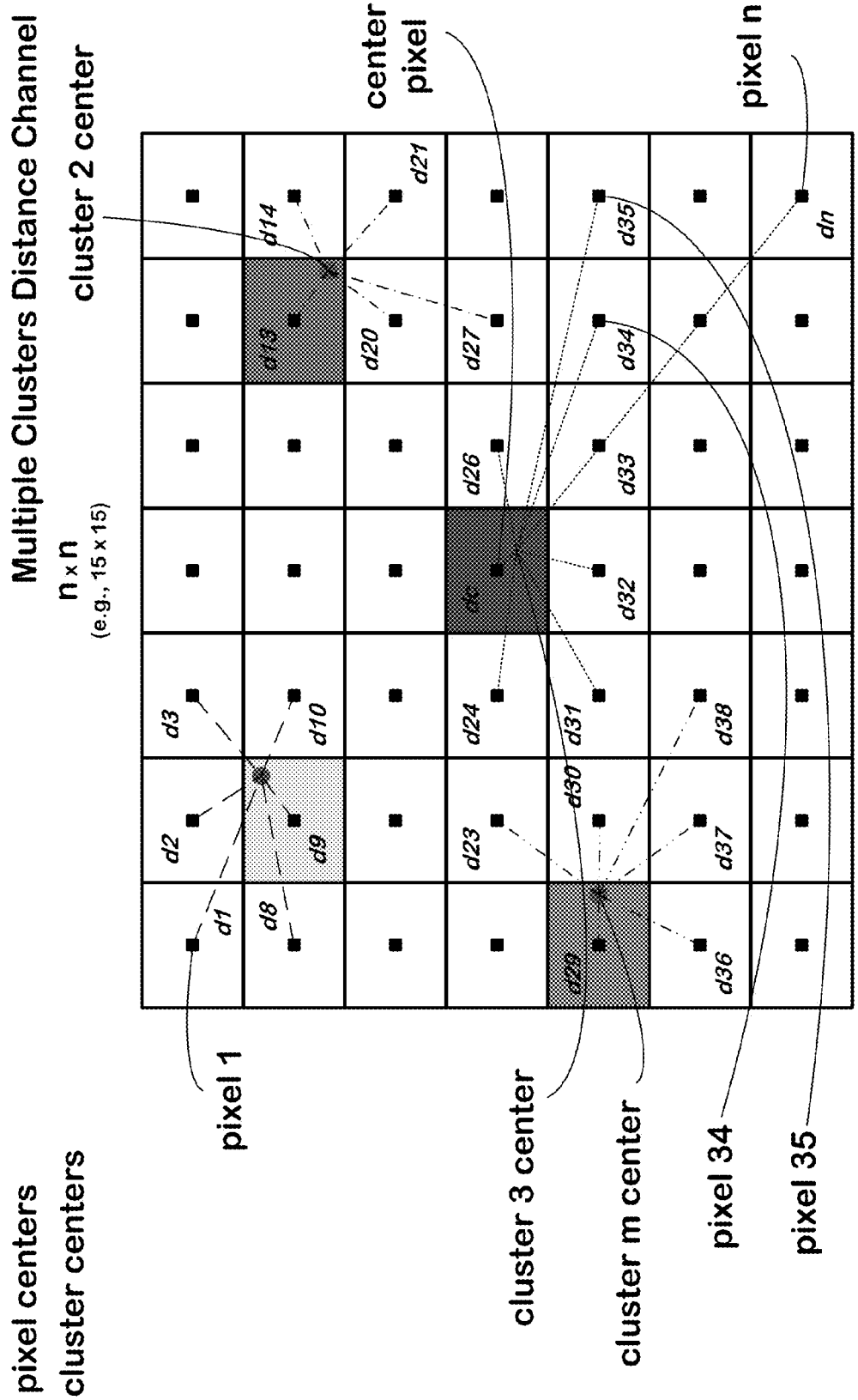
FIG. 85b shows, for each of the target clusters, some nearest pixels determined based on the pixel center-to-nearest cluster center distances.

FIG. 85*b* shows, for each of the target clusters 1-m, some nearest pixels determined based on the pixel center-to-nearest cluster center distances 8504 (d1, d2, d23, d29, d24, d32, dn, d13, d14, and etc.).

FIG. 86 shows one implementation of pixel-wise encoding 8602 the minimum distance values that are calculated between the pixels and the nearest one of the clusters. In other implementations, when the image patches are in the upsampled, subpixel resolution, the distance channels are encoded on a subpixel-by-subpixel basis.

Distance Calculation for Multiple Target Clusters based on Cluster Shapes

Figure 87:
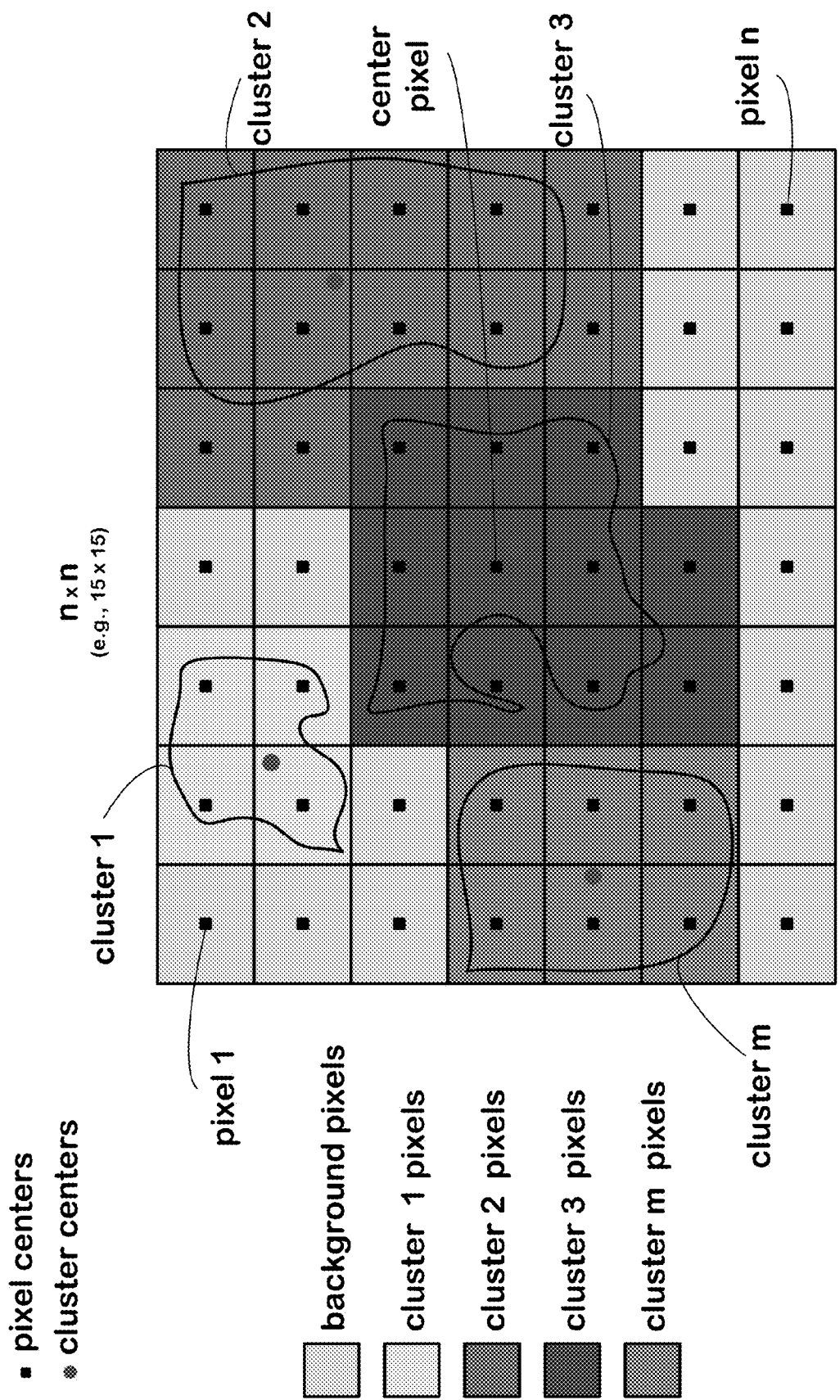
FIG. 87 illustrates one implementation using pixel-to-cluster classification/attribution/categorization, referred to herein as "cluster shape data".

FIG. 87 illustrates one implementation using pixel-to-cluster classification/attribution/categorization 8702, referred to herein as "cluster shape data" or "cluster shape information", to determine cluster distance values 8802 for a distance channel when multiple target clusters 1-m are being simultaneously base called by the neural network-based base caller 1514. First, what follows is a brief review of how the cluster shape data is generated.

As discussed above, the output of the neural network-based template generator 1512 is used to classify the pixels as: background pixels, center pixels, and cluster/cluster interior pixels depicting/contributing to/belonging to a same cluster. This pixel-to-cluster classification information is used to attribute each pixel to only one cluster, irrespective of the distances between the pixel centers and the cluster centers, and is stored as the cluster shape data.

In the implementation illustrated in FIG. 87, background pixels are colored in grey, pixels belonging to cluster 1 are colored in yellow (cluster 1 pixels), pixels belonging to cluster 2 are colored in green (cluster 2 pixels), pixels belonging to cluster 3 are colored in red (cluster 3 pixels), and pixels belonging to cluster m are colored in blue (cluster m pixels).

Figure 88:
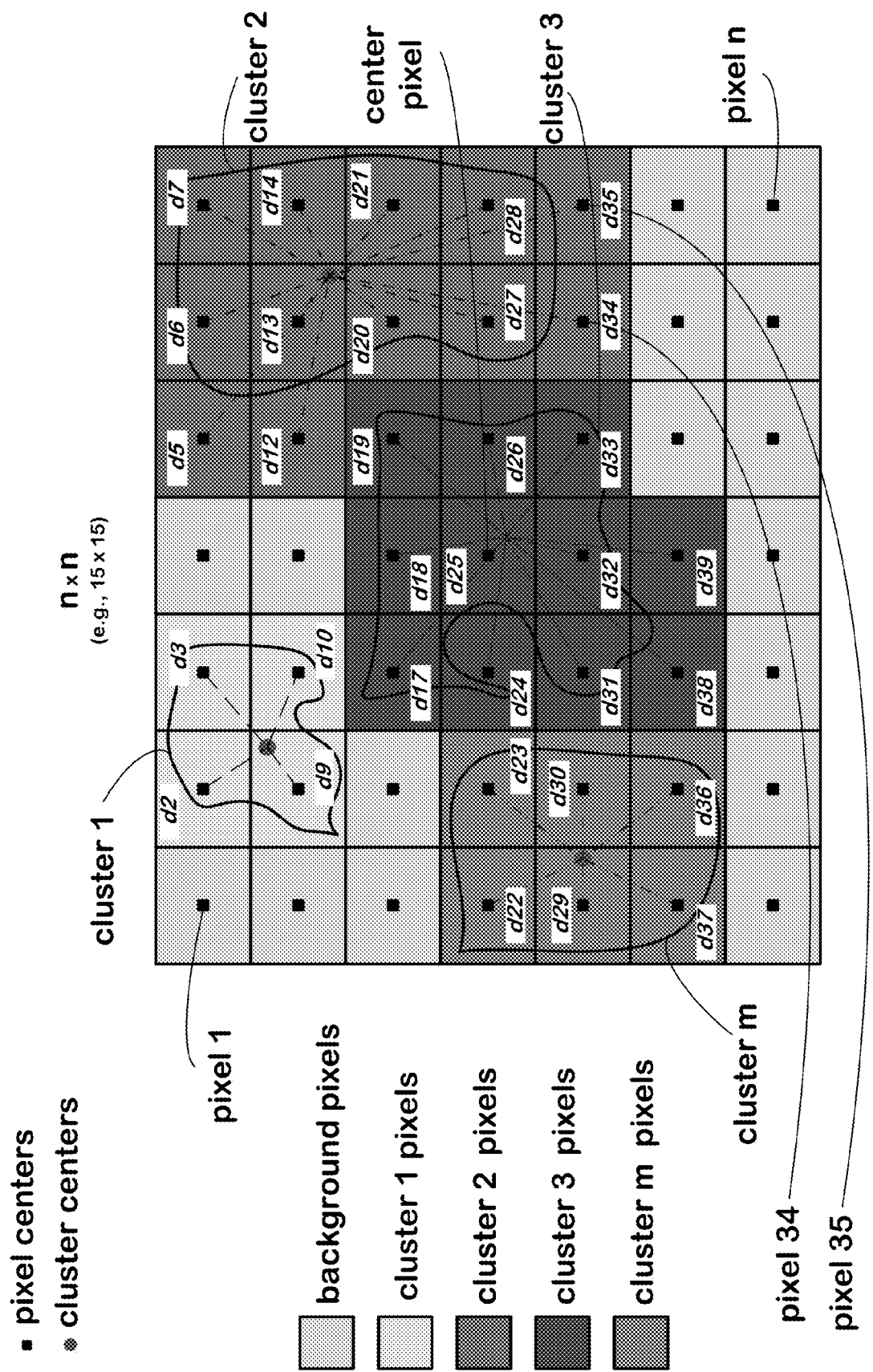
FIG. 88 shows one implementation of calculating the distance values using the cluster shape data.

FIG. 88 shows one implementation of calculating the distance values 8802 using the cluster shape data. First, we explain why distance information calculated without accounting for cluster shapes is prone to error. We then explain how the cluster shape data overcomes this limitation.

In the "multi-cluster" base calling implementation that does not use cluster shape data (FIGS. 85*a-b* and 86), the center-to-center distance value for a pixel is calculated with respect to the nearest cluster from among a plurality of clusters. Now, consider the scenario when a pixel that belongs to cluster A is further away from the center of cluster A but nearer to the center of cluster B. In such a case, without the cluster shape data, the pixel is assigned a distance value that is calculated with respect to cluster B (to which it does not belong), instead of being assigned a distance value vis-a-vis cluster A (to which it truly belongs).

The "multi-cluster shape-based" base calling implementation avoids this by using the true pixel-to-cluster mapping, as defined in the raw image data and produced by the neural network-based template generator 1512.

Contrast between the two implementations can be seen with regards to pixels 34 and 35. In FIG. 85*b*, distance values of pixels 34 and 35 are calculated with respect to the nearest center of cluster 3, without accounting for the cluster shape data. However, in FIG. 88, based on the cluster shape data, distance values 8802 of pixels 34 and 35 are calculated with respect to cluster 2 (to which they actually belong).

In FIG. 88, the cluster pixels depict cluster intensities and the background pixels depict background intensities. The cluster distance values identify each cluster pixel's center-to-center distance from an assigned one of the clusters selected based on classifying each cluster pixel to only one of the clusters. In some implementations, the background pixels are assigned a predetermined background distance value, such as 0 or 0.1, or some other minimum value.

In one implementation, as discussed above, the cluster distance values 8802 are calculated using the following distance formula: $d=\sqrt{(x_2-x_1)^2+(y_2-y_1)^2}$, which operates on the transformed cluster centers 8104. In other implementations, a different distance formula can be used such as distance squared, $e^\wedge$-distance, and $e^\wedge$-distance squared.

In other implementations, when the image patches are in the upsampled, subpixel resolution, the cluster distance values 8802 are calculated in the subpixel domain and the cluster and background attribution 8702 occurs on a subpixel-by-subpixel basis.

Thus, in the multi-cluster shape-based base calling implementation, the distance channels are calculated with respect to an assigned cluster from among a plurality of clusters. The assigned cluster is selected based on classifying each cluster pixel to only one of the clusters in accordance with the true pixel-to-cluster mapping defined in the raw image data.

FIG. 89 shows one implementation of pixel-wise encoding the distance values 8702 that are calculated between the pixels and the assigned clusters. In other implementations, when the image patches are in the upsampled, subpixel resolution, the distance channels are encoded on a subpixel-by-subpixel basis.

Deep learning is a powerful machine learning technique that uses many-layered neural networks. One particularly successful network structure in computer vision and image processing domains is the convolutional neural network (CNN), where each layer performs a feed-forward convolutional transformations from an input tensor (an image-like, multi-dimensional dense array) to an output tensor of different shape. CNNs are particularly suited for image-like input due the spatial coherence of images and the advent of general purpose graphics processing units (GPUs) which make training fast on arrays up to 3- or 4-D. Exploiting these image-like properties leads to superior empirical performance compared to other learning methods such as support vector machine (SVM) or multi-layer perceptron (MLP).

We introduce a specialized architecture that augments a standard CNN to handle both image data and supplemental distance and scaling data. More details follow.

Specialized Architecture

Figure 90:
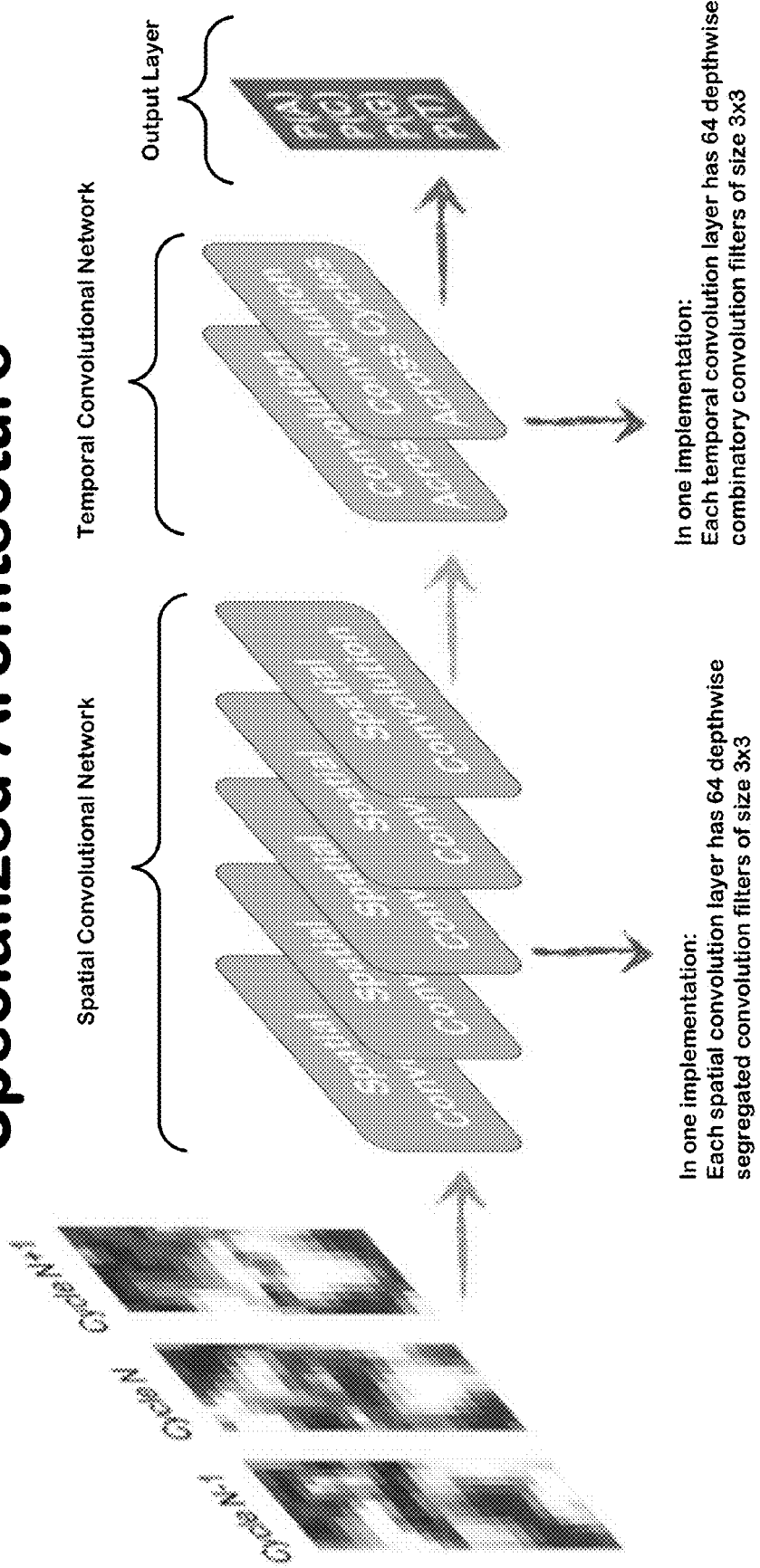
FIG. 90 illustrates one implementation of the specialized architecture of the neural network-based base caller that is used to segregate processing of data for different sequencing cycles.

FIG. 90 illustrates one implementation of the specialized architecture of the neural network-based base caller 1514 that is used to segregate processing of data for different sequencing cycles. The motivation for using the specialized architecture is described first.

As discussed above, the neural network-based base caller 1514 processes data for a current sequencing cycle, one or more preceding sequencing cycles, and one or more successive sequencing cycles. Data for additional sequencing cycles provides sequence-specific context. The neural network-based base caller 1514 learns the sequence-specific context during training and base call them. Furthermore, data for pre and post sequencing cycles provides second order contribution of pre-phasing and phasing signals to the current sequencing cycle.

Spatial Convolution Layers

However, as discussed above, images captured at different sequencing cycles and in different image channels are misaligned and have residual registration error with respect to each other. To account for this misalignment, the specialized architecture comprises spatial convolution layers that do not mix information between sequencing cycles and only mix information within a sequencing cycle.

Spatial convolution layers use so-called "segregated convolutions" that operationalize the segregation by independently processing data for each of a plurality of sequencing cycles through a "dedicated, non-shared" sequence of convolutions. The segregated convolutions convolve over data and resulting feature maps of only a given sequencing cycle, i.e., intra-cycle, without convolving over data and resulting feature maps of any other sequencing cycle.

Consider, for example, that the input data comprises (i) current data for a current (time t) sequencing cycle to be base called, (ii) previous data for a previous (time t−1) sequencing cycle, and (iii) next data for a next (time t+1) sequencing cycle. The specialized architecture then initiates three separate data processing pipelines (or convolution pipelines), namely, a current data processing pipeline, a previous data processing pipeline, and a next data processing pipeline. The current data processing pipeline receives as input the current data for the current (time t) sequencing cycle and independently processes it through a plurality of spatial convolution layers to produce a so-called "current spatially convolved representation" as the output of a final spatial convolution layer. The previous data processing pipeline receives as input the previous data for the previous (time t−1) sequencing cycle and independently processes it through the plurality of spatial convolution layers to produce a so-called "previous spatially convolved representation" as the output of the final spatial convolution layer. The next data processing pipeline receives as input the next data for the next (time t+1) sequencing cycle and independently processes it through the plurality of spatial convolution layers to produce a so-called "next spatially convolved representation" as the output of the final spatial convolution layer.

In some implementations, the current, previous, and next processing pipelines are executed in parallel.

In some implementations, the spatial convolution layers are part of a spatial convolutional network (or subnetwork) within the specialized architecture.

Temporal Convolution Layers

The neural network-based base caller 1514 further comprises temporal convolution layers that mix information between sequencing cycles, i.e., inter-cycles. The temporal convolution layers receive their inputs from the spatial convolutional network and operate on the spatially convolved representations produced by the final spatial convolution layer for the respective data processing pipelines.

The inter-cycle operability freedom of the temporal convolution layers emanates from the fact that the misalignment property, which exists in the image data fed as input to the spatial convolutional network, is purged out from the spatially convolved representations by the cascade of segregated convolutions performed by the sequence of spatial convolution layers.

Temporal convolution layers use so-called "combinatory convolutions" that groupwise convolve over input channels in successive inputs on a sliding window basis. In one implementation, the successive inputs are successive outputs produced by a previous spatial convolution layer or a previous temporal convolution layer.

In some implementations, the temporal convolution layers are part of a temporal convolutional network (or subnetwork) within the specialized architecture. The temporal convolutional network receives its inputs from the spatial convolutional network. In one implementation, a first temporal convolution layer of the temporal convolutional network groupwise combines the spatially convolved representations between the sequencing cycles. In another implementation, subsequent temporal convolution layers of the temporal convolutional network combine successive outputs of previous temporal convolution layers.

The output of the final temporal convolution layer is fed to an output layer that produces an output. The output is used to base call one or more clusters at one or more sequencing cycles.

What follows is a more detailed discussion of the segregated and combinatory convolutions.

Segregated Convolutions

During a forward propagation, the specialized architecture processes information from a plurality of inputs in two stages. In the first stage, segregation convolutions are used to prevent mixing of information between the inputs. In the second stage, combinatory convolutions are used to mix information between the inputs. The results from the second stage are used to make a single inference for the plurality of inputs.

This is different than the batch mode technique where a convolution layer processes multiple inputs in a batch at the same time and makes a corresponding inference for each input in the batch. In contrast, the specialized architecture maps the plurality of inputs to the single inference. The single inference can comprise more than one prediction, such as a classification score for each of the four bases (A, C, T, and G).

In one implementation, the inputs have temporal ordering such that each input is generated at a different time step and has a plurality of input channels. For example, the plurality of inputs can include the following three inputs: a current input generated by a current sequencing cycle at time step (t), a previous input generated by a previous sequencing cycle at time step (t−1), and a next input generated by a next sequencing cycle at time step (t+1). In another implementation, each input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel.

Figure 91:
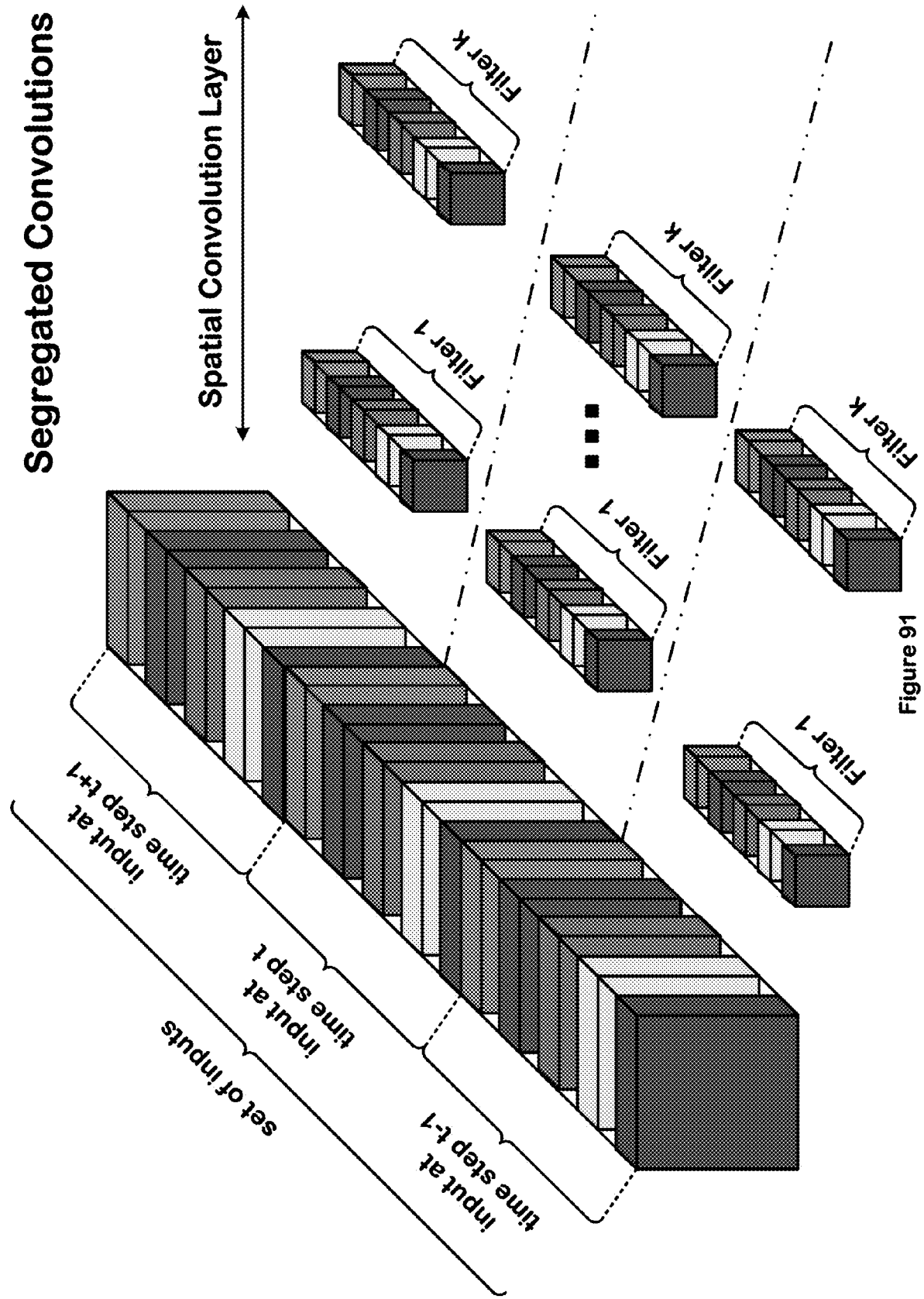
FIG. 91 depicts one implementation of segregated convolutions.

FIG. 91 depicts one implementation of the segregated convolutions. Segregated convolutions process the plurality of inputs at once by applying a convolution filter to each input in parallel. With the segregated convolutions, the convolution filter combines input channels in a same input and does not combine input channels in different inputs. In one implementation, a same convolution filter is applied to each input in parallel. In another implementation, a different convolution filter is applied to each input in parallel. In some implementations, each spatial convolution layer comprises a bank of k convolution filters, each of which applies to each input in parallel.

Combinatory Convolutions

Combinatory convolutions mix information between different inputs by grouping corresponding input channels of the different inputs and applying a convolution filter to each group. The grouping of the corresponding input channels and application of the convolution filter occurs on a sliding window basis. In this context, a window spans two or more successive input channels representing, for instance, outputs for two successive sequencing cycles. Since the window is a sliding window, most input channels are used in two or more windows.

In some implementations, the different inputs originate from an output sequence produced by a preceding spatial or temporal convolution layer. In the output sequence, the different inputs are arranged as successive outputs and therefore viewed by a next temporal convolution layer as successive inputs. Then, in the next temporal convolution layer, the combinatory convolutions apply the convolution filter to groups of corresponding input channels in the successive inputs.

In one implementation, the successive inputs have temporal ordering such that a current input is generated by a current sequencing cycle at time step (t), a previous input is generated by a previous sequencing cycle at time step (t−1), and a next input is generated by a next sequencing cycle at time step (t+1). In another implementation, each successive input is respectively derived from the current, previous, and next inputs by one or more previous convolution layers and includes k feature maps.

In one implementation, each input can include the following five input channels: a red image channel (in red), a red distance channel (in yellow), a green image channel (in green), a green distance channel (in purple), and a scaling channel (in blue). In another implementation, each input can include k feature maps produced by a previous convolution layer and each feature map is treated as an input channel.

The depth B of the convolution filter is dependent upon the number of successive inputs whose corresponding input channels are groupwise convolved by the convolution filter on a sliding window basis. In other words, the depth B is equal to the number of successive inputs in each sliding window and the group size.

Figure 92A:
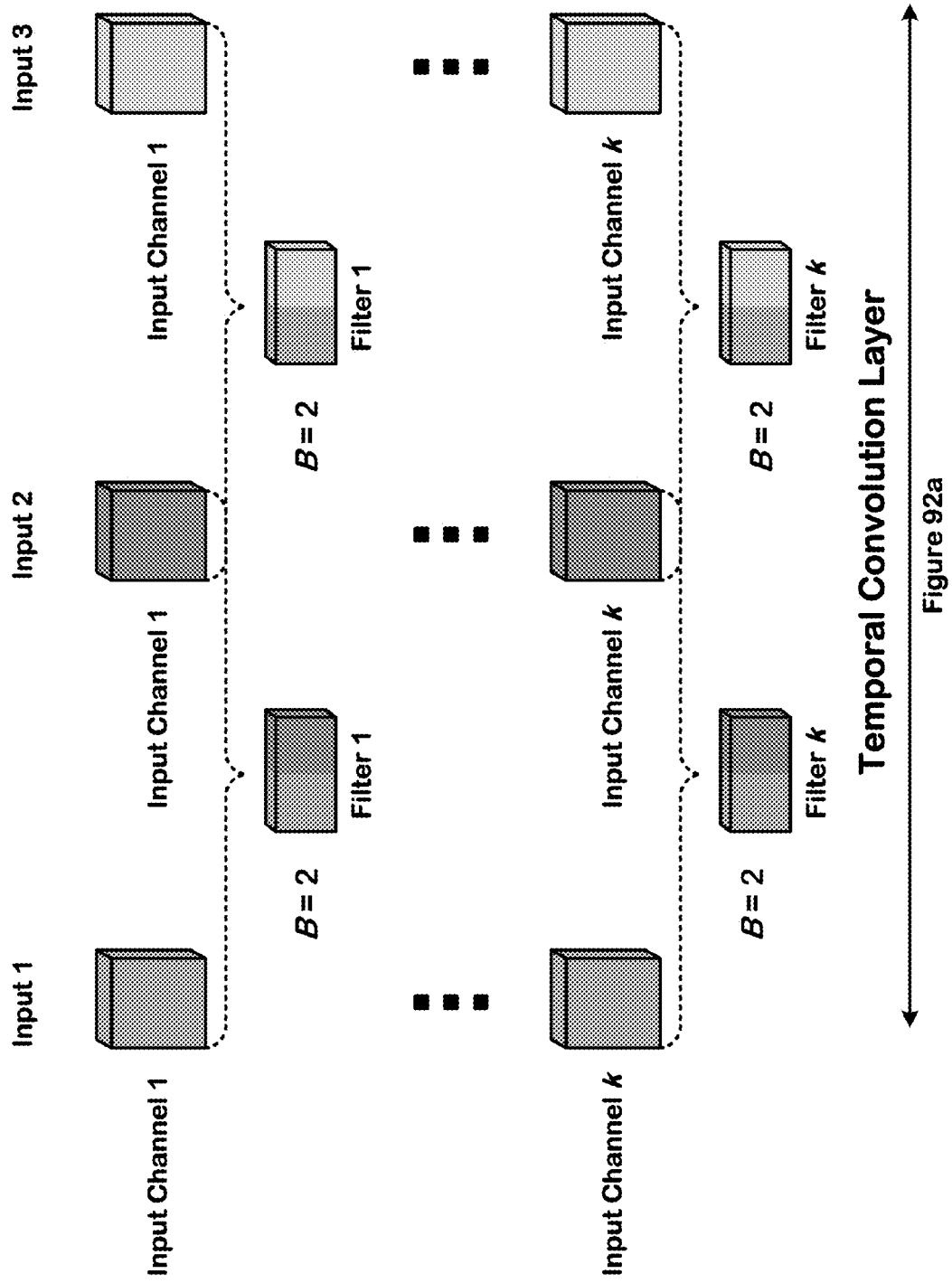
FIG. 92a depicts one implementation of combinatory convolutions.
Figure 92B:
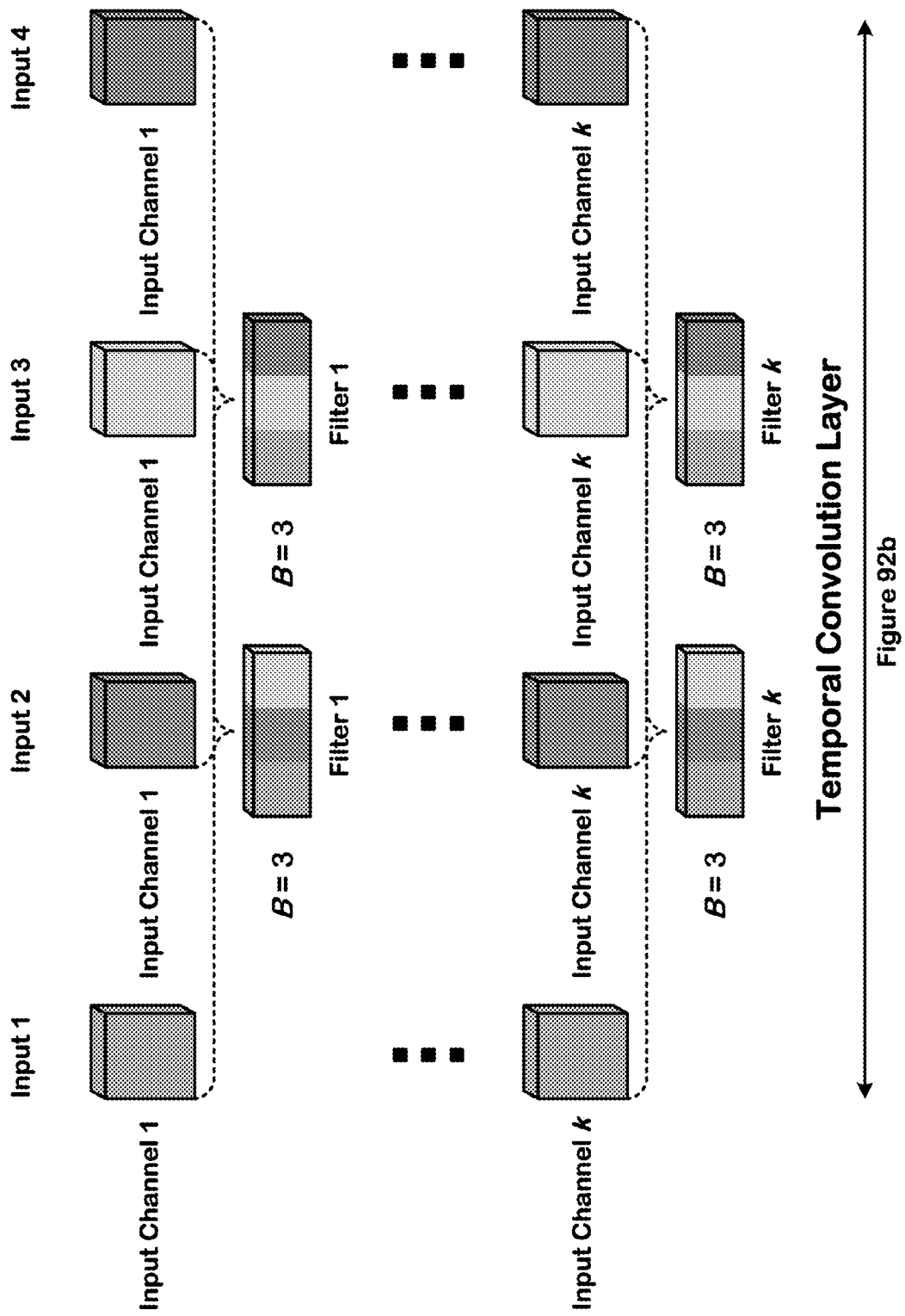
FIG. 92b depicts another implementation of the combinatory convolutions.

In FIG. 92a, corresponding input channels from two successive inputs are combined in each sliding window, and therefore B=2. In FIG. 92b, corresponding input channels from three successive inputs are combined in each sliding window, and therefore B=3.

In one implementation, the sliding windows share a same convolution filter. In another implementation, a different convolution filter is used for each sliding window. In some implementations, each temporal convolution layer comprises a bank of k convolution filters, each of which applies to the successive inputs on a sliding window basis.

Filter Banks

Figure 93:
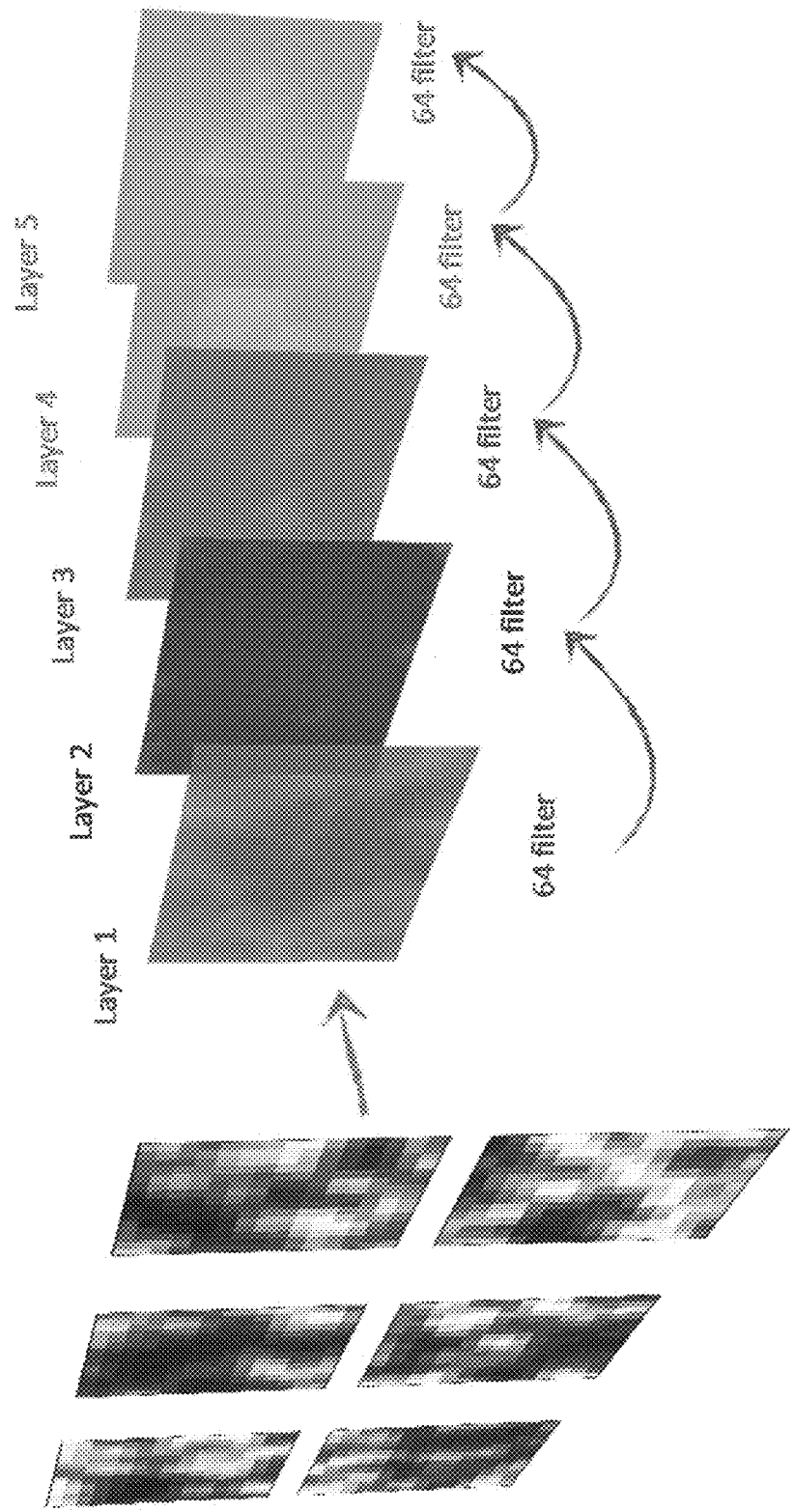
FIG. 93 shows one implementation of convolution layers of the neural network-based base caller in which each convolution layer has a bank of convolution filters.

FIG. 93 shows one implementation of convolution layers of the neural network-based base caller 1514 in which each convolution layer has a bank of convolution filters. In FIG. 93, five convolution layers are shown, each of which has a bank of 64 convolution filters. In some implementations, each spatial convolution layer has a bank of k convolution filters, where k can be any number such as 1, 2, 8, 64, 128, 256, and so on. In some implementations, each temporal convolution layer has a bank of k convolution filters, where k can be any number such as 1, 2, 8, 64, 128, 256, and so on.

The discussion now turns to the supplemental scaling channel and how it is calculated.

Scaling Channel

Figure 94:
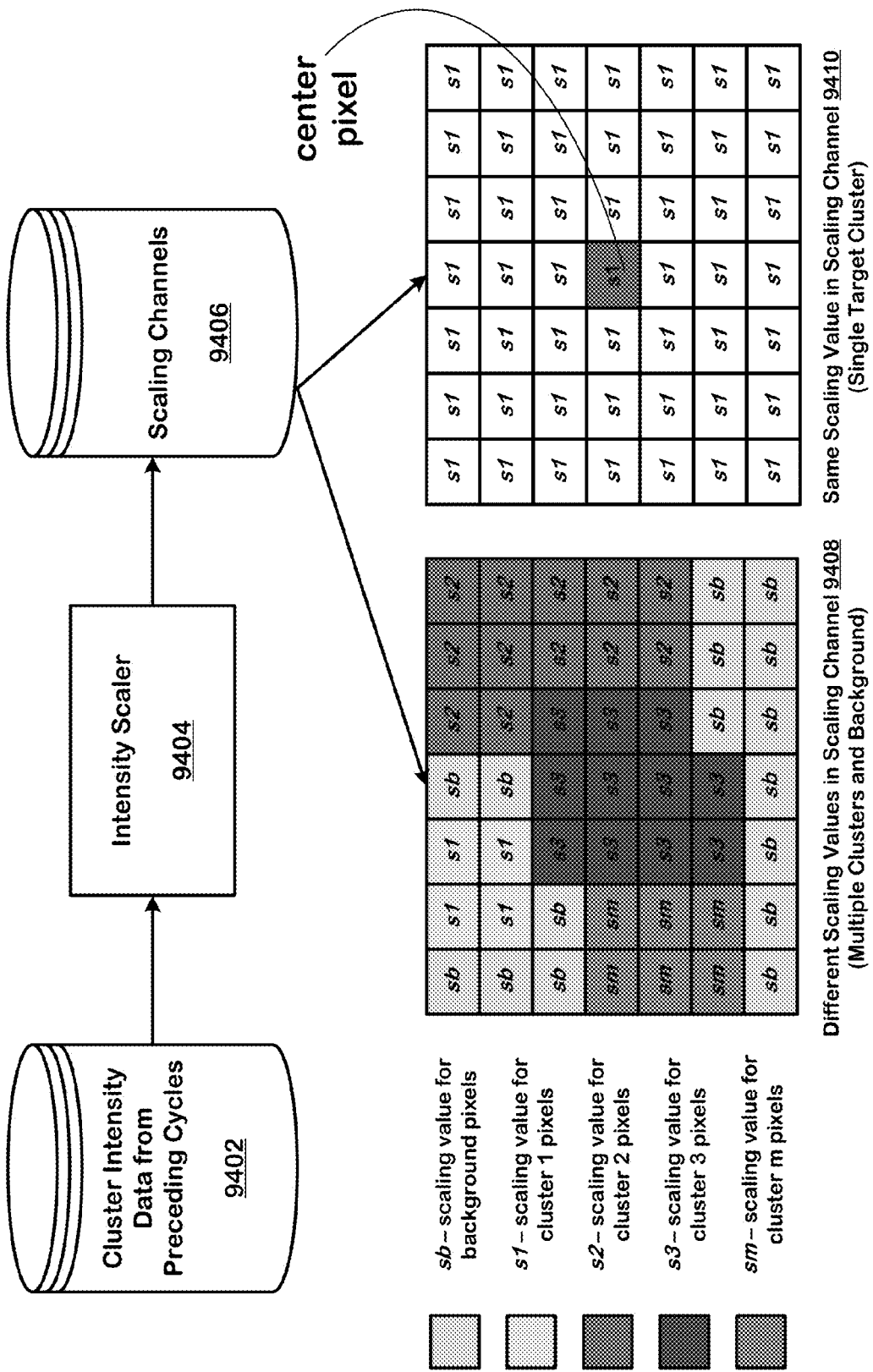
FIG. 94 depicts two configurations of the scaling channel that supplements the image channels.

FIG. 94 depicts two configurations of the scaling channel that supplements the image channels. The scaling channel is pixel-wise encoded in the input data that is fed to the neural network-based base caller 1514. Different cluster sizes and uneven illumination conditions result in a wide range of cluster intensities being extracted. The additive bias supplied by the scaling channel makes cluster intensities comparable across clusters. In other implementations, when the image patches are in the upsampled, subpixel resolution, the scaling channel is encoded on a subpixel-by-subpixel basis.

When a single target cluster is being base called, the scaling channel assigns a same scaling value to all the pixels. When multiple target clusters are being simultaneously base called, the scaling channels assign different scaling values to groups of pixels based on the cluster shape data.

Scaling channel 9410 has a same scaling value (s1) for all the pixels. Scaling value (s1) is based on a mean intensity of the center pixel that contains the center of the target cluster. In one implementation, the mean intensity is calculated by averaging intensity values of the center pixel observe during two or more preceding sequencing cycles that produced an A and a T base call for the target cluster.

Scaling channel 9408 has different scaling values (s1, s2, s3, sm) for respective pixel groups attributed to corresponding clusters based on the cluster shape data. Each pixel group includes a central cluster pixel that contains a center of the corresponding cluster. Scaling value for a particular pixel group is based on the mean intensity of its central cluster pixel. In one implementation, the mean intensity is calculated by averaging intensity values of the central cluster pixel observe during two or more preceding sequencing cycles that produced an A and a T base call for the corresponding cluster.

In some implementations, the background pixels are assigned a background scaling value (sb), which can be 0 or 0.1, or some other minimum value.

In one implementation, the scaling channels 9406 and their scaling values are determined by an intensity scaler 9404. The intensity scaler 9404 uses cluster intensity data 9402 from preceding sequencing cycles to calculate the mean intensities.

In other implementations, the supplemental scaling channel can be provided as input in a different way, such as prior to or to the last layer of the neural network-based base caller 1514, prior to or to the one or more intermediate layers of the neural network-based base caller 1514, and as a single value instead of encoding it pixel-wise to match the image size.

The discussion now turns to the input data that is fed to the neural network-based base caller 1514

Input Data: Image Channels, Distance Channels, and Scaling Channel

Figure 95A:
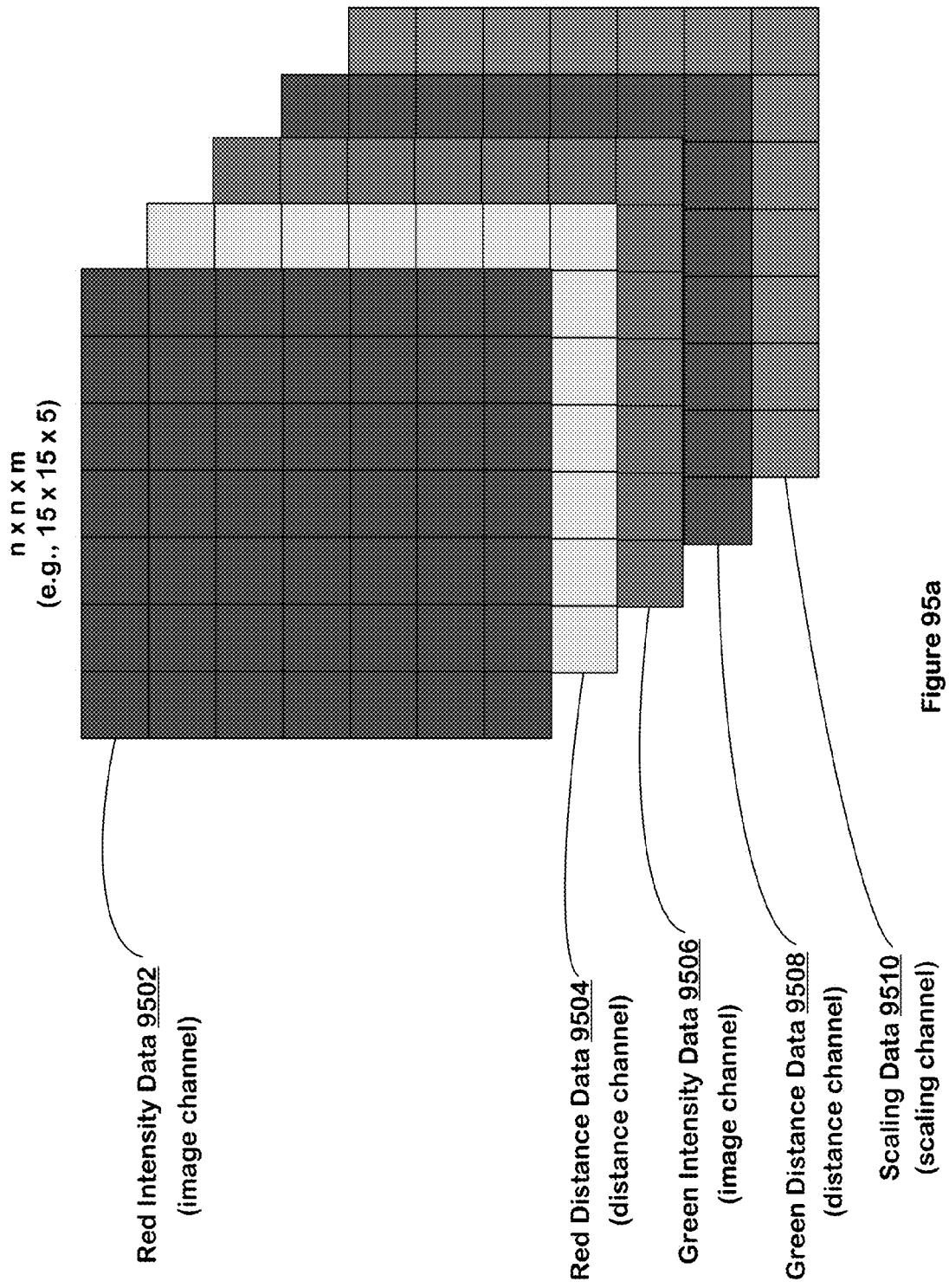
FIG. 95a illustrates one implementation of input data for a single sequencing cycle that produces a red image and a green image.

FIG. 95a illustrates one implementation of input data 9500 for a single sequencing cycle that produces a red image and a green image. The input data 9500 comprises the following:

Red intensity data 9502 (in red) for pixels in an image patch extracted from the red image. The red intensity data 9502 is encoded in a red image channel.

Red distance data 9504 (in yellow) that pixel-wise supplements the red intensity data 9502. The red distance data 9504 is encoded in a red distance channel.

Green intensity data 9506 (in green) for pixels in an image patch extracted from the green image. The green intensity data 9506 is encoded in a green image channel.

Green distance data 9508 (in purple) that pixel-wise supplements the green intensity data 9506. The green distance data 9508 is encoded in a green distance channel.

Scaling data 9510 (in blue) that pixel-wise supplements the red intensity data 9502 and the green intensity data 9506. The scaling data 9510 is encoded in a scaling channel.

In other implementations, the input data can include fewer or greater number of image channels and supplemental distance channels. In one example, for a sequencing run that uses 4-channel chemistry, the input data comprises four image channels for each sequencing cycle and four supplemental distance channels.

The discussion now turns to how the distance channels and the scaling channel contribute to base calling accuracy.

Additive Biasing

Figure 95B:
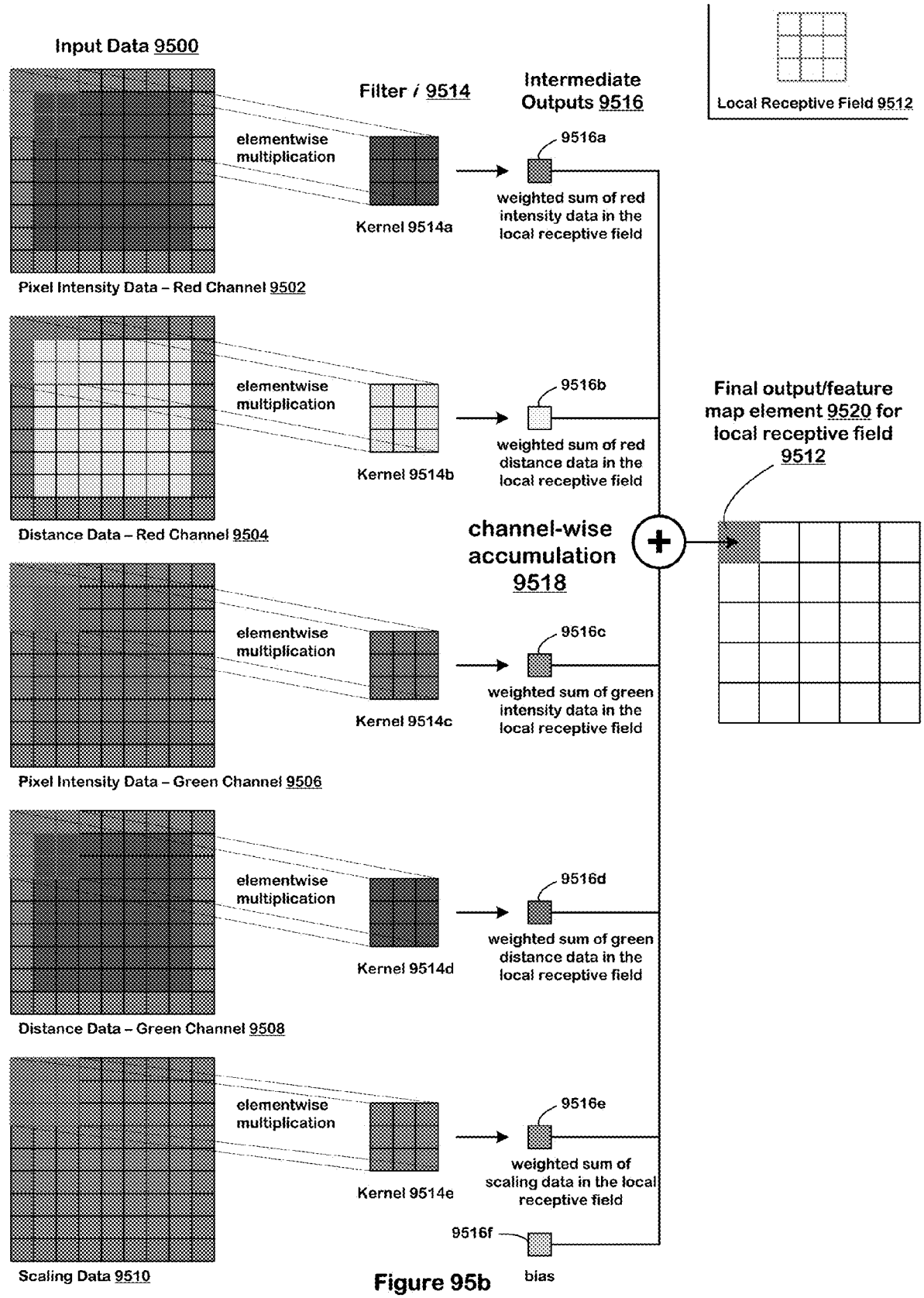
FIG. 95b illustrates one implementation of the distance channels supplying additive bias that is incorporated in the feature maps generated from the image channels.

FIG. 95b illustrates one implementation of the distance channels supplying additive bias that is incorporated in the feature maps generated from the image channels. This additive bias contributes to base calling accuracy because it is based on pixel center-to-cluster center(s) distances, which are pixel-wise encoded in the distance channels.

On average, around 3×3 pixels comprise one cluster. Density at the center of a cluster is expected to be higher than at the fringe because the cluster grows outwards from a substantially central location. Perimeter cluster pixels can contain conflicting signals from nearby clusters. Therefore, the central cluster pixel is considered the maximum intensity region and serves as a beacon that reliably identifies the cluster.

An image patch's pixels depict intensity emissions of a plurality of clusters (e.g., 10 to 200 clusters) and their surround background. Additional clusters incorporate information from a wider radius and contribute to base call prediction by discerning the underlying base whose intensity emissions are depicted in the image patch In other words, intensity emissions from a group of clusters cumulatively create an intensity pattern that can be assigned to a discrete base (A, C, T, or G).

We observe that explicitly communicating to the convolution filters distance of each pixel from the cluster center(s) in the supplemental distance channels results in higher base calling accuracy. The distance channels convey to the convolution filters which pixels contain the cluster centers and which pixels are farther away from the cluster centers. The convolution filters use this information to assign a sequencing signal to its proper source cluster by attending to (a) the central cluster pixels, their neighboring pixels, and feature maps derived from them more than (b) the perimeter cluster pixels, background pixels, and feature maps derived from them. In one example of the attending, the distance channels supply positive additive biases that are incorporated in feature maps resulting from (a), but supply negative additive biases that are incorporated in feature maps resulting from (b).

The distance channels have the same dimensionality as the image channels. This allows the convolution filters to separately evaluate the image channels and the distance channels within a local receptive field and coherently combine the evaluations.

When a single target cluster is being base called, the distance channels identify only one central cluster pixel at the center of the image patches. When multiple target clusters are being simultaneously base called, the distance channels identify multiple central cluster pixels distributed across the image patches.

A "single cluster" distance channel applies to an image patch that contains the center of a single target cluster to be base called in its center pixel. The single cluster distance channel includes center-to-center distance of each pixel in the image patch to the single target cluster. In this implementation, the image patch also includes additional clusters that are adjacent to the single target cluster, but the additional clusters are not base called.

A "multi-cluster" distance channel applies to an image patch that contains the centers of multiple target clusters to be base called in its respective central cluster pixels. The multi-cluster distance channel includes center-to-center distance of each pixel in the image patch to the nearest cluster from among the multiple target clusters. This has the potential of measuring a center-to-center distance to the wrong cluster, but that potential is low.

A "multi-cluster shape-based" distance channel applies to an image patch that contains the centers of multiple target clusters to be base called in its respective central cluster pixels and for which pixel-to-cluster attribution information is known. The multi-cluster distance channel includes center-to-center distance of each cluster pixel in the image patch to the cluster to which it belongs or is attributed to from among the multiple target clusters. Background pixels can be flagged as background, instead of given a calculated distance.

FIG. 95b also illustrates one implementation of the scaling channel supplying additive bias that is incorporated in the feature maps generated from the image channels. This additive bias contributes to base calling accuracy because it is based on mean intensities of central cluster pixel(s), which are pixel-wise encoded in the scaling channel. The discussion about additive biasing in the context of the distance channels analogously applies to the scaling channel.

Example of Additive Biasing

FIG. 95b further shows an example of how the additive biases are derived from the distance and scaling channels and incorporated into the features maps generated from the image channels.

In FIG. 95b, convolution filter i 9514 evaluates a local receptive field 9512 (in magenta) across the two image channels 9502 and 9506, the two distance channels 9504 and 9508, and the scaling channel 9510. Because the distance and scaling channels are separately encoded, the additive biasing occurs when the intermediate outputs 9516a-e of each of the channel-specific convolution kernels (or feature detectors) 9516a-e (plus bias 95160 are channel-wise accumulated 9518 as the final output/feature map element 9520 for the local receptive field 9512. In this example, the additive biases supplied by the two distance channels 9504 and 9508 are the intermediate outputs 9516b and 9516d, respectively. The additive bias supplied by the scaling channel 9510 is the intermediate output 9516e.

The additive biasing guides the feature map compilation process by putting greater emphasis on those features in the image channels that are considered more important and reliable for base calling, i.e., pixel intensities of central cluster pixels and their neighboring pixels. During training, backpropagation of gradients computed from comparison to the ground truth base calls updates weights of the convolution kernels to produce stronger activations for central cluster pixels and their neighboring pixels.

Consider, for example, that a pixel in the group of adjacent pixels covered by the local receptive field 9512 contains a cluster center, then the distance channels 9504 and 9508 reflect the proximity of the pixels to the cluster center. As a result, when the intensity intermediate outputs 9516a and 9516c are merged with the distance channel additive biases 9516b and 9516d at the channelwise accumulation 9518, what results is a positively biased convolved representation 9520 of the pixels.

In contrast, if the pixels covered by the local receptive field 9512 are not near a cluster center, then the distance channels 9504 and 9508 reflect their separation from the cluster center. As a result, when the intensity intermediate outputs 9516a and 9516c are merged with the distance channel additive biases 9516b and 9516d at the channelwise accumulation 9518, what results is a negatively biased convolved representation 9520 of the pixels.

Similarly, the scaling channel additive bias 9516e derived from the scaling channel 9510 can positively or negatively bias the convolved representation 9520 of the pixels.

For clarity's sake, FIG. 95b shows application of a single convolution filter i 9514 on the input data 9500 for a single sequencing cycle. One skilled in the art will appreciate that the discussion can be extended to multiple convolution filters (e.g., a filter bank of k filters, where k can be 8, 16, 32, 64, 128, 256, and so on), to multiple convolutional layers (e.g., multiple spatial and temporal convolution layers), and multiple sequencing cycles (e.g., t, t+1, t−1).

In other implementations, the distance and scaling channels, instead of being separately encoded, are directly applied to the image channels to generate modulated pixel multiplication) since the distance and scaling channels and the image channels have the same dimensionality. In further implementations, weights of the convolution kernels are determined based on the distance and image channels so as to detect most important features in the image channels during the elementwise multiplication. In yet other implementations, instead of being fed to a first layer, the distance and scaling channels are provided as auxiliary input to downstream layers and/or networks (e.g., to a fully-connected network or a classification layer). In yet further implementations, the distance and scaling channels are fed to the first layer and re-fed to the downstream layers and/or networks (e.g., via a residual connection).

The discussion above is for 2D input data with k input channels. The extension to 3D input will be appreciated by one skilled in the art. Briefly, volumetric input is a 4D tensor with dimensions k×l×w×h, with l being the additional dimension, length. Each individual kernel is a 4D tensor swept in a 4D tensor, resulting in a 3D tensor (the channel dimension is collapsed because it is not swept across).

In other implementations, when the input data 9500 is in the upsampled, subpixel resolution, the distance and scaling channels are separately encoded on a subpixel-by-subpixel basis and the additive biasing occurs at the subpixel level.

Base Calling Using the Specialized Architecture and the Input Data

The discussion now turns to how the specialized architecture and the input data are used for the neural network-based base calling.

Single Cluster Base Calling

Figure 96A:
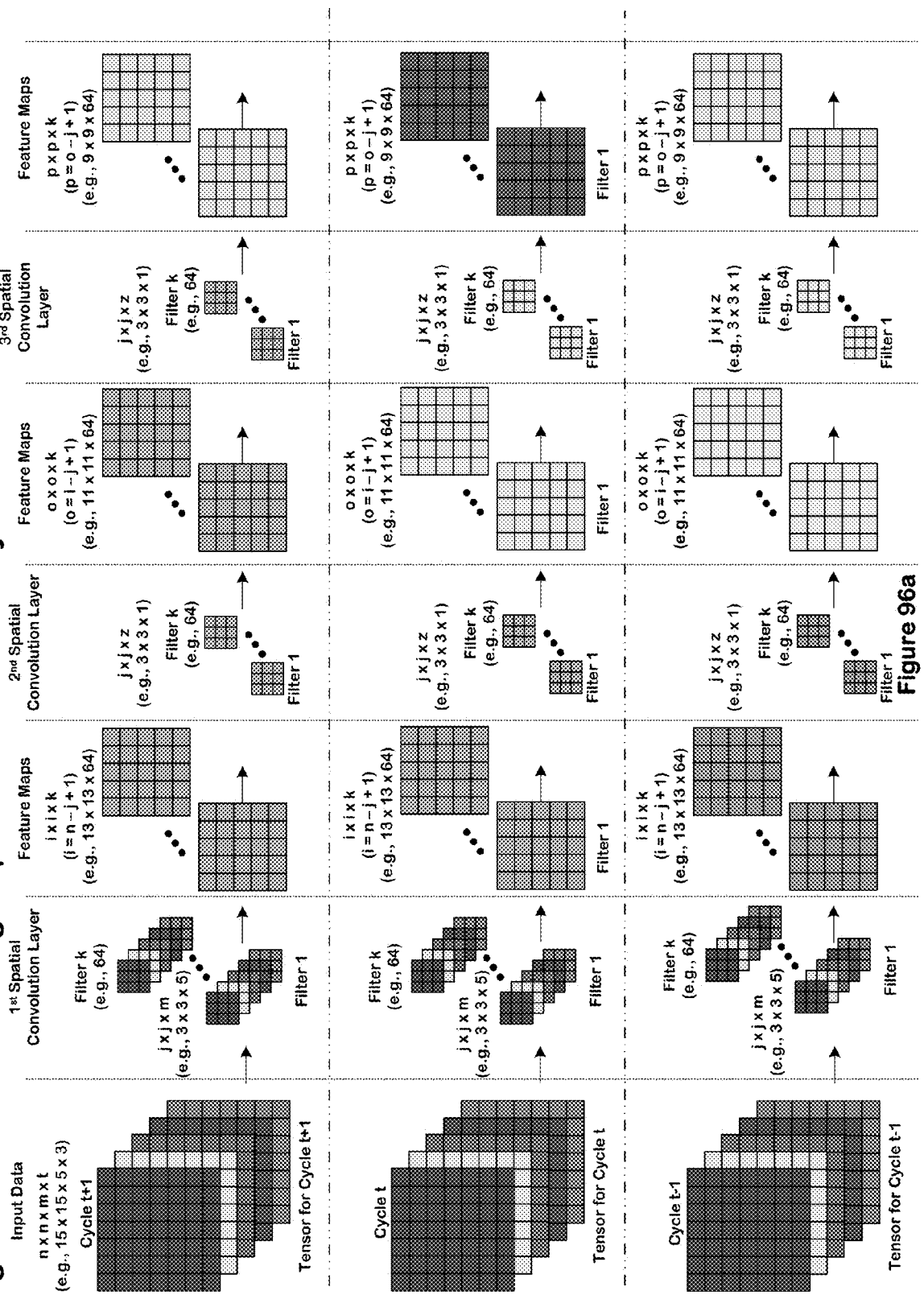
FIGS. 96a, 96b, and 96c depict one implementation of base calling a single target cluster.
Figure 96B:
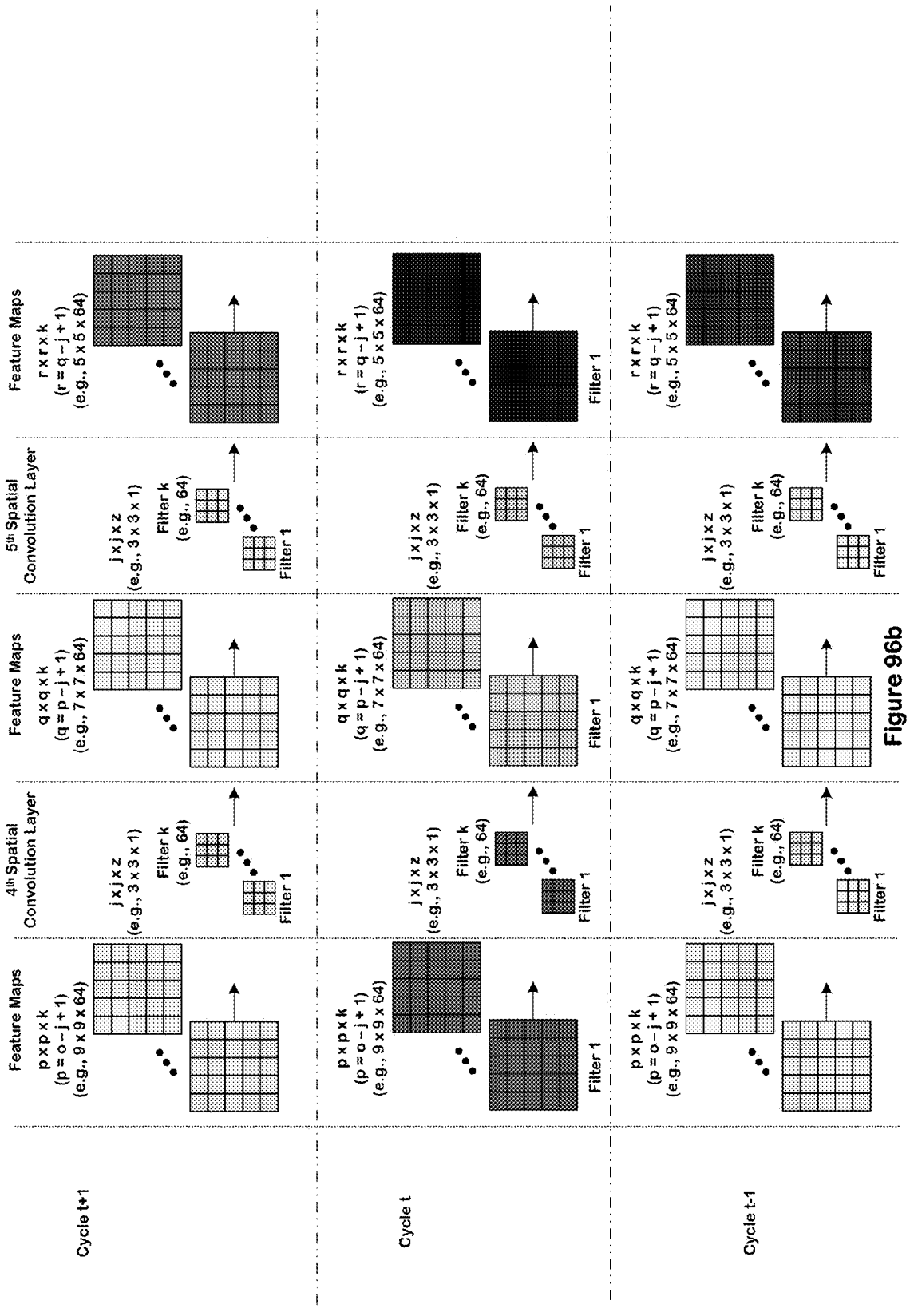
Figure 96C:
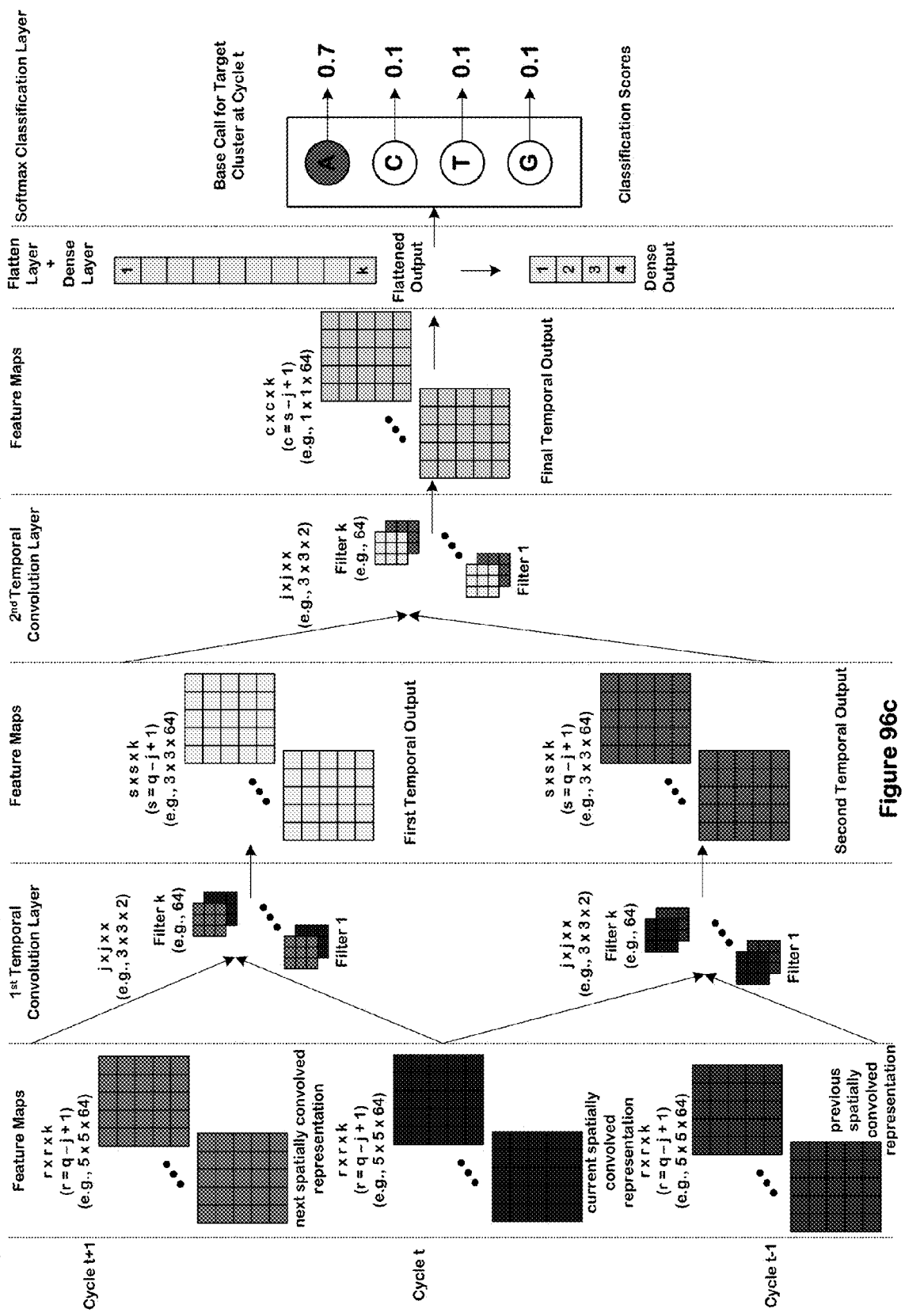

FIGS. 96a, 96b, and 96c depict one implementation of base calling a single target cluster. The specialized architecture processes the input data for three sequencing cycles, namely, a current (time t) sequencing cycle to be base called, a previous (time t−1) sequencing cycle, and a next (time t+1) sequencing cycle and produces a base call for the single target cluster at the current (time t) sequencing cycle.

FIGS. 96a and 96b show the spatial convolution layers. FIG. 96c shows the temporal convolution layers, along with some other non-convolution layers. In FIGS. 96a and 96b, vertical dotted lines demarcate spatial convolution layers from the feature maps and horizontal dashdotted lines demarcate the three convolution pipelines corresponding to the three sequencing cycles.

For each sequencing cycle, the input data includes a tensor of dimensionality n×n×m (e.g., the input tensor 9500 in FIG. 95a), where n represents the width and height of a square tensor and m represents the number of input channels, making the dimensionality of the input data for the three cycles n×n×m×t.

Here, each per-cycle tensor contains, in the center pixel of its image channels, a center of the single target cluster. It also depicts intensity emissions of the single target cluster, of some adjacent clusters, and of their surrounding background captured in each of the image channels at a particular sequencing cycle. In FIG. 96a, two example image channels are depicted, namely, the red image channel and the green image channel.

Each per-cycle tensor also includes distance channels that supplement corresponding image channels (e.g., a red distance channel and a green distance channel). The distance channels identify center-to-center distance of each pixel in the corresponding image channels to the single target cluster. Each per-cycle tensor further includes a scaling channel that pixel-wise scales intensity values in each of the image channels.

The specialized architecture has five spatial convolution layers and two temporal convolution layers. Each spatial convolution layer applies segregated convolutions using a bank of k convolution filters of dimensionality j×j×∂, where j represents the width and height of a square filter and ∂ represents its depth Each temporal convolution layer applies combinatory convolutions using a bank of k convolution filters of dimensionality j×j×∂, where j represents the width and height of a square filter and a represents its depth.

The specialized architecture has pre-classification layers (e.g., a flatten layer and a dense layer) and an output layer (e.g., a softmax classification layer). The pre-classification layers prepare the input for the output layer. The output layer produces the base call for the single target cluster at the current (time t) sequencing cycle.

Consistently Reducing Spatial Dimensionality

FIGS. 96a, 96b, and 96c also show the resulting feature maps (convolved representations or intermediate convolved representations or convolved features or activation maps) produced by the convolution filters. Starting from the per-cycle tensors, the spatial dimensionality of the resulting feature maps reduces by a constant step size from one convolution layer to the next, a concept referred to herein as the "consistently reducing spatial dimensionality". In FIGS. 96a, 96b, and 96c, an example constant step size of two is used for the consistently reducing spatial dimensionality.

The consistently reducing spatial dimensionality is expressed by the following formulation: "current feature map spatial dimensionality=previous feature map spatial dimensionality−convolution filter spatial dimensionality+1". The consistently reducing spatial dimensionality causes the convolution filters to progressively narrow the focus of attention on the central cluster pixels and their neighboring pixels and generate feature maps with features that capture local dependencies among the central cluster pixels and their neighboring pixels. This in turn helps with accurately base calling the clusters whose centers are contained in the central cluster pixels.

The segregated convolutions of the five spatial convolution layers prevent mixing of information between the three sequencing cycles and maintain the three separate convolution pipelines.

The combinatory convolutions of the two temporal convolution layers mix information between the three sequencing cycles. The first temporal convolution layer convolves over the next and current spatially convolved representations respectively produced for the next and current sequencing cycles by a final spatial convolution layer. This yields a first temporal output. The first temporal convolution layer also convolves over the current and previous spatially convolved representations respectively produced for the current and previous sequencing cycles by the final spatial convolution layer. This yields a second temporal output. The second temporal convolution layer convolves over the first and second temporal outputs and produces a final temporal output.

In some implementations, the final temporal output is fed to the flatten layer to produce a flattened output. The flattened output is then fed to the dense layer to produce a dense output. The dense output is processed by the output layer to produce the base call for the single target cluster at the current (time t) sequencing cycle.

In some implementations, the output layer produces likelihoods (classification scores) of a base incorporated in the single target cluster at the current sequencing cycle being A, C, T, and G, and classifies the base as A, C, T, or G based on the likelihoods (e.g., the base with the maximum likelihood is selected, such the base A in FIG. 96a). In such implementations, the likelihoods are exponentially normalized scores produced by a softmax classification layer and sum to unity.

In some implementations, the output layer derives an output pair for the single target cluster. The output pair identifies a class label of a base incorporated in the single target cluster at the current sequencing cycle being A, C, T, or G, and base calls the single target cluster based on the class label. In one implementation, a class label of 1, 0 identifies an A base, a class label of 0, 1 identifies a C base, a class label of 1, 1 identifies a T base, and a class label of 0, 0 identifies a G base. In another implementation, a class label of 1, 1 identifies an A base, a class label of 0, 1 identifies a C base, a class label of 0.5, 0.5 identifies a T base, and a class label of 0, 0 identifies a G base. In yet another implementation, a class label of 1, 0 identifies an A base, a class label of 0, 1 identifies a C base, a class label of 0.5, 0.5 identifies a T base, and a class label of 0, 0 identifies a G base. In yet further implementation, a class label of 1, 2 identifies an A base, a class label of 0, 1 identifies a C base, a class label of 1, 1 identifies a T base, and a class label of 0, 0 identifies a G base.

In some implementations, the output layer derives a class label for the single target cluster that identifies a base incorporated in the single target cluster at the current sequencing cycle being A, C, T, or G, and base calls the single target cluster based on the class label. In one implementation, a class label of 0.33 identifies an A base, a class label of 0.66 identifies a C base, a class label of 1 identifies a T base, and a class label of 0 identifies a G base. In another implementation, a class label of 0.50 identifies an A base, a class label of 0.75 identifies a C base, a class label of 1 identifies a T base, and a class label of 0.25 identifies a G base.

In some implementations, the output layer derives a single output value, compares the single output value against class value ranges corresponding to bases A, C, T, and G, based on the comparison, assigns the single output value to a particular class value range, and base calls the single target cluster based on the assignment. In one implementation, the single output value is derived using a sigmoid function and the single output value ranges from 0 to 1. In another implementation, a class value range of 0-0.25 represents an A base, a class value range of 0.25-0.50 represents a C base, a class value range of 0.50-0.75 represents a T base, and a class value range of 0.75-1 represents a G base.

One skilled in the art will appreciate that, in other implementations, the specialized architecture can process input data for fewer or greater number of sequencing cycles and can comprise fewer or greater number of spatial and temporal convolution layers. Also, the dimensionality of the input data, the per-cycle tensors in the input data, the convolution filters, the resulting feature maps, and the output can be different. Also, the number of convolution filters in a convolution layer can be different. It can use different padding and striding configurations. It can use a different classification function (e.g., sigmoid or regression) and may or may not include a fully-connected layer. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

Having described single cluster base calling, the discussion now turns to multiple clusters base calling.

Multiple Clusters Base Calling

Depending on the size of the input data and cluster density on the flow cell, anywhere between ten to three hundred thousand clusters are simultaneously base called by the neural network-based base caller 1514 on a per-input basis. Extending this to the data parallelism and/or model parallelism strategies implemented on parallel processors, using a batch or mini-batch of size ten results in hundred to three million clusters being simultaneously base called on a per-batch basis or per-mini-batch basis.

Depending on the sequencing configuration (e.g., cluster density, number of tiles on the flow cell), a tile includes twenty thousand to three hundred thousand clusters. In another implementation, Illumina's NovaSeq sequencer has up to four million clusters per tile. Therefore, a sequencing image of the tile (tile image) can depict intensity emissions from twenty thousand to three hundred thousand clusters and their surrounding background. So, in one implementation, using input data which includes the entire tile image results in three hundred thousand clusters being simultaneously base called on a per-input basis. In another implementation, using image patches of size 15×15 pixels in the input data results in less than hundred clusters being simultaneously base called on a per-input basis. One skilled in the art will appreciate that these numbers can vary depending on the sequencing configuration, the parallelism strategy, the details of the architecture (e.g., based on optimal architecture hyperparameters), and available compute.

Figure 97:
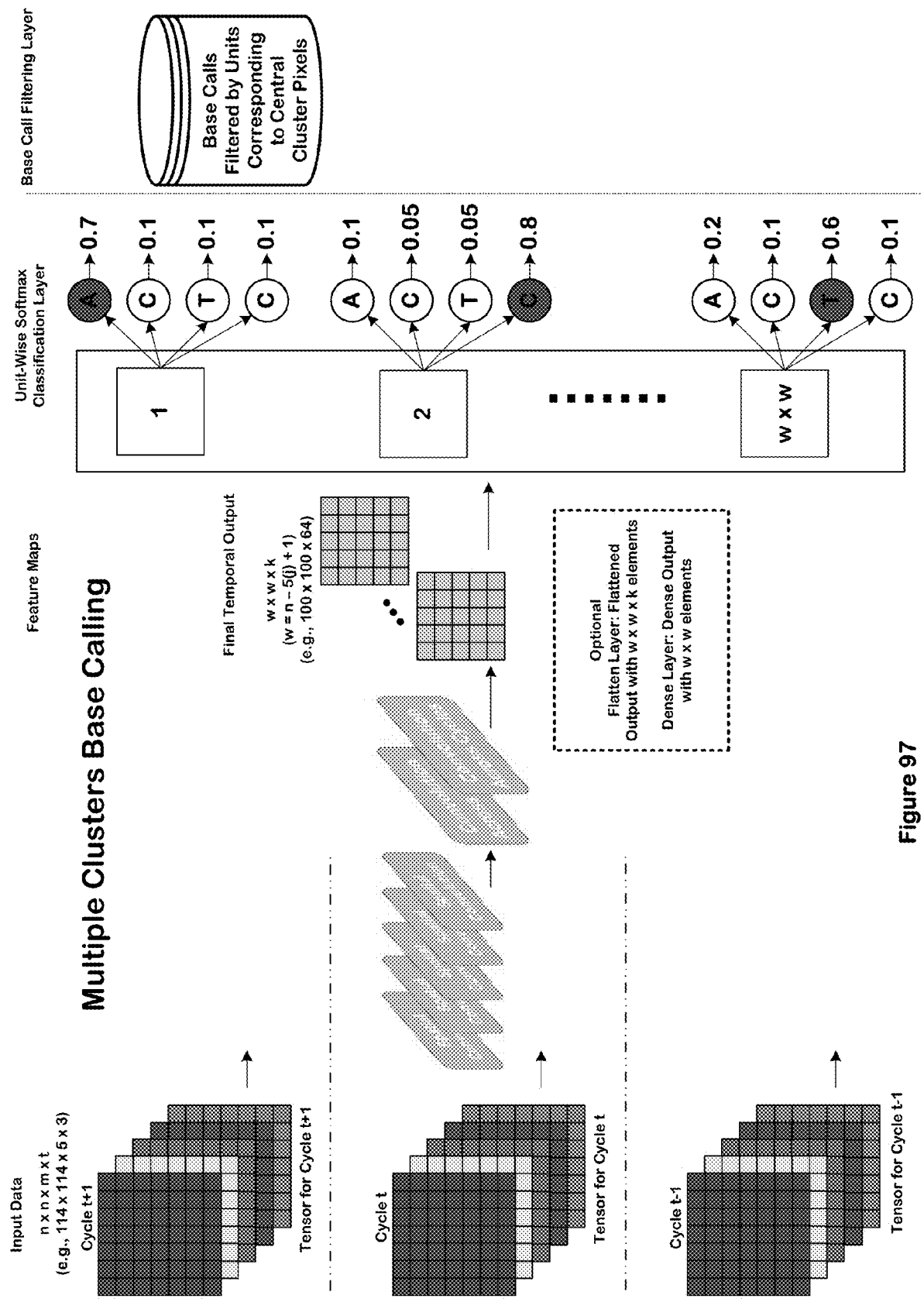
FIG. 97 shows one implementation of simultaneously base calling multiple target clusters.

FIG. 97 shows one implementation of simultaneously base calling multiple target clusters. The input data has three tensors for the three sequencing cycles discussed above. Each per-cycle tensor (e.g., the input tensor 9500 in FIG. 95a) depicts intensity emissions of multiple target clusters to be base called and their surrounding background captured in each of the image channels at a particular sequencing cycle. In other implementations, some additional adjacent clusters, which are not base called, are also included for context.

In the multi-cluster base calling implementation, each per-cycle tensor includes distance channels that supplement corresponding image channels (e.g., a red distance channel and a green distance channel). The distance channels identify center-to-center distance of each pixel in the corresponding image channels to the nearest cluster from among the multiple target clusters.

In the multi-cluster shape-based base calling implementation, each per-cycle tensor includes distance channels that supplement corresponding image channels (e.g., a red distance channel and a green distance channel). The distance channels identify center-to-center distance of each cluster pixel in the corresponding image channels to the cluster to which it belongs or is attributed to from among the multiple target clusters.

Each per-cycle tensor further includes a scaling channel that pixel-wise scales intensity values in each of the image channels.

In FIG. 97, the spatial dimensionality of each per-cycle tensor is great than that shown in FIG. 96a. That is, in the single target cluster base calling implementation in FIG. 96a, the spatial dimensionality of each per-cycle tensor is 15×15, whereas in the multiple cluster base calling implementation in FIG. 97, the spatial dimensionality of each per-cycle tensor is 114×114. Having greater amount of pixelated data that depicts intensity emissions of additional clusters improves the accuracy of base calls simultaneously predicted for the multiple clusters, according to some implementations.

Avoiding Redundant Convolutions

Furthermore, the image channels in each per-cycle tensor are obtained from the image patches extracted from the sequencing images. In some implementations, there are overlapping pixels between extracted image patches that are spatially contiguous (e.g., left, right, top, and bottom contiguous). Accordingly, in one implementation, the overlapping pixels are not subjected to redundant convolutions and results from a prior convolution are reused in later instances when the overlapping pixels are part of the subsequent inputs.

Consider, for example, that a first image patch of size n×n pixels is extracted from a sequencing image and a second image patch of size m×m pixels is also extracted from the same sequencing image, such that the first and second image patches are spatially contiguous and share an overlapping region of o×o pixels. Further consider that the o×o pixels are convolved as part of the first image patch to produce a first convolved representation that is stored in memory. Then, when the second image patch is convolved, the o×o pixels are not convolved again and instead the first convolved representation is retrieved from memory and reused. In some implementations, n=m. In other implementations, they are not equal.

The input data is then processed through the spatial and temporal convolution layers of the specialized architecture to produce a final temporal output of dimensionality w×w×k. Here too, under the consistently reducing spatial dimensionality phenomenon, the spatial dimensionality is reduced by a constant step size of two at each convolution layer. That is, starting with a n×n spatial dimensionality of the input data, a w×w spatial dimensionality of the final temporal output is derived.

Then, based on the final temporal output of spatial dimensionality w×w, an output layer produces a base call for each unit in the w×w set of units. In one implementation, the output layer is a softmax layer that produces four-way classification scores for the four bases (A, C, T, and G) on a unit-by-unit basis. That is, each unit in the w×w set of units is assigned a base call based on the maximum classification score in a corresponding softmax quadruple, as depicted in FIG. 97. In some implementations, the w×w set of units is derived as a result of processing the final temporal output through a flatten layer and a dense layer to produce a flattened output and a dense output, respectively. In such implementations, the flattened output has w×w×k elements and the dense output has w×w elements that form the w×w set of units.

Base calls for the multiple target clusters are obtained by identifying which of the base called units in the w×w set of units coincide with or correspond to central cluster pixels, i.e., pixels in the input data that contain the respective centers of the multiple target clusters. A given target cluster is assigned the base call of the unit that coincides with or corresponds to the pixel that contains the center of the given target cluster. In other words, base calls of units that do not coincide with or correspond to the central cluster pixels are filtered out. This functionality is operationalized by a base call filtering layer, which is part of the specialized architecture in some implementations, or implemented as a post-processing module in other implementations.

In other implementations, base calls for the multiple target clusters are obtained by identifying which groups of base called units in the w×w set of units cover a same cluster, i.e., identifying pixel groups in the input data that depict a same cluster. Then, for each cluster and its corresponding pixel group, an average of classification scores (softmax probabilities) of the respective four base classes (A, C, T, and G) is calculated across pixels in the pixel group and the base class that has the highest average classification score is selected for base calling the cluster.

During training, in some implementations, the ground truth comparison and error computation occurs only for those units that coincide with or correspond to the central cluster pixels, such that their predicted base calls are evaluated against the correct base calls identified as ground truth labels.

Having described multiple clusters base calling, the discussion now turns to multiple clusters and multiple cycles base calling.

Multiple Clusters and Multiple Cycles Base Calling

Figure 98:
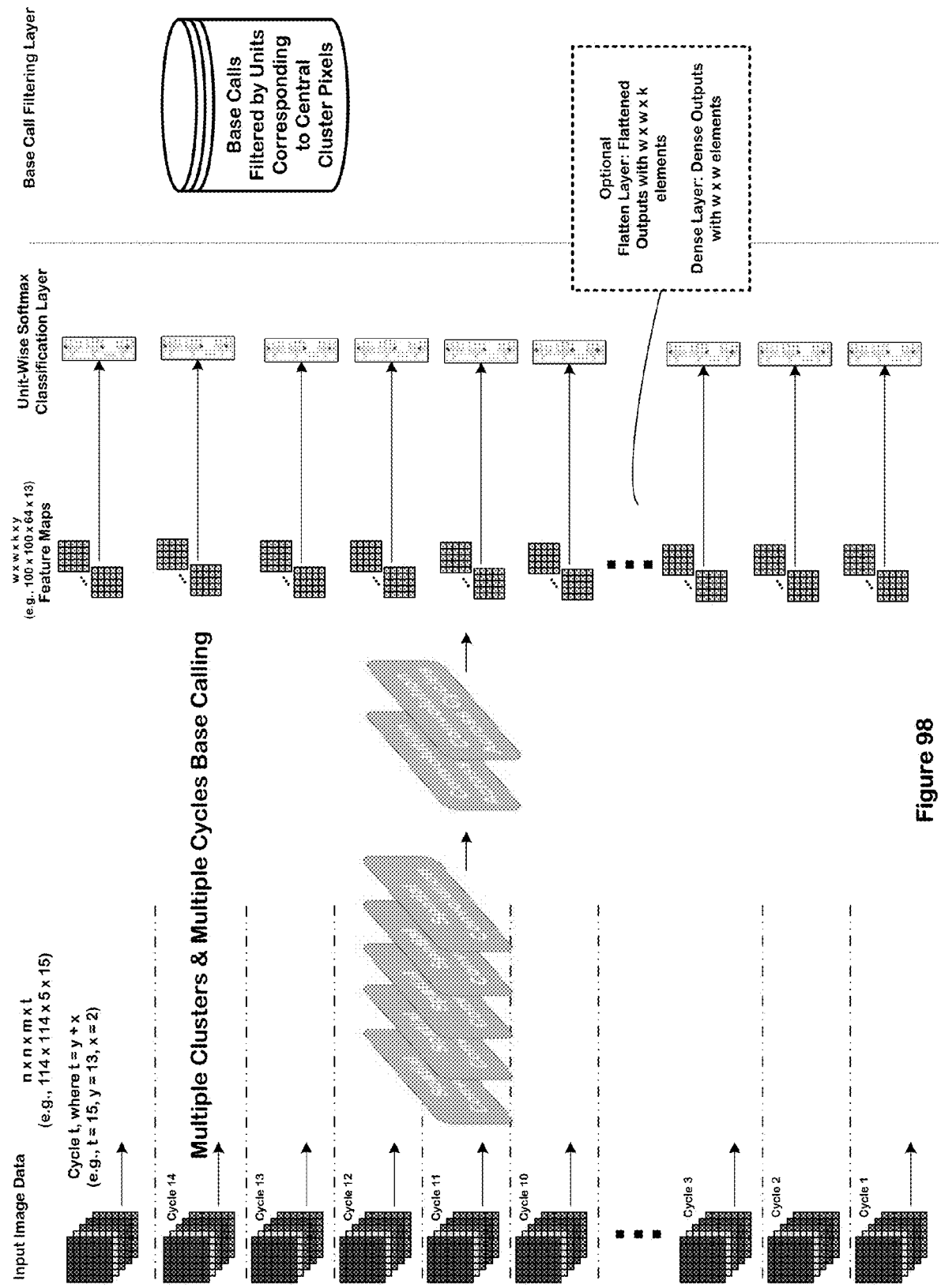
FIG. 98 shows one implementation of simultaneously base calling multiple target clusters at a plurality of successive sequencing cycles, thereby simultaneously producing a base call sequence for each of the multiple target clusters.

FIG. 98 shows one implementation of simultaneously base calling multiple target clusters at a plurality of successive sequencing cycles, thereby simultaneously producing a base call sequence for each of the multiple target clusters.

In the single and multiple base calling implementations discussed above, base call at one sequencing cycle (the current (time t) sequencing cycle) is predicted using data for three sequencing cycles (the current (time t), the previous/left flanking (time t−1), and the next/right flanking (time t+1) sequencing cycles), where the right and left flanking sequencing cycles provide sequence-specific context for base triplet motifs and second order contribution of pre-phasing and phasing signals. This relationship is expressed by the following formulation: "number of sequencing cycles for which data is included in the input data (t)=number of sequencing cycles being base called (y)+number of right and left flanking sequencing cycles (x)."

In FIG. 98, the input data includes t per-cycle tensors for t sequencing cycles, making its dimensionality n×n×m×t, where n=114, m=5, and t=15. In other implementations, these dimensionalities are different. Of the t sequencing cycles, the $t^{th}$ sequencing cycle and the first sequencing cycle serve as right and left flanking contexts x, and y sequencing cycles between them are base called. Thus, y=13, x=2, and t=y+x. Each per-cycle tensor includes image channels, corresponding distance channels, and a scaling channel, such as the input tensor 9500 in FIG. 95*a*.

The input data with t per-cycle tensors is then processed through the spatial and temporal convolution layers of the specialized architecture to produce y final temporal outputs, each of which corresponds to a respective one of the y sequencing cycles being base called. Each of the y final temporal outputs has a dimensionality of w×w×k. Here too, under the consistently reducing spatial dimensionality phenomenon, the spatial dimensionality is reduced by a constant step size of two at each convolution layer. That is, starting with a n×n spatial dimensionality of the input data, a w×w spatial dimensionality of each of the y final temporal outputs is derived.

Then, each of the y final temporal outputs is processed in parallel by an output layer. For each of the y final temporal outputs, the output layer produces a base call for each unit in the w×w set of units. In one implementation, the output layer is a softmax layer that produces four-way classification scores for the four bases (A, C, T, and G) on a unit-by-unit basis. That is, each unit in the w×w set of units is assigned a base call based on the maximum classification score in a corresponding softmax quadruple, as depicted in FIG. 97. In some implementations, the w×w set of units is derived for each of the y final temporal outputs as a result of respectively processing the later through a flatten layer and a dense layer to produce corresponding flattened outputs and dense outputs. In such implementations, each flattened output has w×w×k elements and each dense output has w×w elements that form the w×w set of units.

For each of the y sequencing cycles, base calls for the multiple target clusters are obtained by identifying which of the base called units in the corresponding w×w set of units coincide with or correspond to central cluster pixels, i.e., pixels in the input data that contain the respective centers of the multiple target clusters. A given target cluster is assigned the base call of the unit that coincides with or corresponds to the pixel that contains the center of the given target cluster. In other words, base calls of units that do not coincide with or correspond to the central cluster pixels are filtered out. This functionality is operationalized by a base call filtering layer, which is part of the specialized architecture in some implementations, or implemented as a post-processing module in other implementations.

During training, in some implementations, the ground truth comparison and error computation occurs only for those units that coincide with or correspond to the central cluster pixels, such that their predicted base calls are evaluated against the correct base calls identified as ground truth labels.

On a per-input basis, what results is a base call for each of the multiple target clusters at each of they sequencing cycles, i.e., a base call sequence of length y for each of the multiple target clusters. In other implementations, y is 20, 30, 50, 150, 300, and so on. One skilled in the art will appreciate that these numbers can vary depending on the sequencing configuration, the parallelism strategy, the details of the architecture (e.g., based on optimal architecture hyperparameters), and available compute.

End-to-End Dimensionality Diagrams

The following discussion uses dimensionality diagrams to illustrate different implementations of underlying data dimensionality changes involved in producing base calls from image data, together with dimensionality of data operators that effectuate the said data dimensionality changes.

Figure 99:
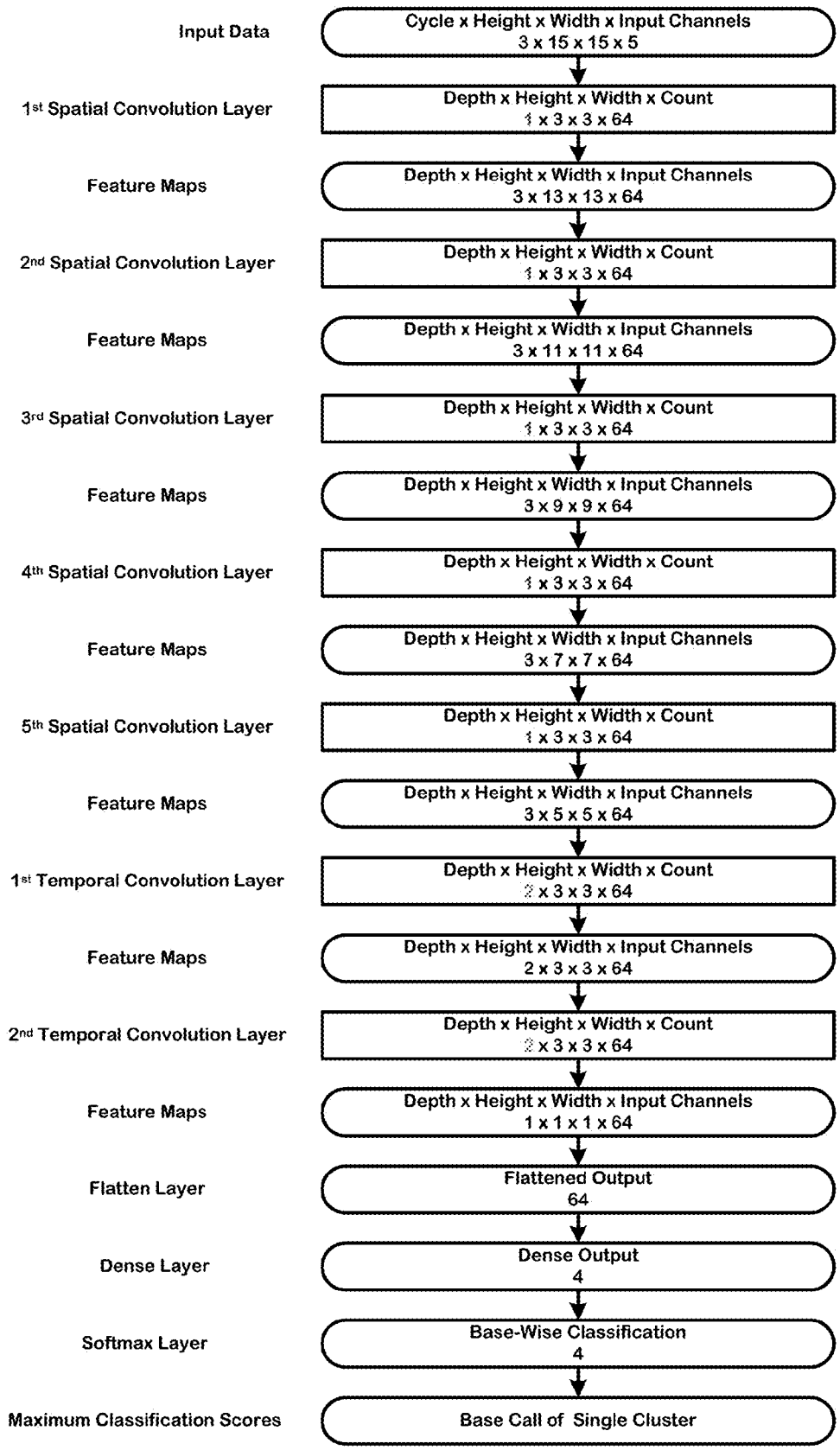
FIG. 99 illustrates the dimensionality diagram for the single cluster base calling implementation.
Figure 100:
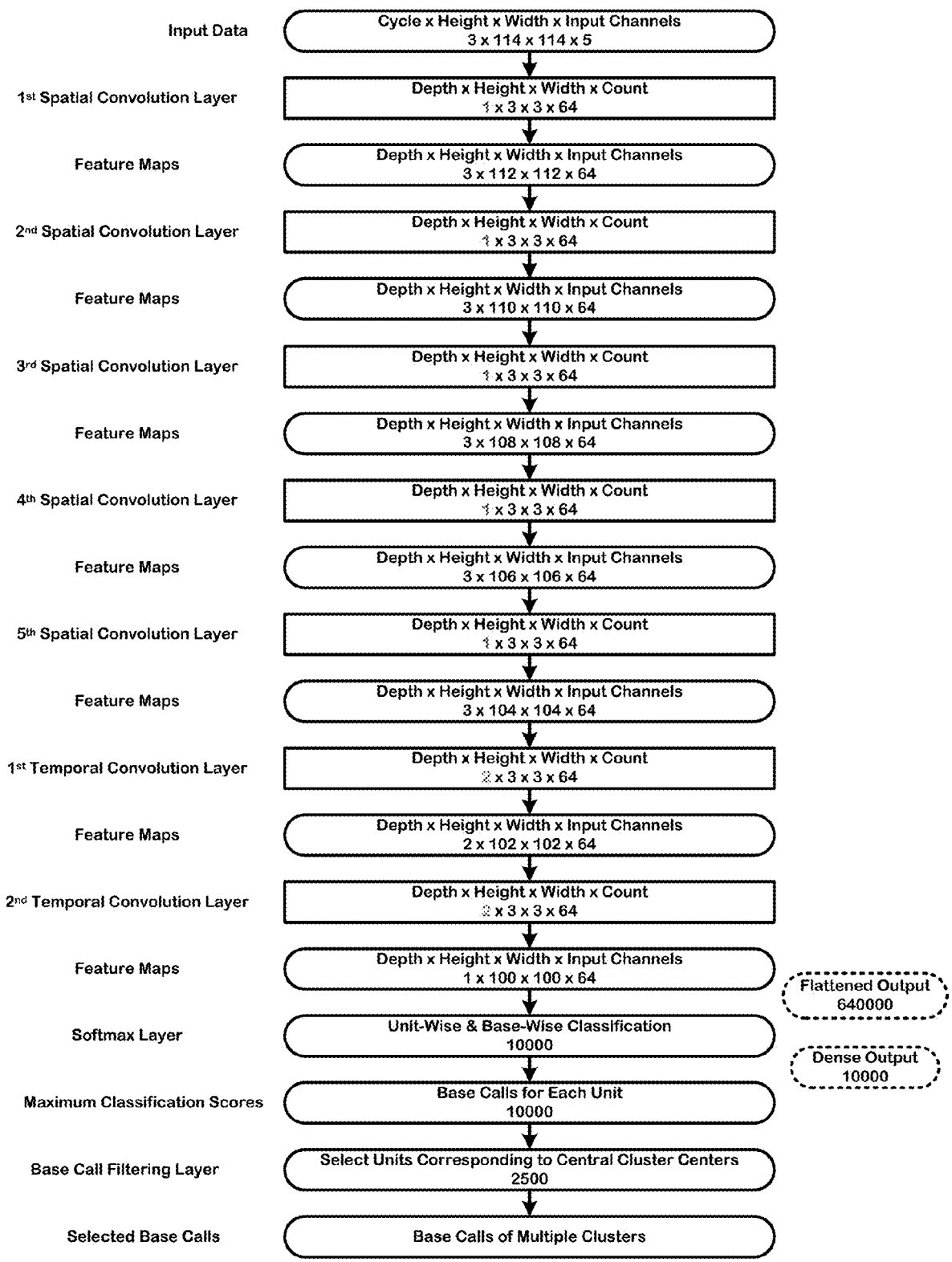
FIG. 100 illustrates the dimensionality diagram for the multiple clusters, single sequencing cycle base calling implementation.
Figure 101:
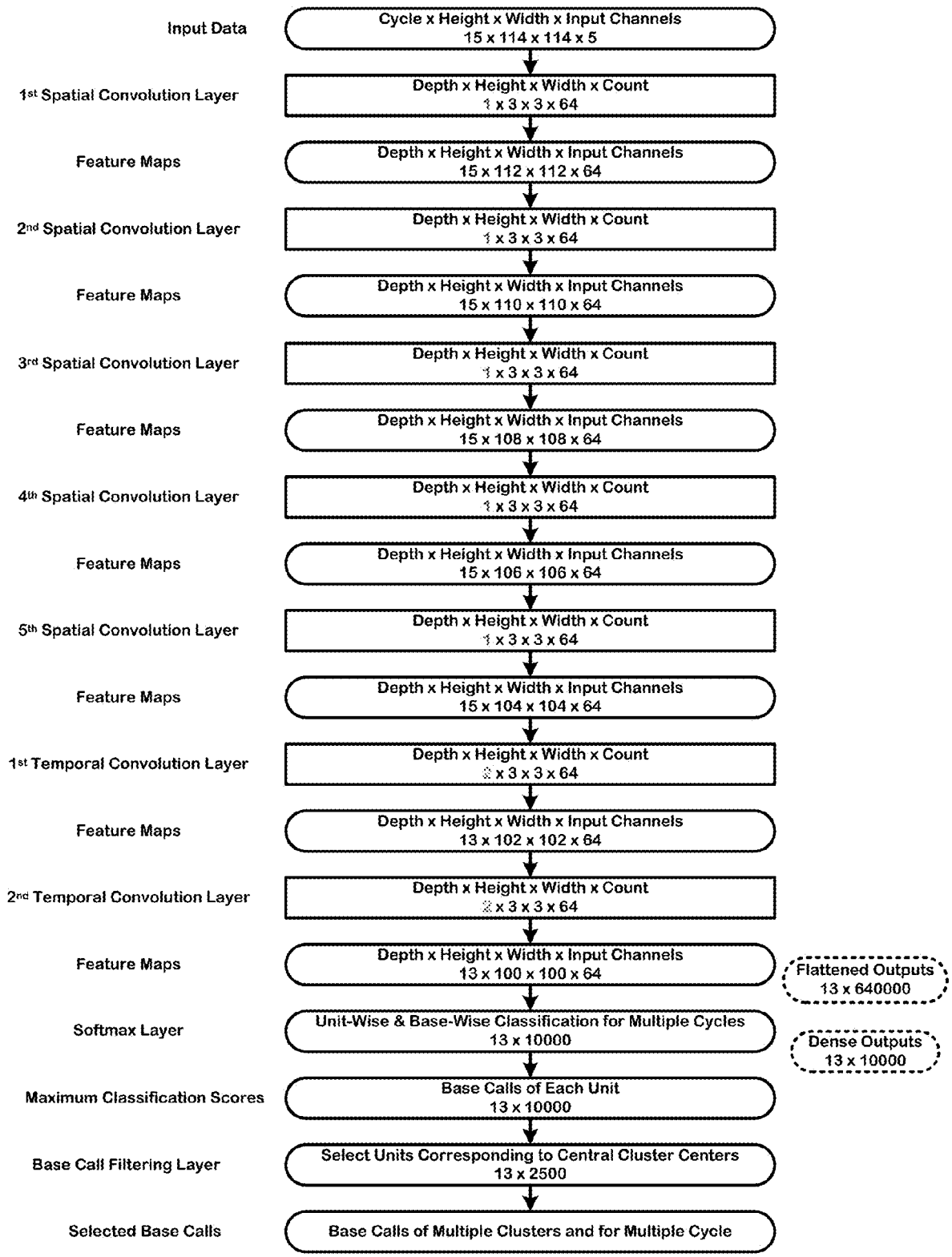
FIG. 101 illustrates the dimensionality diagram for the multiple clusters, multiple sequencing cycles base calling implementation.

In FIGS. 99, 100, and 101, rectangles represent data operators like spatial and temporal convolution layers and softmax classification layer, and rounded corner rectangles represent data (e.g., feature maps) produced by the data operators.

FIG. 99 illustrates the dimensionality diagram 9900 for the single cluster base calling implementation. Note that the "cycle dimension" of the input is three and continues to be that for the resulting feature maps up until the first temporal convolution layer. Cycle dimension of three presents the three sequencing cycles, and its continuity represents that feature maps for the three sequencing cycles are separately generated and convolved upon and no features are mixed between the three sequencing cycles. The segregated convolution pipelines are effectuated by the depth-wise segregated convolution filters of the spatial convolution layers. Note that the "depth dimensionality" of the depth-wise segregated convolution filters of the spatial convolution layers is one. This is what enables the depth-wise segregated convolution filters to convolve over data and resulting feature maps of only a given sequencing cycle, i.e., intra-cycle, and prevents them from convolving over data and resulting feature maps of any other sequencing cycle.

In contrast, note that the depth dimensionality of the depth-wise combinatory convolution filters of the temporal convolution layers is two. This is what enables the depth-wise combinatory convolution filters to groupwise convolve over resulting features maps from multiple sequencing cycles and mix features between the sequencing cycles.

Also note the consistent reduction in the "spatial dimensionality" by a constant step size of two.

Further, a vector with four elements is exponentially normalized by the softmax layer to produce classification scores (i.e., confidence scores, probabilities, likelihoods, softmax scores) for the four bases (A, C, T, and G). The base with the highest (maximum) softmax score is assigned to the single target cluster being base called at the current sequencing cycle.

One skilled in the art will appreciate that, in other implementations, the illustrated dimensionalities can vary depending on the sequencing configuration, the parallelism strategy, the details of the architecture (e.g., based on optimal architecture hyperparameters), and available compute.

FIG. 100 illustrates the dimensionality diagram 10000 for the multiple clusters, single sequencing cycle base calling implementation. The above discussion about the cycle, depth, and spatial dimensionality with respect to the single cluster base calling applies to this implementation.

Here, the softmax layer operates independently on each of the 10,000 units and produces a respective quadruple of softmax scores for each of the 10,000 units. The quadruple corresponds to the four bases (A, C, T, and G). In some implementations, the 10,000 units are derived from the transformation of 64,0000 flattened units to 10,000 dense units.

Then, from the softmax score quadruple of each of the 10,000 units, the base with the highest softmax score in each quadruple is assigned to a respective one of the 10,000 units.

Then, of the 10,000 units, those 2500 units are selected which correspond the 2,500 central cluster pixels containing respective centers of the 2,500 target clusters being simultaneously base called at the current sequencing cycle. The bases assigned to the selected 2,500 units are in turn assigned to the corresponding ones of the 2,500 target clusters.

One skilled in the art will appreciate that, in other implementations, the illustrated dimensionalities can vary depending on the sequencing configuration, the parallelism strategy, the details of the architecture (e.g., based on optimal architecture hyperparameters), and available compute.

FIG. 101 illustrates the dimensionality diagram 10100 for the multiple clusters, multiple sequencing cycles base calling implementation. The above discussion about the cycle, depth, and spatial dimensionality with respect to the single cluster base calling applies to this implementation.

Further, the above discussion about the softmax-based base call classification with respect to the multiple clusters base calling applies here too. However, here, the softmax-based base call classification of the 2,500 target clusters occurs in parallel for each of the thirteen sequencing cycles base called, thereby simultaneously producing thirteen base calls for each of the 2,500 target clusters.

One skilled in the art will appreciate that, in other implementations, the illustrated dimensionalities can vary depending on the sequencing configuration, the parallelism strategy, the details of the architecture (e.g., based on optimal architecture hyperparameters), and available compute.

Arrayed Input v/s Stacked Input

The discussion now turns to the two configurations in which the multi-cycle input data to the neural network-based caller can be arranged. The first configuration is called "arrayed input" and the second configuration is called "stacked input". The arrayed input is shown in FIG. 102a and is discussed above with respect to FIGS. 96a to 101. The arrayed input encodes each sequencing cycle's input in a separate column/block because image patches in the per-cycle inputs are misaligned with respect to each other due to residual registration error. The specialized architecture is used with the arrayed input to segregate processing of each of the separate columns/blocks. Also, the distance channels are calculated using the transformed cluster centers to account for the misalignments between image patches in a cycle and between image patches across cycles.

In contrast, the stacked input, shown in FIG. 102b, encodes the inputs from different sequencing cycles in a single column/block. In one implementation, this obviates the need of using the specialized architecture because the image patches in the stacked input are aligned with each other through affine transformation and intensity interpolation, which eliminate the inter-cycle and intra-cycle residual registration error. In some implementations, the stacked input has a common scaling channel for all the inputs.

Figure 104:
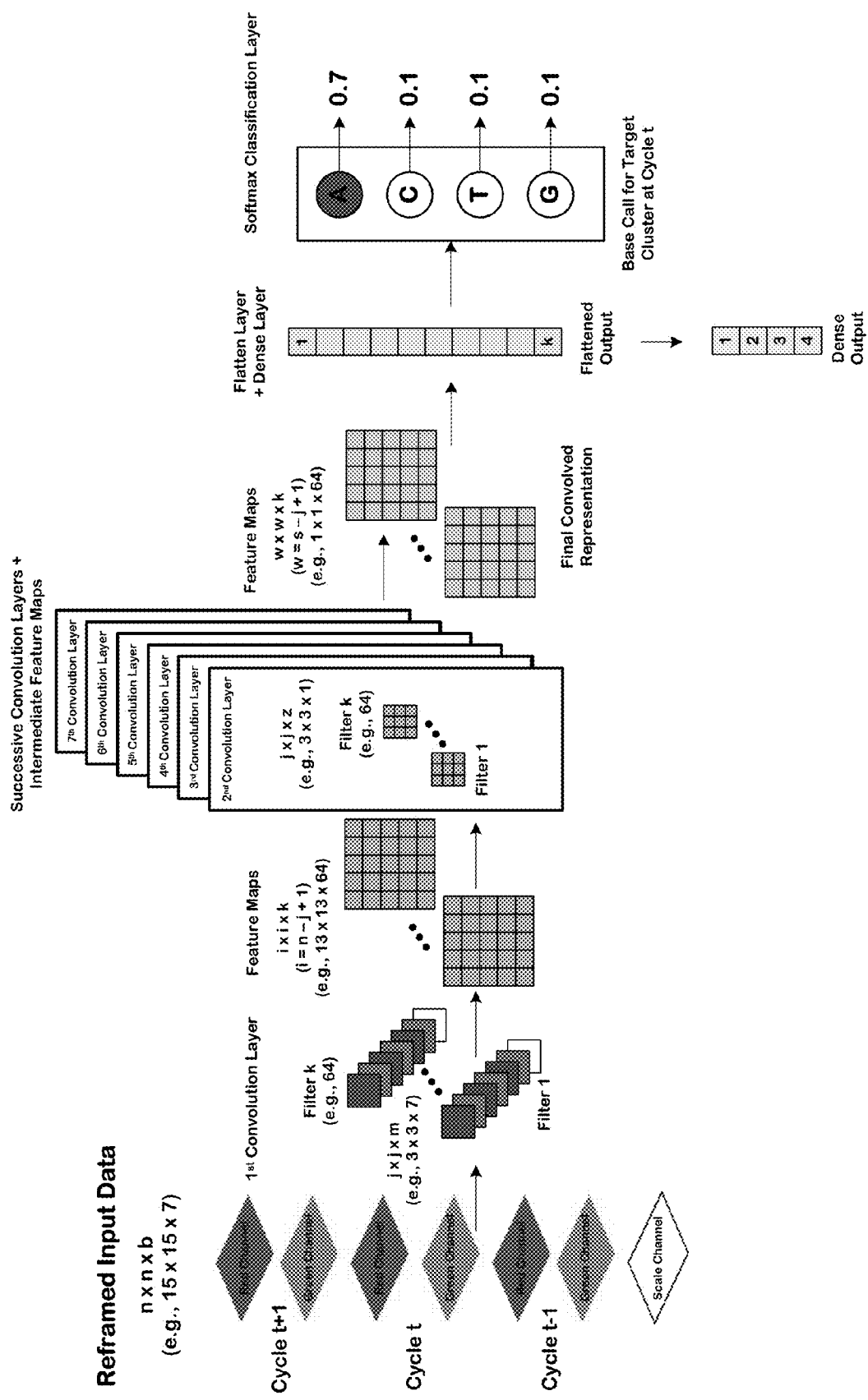
FIG. 104 shows one implementation of base calling a single target cluster at a current sequencing cycle using a standard convolution neural network and the reframed input.

In another implementation, intensity interpolation is used to reframe or shift the image patches such that the center of the center pixel of each image patch coincides with the center of the single target cluster being base called. This obviates the need of using the supplemental distance channels because all the non-center pixels are equidistant from the center of the single target cluster. Stacked input without the distance channels is referred to herein as the "reframed input" and is illustrated in FIG. 104.

Figure 105:
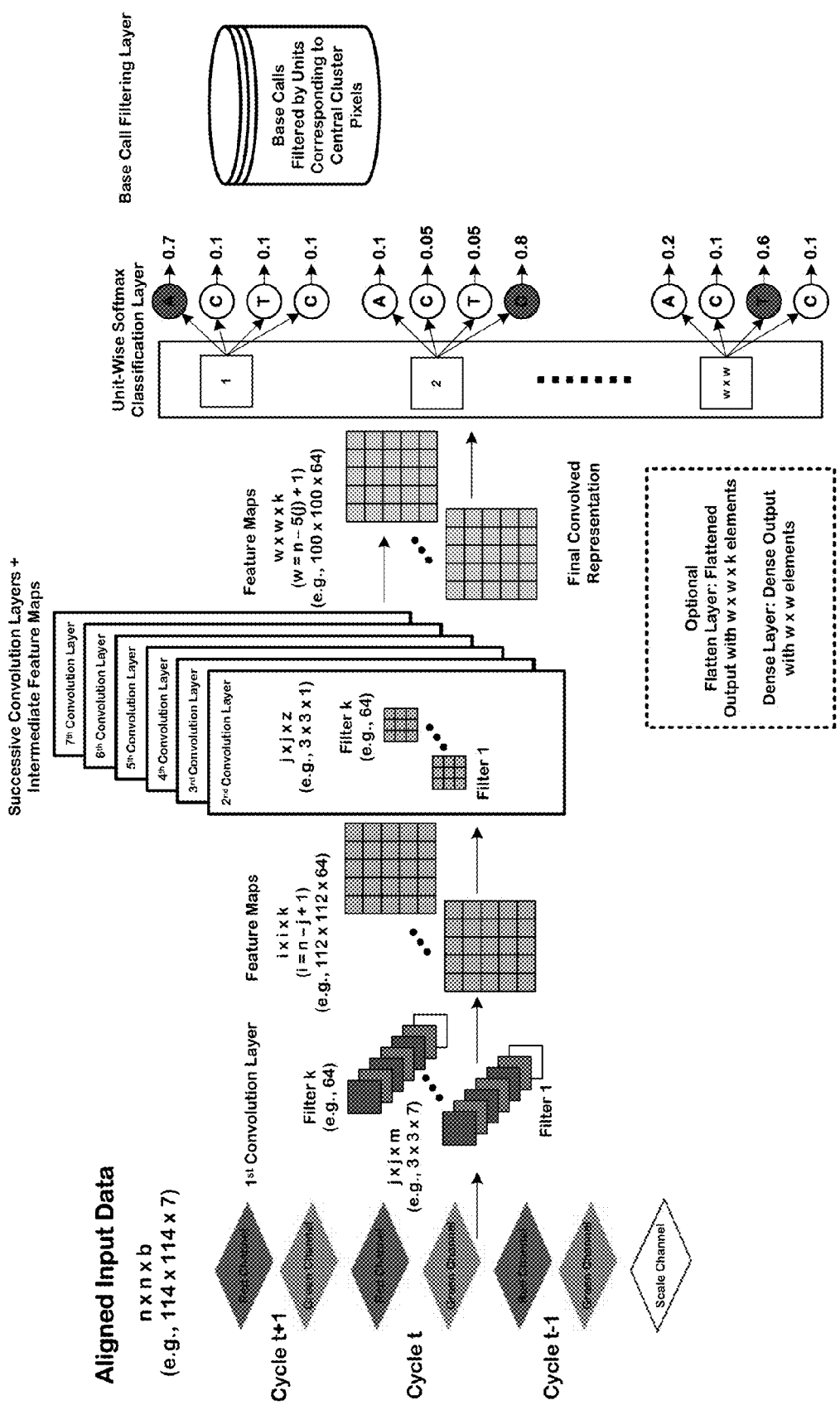
FIG. 105 shows one implementation of base calling multiple target clusters at the current sequencing cycle using the standard convolution neural network and the aligned input.
Figure 106:
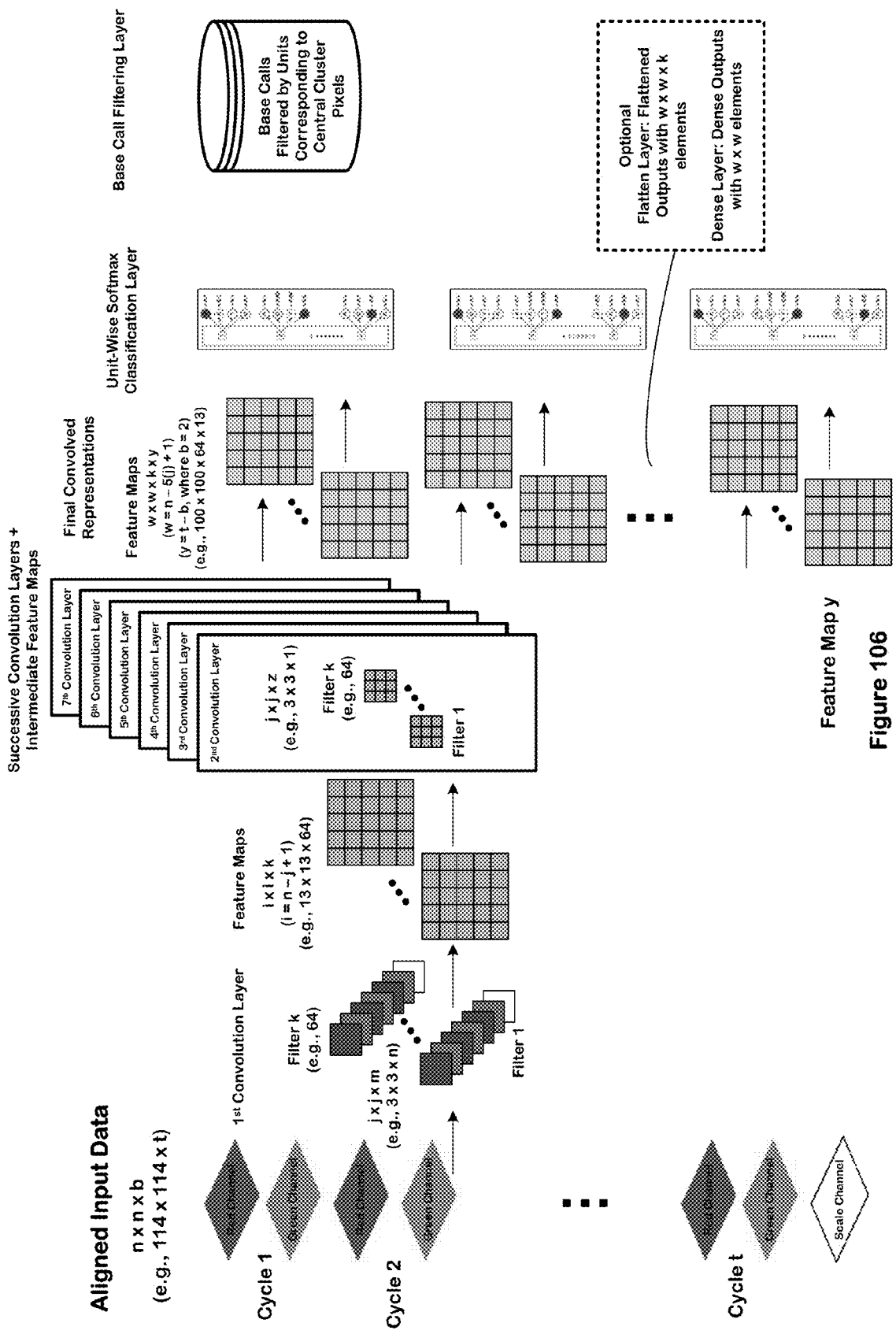
FIG. 106 shows one implementation of base calling multiple target clusters at a plurality of sequencing cycles using the standard convolution neural network and the aligned input.

However, the reframing may not be feasible with base calling implementations involving multiple clusters because there the image patches contain multiple central cluster pixels that are base called. Stacked input without the distance channels and without the reframing is referred to herein as the "aligned input" and is illustrated in FIGS. 105 and 106. Aligned input may be used when calculation of the distance channels is not desired (e.g., due to compute limitations) and reframing is not feasible.

The following section discusses various base calling implementations that do not use the specialized architecture and the supplemental distance channels, and instead using standard convolution layers and filters.

Reframed Input: Aligned Imam Patches without the Distance Channels

FIG. 103a depicts one implementation of reframing 10300a pixels of an image patch 10302 to center a center of a target cluster being base called in a center pixel. The center of the target cluster (in purple) falls within the center pixel of the image patch 10302, but is at an offset (in red) from the center pixel's center, as depicted in FIG. 10300a.

To eliminate the offset, a reframer 10304 shifts the image patch 10302 by interpolating intensity of the pixels to compensate for the reframing and produces a reframed/shifted image patch 10306. In the shifted image patch 10306, the center of the center pixel coincides with the center of the target cluster. Also, the non-center pixels are equidistant from the center of the target cluster. The interpolation can be performed by nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. These techniques are described in detail in Appendix entitled "Intensity Extraction Methods".

Figure 103B:
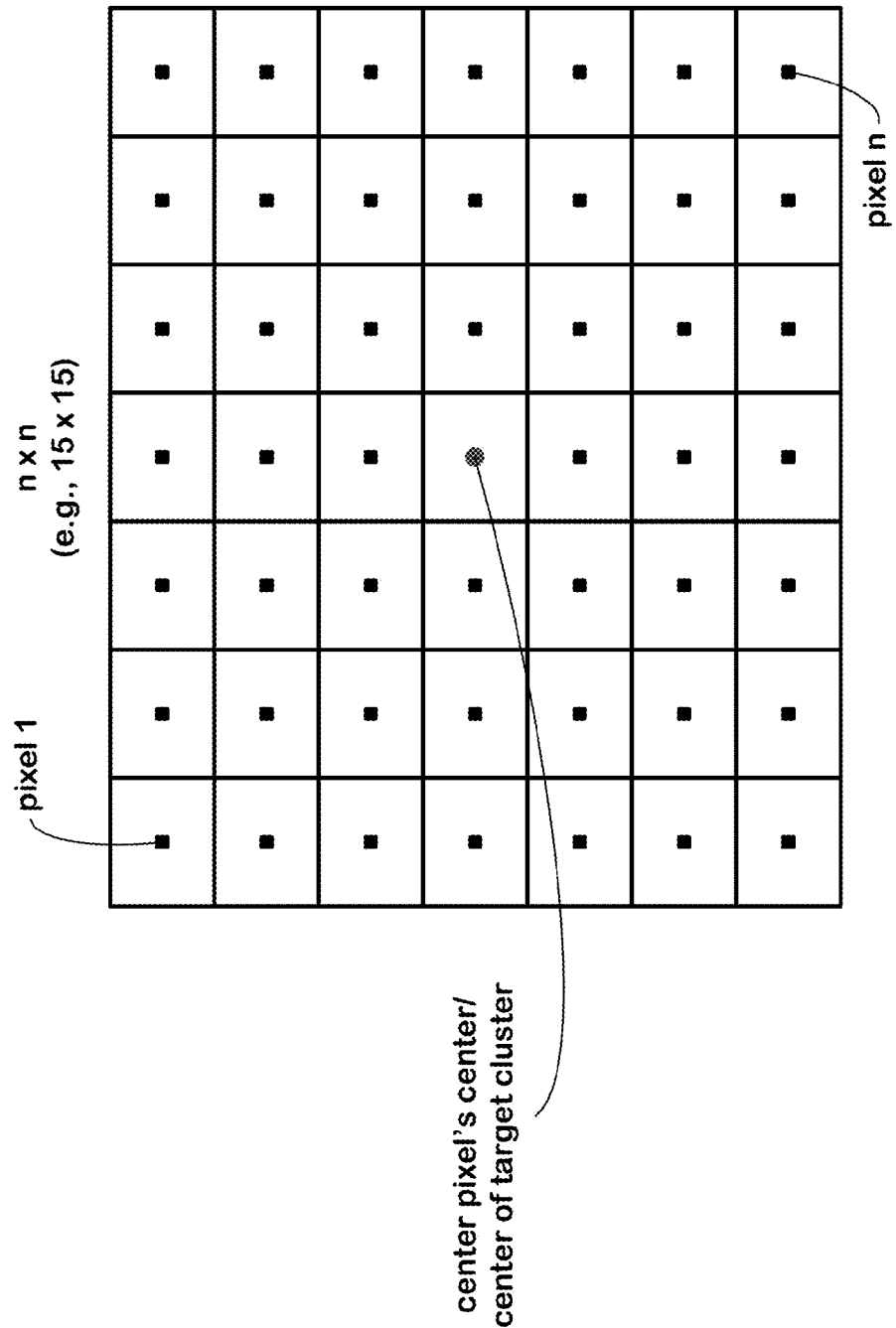
FIG. 103b depicts another example reframed/shifted image patch in which (i) the center of the center pixel coincides with the center of the target cluster and (ii) the non-center pixels are equidistant from the center of the target cluster.

FIG. 103b depicts another example reframed/shifted image patch 10300b in which (i) the center of the center pixel coincides with the center of the target cluster and (ii) the non-center pixels are equidistant from the center of the target cluster. These two factors obviate the need of providing a supplemental distance channel because all the non-center pixels have the same degree of proximity to the center of the target cluster.

FIG. 104 shows one implementation of base calling a single target cluster at a current sequencing cycle using a standard convolution neural network and the reframed input. In the illustrated implementation, the reframed input includes a current image patch set for a current (t) sequencing cycle being base called, a previous image patch set for a previous (t−1) sequencing cycle, and a next image patch set for a next (t+1) sequencing cycle. Each image patch set has an image patch for a respective one of one or more image channels. FIG. 104 depicts two image channels, a red channel and a green channel. Each image patch has pixel intensity data for pixels covering a target cluster being base called, some adjacent clusters, and their surrounding background. The reframed input also includes a common scaling channel.

The reframed input does not include any distance channels because the image patches are reframed or shifted to center at the center the target cluster, as explained above with respect to FIGS. 103a-b. Also, the image patches are aligned with each other to remove inter-cycle and intra-cycle residual registration error. In one implementation, this is done using affine transformation and intensity interpolation, additional details of which can be found in Appendices 1, 2, 3, and 4. These factors obviate the need of using the specialized architecture, and instead a standard convolutional neural network is used with the reframed input.

In the illustrated implementation, the standard convolutional neural network 10400 includes seven standard convolution layers that use standard convolution filters. This means that there are no segregated convolution pipelines to prevent mixing of data between the sequencing cycles (since the data is aligned and can be mixed). In some implementations, the consistently reducing spatial dimensionality phenomenon is used to teach the standard convolution filters to attend to the central cluster center and its neighboring pixels more than to other pixels.

The reframed input is then processed through the standard convolution layers to produce a final convolved representation. Based on the final convolved representation, the base call for the target cluster at the current sequencing cycle is obtained in the similar fashion using flatten, dense, and classification layers as discussed above with respect to FIG. 96c.

In some implementations, the process is iterated over a plurality of sequencing cycles to produce a sequence of base calls for the target cluster.

In other implementations, the process is iterated over a plurality of sequencing cycles for a plurality of target clusters to produce a sequence of base calls for each target cluster in the plurality of target clusters.

Aligned Input: Aligned Image Patches without the Distance Channels and the Reframing FIG. 105 shows one implementation of base calling multiple target clusters at the current sequencing cycle using the standard convolution neural network and the aligned input. The reframing is not feasible here because the image patches contain multiple central cluster pixels that are being base called. As a result, the image patches in the aligned input are not reframed. Further, the supplemental distance channels are not included due to compute considerations, according to one implementation.

The aligned input is then processed through the standard convolution layers to produce a final convolved representation. Based on the final convolved representation, a base call for each of the target clusters is obtained at the current sequencing cycle in the similar fashion using flatten (optional), dense (optional), classification, and base call filtering layers as discussed above with respect to FIG. 97.

FIG. 106 shows one implementation of base calling multiple target clusters at a plurality of sequencing cycles using the standard convolution neural network and the aligned input. The aligned input is processed through the standard convolution layers to produce a final convolved representation for each of they sequencing cycles being base called. Based on they final convolved representations, a base call for each of the target clusters is obtained for each of they sequencing cycles being base called in the similar fashion using flatten (optional), dense (optional), classification, and base call filtering layers as discussed above with respect to FIG. 98.

One skilled in the art will appreciate that, in other implementations, the standard convolutional neural network can process reframed input for fewer or greater number of sequencing cycles and can comprise fewer or greater number of standard convolution layers. Also, the dimensionality of the reframed input, the per-cycle tensors in the reframed input, the convolution filters, the resulting feature maps, and the output can be different. Also, the number of convolution filters in a convolution layer can be different. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

Training

Figure 107:
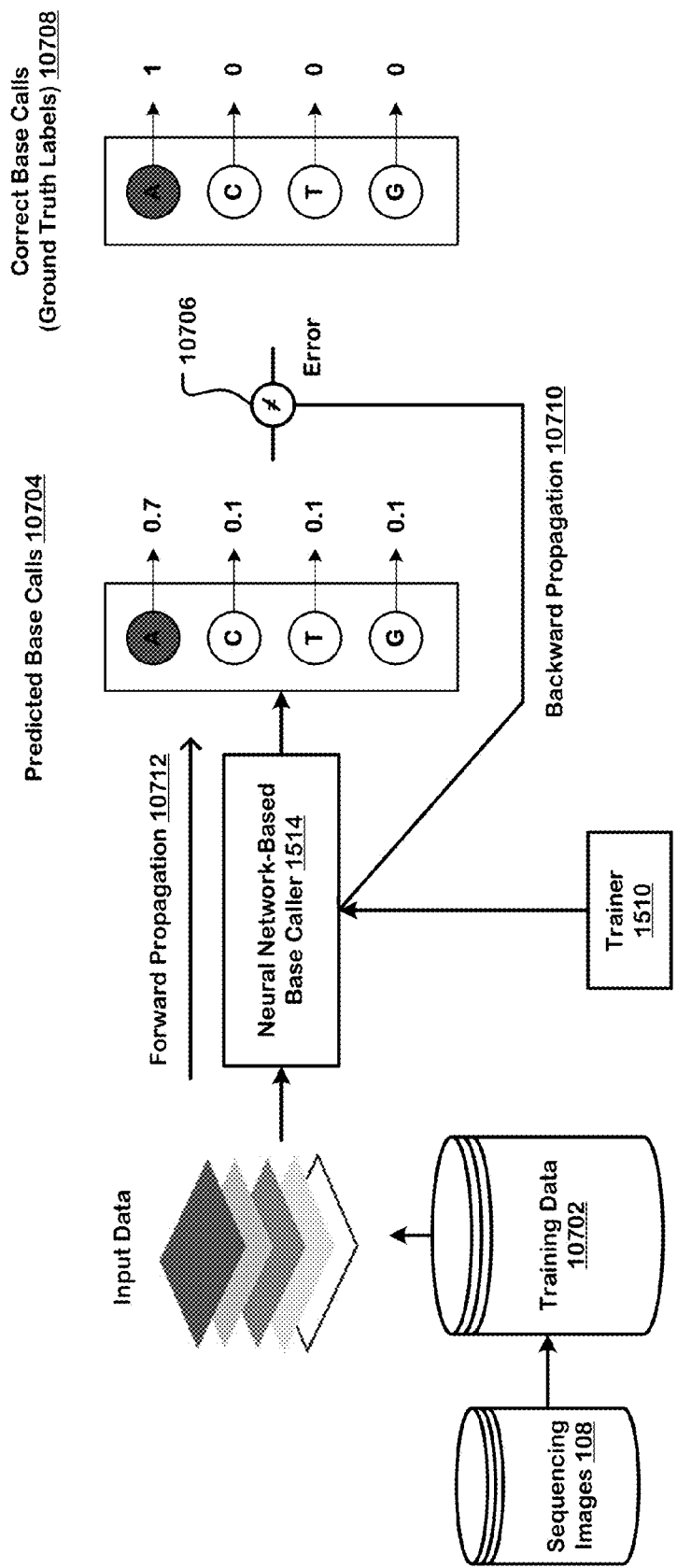
FIG. 107 shows one implementation of training the neural network-based base caller.

FIG. 107 shows one implementation of training 10700 the neural network-based base caller 1514. With both the specialized and standard architectures, the neural network-based base caller 1514 is trained using a backpropagation-based gradient update technique that compares the predicted base calls 10704 against the correct base calls 10708 and computes an error 10706 based on the comparison. The error 10706 is then used to calculate gradients, which are applied to the weights and parameters of the neural network-based base caller 1514 during backward propagation 10710. The training 10700 is operationalized by the trainer 1510 using a stochastic gradient update algorithm such as ADAM.

The trainer 1510 uses training data 10702 (derived from the sequencing images 108) to train the neural network-based base caller 1514 over thousands and millions of iterations of the forward propagation 10712 that produces the predicted base calls 10704 and the backward propagation 10710 that updates the weights and parameters based on the error 10706. Additional details about the training 10700 can be found in Appendix entitled "Deep Learning Tools".

CNN—RNN-Based Base Caller

Hybrid Neural Network

Figure 108A:
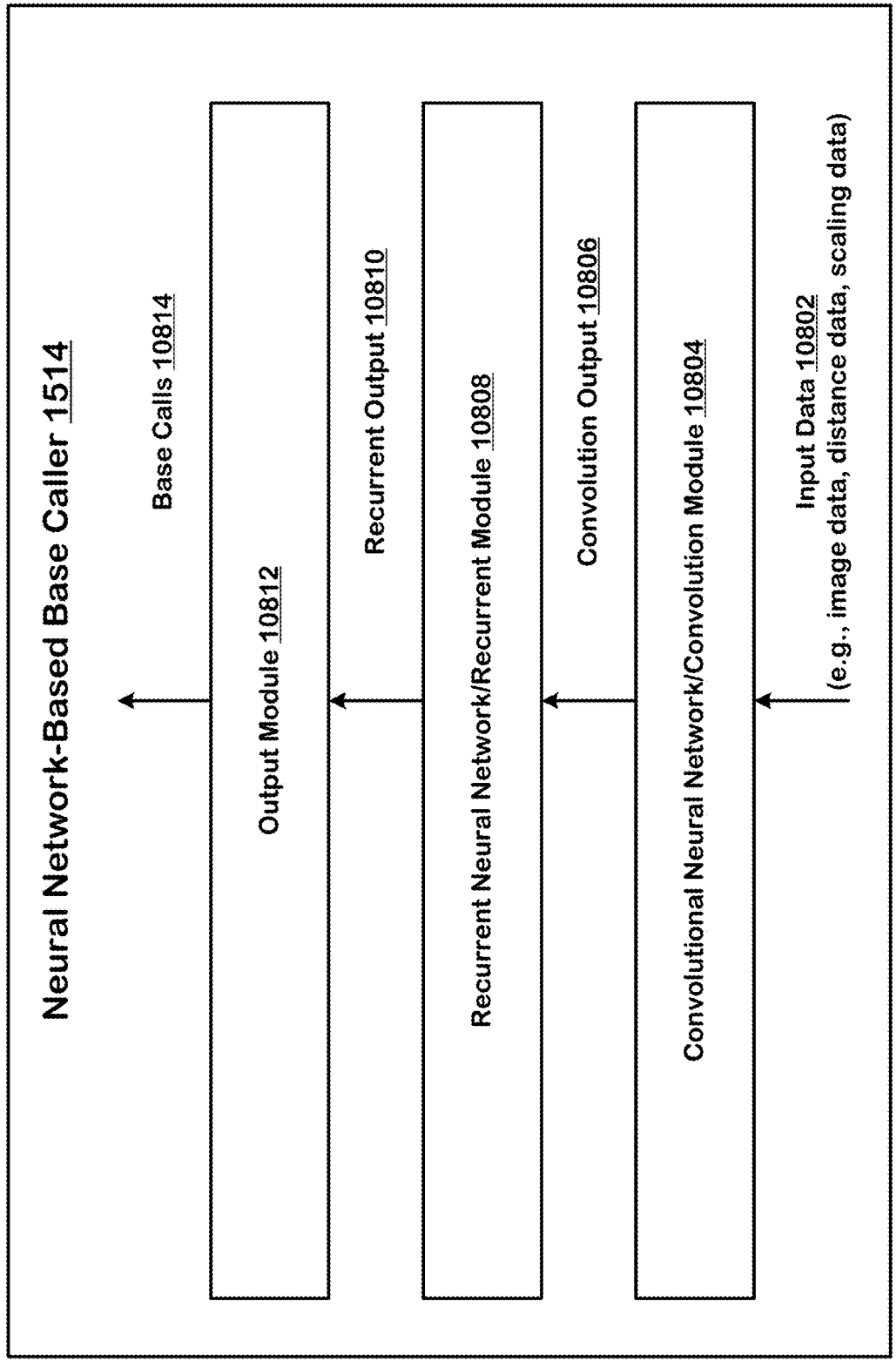

FIG. 108a depicts one implementation of a hybrid neural network 10800a that is used as the neural network-based base caller 1514. The hybrid neural network 10800a comprises at least one convolution module 10804 (or convolutional neural network (CNN)) and at least one recurrent module 10808 (or recurrent neural network (RNN)). The recurrent module 10808 uses and/or receives inputs from the convolution module 10804.

The convolution module 10804 processes input data 10802 through one or more convolution layers and produces convolution output 10806. In one implementation, the input data 10802 includes only image channels or image data as the main input, as discussed above in the Section entitled "Input". The image data fed to the hybrid neural network 10800a can be the same as the image data 7902 described above.

In another implementation, the input data 10802, in addition to the image channels or the image data, also includes supplemental channels such as the distance channels, the scaling channel, the cluster center coordinates, and/or cluster attribution information, as discussed above in the Section entitled "Input".

The image data (i.e., the input data 10802) depicts intensity emissions of one or more clusters and their surrounding background. The convolution module 10804 processes the image data for a series of sequencing cycles of a sequencing run through the convolution layers and produces one or more convolved representations of the image data (i.e., the convolved output 10806).

The series of sequencing cycles can include image data for t sequencing cycles that are to be base called, where t is any number between 1 and 1000. We observe accurate base calling results when t is between fifteen and twenty-one.

The recurrent module 10810 convolves the convolved output 10806 and produces recurrent output 10810. In particular, the recurrent module 10810 produces current hidden state representations (i.e., the recurrent output 10810) based on convolving the convolved representations and previous hidden state representations.

In one implementation, the recurrent module 10810 applies three-dimensional (3D) convolutions to the convolved representations and previous hidden state representations and produces the current hidden state representations, mathematically formulated as:

$h_t = W1_{3DCONV} V_t + W2_{3DCONV} h_{t-1}$, where $h_t$ represents a current hidden state representation produced at a current time step t, $V_t$ represents a set or group of convolved representations that form an input volume at a current sliding window at the current time step t, $W1_{3DCONV}$ represents weights of a first 3D convolution filter applied to $V_t$, $h_{t-1}$ represents a previous hidden state representation produced at a previous time step t−1, and $W2_{3DCONV}$ represents weights of a second 3D convolution filter applied to $h_{t-1}$.

In some implementations, $W1_{3DCONV}$ and $W2_{3DCONV}$ are the same because the weights are shared.

An output module 10812 then produces base calls 10814 based on the recurrent output 10810. In some implementations, the output module 10812 comprises one or more fully-connected layers and a classification layer (e.g., softmax). In such implementations, the current hidden state representations are processed through the fully-connected layers and the outputs of the fully-connected layers are processed through the classification layer to produce the base calls 10814.

The base calls 10814 include a base call for at least one of the clusters and for at least one of the sequencing cycles. In some implementations, the base calls 10814 include a base call for each of the clusters and for each of sequencing cycles. So, for example, when the input data 10802 includes image data for twenty-five clusters and for fifteen sequencing cycles, the base calls 10802 include a base call sequence of fifteen base calls for each of the twenty-five clusters.

3D Convolutions

Figure 108B:
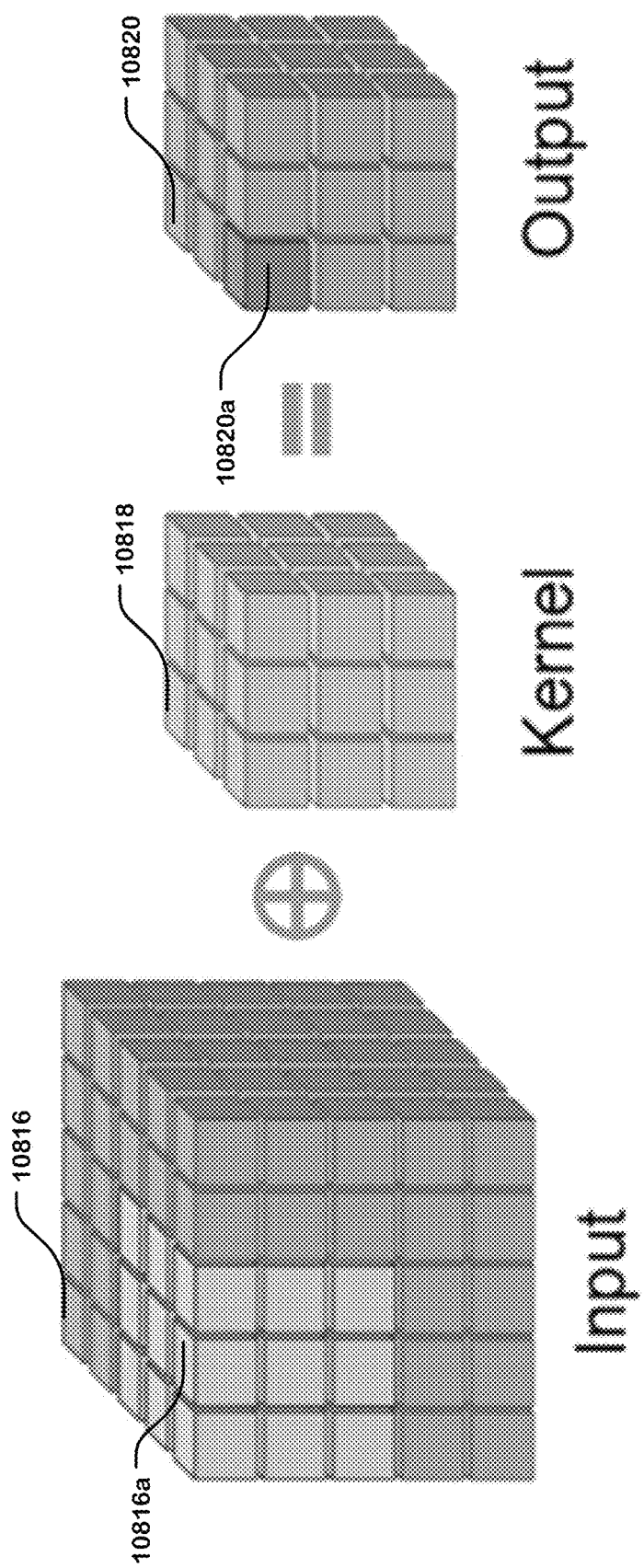

FIG. 108b shows one implementation of 3D convolutions 10800b used by the recurrent module 10810 of the hybrid neural network 10800b to produce the current hidden state representations.

A 3D convolution is a mathematical operation where each voxel present in the input volume is multiplied by a voxel in the equivalent position of the convolution kernel. At the end, the sum of the results is added to the output volume. In FIG. 108b, it is possible to observe the representation of the 3D convolution operation, where the voxels 10816a highlighted in the input 10816 are multiplied with their respective voxels in the kernel 10818. After these calculations, their sum 10820a is added to the output 10820.

Since the coordinates of the input volume are given by (x, y, z) and the convolution kernel has size (P, Q, R), the 3D convolution operation can be mathematically defined as:

$$O_{xyz} = \sum_{p=0}^{P-1} \sum_{q=0}^{Q-1} \sum_{r=0}^{R-1} K_{pqr} I_{(x+p)(y+q)(z+r)},$$

where
O is the result of the convolution,
I is the input volume,
K is the convolution kernel, and
(p,q,r) are the coordinates of K.

The bias term is omitted from the above equation to improve clarity.

3D convolutions, in addition to extracting spatial information from matrices like 2D convolutions, extract information present between consecutive matrices. This allows them to map both spatial information of 3D objects and temporal information of a set of sequential images.

Convolution Module

Figure 109:
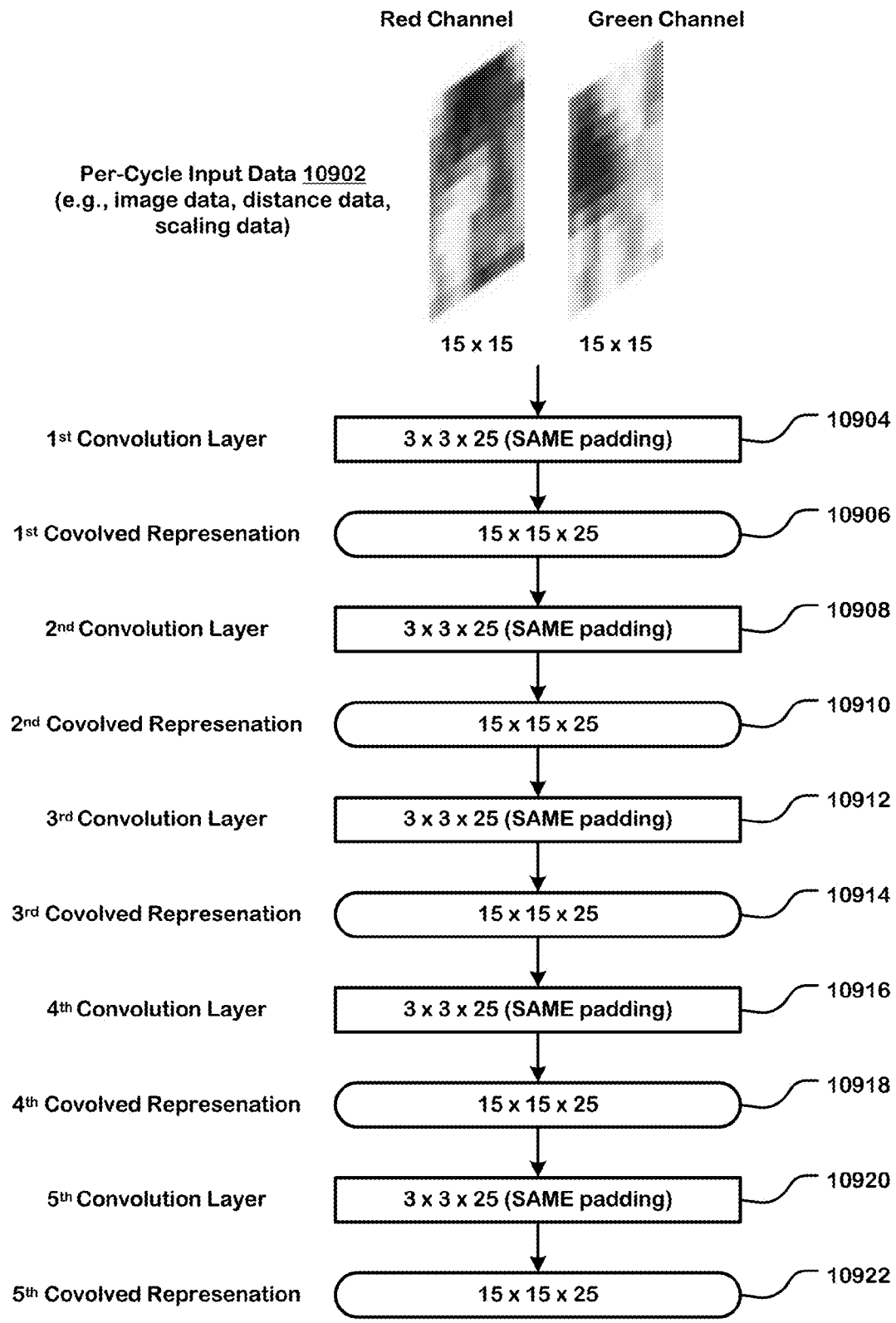

FIG. 109 illustrates one implementation of processing, through a cascade of convolution layers 10900 of the convolution module 10804, per-cycle input data 10902 for a single sequencing cycle among the series of t sequencing cycles to be base called.

The convolution module 10804 separately processes each per-cycle input data in a sequence of per-cycle input data through the cascade of convolution layers 10900. The sequence of per-cycle input data is generated for a series of t sequencing cycles of a sequencing run that are to be base called, where t is any number between 1 and 1000. So, for example, when the series includes fifteen sequencing cycles, the sequence of per-cycle input data comprises fifteen different per-cycle input data.

In one implementation, each per-cycle input data includes only image channels (e.g., a red channel and a green channel) or image data (e.g., the image data 7902 described above). The image channels or the image data depict intensity emissions of one or more clusters and their surrounding background captured at a respective sequencing cycle in the series. In another implementation, each per-cycle input data, in addition to the image channels or the image data, also includes supplemental channels such as the distance channels and the scaling channel (e.g., the input data 9500 described above).

In the illustrated implementation, the per-cycle input data 10902 includes two image channels, namely, a red channel and a green channel, for the single sequencing cycle among the series of t sequencing cycles to be base called. Each image channel is encoded in an image patch of size 15×15. The convolution module 10804 comprises five convolution layers. Each convolution layer has a bank of twenty-five convolution filters of size 3×3. Further, the convolution filters use so-called SAME padding that preserves the height and width of the input images or tensors. With the SAME padding, a padding is added to the input features such that the output feature map has the same size as the input features. In contrast, so-called VALID padding means no padding.

The first convolution layer 10904 processes the per-cycle input data 10902 and produces a first convolved representation 10906 of size 15×15×25. The second convolution layer 10908 processes the first convolved representation 10906 and produces a second convolved representation 10910 of size 15×15×25. The third convolution layer 10912 processes the second convolved representation 10910 and produces a third convolved representation 10914 of size 15×15×25. The fourth convolution layer 10916 processes the third convolved representation 10914 and produces a fourth convolved representation 10918 of size 15×15×25. The fifth convolution layer 10920 processes the fourth convolved representation 10918 and produces a fifth convolved representation 10922 of size 15×15×25. Note that the SAME padding preserves the spatial dimensions of the resulting convolved representations (e.g., 15×15). In some implementations, the number of convolution filters in the convolution layers are a power of two, such as 2, 4, 16, 32, 64, 128, 256, 512, and 1024.

As convolutions become deeper, information can be lost. To account for this, in some implementations, we use skip connections (1) to reintroduce the original per-cycle input data and (2) to combine low-level spatial features extracted by earlier convolution layers with high-level spatial features extracted by later convolution layers. We observe that this improves base calling accuracy.

Figure 110:
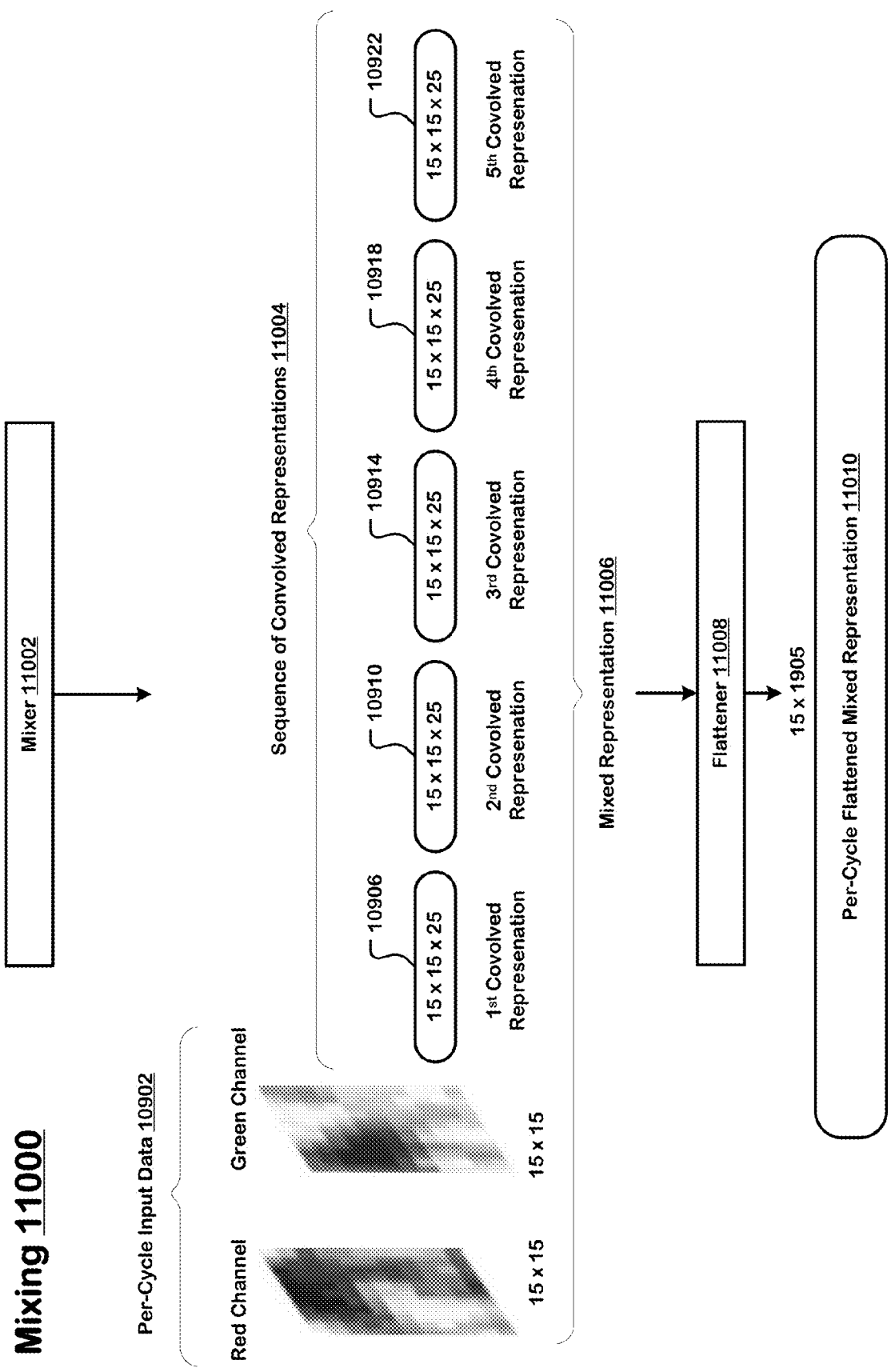

FIG. 110 depicts one implementation of mixing 11000 the single sequencing cycle's per-cycle input data 10902 with its corresponding convolved representations 10906, 10910, 10914, 10918, and 10922 produced by the cascade of convolution layers 10900 of the convolution module 10804. The convolved representations 10906, 10910, 10914, 10918, and 10922 are concatenated to form a sequence of convolved representations 11004, which in turn is concatenated with the per-cycle input data 10902 to produce a mixed representation 11006. In other implementations, summation is used instead of concatenation. Also, the mixing 11000 is operationalized by the mixer 11002.

A flattener 11008 then flattens the mixed representation 11006 and produces a per-cycle flattened mixed representation 11010. In some implementations, the flattened mixed representation 11010 is a high dimensional vector or two-dimensional (2D) array that shares at least one dimension size with the per-cycle input data 10902 and the convolved representations 10906, 10910, 10914, 10918, and 10922 (e.g., 15×1905, i.e., same row-wise dimension). This induces symmetry in the data that facilitates feature extraction in downstream 3D convolutions.

FIGS. 109 and 110 illustrate processing of the per-cycle image data 10902 for the single sequencing cycle among the series of t sequencing cycles to be base called. The convolution module 10804 separately processes respective per-cycle image data for each of the t sequencing cycles and produces a respective per-cycle flattened mixed presentation for each of the t sequencing cycles.

Stacking

Figure 111:
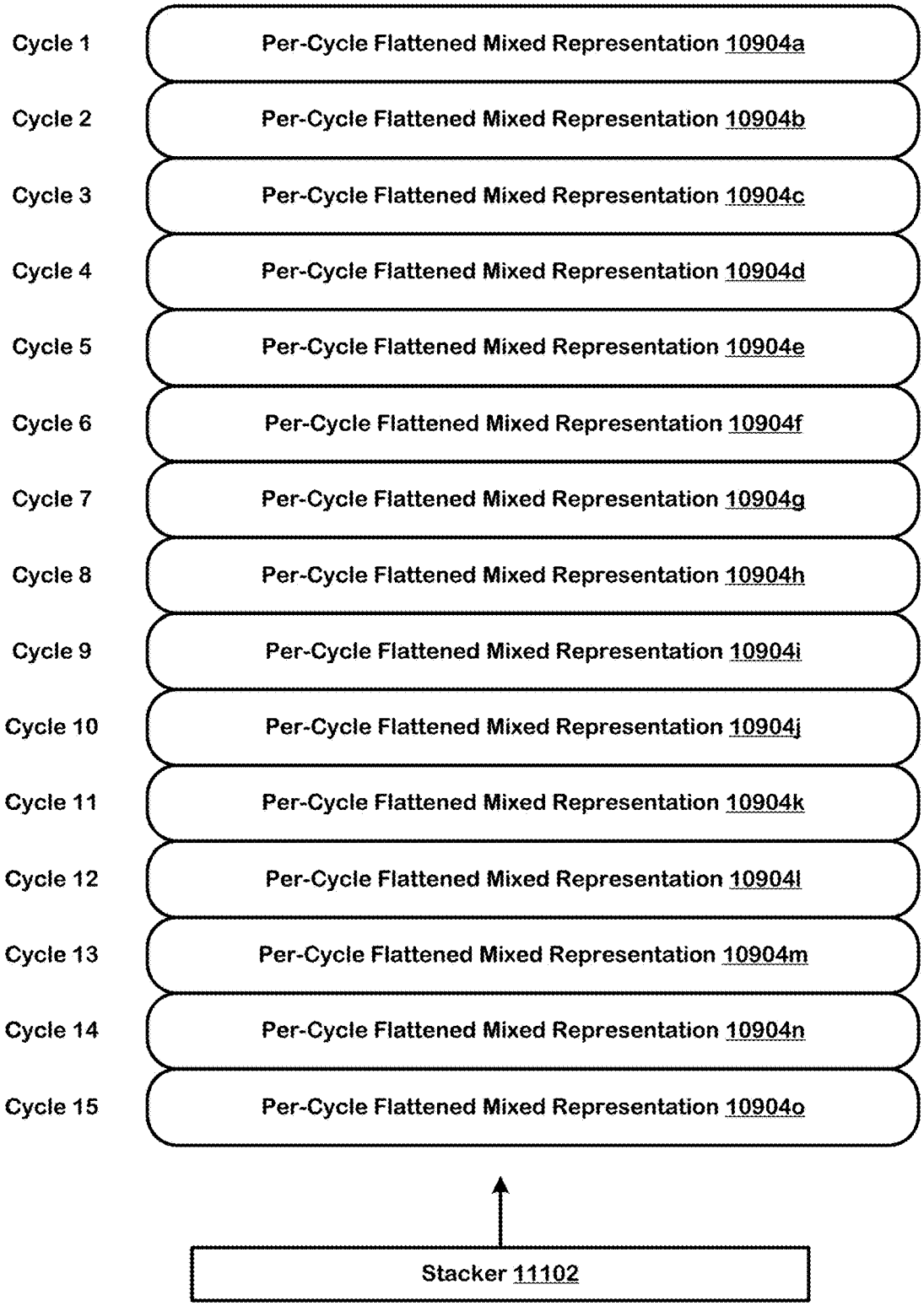

FIG. 111 shows one implementation of arranging flattened mixed representations of successive sequencing cycles as a stack 11100. In the illustrated implementation, fifteen flattened mixed representations 10904a to 10904o for fifteen sequencing cycles are stacked in the stack 11100. Stack 11100 is a 3D input volume that makes available features from both spatial and temporal dimensions (i.e., multiple sequencing cycles) in a same receptive field of a 3D convolution filter. The stacking is operationalized by the stacker 11102. In other implementations, stack 11100 can be a tensor of any dimensionality (e.g., 1D, 2D, 4D, 5D, etc.).

Recurrent Module

We use recurrent processing to capture long-term dependencies in the sequencing data and, in particular, to account for second order contributions in cross-cycle sequencing images from pre-phasing and phasing. Recurrent processing is used for analysis of sequential data because of the usage of time steps. A current hidden state representation at a current time step is a function of (i) the previous hidden state representation from a previous time step and (ii) the current input at the current time step.

Figure 112A:
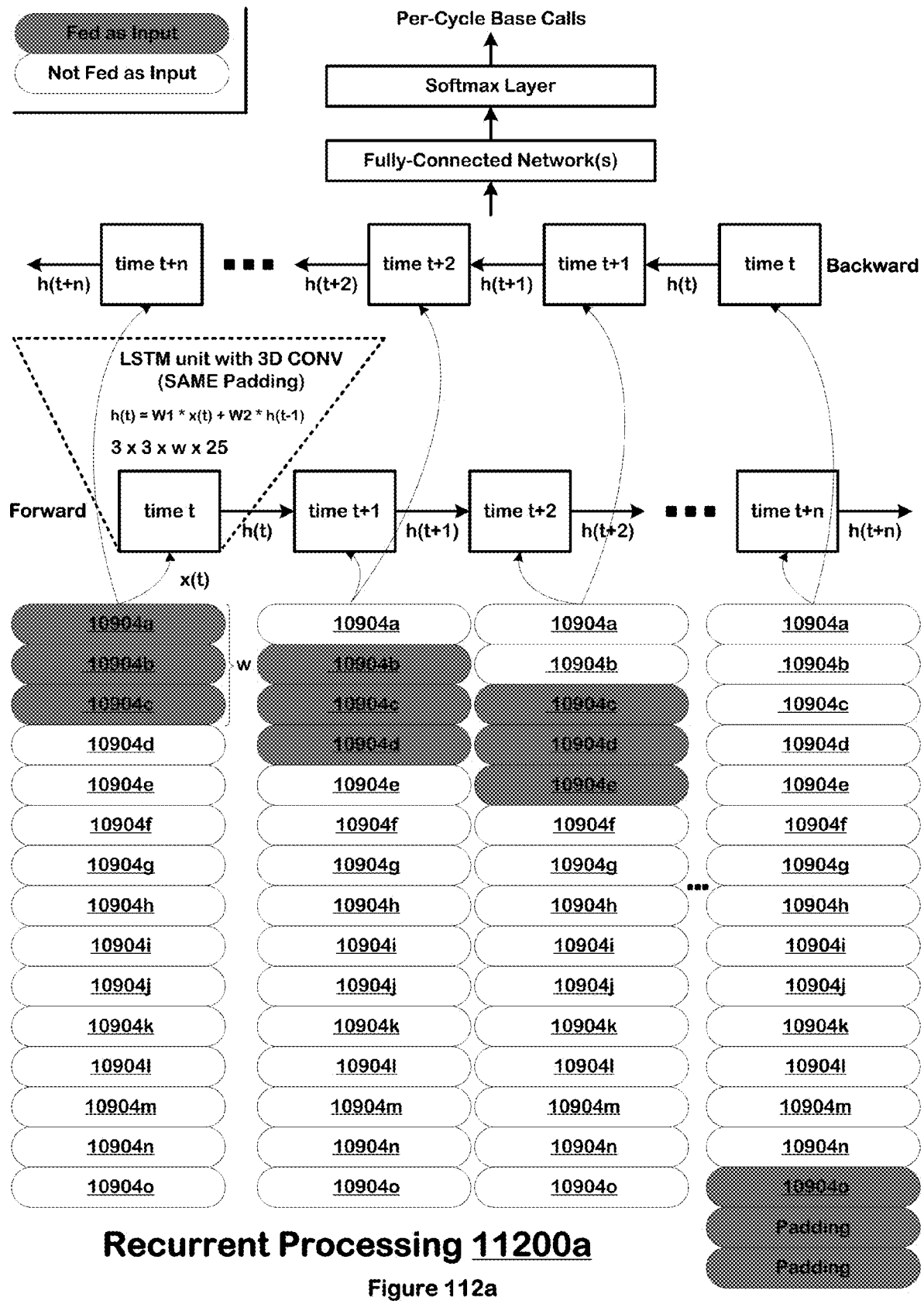

The recurrent module 10808 subjects the stack 11100 to recurrent application of 3D convolutions (i.e., recurrent processing 11200) in forward and backward directions and produces base calls for each of the clusters at each of the t sequencing cycles in the series. The 3D convolutions are used to extract spatio-temporal features from a subset of the flattened mixed representations in the stack 11100 on a sliding window basis. Each sliding window (w) corresponds to a respective sequencing cycle and is highlighted in FIG. 112*a* in orange. In some implementations, w is parameterized to be 1, 2, 3, 5, 7, 9, 15, 21, etc., depending on the total number of sequencing cycles being simultaneously base called. In one implementation, w is a fraction of the total number of sequencing cycles being simultaneously base called.

So, for example, consider that each sliding window contains three successive flattened mixed representations from the stack 11100 that comprises the fifteen flattened mixed representations 10904*a* to 10904*o*. Then, the first three flattened mixed representations 10904*a* to 10904*c* in the first sliding window correspond to the first sequencing cycle, the next three flattened mixed representations 10904*b* to 10904*d* in the second sliding window correspond to the second sequencing cycle, and so on. In some implementations, padding is used to encode adequate number of flattened mixed representations in the final sliding window corresponding to the final sequencing cycle, starting with the final flattened mixed representation 10904*o*.

At each time step, the recurrent module 10808 accepts (1) the current input $x(t)$ and (2) the previous hidden state representation $h(t-1)$ and computes the current hidden state representation $h(t)$. The current input $x(t)$ includes only a subset of the flattened mixed representations from the stack 11100 that fall within the current sliding window ((w), in orange). Therefore, each current input $x(t)$, at each time step, is a 3D volume of a plurality of flattened mixed representations (e.g., 1, 2, 3, 5, 7, 9, 15, or 21 flattened mixed representations, depending on w). For example, when (i) a single flattened mixed representation is two-dimensional (2D) with dimensions 15×1905 and (ii) w is 7, then each current input $x(t)$, at each time step, is a 3D volume with dimensions 15×1905×7.

The recurrent module 10808 applies a first 3D convolution ($W1_{3DCONV}$) to the current input $x(t)$ and a second 3D convolution) ($W2_{3DCONV}$) to the previous hidden state representation $h(t-1)$ to produce the current hidden state representation $h(t)$. In some implementations, $W1_{3DCONV}$ and $W2_{3DCONV}$ are the same because the weights are shared.

Gated Processing

In one implementation, the recurrent module 10808 processes the current input $x(t)$ and the previous hidden state representation $h(t-1)$ through a gated network such as long short-term memory (LSTM) network or gated recurrent unit (GRU) network. For example, in the LSTM implementation, the current input $x(t)$, along with the previous hidden state representation $h(t-1)$, is processed through each of the four gates of an LSTM unit: input gate, activation gate, forget gate, and output gate. This is illustrated in FIG. 112*b*, which shows one implementation of processing 11200*b* the current input $x(t)$ and the previous hidden state representation $h(t-1)$ through an LSTM unit that applies 3D convolutions to the current input $x(t)$ and the previous hidden state representation $h(t-1)$ and produces the current hidden state representation $h(t)$ as output. In such an implementation, the weights of the input, activation, forget, and output gates apply 3D convolutions.

In some implementations, the gated units (LSTM or GRU) do not use the non-linearity/squashing functions like hyperbolic tangent and sigmoid.

In one implementation, the current input $x(t)$, the previous hidden state representation $h(t-1)$, and the current hidden state representation $h(t)$ are all 3D volume with same dimensionality and are processed through or produced by the input, activation, forget, and output gates as 3D volume.

In one implementation, the 3D convolutions of the recurrent module 10808 use a bank of twenty-five convolution filters of size 3×3, along with the SAME padding. In some implementations, the size of the convolution filters is 5×5. In some implementations, the number of convolution filters used by the recurrent module 10808 are factorized by a power of two, such as 2, 4, 16, 32, 64, 128, 256, 512, and 1024.

Bi-Directional Processing

The recurrent module 10808 first processes the stack 11100 from the beginning to the end (top-down) on the sliding window basis and produces a sequence of current hidden state representations (vectors) for the forward traversal $\vec{h}_t = 3DCONV(x_t + \vec{h}_{t-1})$.

The recurrent module 10808 then processes the stack 11100 from the end to the beginning (bottom-up) on the sliding window basis and produces a sequence of current hidden state representations (vectors) for the backward/reverse traversal $\overleftarrow{h}_t = 3DCONV(x_t + \overleftarrow{h}_{t-1})$.

In some implementations, for both the directions, at each time step, the processing uses the gates of an LSTM or a GRU. For example, at each time step, a forward current input $x(t)$ is processed through the input, activation, forget, and output gates of an LSTM unit to produce a forward current hidden state representation $\vec{h}_t$ and a backward current input $x(t)$ is processed through the input, activation, forget, and output gates of another LSTM unit to produce a backward current hidden state representation $\overleftarrow{h}_t$.

Then, for each time step/sliding window/sequencing cycle, the recurrent module 10808 combines (concatenates or sums or averages) the corresponding forward and backward current hidden state representations and produces a combined hidden state representation $$_t = [\vec{h}_t; \overleftarrow{h}_t].$$

The combined hidden representation $h_t$ is then processed through one or more fully-connected networks to produce a dense representation. The dense representation is then processed through a softmax layer to produce likelihoods of bases incorporated in each of the clusters at a given sequencing cycle being A, C, T, and G. The bases are classified as A, C, T, or G based on the likelihoods. This is done for each of the t sequencing cycles in the series (or each time step/sliding window), either in parallel or sequentially.

One skilled in the art will appreciate that, in other implementations, the hybrid architecture can process input data for fewer or greater number of sequencing cycles and can comprise fewer or greater number of convolution and recurrent layers. Also, the dimensionality of the input data, the current and previous hidden representations, the convolution filters, the resulting feature maps, and the output can be different. Also, the number of convolution filters in a convolution layer can be different. It can use different padding and striding configurations. It can use a different classification function (e.g., sigmoid or regression) and may or may not include a fully-connected layer. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

Experimental Results and Observations

Figure 113:
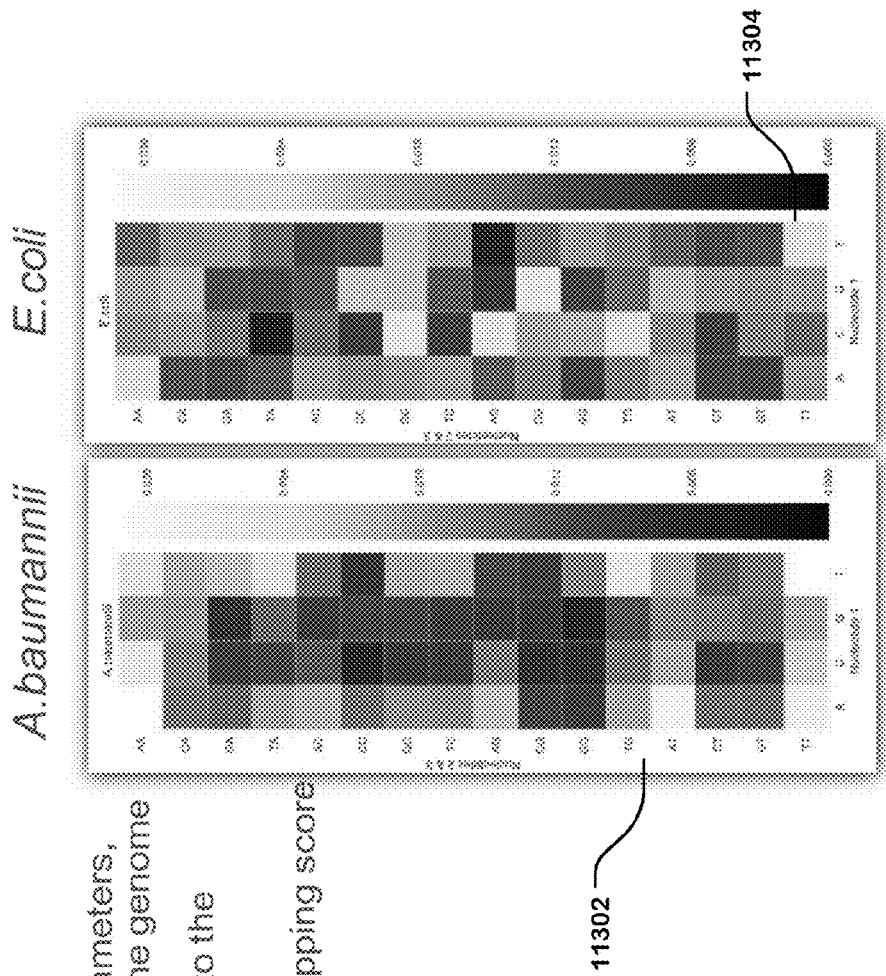

FIG. 113 shows one implementation of balancing trinucleotides (3-mers) in the training data used to train the neural network-based base caller 1514. Balancing results in very little learning of statistics about genome in the training data and in turn improves generalization. Heat map 11302 shows balanced 3-mers in the training data for a first organism called "*A. baumanni*". Heap map 11304 shows balanced 3-mers in the training data for a second organism called "*E. coli*".

FIG. 114 compares base calling accuracy of the RTA base caller against the neural network-based base caller 1514. As illustrated in FIG. 114, the RTA base caller has a higher error percentage in two sequencing runs (Read: 1 and Read: 2). That is, the neural network-based base caller 1514 outperforms the RTA base caller in both the sequencing runs.

FIG. 115 compares tile-to-tile generalization of the RTA base caller with that of the neural network-based base caller 1514 on a same tile. That is, with the neural network-based base caller 1514, the inference (testing) is performed on data for the same tile whose data is used in the training.

FIG. 116 compares tile-to-tile generalization of the RTA base caller with that of the neural network-based base caller 1514 on a same tile and on different tiles. That is, the neural network-based base caller 1514 is trained on data for clusters on a first tile, but performs inference on data from clusters on a second tile. In the same tile implementation, the neural network-based base caller 1514 is trained on data from clusters on tile five and tested on data from clusters on tile five. In the different tile implementation, the neural network-based base caller 1514 is trained on data from clusters on tile ten and tested on data from clusters on tile five.

FIG. 117 also compares tile-to-tile generalization of the RTA base caller with that of the neural network-based base caller 1514 on different tiles. In the different tile implementations, the neural network-based base caller 1514 is once trained on data from clusters on tile ten and tested on data from clusters on tile five, and then trained on data from clusters on tile twenty and tested on data from clusters on tile five.

FIG. 118 shows how different sizes of the image patches fed as input to the neural network-based base caller 1514 effect the base calling accuracy. In both sequencing runs (Read: 1 and Read: 2), the error percentage decreases as the patch size increases from 3×3 to 11×11. That is, the neural network-based base caller 1514 produces more accurate base calls with larger image patches. In some implementations, base calling accuracy is balanced against compute efficiency by using image patches that are not larger than 100×100 pixels. In other implementations, image patches as large as 3000×3000 pixels (and larger) are used.

FIGS. 119, 120, 121, and 122 show lane-to-lane generalization of the neural network-based base caller 1514 on training data from *A. baumanni* and *E. coli*.

Turning to FIG. 120, in one implementation, the neural network-based base caller 1514 is trained on *E. coli* data from clusters on a first lane of a flow cell and tested on *A. baumanni* data from clusters on both the first and second lanes of the flow cell. In another implementation, the neural network-based base caller 1514 is trained on *A. baumanni* data from clusters on the first lane and tested on the *A. baumanni* data from clusters on both the first and second lanes. In yet another implementation, the neural network-based base caller 1514 is trained on *E. coli* data from clusters on the second lane and tested on the *A. baumanni* data from clusters on both the first and second lanes. In yet further implementation, the neural network-based base caller 1514 is trained on *A. baumanni* data from clusters on the second lane and tested on the *A. baumanni* data from clusters on both the first and second lanes.

In one implementation, the neural network-based base caller 1514 is trained on *E. coli* data from clusters on a first lane of a flow cell and tested on *E. coli* data from clusters on both the first and second lanes of the flow cell. In another implementation, the neural network-based base caller 1514 is trained on *A. baumanni* data from clusters on the first lane and tested on the *E. coli* data from clusters on both the first and second lanes. In yet another implementation, the neural network-based base caller 1514 is trained on *E. coli* data from clusters on the second lane and tested on the *E. coli* data from clusters on the first lane. In yet further implementation, the neural network-based base caller 1514 is trained on *A. baumanni* data from clusters on the second lane and tested on the *E. coli* data from clusters on both the first and second lanes.

In FIG. 120, the base calling accuracy (measured by the error percentage) is shown for each of these implementations for two sequencing runs (e.g., Read: 1 and Read: 2).

Turning to FIG. 121, in one implementation, the neural network-based base caller 1514 is trained on *E. coli* data from clusters on a first lane of a flow cell and tested on *A. baumanni* data from clusters on the first lane. In another implementation, the neural network-based base caller 1514 is trained on *A. baumanni* data from clusters on the first lane and tested on the *A. baumanni* data from clusters on the first lane. In yet another implementation, the neural network-based base caller 1514 is trained on *E. coli* data from clusters on the second lane and tested on the *A. baumanni* data from clusters on the first lane. In yet further implementation, the neural network-based base caller 1514 is trained on *A. baumanni* data from clusters on the second lane and tested on the *A. baumanni* data from clusters on the first lane.

In one implementation, the neural network-based base caller 1514 is trained on *E. coli* data from clusters on a first lane of a flow cell and tested on *E. coli* data from clusters on the first lane. In another implementation, the neural network-based base caller 1514 is trained on *A. baumanni* data from clusters on the first lane and tested on the *E. coli* data from clusters on the first lane. In yet another implementation, the neural network-based base caller 1514 is trained on *E. coli* data from clusters on the second lane and tested on the *E. coli* data from clusters on the first lane. In yet further implementation, the neural network-based base caller 1514 is trained on *A. baumanni* data from clusters on the second lane and tested on the *E. coli* data from clusters on the first lane.

In FIG. 121, the base calling accuracy (measured by the error percentage) is shown for each of these implementations for two sequencing runs (e.g., Read: 1 and Read: 2). Comparing FIG. 120 with FIG. 121, it can be seen that the implementations covered by the later result in an error reduction between fifty to eighty percent.

Turning to FIG. 122, in one implementation, the neural network-based base caller 1514 is trained on *E. coli* data from clusters on a first lane of a flow cell and tested on *A. baumanni* data from clusters on the second lane. In another implementation, the neural network-based base caller 1514 is trained on *A. baumanni* data from clusters on the first lane and tested on the *A. baumanni* data from clusters on the second lane. In yet another implementation, the neural network-based base caller 1514 is trained on *E. coli* data from clusters on the second lane and tested on the *A. baumanni* data from clusters on the first lane. In second first lane. In yet further implementation, the neural network-based base caller 1514 is trained on *A. baumanni* data from clusters on the second lane and tested on the *A. baumanni* data from clusters on the second lane.

In one implementation, the neural network-based base caller 1514 is trained on *E. coli* data from clusters on a first lane of a flow cell and tested on *E. coli* data from clusters on the second lane. In another implementation, the neural network-based base caller 1514 is trained on *A. baumanni* data from clusters on the first lane and tested on the *E. coli* data from clusters on the second lane. In yet another implementation, the neural network-based base caller 1514 is trained on *E. coli* data from clusters on the second lane and tested on the *E. coli* data from clusters on the second lane. In yet further implementation, the neural network-based base caller 1514 is trained on *A. baumanni* data from clusters on the second lane and tested on the *E. coli* data from clusters on the second lane.

In FIG. 122, the base calling accuracy (measured by the error percentage) is shown for each of these implementations for two sequencing runs (e.g., Read: 1 and Read: 2). Comparing FIG. 120 with FIG. 122, it can be seen that the implementations covered by the later result in an error reduction between fifty to eighty percent.

FIG. 123 depicts an error profile for the lane-to-lane generalization discussed above with respect to FIGS. 119, 120, 121, and 122. In one implementation, the error profile detects error in base calling A and T bases in the green channel.

FIG. 124 attributes the source of the error detected by the error profile of FIG. 123 to low cluster intensity in the green channel.

FIG. 125 compares error profiles of the RTA base caller and the neural network-based base caller 1514 for two sequencing runs (Read 1 and Read 2). The comparison confirms superior base calling accuracy of the neural network-based base caller 1514.

FIG. 126*a* shows run-to-run generalization of the neural network-based base caller 1514 on four different instruments.

FIG. 126*b* shows run-to-run generalization of the neural network-based base caller 1514 on four different runs executed on a same instrument.

FIG. 127 shows the genome statistics of the training data used to train the neural network-based base caller 1514.

FIG. 128 shows the genome context of the training data used to train the neural network-based base caller 1514.

FIG. 129 shows the base calling accuracy of the neural network-based base caller 1514 in base calling long reads (e.g., 2×250).

FIG. 130 illustrates one implementation of how the neural network-based base caller 1514 attends to the central cluster pixel(s) and its neighboring pixels across image patches.

FIG. 131 shows various hardware components and configurations used to train and run the neural network-based base caller 1514, according to one implementation. In other implementations, different hardware components and configurations are used.

FIG. 132 shows various sequencing tasks that can be performed using the neural network-based base caller 1514. Some examples include quality scoring (QScoring) and variant classification. FIG. 132 also lists some example sequencing instruments for which the neural network-based base caller 1514 performs base calling.

FIG. 133 is a scatter plot 13300 visualized by t-Distributed Stochastic Neighbor Embedding (t-SNE) and portrays base calling results of the neural network-based base caller 1514. Scatter plot 13300 shows that the base calling results are clustered into 64 ($4^3$) groups, with each group mostly corresponding to a particular input 3-mer (trinucleotide repeating pattern). This is the case because the neural network-based base caller 1514 processes input data for at least three sequencing cycles and learns sequence-specific motifs to produce a current base call based on the previous and successive base calls.

Quality Scoring

Quality scoring refers to the process of assigning a quality score to each base call. Quality scores are defined according to the Phred framework, which transforms the values of predictive features of sequencing traces to a probability based on a quality table. The quality table is obtained by training on calibration data sets and is updated when characteristics of the sequencing platform change. The probabilistic interpretation of quality scores allows fair integration of different sequencing reads in the downstream analysis such as variant calling and sequence assembly. Thus, a valid model to define quality scores is indispensable for any base caller.

We first describe what quality scores are. A quality score is a measure of the probability of a sequencing error in a base call. A high quality score implies that a base call is more reliable and less likely to be incorrect. For example, if the quality score of a base is Q30, the probability that this base is called incorrectly is 0.001. This also indicates that the base call accuracy is 99.9%.

The following table shows the relationship between the base call quality scores and their corresponding error probability, base call accuracy rate, and base call error rate:

| Quality Score | Error Probability | Base Call Error Rate | Base Call Accuracy Rate |
|---|---|---|---|
| Q10 | 0.1 (1 in 10) | 10% | 90% |
| Q20 | 0.01 (1 in 100) | 1% | 99% |
| Q30 | 0.001 (1 in 1,000) | 0.1% | 99.9% |
| Q40 | 0.0001 (1 in 10,000) | 0.01% | 99.99% |
| Q50 | 0.00001 (1 in 100,000) | 0.001% | 99.999% |
| Q60 | 0.000001 (1 in 1,000,000) | 0.0001% | 99.9999% |

We now describe how quality scores are generated. During a sequencing run, a quality score is assigned to each base call for every cluster, on every tile, for every sequencing cycle. Illumina quality scores are calculated for each base call in a two-step process. For each base call, a number of quality predictor values are computed. Quality predictor values are observable properties of clusters from which base calls are extracted. These include properties such as intensity profiles and signal-to-noise ratios and measure various aspects of base call reliability. They have been empirically determined to correlate with the quality of the base call.

A quality model, also known as a quality table or Q-table, lists combinations of quality predictor values and relates them to corresponding quality scores; this relationship is determined by a calibration process using empirical data. To estimate a new quality score, the quality predictor values are computed for a new base call and compared to values in the pre-calibrated quality table.

We now describe how a quality table is calibrated. Calibration is a process in which a statistical quality table is derived from empirical data that includes various well-characterized human and non-human samples sequenced on a number of instruments. Using a modified version of the Phred algorithm, a quality table is developed and refined using characteristics of the raw signals and error rates determined by aligning reads to the appropriate references.

We now describe why quality tables change from time to time. Quality tables provide quality scores for runs generated by specific instrument configurations and versions of chemistry. When significant characteristics of the sequencing platform change, such as new hardware, software, or chemistry versions, the quality model requires recalibration. For example, improvements in sequencing chemistry require quality table recalibration to accurately score the new data, which consumes a substantial amount of processing time and computational resources.

Neural Network-Based Quality Scoring

We disclose neural network-based techniques for quality scoring that do not use the quality predictor values or the quality tables and instead infer quality scores from confidence over predictions of well-calibrated neural networks. In the context of neural networks, "calibration" refers to the consistency or correlation between subjective forecasts and empirical long-run frequencies. This is a frequentist notion of certainty: if a neural network claims that 90% of the time a particular label is the correct label, then, during evaluation, 90% of all labels ascribed probability 90% of being correct, should be the correct label. Note that calibration is an orthogonal concern to accuracy: a neural network's predictions may be accurate and yet miscalibrated.

The disclosed neural networks are well-calibrated because they are trained on large-scale training sets with diverse sequencing characteristics that adequately model the base calling domain of real-world sequencing runs. In particular, sequencing images obtained from a variety of sequencing platforms, sequencing instruments, sequencing protocols, sequencing chemistries, sequencing reagents, cluster densities, and flow cells are used as training examples to train the neural networks. In other implementations, different base calling and quality scoring models are respectively used for different sequencing platforms, sequencing instruments, sequencing protocols, sequencing chemistries, sequencing reagents, cluster densities, and/or flow cells.

For each of the four base call classes (A, C, T, and G), large numbers of sequencing images are used as training examples that identify intensity patterns representative of the respective base call class under a wide range of sequencing conditions. This in turn obviates the need of extending classification capabilities of the neural networks to new classes not present in the training. Furthermore, each training example is accurately labelled with a corresponding ground truth based on aligning reads to the appropriate references. What results is well-calibrated neural networks whose confidence over predictions can be interpreted as a certainty measure for quality scoring, expressed mathematically below.

Let $Y=\{A,C,T,G\}$ denote the set of class labels for the base call classes A, C, T, and G and X denote a space of inputs. Let $N_\theta(y|x)$ denote the probability distribution one of the disclosed neural networks predicts on an input $x \in X$ and $\theta$ denote the neural network's parameters. For a training example $x_i$ with correct label $y_i$, the neural network predicts label $\hat{y}_i = \text{argmax}_{y \in Y} N_\theta(y|x_i)$. The prediction gets correctness score $c_i=1$ if $\hat{y}_i = y_i$ and 0 otherwise and a confidence score $r_i = N_\theta(\hat{y}_i|x_i)$.

The neural network $N_\theta(y|x)$ is well-calibrated over a data distribution D because over all $(x_i,y_i) \in D$ and $r_i = \alpha$ the probability that $c_i=1$ is $\alpha$. For example, out of a sample from D, given 100 predictions, each with confidence 0.8, 80 are correctly classified by the neural network $N_\theta(y|x)$. More formally, $P_{\theta, D}(r,c)$ denotes the distribution over r and c values of the predictions of the neural network $N_\theta(y|x)$ on D and is expressed as $P_{\theta,D}(c=1|r=I_\alpha)=\alpha \; \forall_\alpha \in [0,1]$, where $I_\alpha$ denotes a small non-zero interval around $\alpha$.

Because the well-calibrated neural networks are trained on diverse training sets, unlike the quality predictor values or the quality tables, they are not specific to instrument configurations and chemistry versions. This has two advantages. First, for different types of sequencing instruments, the well-calibrated neural networks obviate the need of deriving different quality tables from separate calibration processes. Second, for a same sequencing instrument, they obviate the need of recalibration when characteristics of the sequencing instrument change. More details follow.

Inferring Quality Scores from Softmax Confidence Probabilities

The first well-calibrated neural network is the neural network-based base caller 1514 that processes input data derived from the sequencing images 108 and produces base call confidence probabilities for the base being A, C, T, and G. Base call confidence probabilities can also be considered likelihoods or classification scores. In one implementation, the neural network-based base caller 1514 uses a softmax function to generate the base call confidence probabilities as softmax scores.

Quality scores are inferred from the base call confidence probabilities generated by the softmax function of the neural network-based base caller 1514 because the softmax scores are calibrated (i.e., they are representative of the ground truth correctness likelihood) and thus naturally correspond to the quality scores.

We demonstrate correspondence between the base call confidence probabilities and the quality scores by selecting a set of the base call confidence probabilities produced by the neural network-based base caller 1514 during training and determining their base calling error rate (or base calling accuracy rate).

So, for example, we select the base call confidence probability "0.90" produced by the neural network-based base caller 1514. We take numerous (e.g., ranging from 10000 to 1000000) instances when the neural network-based base caller 1514 made the base call prediction with 0.90 softmax score. The numerous instances can be obtained either from the validation set or the test set. We then, based on comparison to corresponding ground truth base calls associated with respective ones of the numerous instances, determine in how many of the numerous instances the base call prediction was correct.

We observe that the base call was correctly predicted in ninety percent of the numerous instances, with ten percent miscalls. This means that for the 0.90 softmax score, the base calling error rate is 10% and the base calling accuracy rate is 90%, which in turn corresponds to quality score Q10 (see table above). Similarly, for other softmax scores like 0.99, 0.999, 0.9999, 0.99999, and 0.999999 we observe correspondence with quality scores Q20, Q30, Q40, Q50, and Q60, respectively. This is illustrated in FIG. 136a. In other implementations, we observe correspondence between the softmax scores and quality scores such as Q9, Q11, Q12, Q23, Q25, Q29, Q37, and Q39.

We also observe correspondence with binned quality scores. For example, 0.80 softmax score corresponds to binned quality score Q06, 0.95 softmax score corresponds to binned quality score Q15, 0.993 softmax score corresponds to binned quality score Q22, 0.997 softmax score corresponds to binned quality score Q27, 0.9991 softmax score corresponds to binned quality score Q33, 0.9995 softmax score corresponds to binned quality score Q37, and 0.9999 softmax score corresponds to binned quality score Q40. This is illustrated in FIG. 136b.

The sample size used herein are large to avoid small sample issues and can, for example, range from 10000 to 1000000. In some implementations, the sample size of instances used to determine the base calling error rates (or the base calling accuracy rates) is selected based on the softmax score being evaluated. For example, for 0.99 softmax score, the sample includes one hundred instances, for 0.999 softmax score, the sample includes one thousand instances, for 0.9999 softmax score, the sample includes ten thousand instances, for 0.99999 softmax score, the sample includes hundred thousand instances, and for 0.999999 softmax score, the sample includes one million instances.

Regarding softmax, softmax is an output activation function for multiclass classification. Formally, training a so-called softmax classifier is regression to a class probability, rather than a true classifier as it does not return the class but rather a confidence prediction of each class's likelihood. The softmax function takes a class of values and converts them to probabilities that sum to one. The softmax function squashes a k-dimensional vector of arbitrary real values to k-dimensional vector of real values within the range zero to one. Thus, using the softmax function ensures that the output is a valid, exponentially normalized probability mass function (nonnegative and summing to one).

Consider that $\hat{y}_i$ is the i th element of the vector $\tilde{y}=[\tilde{y}_1, \tilde{y}_2, \ldots, \tilde{y}_n]$:

$$\tilde{y}_i = (\text{softmax}(\tilde{z}))_i = \frac{\exp(\tilde{z}_i)}{\sum_{j=1}^{j=N} \exp(\tilde{z}_j)},$$

where
$\tilde{y}$ is a vector of length n, where n is the number of classes in the classification. These elements have values between zero and one, and sum to one so that they represent a valid probability distribution.

An example softmax activation function 13406 is shown in FIG. 134. Softmax 13406 is applied to three classes as $$z \mapsto \text{softmax}\left(\left[z; \frac{z}{10}; -2z\right]\right).$$

Note that the three outputs always sum to one. They thus define a discrete probability mass function.

When used for classification, $\tilde{y}_i$ gives the probability of being in class i.

$P(Y=i|\tilde{z})=(\text{softmax}(\tilde{z}))_i=\tilde{y}_i$

The name "softmax" can be somewhat confusing. The function is more closely related to the argmax function than the max function. The term "soft" derives from the fact that the softmax function is continuous and differentiable. The argmax function, with its result represented as a one-hot vector, is not continuous or differentiable. The softmax function thus provides a "softened" version of the argmax. It would perhaps be better to call the softmax function "softargmax," but the current name is an entrenched convention.

FIG. 134 illustrates one implementation of selecting 13400 the base call confidence probabilities 10704 of the neural network-based base caller 1514 for quality scoring. The base call confidence probabilities 10704 of the neural network-based base caller 1514 can be classification scores (e.g., softmax scores or sigmoid scores) or regression scores. In one implementation, the base call confidence probabilities 10704 are produced during the training 10700.

In some implementations, the selection 13400 is done based on quantization, which is performed by a quantizer 13402 that accesses the base call confidence probabilities 10704 and produces quantized classification scores 13404. The quantized classification scores 13404 can be any real-number. In one implementation, the quantized classification scores 13404 are selected based on a selection formula defined as $$0.9 \sum_{i=1}^{n} 0.1^{(i-1)}.$$

In another implementation, the quantized classification scores 13404 are selected based on a selection formula defined as $$\bigvee_{i=1}^{n=10} 0.1i.$$

FIG. 135 shows one implementation of the neural network-based quality scoring 13500. For each of the quantized classification scores 13404, a base calling error rate 13508 and/or a base calling accuracy rate 13510 is determined by comparing its base call predictions 10704 against corresponding ground truth base calls 10708 (e.g., over batches with varying sample size). The comparison is performed by a comparer 13502, which in turn includes a base calling error rate determiner 13504 and a base calling accuracy rate determiner 13506.

Then, to establish the correspondence between the quantized classification scores 13404 and the quality scores, a fit is determined between the quantized classification scores 13404 and their base calling error rate 13508 (and/or their base calling accuracy rate 13510) by a fit determiner 13512. In one implementation, the fit determiner 13512 is a regression model.

Based on the fit, the quality scores are correlated with the quantized classification scores 13404 by a correlator 13514.

FIGS. 136a-136b depict one implementation of correspondence 13600 between the quality scores and the base call confidence predictions made by the neural network-based base caller 1514. The base call confidence probabilities of the neural network-based base caller 1514 can be classification scores (e.g., softmax scores or sigmoid scores) or regression scores. FIG. 136a is a quality score correspondence scheme 13600a for quality scores. FIG. 136b is a quality score correspondence scheme 13600a for binned quality scores.

Inference

FIG. 137 shows one implementation of inferring quality scores from base call confidence predictions made by the neural network-based base caller 1514 during inference 13700. The base call confidence probabilities of the neural network-based base caller 1514 can be classification scores (e.g., softmax scores or sigmoid scores) or regression scores.

During the inference 13700, the predicted base call 13706 is assigned the quality score 13708 to which its base call confidence probability (i.e., the highest softmax score (in red)) most corresponds to. In some implementations, the quality score correspondence 13600 is made by looking up the quality score correspondence schemes 13600a-13600b and is operationalized by a quality score inferrer 13712.

In some implementations, a chastity filter 13710 terminates the base calling of a given cluster when the quality score 13708 assigned to its called base, or an average quality score over successive base calling cycles, falls below a preset threshold.

The inference 13700 includes hundreds, thousands, and/or millions of iterations of forward propagation 13714, including parallelization techniques such as batching. The inference 13700 is performed on inference data 13702 that includes the input data (with the image channels derived from the sequencing images 108 and/or the supplemental channels (e.g., the distance channels, the scaling channel)). The inference 13700 is operationalized by a tester 13704.

Directly Predicting Base Call Quality

The second well-calibrated neural network is the neural network-based quality scorer 13802 that processes input data derived from the sequencing images 108 and directly produces a quality indication.

In one implementation, the neural network-based quality scorer 13802 is a multilayer perceptron (MLP). In another implementation, the neural network-based quality scorer 13802 is a feedforward neural network. In yet another implementation, the neural network-based quality scorer 13802 is a fully-connected neural network. In a further implementation, the neural network-based quality scorer 13802 is a fully convolutional neural network. In yet further implementation, the neural network-based quality scorer 13802 is a semantic segmentation neural network.

In one implementation, the neural network-based quality scorer 13802 is a convolutional neural network (CNN) with a plurality of convolution layers. In another implementation, it is a recurrent neural network (RNN) such as a long short-term memory network (LSTM), bi-directional LSTM (Bi-LSTM), or a gated recurrent unit (GRU). In yet another implementation, it includes both a CNN and a RNN.

In yet other implementations, the neural network-based quality scorer 13802 can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

In some implementations, the neural network-based quality scorer 13802 has the same architecture as the neural network-based base caller 1514.

The input data can include the image channels derived from the sequencing images 108 and/or the supplemental channels (e.g., the distance channels, the scaling channel). The neural network-based quality scorer 13802 processes the input data and produces an alternative representation of the input data. The alternative representation is a convolved representation in some implementations and a hidden representation in other implementations. The alternative representation is then processed by an output layer to produce an output. The output is used to produce the quality indication.

In one implementation, the same input data is fed to the neural network-based base caller 1514 and the neural network-based quality scorer 13802 to produce (i) a base call from the neural network-based base caller 1514 and (ii) a corresponding quality indication from the neural network-based quality scorer 13802. In some implementations, the neural network-based base caller 1514 and the neural network-based quality scorer 13802 are jointly trained with end-to-end backpropagation.

In one implementation, the neural network-based quality scorer 13802 outputs a quality indication for a single target cluster for a particular sequencing cycle. In another implementation, it outputs a quality indication for each target cluster in a plurality of target clusters for the particular sequencing cycle. In yet another implementation, it outputs a quality indication for each target cluster in a plurality of target clusters for each sequencing cycle in a plurality of sequencing cycles, thereby producing a quality indication sequence for each target cluster.

In one implementation, the neural network-based quality scorer 13802 is a convolutional neural network trained on training examples comprising data from the sequencing images 108 and labeled with base call quality ground truths. The neural network-based quality scorer 13802 is trained using a backpropagation-based gradient update technique that progressively matches base call quality predictions 13804 of the convolutional neural network 13802 with the base call quality ground truths 13808. In some implementations, we label a base as 0 if it was a wrong base call and 1 if otherwise. As a result, the output corresponds to the probability of error. In one implementation, this obviates the need of using the sequence context as input features.

An input module of the convolutional neural network 13802 feeds data from the sequencing images 108 captured at one or more sequencing cycles to the convolutional neural network 13802 for determining quality of one or more bases called for one or more clusters.

An output module of the convolutional neural network 13802 translates analysis by the convolutional neural network 13802 into an output 13902 that identifies the quality of the one or more bases called for the one or more clusters.

In one implementation, the output module further comprises a softmax classification layer that produces likelihoods for the quality status being high-quality, medium-quality (optional, as indicated by dotted lines), and low-quality. In another implementation, the output module further comprises a softmax classification layer that produces likelihoods for the quality status being high-quality and low-quality. A person skilled in the art will appreciate that other classes that bucket quality scores differently and discernably can be used. The softmax classification layer produces likelihoods for the quality being assigned a plurality of quality scores. Based on the likelihoods, the quality is assigned a quality score from one of the plurality of quality scores. The quality scores are logarithmically based on base calling error probabilities. The plurality of quality scores includes Q6, Q10, Q15, Q20, Q22, Q27, Q30, Q33, Q37, Q40, and Q50. In another implementation, the output module further comprises a regression layer that produces continuous values which identify the quality.

In some implementations, the neural network-based quality scorer 13802 further comprises a supplemental input module that supplements the data from the sequencing images 108 with quality predictor values for the bases called and feeds the quality predictor values to the convolutional neural network 13802 along with the data from the sequencing images.

In some implementations, the quality predictor values include online overlap, purity, phasing, starts, hexamer score, motif accumulation, endiness, approximate homopolymer, intensity decay, penultimate chastity, signal overlap with background (SOWB), and/or shifted purity G adjustment. In other implementations, the quality predictor values include peak height, peak width, peak location, relative peak locations, peak height ration, peak spacing ration, and/or peak correspondence. Additional details about the quality predictor values can be found in US Patent Publication Nos. 2018/0274023 and 2012/0020537, which are incorporated by reference as if fully set forth herein.

Training

FIG. 138 shows one implementation of training 13800 the neural network-based quality scorer 13802 to process input data derived from the sequencing images 108 and directly produce quality indications. The neural network-based quality scorer 13802 is trained using a backpropagation-based gradient update technique that compares the predicted quality indications 13804 against the correct quality indications 13808 and computes an error 13806 based on the comparison. The error 13806 is then used to calculate gradients, which are applied to the weights and parameters of the neural network-based quality scorer 13802 during backward propagation 13810. The training 13800 is operationalized by the trainer 1510 using a stochastic gradient update algorithm such as ADAM.

The trainer 1510 uses training data 13812 (derived from the sequencing images 108) to train the neural network-based quality scorer 13802 over thousands and millions of iterations of the forward propagation 13816 that produces the predicted quality indications and the backward propagation 13810 that updates the weights and parameters based on the error 13806. In some implementations, the training data 13812 is supplemented with the quality predictor values 13814. Additional details about the training 13800 can be found in Appendix entitled "Deep Learning Tools".

Inference

FIG. 139 shows one implementation of directly producing quality indications as outputs of the neural network-based quality scorer 13802 during inference 13900. The inference 13900 includes hundreds, thousands, and/or millions of iterations of forward propagation 13908, including parallelization techniques such as batching. The inference 13900 is performed on inference data 13904 that includes the input data (with the image channels derived from the sequencing images 108 and/or the supplemental channels (e.g., the distance channels, the scaling channel)). In some implementations, the inference data 13904 is supplemented with the quality predictor values 13906. The inference 13900 is operationalized by a tester 13910.

Lossless Transformations

FIG. 140 depicts one implementation of using lossless transformation 1400 to generate transformed data 14004 that can be fed as input to the neural network-based template generator 1512, the neural network-based base caller 1514, and the neural network-based quality scorer 13802. Some examples of the lossless transformation 1400 include convolutions, deconvolutions, and Fourier transforms.

The lossless transformation 1400 can be applied by a lossless transformer 14002 that comprises a plurality of filters 1–n (e.g., convolution filters with convolution kernels). The lossless transformation 1400 can be applied on the input data 9500 and/or the input image data 1702 to produce the transformed data 14004.

The transformed data 14004 can be fed as input to the neural network-based template generator 1512 to produce the cluster metadata, to the neural network-based base caller 1514 to produce the base calls, and/or to the neural network-based quality scorer 13802 to produce the quality scores.

In some implementations, the transformed data 14004 is deconvolved by a deconvolution layer 14006 to reconstruct essential features of the input data 9500 and/or the input image data 1702. The deconvolution layer 14006 can be an initial layer of the neural network-based template generator 1512, the neural network-based base caller 1514, and/or the neural network-based quality scorer 13802.

End-to-End Integration with Intensity Modification

The discussion now turns to how the neural network-based template generator 1512 is integrated with the neural network-based base caller 1514 using intensity modification techniques.

In many of the base calling implementations discussed above, the input data 9500 that is fed as input to the neural network-based base caller 1514 comprises: (i) the image data 7902 (image channels) derived from the sequencing images 108, (ii) the supplemental distance data (distance channels) derived from the output 1714 of the neural network-based template generator 1512 (e.g., the decay map 1716, the ternary map 1718, or the binary map 1720), and (iii) the supplemental scaling data (scaling channel). In these implementations, intensity values in the image data 7902 are not modified, but rather supplemented with distance values that communicate the cluster shape information by conveying which pixels in the image data 7902 contain the cluster centers and which pixels in the image data 7902 are farther away from the cluster centers.

We now disclose base calling implementations that modify the image data 7902 to incorporate the cluster shape information, thus obviating the need of calculating and using the supplemental distance channels. The image data 7902 is modified based on the decay map 1716, the ternary map 1718, and the binary map 1720, which are in turn the output 1714 of the neural network-based template generator 1512. Thus, in this context, "integration" refers to modifying data processed by the neural network-based base caller 1514 based on information produced by the neural network-based template generator 1512 (e.g., the decay map 1716, the ternary map 1718, and the binary map 1720), as opposed to supplementing the former with the latter.

Both the decay and ternary maps contain the cluster shape information that identifies the subpixels as: (1) background subpixels, (2) cluster center subpixels, and (3) cluster or cluster interior subpixels belonging to a same cluster. The cluster shape information is included in the template image in the upsampled, subpixel domain to distinguish the cluster boundaries at a fine-grained level. However, the image data 7902, which contains the cluster and background intensities, is typically in the optical, pixel domain.

Though the template image and the image data 7902 are in different domains, they represent the same imaged area. The template image is derived from processing of the input image data 1702 for a certain number of initial sequencing cycles of a sequencing run and post-processing of the decay map 1716, the ternary map 1718, or the binary map 1720. In contrast, modifications for cluster shape information incorporation are not limited to the image data 7902 for the initial sequencing cycles, but instead applied to the image data 7902 for each sequencing cycle that is to be base called.

In some implementations though, when the cluster sizes are large enough, the output of the neural network-based base caller 1514, i.e., the decay map 1716, the ternary map 1718, and the binary map 1720 are in the optical, pixel domain. Accordingly, in such implementations, the template image is also in the optical, pixel domain.

So, consider, for example, that the sequencing run comprises 300 sequencing cycles that are to be base called. Then, the template image is derived from the processing the input image data 1702 for the first 2 to 7 sequencing cycles through the neural network-based template generator 1512 and post-processing of the decay map 1716, the ternary map 1718, or the binary map 1720 produced by the neural network-based template generator 1512 as output. Whereas the image data 7902 for each of the 300 sequencing cycles is modified for cluster shape information and then processed through the neural network-based base caller 1514 to produce a base call for each of the 300 sequencing cycles.

We disclose intensity modification techniques that incorporate the cluster shape information in the image data 7902 for base calling by the neural network-based base caller 1514. More details follow.

Area Weighting Factoring (AWF)

The first type of intensity modification techniques are area weighting factoring techniques in which the intensity modifications are applied to pixels in the image data 7902 in the optical, pixel domain.

Since the template image and the image data 7902 represent the same imaged area, there is many-to-one correspondence between subpixel blocks in the template image and respective pixels in the image data 7902. For example, the first block of 16 subpixels in the template image corresponds to the first pixel in the image data 7902, the second block of 16 subpixels in the template image corresponds to the second pixel in the image data 7902, and so on.

For a given cluster that is to be base called, we access its cluster shape information from the template image and identify which pixels in the image data 7902 contain parts of the given cluster, i.e., which pixels in the image data 7902 cover the given cluster or depict intensity emissions from the given cluster.

Then, for each identified pixel in the image data 7902, we determine how many subpixels in the template image that correspond to the identified pixel in the image data 7902 contain parts of the given cluster, i.e., how many subpixels in the template image that correspond to the identified pixel in the image data 7902 cover the given cluster or depict intensity emissions from the given cluster. Then, based on the determined subpixel count, we calculate and assign an area weighting factor (AWF) to each identified pixel in the image data 7902.

Factoring a Single Cluster Per Pixel

AWF for a single pixel i is calculated as follows:

$$AWF \text{ for pixel } i = \frac{\text{Number of subpixels in the template image that correspond to pixel } i \text{ and depict the given cluster}}{\text{Total number of subpixels that correspond to pixel } i}$$

The above AWF calculation excludes from the subpixel count: (i) background subpixels and (ii) subpixels containing parts of any other cluster (i.e., subpixels depicting clusters other than the given cluster). An example of this is illustrated in FIG. 143.

We then modify each identified pixel's intensity value based on its AWF. This yields a modified version of the image data 7902, which is processed by the neural network-based base caller 1514 to base call the given cluster.

Modified intensity value (MIV) of pixel i is calculated as follows:

MIV of pixel $i$=AWF for pixel $i$×optical intensity value of pixel $i$ (in the image data 7902)

FIG. 143 depicts one example of area weighting factoring 14300 for contribution from only a single cluster per pixel. In FIG. 143, intensities of pixels in sequencing image 14304 of the image data 7902 are modified. The sequencing image 14304 comprises four pixels with intensities 100, 140, 160, and 320, respectively.

Template image 14302 contains the cluster shape information for the sequencing image 14304. The template image 14302 includes four subpixel blocks respectively corresponding to the four pixels in the sequencing image 14304

(i.e., sixteen subpixels in the template image 14302 per pixel in the sequencing image 14304). The template image 14302 also identifies background subpixels and cluster subpixels for three clusters A, B, and C.

An AWF for each of the four pixels in the sequencing image 14304 is then calculated to account only for cluster A per pixel and stored as AWFs 14306 in the template image 14302. Note that the AWFs for the second and third pixels are $7/16$ and $8/16$, respectively. Even though the second pixel receives contributions from two clusters A and C, its AWF takes into account only the seven subpixels that cover cluster A (in red) and ignores the four subpixels that cover cluster C (in orange). Similarly, even though the third pixel receives contributions from two clusters A and B, its AWF takes into account only the eight subpixels that cover cluster A (in red) and ignores the four subpixels that cover cluster B (in green). Background subpixels are not counted.

The AWFs 14306 are further used to modify intensities of each of the four pixels and to produce a modified sequencing image 14308. The modified sequencing image 14308 is processed by the neural network-based base caller 1514 for base calling.

Factoring Multiple Clusters Per Pixel

In some implementations, we account for contributions from multiple clusters to a single pixel in the image data 7902. AWF for a single pixel i that receives contributions from multiple clusters is calculated as following:

$$AWF \text{ for pixel } i = \frac{\text{Number of subpixels in the template image that correspond to pixel } i \text{ and depict at least one cluster}}{\text{Total number of subpixels that correspond to pixel } i}$$

The above AWF calculation excludes background subpixels from the subpixel count, but includes in the subpixel count those subpixels that contain parts of other clusters (i.e., subpixels depicting clusters other than the given cluster). An example of this is illustrated in FIG. 144.

FIG. 144 depicts one example of area weighting factoring 14400 for contributions from multiple clusters per pixel. In FIG. 144, intensities of pixels in sequencing image 14404 of the image data 7902 are modified. The sequencing image 14404 comprises four pixels with intensities 100, 140, 160, and 320, respectively.

Template image 14402 contains the cluster shape information for the sequencing image 14404. The template image 14402 includes four subpixel blocks respectively corresponding to the four pixels in the sequencing image 14404 (i.e., sixteen subpixels in the template image 14302 per pixel in the sequencing image 14404). The template image 14402 also identifies background subpixels and cluster subpixels for three clusters A, B, and C.

An AWF for each of the four pixels in the sequencing image 14404 is then calculated to account for all the three clusters A, B, and C per pixel and stored as AWFs 14406 in the template image 14402. Note that the AWFs for the second and third pixels are $11/16$ and $12/16$, respectively. Since the second pixel receives contributions from two clusters A and C, its AWF takes into account the seven subpixels that cover cluster A (in red) and also the four subpixels that cover cluster C (in orange). Similarly, since the third pixel receives contributions from two clusters A and B, its AWF takes into account the eight subpixels that cover cluster A (in red) and also the four subpixels that cover cluster B (in green). Background subpixels are not counted.

The AWFs 14406 are further used to modify intensities of each of the four pixels and to produce a modified sequencing image 14408. The modified sequencing image 14408 is processed by the neural network-based base caller 1514 for base calling.

The area weighting factoring techniques described above can be used for base calling a single target cluster and also for simultaneously base calling multiple target clusters.

Upsampling and Background Masking

The second type of intensity modification techniques are upsampling and background masking techniques in which the image data 7902 is first upsampled to be in the same upsampled, subpixel domain as the template image and then the intensity modifications are applied to subpixels in the upsampled version of the image data 7902.

Since the template image and the image data 7902 represent the same imaged area, there is one-to-one correspondence between subpixels in the template image and respective subpixels in the upsampled version of the image data 7902. For example, the first subpixel in the template image corresponds to the first subpixel in the upsampled version of the image data 7902, the second subpixel in the template image corresponds to the second subpixel in the upsampled version of the image data 7902, and so on.

In some implementations though, when the cluster sizes are large enough, the output of the neural network-based base caller 1514, i.e., the decay map 1716, the ternary map 1718, and the binary map 1720 are in the optical, pixel domain. Accordingly, in such implementations, the template image is also in the optical, pixel domain.

Interpolation

Using the cluster shape information in the template image, we first identify, among the subpixels in the template image that blockwise correspond to the pixels in the image data 7902, which subpixels in the template image are background subpixels not contributing to/depicting intensity emissions from/covering any cluster and which are cluster subpixels contributing to/depicting intensity emissions from/covering at least one cluster.

We then use interpolation to upsample the image data 7902 in the upsampled, subpixel domain and produce the upsampled version of the image data 7902 such that (1) those subpixels in the upsampled version of the image data 7902 that respectively correspond to the identified background subpixels in the template image are assigned a same background intensity (e.g., a zero value or a near zero value) and (2) those subpixels in the upsampled version of the image data 7902 that respectively correspond to the identified cluster subpixels in the template image are assigned cluster intensities that are interpolated from the pixel intensities in the optical, pixel domain. An example of this is illustrated in FIG. 145.

FIG. 145 depicts one example of using interpolation for upsampling and background masking 14500. In FIG. 145, intensities of pixels in sequencing image 14504 of the image data 7902 are modified. The sequencing image 14504 comprises four pixels with intensities 160, 80, 320, and 200, respectively.

Template image 14502 contains the cluster shape information for the sequencing image 14504. The template image 14502 includes four subpixel blocks respectively corresponding to the four pixels in the sequencing image 14504 (i.e., sixteen subpixels in the template image 14502 per pixel in the sequencing image 14504). The template image 14502 also identifies background subpixels and cluster subpixels for three clusters A, B, and C.

Interpolation is used to upsample the sequencing image 14504 and to produce an upsampled sequencing image 14506 with subpixels. The interpolation assigns the background subpixels the background intensity and assigns the cluster subpixels the cluster intensities interpolated from the pixel intensities.

Subpixel Count Weighting

Here, the cluster intensities are calculated differently. That is, instead of interpolating the pixel intensities, each pixel's intensity in the optical, pixel domain is distributed equally among those cluster subpixels in the upsampled version of the image data 7902 that constitute the corresponding pixel. For each pixel, the count of its constituent cluster subpixels among which its intensity is equally distributed can be determined based on the area weighting factor (AWF) described above that takes into account contributions from multiple clusters. The background subpixels are assigned the background intensity, as discussed above. An example of this is illustrated in FIG. 146.

FIG. 146 depicts one example of using subpixel count weighting for upsampling and background masking 14600. In FIG. 146, intensities of pixels in sequencing image 14604 of the image data 7902 are modified. The sequencing image 14604 comprises four pixels with intensities 160, 80, 320, and 200, respectively.

Template image 14602 contains the cluster shape information for the sequencing image 14604. The template image 14602 includes four subpixel blocks respectively corresponding to the four pixels in the sequencing image 14604 (i.e., sixteen subpixels in the template image 14602 per pixel in the sequencing image 14604). The template image 14602 also identifies background subpixels and cluster subpixels for three clusters A, B, and C.

Subpixel count weighting is used to upsample the sequencing image 14604 and produce an upsampled sequencing image 14606 with subpixels. The subpixel count weighting assigns the background subpixels the background intensity and distributes each pixel's entire intensity to its constituent cluster subpixels. That is, the intensity allocation from the pixel to its constituent cluster subpixels utilizes all of the pixel's intensity, without wasting some of the pixel's intensity on no or minimal allocation to the background subpixels constituting the pixel. In some implementations, the pixel's intensity is equally distributed among its constituent cluster subpixels.

In other implementations, the upsampling is performed using at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage.

In some implementations, prior to the upsampling, the image data 7902 is aligned with the template image using cycle-specific and imaging channel-specific transformations.

The upsampled version of the image data 7902, containing the cluster intensities and the background intensity, is processed by the neural network-based base caller 1514 for base calling.

In other implementations, the values in the decay map, the binary map, and/or the ternary map are used to directly modulate the intensities of pixels in the image data 7902 or the intensities of subpixels in the upsampled version of the image data 7902.

Integration Workflow

Area Weighting Factoring

FIG. 141 illustrates one implementation of integrating the neural network-based template generator 1512 with the neural network-based base caller 1514 using area weighting factoring.

First, the neural network-based template generator 1512 processes the input image data 1702 for some initial sequencing cycles of a sequencing run and produces as output the decay map 1716, the ternary map 1718, or the binary map 1720. The input image data 1702 is in turn derived from the sequencing images 108, as described above with reference to FIG. 21b to FIG. 24. In one implementation, the input image data 1702 is in the upsampled, subpixel domain/resolution prior to being fed as input to the neural network-based template generator 1512. In another implementation, an upsampling layer of the neural network-based template generator 1512 upsamples the input image data 1702 to be in the upsampled, subpixel domain/resolution. The upsampling can be achieved by interpolation techniques such as bicubic interpolation.

From the output 1714 (the decay map 1716, the ternary map 1718, or the binary map 1720) of the neural network-based template generator 1512, the template image 14102 is derived through post-processing as discussed above. The template image 14202 contains the cluster metadata in the upsampled, subpixel domain/resolution. The cluster metadata 1812 identifies cluster centers, cluster shapes, cluster boundaries, and/or cluster background. "Template image" or "template" can refer to a data structure that contains or identifies the cluster metadata 1812 derived from the decay map 1716, the ternary map 1718, and/or the binary map 1718.

In some implementations though, when the cluster sizes are large enough, the output of the neural network-based base caller 1514, i.e., the decay map 1716, the ternary map 1718, and the binary map 1720 are in the optical, pixel domain. Accordingly, in such implementations, the template image 14202 is also in the optical, pixel domain.

Then, an area weighting factor determiner 14104 uses the template image 14102 to determine the area weighting factors and store them in the template image 14102, as discussed above.

Then, for each of the sequencing cycles of the sequencing run, the image data 7902 is modified by an intensity modifier 14106 based on the area weighting factors stored in the template image 14102. In other implementations, the area weighting factors can be stored elsewhere.

What results is intensity modified images 14108, which are processed by the neural network-based base caller 1514 to produce the base calls 14110. Note that the intensity modified images 14108 do not include any supplemental distance channels, but can include the supplemental scaling channel.

In other implementations, the intensity modification is performed only for a subset of the sequencing cycles of the sequencing run.

Upsampling and Background Masking

FIG. 142 illustrates another implementation of integrating the neural network-based template generator 1512 with the neural network-based base caller 1514 using upsampling and background masking.

First, the neural network-based template generator 1512 processes the input image data 1702 for some initial sequencing cycles of a sequencing run and produces as output the decay map 1716, the ternary map 1718, or the binary map 1720. The input image data 1702 is in turn derived from the sequencing images 108, as described above with reference to FIG. 21b to FIG. 24. In one implementation, the input image data 1702 is in the upsampled, subpixel domain/resolution prior to being fed as input to the neural network-based template generator 1512. In another implementation, an upsampling layer of the neural network-based template generator 1512 upsamples the input image data 1702 to be in the upsampled, subpixel domain/resolution. The upsampling can be achieved by interpolation techniques such as bicubic interpolation.

From the output (the decay map 1716, the ternary map 1718, or the binary map 1720) of the neural network-based template generator 1512, the template image 14202 is derived through post-processing as discussed above. The template image 14202 contains the cluster metadata in the upsampled, subpixel domain/resolution. The cluster metadata 1812 identifies cluster centers, cluster shapes, cluster boundaries, and/or cluster background. "Template image" or "template" can refer to a data structure that contains or identifies the cluster metadata 1812 derived from the decay map 1716, the ternary map 1718, and/or the binary map 1718.

In some implementations though, when the cluster sizes are large enough, the output of the neural network-based base caller 1514, i.e., the decay map 1716, the ternary map 1718, and the binary map 1720 are in the optical, pixel domain. Accordingly, in such implementations, the template image 14202 is also in the optical, pixel domain.

Then, an image integrator 14204 uses the template image 14202 to upsample the image data 7902 for each of the sequencing cycles of the sequencing run using interpolation or subpixel count weighting and to produce an upsampled version 14212 of the image data 7902 for each of the sequencing cycles of the sequencing run, as discussed above.

The upsampling is operationalized by an image upsampler 14208. In one implementation, the upsampled version 14212 of the image data 7902 is generated prior to being fed as input to the neural network-based base caller 1514. In another implementation, an upsampling layer the neural network-based base caller 1514 upsamples the image data 7902 and generates the upsampled version 14212 of the image data 7902. The upsampling can be achieved by interpolation techniques such as bicubic interpolation.

The image integrator 14204 also applies a background mask to the background subpixels in the upsampled version 14212 of the image data 7902 for each of the sequencing cycles of the sequencing run, as discussed above. The background masking is applied by a background masker 14210.

In some implementations, prior to the upsampling, the image integrator 14204 also aligns the image data 7902 for each of the sequencing cycles of the sequencing run with the template image 14202, as discussed above. The aligning is operationalized by an image aligner 14206.

Then, for each of the sequencing cycles of the sequencing run, the upsampled version 14212 of the image data 7902 is processed by the neural network-based base caller 1514 to produce the base calls 14214. Note that the upsampled version 14212 of the image data 7902 does not include any supplemental distance channels, but can include the supplemental scaling channel.

In other implementations, the upsampling and background masking is performed only for a subset of the sequencing cycles of the sequencing run.

End-to-End Integration without Intensity Modification, Instead Using Non-Distance Supplemental Channels The discussion now turns to how the neural network-based template generator 1512 is integrated with the neural network-based base caller 1514 without modifying intensity data of the sequencing images. The implementations discussed below provide new supplemental channels that are different than the supplemental distance channel discussed above. These new supplemental channels also convey the cluster shape information.

1. Decay Map, Ternary Map, Binary Map as Supplemental Channels

We now disclose base calling implementations that supplement the image data 7902 with the output 1714 of the neural network-based template generator 1512, i.e., the decay map 1716, the ternary map 1718, and the binary map 1720. Thus, in this context, "integration" refers to supplementing data processed by the neural network-based base caller 1514 with information produced by the neural network-based template generator 1512 (e.g., the decay map 1716, the ternary map 1718, and the binary map 1720).

The decay map 1716, the ternary map 1718, and the binary map 1720 are in the upsampled, subpixel domain; however, the image data 7902, which contains the cluster and background intensities, is typically in the optical, pixel domain.

In some implementations though, when the cluster sizes are large enough, the output of the neural network-based base caller 1514, i.e., the decay map 1716, the ternary map 1718, and the binary map 1720 are in the optical, pixel domain. Accordingly, in such implementations, the template image is also in the optical, pixel domain.

Upsampling the Input Image Data

When the decay map 1716, the ternary map 1718, and the binary map 1720 are in the upsampled, subpixel domain, in some implementations, the input image data 1702 is upsampled to be in the upsampled, subpixel domain. In one implementation, the upsampler 2302 uses interpolation (e.g., bicubic interpolation) to upsample the sequencing images 108 in the series of image sets 2100 by an upsampling factor (e.g., 4×) and the series of upsampled image sets 2300.

Then, the decay map 1716, the ternary map 1718, or the binary map 1720 are subpixel-wise supplemented with the input image data 1702 (also in the upsampled, subpixel domain) and fed as a supplemental channel to the neural network-based base caller 1514, along with the input image data 1702 (also in the upsampled, subpixel domain).

Downsampling the Decay Map, Ternary Map, Binary Man

In other implementations, when the decay map 1716, the ternary map 1718, and the binary map 1720 are produced in the upsampled, subpixel domain, they are downsampled to be in the optical, pixel domain. In one implementation, the downsampling can involve grouping subpixels based on a downsampling factor and taking an average of the output values of the grouped subpixels and assigning it to a corresponding pixel in the optical, pixel domain. The output values are weighted decay values in the case of the decay map 1716. The output values are three-way classification scores in the case of the ternary map 1718. The output values are two-way classification scores in the case of the binary map 1720. In another implementation, the downsampling can involve grouping subpixels based on belonging to a same cluster and taking an average of the output values of the grouped subpixels and assigning it to corresponding pixel(s) in the optical, pixel domain.

Then, the decay map 1716, the ternary map 1718, or the binary map 1720 in the optical, pixel domain are pixel-wise supplemented with the input image data 1702 (also in the optical, pixel domain) and fed as a supplemental channel to the neural network-based base caller 1514, along with the input image data 1702 (also in the optical, pixel domain).

2. Area Weighting Factors as Supplemental Channels

In one implementation, area weighting factors contained in the template image (e.g., 14306 and 14406) are calculated as described above, but instead of being used to modify the intensity values and generate modified sequencing images (e.g., 14308 and 14408), they themselves are provided as supplemental channels that accompany the unmodified, original sequencing images (e.g., 14304 and 14404). That is, since the area weighting factors contained in the template image (e.g., 14306 and 14406) are in the optical, pixel domain, they are pixel-wise supplemented with the unmodified input image data 1702 (also in the optical, pixel domain) and fed as a supplemental channel to the neural network-based base caller 1514, along with the unmodified input image data 1702 (also in the optical, pixel domain).

Thus, in this context, "integration" refers to supplementing data processed by the neural network-based base caller 1514 with information (e.g., area weighting factors) derived from the output of the neural network-based template generator 1512 (e.g., the decay map 1716, the ternary map 1718, and the binary map 1720).

Data Pre-Processing

In some implementations, the technology disclosed uses pre-processing techniques that apply to pixels in the image data 202 and produce pre-processed image data 202p. In such implementations, instead of the image data 202, the pre-processed image data 202p is provided as input to the neural network-based base caller 1514. The data pre-processing is operationalized by a data pre-processor 15002, which in turn can contain a data normalizer 15032 and a data augmenter 15034.

FIG. 150 shows different implementations of data pre-processing, which can include data normalization and data augmentation.

Data Normalization

In one implementation, data normalization is applied on pixels in the image data 202 on an image patch-by-image patch basis. This includes normalizing intensity values of pixels in an image patch such that a pixel intensity histogram of the resulting normalized image patch has a fifth percentile of zero and a ninety-fifth percentile of one. That is, in the normalized image patch, (i) 5% of the pixels have intensity values less than zero and (ii) another 5% of the pixels have intensity values greater than one. Respective image patches of the image data 202 can be normalized separately, or the image data 202 can be normalized all at once. What results is normalized image patches 15016, which are one example of the pre-processed image data 202p. The data normalization is operationalized by the data normalizer 15032.

Data Augmentation

In one implementation, data augmentation is applied on the intensity values of the pixels in the image data 202. This includes (i) multiplying the intensity values of all the pixels in the image data 202 with a same scaling factor and (ii) adding a same offset value to the scaled intensity values of all the pixels in the image data 202. For a single pixel, this can be expressed by the following formulation:

augmented pixel intensity(API)=$aX+b$ where a is the scaling factor, X is the original pixel intensity, b is the offset value, aX is the scaled pixel intensity What results is augmented image patches 15026, which are also one example of the pre-processed image data 202p. The data augmentation is operationalized by the data augmenter 15034.

FIG. 151 shows that the data normalization technique (DeepRTA (norm)) and the data augmentation technique (DeepRTA (augment)) of FIG. 150 reduce the base calling error percentage when the neural network-based base caller 1514 is trained on bacterial data and tested on human data, where the bacterial data and the human data share the same assay (e.g., both contain intronic data).

FIG. 152 shows that the data normalization technique (DeepRTA (norm)) and the data augmentation technique (DeepRTA (augment)) of FIG. 150 reduce the base calling error percentage when the neural network-based base caller 1514 is trained on non-exonic data (e.g., intronic data) and tested on exonic data.

In other words, the data normalization and the data augmentation techniques of FIG. 150 allow the neural network-based base caller 1514 to generalize better on data not seen in training and thus reduce overfitting.

In one implementation, the data augmentation is applied during both training and inference. In another implementation, the data augmentation is applied only during the training. In yet another implementation, the data augmentation is applied only during the inference.

FIGS. 147A and 147B depict one implementation of a sequencing system. The sequencing system comprises a configurable processor.

FIG. 147C is a simplified block diagram of a system for analysis of sensor data from the sequencing system, such as base call sensor outputs.

FIG. 148A is a simplified diagram showing aspects of the base calling operation, including functions of a runtime program executed by a host processor.

FIG. 148B is a simplified diagram of a configuration of a configurable processor such as the one depicted in FIG. 147C.

FIG. 149 is a computer system that can be used by the sequencing system of FIG. 147A to implement the technology disclosed herein.

Sequencing System

FIGS. 147A and 147B depict one implementation of a sequencing system 14700A. The sequencing system 14700A comprises a configurable processor 14746. The configurable processor 14746 implements the base calling techniques disclosed herein. The sequencing system is also referred to as a "sequencer."

The sequencing system 14700A can operate to obtain any information or data that relates to at least one of a biological or chemical substance. In some implementations, the sequencing system 14700A is a workstation that may be similar to a bench-top device or desktop computer. For example, a majority (or all) of the systems and components for conducting the desired reactions can be within a common housing 14702.

In particular implementations, the sequencing system 14700A is a nucleic acid sequencing system configured for various applications, including but not limited to de novo sequencing, resequencing of whole genomes or target genomic regions, and metagenomics. The sequencer may also be used for DNA or RNA analysis. In some implementations, the sequencing system 14700A may also be configured to generate reaction sites in a biosensor. For example, the sequencing system 14700A may be configured to receive a sample and generate surface attached clusters of clonally amplified nucleic acids derived from the sample. Each cluster may constitute or be part of a reaction site in the biosensor.

The exemplary sequencing system 14700A may include a system receptacle or interface 14710 that is configured to interact with a biosensor 14712 to perform desired reactions within the biosensor 14712. In the following description with respect to FIG. 147A, the biosensor 14712 is loaded into the system receptacle 14710. However, it is understood that a cartridge that includes the biosensor 14712 may be inserted into the system receptacle 14710 and in some states the cartridge can be removed temporarily or permanently. As described above, the cartridge may include, among other things, fluidic control and fluidic storage components.

In particular implementations, the sequencing system 14700A is configured to perform a large number of parallel reactions within the biosensor 14712. The biosensor 14712 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 14712 may include a solid-state imaging device (e.g., CCD or CMOS imager) and a flow cell mounted thereto. The flow cell may include one or more flow channels that receive a solution from the sequencing system 14700A and direct the solution toward the reaction sites. Optionally, the biosensor 14712 can be configured to engage a thermal element for transferring thermal energy into or out of the flow channel.

The sequencing system 14700A may include various components, assemblies, and systems (or sub-systems) that interact with each other to perform a predetermined method or assay protocol for biological or chemical analysis. For example, the sequencing system 14700A includes a system controller 14706 that may communicate with the various components, assemblies, and sub-systems of the sequencing system 14700A and also the biosensor 14712. For example, in addition to the system receptacle 14710, the sequencing system 14700A may also include a fluidic control system 14708 to control the flow of fluid throughout a fluid network of the sequencing system 14700A and the biosensor 14712; a fluid storage system 14714 that is configured to hold all fluids (e.g., gas or liquids) that may be used by the bioassay system; a temperature control system 14704 that may regulate the temperature of the fluid in the fluid network, the fluid storage system 14714, and/or the biosensor 14712; and an illumination system 14716 that is configured to illuminate the biosensor 14712. As described above, if a cartridge having the biosensor 14712 is loaded into the system receptacle 14710, the cartridge may also include fluidic control and fluidic storage components.

Also shown, the sequencing system 14700A may include a user interface 14718 that interacts with the user. For example, the user interface 14718 may include a display 14720 to display or request information from a user and a user input device 14722 to receive user inputs. In some implementations, the display 14720 and the user input device 14722 are the same device. For example, the user interface 14718 may include a touch-sensitive display configured to detect the presence of an individual's touch and also identify a location of the touch on the display. However, other user input devices 14722 may be used, such as a mouse, touchpad, keyboard, keypad, handheld scanner, voice-recognition system, motion-recognition system, and the like. As will be discussed in greater detail below, the sequencing system 14700A may communicate with various components, including the biosensor 14712 (e.g., in the form of a cartridge), to perform the desired reactions. The sequencing system 14700A may also be configured to analyze data obtained from the biosensor to provide a user with desired information.

The system controller 14706 may include any processor-based or microprocessor-based system, including systems using microcontrollers, reduced instruction set computers (RISC), application specific integrated circuits (ASICs), field programmable gate array (FPGAs), coarse-grained reconfigurable architectures (CGRAs), logic circuits, and any other circuit or processor capable of executing functions described herein. The above examples are exemplary only, and are thus not intended to limit in any way the definition and/or meaning of the term system controller. In the exemplary implementation, the system controller 14706 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the sequencing system 14700A.

The set of instructions may include various commands that instruct the sequencing system 14700A or biosensor 14712 to perform specific operations such as the methods and processes of the various implementations described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the sequencing system 14700A, processed in response to user inputs, or processed in response to a request made by another processing machine (e.g., a remote request through a communication link). In the illustrated implementation, the system controller 14706 includes an analysis module 14744. In other implementations, system controller 14706 does not include the analysis module 14744 and instead has access to the analysis module 14744 (e.g., the analysis module 14744 may be separately hosted on cloud).

The system controller 14706 may be connected to the biosensor 14712 and the other components of the sequencing system 14700A via communication links. The system controller 14706 may also be communicatively connected to off-site systems or servers. The communication links may be hardwired, corded, or wireless. The system controller 14706 may receive user inputs or commands, from the user interface 14718 and the user input device 14722.

The fluidic control system 14708 includes a fluid network and is configured to direct and regulate the flow of one or more fluids through the fluid network. The fluid network may be in fluid communication with the biosensor 14712 and the fluid storage system 14714. For example, select fluids may be drawn from the fluid storage system 14714 and directed to the biosensor 14712 in a controlled manner, or the fluids may be drawn from the biosensor 14712 and directed toward, for example, a waste reservoir in the fluid storage system 14714. Although not shown, the fluidic control system 14708 may include flow sensors that detect a flow rate or pressure of the fluids within the fluid network. The sensors may communicate with the system controller 14706.

The temperature control system 14704 is configured to regulate the temperature of fluids at different regions of the fluid network, the fluid storage system 14714, and/or the biosensor 14712. For example, the temperature control system 14704 may include a thermocycler that interfaces with the biosensor 14712 and controls the temperature of the fluid that flows along the reaction sites in the biosensor 14712. The temperature control system 14704 may also regulate the temperature of solid elements or components of the sequencing system 14700A or the biosensor 14712. Although not shown, the temperature control system 14704 may include sensors to detect the temperature of the fluid or other components. The sensors may communicate with the system controller 14706.

The fluid storage system 14714 is in fluid communication with the biosensor 14712 and may store various reaction components or reactants that are used to conduct the desired reactions therein. The fluid storage system 14714 may also store fluids for washing or cleaning the fluid network and biosensor 14712 and for diluting the reactants. For example, the fluid storage system 14714 may include various reservoirs to store samples, reagents, enzymes, other biomolecules, buffer solutions, aqueous, and non-polar solutions, and the like. Furthermore, the fluid storage system 14714 may also include waste reservoirs for receiving waste products from the biosensor 14712. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 14716 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 14716 may be configured to direct an excitation light to reaction sites. As one example, fluorophores may be excited by green wavelengths of light, as such the wavelength of the excitation light may be approximately 532 nm. In one implementation, the illumination system 14716 is configured to produce illumination that is parallel to a surface normal of a surface of the biosensor 14712. In another implementation, the illumination system 14716 is configured to produce illumination that is off-angle relative to the surface normal of the surface of the biosensor 14712. In yet another implementation, the illumination system 14716 is configured to produce illumination that has plural angles, including some parallel illumination and some off-angle illumination.

The system receptacle or interface 14710 is configured to engage the biosensor 14712 in at least one of a mechanical, electrical, and fluidic manner. The system receptacle 14710 may hold the biosensor 14712 in a desired orientation to facilitate the flow of fluid through the biosensor 14712. The system receptacle 14710 may also include electrical contacts that are configured to engage the biosensor 14712 so that the sequencing system 14700A may communicate with the biosensor 14712 and/or provide power to the biosensor 14712. Furthermore, the system receptacle 14710 may include fluidic ports (e.g., nozzles) that are configured to engage the biosensor 14712. In some implementations, the biosensor 14712 is removably coupled to the system receptacle 14710 in a mechanical manner, in an electrical manner, and also in a fluidic manner.

In addition, the sequencing system 14700A may communicate remotely with other systems or networks or with other bioassay systems 14700A. Detection data obtained by the bioassay system(s) 14700A may be stored in a remote database.

FIG. 147B is a block diagram of a system controller 14706 that can be used in the system of FIG. 147A. In one implementation, the system controller 14706 includes one or more processors or modules that can communicate with one another. Each of the processors or modules may include an algorithm (e.g., instructions stored on a tangible and/or non-transitory computer readable storage medium) or sub-algorithms to perform particular processes. The system controller 14706 is illustrated conceptually as a collection of modules, but may be implemented utilizing any combination of dedicated hardware boards, DSPs, processors, etc. Alternatively, the system controller 14706 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 14750 may transmit information (e.g., commands) to or receive information (e.g., data) from the biosensor 14712 (FIG. 147A) and/or the sub-systems 14708, 14714, 14704 (FIG. 147A). In implementations, the communication port 14750 may output a plurality of sequences of pixel signals. A communication link 14734 may receive user input from the user interface 14718 (FIG. 147A) and transmit data or information to the user interface 14718. Data from the biosensor 14712 or sub-systems 14708, 14714, 14704 may be processed by the system controller 14706 in real-time during a bioassay session. Additionally or alternatively, data may be stored temporarily in a system memory during a bioassay session and processed in slower than real-time or off-line operation.

As shown in FIG. 147B, the system controller 14706 may include a plurality of modules 14726-14748 that communicate with a main control module 14724, along with a central processing unit (CPU) 14752. The main control module 14724 may communicate with the user interface 14718

(FIG. 147A). Although the modules 14726-14748 are shown as communicating directly with the main control module 14724, the modules 14726-14748 may also communicate directly with each other, the user interface 14718, and the biosensor 14712. Also, the modules 14726-14748 may communicate with the main control module 14724 through the other modules.

The plurality of modules 14726-14748 include system modules 14728-14732, 14726 that communicate with the sub-systems 14708, 14714, 14704, and 14716, respectively. The fluidic control module 14728 may communicate with the fluidic control system 14708 to control the valves and flow sensors of the fluid network for controlling the flow of one or more fluids through the fluid network. The fluid storage module 14730 may notify the user when fluids are low or when the waste reservoir is at or near capacity. The fluid storage module 14730 may also communicate with the temperature control module 14732 so that the fluids may be stored at a desired temperature. The illumination module 14726 may communicate with the illumination system 14716 to illuminate the reaction sites at designated times during a protocol, such as after the desired reactions (e.g., binding events) have occurred. In some implementations, the illumination module 14726 may communicate with the illumination system 14716 to illuminate the reaction sites at designated angles.

The plurality of modules 14726-14748 may also include a device module 14736 that communicates with the biosensor 14712 and an identification module 14738 that determines identification information relating to the biosensor 14712. The device module 14736 may, for example, communicate with the system receptacle 14710 to confirm that the biosensor has established an electrical and fluidic connection with the sequencing system 14700A. The identification module 14738 may receive signals that identify the biosensor 14712. The identification module 14738 may use the identity of the biosensor 14712 to provide other information to the user. For example, the identification module 14738 may determine and then display a lot number, a date of manufacture, or a protocol that is recommended to be run with the biosensor 14712.

The plurality of modules 14726-14748 also includes an analysis module 14744 (also called signal processing module or signal processor) that receives and analyzes the signal data (e.g., image data) from the biosensor 14712. Analysis module 14744 includes memory (e.g., RAM or Flash) to store detection/image data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 14718 to display desired information to the user. In some implementations, the signal data may be processed by the solid-state imager (e.g., CMOS image sensor) before the analysis module 14744 receives the signal data The analysis module 14744 is configured to obtain image data from the light detectors at each of a plurality of sequencing cycles. The image data is derived from the emission signals detected by the light detectors and process the image data for each of the plurality of sequencing cycles through the neural network-based quality scorer 6102 and/or the neural network-based base caller 218 and produce a base call for at least some of the analytes at each of the plurality of sequencing cycle. The light detectors can be part of one or more over-head cameras (e.g., Illumina's GAIIx's CCD camera taking images of the clusters on the biosensor 14712 from the top), or can be part of the biosensor 14712 itself (e.g., Illumina's iSeq's CMOS image sensors underlying the clusters on the biosensor 14712 and taking images of the clusters from the bottom).

The output of the light detectors is the sequencing images, each depicting intensity emissions of the clusters and their surrounding background. The sequencing images depict intensity emissions generated as a result of nucleotide incorporation in the sequences during the sequencing. The intensity emissions are from associated analytes and their surrounding background. The sequencing images are stored in memory 14748.

Protocol modules 14740 and 14742 communicate with the main control module 14724 to control the operation of the sub-systems 14708, 14714, and 14704 when conducting predetermined assay protocols. The protocol modules 14740 and 14742 may include sets of instructions for instructing the sequencing system 14700A to perform specific operations pursuant to predetermined protocols. As shown, the protocol module may be a sequencing-by-synthesis (SBS) module 14740 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 14716 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (200147); WO 04/01147497; U.S. Pat. No. 7,057,026; WO 91/0667147; WO 07/123744; U.S. Pat. Nos. 7,329,492; 7,211,414; 7,315,019; 7,405,21471, and US 200147/0147014701472, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in US Pat. App. Ser. Nos. 61/53147,294 and 61/619,1477147, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 14742 that is configured to issue commands to the fluidic control system 14708 and the temperature control system 14704 for amplifying a product within the biosensor 14712. For example, the biosensor 14712 may be engaged to the sequencing system 14700A. The amplification module 14742 may issue instructions to the fluidic control system 14708 to deliver necessary amplification components to reaction chambers within the biosensor 14712. In other implementations, the reaction sites may already contain some components for amplification, such as the template DNA and/or primers. After delivering the amplification components to the reaction chambers, the amplification module 14742 may instruct the temperature control system 14704 to cycle through different temperature stages according to known amplification protocols. In some implementations, the amplification and/or nucleotide incorporation is performed isothermally.

The SBS module 14740 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 14740 may instruct the fluidic control system 14708 to direct a flow of reagent and enzyme solutions through the biosensor 14712. Exemplary reversible terminator-based SBS methods which can be utilized with the apparatus and methods set forth herein are described in US Patent Application Publication No. 2007/0166705 A1, US Patent Application Publication No. 2006/01147147901 A1, U.S. Pat. No. 7,057,026, US Patent Application Publication No. 2006/0240439 A1, US Patent Application Publication No. 2006/0214714714709 A1, PCT Publication No. WO 05/014914714, US Patent Application Publication No. 2005/014700900 A1, PCT Publication No. WO 06/0147B199 and PCT Publication No. WO 07/01470251, each of which is incorporated herein by reference in its entirety. Exemplary reagents for reversible terminator-based SBS are described in U.S. Pat. Nos. 7,541,444; 7,057,026; 7,414,14716; U.S. Pat. Nos. 7,427,673; 7,566,537; 7,592,435 and WO 07/141473536147, each of which is incorporated herein by reference in its entirety.

In some implementations, the amplification and SBS modules may operate in a single assay protocol where, for example, template nucleic acid is amplified and subsequently sequenced within the same cartridge.

The sequencing system 14700A may also allow the user to reconfigure an assay protocol. For example, the sequencing system 14700A may offer options to the user through the user interface 14718 for modifying the determined protocol. For example, if it is determined that the biosensor 14712 is to be used for amplification, the sequencing system 14700A may request a temperature for the annealing cycle. Furthermore, the sequencing system 14700A may issue warnings to a user if a user has provided user inputs that are generally not acceptable for the selected assay protocol.

In implementations, the biosensor 14712 includes millions of sensors (or pixels), each of which generates a plurality of sequences of pixel signals over successive base calling cycles. The analysis module 14744 detects the plurality of sequences of pixel signals and attributes them to corresponding sensors (or pixels) in accordance to the row-wise and/or column-wise location of the sensors on an array of sensors.

FIG. 147C is a simplified block diagram of a system for analysis of sensor data from the sequencing system 14700A, such as base call sensor outputs. In the example of FIG. 147C, the system includes the configurable processor 14746. The configurable processor 14746 can execute a base caller (e.g., the neural network-based quality scorer 6102 and/or the neural network-based base caller 218) in coordination with a runtime program executed by the central processing unit (CPU) 14752 (i.e., a host processor). The sequencing system 14700A comprises the biosensor 14712 and flow cells. The flow cells can comprise one or more tiles in which clusters of genetic material are exposed to a sequence of analyte flows used to cause reactions in the clusters to identify the bases in the genetic material. The sensors sense the reactions for each cycle of the sequence in each tile of the flow cell to provide tile data. Genetic sequencing is a data intensive operation, which translates base call sensor data into sequences of base calls for each cluster of genetic material sensed in during a base call operation.

The system in this example includes the CPU 14752, which executes a runtime program to coordinate the base call operations, memory 14748B to store sequences of arrays of tile data, base call reads produced by the base calling operation, and other information used in the base call operations. Also, in this illustration the system includes memory 14748A to store a configuration file (or files), such as FPGA bit files, and model parameters for the neural networks used to configure and reconfigure the configurable processor 14746, and execute the neural networks. The sequencing system 14700A can include a program for configuring a configurable processor and in some embodiments a reconfigurable processor to execute the neural networks.

The sequencing system 14700A is coupled by a bus 14789 to the configurable processor 14746. The bus 14789 can be implemented using a high throughput technology, such as in one example bus technology compatible with the PCIe standards (Peripheral Component Interconnect Express) currently maintained and developed by the PCI-SIG (PCI Special Interest Group). Also in this example, a memory 14748A is coupled to the configurable processor 14746 by bus 14793. The memory 14748A can be on-board memory, disposed on a circuit board with the configurable processor 14746. The memory 14748A is used for high speed access by the configurable processor 14746 of working data used in the base call operation. The bus 14793 can also be implemented using a high throughput technology, such as bus technology compatible with the PCIe standards.

Configurable processors, including field programmable gate arrays FPGAs, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor. The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include Google's Tensor Processing Unit (TPU)™, rackmount solutions like GX4 Rackmount Series™, GX9 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, Xilinx Alveo™ U200, Xilinx Alveo™ U250, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Embodiments described herein implement the neural network-based quality scorer 6102 and/or the neural network-based base caller 218 using the configurable processor 14746. The configuration file for the configurable processor 14746 can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor configurable processor 14746, in all embodiments described herein, therefore include a configured processor comprising an application specific ASIC or special purpose integrated circuit or set of integrated circuits, or a system-on-a-chip SOC device, or a graphics processing unit (GPU) processor or a coarse-grained reconfigurable architecture (CGRA) processor, configured to execute a neural network based base call operation as described herein.

In general, configurable processors and configured processors described herein, as configured to execute runs of a neural network, are referred to herein as neural network processors.

The configurable processor 14746 is configured in this example by a configuration file loaded using a program executed by the CPU 14752, or by other sources, which configures the array of configurable elements 14791 (e.g., configuration logic blocks (CLB) such as look up tables (LUTs), flip-flops, compute processing units (PMUs), and compute memory units (CMUs), configurable I/O blocks, programmable interconnects), on the configurable processor to execute the base call function. In this example, the configuration includes data flow logic 14797 which is coupled to the buses 14789 and 14793 and executes functions for distributing data and control parameters among the elements used in the base call operation.

Also, the configurable processor 14746 is configured with base call execution logic 14797 to execute the neural network-based quality scorer 6102 and/or the neural network-based base caller 218. The logic 14797 comprises multi-cycle execution clusters (e.g., 14779) which, in this example, includes execution cluster 1 through execution cluster X. The number of multi-cycle execution clusters can be selected according to a trade-off involving the desired throughput of the operation, and the available resources on the configurable processor 14746.

The multi-cycle execution clusters are coupled to the data flow logic 14797 by data flow paths 14799 implemented using configurable interconnect and memory resources on the configurable processor 14746. Also, the multi-cycle execution clusters are coupled to the data flow logic 14797 by control paths 14795 implemented using configurable interconnect and memory resources for example on the configurable processor 14746, which provide control signals indicating available execution clusters, readiness to provide input units for execution of a run of the neural network-based quality scorer 6102 and/or the neural network-based base caller 218 to the available execution clusters, readiness to provide trained parameters for the neural network-based quality scorer 6102 and/or the neural network-based base caller 218, readiness to provide output patches of base call classification data, and other control data used for execution of the neural network-based quality scorer 6102 and/or the neural network-based base caller 218.

The configurable processor 14746 is configured to execute runs of the neural network-based quality scorer 6102 and/or the neural network-based base caller 218 using trained parameters to produce classification data for the sensing cycles of the base calling operation. A run of the neural network-based quality scorer 6102 and/or the neural network-based base caller 218 is executed to produce classification data for a subject sensing cycle of the base calling operation. A run of the neural network-based quality scorer 6102 and/or the neural network-based base caller 218 operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 14797 is configured to move tile data and at least some trained parameters of the model parameters from the memory 14748A to the configurable processor 14746 for runs of the neural network-based quality scorer 6102 and/or the neural network-based base caller 218, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in embodiments of the base calling operation, the tile data can comprise information about alignment of the images with the clusters such as distance from center information indicating the distance of each pixel in the array of sensor data from the center of a cluster of genetic material on the tile.

During execution of the neural network-based quality scorer 6102 and/or the neural network-based base caller 218 as described below, tile data can also include data produced during execution of the neural network-based quality scorer 6102 and/or the neural network-based base caller 218, referred to as intermediate data, which can be reused rather than recomputed during a run of the neural network-based quality scorer 6102 and/or the neural network-based base caller 218. For example, during execution of the neural network-based quality scorer 6102 and/or the neural network-based base caller 218, the data flow logic 14797 can write intermediate data to the memory 14748A in place of the sensor data for a given patch of an array of tile data. Embodiments like this are described in more detail below.

As illustrated, a system is described for analysis of base call sensor output, comprising memory (e.g., 14748A) accessible by the runtime program storing tile data including sensor data for a tile from sensing cycles of a base calling operation. Also, the system includes a neural network processor, such as configurable processor 14746 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 14797 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution clusters in the plurality of execution clusters configured to execute a neural network. The data flow logic 14797 has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

FIG. 148A is a simplified diagram showing aspects of the base calling operation, including functions of a runtime program executed by a host processor. In this diagram, the output of image sensors from a flow cell are provided on lines 14800 to image processing threads 14801, which can perform processes on images such as alignment and arrangement in an array of sensor data for the individual tiles and resampling of images, and can be used by processes which calculate a tile cluster mask for each tile in the flow cell, which identifies pixels in the array of sensor data that correspond to clusters of genetic material on the corresponding tile of the flow cell. The outputs of the image processing threads 14801 are provided on lines 14806 to a dispatch logic 14810 in the CPU which routes the arrays of tile data to a data cache 14804 (e.g., SSD storage) on a high-speed bus 14807, or on high-speed bus 14805 to the neural network processor hardware 14820, such as the configurable processor 14746 of FIG. 147C, according to the state of the base calling operation. The processed and transformed images can be stored on the data cache 14804 for sensing cycles that were previously used. The hardware 14820 returns classification data output by the neural network to the dispatch logic 148148, which passes the information to the data cache 14804, or on lines 14811 to threads 14802 that perform base call and quality score computations using the classification data, and can arrange the data in standard formats for base call reads. The outputs of the threads 14802 that perform base calling and quality score computations are provided on lines 14812 to threads 14803 that aggregate the base call reads, perform other operations such as data compression, and write the resulting base call outputs to specified destinations for utilization by the customers.

In some embodiments, the host can include threads (not shown) that perform final processing of the output of the hardware 14820 in support of the neural network. For example, the hardware 14820 can provide outputs of classification data from a final layer of the multi-cluster neural network. The host processor can execute an output activation function, such as a softmax function, over the classification data to configure the data for use by the base call and quality score threads 14802. Also, the host processor can execute input operations (not shown), such as batch normalization of the tile data prior to input to the hardware 14820.

FIG. 148B is a simplified diagram of a configuration of a configurable processor 14746 such as that of FIG. 147C. In FIG. 148B, the configurable processor 14746 comprises an FPGA with a plurality of high speed PCIe interfaces. The FPGA is configured with a wrapper 14890 which comprises the data flow logic 14797 described with reference to FIG. 147C. The wrapper 14890 manages the interface and coordination with a runtime program in the CPU across the CPU communication link 14877 and manages communication with the on-board DRAM 14899 (e.g., memory 14748A) via DRAM communication link 14897. The data flow logic 14797 in the wrapper 14890 provides patch data retrieved by traversing the arrays of tile data on the on-board DRAM 14899 for the number N cycles to a cluster 14885, and retrieves process data 14887 from the cluster 14885 for delivery back to the on-board DRAM 14899. The wrapper 14890 also manages transfer of data between the on-board DRAM 14899 and host memory, for both the input arrays of tile data, and for the output patches of classification data. The wrapper transfers patch data on line 14883 to the allocated cluster 14885. The wrapper provides trained parameters, such as weights and biases on line 14881 to the cluster 14885 retrieved from the on-board DRAM 14899. The wrapper provides configuration and control data on line 14879 to the cluster 14885 provided from, or generated in response to, the runtime program on the host via the CPU communication link 14877. The cluster can also provide status signals on line 14889 to the wrapper 14890, which are used in cooperation with control signals from the host to manage traversal of the arrays of tile data to provide spatially aligned patch data, and to execute the multi-cycle neural network over the patch data using the resources of the cluster 14885.

As mentioned above, there can be multiple clusters on a single configurable processor managed by the wrapper 14890 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some embodiments. For example, the model trained parameters may be updated once every 20 cycles (or other number of cycles), or according to update patterns implemented for particular systems and neural network models. In some embodiments including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 14890. The wrapper 14890 can optionally do some pre-processing and transformation of the sensing data and write the information to the on-board DRAM 14899. The input tile data for each sensing cycle can include arrays of sensor data including on the order of 4000×3000 pixels per sensing cycle per tile or more, with two features representing colors of two images of the tile, and one or two bytes per feature per pixel. For an embodiment in which the number N is three sensing cycles to be used in each run of the multi-cycle neural network, the array of tile data for each run of the multi-cycle neural network can consume on the order of hundreds of megabytes per tile. In some embodiments of the system, the tile data also includes an array of DFC data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various embodiments.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 14899. When the processing of the entire tile has been completed, and the output patches of data transferred to the DRAM, the wrapper sends the processed output array for the tile back to the host/CPU in a specified format. In some embodiments, the on-board DRAM 14899 is managed by memory management logic in the wrapper 14890. The runtime program can control the sequencing operations to complete analysis of all the arrays of tile data for all the cycles in the run in a continuous flow to provide real time analysis.

Computer System

FIG. 149 is a computer system 14900 that can be used by the sequencing system 800A to implement the technology disclosed herein. Computer system 14900 includes at least one central processing unit (CPU) 14972 that communicates with a number of peripheral devices via bus subsystem 14955. These peripheral devices can include a storage subsystem 14910 including, for example, memory devices and a file storage subsystem 14936, user interface input devices 14938, user interface output devices 14976, and a network interface subsystem 14974. The input and output devices allow user interaction with computer system 14900. Network interface subsystem 14974 provides an interface to outside networks, including an interface to corresponding interface devices in other computer systems.

In one implementation, the system controller 7806 is communicably linked to the storage subsystem 14910 and the user interface input devices 14938.

User interface input devices 14938 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 14900.

User interface output devices 14976 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 14900 to the user or to another machine or computer system.

Storage subsystem 14910 stores programming and data constructs that provide the functionality of some or all of the modules and methods described herein. These software modules are generally executed by deep learning processors 14978.

Deep learning processors 14978 can be graphics processing units (GPUs), field-programmable gate arrays (FPGAs), application-specific integrated circuits (ASICs), and/or coarse-grained reconfigurable architectures (CGRAs). Deep learning processors 14978 can be hosted by a deep learning cloud platform such as Google Cloud Platform™, Xilinx™, and Cirrascale™. Examples of deep learning processors 14978 include Google's Tensor Processing Unit (TPU)™, rackmount solutions like GX4 Rackmount Series™, GX149 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™ Fujitsu DPI™, ARM's DynamicIQ™, IBM TrueNorth™, Lambda GPU Server with Testa V100s™, and others.

Memory subsystem 14922 used in the storage subsystem 14910 can include a number of memories including a main random access memory (RAM) 14932 for storage of instructions and data during program execution and a read only memory (ROM) 14934 in which fixed instructions are stored. A file storage subsystem 14936 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 14936 in the storage subsystem 14910, or in other machines accessible by the processor.

Bus subsystem 14955 provides a mechanism for letting the various components and subsystems of computer system 14900 communicate with each other as intended. Although bus subsystem 14955 is shown schematically as a single bus, alternative implementations of the bus subsystem can use multiple busses.

Computer system 14900 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 14900 depicted in FIG. 149 is intended only as a specific example for purposes of illustrating the preferred implementations of the present invention. Many other configurations of computer system 14900 are possible having more or less components than the computer system depicted in FIG. 149.

Sequencing Process

Implementations set forth herein may be applicable to analyzing nucleic acid sequences to identify sequence variations. Implementations may be used to analyze potential variants/alleles of a genetic position/locus and determine a genotype of the genetic locus or, in other words, provide a genotype call for the locus. By way of example, nucleic acid sequences may be analyzed in accordance with the methods and systems described in US Patent Application Publication No. 2016/0085910 and US Patent Application Publication No. 2013/0296175, the complete subject matter of which are expressly incorporated by reference herein in their entirety.

In one implementation, a sequencing process includes receiving a sample that includes or is suspected of including nucleic acids, such as DNA. The sample may be from a known or unknown source, such as an animal (e.g., human), plant, bacteria, or fungus. The sample may be taken directly from the source. For instance, blood or saliva may be taken directly from an individual. Alternatively, the sample may not be obtained directly from the source. Then, one or more processors direct the system to prepare the sample for sequencing. The preparation may include removing extraneous material and/or isolating certain material (e.g., DNA). The biological sample may be prepared to include features for a particular assay. For example, the biological sample may be prepared for sequencing-by-synthesis (SBS). In certain implementations, the preparing may include amplification of certain regions of a genome. For instance, the preparing may include amplifying predetermined genetic loci that are known to include STRs and/or SNPs. The genetic loci may be amplified using predetermined primer sequences.

Next, the one or more processors direct the system to sequence the sample. The sequencing may be performed through a variety of known sequencing protocols. In particular implementations, the sequencing includes SBS. In SBS, a plurality of fluorescently-labeled nucleotides are used to sequence a plurality of clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders.

The nucleic acids can be prepared such that they comprise a known primer sequence that is adjacent to an unknown target sequence. To initiate the first SBS sequencing cycle, one or more differently labeled nucleotides, and DNA polymerase, etc., can be flowed into/through the flow cell by a fluid flow subsystem. Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g., A, C, T, G). The nucleotides can include detectable label moieties such as fluorophores. Where the four nucleotides are mixed together, the polymerase is able to select the correct base to incorporate and each sequence is extended by a single base. Non-incorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection operations can be repeated several times to complete a sequencing run. Example sequencing methods are described, for example, in Bentley et al., Nature 456:53-59 (2008), International Publication No. WO 04/018497; U.S. Pat. No. 7,057,026; International Publication No. WO 91/06678; International Publication No. WO 07/123744; U.S. Pat. Nos. 7,329,492; 7,211,414; 7,315,019; 7,405,281, and U.S. Patent Application Publication No. 2008/0108082, each of which is incorporated herein by reference.

In some implementations, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; U.S. Patent Application Publication No. 2002/0055100; U.S. Pat. No. 7,115,400; U.S. Patent Application Publication No. 2004/0096853; U.S. Patent Application Publication No. 2004/0002090; U.S. Patent Application Publication No. 2007/0128624; and U.S. Patent Application Publication No. 2008/0009420, each of which is incorporated herein by reference in its entirety. Another useful method for amplifying nucleic acids on a surface is rolling circle amplification (RCA), for example, as described in Lizardi et al., Nat. Genet. 19:225-232 (1998) and U.S. Patent Application Publication No. 2007/0099208 A1, each of which is incorporated herein by reference.

One example SBS protocol exploits modified nucleotides having removable 3' blocks, for example, as described in International Publication No. WO 04/018497, U.S. Patent Application Publication No. 2007/0166705A1, and U.S. Pat. No. 7,057,026, each of which is incorporated herein by reference. For example, repeated cycles of SBS reagents can be delivered to a flow cell having target nucleic acids attached thereto, for example, as a result of the bridge amplification protocol. The nucleic acid clusters can be converted to single stranded form using a linearization solution. The linearization solution can contain, for example, a restriction endonuclease capable of cleaving one strand of each cluster. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example 'USER', as supplied by NEB, Ipswich, Mass., USA, part number M5505S), by exposure to heat or alkali, cleavage of ribonucleotides incorporated into amplification products otherwise comprised of deoxyribonucleotides, photochemical cleavage or cleavage of a peptide linker. After the linearization operation a sequencing primer can be delivered to the flow cell under conditions for hybridization of the sequencing primer to the target nucleic acids that are to be sequenced.

A flow cell can then be contacted with an SBS extension reagent having modified nucleotides with removable 3' blocks and fluorescent labels under conditions to extend a primer hybridized to each target nucleic acid by a single nucleotide addition. Only a single nucleotide is added to each primer because once the modified nucleotide has been incorporated into the growing polynucleotide chain complementary to the region of the template being sequenced there is no free 3'—OH group available to direct further sequence extension and therefore the polymerase cannot add further nucleotides. The SBS extension reagent can be removed and replaced with scan reagent containing components that protect the sample under excitation with radiation. Example components for scan reagent are described in U.S. Patent Application Publication No. 2008/0280773 A1 and U.S. patent application Ser. No. 13/018,255, each of which is incorporated herein by reference. The extended nucleic acids can then be fluorescently detected in the presence of scan reagent. Once the fluorescence has been detected, the 3' block may be removed using a deblock reagent that is appropriate to the blocking group used. Example deblock reagents that are useful for respective blocking groups are described in WO004018497, US 2007/0166705A1 and U.S. Pat. No. 7,057,026, each of which is incorporated herein by reference. The deblock reagent can be washed away leaving target nucleic acids hybridized to extended primers having 3'—OH groups that are now competent for addition of a further nucleotide. Accordingly the cycles of adding extension reagent, scan reagent, and deblock reagent, with optional washes between one or more of the operations, can be repeated until a desired sequence is obtained. The above cycles can be carried out using a single extension reagent delivery operation per cycle when each of the modified nucleotides has a different label attached thereto, known to correspond to the particular base. The different labels facilitate discrimination between the nucleotides added during each incorporation operation. Alternatively, each cycle can include separate operations of extension reagent delivery followed by separate operations of scan reagent delivery and detection, in which case two or more of the nucleotides can have the same label and can be distinguished based on the known order of delivery.

Although the sequencing operation has been discussed above with respect to a particular SBS protocol, it will be understood that other protocols for sequencing any of a variety of other molecular analyses can be carried out as desired.

Then, the one or more processors of the system receive the sequencing data for subsequent analysis. The sequencing data may be formatted in various manners, such as in a .BAM file. The sequencing data may include, for example, a number of sample reads. The sequencing data may include a plurality of sample reads that have corresponding sample sequences of the nucleotides. Although only one sample read is discussed, it should be understood that the sequencing data may include, for example, hundreds, thousands, hundreds of thousands, or millions of sample reads. Different sample reads may have different numbers of nucleotides. For example, a sample read may range between 10 nucleotides to about 500 nucleotides or more. The sample reads may span the entire genome of the source(s). As one example, the sample reads are directed toward predetermined genetic loci, such as those genetic loci having suspected STRs or suspected SNPs.

Each sample read may include a sequence of nucleotides, which may be referred to as a sample sequence, sample fragment or a target sequence. The sample sequence may include, for example, primer sequences, flanking sequences, and a target sequence. The number of nucleotides within the sample sequence may include 30, 40, 50, 60, 70, 80, 90, 100 or more. In some implementations, one or more the sample reads (or sample sequences) includes at least 150 nucleotides, 200 nucleotides, 300 nucleotides, 400 nucleotides, 500 nucleotides, or more. In some implementations, the sample reads may include more than 1000 nucleotides, 2000 nucleotides, or more. The sample reads (or the sample sequences) may include primer sequences at one or both ends.

Next, the one or more processors analyze the sequencing data to obtain potential variant call(s) and a sample variant frequency of the sample variant call(s). The operation may also be referred to as a variant call application or variant caller. Thus, the variant caller identifies or detects variants and the variant classifier classifies the detected variants as somatic or germline. Alternative variant callers may be utilized in accordance with implementations herein, wherein different variant callers may be used based on the type of sequencing operation being performed, based on features of the sample that are of interest and the like. One non-limiting example of a variant call application, such as the Pisces™ application by Illumina Inc. (San Diego, Calif.) hosted at https://github.com/Illumina/Pisces and described in the article Dunn, Tamsen & Berry, Gwenn & Emig-Agius, Dorothea & Jiang, Yu & Iyer, Anita & Udar, Nitin & Strömberg, Michael. (2017). Pisces: An Accurate and Versatile Single Sample Somatic and Germline Variant Caller. 595-595. 10.1145/3107411.3108203, the complete subject matter of which is expressly incorporated herein by reference in its entirety.

Such a variant call application can comprise four sequentially executed modules:

(1) Pisces Read Stitcher: Reduces noise by stitching paired reads in a BAM (read one and read two of the same molecule) into consensus reads. The output is a stitched BAM.

(2) Pisces Variant Caller: Calls small SNVs, insertions and deletions. Pisces includes a variant-collapsing algorithm to coalesce variants broken up by read boundaries, basic filtering algorithms, and a simple Poisson-based variant confidence-scoring algorithm. The output is a VCF.

(3) Pisces Variant Quality Recalibrator (VQR): In the event that the variant calls overwhelmingly follow a pattern associated with thermal damage or FFPE deamination, the VQR step will downgrade the variant Q score of the suspect variant calls. The output is an adjusted VCF.

(4) Pisces Variant Phaser (Scylla): Uses a read-backed greedy clustering method to assemble small variants into complex alleles from clonal subpopulations. This allows for the more accurate determination of functional consequence by downstream tools. The output is an adjusted VCF.

Additionally or alternatively, the operation may utilize the variant call application Strelka™ application by Illumina Inc. hosted at https://github.com/Illumina/strelka and described in the article T Saunders, Christopher & Wong, Wendy & Swamy, Sajani & Becq, Jennifer & J Murray, Lisa & Cheetham, Keira. (2012). Strelka: Accurate somatic small-variant calling from sequenced tumor-normal sample pairs. Bioinformatics (Oxford, England). 28. 1811-7. 10.1093/bioinformatics/bts271, the complete subject matter of which is expressly incorporated herein by reference in its entirety. Furthermore, additionally or alternatively, the operation may utilize the variant call application Strelka2™ application by Illumina Inc. hosted at https://github.com/Illumina/strelka and described in the article Kim, S., Scheffler, K., Halpern, A. L., Bekritsky, M. A., Noh, E., Kallberg, M., Chen, X., Beyter, D., Krusche, P., and Saunders, C. T. (2017). Strelka2: Fast and accurate variant calling for clinical sequencing applications, the complete subject matter of which is expressly incorporated herein by reference in its entirety. Moreover, additionally or alternatively, the operation may utilize a variant annotation/call tool, such as the Nirvana™ application by Illumina Inc. hosted at https://github.com/Illumina/Nirvana/wiki and described in the article Stromberg, Michael & Roy, Rajat & Lajugie, Julien & Jiang, Yu & Li, Haochen & Margulies, Elliott. (2017). Nirvana: Clinical Grade Variant Annotator. 596-596. 10.1145/3107411.3108204, the complete subject matter of which is expressly incorporated herein by reference in its entirety.

Such a variant annotation/call tool can apply different algorithmic techniques such as those disclosed in Nirvana:

a Identifying all overlapping transcripts with Interval Array: For functional annotation, we can identify all transcripts overlapping a variant and an interval tree can be used. However, since a set of intervals can be static, we were able to further optimize it to an Interval Array. An interval tree returns all overlapping transcripts in $O(min(n, k \lg n))$ time, where n is the number of intervals in the tree and k is the number of overlapping intervals. In practice, since k is really small compared to n for most variants, the effective runtime on interval tree would be $O(k \lg n)$. We improved to $O(\lg n+k)$ by creating an interval array where all intervals are stored in a sorted array so that we only need to find the first overlapping interval and then enumerate through the remaining (k−1).

b. CNVs/SVs (Yu): annotations for Copy Number Variation and Structural Variants can be provided. Similar to the annotation of small variants, transcripts overlapping with the SV and also previously reported structural variants can be annotated in online databases. Unlike the small variants, not all overlapping transcripts need be annotated, since too many transcripts will be overlapped with a large SVs. Instead, all overlapping transcripts can be annotated that belong to a partial overlapping gene. Specifically, for these transcripts, the impacted introns, exons and the consequences caused by the structural variants can be reported. An option to allow output all overlapping transcripts is available, but the basic information for these transcripts can be reported, such as gene symbol, flag whether it is canonical overlap or partial overlapped with the transcripts. For each SV/CNV, it is also of interest to know if these variants have been studied and their frequencies in different populations. Hence, we reported overlapping SVs in external databases, such as 1000 genomes, DGV and ClinGen. To avoid using an arbitrary cutoff to determine which SV is overlapped, instead all overlapping transcripts can be used and the reciprocal overlap can be calculated, i.e. the overlapping length divided by the minimum of the length of these two SVs.

c. Reporting supplementary annotations: Supplementary annotations are of two types: small and structural variants (SVs). SVs can be modeled as intervals and use the interval array discussed above to identify overlapping SVs. Small variants are modeled as points and matched by position and (optionally) allele. As such, they are searched using a binary-search-like algorithm. Since the supplementary annotation database can be quite large, a much smaller index is created to map chromosome positions to file locations where the supplementary annotation resides. The index is a sorted array of objects (made up of chromosome position and file location) that can be binary searched using position. To keep the index size small, multiple positions (up to a certain max count) are compressed to one object that stores the values for the first position and only deltas for subsequent positions. Since we use Binary search, the runtime is $O(\lg n)$, where n is the number of items in the database.

d. VEP cache files e. Transcript Database: The Transcript Cache (cache) and Supplementary database (SAdb) files are serialized dump of data objects such as transcripts and supplementary annotations. We use Ensembl VEP cache as our data source for cache. To create the cache, all transcripts are inserted in an interval array and the final state of the array is stored in the cache files. Thus, during annotation, we only need to load a pre-computed interval array and perform searches on it. Since the cache is loaded up in memory and searching is very fast (described above), finding overlapping transcripts is extremely quick in Nirvana (profiled to less than 1% of total runtime?).

f. Supplementary Database: The data sources for SAdb are listed under supplementary material. The SAdb for small variants is produced by a k-way merge of all data sources such that each object in the database (identified by reference name and position) holds all relevant supplementary annotations. Issues encountered during parsing data source files have been documented in detail in Nirvana's home page. To limit memory usage, only the SA index is loaded up in memory. This index allows a quick lookup of the file location for a supplementary annotation. However, since the data has to be fetched from disk, adding supplementary annotation has been identified as Nirvana's largest bottleneck (profiled at ~30% of total runtime.)

g. Consequence and Sequence Ontology: Nirvana's functional annotation (when provided) follows the Sequence Ontology (SO) (http://www.sequenceontology.org/) guidelines. On occasions, we had the opportunity to identify issues in the current SO and collaborate with the SO team to improve the state of annotation.

Such a variant annotation tool can include pre-processing. For example, Nirvana included a large number of annotations from External data sources, like ExAC, EVS, 1000 Genomes project, dbSNP, ClinVar, Cosmic, DGV and ClinGen. To make full use of these databases, we have to sanitize the information from them. We implemented different strategy to deal with different conflicts that exist from different data sources. For example, in case of multiple dbSNP entries for the same position and alternate allele, we join all ids into a comma separated list of ids; if there are multiple entries with different CAF values for the same allele, we use the first CAF value. For conflicting ExAC and EVS entries, we consider the number of sample counts and the entry with higher sample count is used. In 1000 Genome Projects, we removed the allele frequency of the conflicting allele. Another issue is inaccurate information. We mainly extracted the allele frequencies information from 1000 Genome Projects, however, we noticed that for GRCh38, the allele frequency reported in the info field did not exclude samples with genotype not available, leading to deflated frequencies for variants which are not available for all samples. To guarantee the accuracy of our annotation, we use all of the individual level genotype to compute the true allele frequencies. As we know, the same variants can have different representations based on different alignments. To make sure we can accurately report the information for already identified variants, we have to preprocess the variants from different resources to make them have consistent representation. For all external data sources, we trimmed alleles to remove duplicated nucleotides in both reference allele and alternative allele. For ClinVar, we directly parsed the xml file we performed a five-prime alignment for all variants, which is often used in vcf file. Different databases can contain the same set of information. To avoid unnecessary duplicates, we removed some duplicated information. For example, we removed variants in DGV which has data source as 1000 genome projects, since we already reported these variants in 1000 genomes with more detailed information.

In accordance with at least some implementations, the variant call application provides calls for low frequency variants, germline calling and the like. As non-limiting example, the variant call application may run on tumor-only samples and/or tumor-normal paired samples. The variant call application may search for single nucleotide variations (SNV), multiple nucleotide variations (MNV), indels and the like. The variant call application identifies variants, while filtering for mismatches due to sequencing or sample preparation errors. For each variant, the variant caller identifies the reference sequence, a position of the variant, and the potential variant sequence(s) (e.g., A to C SNV, or AG to A deletion). The variant call application identifies the sample sequence (or sample fragment), a reference sequence/fragment, and a variant call as an indication that a variant is present. The variant call application may identify raw fragments, and output a designation of the raw fragments, a count of the number of raw fragments that verify the potential variant call, the position within the raw fragment at which a supporting variant occurred and other relevant information. Non-limiting examples of raw fragments include a duplex stitched fragment, a simplex stitched fragment, a duplex un-stitched fragment and a simplex un-stitched fragment.

The variant call application may output the calls in various formats, such as in a .VCF or .GVCF file. By way of example only, the variant call application may be included in a MiSeqReporter pipeline (e.g., when implemented on the MiSeq® sequencer instrument). Optionally, the application may be implemented with various workflows. The analysis may include a single protocol or a combination of protocols that analyze the sample reads in a designated manner to obtain desired information.

Then, the one or more processors perform a validation operation in connection with the potential variant call. The validation operation may be based on a quality score, and/or a hierarchy of tiered tests, as explained hereafter. When the validation operation authenticates or verifies that the potential variant call, the validation operation passes the variant call information (from the variant call application) to the sample report generator. Alternatively, when the validation operation invalidates or disqualifies the potential variant call, the validation operation passes a corresponding indication (e.g., a negative indicator, a no call indicator, an in-valid call indicator) to the sample report generator. The validation operation also may pass a confidence score related to a degree of confidence that the variant call is correct or the in-valid call designation is correct.

Next, the one or more processors generate and store a sample report. The sample report may include, for example, information regarding a plurality of genetic loci with respect to the sample. For example, for each genetic locus of a predetermined set of genetic loci, the sample report may at least one of provide a genotype call; indicate that a genotype call cannot be made; provide a confidence score on a certainty of the genotype call; or indicate potential problems with an assay regarding one or more genetic loci. The sample report may also indicate a gender of an individual that provided a sample and/or indicate that the sample include multiple sources. As used herein, a "sample report" may include digital data (e.g., a data file) of a genetic locus or predetermined set of genetic locus and/or a printed report of the genetic locus or the set of genetic loci. Thus, generating or providing may include creating a data file and/or printing the sample report, or displaying the sample report.

The sample report may indicate that a variant call was determined, but was not validated. When a variant call is determined invalid, the sample report may indicate additional information regarding the basis for the determination to not validate the variant call. For example, the additional information in the report may include a description of the raw fragments and an extent (e.g., a count) to which the raw fragments support or contradicted the variant call. Additionally or alternatively, the additional information in the report may include the quality score obtained in accordance with implementations described herein.

Variant Call Application

Implementations disclosed herein include analyzing sequencing data to identify potential variant calls. Variant calling may be performed upon stored data for a previously performed sequencing operation. Additionally or alternatively, it may be performed in real time while a sequencing operation is being performed. Each of the sample reads is assigned to corresponding genetic loci. The sample reads may be assigned to corresponding genetic loci based on the sequence of the nucleotides of the sample read or, in other words, the order of nucleotides within the sample read (e.g., A, C, G, T). Based on this analysis, the sample read may be designated as including a possible variant/allele of a particular genetic locus. The sample read may be collected (or aggregated or binned) with other sample reads that have been designated as including possible variants/alleles of the genetic locus. The assigning operation may also be referred to as a calling operation in which the sample read is identified as being possibly associated with a particular genetic position/locus. The sample reads may be analyzed to locate one or more identifying sequences (e.g., primer sequences) of nucleotides that differentiate the sample read from other sample reads. More specifically, the identifying sequence(s) may identify the sample read from other sample reads as being associated with a particular genetic locus.

The assigning operation may include analyzing the series of n nucleotides of the identifying sequence to determine if the series of n nucleotides of the identifying sequence effectively matches with one or more of the select sequences. In particular implementations, the assigning operation may include analyzing the first n nucleotides of the sample sequence to determine if the first n nucleotides of the sample sequence effectively matches with one or more of the select sequences. The number n may have a variety of values, which may be programmed into the protocol or entered by a user. For example, the number n may be defined as the number of nucleotides of the shortest select sequence within the database. The number n may be a predetermined number. The predetermined number may be, for example, 10, 11, 12, 13, 14, 15, 16, 17, 18, 19, 20, 21, 22, 23, 24, 25, 26, 27, 28, 29, or 30 nucleotides. However, fewer or more nucleotides may be used in other implementations. The number n may also be selected by an individual, such as a user of the system. The number n may be based on one or more conditions. For instance, the number n may be defined as the number of nucleotides of the shortest primer sequence within the database or a designated number, whichever is the smaller number. In some implementations, a minimum value for n may be used, such as 15, such that any primer sequence that is less than 15 nucleotides may be designated as an exception.

In some cases, the series of n nucleotides of an identifying sequence may not precisely match the nucleotides of the select sequence. Nonetheless, the identifying sequence may effectively match the select sequence if the identifying sequence is nearly identical to the select sequence. For example, the sample read may be called for a genetic locus if the series of n nucleotides (e.g., the first n nucleotides) of the identifying sequence match a select sequence with no more than a designated number of mismatches (e.g., 3) and/or a designated number of shifts (e.g., 2). Rules may be established such that each mismatch or shift may count as a difference between the sample read and the primer sequence. If the number of differences is less than a designated number, then the sample read may be called for the corresponding genetic locus (i.e., assigned to the corresponding genetic locus). In some implementations, a matching score may be determined that is based on the number of differences between the identifying sequence of the sample read and the select sequence associated with a genetic locus. If the matching score passes a designated matching threshold, then the genetic locus that corresponds to the select sequence may be designated as a potential locus for the sample read. In some implementations, subsequent analysis may be performed to determine whether the sample read is called for the genetic locus.

If the sample read effectively matches one of the select sequences in the database (i.e., exactly matches or nearly matches as described above), then the sample read is assigned or designated to the genetic locus that correlates to the select sequence. This may be referred to as locus calling or provisional-locus calling, wherein the sample read is called for the genetic locus that correlates to the select sequence. However, as discussed above, a sample read may be called for more than one genetic locus. In such implementations, further analysis may be performed to call or assign the sample read for only one of the potential genetic loci. In some implementations, the sample read that is compared to the database of reference sequences is the first read from paired-end sequencing. When performing paired-end sequencing, a second read (representing a raw fragment) is obtained that correlates to the sample read. After assigning, the subsequent analysis that is performed with the assigned reads may be based on the type of genetic locus that has been called for the assigned read.

Next, the sample reads are analyzed to identify potential variant calls. Among other things, the results of the analysis identify the potential variant call, a sample variant frequency, a reference sequence and a position within the genomic sequence of interest at which the variant occurred. For example, if a genetic locus is known for including SNPs, then the assigned reads that have been called for the genetic locus may undergo analysis to identify the SNPs of the assigned reads. If the genetic locus is known for including polymorphic repetitive DNA elements, then the assigned reads may be analyzed to identify or characterize the polymorphic repetitive DNA elements within the sample reads. In some implementations, if an assigned read effectively matches with an STR locus and an SNP locus, a warning or flag may be assigned to the sample read. The sample read may be designated as both an STR locus and an SNP locus. The analyzing may include aligning the assigned reads in accordance with an alignment protocol to determine sequences and/or lengths of the assigned reads. The alignment protocol may include the method described in International Patent Application No. PCT/US2013/030867 (Publication No. WO 2014/142831), filed on Mar. 15, 2013, which is herein incorporated by reference in its entirety.

Then, the one or more processors analyze raw fragments to determine whether supporting variants exist at corresponding positions within the raw fragments. Various types of raw fragments may be identified. For example, the variant caller may identify a type of raw fragment that exhibits a variant that validates the original variant call. For example, the type of raw fragment may represent a duplex stitched fragment, a simplex stitched fragment, a duplex un-stitched fragment or a simplex un-stitched fragment. Optionally other raw fragments may be identified instead of or in addition to the foregoing examples. In connection with identifying each type of raw fragment, the variant caller also identifies the position, within the raw fragment, at which the supporting variant occurred, as well as a count of the number of raw fragments that exhibited the supporting variant. For example, the variant caller may output an indication that 10 reads of raw fragments were identified to represent duplex stitched fragments having a supporting variant at a particular position X. The variant caller may also output indication that five reads of raw fragments were identified to represent simplex un-stitched fragments having a supporting variant at a particular position Y. The variant caller may also output a number of raw fragments that corresponded to reference sequences and thus did not include a supporting variant that would otherwise provide evidence validating the potential variant call at the genomic sequence of interest.

Next, a count is maintained of the raw fragments that include supporting variants, as well as the position at which the supporting variant occurred. Additionally or alternatively, a count may be maintained of the raw fragments that did not include supporting variants at the position of interest (relative to the position of the potential variant call in the sample read or sample fragment). Additionally or alternatively, a count may be maintained of raw fragments that correspond to a reference sequence and do not authenticate or confirm the potential variant call. The information determined is output to the variant call validation application, including a count and type of the raw fragments that support the potential variant call, positions of the supporting variance in the raw fragments, a count of the raw fragments that do not support the potential variant call and the like.

When a potential variant call is identified, the process outputs an indicating of the potential variant call, the variant sequence, the variant position and a reference sequence associated therewith. The variant call is designated to represent a "potential" variant as errors may cause the call process to identify a false variant. In accordance with implementations herein, the potential variant call is analyzed to reduce and eliminate false variants or false positives. Additionally or alternatively, the process analyzes one or more raw fragments associated with a sample read and outputs a corresponding variant call associated with the raw fragments.

Technical Improvements and Terminology

Base calling includes incorporation or attachment of a fluorescently-labeled tag with an analyte. The analyte can be a nucleotide or an oligonucleotide, and the tag can be for a particular nucleotide type (A, C, T, or G). Excitation light is directed toward the analyte having the tag, and the tag emits a detectable fluorescent signal or intensity emission. The intensity emission is indicative of photons emitted by the excited tag that is chemically attached to the analyte.

Throughout this application, including the claims, when phrases such as or similar to "images, image data, or image regions depicting intensity emissions of analytes and their surrounding background" are used, they refer to the intensity emissions of the tags attached to the analytes. A person skilled in the art will appreciate that the intensity emissions of the attached tags are representative of or equivalent to the intensity emissions of the analytes to which the tags are attached, and are therefore used interchangeably. Similarly, properties of the analytes refer to properties of the tags attached to the analytes or of the intensity emissions from the attached tags. For example, a center of an analyte refers to the center of the intensity emissions emitted by a tag attached to the analyte. In another example, the surrounding background of an analyte refers to the surrounding background of the intensity emissions emitted by a tag attached to the analyte.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The technology disclosed uses neural networks to improve the quality and quantity of nucleic acid sequence information that can be obtained from a nucleic acid sample such as a nucleic acid template or its complement, for instance, a DNA or RNA polynucleotide or other nucleic acid sample. Accordingly, certain implementations of the technology disclosed provide higher throughput polynucleotide sequencing, for instance, higher rates of collection of DNA or RNA sequence data, greater efficiency in sequence data collection, and/or lower costs of obtaining such sequence data, relative to previously available methodologies.

The technology disclosed uses neural networks to identify the center of a solid-phase nucleic acid cluster and to analyze optical signals that are generated during sequencing of such clusters, to discriminate unambiguously between adjacent, abutting or overlapping clusters in order to assign a sequencing signal to a single, discrete source cluster. These and related implementations thus permit retrieval of meaningful information, such as sequence data, from regions of high-density cluster arrays where useful information could not previously be obtained from such regions due to confounding effects of overlapping or very closely spaced adjacent clusters, including the effects of overlapping signals (e.g., as used in nucleic acid sequencing) emanating therefrom.

As described in greater detail below, in certain implementations there is provided a composition that comprises a solid support having immobilized thereto one or a plurality of nucleic acid clusters as provided herein. Each cluster comprises a plurality of immobilized nucleic acids of the same sequence and has an identifiable center having a detectable center label as provided herein, by which the identifiable center is distinguishable from immobilized nucleic acids in a surrounding region in the cluster. Also described herein are methods for making and using such clusters that have identifiable centers.

The presently disclosed implementations will find uses in numerous situations where advantages are obtained from the ability to identify, determine, annotate, record or otherwise assign the position of a substantially central location within a cluster, such as high-throughput nucleic acid sequencing, development of image analysis algorithms for assigning optical or other signals to discrete source clusters, and other applications where recognition of the center of an immobilized nucleic acid cluster is desirable and beneficial.

In certain implementations, the present invention contemplates methods that relate to high-throughput nucleic acid analysis such as nucleic acid sequence determination (e.g., "sequencing"). Exemplary high-throughput nucleic acid analyses include without limitation de novo sequencing, re-sequencing, whole genome sequencing, gene expression analysis, gene expression monitoring, epigenetic analysis, genome methylation analysis, allele specific primer extension (APSE), genetic diversity profiling, whole genome polymorphism discovery and analysis, single nucleotide polymorphism analysis, hybridization based sequence determination methods, and the like. One skilled in the art will appreciate that a variety of different nucleic acids can be analyzed using the methods and compositions of the present invention.

Although the implementations of the present invention are described in relation to nucleic acid sequencing, they are applicable in any field where image data acquired at different time points, spatial locations or other temporal or physical perspectives is analyzed. For example, the methods and systems described herein are useful in the fields of molecular and cell biology where image data from microarrays, biological specimens, cells, organisms and the like is acquired and at different time points or perspectives and analyzed. Images can be obtained using any number of techniques known in the art including, but not limited to, fluorescence microscopy, light microscopy, confocal microscopy, optical imaging, magnetic resonance imaging, tomography scanning or the like. As another example, the methods and systems described herein can be applied where image data obtained by surveillance, aerial or satellite imaging technologies and the like is acquired at different time points or perspectives and analyzed. The methods and systems are particularly useful for analyzing images obtained for a field of view in which the analytes being viewed remain in the same locations relative to each other in the field of view. The analytes may however have characteristics that differ in separate images, for example, the analytes may appear different in separate images of the field of view. For example, the analytes may appear different with regard to the color of a given analyte detected in different images, a change in the intensity of signal detected for a given analyte in different images, or even the appearance of a signal for a given analyte in one image and disappearance of the signal for the analyte in another image.

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channel that delivers reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially alkaline/basic, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7.

In some examples, the reaction sites are provided or spaced apart in a predetermined manner, such as in a uniform or repeating pattern. In some other examples, the reaction sites are randomly distributed. Each of the reaction sites may be associated with one or more light guides and one or more light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, a designated reaction is a positive binding event, such as incorporation of a fluorescently labeled biomolecule with an analyte-of-interest, for example. More generally, a designated reaction may be a chemical transformation, chemical change, or chemical interaction. A designated reaction may also be a change in electrical properties. In particular examples, a designated reaction includes the incorporation of a fluorescently-labeled molecule with an analyte. The analyte may be an oligonucleotide and the fluorescently-labeled molecule may be a nucleotide. A designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Forster) resonance energy transfer (FRET), for example, by bringing a donor fluorophore in proximity to an acceptor fluorophore, decrease FRET by separating donor and acceptor fluorophores, increase fluorescence by separating a quencher from a fluorophore, or decrease fluorescence by co-locating a quencher and fluorophore.

As used herein, a "reaction solution," "reaction component" or "reactant" includes any substance that may be used to obtain at least one designated reaction. For example, potential reaction components include reagents, enzymes, samples, other biomolecules, and buffer solutions, for example. The reaction components may be delivered to a reaction site in a solution and/or immobilized at a reaction site. The reaction components may interact directly or indirectly with another substance, such as an analyte-of-interest immobilized at a reaction site. As noted above, the reaction solution may be substantially acidic (i.e., include a relatively high acidity) (e.g., comprising a pH of less than or equal to about 5, a pH less than or equal to about 4, or a pH less than or equal to about 3) or substantially alkaline/basic (i.e., include a relatively high alkalinity/basicity) (e.g., comprising a pH of greater than or equal to about 8, a pH of greater than or equal to about 9, or a pH of greater than or equal to about 10).

As used herein, the term "reaction site" is a localized region where at least one designated reaction may occur. A reaction site may include support surfaces of a reaction structure or substrate where a substance may be immobilized thereon. For example, a reaction site may include a surface of a reaction structure (which may be positioned in a channel of a flow cell) that has a reaction component thereon, such as a colony of nucleic acids thereon. In some such examples, the nucleic acids in the colony have the same sequence, being for example, clonal copies of a single stranded or double stranded template. However, in some examples a reaction site may contain only a single nucleic acid molecule, for example, in a single stranded or double stranded form.

A plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" or "reaction recess" includes a defined spatial region of the support structure (which is often in fluid communication with a flow channel). A reaction recess may be at least partially separated from the surrounding environment other or spatial regions. For example, a plurality of reaction recesses may be separated from each other by shared walls, such as a detection surface. As a more specific example, the reaction recesses may be nanowells comprising an indent, pit, well, groove, cavity or depression defined by interior surfaces of a detection surface and have an opening or aperture (i.e., be open-sided) so that the nanowells can be in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids or solutions that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include four types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

As used herein, the term "analyte" is intended to mean a point or area in a pattern that can be distinguished from other points or areas according to relative location. An individual analyte can include one or more molecules of a particular type. For example, an analyte can include a single target nucleic acid molecule having a particular sequence or an analyte can include several nucleic acid molecules having the same sequence (and/or complementary sequence, thereof). Different molecules that are at different analytes of a pattern can be differentiated from each other according to the locations of the analytes in the pattern. Example analytes include without limitation, wells in a substrate, beads (or other particles) in or on a substrate, projections from a substrate, ridges on a substrate, pads of gel material on a substrate, or channels in a substrate.

Any of a variety of target analytes that are to be detected, characterized, or identified can be used in an apparatus, system or method set forth herein. Exemplary analytes include, but are not limited to, nucleic acids (e.g., DNA, RNA or analogs thereof), proteins, polysaccharides, cells, antibodies, epitopes, receptors, ligands, enzymes (e.g. kinases, phosphatases or polymerases), small molecule drug candidates, cells, viruses, organisms, or the like.

The terms "analyte", "nucleic acid", "nucleic acid molecule", and "polynucleotide" are used interchangeably herein. In various implementations, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain implementations include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other implementations, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular implementations, a nucleic acid may have one or more detectable labels, as described elsewhere herein.

The terms "analyte", "cluster", "nucleic acid cluster", "nucleic acid colony", and "DNA cluster" are used interchangeably and refer to a plurality of copies of a nucleic acid template and/or complements thereof attached to a solid support. Typically and in certain preferred implementations, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

Colonies of nucleic acids can also be referred to as "nucleic acid clusters". Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. In a particular implementation, the diameter of a nucleic acid cluster is about 0.5 µm, about 1 µm, about 1.5 µm, about 2 µm, about 2.5 µm, about 3 µm, about 4 µm, about 5 µm, or about 6 µm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, $100,000/mm^2$ to $1,000,000/mm^2$ and $1,000,000/mm^2$ to $10,000,000/mm^2$.

As used herein, an "analyte" is an area of interest within a specimen or field of view. When used in connection with microarray devices or other molecular analytical devices, an analyte refers to the area occupied by similar or identical molecules. For example, an analyte can be an amplified oligonucleotide or any other group of a polynucleotide or polypeptide with a same or similar sequence. In other implementations, an analyte can be any element or group of elements that occupy a physical area on a specimen. For example, an analyte could be a parcel of land, a body of water or the like. When an analyte is imaged, each analyte will have some area. Thus, in many implementations, an analyte is not merely one pixel.

The distances between analytes can be described in any number of ways. In some implementations, the distances between analytes can be described from the center of one analyte to the center of another analyte. In other implementations, the distances can be described from the edge of one analyte to the edge of another analyte, or between the outer-most identifiable points of each analyte. The edge of an analyte can be described as the theoretical or actual physical boundary on a chip, or some point inside the boundary of the analyte. In other implementations, the distances can be described in relation to a fixed point on the specimen or in the image of the specimen.

Generally several implementations will be described herein with respect to a method of analysis. It will be understood that systems are also provided for carrying out the methods in an automated or semi-automated way. Accordingly, this disclosure provides neural network-based template generation and base calling systems, wherein the systems can include a processor; a storage device; and a program for image analysis, the program including instructions for carrying out one or more of the methods set forth herein. Accordingly, the methods set forth herein can be carried out on a computer, for example, having components set forth herein or otherwise known in the art.

The methods and systems set forth herein are useful for analyzing any of a variety of objects. Particularly useful objects are solid supports or solid-phase surfaces with attached analytes. The methods and systems set forth herein provide advantages when used with objects having a repeating pattern of analytes in an xy plane. An example is a microarray having an attached collection of cells, viruses, nucleic acids, proteins, antibodies, carbohydrates, small molecules (such as drug candidates), biologically active molecules or other analytes of interest.

An increasing number of applications have been developed for arrays with analytes having biological molecules such as nucleic acids and polypeptides. Such microarrays typically include deoxyribonucleic acid (DNA) or ribonucleic acid (RNA) probes. These are specific for nucleotide sequences present in humans and other organisms. In certain applications, for example, individual DNA or RNA probes can be attached at individual analytes of an array. A test sample, such as from a known person or organism, can be exposed to the array, such that target nucleic acids (e.g., gene fragments, mRNA, or amplicons thereof) hybridize to complementary probes at respective analytes in the array. The probes can be labeled in a target specific process (e.g., due to labels present on the target nucleic acids or due to enzymatic labeling of the probes or targets that are present in hybridized form at the analytes). The array can then be examined by scanning specific frequencies of light over the analytes to identify which target nucleic acids are present in the sample.

Biological microarrays may be used for genetic sequencing and similar applications. In general, genetic sequencing comprises determining the order of nucleotides in a length of target nucleic acid, such as a fragment of DNA or RNA. Relatively short sequences are typically sequenced at each analyte, and the resulting sequence information may be used in various bioinformatics methods to logically fit the sequence fragments together so as to reliably determine the sequence of much more extensive lengths of genetic material from which the fragments were derived. Automated, computer-based algorithms for characteristic fragments have been developed, and have been used more recently in genome mapping, identification of genes and their function, and so forth. Microarrays are particularly useful for characterizing genomic content because a large number of variants are present and this supplants the alternative of performing many experiments on individual probes and targets. The microarray is an ideal format for performing such investigations in a practical manner.

Any of a variety of analyte arrays (also referred to as "microarrays") known in the art can be used in a method or system set forth herein. A typical array contains analytes, each having an individual probe or a population of probes. In the latter case, the population of probes at each analyte is typically homogenous having a single species of probe. For example, in the case of a nucleic acid array, each analyte can have multiple nucleic acid molecules each having a common sequence. However, in some implementations the populations at each analyte of an array can be heterogeneous. Similarly, protein arrays can have analytes with a single protein or a population of proteins typically, but not always, having the same amino acid sequence. The probes can be attached to the surface of an array for example, via covalent linkage of the probes to the surface or via non-covalent interaction(s) of the probes with the surface. In some implementations, probes, such as nucleic acid molecules, can be attached to a surface via a gel layer as described, for example, in U.S. patent application Ser. No. 13/784,368 and US Pat. App. Pub. No. 2011/0059865 A1, each of which is incorporated herein by reference.

Example arrays include, without limitation, a BeadChip Array available from Illumina, Inc. (San Diego, Calif.) or others such as those where probes are attached to beads that are present on a surface (e.g. beads in wells on a surface) such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in a method or system according to some implementations of the present disclosure. An example spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; WO 91/06678; WO 07/123744; U.S. Pat. Nos. 7,329,492; 7,211,414; 7,315,019; 7,405,281, or 7,057,026; or US Pat.

App. Pub. No. 2008/0108082 A1, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US Pat. App. Pub. No. 2005/0130173 or US Pat. App. Pub. No. 2005/0064460, each of which is incorporated herein by reference in its entirety.

Arrays used for nucleic acid sequencing often have random spatial patterns of nucleic acid analytes. For example, HiSeq or MiSeq sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Example patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The analytes of such patterned arrays can be used to capture a single nucleic acid template molecule to seed subsequent formation of a homogenous colony, for example, via bridge amplification. Such patterned arrays are particularly useful for nucleic acid sequencing applications.

The size of an analyte on an array (or other object used in a method or system herein) can be selected to suit a particular application. For example, in some implementations, an analyte of an array can have a size that accommodates only a single nucleic acid molecule. A surface having a plurality of analytes in this size range is useful for constructing an array of molecules for detection at single molecule resolution. Analytes in this size range are also useful for use in arrays having analytes that each contain a colony of nucleic acid molecules. Thus, the analytes of an array can each have an area that is no larger than about 1 mm$^2$, no larger than about 500 µm$^2$, no larger than about 100 µm$^2$, no larger than about 10 µm$^2$, no larger than about 1 µm$^2$, no larger than about 500 nm$^2$, or no larger than about 100 nm$^2$, no larger than about 10 nm$^2$, no larger than about 5 nm$^2$, or no larger than about 1 nm$^2$. Alternatively or additionally, the analytes of an array will be no smaller than about 1 mm$^2$, no smaller than about 500 µm$^2$, no smaller than about 100 µm$^2$, no smaller than about 10 µm$^2$, no smaller than about 1 µm$^2$, no smaller than about 500 nm$^2$, no smaller than about 100 nm$^2$, no smaller than about 10 nm$^2$, no smaller than about 5 nm$^2$, or no smaller than about 1 nm$^2$. Indeed, an analyte can have a size that is in a range between an upper and lower limit selected from those exemplified above. Although several size ranges for analytes of a surface have been exemplified with respect to nucleic acids and on the scale of nucleic acids, it will be understood that analytes in these size ranges can be used for applications that do not include nucleic acids. It will be further understood that the size of the analytes need not necessarily be confined to a scale used for nucleic acid applications.

For implementations that include an object having a plurality of analytes, such as an array of analytes, the analytes can be discrete, being separated with spaces between each other. An array useful in the invention can have analytes that are separated by edge to edge distance of at most 100 µm, 50 µm, 10 µm, 5 µm, 1 µm, 0.5 µm, or less. Alternatively or additionally, an array can have analytes that are separated by an edge to edge distance of at least 0.5 µm, 1 µm, 5 µm, 10 µm, 50 µm, 100 µm, or more. These ranges can apply to the average edge to edge spacing for analytes as well as to the minimum or maximum spacing.

In some implementations the analytes of an array need not be discrete and instead neighboring analytes can abut each other. Whether or not the analytes are discrete, the size of the analytes and/or pitch of the analytes can vary such that arrays can have a desired density. For example, the average analyte pitch in a regular pattern can be at most 100 µm, 50 µm, 10 µm, 5 µm, 1 µm, 0.5 µm, or less. Alternatively or additionally, the average analyte pitch in a regular pattern can be at least 0.5 µm, 1 µm, 5 µm, 10 µm, 50 µm, 100 µm, or more. These ranges can apply to the maximum or minimum pitch for a regular pattern as well. For example, the maximum analyte pitch for a regular pattern can be at most 100 µm, 50 µm, 10 µm, 5 µm, 1 µm, 0.5 µm, or less; and/or the minimum analyte pitch in a regular pattern can be at least 0.5 µm, 1 µm, 5 µm, 10 µm, 50 µm, 100 µm, or more.

The density of analytes in an array can also be understood in terms of the number of analytes present per unit area. For example, the average density of analytes for an array can be at least about $1 \times 10^3$ analytes/mm$^2$, $1 \times 10^4$ analytes/mm$^2$, $1 \times 10^5$ analytes/mm$^2$, $1 \times 10^6$ analytes/mm$^2$, $1 \times 10^7$ analytes/mm$^2$, $1 \times 10^8$ analytes/mm$^2$, or $1 \times 10^9$ analytes/mm$^2$, or higher. Alternatively or additionally the average density of analytes for an array can be at most about $1 \times 10^9$ analytes/mm$^2$, $1 \times 10^8$ analytes/mm$^2$, $1 \times 10^7$ analytes/mm$^2$, $1 \times 10^6$ analytes/mm$^2$, $1 \times 10^5$ analytes/mm$^2$, $1 \times 10^4$ analytes/mm$^2$, or $1 \times 10^3$ analytes/mm$^2$, or less.

The above ranges can apply to all or part of a regular pattern including, for example, all or part of an array of analytes.

The analytes in a pattern can have any of a variety of shapes. For example, when observed in a two dimensional plane, such as on the surface of an array, the analytes can appear rounded, circular, oval, rectangular, square, symmetric, asymmetric, triangular, polygonal, or the like. The analytes can be arranged in a regular repeating pattern including, for example, a hexagonal or rectilinear pattern. A pattern can be selected to achieve a desired level of packing. For example, round analytes are optimally packed in a hexagonal arrangement. Of course other packing arrangements can also be used for round analytes and vice versa.

A pattern can be characterized in terms of the number of analytes that are present in a subset that forms the smallest geometric unit of the pattern. The subset can include, for example, at least about 2, 3, 4, 5, 6, 10 or more analytes. Depending upon the size and density of the analytes the geometric unit can occupy an area of less than 1 mm$^2$, 500 µm$^2$, 100 µm$^2$, 50 µm$^2$, 10 µm$^2$, 1 µm$^2$, 500 nm$^2$, 100 nm$^2$, 50 nm$^2$, 10 nm$^2$, or less. Alternatively or additionally, the geometric unit can occupy an area of greater than 10 nm$^2$, 50 nm$^2$, 100 nm$^2$, 500 nm$^2$, 1 µm$^2$, 10 µm$^2$, 50 µm$^2$, 100 µm$^2$, 500 µm$^2$, 1 mm$^2$, or more. Characteristics of the analytes in a geometric unit, such as shape, size, pitch and the like, can be selected from those set forth herein more generally with regard to analytes in an array or pattern.

An array having a regular pattern of analytes can be ordered with respect to the relative locations of the analytes but random with respect to one or more other characteristic of each analyte. For example, in the case of a nucleic acid array, the nuclei acid analytes can be ordered with respect to their relative locations but random with respect to one's knowledge of the sequence for the nucleic acid species present at any particular analyte. As a more specific example, nucleic acid arrays formed by seeding a repeating pattern of analytes with template nucleic acids and amplifying the template at each analyte to form copies of the template at the analyte (e.g., via cluster amplification or bridge amplification) will have a regular pattern of nucleic acid analytes but will be random with regard to the distribution of sequences of the nucleic acids across the array. Thus, detection of the presence of nucleic acid material generally on the array can yield a repeating pattern of analytes, whereas sequence specific detection can yield non-repeating distribution of signals across the array.

It will be understood that the description herein of patterns, order, randomness and the like pertain not only to analytes on objects, such as analytes on arrays, but also to analytes in images. As such, patterns, order, randomness and the like can be present in any of a variety of formats that are used to store, manipulate or communicate image data including, but not limited to, a computer readable medium or computer component such as a graphical user interface or other output device.

As used herein, the term "image" is intended to mean a representation of all or part of an object. The representation can be an optically detected reproduction. For example, an image can be obtained from fluorescent, luminescent, scatter, or absorption signals. The part of the object that is present in an image can be the surface or other xy plane of the object. Typically, an image is a 2 dimensional representation, but in some cases information in the image can be derived from 3 or more dimensions. An image need not include optically detected signals. Non-optical signals can be present instead. An image can be provided in a computer readable format or medium such as one or more of those set forth elsewhere herein.

As used herein, "image" refers to a reproduction or representation of at least a portion of a specimen or other object. In some implementations, the reproduction is an optical reproduction, for example, produced by a camera or other optical detector. The reproduction can be a non-optical reproduction, for example, a representation of electrical signals obtained from an array of nanopore analytes or a representation of electrical signals obtained from an ion-sensitive CMOS detector. In particular implementations non-optical reproductions can be excluded from a method or apparatus set forth herein. An image can have a resolution capable of distinguishing analytes of a specimen that are present at any of a variety of spacings including, for example, those that are separated by less than 100 μm, 50 μm, 10 μm, 5 μm, 1 μm or 0.5 μm.

As used herein, "acquiring", "acquisition" and like terms refer to any part of the process of obtaining an image file. In some implementations, data acquisition can include generating an image of a specimen, looking for a signal in a specimen, instructing a detection device to look for or generate an image of a signal, giving instructions for further analysis or transformation of an image file, and any number of transformations or manipulations of an image file.

As used herein, the term "template" refers to a representation of the location or relation between signals or analytes. Thus, in some implementations, a template is a physical grid with a representation of signals corresponding to analytes in a specimen. In some implementations, a template can be a chart, table, text file or other computer file indicative of locations corresponding to analytes. In implementations presented herein, a template is generated in order to track the location of analytes of a specimen across a set of images of the specimen captured at different reference points. For example, a template could be a set of x,y coordinates or a set of values that describe the direction and/or distance of one analyte with respect to another analyte.

As used herein, the term "specimen" can refer to an object or area of an object of which an image is captured. For example, in implementations where images are taken of the surface of the earth, a parcel of land can be a specimen. In other implementations where the analysis of biological molecules is performed in a flow cell, the flow cell may be divided into any number of subdivisions, each of which may be a specimen. For example, a flow cell may be divided into various flow channels or lanes, and each lane can be further divided into 2, 3, 4, 5, 6, 7, 8, 9, 10, 20, 30, 40, 50, 60 70, 80, 90, 100, 110, 120, 140, 160, 180, 200, 400, 600, 800, 1000 or more separate regions that are imaged. One example of a flow cell has 8 lanes, with each lane divided into 120 specimens or tiles. In another implementation, a specimen may be made up of a plurality of tiles or even an entire flow cell. Thus, the image of each specimen can represent a region of a larger surface that is imaged.

It will be appreciated that references to ranges and sequential number lists described herein include not only the enumerated number but all real numbers between the enumerated numbers.

As used herein, a "reference point" refers to any temporal or physical distinction between images. In a preferred implementation, a reference point is a time point. In a more preferred implementation, a reference point is a time point or cycle during a sequencing reaction. However, the term "reference point" can include other aspects that distinguish or separate images, such as angle, rotational, temporal, or other aspects that can distinguish or separate images.

As used herein, a "subset of images" refers to a group of images within a set. For example, a subset may contain 1, 2, 3, 4, 6, 8, 10, 12, 14, 16, 18, 20, 30, 40, 50, 60 or any number of images selected from a set of images. In particular implementations, a subset may contain no more than 1, 2, 3, 4, 6, 8, 10, 12, 14, 16, 18, 20, 30, 40, 50, 60 or any number of images selected from a set of images. In a preferred implementation, images are obtained from one or more sequencing cycles with four images correlated to each cycle. Thus, for example, a subset could be a group of 16 images obtained through four cycles.

A base refers to a nucleotide base or nucleotide, A (adenine), C (cytosine), T (thymine), or G (guanine). This application uses "base(s)" and "nucleotide(s)" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects. The application uses "read(s)" and "sequence read(s)" interchangeably.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual. In other implementations, the "genome" also covers so-called "graph genomes", which use a particular storage format and representation of the genome sequence. In one implementation, graph genomes store data in a linear file. In another implementation, the graph genomes refer to a representation where alternative sequences (e.g., different copies of a chromosome with small differences) are stored as different paths in a graph. Additional information regarding graph genome implementations can be found in https://www.biorxiv.org/content/biorxiv/early/2018/03/20/194530.full.pdf, the content of which is hereby incorporated herein by reference in its entirety.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, the DNA sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "×") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105× with 98% of targeted bases covered >100×.

The terms "base call quality score" or "Q score" refer to a PHRED-scaled probability ranging from 0-50 inversely proportional to the probability that a single sequenced base is correct. For example, a T base call with Q of 20 is considered likely correct with a probability of 99.99%. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Regarding "strandedness" (or DNA strandedness), the genetic message in DNA can be represented as a string of the letters A, G, C, and T. For example, 5'-AGGACA-3'. Often, the sequence is written in the direction shown here, i.e., with the 5' end to the left and the 3' end to the right. DNA may sometimes occur as single-stranded molecule (as in certain viruses), but normally we find DNA as a double-stranded unit. It has a double helical structure with two antiparallel strands. In this case, the word "antiparallel" means that the two strands run in parallel, but have opposite polarity. The double-stranded DNA is held together by pairing between bases and the pairing is always such that adenine (A) pairs with thymine (T) and cytosine (C) pairs with guanine (G). This pairing is referred to as complementarity, and one strand of DNA is said to be the complement of the other. The double-stranded DNA may thus be represented as two strings, like this: 5'-AGGACA-3' and 3'-TCCTGT-5'. Note that the two strands have opposite polarity. Accordingly, the strandedness of the two DNA strands can be referred to as the reference strand and its complement, forward and reverse strands, top and bottom strands, sense and antisense strands, or Watson and Crick strands.

The reads alignment (also called reads mapping) is the process of figuring out where in the genome a sequence is from. Once the alignment is performed, the "mapping quality" or the "mapping quality score (MAPQ)" of a given read quantifies the probability that its position on the genome is correct. The mapping quality is encoded in the phred scale where P is the probability that the alignment is not correct. The probability is calculated as: $P=10^{(-MAPQ/10)}$, where MAPQ is the mapping quality. For example, a mapping quality of 40=10 to the power of −4, meaning that there is a 0.01% chance that the read was aligned incorrectly. The mapping quality is therefore associated with several alignment factors, such as the base quality of the read, the complexity of the reference genome, and the paired-end information. Regarding the first, if the base quality of the read is low, it means that the observed sequence might be wrong and thus its alignment is wrong. Regarding the second, the mappability refers to the complexity of the genome. Repeated regions are more difficult to map and reads falling in these regions usually get low mapping quality. In this context, the MAPQ reflects the fact that the reads are not uniquely aligned and that their real origin cannot be determined. Regarding the third, in case of paired-end sequencing data, concordant pairs are more likely to be well aligned. The higher is the mapping quality, the better is the alignment. A read aligned with a good mapping quality usually means that the read sequence was good and was aligned with few mismatches in a high mappability region. The MAPQ value can be used as a quality control of the alignment results. The proportion of reads aligned with an MAPQ higher than 20 is usually for downstream analysis.

As used herein, a "signal" refers to a detectable event such as an emission, preferably light emission, for example, in an image. Thus, in preferred implementations, a signal can represent any detectable light emission that is captured in an image (i.e., a "spot"). Thus, as used herein, "signal" can refer to both an actual emission from an analyte of the specimen, and can refer to a spurious emission that does not correlate to an actual analyte. Thus, a signal could arise from noise and could be later discarded as not representative of an actual analyte of a specimen.

As used herein, the term "clump" refers to a group of signals. In particular implementations, the signals are derived from different analytes. In a preferred implementation, a signal clump is a group of signals that cluster together. In a more preferred implementation, a signal clump represents a physical region covered by one amplified oligonucleotide. Each signal clump should be ideally observed as several signals (one per template cycle, and possibly more due to cross-talk). Accordingly, duplicate signals are detected where two (or more) signals are included in a template from the same clump of signals.

As used herein, terms such as "minimum," "maximum," "minimize," "maximize" and grammatical variants thereof can include values that are not the absolute maxima or minima. In some implementations, the values include near maximum and near minimum values. In other implementations, the values can include local maximum and/or local minimum values. In some implementations, the values include only absolute maximum or minimum values.

As used herein, "cross-talk" refers to the detection of signals in one image that are also detected in a separate image. In a preferred implementation, cross-talk can occur when an emitted signal is detected in two separate detection channels. For example, where an emitted signal occurs in one color, the emission spectrum of that signal may overlap with another emitted signal in another color. In a preferred implementation, fluorescent molecules used to indicate the presence of nucleotide bases A, C, G and T are detected in separate channels. However, because the emission spectra of A and C overlap, some of the C color signal may be detected during detection using the A color channel. Accordingly, cross-talk between the A and C signals allows signals from one color image to appear in the other color image. In some implementations, G and T cross-talk. In some implementations, the amount of cross-talk between channels is asymmetric. It will be appreciated that the amount of cross-talk between channels can be controlled by, among other things, the selection of signal molecules having an appropriate emission spectrum as well as selection of the size and wavelength range of the detection channel.

As used herein, "register", "registering", "registration" and like terms refer to any process to correlate signals in an image or data set from a first time point or perspective with signals in an image or data set from another time point or perspective. For example, registration can be used to align signals from a set of images to form a template. In another example, registration can be used to align signals from other images to a template. One signal may be directly or indirectly registered to another signal. For example, a signal from image "S" may be registered to image "G" directly. As another example, a signal from image "N" may be directly registered to image "G", or alternatively, the signal from image "N" may be registered to image "5", which has previously been registered to image "G". Thus, the signal from image "N" is indirectly registered to image "G".

As used herein, the term "fiducial" is intended to mean a distinguishable point of reference in or on an object. The point of reference can be, for example, a mark, second object, shape, edge, area, irregularity, channel, pit, post or the like. The point of reference can be present in an image of the object or in another data set derived from detecting the object. The point of reference can be specified by an x and/or y coordinate in a plane of the object. Alternatively or additionally, the point of reference can be specified by a z coordinate that is orthogonal to the xy plane, for example, being defined by the relative locations of the object and a detector. One or more coordinates for a point of reference can be specified relative to one or more other analytes of an object or of an image or other data set derived from the object.

As used herein, the term "optical signal" is intended to include, for example, fluorescent, luminescent, scatter, or absorption signals. Optical signals can be detected in the ultraviolet (UV) range (about 200 to 390 nm), visible (VIS) range (about 391 to 770 nm), infrared (IR) range (about 0.771 to 25 microns), or other range of the electromagnetic spectrum. Optical signals can be detected in a way that excludes all or part of one or more of these ranges.

As used herein, the term "signal level" is intended to mean an amount or quantity of detected energy or coded information that has a desired or predefined characteristic. For example, an optical signal can be quantified by one or more of intensity, wavelength, energy, frequency, power, luminance or the like. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

As used herein, the term "simulate" is intended to mean creating a representation or model of a physical thing or action that predicts characteristics of the thing or action. The representation or model can in many cases be distinguishable from the thing or action. For example, the representation or model can be distinguishable from a thing with respect to one or more characteristic such as color, intensity of signals detected from all or part of the thing, size, or shape. In particular implementations, the representation or model can be idealized, exaggerated, muted, or incomplete when compared to the thing or action. Thus, in some implementations, a representation of model can be distinguishable from the thing or action that it represents, for example, with respect to at least one of the characteristics set forth above. The representation or model can be provided in a computer readable format or medium such as one or more of those set forth elsewhere herein.

As used herein, the term "specific signal" is intended to mean detected energy or coded information that is selectively observed over other energy or information such as background energy or information. For example, a specific signal can be an optical signal detected at a particular intensity, wavelength or color; an electrical signal detected at a particular frequency, power or field strength; or other signals known in the art pertaining to spectroscopy and analytical detection.

As used herein, the term "swath" is intended to mean a rectangular portion of an object. The swath can be an elongated strip that is scanned by relative movement between the object and a detector in a direction that is parallel to the longest dimension of the strip. Generally, the width of the rectangular portion or strip will be constant along its full length. Multiple swaths of an object can be parallel to each other. Multiple swaths of an object can be adjacent to each other, overlapping with each other, abutting each other, or separated from each other by an interstitial area.

As used herein, the term "variance" is intended to mean a difference between that which is expected and that which is observed or a difference between two or more observations. For example, variance can be the discrepancy between an expected value and a measured value. Variance can be represented using statistical functions such as standard deviation, the square of standard deviation, coefficient of variation or the like.

As used herein, the term "xy coordinates" is intended to mean information that specifies location, size, shape, and/or orientation in an xy plane. The information can be, for example, numerical coordinates in a Cartesian system. The coordinates can be provided relative to one or both of the x and y axes or can be provided relative to another location in the xy plane. For example, coordinates of a analyte of an object can specify the location of the analyte relative to location of a fiducial or other analyte of the object.

As used herein, the term "xy plane" is intended to mean a 2 dimensional area defined by straight line axes x and y. When used in reference to a detector and an object observed by the detector, the area can be further specified as being orthogonal to the direction of observation between the detector and object being detected.

As used herein, the term "z coordinate" is intended to mean information that specifies the location of a point, line or area along an axes that is orthogonal to an xy plane. In particular implementations, the z axis is orthogonal to an area of an object that is observed by a detector. For example, the direction of focus for an optical system may be specified along the z axis.

In some implementations, acquired signal data is transformed using an affine transformation. In some such implementations, template generation makes use of the fact that the affine transforms between color channels are consistent between runs. Because of this consistency, a set of default offsets can be used when determining the coordinates of the analytes in a specimen. For example, a default offsets file can contain the relative transformation (shift, scale, skew) for the different channels relative to one channel, such as the A channel. In other implementations, however, the offsets between color channels drift during a run and/or between runs, making offset-driven template generation difficult. In such implementations, the methods and systems provided herein can utilize offset-less template generation, which is described further below.

In some aspects of the above implementations, the system can comprise a flow cell. In some aspects, the flow cell comprises lanes, or other configurations, of tiles, wherein at least some of the tiles comprise one or more arrays of analytes. In some aspects, the analytes comprise a plurality of molecules such as nucleic acids. In certain aspects, the flow cell is configured to deliver a labeled nucleotide base to an array of nucleic acids, thereby extending a primer hybridized to a nucleic acid within a analyte so as to produce a signal corresponding to a analyte comprising the nucleic acid. In preferred implementations, the nucleic acids within a analyte are identical or substantially identical to each other.

In some of the systems for image analysis described herein, each image in the set of images includes color signals, wherein a different color corresponds to a different nucleotide base. In some aspects, each image of the set of images comprises signals having a single color selected from at least four different colors. In some aspects, each image in the set of images comprises signals having a single color selected from four different colors. In some of the systems described herein, nucleic acids can be sequenced by providing four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, the system comprises a flow cell that is configured to deliver additional labeled nucleotide bases to the array of molecules, thereby producing a plurality of cycles of color images.

In preferred implementations, the methods provided herein can include determining whether a processor is actively acquiring data or whether the processor is in a low activity state. Acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. Accordingly, as used herein, the term low activity state refers to the processing capacity of a processor at a given time. In some implementations, a low activity state occurs when a processor is not acquiring and/or storing data. In some implementations, a low activity state occurs when some data acquisition and/or storage is taking place, but additional processing capacity remains such that image analysis can occur at the same time without interfering with other functions.

As used herein, "identifying a conflict" refers to identifying a situation where multiple processes compete for resources. In some such implementations, one process is given priority over another process. In some implementations, a conflict may relate to the need to give priority for allocation of time, processing capacity, storage capacity or any other resource for which priority is given. Thus, in some implementations, where processing time or capacity is to be distributed between two processes such as either analyzing a data set and acquiring and/or storing the data set, a conflict between the two processes exists and can be resolved by giving priority to one of the processes.

Also provided herein are systems for performing image analysis. The systems can include a processor; a storage capacity; and a program for image analysis, the program comprising instructions for processing a first data set for storage and the second data set for analysis, wherein the processing comprises acquiring and/or storing the first data set on the storage device and analyzing the second data set when the processor is not acquiring the first data set. In certain aspects, the program includes instructions for identifying at least one instance of a conflict between acquiring and/or storing the first data set and analyzing the second data set; and resolving the conflict in favor of acquiring and/or storing image data such that acquiring and/or storing the first data set is given priority. In certain aspects, the first data set comprises image files obtained from an optical imaging device. In certain aspects, the system further comprises an optical imaging device. In some aspects, the optical imaging device comprises a light source and a detection device.

As used herein, the term "program" refers to instructions or commands to perform a task or process. The term "program" can be used interchangeably with the term module. In certain implementations, a program can be a compilation of various instructions executed under the same set of commands. In other implementations, a program can refer to a discrete batch or file.

Set forth below are some of the surprising effects of utilizing the methods and systems for performing image analysis set forth herein. In some sequencing implementations, an important measure of a sequencing system's utility is its overall efficiency. For example, the amount of mappable data produced per day and the total cost of installing and miming the instrument are important aspects of an economical sequencing solution. To reduce the time to generate mappable data and to increase the efficiency of the system, real-time base calling can be enabled on an instrument computer and can run in parallel with sequencing chemistry and imaging. This allows much of the data processing and analysis to be completed before the sequencing chemistry finishes. Additionally, it can reduce the storage required for intermediate data and limit the amount of data that needs to travel across the network.

While sequence output has increased, the data per run transferred from the systems provided herein to the network and to secondary analysis processing hardware has substantially decreased. By transforming data on the instrument computer (acquiring computer), network loads are dramatically reduced. Without these on-instrument, off-network data reduction techniques, the image output of a fleet of DNA sequencing instruments would cripple most networks.

The widespread adoption of the high-throughput DNA sequencing instruments has been driven in part by ease of use, support for a range of applications, and suitability for virtually any lab environment. The highly efficient algorithms presented herein allow significant analysis functionality to be added to a simple workstation that can control sequencing instruments. This reduction in the requirements for computational hardware has several practical benefits that will become even more important as sequencing output levels continue to increase. For example, by performing image analysis and base calling on a simple tower, heat production, laboratory footprint, and power consumption are kept to a minimum In contrast, other commercial sequencing technologies have recently ramped up their computing infrastructure for primary analysis, with up to five times more processing power, leading to commensurate increases in heat output and power consumption. Thus, in some implementations, the computational efficiency of the methods and systems provided herein enables customers to increase their sequencing throughput while keeping server hardware expenses to a minimum.

Accordingly, in some implementations, the methods and/or systems presented herein act as a state machine, keeping track of the individual state of each specimen, and when it detects that a specimen is ready to advance to the next state, it does the appropriate processing and advances the specimen to that state. A more detailed example of how the state machine monitors a file system to determine when a specimen is ready to advance to the next state according to a preferred implementation is set forth in Example 1 below.

In preferred implementations, the methods and systems provided herein are multi-threaded and can work with a configurable number of threads. Thus, for example in the context of nucleic acid sequencing, the methods and systems provided herein are capable of working in the background during a live sequencing run for real-time analysis, or it can be run using a pre-existing set of image data for off-line analysis. In certain preferred implementations, the methods and systems handle multi-threading by giving each thread its own subset of specimen for which it is responsible. This minimizes the possibility of thread contention.

A method of the present disclosure can include a step of obtaining a target image of an object using a detection apparatus, wherein the image includes a repeating pattern of analytes on the object. Detection apparatus that are capable of high resolution imaging of surfaces are particularly useful. In particular implementations, the detection apparatus will have sufficient resolution to distinguish analytes at the densities, pitches, and/or analyte sizes set forth herein. Particularly useful are detection apparatus capable of obtaining images or image data from surfaces. Example detectors are those that are configured to maintain an object and detector in a static relationship while obtaining an area image. Scanning apparatus can also be used. For example, an apparatus that obtains sequential area images (e.g., so called 'step and shoot' detectors) can be used. Also useful are devices that continually scan a point or line over the surface of an object to accumulate data to construct an image of the surface. Point scanning detectors can be configured to scan a point (i.e., a small detection area) over the surface of an object via a raster motion in the x-y plane of the surface. Line scanning detectors can be configured to scan a line along they dimension of the surface of an object, the longest dimension of the line occurring along the x dimension. It will be understood that the detection device, object or both can be moved to achieve scanning detection. Detection apparatus that are particularly useful, for example in nucleic acid sequencing applications, are described in US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference.

The implementations disclosed herein may be implemented as a method, apparatus, system or article of manufacture using programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), coarse grained reconfigurable architectures (CGRAs), application-specific integrated circuits (ASICs), complex programmable logic devices (CPLDs), programmable logic arrays (PLAs), microprocessors, or other similar processing devices. In particular implementations, information or algorithms set forth herein are present in non-transient storage media.

In particular implementations, a computer implemented method set forth herein can occur in real time while multiple images of an object are being obtained. Such real time analysis is particularly useful for nucleic acid sequencing applications wherein an array of nucleic acids is subjected to repeated cycles of fluidic and detection steps. Analysis of the sequencing data can often be computationally intensive such that it can be beneficial to perform the methods set forth herein in real time or in the background while other data acquisition or analysis algorithms are in process. Example real time analysis methods that can be used with the present methods are those used for the MiSeq and HiSeq sequencing devices commercially available from Illumina, Inc. (San Diego, Calif.) and/or described in US Pat. App. Pub. No. 2012/0020537 A1, which is incorporated herein by reference.

An example data analysis system, formed by one or more programmed computers, with programming being stored on one or more machine readable media with code executed to carry out one or more steps of methods described herein. In one implementation, for example, the system includes an interface designed to permit networking of the system to one or more detection systems (e.g., optical imaging systems) that are configured to acquire data from target objects. The interface may receive and condition data, where appropriate. In particular implementations the detection system will output digital image data, for example, image data that is representative of individual picture elements or pixels that, together, form an image of an array or other object. A processor processes the received detection data in accordance with a one or more routines defined by processing code. The processing code may be stored in various types of memory circuitry.

In accordance with the presently contemplated implementations, the processing code executed on the detection data includes a data analysis routine designed to analyze the detection data to determine the locations and metadata of individual analytes visible or encoded in the data, as well as locations at which no analyte is detected (i.e., where there is no analyte, or where no meaningful signal was detected from an existing analyte). In particular implementations, analyte locations in an array will typically appear brighter than non-analyte locations due to the presence of fluorescing dyes attached to the imaged analytes. It will be understood that the analytes need not appear brighter than their surrounding area, for example, when a target for the probe at the analyte is not present in an array being detected. The color at which individual analytes appear may be a function of the dye employed as well as of the wavelength of the light used by the imaging system for imaging purposes. Analytes to which targets are not bound or that are otherwise devoid of a particular label can be identified according to other characteristics, such as their expected location in the microarray.

Once the data analysis routine has located individual analytes in the data, a value assignment may be carried out. In general, the value assignment will assign a digital value to each analyte based upon characteristics of the data represented by detector components (e.g., pixels) at the corresponding location. That is, for example when imaging data is processed, the value assignment routine may be designed to recognize that a specific color or wavelength of light was detected at a specific location, as indicated by a group or cluster of pixels at the location. In a typical DNA imaging application, for example, the four common nucleotides will be represented by four separate and distinguishable colors. Each color, then, may be assigned a value corresponding to that nucleotide.

As used herein, the terms "module", "system," or "system controller" may include a hardware and/or software system and circuitry that operates to perform one or more functions. For example, a module, system, or system controller may include a computer processor, controller, or other logic-based device that performs operations based on instructions stored on a tangible and non-transitory computer readable storage medium, such as a computer memory. Alternatively, a module, system, or system controller may include a hard-wired device that performs operations based on hard-wired logic and circuitry. The module, system, or system controller shown in the attached figures may represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or computer microprocessors.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are examples only, and are thus not limiting as to the types of memory usable for storage of a computer program.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the implementations of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year, and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some implementations of the methods and systems presented herein can reduce the time, hardware, networking, and laboratory infrastructure requirements needed to produce usable sequence data.

The present disclosure describes various methods and systems for carrying out the methods. Examples of some of the methods are described as a series of steps. However, it should be understood that implementations are not limited to the particular steps and/or order of steps described herein. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other implementations.

In some implementations, a processing unit, processor, module, or computing system that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

Moreover, the operations of the methods described herein can be sufficiently complex such that the operations cannot be mentally performed by an average human being or a person of ordinary skill in the art within a commercially reasonable time period. For example, the methods may rely on relatively complex computations such that such a person cannot complete the methods within a commercially reasonable time.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

As used herein, the term "each", when used in reference to a collection of items, is intended to identify an individual item in the collection but does not necessarily refer to every item in the collection. Exceptions can occur if explicit disclosure or context clearly dictates otherwise.

Although the invention has been described with reference to the examples provided above, it should be understood that various modifications can be made without departing from the invention.

The modules in this application can be implemented in hardware or software, and need not be divided up in precisely the same blocks as shown in the figures. Some can also be implemented on different processors or computers, or spread among a number of different processors or computers. In addition, it will be appreciated that some of the modules can be combined, operated in parallel or in a different sequence than that shown in the figures without affecting the functions achieved. Also as used herein, the term "module" can include "sub-modules", which themselves can be considered herein to constitute modules. The blocks in the figures designated as modules can also be thought of as flowchart steps in a method.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify".

As used herein, a given signal, event or value is "in dependence upon" a predecessor signal, event or value of the predecessor signal, event or value influenced by the given signal, event or value. If there is an intervening processing element, step or time period, the given signal, event or value can still be "in dependence upon" the predecessor signal, event or value. If the intervening processing element or step combines more than one signal, event or value, the signal output of the processing element or step is considered "in dependence upon" each of the signal, event or value inputs. If the given signal, event or value is the same as the predecessor signal, event or value, this is merely a degenerate case in which the given signal, event or value is still considered to be "in dependence upon" or "dependent on" or "based on" the predecessor signal, event or value. "Responsiveness" of a given signal, event or value upon another signal, event or value is defined similarly.

As used herein, "concurrently" or "in parallel" does not require exact simultaneity. It is sufficient if the evaluation of one of the individuals begins before the evaluation of another of the individuals completes.

Particular Implementations

We describe various implementations of neural network-based template generation and neural network-based base calling. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

Subpixel Base Calling

We disclose a computer-implemented method of determining metadata about analytes on a tile of a flow cell. The method includes accessing a series of image sets generated during a sequencing run, each image set in the series generated during a respective sequencing cycle of the sequencing run, each image in the series depicting the analytes and their surrounding background, and each image in the series having a plurality of subpixels. The method includes obtaining, from a base caller, a base call classifying each of the subpixels as one of four bases (A, C, T, and G), thereby producing a base call sequence for each of the subpixels across a plurality of sequencing cycles of the sequencing run. The method includes generating an analyte map that identifies the analytes as disjointed regions of contiguous subpixels which share a substantially matching base call sequence. The method includes determining spatial distribution of analytes, including their shapes and sizes based on the disjointed regions and storing the analyte map in memory for use as ground truth for training a classifier.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in these implementations can readily be combined with sets of base features identified in other implementations.

In one implementation, the method includes identifying as background those subpixels in the analyte map that do not belong to any of the disjointed regions. In one implementation, the method includes obtaining, from the base caller, the base call classifying each of the subpixels as one of five bases (A, C, T, G, and N). In one implementation, the analyte map identifies analyte boundary portions between two contiguous subpixels whose base call sequences do not substantially match.

In one implementation, the method includes identifying origin subpixels at preliminary center coordinates of the analytes determined by the base caller, and breadth-first searching for substantially matching base call sequences by beginning with the origin subpixels and continuing with successively contiguous non-origin subpixels. In one implementation, the method includes, on an analyte-by-analyte basis, determining hyperlocated center coordinates of the analytes by calculating centers of mass of the disjointed regions of the analyte map as an average of coordinates of respective contiguous subpixels forming the disjointed regions, and storing the hyperlocated center coordinates of the analytes in the memory on the analyte-by-analyte basis for use as ground truth for training the classifier.

In one implementation, the method includes, on the analyte-by-analyte basis, identifying centers of mass subpixels in the disjointed regions of the analyte map at the hyperlocated center coordinates of the analytes, upsampling the analyte map using interpolation and storing the upsampled analyte map in the memory for use as ground truth for training the classifier, and, in the upsampled analyte map, on the analyte-by-analyte basis, assigning a value to each contiguous subpixel in the disjointed regions based on a decay factor that is proportional to distance of a contiguous subpixel from a center of mass subpixel in a disjointed region to which the contiguous subpixel belongs. In one implementation, the value is a intensity value normalized between zero and one. In one implementation, the method includes, in the upsampled analyte map, assigning a same predetermined value to all the subpixels identified as the background. In one implementation, the predetermined value is a zero intensity value.

In one implementation, the method includes generating a decay map from the upsampled analyte map that expresses the contiguous subpixels in the disjointed regions and the subpixels identified as the background based on their assigned values, and storing the decay map in the memory for use as ground truth for training the classifier. In one implementation, each subpixel in the decay map has a value normalized between zero and one. In one implementation, the method includes, in the upsampled analyte map, categorizing, on the analyte-by-analyte basis, the contiguous subpixels in the disjointed regions as analyte interior subpixels belonging to a same analyte, the centers of mass subpixels as analyte center subpixels, subpixels containing the analyte boundary portions as boundary subpixels, and the subpixels identified as the background as background subpixels, and storing the categorizations in the memory for use as ground truth for training the classifier.

In one implementation, the method includes, storing, on the analyte-by-analyte basis, coordinates of the analyte interior subpixels, the analyte center subpixels, the boundary subpixels, and the background subpixels in the memory for use as ground truth for training the classifier, downscaling the coordinates by a factor used to upsample the analyte map, and, storing, on the analyte-by-analyte basis, the downscaled coordinates in the memory for use as ground truth for training the classifier.

In one implementation, the method includes, in a binary ground truth data generated from the upsampled analyte map, using color coding to label the analyte center subpixels as belonging to an analyte center class and all other subpixels are belonging to a non-center class, and storing the binary ground truth data in the memory for use as ground truth for training the classifier. In one implementation, the method includes, in a ternary ground truth data generated from the upsampled analyte map, using color coding to label the background subpixels as belonging to a background class, the analyte center subpixels as belonging to an analyte center class, and the analyte interior subpixels as belonging to an analyte interior class, and storing the ternary ground truth data in the memory for use as ground truth for training the classifier.

In one implementation, the method includes generating analyte maps for a plurality of tiles of the flow cell, storing the analyte maps in memory and determining spatial distribution of analytes in the tiles based on the analyte maps, including their shapes and sizes, in the upsampled analyte maps of the analytes in the tiles, categorizing, on an analyte-by-analyte basis, subpixels as analyte interior subpixels belonging to a same analyte, analyte center subpixels, boundary subpixels, and background subpixels, storing the categorizations in the memory for use as ground truth for training the classifier, storing, on the analyte-by-analyte basis across the tiles, coordinates of the analyte interior subpixels, the analyte center subpixels, the boundary subpixels, and the background subpixels in the memory for use as ground truth for training the classifier, downscaling the coordinates by the factor used to upsample the analyte map, and, storing, on the analyte-by-analyte basis across the tiles, the downscaled coordinates in the memory for use as ground truth for training the classifier.

In one implementation, the base call sequences are substantially matching when a predetermined portion of base calls match on an ordinal position-wise basis. In one implementation, the base caller produces the base call sequences by interpolating intensity of the subpixels, including at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. In one implementation, the subpixels are identified to the base caller based on their integer or non-integer coordinates.

In one implementation, the method includes requiring that at least some of the disjointed regions have a predetermined minimum number of subpixels. In one implementation, the flow cell has at least one patterned surface with an array of wells that occupy the analytes. In such an implementation, the method includes, based on the determined shapes and sizes of the analytes, determining which ones of the wells are substantially occupied by at least one analyte, which ones of the wells are minimally occupied, and which ones of the wells are co-occupied by multiple analytes.

In one implementation, the flow cell has at least one nonpatterned surface and the analytes are unevenly scattered over the nonpatterned surface. In one implementation, the density of the analytes ranges from about 100,000 analytes/$mm^2$ to about 1,000,000 analytes/$mm^2$. In one implementation, the density of the analytes ranges from about 1,000,000 analytes/$mm^2$ to about 10,000,000 analytes/$mm^2$. In one implementation, the subpixels are quarter subpixels. In another implementation, the subpixels are half subpixels. In one implementation, the preliminary center coordinates of the analytes determined by the base caller are defined in a template image of the tile, and a pixel resolution, an image coordinate system, and measurement scales of the image coordinate system are same for the template image and the images. In one implementation, each image set has four images. In another implementation, each image set has two images. In yet another implementation, each image set has one image. In one implementation, the sequencing run utilizes four-channel chemistry. In another implementation, the sequencing run utilizes two-channel chemistry. In yet another implementation, the sequencing run utilizes one-channel chemistry.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method of determining metadata about analytes on a tile of a flow cell. The method includes accessing a set of images of the tile captured during a sequencing run and preliminary center coordinates of the analytes determined by a base caller. The method includes, for each image set, obtaining, from a base caller, a base call classifying, as one of four bases origin subpixels that contain the preliminary center coordinates and a predetermined neighborhood of contiguous subpixels that are successively contiguous to respective ones of the origin subpixels, thereby producing a base call sequence for each of the origin subpixels and for each of the predetermined neighborhood of contiguous subpixels. The method includes generating an analyte map that identifies the analytes as disjointed regions of contiguous subpixels that are successively contiguous to at least some of the respective ones of the origin subpixels and share a substantially matching base call sequence of the one of four bases with the at least some of the respective ones of the origin subpixels. The method includes storing the analyte map in memory and determining the shapes and the sizes of the analytes based on the disjointed regions in the analyte map.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the predetermined neighborhood of contiguous subpixels is a m×n subpixel patch centered at pixels containing the origin subpixels and the subpixel patch is 3×3 pixels. In one implementation, the predetermined neighborhood of contiguous subpixels is a n-connected subpixel neighborhood centered at pixels containing the origin subpixels. In one implementation, the method includes, identifying as background those subpixels in the analyte map that do not belong to any of the disjointed regions.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Data Generation

We disclose a computer-implemented method of generating training data for neural network-based template generation and base calling. The method includes accessing a multitude of images of a flow cell captured over a plurality of cycles of a sequencing run, the flow cell having a plurality of tiles and, in the multitude of images, each of the tiles having a sequence of image sets generated over the plurality of cycles, and each image in the sequence of image sets depicting intensity emissions of analytes and their surrounding background on a particular one of the tiles at a particular one the cycles. The method includes constructing a training set having a plurality of training examples, each training example corresponding to a particular one of the tiles and including image data from at least some image sets in the sequence of image sets of the particular one of the tiles. The method includes generating at least one ground truth data representation for each of the training examples, the ground truth data representation identifying at least one of spatial distribution of analytes and their surrounding background on the particular one of the tiles whose intensity emissions are depicted by the image data, including at least one of analyte shapes, analyte sizes, and/or analyte boundaries, and/or centers of the analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the image data includes images in each of the at least some image sets in the sequence of image sets of the particular one of the tiles, and the images have a resolution of 1800×1800. In one implementation, the image data includes at least one image patch from each of the images, and the image patch covers a portion of the particular one of the tiles and has a resolution of 20×20. In one implementation, the image data includes an upsampled representation of the image patch, and the upsampled representation has a resolution of 80×80. In one implementation, the ground truth data representation has an upsampled resolution of 80×80.

In one implementation, multiple training examples correspond to a same particular one of the tiles and respectively include as image data different image patches from each image in each of at least some image sets in a sequence of image sets of the same particular one of the tiles, and at least some of the different image patches overlap with each other. In one implementation, the ground truth data representation identifies the analytes as disjoint regions of adjoining subpixels, the centers of the analytes as centers of mass subpixels within respective ones of the disjoint regions, and their surrounding background as subpixels that do not belong to any of the disjoint regions. In one implementation, the ground truth data representation uses color coding to identify each subpixel as either being a analyte center or a non-center. In one implementation, the ground truth data representation uses color coding to identify each subpixel as either being analyte interior, analyte center, or surrounding background.

In one implementation, the method includes, storing, in memory, the training examples in the training set and associated ground truth data representations as the training data for the neural network-based template generation and base calling. In one implementation, the method includes generating the training data for a variety of flow cells, sequencing instruments, sequencing protocols, sequencing chemistries, sequencing reagents, and analyte densities.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Metadata & Base Calls Generation

In one implementation, a method includes accessing sequencing images of analytes produced by a sequencer, generating training data from the sequencing images, and using the training data for training a neural network to generate metadata about the analytes. Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a method includes accessing sequencing images of analytes produced by a sequencer, generating training data from the sequencing images, and using the training data for training a neural network to base call the analytes. Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Regression Model

We disclose a computer-implemented method of identifying analytes on a tile of a flow cell and related analyte metadata. The method includes processing input image data from a sequence of image sets through a neural network and generating an alternative representation of the input image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through an output layer and generating an output that identifies analytes, whose intensity emissions are depicted by the input image data, as disjoint regions of adjoining subpixels, centers of the analytes as center subpixels at centers of mass of the respective ones of the disjoint regions, and their surrounding background as background subpixels not belonging to any of the disjoint regions.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the adjoining subpixels in the respective ones of the disjoint regions have intensity values weighted according to distance of an adjoining subpixel from a center subpixel in a disjoint region to which the adjoining subpixel belongs. In one implementation, the center subpixels have highest intensity values within the respective ones of the disjoint regions. In one implementation, the background subpixels all have a same lowest intensity value in the output. In one implementation, the output layer normalizes the intensity values between zero and one.

In one implementation, the method includes applying a peak locator to the output to find peak intensities in the output, determining location coordinates of the centers of the analytes based on the peak intensities, downscaling the location coordinates by an upsampling factor used to prepare the input image data, and storing the downscaled location coordinates in memory for use in base calling the analytes. In one implementation, the method includes categorizing the adjoining subpixels in the respective ones of the disjoint regions as analyte interior subpixels belonging to a same analyte, and storing the categorization and downscaled location coordinates of the analyte interior subpixels in the memory on an analyte-by-analyte basis for use in base calling the analytes. In one implementation, the method includes, on the analyte-by-analyte basis, determining distances of the analyte interior subpixels from respective ones of the centers of the analytes, and storing the distances in the memory on the analyte-by-analyte basis for use in base calling the analytes.

In one implementation, the method includes extracting intensities from the analyte interior subpixels in the respective ones of the disjoint regions, including using at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage, and storing the intensities in the memory on the analyte-by-analyte basis for use in base calling the analytes.

In one implementation, the method includes based on the disjoint regions, determining, as part of the related analyte metadata, spatial distribution of the analytes, including at least one of analyte shapes, analyte sizes, and/or analyte boundaries, and storing the related analyte metadata in the memory on the analyte-by-analyte basis for use in base calling the analytes.

In one implementation, the input image data includes images in the sequence of image sets, and the images have a resolution of 3000×3000. In one implementation, the input image data includes at least one image patch from each of the images in the sequence of image sets, and the image patch covers a portion of the tile and has a resolution of 20×20. In one implementation, the input image data includes an upsampled representation of the image patch from each of the images in the sequence of image sets, and the upsampled representation has a resolution of 80×80. In one implementation, the output has an upsampled resolution of 80×80.

In one implementation, the neural network is a deep fully convolutional segmentation neural network with an encoder subnetwork and a corresponding decoder network, the encoder subnetwork includes a hierarchy of encoders, and the decoder subnetwork includes a hierarchy of decoders that map low resolution encoder feature maps to full input resolution feature maps. In one implementation, the density of the analytes ranges from about 100,000 analytes/mm$^2$ to about 1,000,000 analytes/mm$^2$. In another implementation, the density of the analytes ranges from about 1,000,000 analytes/mm$^2$ to about 10,000,000 analytes/mm$^2$.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Regression Model

We disclose a computer-implemented method of training a neural network to identify analytes and related analyte metadata. The method includes obtaining training data for training the neural network. The training data includes a plurality of training examples and corresponding ground truth data that should be generated by the neural network by processing the training examples. Each training example includes image data from a sequence of image sets. Each image in the sequence of image sets covers a tile of a flow cell and depicts intensity emissions of analytes on the tile and their surrounding background captured for a particular image channel at a particular one of a plurality of sequencing cycles of a sequencing run performed on the flow cell. Each ground truth data identifies analytes, whose intensity emissions are depicted by the image data of a corresponding training example, as disjoint regions of adjoining subpixels, centers of the analytes as center subpixels at centers of mass of the respective ones of the disjoint regions, and their surrounding background as background subpixels not belonging to any of the disjoint regions. The method includes using a gradient descent training technique to train the neural network and generating outputs for the training examples that progressively match the ground truth data, including iteratively optimizing a loss function that minimizes error between the outputs and the ground truth data, and updating parameters of the neural network based on the error.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, upon error convergence after a final iteration, storing the updated parameters of the neural network in memory to be applied to further neural network-based template generation and base calling. In one implementation, in the ground truth data, the adjoining subpixels in the respective ones of the disjoint regions have intensity values weighted according to distance of an adjoining subpixel from a center subpixel in a disjoint region to which the adjoining subpixel belongs. In one implementation, in the ground truth data, the center subpixels have highest intensity values within the respective ones of the disjoint regions. In one implementation, in the ground truth data, the background subpixels all have a same lowest intensity value in the output. In one implementation, in the ground truth data, the intensity values are normalized between zero and one.

In one implementation, the loss function is mean squared error and the error is minimized on a subpixel-basis between the normalized intensity values of corresponding subpixels in the outputs and the ground truth data. In one implementation, the ground truth data identify, as part of the related analyte metadata, spatial distribution of the analytes, including at least one of analyte shapes, analyte sizes, and/or analyte boundaries. In one implementation, the image data includes images in the sequence of image sets, and the images have a resolution of 1800×1800. In one implementation, the image data includes at least one image patch from each of the images in the sequence of image sets, and the image patch covers a portion of the tile and has a resolution of 20×20. In one implementation, the image data includes an upsampled representation of the image patch from each of the images in the sequence of image sets, and the upsampled representation of the image patch has a resolution of 80×80.

In one implementation, in the training data, multiple training examples respectively include as image data different image patches from each image in a sequence of image sets of a same tile, and at least some of the different image patches overlap with each other. In one implementation, the ground truth data has an upsampled resolution of 80×80. In one implementation, the training data includes training examples for a plurality of tiles of the flow cell. In one implementation, the training data includes training examples for a variety of flow cells, sequencing instruments, sequencing protocols, sequencing chemistries, sequencing reagents, and analyte densities. In one implementation, the neural network is a deep fully convolutional segmentation neural network with an encoder subnetwork and a corresponding decoder network, the encoder subnetwork includes a hierarchy of encoders, and the decoder subnetwork includes a hierarchy of decoders that map low resolution encoder feature maps to full input resolution feature maps for subpixel-wise classification by a final classification layer.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Neural Network-Based Template Generator

We disclose a computer-implemented method of determining metadata about analytes on a flow cell. The method includes accessing image data that depicts intensity emissions of the analytes, processing the image data through one or more layers of a neural network and generating an alternative representation of the image data, and processing the alternative representation through an output layer and generating an output that identifies at least one of shapes and sizes of the analytes and/or centers of the analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the image data further depicts intensity emissions of surrounding background of the analytes. In such an implementation, the method includes the output identifying spatial distribution of the analytes on the flow cell, including the surrounding background and boundaries between the analytes. In one implementation, the method includes determining center location coordinates of the analytes on the flow cell based on the output. In one implementation, the neural network is a convolutional neural network. In one implementation, the neural network is a recurrent neural network. In one implementation, the neural network is a deep fully convolutional segmentation neural network with an encoder subnetwork and a corresponding decoder network, followed by the output layer, the encoder subnetwork includes a hierarchy of encoders, and the decoder subnetwork includes a hierarchy of decoders that map low resolution encoder feature maps to full input resolution feature maps.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Binary Classification Model

We disclose a computer-implemented method of identifying analytes on a tile of a flow cell and related analyte metadata. The method includes processing input image data from a sequence of image sets through a neural network and generating an alternative representation of the image data. In one implementation, each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies centers of analytes whose intensity emissions are depicted by the input image data. The output has a plurality of subpixels, and each subpixel in the plurality of subpixels is classified as either an analyte center or a non-center.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the classification layer assigns each subpixel in the output a first likelihood score of being the analyte center, and a second likelihood score of being the non-center. In one implementation, the first and second likelihood scores are determined based on a softmax function and exponentially normalized between zero and one. In one implementation, the first and second likelihood scores are determined based on a sigmoid function and normalized between zero and one. In one implementation, each subpixel in the output is classified as either the analyte center or the non-center based on which one of the first and second likelihood scores is higher than the other. In one implementation, each subpixel in the output is classified as either the analyte center or the non-center based on whether the first and second likelihood scores are above a predetermined threshold likelihood score. In one implementation, the output identifies the centers at centers of mass of respective ones of the analytes. In one implementation, in the output, subpixels classified as analyte centers are assigned a same first predetermined value, and subpixels classified as non-centers are all assigned a same second predetermined value. In one implementation, the first and second predetermined values are intensity values. In one implementation, the first and second predetermined values are continuous values.

In one implementation, the method includes determining location coordinates of subpixels classified as analyte centers, downscaling the location coordinates by an upsampling factor used to prepare the input image data, and storing the downscaled location coordinates in memory for use in base calling the analytes. In one implementation, the input image data includes images in the sequence of image sets, and the images have a resolution of 3000×3000. In one implementation, the input image data includes at least one image patch from each of the images in the sequence of image sets, and the image patch covers a portion of the tile and has a resolution of 20×20. In one implementation, the input image data includes an upsampled representation of the image patch from each of the images in the sequence of image sets, and the upsampled representation has a resolution of 80×80. In one implementation, the output has an upsampled resolution of 80×80.

In one implementation, the neural network is a deep fully convolutional segmentation neural network with an encoder subnetwork and a corresponding decoder network, followed by the classification layer, the encoder subnetwork includes a hierarchy of encoders, and the decoder subnetwork includes a hierarchy of decoders that map low resolution encoder feature maps to full input resolution feature maps for subpixel-wise classification by the classification layer. In one implementation, the density of the analytes ranges from about 100,000 analytes/mm$^2$ to about 1,000,000 analytes/mm$^2$. In another implementation, the density of the analytes ranges from about 1,000,000 analytes/mm$^2$ to about 10,000,000 analytes/mm$^2$.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Binary Classification Model

We disclose a computer-implemented method of training a neural network to identify analytes and related analyte metadata. The method includes obtaining training data for training the neural network. The training data includes a plurality of training examples and corresponding ground truth data that should be generated by the neural network by processing the training examples. Each training example includes image data from a sequence of image sets. Each image in the sequence of image sets covers a tile of a flow cell and depicts intensity emissions of analytes on the tile and their surrounding background captured for a particular image channel at a particular one of a plurality of sequencing cycles of a sequencing run performed on the flow cell. Each ground truth data identifies centers of analytes, whose intensity emissions are depicted by the image data of a corresponding training example. The ground truth data has a plurality of subpixels, and each subpixel in the plurality of subpixels is classified as either an analyte center or a non-center. The method includes using a gradient descent training technique to train the neural network and generating outputs for the training examples that progressively match the ground truth data, including iteratively optimizing a loss function that minimizes error between the outputs and the ground truth data, and updating parameters of the neural network based on the error.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, upon error convergence after a final iteration, storing the updated parameters of the neural network in memory to be applied to further neural network-based template generation and base calling. In one implementation, in the ground truth data, subpixels classified as analyte centers are all assigned a same first predetermined class score, and subpixels classified as non-centers are all assigned a same second predetermined class score. In one implementation, in each output, each subpixel has a first prediction score of being the analyte center, and a second prediction score of being the non-center. In one implementation, the loss function is custom weighted binary cross entropy loss and the error is minimized on a subpixel-basis between the prediction scores and the class scores of corresponding subpixels in the outputs and the ground truth data. In one implementation, the ground truth data identifies the centers at centers of mass of respective ones of the analytes. In one implementation, in the ground truth data, subpixels classified as analyte centers are all assigned a same first predetermined value, and subpixels classified as non-centers are all assigned a same second predetermined value. In one implementation, the first and second predetermined values are intensity values. In another implementation, the first and second predetermined values are continuous values.

In one implementation, the ground truth data identify, as part of the related analyte metadata, spatial distribution of the analytes, including at least one of analyte shapes, analyte sizes, and/or analyte boundaries. In one implementation, the image data includes images in the sequence of image sets, and the images have a resolution of 1800×1800. In one implementation, the image data includes at least one image patch from each of the images in the sequence of image sets, and the image patch covers a portion of the tile and has a resolution of 20×20. In one implementation, the image data includes an upsampled representation of the image patch from each of the images in the sequence of image sets, and the upsampled representation of the image patch has a resolution of 80×80. In one implementation, in the training data, multiple training examples respectively include as image data different image patches from each image in a sequence of image sets of a same tile, and at least some of the different image patches overlap with each other. In one implementation, the ground truth data has an upsampled resolution of 80×80. In one implementation, the training data includes training examples for a plurality of tiles of the flow cell. In one implementation, the training data includes training examples for a variety of flow cells, sequencing instruments, sequencing protocols, sequencing chemistries, sequencing reagents, and analyte densities. In one implementation, the neural network is a deep fully convolutional segmentation neural network with an encoder subnetwork and a corresponding decoder network, followed by a classification layer, the encoder subnetwork includes a hierarchy of encoders, and the decoder subnetwork includes a hierarchy of decoders that map low resolution encoder feature maps to full input resolution feature maps for subpixel-wise classification by the classification layer.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Ternary Classification Model

We disclose a computer-implemented method of identifying analytes on a tile of a flow cell and related analyte metadata. The method includes processing input image data from a sequence of image sets through a neural network and generating an alternative representation of the image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies spatial distribution of analytes and their surrounding background whose intensity emissions are depicted by the input image data, including at least one of analyte centers, analyte shapes, analyte sizes, and/or analyte boundaries. The output has a plurality of subpixels, and each subpixel in the plurality of subpixels is classified as either background, analyte center, or analyte interior.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the classification layer assigns each subpixel in the output a first likelihood score of being the background, a second likelihood score of being the analyte center, and a third likelihood score of being the analyte interior. In one implementation, the first, second, and third likelihood scores are determined based on a softmax function and exponentially normalized between zero and one. In one implementation, each subpixel in the output is classified as either the background, the analyte center, or the analyte interior based on which one among the first, second, and third likelihood scores is highest. In one implementation, each subpixel in the output is classified as either the background, the analyte center, or the analyte interior based on whether the first, second, and third likelihood scores are above a predetermined threshold likelihood score. In one implementation, the output identifies the analyte centers at centers of mass of respective ones of the analytes. In one implementation, in the output, subpixels classified as background are all assigned a same first predetermined value, subpixels classified as analyte centers are all assigned a same second predetermined value, and subpixels classified as analyte interior are all assigned a same third predetermined value. In one implementation, the first, second, and third predetermined values are intensity values. In one implementation, the first, second, and third predetermined values are continuous values.

In one implementation, the method includes determining location coordinates of subpixels classified as analyte centers on an analyte-by-analyte basis, downscaling the location coordinates by an upsampling factor used to prepare the input image data, and storing the downscaled location coordinates in memory on the analyte-by-analyte basis for use in base calling the analytes. In one implementation, the method includes determining location coordinates of subpixels classified as analyte interior on the analyte-by-analyte basis, downscaling the location coordinates by an upsampling factor used to prepare the input image data, and storing the downscaled location coordinates in memory on the analyte-by-analyte basis for use in base calling the analytes. In one implementation, the method includes, on the analyte-by-analyte basis, determining distances of the subpixels classified as analyte interior from respective ones of the subpixels classified as analyte centers, and storing the distances in the memory on the analyte-by-analyte basis for use in base calling the analytes. In one implementation, the method includes, on the analyte-by-analyte basis, extracting intensities from the subpixels classified as analyte interior, including using at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage, and storing the intensities in the memory on the analyte-by-analyte basis for use in base calling the analytes.

In one implementation, the input image data includes images in the sequence of image sets, and the images have a resolution of 3000×3000. In one implementation, the input image data includes at least one image patch from each of the images in the sequence of image sets, and the image patch covers a portion of the tile and has a resolution of 20×20. In one implementation, the input image data includes an upsampled representation of the image patch from each of the images in the sequence of image sets, and the upsampled representation has a resolution of 80×80. In one implementation, the output has an upsampled resolution of 80×80. In one implementation, the neural network is a deep fully convolutional segmentation neural network with an encoder subnetwork and a corresponding decoder network, followed by the classification layer, the encoder subnetwork includes a hierarchy of encoders, and the decoder subnetwork includes a hierarchy of decoders that map low resolution encoder feature maps to full input resolution feature maps for subpixel-wise classification by the classification layer. In one implementation, the density of the analytes ranges from about 100,000 analytes/mm$^2$ to about 1,000,000 analytes/mm$^2$. In another implementation, the density of the analytes ranges from about 1,000,000 analytes/mm$^2$ to about 10,000,000 analytes/mm$^2$.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Ternary Classification Model

We disclose a computer-implemented method of training a neural network to identify analytes and related analyte metadata. The method includes obtaining training data for training the neural network. The training data includes a plurality of training examples and corresponding ground truth data that should be generated by the neural network by processing the training examples. Each training example includes image data from a sequence of image sets. Each image in the sequence of image sets covers a tile of a flow cell and depicts intensity emissions of analytes on the tile and their surrounding background captured for a particular image channel at a particular one of a plurality of sequencing cycles of a sequencing run performed on the flow cell. Each ground truth data identifies spatial distribution of analytes and their surrounding background whose intensity emissions are depicted by the input image data, including analyte centers, analyte shapes, analyte sizes, and analyte boundaries. The ground truth data has a plurality of subpixels, and each subpixel in the plurality of subpixels is classified as either background, analyte center, or analyte interior. The method includes using a gradient descent training technique to train the neural network and generating outputs for the training examples that progressively match the ground truth data, including iteratively optimizing a loss function that minimizes error between the outputs and the ground truth data, and updating parameters of the neural network based on the error.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, upon error convergence after a final iteration, storing the updated parameters of the neural network in memory to be applied to further neural network-based template generation and base calling. In one implementation, in the ground truth data, subpixels classified as background are all assigned a same first predetermined class score, subpixels classified as analyte centers are all assigned a same second predetermined class score, and subpixels classified as analyte interior are all assigned a same third predetermined class score.

In one implementation, in each output, each subpixel has a first prediction score of being the background, a second prediction score of being the analyte center, and a third prediction score of being the analyte interior. In one implementation, the loss function is custom weighted ternary cross entropy loss and the error is minimized on a subpixel-basis between the prediction scores and the class scores of corresponding subpixels in the outputs and the ground truth data. In one implementation, the ground truth data identifies the analyte centers at centers of mass of respective ones of the analytes. In one implementation, in the ground truth data, subpixels classified as background are all assigned a same first predetermined value, subpixels classified as analyte centers are all assigned a same second predetermined value, and subpixels classified as analyte interior are all assigned a same third predetermined value. In one implementation, the first, second, and third predetermined values are intensity values. In one implementation, the first, second, and third predetermined values are continuous values. In one implementation, the image data includes images in the sequence of image sets, and the images have a resolution of 1800×1800. In one implementation, the image data includes images in the sequence of image sets, and the images have a resolution of 1800×1800.

In one implementation, the image data includes at least one image patch from each of the images in the sequence of image sets, and the image patch covers a portion of the tile and has a resolution of 20×20. In one implementation, the image data includes an upsampled representation of the image patch from each of the images in the sequence of image sets, and the upsampled representation of the image patch has a resolution of 80×80. In one implementation, in the training data, multiple training examples respectively include as image data different image patches from each image in a sequence of image sets of a same tile, and at least some of the different image patches overlap with each other. In one implementation, the ground truth data has an upsampled resolution of 80×80. In one implementation, the training data includes training examples for a plurality of tiles of the flow cell. In one implementation, the training data includes training examples for a variety of flow cells, sequencing instruments, sequencing protocols, sequencing chemistries, sequencing reagents, and analyte densities. In one implementation, the neural network is a deep fully convolutional segmentation neural network with an encoder subnetwork and a corresponding decoder network, followed by a classification layer, the encoder subnetwork includes a hierarchy of encoders, and the decoder subnetwork includes a hierarchy of decoders that map low resolution encoder feature maps to full input resolution feature maps for sub-pixel-wise classification by the classification layer.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Segmentation

We disclose a computer-implemented method of determining analyte metadata. The method includes processing input image data derived from a sequence of image sets through a neural network and generating an alternative representation of the input image data. The input image data has an array of units that depicts analytes and their surrounding background. The method includes processing the alternative representation through an output layer and generating an output value for each unit in the array. The method includes thresholding output values of the units and classifying a first subset of the units as background units depicting the surrounding background. The method includes locating peaks in the output values of the units and classifying a second subset of the units as center units containing centers of the analytes. The method includes applying a segmenter to the output values of the units and determining shapes of the analytes as non-overlapping regions of contiguous units separated by the background units and centered at the center units. The segmenter begins with the center units and determines, for each center unit, a group of successively contiguous units that depict a same analyte whose center is contained in the center unit.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. In one implementation, the output values are continuous values. In another implementation, the output values are softmax scores. In one implementation, the contiguous units in the respective ones of the non-overlapping regions have output values weighted according to distance of a contiguous unit from a center unit in a non-overlapping region to which the contiguous unit belongs. In one implementation, the center units have highest output values within the respective ones of the non-overlapping regions.

In one implementation, the non-overlapping regions have irregular contours and the units are subpixels. In such an implementation, the method includes determining analyte intensity of a given analyte by identifying subpixels that contribute to the analyte intensity of the given analyte based on a corresponding non-overlapping region of contiguous subpixels that identifies a shape of the given analyte, locating the identified subpixels in one or more optical, pixel-resolution images generated for one or more image channels at a current sequencing cycle, in each of the images, interpolating intensities of the identified subpixels, combining the interpolated intensities, and normalizing the combined interpolated intensities to produce a per-image analyte intensity for the given analyte in each of the images, and combining the per-image analyte intensity for each of the images to determine the analyte intensity of the given analyte at the current sequencing cycle. In one implementation, the normalizing is based on a normalization factor, and the normalization factor is a number of the identified subpixels. In one implementation, the method includes base calling the given analyte based on the analyte intensity at the current sequencing cycle.

In one implementation, the non-overlapping regions have irregular contours and the units are subpixels. In such an implementation, the method includes determining analyte intensity of a given analyte by identifying subpixels that contribute to the analyte intensity of the given analyte based on a corresponding non-overlapping region of contiguous subpixels that identifies a shape of the given analyte, locating the identified subpixels in one or more subpixel resolution images upsampled from corresponding optical, pixel-resolution images generated for one or more image channels at a current sequencing cycle, in each of the upsampled images, combining intensities of the identified subpixels and normalizing the combined intensities to produce a per-image analyte intensity for the given analyte in each of the upsampled images, and combining the per-image analyte intensity for each of the upsampled images to determine the analyte intensity of the given analyte at the current sequencing cycle. In one implementation, the normalizing is based on a normalization factor, and the normalization factor is a number of the identified subpixels. In one implementation, the method includes base calling the given analyte based on the analyte intensity at the current sequencing cycle.

In one implementation, each image in the sequence of image sets covers a tile, and depicts intensity emissions of analytes on a tile and their surrounding background captured for a particular image channel at a particular one of a plurality of sequencing cycles of a sequencing run performed on a flow cell. In one implementation, the input image data includes at least one image patch from each of the images in the sequence of image sets, and the image patch covers a portion of the tile and has a resolution of 20×20. In one implementation, the input image data includes an upsampled, subpixel resolution representation of the image patch from each of the images in the sequence of image sets, and the upsampled, subpixel representation has a resolution of 80×80.

In one implementation, the neural network is a convolutional neural network. In another implementation, the neural network is a recurrent neural network. In yet another implementation, the neural network is a residual neural network with residual bocks and residual connections. In yet further implementation, the neural network is a deep fully convolutional segmentation neural network with an encoder subnetwork and a corresponding decoder network, the encoder subnetwork includes a hierarchy of encoders, and the decoder subnetwork includes a hierarchy of decoders that map low resolution encoder feature maps to full input resolution feature maps.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Peak Detection

We disclose a computer-implemented method of determining analyte metadata. The method includes processing input image data derived from a sequence of image sets through a neural network and generating an alternative representation of the input image data. The input image data has an array of units that depicts analytes and their surrounding background. The method includes processing the alternative representation through an output layer and generating an output value for each unit in the array. The method includes thresholding output values of the units and classifying a first subset of the units as background units depicting the surrounding background. The method includes locating peaks in the output values of the units and classifying a second subset of the units as center units containing centers of the analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes applying a segmenter to the output values of the units and determining shapes of the analytes as non-overlapping regions of contiguous units separated by the background units and centered at the center units. The segmenter begins with the center units and determines, for each center unit, a group of successively contiguous units that depict a same analyte whose center is contained in the center unit.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Neural Network-Based Analyte Metadata Generator

In one implementation, a method includes processing image data through a neural network and generating an alternative representation of the image data. The image data depicts intensity emissions of analytes. The method includes processing the alternative representation through an output layer and generating an output that identifies metadata about the analytes, including at least one of spatial distribution of the analytes, shapes of the analytes, centers of the analytes, and/or boundaries between the analytes, i.e. analyte boundary/boundaries. Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Units-Based Regression Model

We disclose a computer-implemented method of identifying analytes on a tile of a flow cell and related analyte metadata. The method includes processing input image data from a sequence of image sets through a neural network and generating an alternative representation of the input image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through an output layer and generating an output that identifies analytes, whose intensity emissions are depicted by the input image data, as disjoint regions of adjoining units, centers of the analytes as center units at centers of mass of the respective ones of the disjoint regions, and their surrounding background as background units not belonging to any of the disjoint regions.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Units-Based Binary Classification Model

We disclose a computer-implemented method of identifying analytes on a tile of a flow cell and related analyte metadata. The method includes processing input image data from a sequence of image sets through a neural network and generating an alternative representation of the image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies centers of analytes whose intensity emissions are depicted by the input image data. The output has a plurality of units, and each unit in the plurality of units is classified as either an analyte center or a non-center.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Units-Based Ternary Classification Model We disclose a computer-implemented method of identifying analytes on a tile of a flow cell and related analyte metadata. The method includes processing input image data from a sequence of image sets through a neural network and generating an alternative representation of the image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies spatial distribution of analytes and their surrounding background whose intensity emissions are depicted by the input image data, including at least one of analyte centers, analyte shapes, analyte sizes, and/or analyte boundaries. The output has a plurality of units, and each unit in the plurality of units is classified as either background, analyte center, or analyte interior.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Base Calling—Single Analyte Distance Channel

We disclose a neural network-implemented method of base calling analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels. The method includes processing initial image sets respectively generated at initial ones of the plurality of sequencing cycles through a template generator to identify reference centers of the analytes in a template image. The method includes accessing one or more images in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles. The method includes registering each of the images in the current, preceding, and succeeding image sets with the template image to determine cycle-specific and image channel-specific transformations. The method includes applying the transformations to the reference centers of the analytes to identify transformed centers of the analytes in each of the images. The method includes for a particular one of the analytes being base called, extracting an image patch from each of the images in the current, preceding, succeeding image sets such that each image patch contains in its center pixel a transformed center of the particular one of the analytes identified in a respective one of the images, and depicts intensity emissions of the particular one of the analytes, of some adjacent ones of the analytes, and of their surrounding background in a corresponding one of the image channels. The method includes, for each image patch, generating distance information that identifies distances of its pixels' centers from the transformed center of the particular one of the analytes contained its center pixel. The method includes constructing input data by pixel-wise encoding the distance information into each image patch. The method includes convolving the input data through a convolutional neural network to generate a convolved representation of the input data. The method includes processing the convolved representation through an output layer to produce likelihoods of a base incorporated in the particular one of the analytes at the current one of the plurality of sequencing cycles being A, C, T, and G. The method includes classifying the base as A, C, T, or G based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, for each image patch, generating analyte-attribution information that identifies which of its pixels cover the particular one of the analytes and which of its pixels do not, and constructing the input data by pixel-wise encoding the analyte-attribution information into each image patch In one implementation, the pixels that cover the particular one of the analytes are assigned a non-zero value in the analyte-attribution information. In one implementation, the pixels that do not cover the particular one of the analytes are assigned a zero value in the analyte-attribution information. In one implementation, the method includes providing as input to the convolutional neural network position coordinates of the transformed centers of the analytes. In one such implementation, the input is fed to a first layer of the convolutional neural network. In another such implementation, the input is fed to one or more intermediate layers of the convolutional neural network. In yet another such implementation, the input is fed to a final layer of the convolutional neural network. In one implementation, the method includes providing as input to the convolutional neural network an intensity scaling channel that has scaling values corresponding to pixels of the image patch. In such an implementation, the scaling values are based on a mean intensity of the center pixel of the image patch containing the center of the particular one of the analytes. In one implementation, the intensity scaling channel pixel-wise includes a same scaling value for all the pixels of the image patch. In one implementation, the mean intensity of the center pixel is determined for each of the corresponding one of the image channels.

In one implementation, the mean intensity of the center pixel is determined for a first image channel by averaging intensity values of the center pixel observed during two or more preceding sequencing cycles that produced an A and a T base call for the particular one of the analytes. In one implementation, the mean intensity of the center pixel is determined for a second image channel by averaging intensity values of the center pixel observed during the two or more preceding sequencing cycles that produced an A and a C base call for the particular one of the analytes. In one implementation, the mean intensity of the center pixel is determined for a first image channel by averaging intensity values of the center pixel observed during the two or more preceding sequencing cycles that produced an A base call for the particular one of the analytes. In one implementation, the mean intensity of the center pixel is determined for a second image channel by averaging intensity values of the center pixel observed during the two or more preceding sequencing cycles that produced a G base call for the particular one of the analytes. In one implementation, the mean intensity of the center pixel is determined for a third image channel by averaging intensity values of the center pixel observed during the two or more preceding sequencing cycles that produced a T base call for the particular one of the analytes. In one implementation, the mean intensity of the center pixel is determined for a third image channel by averaging intensity values of the center pixel observed during the two or more preceding sequencing cycles that produced a C base call for the particular one of the analytes.

In one implementation, the sequencing run implements paired-end sequencing that sequences both ends of fragments in the analytes in a forward direction and a reverse direction using a first read primer and a second read primer, thereby producing a read pair for each fragment, the read pair having a forward read and a reverse read. In one implementation, the both ends of the fragments are sequenced serially to produce the forward and reverse reads one after the other. In one implementation, the both ends of the fragments are sequenced simultaneously to produce the forward and reverse reads concurrently. In one implementation, the forward and reverse reads each contain one or more of the fragments. In one implementation, the one or more of the fragments are sequenced serially. In one implementation, the one or more of the fragments are sequenced simultaneously. In one implementation, the sequencing run implements single-read sequencing that sequences the fragments in one direction using a single read primer. In one implementation, the sequencing run implements circular sequencing that sequences double stranded copies of the fragments in a loop, and the loop iterates over a double stranded copy of a given fragment multiple times. In one implementation, the sequencing run implements stacked sequencing that sequences stacked copies of the fragments, and the stacked copies of a given fragment are stacked vertically or horizontally. In one implementation, the size of the image patch ranges from 3×3 pixels to 10000×10000 pixels.

In one implementation, the transformed center is a floating point coordinate value. In such an implementation, the method includes rounding the floating point coordinate value using a rounding operation to produce an integer coordinate value for the transformed center, and identifying the center pixel based on an overlap between its integer coordinates and the integer coordinate value produced for the transformed center. In one implementation, the rounding operation is at least one of floor function, ceil function, and/or round function. In one implementation, the rounding operation is at least one of integer function and/or integer plus sign function. In one implementation, the template generator is a neural network-based template generator. In one implementation, the output layer is a softmax layer, and the likelihoods are exponentially normalized score distribution of the base incorporated in the particular one of the analytes at the current one of the plurality of sequencing cycles being A, C, T, and G.

In one implementation, each one of the image channels is one of a plurality of filter wavelength bands. In another implementation, each one of the image channels is one of a plurality of image events. In one implementation, the flow cell has at least one patterned surface with an array of wells that occupy the analytes. In another implementation, the flow cell has at least one nonpatterned surface and the analytes are unevenly scattered over the nonpatterned surface. In one implementation, the image set has four images. In another implementation, the image set has two images. In yet another implementation, the image set has one image. In one implementation, the sequencing run utilizes four-channel chemistry. In another implementation, the sequencing run utilizes two-channel chemistry. In yet another implementation, the sequencing run utilizes one-channel chemistry.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized during a sequencing run. The method includes convolving input data through a convolutional neural network to generate a convolved representation of the input data. The input data includes image patches extracted from one or more images in each of a current image set generated at a current sequencing cycle of the sequencing run, of one or more preceding image sets respectively generated at one or more sequencing cycles of the sequencing run preceding the current sequencing cycle, and of one or more succeeding image sets respectively generated at one or more sequencing cycles of the sequencing run succeeding the current sequencing cycle. Each of the image patches depicts intensity emissions of a target analyte being base called, of some adjacent analytes, and of their surrounding background in a corresponding image channel. The input data further includes distance information which is pixel-wise encoded in each of the image patches to identify distances of an image patch's pixels' centers from a center of the target analyte located in a center pixel of the image patch. The method includes processing the convolved representation through an output layer to produce an output. The method includes base calling the target analyte at the current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes processing the convolved representation through the output layer to produce likelihoods of a base incorporated in the target analyte at the current sequencing cycle being A, C, T, and G, and classifying the base as A, C, T, or G based on the likelihoods. In one implementation, the likelihoods are exponentially normalized scores produced by a softmax layer.

In one implementation, the method includes deriving, from the output, an output pair for the target analyte that identifies a class label of a base incorporated in the target analyte at the current sequencing cycle being A, C, T, or G, and base calling the target analyte based on the class label. In one implementation, a class label of 1, 0 identifies an A base, a class label of 0, 1 identifies a C base, a class label of 1, 1 identifies a T base, and a class label of 0, 0 identifies a G base. In another implementation, a class label of 1, 1 identifies an A base, a class label of 0, 1 identifies a C base, a class label of 0.5, 0.5 identifies a T base, and a class label of 0, 0 identifies a G base. In yet another implementation, a class label of 1, 0 identifies an A base, a class label of 0, 1 identifies a C base, a class label of 0.5, 0.5 identifies a T base, and a class label of 0, 0 identifies a G base. In yet further implementation, a class label of 1, 2 identifies an A base, a class label of 0, 1 identifies a C base, a class label of 1, 1 identifies a T base, and a class label of 0, 0 identifies a G base. In one implementation, the method includes deriving, from the output, a class label for the target analyte that identifies a base incorporated in the target analyte at the current sequencing cycle being A, C, T, or G, and base calling the target analyte based on the class label. In one implementation, a class label of 0.33 identifies an A base, a class label of 0.66 identifies a C base, a class label of 1 identifies a T base, and a class label of 0 identifies a G base. In another implementation, a class label of 0.50 identifies an A base, a class label of 0.75 identifies a C base, a class label of 1 identifies a T base, and a class label of 0.25 identifies a G base. In one implementation, the method includes deriving, from the output, a single output value, comparing the single output value against class value ranges corresponding to bases A, C, T, and G, based on the comparing, assigning the single output value to a particular class value range, and base calling the target analyte based on the assigning. In one implementation, the single output value is derived using a sigmoid function, and the single output value ranges from 0 to 1. In another implementation, a class value range of 0-0.25 represents an A base, a class value range of 0.25-0.50 represents a C base, a class value range of 0.50-0.75 represents a T base, and a class value range of 0.75-1 represents a G base.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels. The method includes processing initial image sets respectively generated at initial ones of the plurality of sequencing cycles through a template generator to identify reference centers of the analytes in a template image. The method includes accessing one or more images in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles. The method includes registering each of the images in the current, preceding, and succeeding image sets with the template image to determine cycle-specific and image channel-specific transformations. The method includes applying the transformations to the reference centers of the analytes to identify transformed centers of the analytes in each of the images. The method includes, for a particular one of the analytes being base called, extracting an image patch from each of the images in the current, preceding, succeeding image sets such that each image patch contains in its center pixel a transformed center of the particular one of the analytes identified in a respective one of the images, and depicts intensity emissions of the particular one of the analytes, of some adjacent ones of the analytes, and of their surrounding background in a corresponding one of the image channels. The method includes, for each image patch, generating distance information that identifies distances of its pixels' centers from the transformed center of the particular one of the analytes contained its center pixel. The method includes constructing input data by pixel-wise encoding the distance information into each image patch. The method includes convolving the input data through a convolutional neural network to generate a convolved representation of the input data. The method includes processing the convolved representation through an output layer to produce an output. The method includes base calling the particular one of the analytes at the current one of the plurality of sequencing cycles based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes processing the convolved representation through the output layer to produce likelihoods of a base incorporated in the particular one of the analytes at the current one of the plurality of sequencing cycles being A, C, T, and G, and classifying the base as A, C, T, or G based on the likelihoods.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, computer-implemented method includes processing input data through a neural network and producing an alternative representation of the input data. The input data includes per-cycle image data for each of one or more sequencing cycles of a sequencing run. The per-cycle image data depicts intensity emissions of one or more analytes and their surrounding background captured at a respective sequencing cycle. The method includes processing the alternative representation through an output layer and producing an output. The method includes base calling one or more of the analytes at one or more of the sequencing cycles based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes accompanying the per-cycle image data with supplemental distance information that identifies distances between pixels of the per-cycle image data and one or more of the analytes. In such an implementation, the distances incorporate context about centers, shapes, and/or boundaries of one or more of the analytes in the processing by the neural network and the output layer. In one implementation, the method includes accompanying the per-cycle image data with supplemental scaling information that assigns scaling values to the pixels of the per-cycle image data. In such an implementation, the scaling values account for variance in intensities of one or more of the analytes.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Base Calling—Multi-Analyte Distance Channel

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch has pixel intensity data for pixels that cover a plurality of analytes and their surrounding background, and pixel distance data that identifies each pixel's center-to-center distance from a nearest one of the analytes selected based on center-to-center distances between the pixel and each of the analytes. The method includes convolving the input data through a convolutional neural network to generate a convolved representation of the input data. The method includes processing the convolved representation through an output layer to produce a score distribution for each of the analytes that identifies likelihoods of a base incorporated in a respective one of the analytes at a current sequencing cycle being A, C, T, and G. The method includes base calling each of the analytes based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the pixel distance data is pixel-wise encoded into each image patch. In one implementation, the center-to-center distance is derived from a distance formula that uses position coordinates of transformed centers of the analytes and position coordinates of pixel centers.

In one implementation, the method includes providing as input to the convolutional neural network intensity scaling channels that have scaling values corresponding to pixels of each image patch, and the scaling values are based on a combination of mean intensities of center pixels in each image patch that contain the transformed centers of the analytes. In one implementation, the intensity scaling channels pixel-wise apply same scaling values to the pixel intensity data of all the pixels of an image patch. In one implementation, the intensity scaling channels pixel-wise apply different scaling values to the pixel intensity data of the pixels of the image patch on a pixel neighborhood basis such that a first scaling value derived from a mean intensity of a first center pixel is applied to a first pixel neighborhood of adjoining pixels that are successively contiguous to the first center pixel, and another scaling value derived from a mean intensity of another center pixel is applied to another pixel neighborhood of adjoining pixels that are successively contiguous to the another center pixel. In one implementation, the pixel neighborhood is a m×n pixel patch centered at the center pixels, and the pixel patch is 3×3 pixels. In one implementation, the pixel neighborhood is a n-connected pixel neighborhood centered at the center pixels. In one implementation, the mean intensities of the center pixels are determined for each of the corresponding one of the image channels. In one implementation, the mean intensities of the center pixels are determined for a first image channel by averaging intensity values of the center pixels observed during two or more preceding sequencing cycles that produced an A and a T base call for respective ones of the analytes. In one implementation, the mean intensities of the center pixels are determined for a second image channel by averaging intensity values of the center pixel observed during the two or more preceding sequencing cycles that produced an A and a C base call for respective ones of the analytes. In one implementation, the mean intensities of the center pixels are determined for a first image channel by averaging intensity values of the center pixel observed during the two or more preceding sequencing cycles that produced an A base call for respective ones of the analytes. In one implementation, the mean intensities of the center pixels are determined for a second image channel by averaging intensity values of the center pixel observed during the two or more preceding sequencing cycles that produced a G base call for respective ones of the analytes. In one implementation, the mean intensities of the center pixels are determined for a third image channel by averaging intensity values of the center pixel observed during the two or more preceding sequencing cycles that produced a T base call for respective ones of the analytes. In one implementation, the mean intensities of the center pixels are determined for a third image channel by averaging intensity values of the center pixel observed during the two or more preceding sequencing cycles that produced a C base call for respective ones of the analytes. In one implementation, the method includes, for each image patch, generating analyte-attribution information that identifies which of its pixels cover the analytes and which of its pixels do not, and constructing the input data by pixel-wise encoding the analyte-attribution information into each image patch In one implementation, the pixels that cover the analytes are assigned a non-zero value in the analyte-attribution information. In one implementation, the pixels that do not cover the analytes are assigned a zero value in the analyte-attribution information. In one implementation, the size of each image patch ranges from 3×3 pixels to 10000×10000 pixels. In one implementation, the output layer is a softmax layer, and the score distribution is an exponentially normalized score distribution.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch has pixel intensity data for pixels that cover a plurality of analytes and their surrounding background, and pixel distance data that identifies each pixel's center-to-center distance from a nearest one of the analytes selected based on center-to-center distances between the pixel and each of the analytes. The method includes convolving the input data through a convolutional neural network to generate a convolved representation of the input data. The method includes processing the convolved representation through an output layer to produce an output. The method includes base calling each of the analytes at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes deriving, from the output, a score distribution for each of the analytes that identifies likelihoods of a base incorporated in a respective one of the analytes at the current sequencing cycle being A, C, T, and G, and base calling each of the analytes based on the likelihoods. In one implementation, the output layer is a softmax layer, and the score distribution is an exponentially normalized score distribution. In one implementation, the method includes deriving, from the output, an output pair for each of the analytes that identifies a class label of a base incorporated in a respective one of the analytes at the current sequencing cycle being A, C, T, and G, and base calling each of the analytes based on the class label. In one implementation, the method includes deriving, from the output, a single output value, comparing the single output value against class value ranges corresponding to bases A, C, T, and G, based on the comparing, assigning the single output value to a particular class value range, and base calling each of the analytes based on the assigning. In one implementation, the single output value is derived using a sigmoid function, and the single output value ranges from 0 to 1.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Base Calling—Multi-Analyte Shape-Based Distance Channel

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch depicts intensity emissions of a plurality of analytes and their surrounding background using analyte pixels that depict analyte intensities and background pixels that depict background intensities. Each image patch is encoded with analyte distance data that identifies each analyte pixel's center-to-center distance from an assigned one of the analytes selected based on classifying each analyte pixel to only one of the analytes. The method includes convolving the input data through a convolutional neural network to generate a convolved representation of the input data. The method includes processing the convolved representation through an output layer to produce a score distribution for each of the analytes that identifies likelihoods of a base incorporated in a respective one of the analytes at a current sequencing cycle being A, C, T, and G. The method includes base calling each of the analytes based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the analytes have irregular shapes that span multiple analyte pixels and pixel-to-analyte classification is based on the irregular shapes. In one implementation, all background pixels are assigned a same minimum center-to-center distance in the analyte distance data. In one implementation, all background pixels are assigned a same minimum intensity. In one implementation, each analyte pixel is classified to only one of the analytes based on a decay map produced by a neural network-based template generator. In such an implementation, the decay map identifies the analytes as disjointed regions of adjoining pixels, centers of the analytes as center pixels at centers of mass of the respective ones of the disjointed regions, and their surrounding background as background pixels not belonging to any of the disjointed regions. In one implementation, the adjoining pixels in the respective ones of the disjointed regions have intensity values weighted according to distance of an adjoining pixel from a center pixel in a disjointed region to which the adjoining pixel belongs. In one implementation, the adjoining pixels in the respective ones of the disjointed regions are categorized as analyte interior pixels belonging to and co-depicting a same analyte and stored in memory on an analyte-by-analyte basis. In one implementation, the center pixels have highest intensity values within the respective ones of the disjointed regions. In one implementation, the background pixels all have a same lowest intensity value in the decay map. In one implementation, the analyte distance data is pixel-wise encoding into each image patch. In one implementation, the center-to-center distance is derived from a distance formula that uses position coordinates of transformed centers of the analytes and position coordinates of pixel centers. In one implementation, the transformed centers of the analytes are derived by applying cycle-specific and image channel-specific transformations to the centers of the analytes identified by the decay map.

In one implementation, the method includes providing as input to the convolutional neural network intensity scaling channels that have scaling values corresponding to pixels of each image patch In such an implementation, the scaling values are based on a combination of mean intensities of center pixels in each image patch that contain the transformed centers of the analytes. In one implementation, the intensity scaling channels pixel-wise apply different scaling values to the pixel intensity data of the pixels of an image patch on a pixel group basis such that a first scaling value derived from a mean intensity of a first center pixel containing a center of a first analyte is applied to a first pixel group of adjoining pixels that belong to and co-depict the first analyte, and another scaling value derived from a mean intensity of another center pixel containing a center of another analyte is applied to another pixel group of adjoining pixels that belong to and co-depict the another analyte. In one implementation, the mean intensities of the center pixels are determined for each of the corresponding one of the image channels. In one implementation, the method includes, for each image patch, generating analyte-attribution information that identifies which of its pixels cover the analytes and which of its pixels do not, and constructing the input data by pixel-wise encoding the analyte-attribution information into each image patch. In one implementation, the pixels that cover the analytes are assigned a non-zero value in the analyte-attribution information. In another implementation, the pixels that do not cover the analytes are assigned a zero value in the analyte-attribution information.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-implemented method of base calling analytes synthesized during a sequencing run. The method includes accessing input data that includes a sequence of per-cycle image patch sets generated for a series of sequencing cycles of a sequencing run. Each per-cycle image patch set in the sequence has an image patch for a respective one of one or more image channels. Each image patch depicts intensity emissions of a plurality of analytes and their surrounding background using analyte pixels that depict analyte intensities and background pixels that depict background intensities. Each image patch is encoded with analyte distance data that identifies each analyte pixel's center-to-center distance from an assigned one of the analytes selected based on classifying each analyte pixel to only one of the analytes. The method includes convolving the input data through a convolutional neural network to generate a convolved representation of the input data. The method includes processing the convolved representation through an output layer to produce an output. The method includes base calling each of the analytes at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Specialized Architecture

We disclose a network-implemented method of base calling analytes using sequencing images that have registration error with respect to each other. The method includes accessing a sequence of per-cycle image patch sets generated for a series of sequencing cycles of a sequencing run. The sequence has registration error between image patches across the per-cycle image patch sets and within the per-cycle image patch sets. Each image patch in the sequence depicts intensity information of a target analyte being base called, of some adjacent analytes, and of their surrounding background in a corresponding image channel at a corresponding sequencing cycle in the series. Each image patch in the sequence is pixel-wise encoded with distance information that identifies distances of its pixels' centers from a center of the target analyte located in its center pixel. The method includes separately processing each per-cycle image patch set through a first convolutional subnetwork to produce an intermediate convolved representation for each sequencing cycle, including applying convolutions that combine the intensity and distance information and combine resulting convolved representations only within a sequencing cycle and not between sequencing cycles. The method includes groupwise processing intermediate convolved representations for successive sequencing cycles in the series through a second convolutional subnetwork to produce a final convolved representation for the series, including applying convolutions that combine the intermediate convolved representations and combine resulting convolved representations between the sequencing cycles. The method includes processing the final convolved representation through an output layer to produce an output. The method includes base calling the target analyte at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, each image patch in the sequence has pixel intensity data for pixels that cover a plurality of analytes and their surrounding background, and pixel distance data that identifies each pixel's center-to-center distance from a nearest one of the analytes selected based on center-to-center distances between the pixel and each of the analytes. In such an implementation, the method includes base calling each of the analytes at the current sequencing cycle based on the output. In one implementation, each image patch in the sequence depicts intensity emissions of a plurality of analytes and their surrounding background using analyte pixels that depict analyte intensities and background pixels that depict background intensities, and is encoded with analyte distance data that identifies each analyte pixel's center-to-center distance from an assigned one of the analytes selected based on classifying each analyte pixel to only one of the analytes. In such an implementation, the method includes base calling each of the analytes at the current sequencing cycle based on the output. In one implementation, the method includes providing as input to the first convolutional subnetwork position coordinates of the target analyte and/or the adjacent analytes. In one implementation, the method includes providing as input to the second convolutional subnetwork position coordinates of the target analyte and/or the adjacent analytes. In one implementation, the method includes providing as input to the output layer position coordinates of the target analyte and/or the adjacent analytes.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a network-implemented method of base calling analytes using image data with registration error. The method includes accessing input data for a series of sequencing cycles of a sequencing run. The input data has an image tensor for each sequencing cycle. Each image tensor has data for one or more image channels, including, for each image channel, pixel intensity data for pixels covering a target analyte being base called, some adjacent analytes, and surrounding background, and pixel distance data for distances from a center of the target analyte to centers of the pixels. The input data has cross-cycle registration error between pixels across the image tensors and cross-image channel registration error between pixels within the image tensors. The method includes separately processing each input tensor through a spatial convolutional network with a sequence of spatial convolution layers to produce a spatially convolved representation for each sequencing cycle, including beginning with a first spatial convolution layer that combines the pixel intensities and distances only within a sequencing cycle and not between sequencing cycles, and continuing with successive spatial convolution layers that combine outputs of preceding spatial convolution layers only within each sequencing cycle in the series of sequencing cycles and not between the sequencing cycles. The method includes groupwise processing spatially convolved representations for successive sequencing cycles through a temporal convolutional network with a sequence of temporal convolution layers to produce a temporally convolved representation for the series, including beginning with a first temporal convolution layer that combines the spatially convolved representations between the sequencing cycles in the series of sequencing cycles, and continuing with successive temporal convolution layers that combine successive outputs of preceding temporal convolution layers. The method includes processing the temporally convolved representation through an output layer to produce an output. The method includes base calling the target analyte at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the groupwise processing further includes convolving over successive intermediate convolved representations within overlapping sliding windows. In one implementation, the successive temporal convolution layers combine the successive outputs within overlapping sliding windows. In one implementation, the pixel distance data is pixel-wise encoding into each image tensor. In one implementation, each image tensor in the sequence has pixel intensity data for pixels that cover a plurality of analytes and their surrounding background, and pixel distance data that identifies each pixel's center-to-center distance from a nearest one of the analytes selected based on center-to-center distances between the pixel and each of the analytes. In one implementation, the method includes base calling each of the analytes at the current sequencing cycle based on the output. In one implementation, each image tensor in the sequence depicts intensity emissions of a plurality of analytes and their surrounding background using analyte pixels that depict analyte intensities and background pixels that depict background intensities, and is encoded with analyte distance data that identifies each analyte pixel's center-to-center distance from an assigned one of the analytes selected based on classifying each analyte pixel to only one of the analytes. In one implementation, the method includes base calling each of the analytes at the current sequencing cycle based on the output. In one implementation, the method includes providing as input to the first convolutional subnetwork position coordinates of the target analyte and/or the adjacent analytes. In one implementation, the method includes providing as input to the second convolutional subnetwork position coordinates of the target analyte and/or the adjacent analytes. In one implementation, the method includes providing as input to the output layer position coordinates of the target analyte and/or the adjacent analytes.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Reframing

We disclose a neural network-implemented method of base calling analytes synthesized during a sequencing run. The method includes accessing a sequence of per-cycle image patch sets generated for a series of sequencing cycles of a sequencing run. Each per-cycle image patch set in the sequence has an image patch for a respective one of one or more image channels. Each image patch has pixel intensity data for pixels covering a target analyte being base called, some adjacent analytes, and surrounding background. The method includes reframing the pixels of each image patch to center a center of the target analyte in a center pixel. The method includes convolving reframed image patches through a convolutional neural network to generate a convolved representation of the reframed image patches. The method includes processing the convolved representation through an output layer to produce an output. The method includes base calling the target analyte at a current sequencing cycle based on the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the reframing further includes intensity interpolation of the pixels of each image patch to compensate for the reframing. In one implementation, the intensity interpolation further includes at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. In one implementation, prior to the reframing, the center of the target analyte is located in the center pixel of each image patch at an offset from a center of the center pixel. In one implementation, the reframing further includes requiring that non-center pixels of each image patch are equidistant from respective centers of the target analyte. In one implementation, each image patch in the sequence has pixel intensity data for pixels that depict a plurality of analytes and their surrounding background, and pixel distance data that identifies each pixel's center-to-center distance from a nearest one of the analytes selected based on center-to-center distances between the pixel and each of the analytes. In one implementation, the method includes base calling each of the analytes at the current sequencing cycle based on the output. In one implementation, each image patch in the sequence depicts intensity emissions of a plurality of analytes and their surrounding background using analyte pixels that depict analyte intensities and background pixels that depict background intensities, and is encoded with analyte distance data that identifies each analyte pixel's center-to-center distance from an assigned one of the analytes selected based on classifying each analyte pixel to only one of the analytes. In one implementation, the method includes base calling each of the analytes at the current sequencing cycle based on the output. In one implementation, the method includes providing as input to the first convolutional subnetwork position coordinates of the target analyte and/or the adjacent analytes. In one implementation, the method includes providing as input to the second convolutional subnetwork position coordinates of the target analyte and/or the adjacent analytes. In one implementation, the method includes providing as input to the output layer position coordinates of the target analyte and/or the adjacent analytes.

We disclose a neural network-implemented method of base calling analytes on a flow cell. The method includes accessing a sequence of image sets generated over a plurality of sequencing cycles of a sequencing run that synthesizes the analytes on the flow cell. Each image in the sequence of image sets covers a non-overlapping region of the flow cell and depicts intensity emissions of a subset of the analytes on the non-overlapping region and their surrounding background captured in a corresponding image channel at a respective one of the plurality of sequencing cycles. The method includes determining a nucleotide base (A, C, T, or G) incorporated at a particular one of the plurality of sequencing cycles in a particular one of the subset of the analytes by selecting, from the sequence of image sets, a current image set generated at the particular one of the plurality of sequencing cycles, one or more preceding image sets respectively generated at one or more of the plurality of sequence cycles preceding the particular one of the plurality of sequencing cycles, and one or more succeeding image sets respectively generated at one or more of the plurality of sequencing cycles succeeding the particular one of the plurality of sequencing cycles. The method includes extracting images patches from images in each of the selected image sets. The images patches are centered at the particular one of the subset of the analytes and include additional adjacent analytes from the subset of the analytes. The method includes convolving the image patches through one or more layers of a convolutional neural network to generate a convolved representation of the image patches. The method includes processing the convolved representation through an output layer to produce likelihoods for the nucleotide base being A, C, T, and G. The method includes classifying the nucleotide base as A, C, T, or G based on the likelihoods.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes producing a sequence of base calls for the particular one of the subset of the analytes over the plurality of sequencing cycles by iterating the selecting, the extracting, the convolving, the processing, and the classifying for each of the plurality of sequencing cycles. In one implementation, the method includes producing a sequence of base calls for a plurality of analytes in the subset over the plurality of sequencing cycles by iterating the selecting, the extracting, the convolving, the processing, and the classifying for each of the plurality of sequencing cycles for each of the plurality of analytes in the subset. In one implementation, the non-overlapping region of the flow cell is a tile. In one implementation, the corresponding image channel is one of a plurality of filter wavelength bands. In one implementation, the corresponding image channel is one of a plurality of image events.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Simultaneously Base Calling Multiple Clusters at Multiple Cycles

We disclose a neural network-implemented method of base calling analytes on a flow cell. The method includes obtaining input image data from a sequence of image sets. The sequence of image sets is generated over a plurality of sequencing cycles of a sequencing run that synthesizes the analytes on the flow cell. Each image in the sequence of image sets covers a non-overlapping region of the flow cell and depicts intensity emissions of a subset of the analytes on the non-overlapping region and their surrounding background captured in a corresponding image channel at a respective one of the plurality of sequencing cycles. The method includes processing the input image data through one or more layers of a neural network to generate an alternative representation of the input image data. The method includes processing the alternative representation through an output layer to generate an output that identifies a nucleotide base (A, C, T, or G) incorporated in at least some of the analytes in the subset at each of the each of the plurality of sequencing cycles, thereby producing a sequence of base calls for each of the at least some of the analytes in the subset over the plurality of sequencing cycles.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the output layer is a softmax layer, and the output is an exponentially normalized score distribution of the nucleotide base incorporated at each of the plurality of sequencing cycles in each of the at least some of the analytes in subset being A, C, T, and G. In one implementation, the input image data includes images in the sequence of image sets. In one implementation, the input image data includes at least one image patch from each of the images in the sequence of image sets. In one implementation, the neural network is a convolutional neural network. In another implementation, the neural network is a residual neural network. In yet another implementation, the neural network is a recurrent neural network.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Recurrent Convolution-Based Base Calling

We disclose a neural network-based system for base calling. The system comprises a hybrid neural network with a recurrent module and a convolution module. The recurrent module uses inputs from the convolution module. The convolution module processes image data for a series of sequencing cycles of a sequencing run through one or more convolution layers and produces one or more convolved representations of the image data. The image data depicts intensity emissions of one or more analytes and their surrounding background. The recurrent module produces current hidden state representations based on convolving the convolved representations and previous hidden state representations. The output module produces a base call for at least one of the analytes and for at least one of the sequencing cycles based on the current hidden state representations.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

We disclose a neural network-implemented method of base calling. The method includes separately processing each per-cycle input data in a sequence of per-cycle input data through a cascade of convolution layers of a convolutional neural network. The sequence of per-cycle input data is generated for a series of sequencing cycles of a sequencing run, and each per-cycle input data includes image channels that depict intensity emissions of one or more analytes and their surrounding background captured at a respective sequencing cycle. The method includes, for each sequencing cycle, based on the separate processing, producing a convolved representation at each of the convolution layers, thereby producing a sequence of convolved representations, mixing its per-cycle input data with its corresponding sequence of convolved representations and producing a mixed representation, and flattening its mixed representation and producing a flattened mixed representation. The method includes arranging flattened mixed representations of successive sequencing cycles as a stack. The method includes processing the stack in forward and backward directions through a recurrent neural network that convolves over a subset of the flattened mixed representations in the stack on a sliding window basis, with each sliding window corresponding to a respective sequencing cycle, and successively produces a current hidden state representation at each time step for each sequencing cycle based on (i) the subset of the flattened mixed representations in a current sliding window over the stack and (ii) a previous hidden state representation. The method includes base calling each of the analytes at each of the sequencing cycles based on results of processing the stack in forward and backward directions. The recurrent neural network can be a gated recurrent neural network, such as an LSTM and a GRU.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

The method includes base calling each of the analytes at a given sequencing cycle by combining forward and backward current hidden state representations of the given sequencing cycle on a time step-basis and producing a combined hidden state representation, processing the combined hidden state representation through one or more fully-connected networks and producing a dense representation, processing the dense representation through a softmax layer to produce likelihoods of bases incorporated in each of the analytes at the given sequencing cycle being A, C, T, and G, and classifying the bases as A, C, T, or G based on the likelihoods. In one implementation, the combining includes concatenation. In another implementation, the combining includes summation. In yet another implementation, the combining includes averaging.

In one implementation, each per-cycle input data includes distance channels that supplement the image channels and contain center-to-center distances between pixels in the corresponding image channels and one or more analyte centers. In one implementation, each per-cycle input data includes a scaling channel that supplements the image channels and contains scaling values based on mean intensities of one or more pixels in the image channels. In one implementation, the mixing further includes concatenating the convolved representations and the per-cycle input data. In one implementation, the mixing further includes summing the convolved representations and the per-cycle input data. In one implementation, the flattened mixed representation is a two-dimensional array. In one implementation, the subset of the flattened mixed representations is a three-dimensional volume. In one implementation, the recurrent neural network applies three-dimensional convolutions to the three-dimensional volume. In one implementation, the three-dimensional convolutions use SAME padding. In one implementation, the convolution layers use SAME padding. In one implementation, the recurrent neural network is a long short-term memory (LSTM) network that comprises an input gate, an activation gate, a forget gate, and an output gate. In such an implementation, the method includes processing (i) the subset of the flattened mixed representations in the current sliding window over the stack and (ii) the previous hidden state representation through the input gate, the activation gate, the forget gate, and the output gate and producing the current hidden state representation at each time step for each sequencing cycle. The input gate, the activation gate, the forget gate, and the output gate apply convolutions on (i) the subset of the flattened mixed representations in the current sliding window over the stack and (ii) the previous hidden state representation.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a neural network-implemented method of base calling includes convolving image data for a series of sequencing cycles of a sequencing run through one or more convolution layers of a convolution module and producing one or more convolved representations of the image data. The image data depicts intensity emissions of one or more analytes and their surrounding background. The method includes convolving the convolved representations and previous hidden state representations through a recurrent module and producing current hidden state representations. The method includes processing the current hidden state representations through an output module and producing a base call for at least one of the analytes and for at least one of the sequencing cycles.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Inferring Quality Scores

We disclose a computer-implemented method of assigning quality scores to bases called by a neural network-based base caller. The method includes quantizing classification scores of predicted base calls produced by the neural network-based base caller in response to processing training data during training. The method includes determining a fit between the quantized classification scores and their base calling error rates. That is, for each quantized classification score, a set of training examples in the training data that are assigned the quantized classification score is determined. For each training example in the determined set of training examples, the predicted base call for the training example is compared to the ground truth base call for the training example and an error rate is determined from the comparison across the determined set of training examples to provide the error rate for the particular quantized classification score. The method includes correlating the quality scores to the quantized classification scores based on the fit.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the set of quantized classification scores includes a subset of the classification scores of predicted base calls produced by the neural network-based base caller in response to processing the training data during the training, and the classification scores are real numbers. In one implementation, the set of quantized classification scores includes all the classification scores of predicted base calls produced by the neural network-based base caller in response to processing the training data during the training, and the classification scores are real numbers. In one implementation, the classification scores are exponentially normalized softmax scores that sum to unity and are produced by a softmax output layer of the neural network-based base caller. In one implementation, the set of quantized classification scores is selected based on a selection formula defined as $$0.9 \sum_{i=1}^{n} 0.1^{(i-1)}$$

and applied to the softmax scores. In one implementation, the set of quantized classification scores is selected based on a selection formula defined as $$\bigvee_{i=1}^{n=10} 0.1i$$

and applied to the softmax scores. In one implementation, the method includes, based on the correlation, assigning the quality scores to bases called by the neural network-based base caller during inference. In one implementation, the method includes assigning the quality scores based on applying a quality score correspondence scheme to the bases called by the neural network-based base caller during the inference. In such an implementation, the scheme maps ranges of classification scores, produced by the neural network-based base caller in response to processing inference data, during the inference, to corresponding quantized classification scores in the set. In one implementation, the method includes, during the inference, stopping base calling an analyte whose quality score is below a set threshold for a current base calling cycle. In one implementation, the method includes, during the inference, stopping base calling an analyte whose average quality score is below a set threshold after successive base calling cycles. In one implementation, a sample size used for comparing the predicted base calls to the corresponding ground truth base calls is specific to each quantized classification score. In one implementation, a sample size used for comparing the predicted base calls to the corresponding ground truth base calls is specific to each quantized classification score. In one implementation, the fit is determined using a regression model. In one implementation, the method includes for each quantized classification score, determining a base calling accuracy rate by comparing its predicted base calls to corresponding ground truth base calls, and determining the fit between the quantized classification scores and their base calling accuracy rates. In one implementation, the corresponding ground truth base calls are derived from well-characterized human and non-human samples sequenced on a number of sequencing instruments, sequencing chemistries, and sequencing protocols.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Predicting Quality Scores

We disclose a neural network-based quality scorer that runs on numerous processors operating in parallel and is coupled to memory. The system comprises a convolutional neural network running on the numerous processors. The convolutional neural network is trained on training examples comprising data from sequencing images and labeled with base call quality ground truths using a backpropagation-based gradient update technique that progressively matches base call quality predictions of the convolutional neural network with the base call quality ground truths. The system comprises an input module of the convolutional neural network which runs on at least one of the numerous processors and feeds data from sequencing images captured at one or more sequencing cycles to the convolutional neural network for determining quality status of one or more bases called for one or more analytes. The system comprises an output module of the convolutional neural network which runs on at least one of the numerous processors and translates analysis by the convolutional neural network into an output that identifies the quality status of the one or more bases called for the one or more analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the output module further comprises a softmax classification layer that produces likelihoods for the quality status being high-quality, medium-quality, and low-quality. In such an implementation, based on the likelihoods, the quality status is classified as high-quality, medium-quality, or low-quality. In one implementation, the softmax classification layer produces likelihoods for the quality status being assigned a plurality of quality scores. In such an implementation, based on the likelihoods, the quality status is assigned a quality score from one of the plurality of quality scores. In one implementation, the quality scores are logarithmically based on base calling error probabilities, and the plurality of quality scores includes Q6, Q10, Q43, Q20, Q22, Q27, Q30, Q33, Q37, Q40, and Q50. In one implementation, the output module further comprises a regression layer that produces continuous values which identify the quality status. In one implementation, the system comprises a supplemental input module that supplements the data from the sequencing images with quality predictor values for the bases called, and feeds the quality predictor values to the convolutional neural network along with the data from the sequencing images. In one implementation, the quality predictor values include online overlap, purity, phasing, starts, hexamer score, motif accumulation, endiness, approximate homopolymer, intensity decay, penultimate chastity, signal overlap with background (SOWS), and/or shifted purity G adjustment. In one implementation, the quality predictor values include peak height, peak width, peak location, relative peak locations, peak height ratio, peak spacing ratio, and/or peak correspondence.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We also disclose a neural network-implemented method of quality scoring. The method includes feeding data from sequencing images captured at one or more sequencing cycles to a convolutional neural network for determining quality status of one or more bases called for one or more analytes. The convolutional neural network is trained on training examples comprising data from sequencing images and labeled with base call quality ground truths. The training comprises using a backpropagation-based gradient update technique that progressively matches base call quality predictions of the convolutional neural network with the base call quality ground truths. The method includes translating analysis by the convolutional neural network into an output that identifies the quality status of the one or more bases called for the one or more analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, a computer-implemented method includes processing input data for one or more analytes through a neural network and producing an alternative representation of the input data, processing the alternative representation through an output layer to produce an output, the output identifies likelihoods of a base incorporated in a particular one of the analytes being A, C, T, and G, calling bases for one or more of the analytes based on the output, and determining quality of the called bases based on the likelihoods identified by the output.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a neural network-based quality scorer, which runs on numerous processors operating in parallel and is coupled to memory. The system comprises a neural network running on the numerous processors, trained on training examples comprising data from sequencing images and labeled with base call quality ground truths using a backpropagation-based gradient update technique that progressively matches base call quality predictions of the neural network with the base call quality ground truths. The system comprises an input module of the neural network which runs on at least one of the numerous processors and feeds data from sequencing images captured at one or more sequencing cycles to the neural network for determining quality status of one or more bases called for one or more analytes. The system comprises an output module of the neural network which runs on at least one of the numerous processors and translates analysis by the neural network into an output that identifies the quality status of the one or more bases called for the one or more analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

End-to-End Integration

There is provided a computer implemented method, the method comprising processing first image data comprising images of analytes and their surrounding background captured by a sequencing system for one or more sequencing cycles of a sequencing run through a neural network and producing a base call for one or more of the analytes of the one or more sequencing cycles of the sequencing run. The method may comprise performing one or more sequencing cycles to capture the images of analytes and their surrounding background. In some embodiments the method comprises performing a plurality of sequencing cycles, wherein each of the plurality of sequencing cycles generates image data. The computer-implemented method may include processing a first input through a first neural network and producing a first output. The first input comprises first image data derived from images of analytes and their surrounding background captured by a sequencing system for a sequencing run. The method may include processing the first output through a post-processor and producing template data indicating one or more properties of respective portions of the first image data, i.e. about the analytes and their surrounding background. The method may include processing a second input through a second neural network and producing a second output. The second input may comprise the first image data modified using the template data, second image data modified using the template data and/or first and/or second image data and supplemental data. The supplemental data may comprise the template data. The second image data is derived from images of the analytes and their surrounding background. The second output identifies base calls for one or more of the analytes at one or more sequencing cycles of the sequencing run.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the metadata comprises a template image at an upsampled, subpixel resolution, and, based on the metadata, each subpixel in the template image is identified as either background subpixel, analyte center subpixel, or analyte interior subpixel. In one implementation, the images of the analytes and their surrounding background are captured at an optical, pixel-resolution. In one implementation, the method includes determining area weighting factors for pixels in the images based on how many subpixels in the template image, corresponding to a pixel in the images, contain parts of one or more of the analytes, and modifying intensities of the pixels based on the area weighting factors and including the pixels with the modified intensities in the second input as the third image data for base calling by the second neural network. In one implementation, the method includes upsampling the images to the upsampled, subpixel resolution and producing upsampled images. The upsampling includes assigning a background intensity to those subpixels in the upsampled images that correspond to background subpixels in the template image and assigning analyte intensities to those subpixels in the upsampled images that correspond to analyte center subpixels and analyte interior subpixels in the template image, and including the upsampled images in the second input as the third image data for base calling by the second neural network. In one implementation, the background intensity has a zero or minimal value. In one implementation, the analyte intensities are determined by interpolating intensities of the pixels in the optical, pixel-resolution. In one implementation, the method includes upsampling the images to the upsampled, subpixel resolution and producing upsampled images. The upsampling includes distributing entire intensity of a pixel in the optical, pixel domain among only those constituent subpixels of the pixel in the upsampled images that correspond to the analyte center subpixels and the analyte interior subpixels in the template image, and including the upsampled images in the second input as the third image data for base calling by the second neural network. In one implementation, the metadata identifies centers of the analytes. In another implementation, the metadata identifies shapes of the analytes. In yet another implementation, the metadata identifies boundaries between the analytes. In one implementation, the method includes determining quality of the base calls based on the second output.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method that includes using a first neural network to determine metadata about analytes, the metadata identifies centers of the analytes, shapes of the analytes, and/or boundaries between the analytes, and using a second neural network to base call the analytes based on the determined metadata.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, based on the determined metadata, constructing an input for processing by the second neural network. The input includes modified intensity values that incorporate context about the centers, shapes, and/or boundaries of the analytes in the processing by the second neural network. In one implementation, the method includes processing the modified intensity values through the second neural network to base call the analytes. In one implementation, the method includes accompanying an input that is fed to the second neural network for processing with supplemental data derived based on the determined metadata. The supplemental data incorporates context about the centers, shapes, and/or boundaries of the analytes in the processing by the second neural network. In one implementation, the method includes processing the input and the supplemental data through the second neural network to base call the analytes.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method that includes performing a sequencing procedure on analytes. The sequencing procedure comprises a plurality of sequencing cycles and each of the plurality of sequencing cycles generates image data. In one implementation, the method includes processing the image data for each of the plurality of sequencing cycles through a neural network and producing a base call for at least some of the analytes at each of the plurality of sequencing cycles.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, prior to processing the image data for each of the plurality of sequencing cycles through the neural network, processing the image data for some of the plurality of sequencing cycles through another neural network and determining metadata about the analytes. The metadata identifies centers and/or shapes of the analytes. In one implementation, the method includes, based on the determined metadata, base calling at least some of the analytes at each of the plurality of sequencing cycles using the neural network.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a sequencing system that comprises a receptacle coupled to a biosensor system, an illumination system, and a system controller coupled to the receptacle and having an analysis module. The biosensor system is configured to have an array of light detectors, the biosensor system has a biosensor, and the biosensor has reaction sites configured to contain analytes. The illumination system is configured to direct excitation light toward the biosensor and illuminate the analytes in the reaction sites. At least some of the analytes provide emission signals when illuminated. The system controller is coupled to the receptacle and has an analysis module. The analysis module is configured to obtain image data from the light detectors at each of a plurality of sequencing cycles. The image data is derived from the emission signals detected by the light detectors and process the image data for each of the plurality of sequencing cycles through a neural network and produce a base call for at least some of the analytes at each of the plurality of sequencing cycles.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

We disclose a computer-implemented method of using analyte centers, shapes, and boundaries identified in a template image at an upsampled, subpixel resolution to interpret images captured at an optical, pixel-resolution to base call analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels captured at the optical, pixel-resolution. The method includes generating the template image with area weighting factors, including processing initial image sets respectively generated at initial ones of the plurality of sequencing cycles through a neural network-based template generator to identify the analyte centers, shapes, and boundaries of the analytes at the upsampled, subpixel resolution, evaluating analyte shape and boundaries of a particular analyte to identify at least one pixel that contains part of the particular analyte, to set an area weighting factor based on how many subpixels in the identified pixel contain parts of the particular analyte, and to store the area weighting factor in the template image, and performing the evaluating to identify, to set, and to store for pixels that also contain part of the particular analyte, for pixels in each of the images captured at the optical, pixel-resolution, modifying a pixel intensity value based on the area weighting factor in the template image for a respective pixel, generating a modified version of each of the images with pixels having modified pixel intensity values, processing modified versions of the images through a neural network-based base caller to generate an alternative representation of the modified versions, and base calling the particular analyte using the alternative representation.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the base calling further includes accessing one or more images at the optical, pixel-resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles, for pixels in each of the images, modifying a pixel intensity value based on the area weighting factor in the template image for a respective pixel, generating a modified version of each of the images with pixels having modified pixel intensity values, for the particular analyte, extracting an image patch from each modified version such that each image patch has an array of pixels, and contains in its center pixel a center of the particular analyte identified in the template image, convolving image patches extracted from modified versions of the images through a convolutional neural network to generate a convolved representation of the image patches, processing the convolved representation through an output layer to produce, for the center pixel, likelihoods of a base incorporated in the particular analyte at the current one of the plurality of sequencing cycles being A, C, T, and G, and classifying the base as A, C, T, or G based on the likelihoods. In one implementation, the method includes, prior to modifying the pixel intensity values, aligning each of the images captured at the optical, pixel-resolution with the template image using cycle-specific and image channel-specific transformations.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method of using analyte centers, shapes, and boundaries identified in a template image at an upsampled, subpixel resolution to interpret images captured at an optical, pixel-resolution to base call analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels captured at the optical, pixel-resolution. The method includes generating the template image with area weighting factors, including processing initial image sets respectively generated at initial ones of the plurality of sequencing cycles through a neural network-based template generator to determine at least one primary analyte for which a pixel contains part of the primary analyte and to set an area weighting factor based on how many subpixels in the pixel contain parts of the primary analyte, and performing the evaluating to determine and to set for numerous analytes and numerous pixels, for pixels in each of the images captured at the optical, pixel-resolution, modifying a pixel intensity value based on the area weighting factor in the template image for a respective pixel, generating a modified version of each of the images with pixels having modified pixel intensity values, as input to a forward pass of a neural network-based base caller, processing modified versions of the images through the neural network-based base caller to generate an alternative representation of the modified versions, and as output of the forward pass, simultaneously base calling each one of the numerous analytes using the alternative representation.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the base calling further includes accessing one or more images at the optical, pixel-resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles, for pixels in each of the images, modifying a pixel intensity value based on the area weighting factor in the template image for a respective pixel, generating a modified version of each of the images with pixels having modified pixel intensity values, extracting an image patch from each modified version such that each image patch has an array of pixels, convolving image patches extracted from modified versions of the images through a convolutional neural network to generate a convolved representation of the image patches, processing the convolved representation through an output layer to produce, for each pixel in the array, likelihoods of a base incorporated at the current one of the plurality of sequencing cycles being A, C, T, and G, classifying the base as A, C, T, or G based on the likelihoods, and base calling each one of the numerous analytes based on a base classification assigned to a respective pixel containing a center of a corresponding analyte. In one implementation, the method includes, prior to modifying the pixel intensity values, aligning each of the images captured at the optical, pixel-resolution with the template image using cycle-specific and image channel-specific transformations.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method of using analyte centers, shapes, and boundaries identified in a template image at an upsampled, subpixel resolution to interpret images captured at an optical, pixel-resolution to base call analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels captured at the optical, pixel-resolution. The method includes processing initial image sets respectively generated at initial ones of the plurality of sequencing cycles through a neural network-based template generator to generate the template image at the upsampled, subpixel resolution. By "initial ones of the plurality of sequencing cycles" this will be understood to refer to one or more initial sequencing cycles, for example one or more of sequencing cycle 1 to 10, 2 to 10, 2 to 8 or 2 to 7. The template image classifies subpixels into classes including analyte center, background, and belonging to an analyte upsampling each of the images captured at the optical, pixel-resolution into subpixel domain, the upsampling includes assigning a background intensity to subpixels identified in the template image as not contributing to any analyte, as input to a forward pass of a neural network-based base caller, processing upsampled images through the neural network-based base caller to generate an alternative representation of the upsampled images, and as output of the forward pass, simultaneously base calling a plurality of the analytes using the alternative representation.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the base calling further includes accessing one or more images at the optical, pixel-resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles, upsampling each of the images captured at the optical, pixel-resolution into subpixel domain, the upsampling includes assigning a background intensity to subpixels identified in the template image as not contributing to any analyte, extracting an image patch from each upsampled image such that each image patch has an array of subpixels, convolving image patches extracted from the upsampled images through a convolutional neural network to generate a convolved representation of the image patches, processing the convolved representation through an output layer to produce, for each subpixel in the array, likelihoods of a base incorporated at the current one of the plurality of sequencing cycles being A, C, T, and G, classifying the base as A, C, T, or G based on the likelihoods, and base calling each one of the plurality of the analytes based on a base classification assigned to a respective subpixel containing a center of a corresponding analyte.

In one implementation, the method includes, prior to the upsampling, aligning each of the images captured at the optical, pixel-resolution with the template image using cycle-specific and image channel-specific transformations. In one implementation, the upsampling is performed using at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. In one implementation, the background intensity has a zero value. In one implementation, the background intensity has a near zero value.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method of using analyte centers, shapes, and boundaries identified in a template image at an upsampled, subpixel resolution to interpret images captured at an optical, pixel-resolution to base call analytes synthesized on a tile of a flow cell during a sequencing run, the sequencing run having a plurality of sequencing cycles, each of the plurality of sequencing cycles generating an image set with one or more images, and each of the images depicting intensity emissions of the analytes and their surrounding background in a respective one of one or more image channels captured at the optical, pixel-resolution. The method includes generating the template image with per-subpixel area weighting factors, including processing initial image sets respectively generated at initial ones of the plurality of sequencing cycles through a neural network-based template generator to identify the analyte centers, shapes, and boundaries of the analytes at the upsampled, subpixel resolution, and evaluating analyte shape and boundaries of the analytes to determine how many subpixels in a respective pixel contain parts of any analyte, to set a per-subpixel area weighting factor for the subpixels in the respective pixel, and to store the per-subpixel area weighting factor in the template image, upsampling each of the images captured at the optical, pixel-resolution into subpixel domain, the upsampling includes distributing intensity of a respective pixel among first subpixels of the respective pixel identified in the template image as contributing to any analyte by applying the per-subpixel area weighting factor, and assigning a background intensity to second subpixels in the respective pixel identified in the template image as not contributing to any analyte, as input to a forward pass of a neural network-based base caller, processing upsampled images through the neural network-based base caller to generate an alternative representation of the upsampled images, and as output of the forward pass, simultaneously base calling a plurality of the analytes using the alternative representation.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the base calling further includes accessing one or more images at the optical, pixel-resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles, upsampling each of the images captured at the optical, pixel-resolution into subpixel domain, the upsampling includes distributing intensity of a respective pixel among first subpixels of the respective pixel identified in the template image as contributing to any analyte by applying the per-subpixel area weighting factor, and assigning a background intensity to second subpixels in the respective pixel identified in the template image as not contributing to any analyte, extracting an image patch from each upsampled image such that each image patch has an array of subpixels, convolving image patches extracted from the upsampled images through a convolutional neural network to generate a convolved representation of the image patches, processing the convolved representation through an output layer to produce, for each subpixel in the array, likelihoods of a base incorporated at the current one of the plurality of sequencing cycles being A, C, T, and G, classifying the base as A, C, T, or G based on the likelihoods, and base calling each one of the plurality of the analytes based on a base classification assigned to a respective subpixel containing a center of a corresponding analyte.

In one implementation, the method includes, prior to the upsampling, aligning each of the images captured at the optical, pixel-resolution with the template image using cycle-specific and image channel-specific transformations. In one implementation, the background intensity has a zero value. In another implementation, the background intensity has a near zero value.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a computer-implemented method includes evaluating a template image in an upsampled subpixel domain for a particular analyte to identify at least one pixel that contains part of the particular analyte and to set an area weighting factor based on how many subpixels in the identified pixel contain parts of the particular analyte, performing the evaluating to determine and to set for adjoining pixels to the identified pixel that also contain part of the particular analyte, and modifying a pixel intensity value of the identified pixel and the adjoining pixels for processing based on the area weighting factor for a respective pixel.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a computer-implemented method includes evaluating a pixel in a template image in an upsampled subpixel domain to determine at least a primary analyte for which the pixel contains part of the primary analyte and to set an area weighting factor based on how many subpixels in the identified pixel contain parts of the primary analyte, performing the evaluating to determine and to set for numerous pixels in a field of an optical image, and modifying a pixel intensity value of the identified pixel and adjoining pixels for processing based on the area weighting factor for a respective pixel.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a computer-implemented method includes accessing a template image in an upsampled subpixel domain, the template image identifies subpixels that contain parts of any analyte and, during upsampling of a field of optical images into the subpixel domain, assigning a background intensity to subpixels identified in the template image as not contributing to any analyte.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a computer-implemented method includes evaluating an identified pixel in a template image in an upsampled subpixel domain to determine how many subpixels in the identified pixel contain parts of any analyte and to set a per-subpixel area weighting factor for the subpixels in the identified pixel, performing the evaluating to determine and to set for numerous pixels in a field of an optical image and storing the per-subpixel area weighting factors for the numerous pixels in the template image, and, during upsampling of the field of the optical image into the subpixel domain, distributing intensity of a particular pixel among first subpixels of a particular pixel identified in the template as contributing to any analyte by applying the per-subpixel area weighting factor and assigning a background intensity to second subpixels a particular pixel identified in the template as not contributing to any analyte.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method of using cluster centers, shapes, and boundaries identified in a template image at an upsampled, subpixel resolution to interpret images captured at an optical, pixel-resolution to base call deoxyribonucleic acid (DNA) clusters synthesized on a tile of a flow cell during a sequencing run, the sequencing run having a plurality of sequencing cycles, each of the plurality of sequencing cycles generating an image set with one or more images, and each of the images depicting intensity emissions of the DNA clusters and their surrounding background in a respective one of one or more imaging channels captured at the optical, pixel-resolution. The method includes generating the template image with area weighting factors, including processing initial image sets respectively generated at initial ones of the plurality of sequencing cycles through a neural network-based template generator to determine at least one primary DNA cluster for which a pixel contains part of the primary DNA cluster and to set an area weighting factor based on how many subpixels in the pixel contain parts of the primary DNA cluster, and performing the evaluating to determine and to set for numerous DNA clusters and numerous pixels, supplementing each of the images captured at the optical, pixel-resolution with the template image with the area weighting factors by pixel-wise encoding the area weighting factors with pixels in the images, as input to a forward pass of a neural network-based base caller, processing the images and the supplemental template image through the neural network-based base caller to generate an alternative representation of the input, and as output of the forward pass, simultaneously base calling each one of the numerous DNA clusters using the alternative representation.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Clauses

The disclosure also includes the following clauses:

Clauses Set 1

1. A computer-implemented method, comprising:
processing first image data comprising images of analytes and their surrounding background captured by a sequencing system for one or more sequencing cycles of a sequencing run through a neural network and producing a base call for one or more of the analytes of the one or more sequencing cycles of the sequencing run.

2. The computer-implemented method of clause 1, wherein processing the first image data comprises:
processing a first input through a first neural network to produce a first output, wherein the first input comprises the first image data;
processing the first output through a post-processor to produce template data indicating one or more properties of respective portions of the first image data; and
processing a second input through a second neural network to produce a second output, wherein the second input comprises the first image data and supplemental data; wherein the supplemental data comprises the template data, and wherein the second output identifies base calls for one or more of the analytes at one or more sequencing cycles of the sequencing run.

3. The computer-implemented method of clause 1, wherein processing the first image data comprises:
processing a first input through a first neural network to produce a first output, wherein the first input comprises the first image data;
processing the first output through a post-processor to produce template data indicating one or more properties of respective portions of the first image data; and
processing a second input through a second neural network to produce a second output, wherein the second input comprises the first image data modified using the template data, and wherein the second output identifies base calls for one or more of the analytes at one or more sequencing cycles of the sequencing run.

4. The computer-implemented method of clause 3, wherein the second input further comprises second image data modified using the template data, the second image data comprising images of analytes and their surrounding background captured by the sequencing system for one or more additional sequencing cycles of the sequencing run.

5. The computer-implemented method of any of clauses 2 to 5, wherein the template data comprises a template image, wherein the template image is at an upsampled, subpixel resolution.

6. The computer-implemented method of clause 5, wherein each subpixel in the template image is identified as either background subpixel, analyte center subpixel, or analyte interior subpixel.

7. The computer-implemented method of any of clauses 1 to 6, wherein the images of the analytes and their surrounding background are captured at an optical, pixel resolution.

8. The computer-implemented method of any of clauses 3 to 7, wherein modification using the template data comprises:
calculating an area weighting factor for one or more pixels in the first and/or second image data based on how many subpixels in the template data that correspond to a pixel in the images of the first and/or second image data contain parts of one or more of the analytes; and
modifying intensities of the pixels based on the area weighting factor.

9. The computer-implemented method of clause 6 or any of clauses 7 or 8 when dependent on clause 6, wherein modification using the template data comprises:
upsampling the images of analytes and their surrounding background to the upsampled, subpixel resolution to produce upsampled images, and assigning a background intensity to those subpixels in the upsampled images that correspond to background subpixels in the template image and assigning analyte intensities to those subpixels in the upsampled images that correspond to analyte center subpixels and analyte interior subpixels in the template image.

10. The computer-implemented method of clause 9, wherein the background intensity has a zero value.

11. The computer-implemented method of clause 9 or clause 10, wherein the analyte intensities are determined by interpolating intensities of the pixels in the optical, pixel resolution.

12. The computer-implemented method of clause 6 or any of clauses 7-11 when dependent on clause 6, wherein modification using the template image comprises:

upsampling the images of analytes and their surrounding background to the upsampled, subpixel resolution to produce upsampled images, and distributing an entire intensity of a pixel in the optical, pixel domain among only those constituent subpixels of the pixel in the upsampled images that correspond to the analyte center subpixels and the analyte interior subpixels in the template image.

13. The computer-implemented method of any of clauses 2-12, wherein the template data identifies at least one of the properties selected from the group consisting of: spatial distribution of the analytes, analyte shape, centers of the analytes and analyte boundary.

14. The computer-implemented method of any of clauses 2-13, further comprising calculating a quality of the base calls based on the second output.

15. The computer-implemented method according to any one of clauses 1-14, further comprising performing one or more sequencing cycles to capture the images of analytes and their surrounding background.

16. The computer-implemented method of any one of clauses 1-15, further comprising performing a plurality of sequencing cycles, wherein each of the plurality of sequencing cycles generates image data.

17. A computer-implemented method, comprising:

using a first neural network to determine template data about analytes, wherein the template data identifies at least one of the properties selected from the group consisting of: spatial distribution of the analytes, analyte shape, centers of the analytes and analyte boundary; and using a second neural network to base call the analytes based on the template data.

18. The computer-implemented method of clause 17, wherein the template data comprises modified intensity values to identify at least one of the properties selected from the group consisting of: spatial distribution of the analytes, analyte shape, centers of the analytes and analyte boundary; and processing the modified intensity values through the second neural network to base call the analytes.

19. The computer-implemented method of clause 17 or 18, wherein the template data comprises a template image.

20. The computer-implemented method of clause 19, further comprising:

evaluating the template image in an upsampled subpixel domain for at least one particular analyte to identify a pixel that contains part of the at least one particular analyte and adjoining pixels to the pixel that also contain part of the at least one particular analyte;

calculating an area weighting factor for each pixel based on how many subpixels in each of the identified pixels contain parts of the at least one particular analyte; and modifying a pixel intensity value of the identified pixel and the adjoining pixels for processing based on the area weighting factor for a respective pixel.

21. The computer-implemented method of clause 20, wherein evaluating the template image further comprises:

processing one or more initial image sets respectively generated at one or more initial sequencing cycles of a plurality of sequencing cycles through the first neural network to produce the template image to identify the centers, shapes, and boundaries of the analytes at the upsampled, subpixel resolution; wherein each image set comprises one or more images, each of the images depicting intensity emissions of the analytes and their surrounding background in a respective one of one or more imaging channels captured at the optical, pixel resolution.

22. The computer-implemented method of clause 20 or 21, wherein evaluating the template image further comprises:

evaluating the analyte shape and boundaries of the at least one particular analyte to identify at least one pixel that contains part of the at least one particular analyte and adjoining pixels to the pixel that also contain part of the at least one particular analyte; and wherein the method further comprises storing the area weighting factor in the template image; and generating a modified version of each of the images with pixels having modified pixel intensity values;

processing modified versions of the images through the second neural network to generate an alternative representation of the modified versions; and base calling the at least one particular analyte using the alternative representation.

23. The computer-implemented method of clause 22, wherein the base calling further comprises:

accessing one or more images at the optical, pixel resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles;

for pixels in each of the images, modifying a pixel intensity value based on the area weighting factor in the template image for a respective pixel;

generating a modified version of each of the images with pixels having modified pixel intensity values;

for the at least one particular analyte, extracting an image patch from each modified version such that each image patch has an array of pixels, and contains in its center pixel a center of the particular analyte identified in the template image;

convolving image patches extracted from modified versions of the images through a convolutional neural network of the second neural network to generate a convolved representation of the image patches;

processing the convolved representation through an output layer to produce, for the center pixel, likelihoods of a base incorporated in the at least one particular analyte at the current one of the plurality of sequencing cycles being A, C, T, and G; and classifying the base as A, C, T, or G based on the likelihoods.

24. The computer-implemented method according to clause 22 or 23, further comprising:

prior to modifying the pixel intensity values, aligning each of the images captured at the optical, pixel resolution with the template image using cycle-specific and imaging channel-specific transformations.

25. The computer-implemented method of clause 19, further comprising:

evaluating the template image in an upsampled subpixel domain to identify subpixels that contain parts of any analyte; and assigning a background intensity to subpixels identified in the template image as not contributing to any analyte.

26. The computer-implemented method of clause 25, wherein evaluating the template image in an upsampled subpixel domain further comprises:

calculating how many subpixels in at least one pixel contain parts of any analyte and calculating a per-subpixel area weighting factor for the subpixels in the at least one pixel.

27. The computer-implemented method of clause 25 or 26, wherein the method comprises:

processing one or more initial image sets respectively generated at one or more initial sequencing cycles of a plurality of sequencing cycles through the first neural network to produce the template image at the upsampled, subpixel resolution, wherein each image set comprises one or more images, each of the images depicting intensity emissions of the analytes and their surrounding background in a respective one of one or more imaging channels captured at the optical, pixel resolution and wherein the template image classifies subpixels into classes including analyte center, background, and analyte interior;

upsampling each of the images captured at the optical, pixel resolution into a subpixel domain and assigning a background intensity to subpixels of each of the images identified in the template image as not contributing to any analyte;

processing the upsampled images through the second neural network to generate an alternative representation of the upsampled images; and base calling a plurality of the analytes using the alternative representation.

28. The computer-implemented method of clause 27, wherein upsampling each of the images further comprises:

distributing intensity of a particular pixel among first subpixels of the particular pixel identified in the template image as contributing to any analyte by applying the per-subpixel area weighting factor and assigning a background intensity to second subpixels of the particular pixel identified in the template as not contributing to any analyte.

29. The computer-implemented method of clause 28, wherein the prior to upsampling the method comprises:

accessing one or more images at the optical, pixel resolution in each
of a current image set generated at a current one of the plurality of sequencing cycles,
of a one or more preceding image sets respectively generated at one or more of the plurality of sequencing cycles preceding the current one of the plurality of sequencing cycles, and
of a one or more succeeding image sets respectively generated at one or more of the plurality of sequencing cycles succeeding the current one of the plurality of sequencing cycles; and after upsampling the method comprises:

extracting an image patch from each upsampled image such that each image patch has an array of subpixels;

convolving image patches extracted from the upsampled images through the convolutional neural network of the second neural network to generate a convolved representation of the image patches;

processing the convolved representation through an output layer to produce, for each subpixel in the array, likelihoods of a base incorporated at the current one of the plurality of sequencing cycles being A, C, T, and G;

classifying the base as A, C, T, or G based on the likelihoods; and base calling each one of the plurality of the analytes based on a base classification assigned to a respective subpixel containing a center of a corresponding analyte.

30. The computer-implemented method of clause 28 or 29, further comprising:

prior to the upsampling, aligning each of the images captured at the optical, pixel resolution with the template image using cycle-specific and imaging channel-specific transformations.

31. The computer-implemented method of any one of clauses 29 to 30, wherein the upsampling is performed using at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage.

32. A sequencing system, comprising:

a receptacle coupled to a biosensor system, the biosensor system configured to comprise an array of light detectors, the biosensor system comprising a biosensor, and the biosensor comprising reaction sites configured to contain analytes;

an illumination system configured to direct excitation light toward the biosensor and illuminate the analytes in the reaction sites, wherein at least some of the analytes provide emission signals when illuminated; and a system controller coupled to the receptacle and comprising an analysis module, the analysis module configured to:
obtain image data from the light detectors at each of a plurality of sequencing cycles, wherein the image data is derived from the emission signals detected by the light detectors; and
process the image data for each of the plurality of sequencing cycles through a neural network and produce a base call for at least some of the analytes at each of the plurality of sequencing cycles.

Clauses Set 2

1. A computer-implemented method of end-to-end sequencing, including template generation and base calling, comprising:

accessing first image data and second image data that contain pixels in an optical, pixel resolution,
wherein the first image data comprises images of clusters and their surrounding background captured by a sequencing system for initial ones of sequencing cycles of a sequencing run, and
wherein the second image data comprises images of the clusters and their surrounding background captured by the sequencing system for the sequencing cycles of the sequencing run;

processing the first image data through a neural network-based template generator, and producing a cluster map that identifies cluster metadata,
wherein the cluster metadata includes cluster centers, cluster shapes, cluster sizes, cluster background, and/or cluster boundaries, and
wherein the neural network-based template generator is trained on a task of mapping the images of the clusters to the cluster metadata;

encoding the cluster metadata in a template image in an upsampled, subpixel resolution,
wherein subpixels of the template and the pixels of the images of the clusters represent a same image area;

modifying intensity values of the pixels of the second image data based on the template image, and producing an intensity modified version of the second image data with an intensity distribution that accounts for the cluster metadata; and processing the intensity modified version of the second image data through a neural network-based base caller, and producing base calls for one or more of the clusters at one or more sequencing cycles of the sequencing run, wherein the neural network-based base caller is trained on a task of mapping the images of the clusters to the base calls.

2. The computer-implemented method of clause 1, further including:

supplementing the second image data with the template image; and processing the second image data, supplemented with the template image, through the neural network-based base caller, and producing base calls for one or more of the clusters at one or more sequencing cycles of the sequencing run.

3. The computer-implemented method of clause 1, wherein each subpixel in the template image is identified as either background subpixel, cluster center subpixel, or cluster interior subpixel.

4. The computer-implemented method of any of clauses 1 to 3, wherein modifying intensity values of the pixels of the second image data comprises:

calculating an area weighting factor for one or more pixels in the second image data based on how many subpixels in the template image that correspond to a pixel in the images of the second image data contain parts of one or more of the clusters; and modifying intensities of the pixels based on the area weighting factor.

5. The computer-implemented method of any of clauses 1 to 4, wherein modifying intensity values of the pixels of the second image data comprises:

upsampling the images of clusters and their surrounding background to the upsampled, subpixel resolution to produce upsampled images, and assigning a background intensity to those subpixels in the upsampled images that correspond to background subpixels in the template image and assigning cluster intensities to those subpixels in the upsampled images that correspond to cluster center subpixels and cluster interior subpixels in the template image.

6. The computer-implemented method of clause 5, wherein the background intensity has a zero value.

7. The computer-implemented method of any of clauses 1 to 6, wherein the cluster intensities are determined by interpolating intensities of the pixels in the optical, pixel resolution.

8. The computer-implemented method of any of clauses 1 to 7, wherein modifying intensity values of the pixels of the second image data comprises:

upsampling the images of clusters and their surrounding background to the upsampled, subpixel resolution to produce upsampled images, and distributing an entire intensity of a pixel in the optical, pixel domain among only those constituent subpixels of the pixel in the upsampled images that correspond to the cluster center subpixels and the cluster interior subpixels in the template image.

9. A computer-implemented method, comprising:

using a first neural network to determine template image about clusters, wherein the template image identifies at least one of the properties selected from the group consisting of: spatial distribution of the clusters, cluster shape, centers of the clusters and cluster boundary; and using a second neural network to base call the clusters based on the template image.

10. The computer-implemented method of clause 10, wherein the template image comprises modified intensity values to identify at least one of the properties selected from the group consisting of: spatial distribution of the clusters, cluster shape, centers of the clusters and cluster boundary; and processing the modified intensity values through the second neural network to base call the clusters.

11. The computer-implemented method of clause 9 or 10, wherein the template image comprises a template image.

12. The computer-implemented method of clause 11, further comprising:

evaluating the template image in an upsampled subpixel domain for at least one particular cluster to identify a pixel that contains part of the at least one particular cluster and adjoining pixels to the pixel that also contain part of the at least one particular cluster;

calculating an area weighting factor for each pixel based on how many subpixels in each of the identified pixels contain parts of the at least one particular cluster; and modifying a pixel intensity value of the identified pixel and the adjoining pixels for processing based on the area weighting factor for a respective pixel.

13. The computer-implemented method of clause 12, wherein evaluating the template image further comprises:

processing one or more initial image sets respectively generated at one or more initial sequencing cycles of a plurality of sequencing cycles through the first neural network to produce the template image to identify the centers, shapes, and boundaries of the clusters at the upsampled, subpixel resolution; wherein each image set comprises one or more images, each of the images depicting intensity emissions of the clusters and their surrounding background in a respective one of one or more imaging channels captured at the optical, pixel resolution.

14. The computer-implemented method of clause 12 or 13, wherein evaluating the template image further comprises:

evaluating the cluster shape and boundaries of the at least one particular cluster to identify at least one pixel that contains part of the at least one particular cluster and adjoining pixels to the pixel that also contain part of the at least one particular cluster; and wherein the method further comprises storing the area weighting factor in the template image; and generating a modified version of each of the images with pixels having modified pixel intensity values;

processing modified versions of the images through the second neural network to generate an alternative representation of the modified versions; and base calling the at least one particular cluster using the alternative representation.

15. The computer-implemented method of clause 14, wherein the base calling further comprises:

accessing one or more images at the optical, pixel resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles;

for pixels in each of the images, modifying a pixel intensity value based on the area weighting factor in the template image for a respective pixel;

generating a modified version of each of the images with pixels having modified pixel intensity values;

for the at least one particular cluster, extracting an image patch from each modified version such that each image patch has an array of pixels, and contains in its center pixel a center of the particular cluster identified in the template image;

convolving image patches extracted from modified versions of the images through a convolutional neural network of the second neural network to generate a convolved representation of the image patches;

processing the convolved representation through an output layer to produce, for the center pixel, likelihoods of a base incorporated in the at least one particular cluster at the current one of the plurality of sequencing cycles being A, C, T, and G; and classifying the base as A, C, T, or G based on the likelihoods.

16. The computer-implemented method any of clauses 14 or 15, further comprising:

prior to modifying the pixel intensity values, aligning each of the images captured at the optical, pixel resolution with the template image using cycle-specific and imaging channel-specific transformations.

17. The computer-implemented method of clause 9, further comprising:

evaluating the template image in an upsampled subpixel domain to identify subpixels that contain parts of any cluster; and assigning a background intensity to subpixels identified in the template image as not contributing to any cluster.

18. The computer-implemented method of clause 17, wherein evaluating the template image in an upsampled subpixel domain further comprises:

calculating how many subpixels in at least one pixel contain parts of any cluster and calculating a per-subpixel area weighting factor for the subpixels in the at least one pixel.

19. The computer-implemented method of clause 17 or 18, wherein the method comprises:

processing one or more initial image sets respectively generated at one or more initial sequencing cycles of a plurality of sequencing cycles through the first neural network to produce the template image at the upsampled, subpixel resolution, wherein each image set comprises one or more images, each of the images depicting intensity emissions of the clusters and their surrounding background in a respective one of one or more imaging channels captured at the optical, pixel resolution and wherein the template image classifies subpixels into classes including cluster center, background, and cluster interior;

upsampling each of the images captured at the optical, pixel resolution into a subpixel domain and assigning a background intensity to subpixels of each of the images identified in the template image as not contributing to any cluster;

processing the upsampled images through the second neural network to generate an alternative representation of the upsampled images; and base calling a plurality of the clusters using the alternative representation.

20. The computer-implemented method of clause 19, wherein upsampling each of the images further comprises:

distributing intensity of a particular pixel among first subpixels of the particular pixel identified in the template image as contributing to any cluster by applying the per-subpixel area weighting factor and assigning a background intensity to second subpixels of the particular pixel identified in the template as not contributing to any cluster.

21. The computer-implemented method of clause 20, wherein the prior to upsampling the method comprises:

accessing one or more images at the optical, pixel resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles; and after upsampling the method comprises:

extracting an image patch from each upsampled image such that each image patch has an array of subpixels;

convolving image patches extracted from the upsampled images through the convolutional neural network of the second neural network to generate a convolved representation of the image patches;

processing the convolved representation through an output layer to produce, for each subpixel in the array, likelihoods of a base incorporated at the current one of the plurality of sequencing cycles being A, C, T, and G;

classifying the base as A, C, T, or G based on the likelihoods; and base calling each one of the plurality of the clusters based on a base classification assigned to a respective subpixel containing a center of a corresponding cluster.

22. The computer-implemented method of clause 20 or 21, further comprising:

prior to the upsampling, aligning each of the images captured at the optical, pixel resolution with the template image using cycle-specific and imaging channel-specific transformations.

23. A sequencing system, comprising:

a receptacle coupled to a biosensor system, the biosensor system configured to comprise an array of light detectors, the biosensor system comprising a biosensor, and the biosensor comprising reaction sites configured to contain clusters;

an illumination system configured to direct excitation light toward the biosensor and illuminate the clusters in the reaction sites, wherein at least some of the clusters provide emission signals when illuminated; and a system controller coupled to the receptacle and comprising an analysis module, the analysis module configured to:

obtain image data from the light detectors at each of a plurality of sequencing cycles, wherein the image data is derived from the emission signals detected by the light detectors; and process the image data for each of the plurality of sequencing cycles through a neural network and produce a base call for at least some of the clusters at each of the plurality of sequencing cycles.

Clauses Set 3

1. A computer-implemented method, including:
processing input data through a neural network and producing an alternative representation of the input data, wherein the input data includes per-cycle data for each of one or more sequencing cycles of a sequencing run, and wherein the per-cycle data is indicative of one or more analytes at a respective sequencing cycle;
processing the alternative representation through an output layer and producing an output; and
base calling one or more of the analytes at one or more of the sequencing cycles based on the output.

2. The neural network-implemented method of clause 1, wherein the per-cycle data is indicative of a surrounding background at the respective sequencing cycle.

3. The neural network-implemented method of any of clauses 1-2, wherein the input data is image data and the per-cycle data comprises intensity emissions indicative of the one or more analytes and of the surrounding background captured at the respective sequencing cycle.

4. The computer-implemented method of clause 3, further including accompanying the per-cycle data with supplemental distance information that identifies distances between pixels of the per-cycle data and those pixels that depict the intensity emissions indicative of the one or more of the analytes.

5. The computer-implemented method of clause 3, further including accompanying the per-cycle data with supplemental scaling information that assigns scaling values to the pixels of the per-cycle data.

6. The neural network-implemented method of clause 1, wherein the per-cycle data is indicative of a voltage change detected at the respective sequencing cycle.

7. The neural network-implemented method of clause 1, wherein the per-cycle data is indicative of an electric current signal measured at the respective sequencing cycle.

8. A neural network-implemented method of base calling analytes synthesized during a sequencing run comprising a plurality of sequencing cycles, the method including:
convolving input data through a convolutional neural network to generate a convolved representation of the input data,
wherein the input data includes image patches extracted from one or more images in each of a current image set generated at a current sequencing cycle of the sequencing run, of one or more preceding image sets respectively generated at one or more sequencing cycles of the sequencing run preceding the current sequencing cycle, and of one or more succeeding image sets respectively generated at one or more sequencing cycles of the sequencing run succeeding the current sequencing cycle,
wherein each of the image patches depicts intensity emissions of a target analyte being base called, and
wherein the input data further includes distance information indicating respective distances of pixels of the image patch from a center pixel of the image patch;
processing the convolved representation through an output layer to produce an output; and
base calling the target analyte at the current sequencing cycle based on the output.

9. The neural network-implemented method of clause 8, further including:
providing as input to the convolutional neural network position coordinates of centers of image regions representing respective analytes,
wherein the input is provided to a first layer of the convolutional neural network,
wherein the input is provided to one or more intermediate layers of the convolutional neural network, and
wherein the input is provided to a final layer of the convolutional neural network.

10. The neural network-implemented method of any of clauses 8-9, further including:
providing as input to the convolutional neural network an intensity scaling channel that has scaling values corresponding to pixels of the image patches, and
wherein the scaling values are based on a mean intensity of center pixels of the image patches that each contain a particular target analyte.

11. The neural network-implemented method of any of clauses 8-10, wherein the intensity scaling channel pixel-wise includes a same scaling value for all the pixels of the image patches.

12. The neural network-implemented method of clause 8, wherein each image patch further comprises pixel distance data indicating a distance between respective pixels and a nearest one of the plurality of analytes, the nearest one of the plurality of analytes selected based on center-to-center distances between the pixel and each of the analytes.

13. The neural network-implemented method of clause 8, wherein each image patch further comprises analyte distance data that identifies a distance of each analyte pixel from an assigned one of the plurality of analytes selected based on classifying each analyte pixel to only one of the analytes.

14. The neural network-implemented method of any of clauses 8-13, wherein convolving the input data through the convolutional neural network to generate the convolved representation of the input data comprises:
separately processing each per-cycle image patch set through a first convolutional subnetwork of the convolutional neural network to produce an intermediate convolved representation for each sequencing cycle, including applying convolutions that combine the intensity and distance information and combine resulting convolved representations only within a sequencing cycle and not between sequencing cycles;
groupwise processing intermediate convolved representations for successive sequencing cycles in the series through a second convolutional subnetwork of the convolutional neural network to produce a final convolved representation for the series, including applying convolutions that combine the intermediate convolved representations and combine resulting convolved representations between the sequencing cycles;
and wherein processing the convolved representation through the output layer to produce the output comprises processing the final convolved representation through the output layer.

15. The neural network-implemented method of any of clauses 8-14, further including: reframing the pixels of each image patch to center a center of the target analyte in a center pixel to generate reframed image patches; and
wherein convolving the input data through the convolutional neural network to generate the convolved representation of the input data comprises convolving the reframed image patches through the convolutional neural network to generate the convolved representation.

16. The neural network-implemented method of clause 15, wherein the reframing further includes intensity interpolation of the pixels of each image patch to compensate for the reframing.

17. A neural network-implemented method of base calling, the method including:

separately processing each per-cycle input data in a sequence of per-cycle input data through a cascade of convolution layers of the convolutional neural network, wherein the sequence of per-cycle input data is generated for a series of sequencing cycles of a sequencing run, and each per-cycle input data includes image channels that depict intensity emissions of one or more analytes and their surrounding background captured at a respective sequencing cycle;

for each sequencing cycle, based on the separate processing, producing a convolved representation at each of the convolution layers, thereby producing a sequence of convolved representations, mixing its per-cycle input data with its corresponding sequence of convolved representations and producing a mixed representation, and flattening its mixed representation and producing a flattened mixed representation;

arranging flattened mixed representations of successive sequencing cycles as a stack;

processing the stack in forward and backward directions through a recurrent neural network that convolves over a subset of the flattened mixed representations in the stack on a sliding window basis, with each sliding window corresponding to a respective sequencing cycle, and successively produces a current hidden state representation at each time step for each sequencing cycle based on (i) the subset of the flattened mixed representations in a current sliding window over the stack and (ii) a previous hidden state representation; and base calling each of the analytes at each of the sequencing cycles based on results of processing the stack in forward and backward directions.

18. The neural network-implemented method of clause 17, further including:

base calling each of the analytes at a given sequencing cycle by:

combining forward and backward current hidden state representations of the given sequencing cycle on a time step-basis and producing a combined hidden state representation, wherein the combining includes concatenation or summation or averaging;

processing the combined hidden state representation through one or more fully-connected networks and producing a dense representation;

processing the dense representation through a softmax layer to produce likelihoods of bases incorporated in each of the analytes at the given sequencing cycle being A, C, T, and G; and classifying the bases as A, C, T, or G based on the likelihoods.

19. A neural network-based system for base calling, the system comprising:

a hybrid neural network with a recurrent module and a convolution module, wherein the recurrent module uses inputs from the convolution module;

the convolution module processing image data for a series of sequencing cycles of a sequencing run through one or more convolution layers and producing one or more convolved representations of the image data, wherein the image data depicts intensity emissions of one or more analytes and their surrounding background;

the recurrent module producing current hidden state representations based on convolving the convolved representations and previous hidden state representations; and an output module producing a base call for at least one of the analytes and for at least one of the sequencing cycles based on the current hidden state representations.

20. A computer-implemented method of base calling clusters, including:

processing input data through a neural network and producing an alternative representation of the input data, wherein the input data includes (i) per-cycle data for each of one or more sequencing cycles of a sequencing run and (ii) supplemental distance information, wherein the per-cycle data comprises pixels that depict intensity emissions indicative of the one or more clusters and of the surrounding background captured at a respective one of the sequencing cycles, wherein the per-cycle data is accompanied with the supplemental distance information that identifies distances between the pixels of the per-cycle data;

wherein, during the processing of the pixels of the per-cycle data by the neural network, the supplemental distance information supplies additive bias that conveys to the neural network which of the pixels of the per-cycle data contain centers of the clusters and which of the pixels of the per-cycle data are farther away from the centers of the clusters;

processing the alternative representation through an output layer and producing an output; and base calling one or more of the clusters at one or more of the sequencing cycles based on the output.

21. The computer-implemented method of clause 20, wherein the additive bias improves accuracy of the base calling.

22. The computer-implemented method of clause 21, wherein the neural network uses the supplemental distance information to assign a sequencing signal to its proper source cluster by attending to central cluster pixels, their neighboring pixels, and alternative representations derived from them more than perimeter cluster pixels, background pixels, and alternative representations derived from them.

Clauses Set 4

1. A computer-implemented method, including:

processing input data for one or more analytes through a neural network-based base caller and producing an alternative representation of the input data;

processing the alternative representation through an output layer to produce an output, wherein the output identifies likelihoods of a base incorporated in a particular one of the analytes being A, C, T, and G;

calling bases for one or more of the analytes based on the output; and determining quality scores of the called bases based on the likelihoods identified by the output.

2. The computer-implemented method of clause 1, wherein determining the quality scores of the called bases based on the likelihoods comprises:

quantizing classification scores of base calls produced by the neural network-based base caller in response to processing training data during training;

selecting a set of quantized classification scores;

for each quantized classification score in the set, determining a base calling error rate by comparing its predicted base calls to corresponding ground truth base calls;

determining a fit between the quantized classification scores and their base calling error rates; and correlating the quality scores to the quantized classification scores based on the fit.

3. The computer-implemented method of any of clauses 1-2, wherein the set of quantized classification scores includes a subset of the classification scores of predicted base calls produced by the neural network-based base caller in response to processing the training data during the training, and wherein the classification scores are real numbers.

4. The computer-implemented method of any of clauses 1-3, wherein the set of quantized classification scores includes all the classification scores of predicted base calls produced by the neural network-based base caller in response to processing the training data during the training, and wherein the classification scores are real numbers.

5. The computer-implemented method of any of clauses 1-4, wherein the classification scores are exponentially normalized softmax scores that sum to unity and are produced by a softmax output layer of the neural network-based base caller.

6. The computer-implemented method of any of clauses 1-5, wherein the set of quantized classification scores is selected based on a selection formula defined as $$0.9 \sum_{i=1}^{n} 0.1^{(i-1)}$$

and applied to the softmax scores.

7. The computer-implemented method of any of clauses 1-6, wherein the set of quantized classification scores is selected based on a selection formula defined as $$\bigvee_{i=1}^{n=10} 0.1i$$

and applied to the softmax scores.

8. The computer-implemented method of any of clauses 1-7, further including:

based on the correlation, assigning the quality scores to bases called by the neural network-based base caller during inference.

9. The computer-implemented method of clause 8, further including:

assigning the quality scores based on applying a quality score correspondence scheme to the bases called by the neural network-based base caller during the inference; and wherein the scheme maps ranges of classification scores, produced by the neural network-based base caller in response to processing inference data during the inference, to corresponding quantized classification scores in the set.

10. The computer-implemented method of any of clauses 8-9, further including:

during the inference, stopping base calling an analyte whose quality score is below a set threshold for a current base calling cycle.

11. The computer-implemented method of any of clauses 8-10, further including:

during the inference, stopping base calling an analyte whose average quality score is below a set threshold after successive base calling cycles.

12. The computer-implemented method of any of clauses 8-11, wherein a sample size used for comparing the predicted base calls to the corresponding ground truth base calls is specific to each quantized classification score.

13. The computer-implemented method of any of clauses 8-12, wherein the fit is determined using a regression model.

14. The computer-implemented method of any of clauses 8-13, further including:

for each quantized classification score, determining a base calling accuracy rate by comparing its predicted base calls to corresponding ground truth base calls; and determining the fit between the quantized classification scores and their base calling accuracy rates.

15. The computer-implemented method of any of clauses 8-14, wherein the corresponding ground truth base calls are derived from well-characterized human and non-human samples sequenced on a number of sequencing instruments, sequencing chemistries, and sequencing protocols.

16. A neural network-based quality scorer, comprising:

numerous processors operating in parallel and coupled to memory;

a neural network running on the numerous processors, trained on training examples comprising data from sequencing images and labeled with base call quality ground truths using a backpropagation-based gradient update technique that progressively matches base call quality predictions of the neural network with the base call quality ground truths that identify known correct base calls;

an input module of the neural network which runs on at least one of the numerous processors and feeds data from sequencing images captured at one or more sequencing cycles to the neural network for determining quality of one or more bases called for one or more analytes; and an output module of the neural network which runs on at least one of the numerous processors and translates analysis by the neural network into an output that identifies the quality of the one or more bases called for the one or more analytes.

17. The neural network-based quality scorer of clause 16, wherein the neural network is a convolutional neural network.

18. The neural network-based quality scorer of clause 16, wherein the output module further comprises a softmax classification layer that produces likelihoods for the quality being high-quality, medium-quality, and low-quality, further comprising:

based on the likelihoods, classifying the quality as high-quality, medium-quality, or low-quality.

19. The neural network-based quality scorer of clause 16, wherein the softmax classification layer produces likelihoods for the quality being assigned a plurality of quality scores, further comprising:

based on the likelihoods, assigning the quality a quality score from one of the plurality of quality scores.

20. The neural network-based quality scorer of any of clauses 16-19, wherein the quality scores are logarithmically based on base calling error probabilities, and wherein the plurality of quality scores includes Q6, Q10, Q15, Q20, Q22, Q27, Q30, Q33, Q37, Q40, and Q50.

21. The neural network-based quality scorer of any of clauses 16-20, wherein the output module further comprises a regression layer that produces continuous values which identify the quality.

22. The neural network-based quality scorer of any of clauses 16-21, further comprising:

a supplemental input module that
supplements the data from the sequencing images with
quality predictor values for the bases called, and feeds the quality predictor values to the convolutional neural network along with the data from the sequencing images.

23. The neural network-based quality scorer of clause 22, wherein the quality predictor values include online overlap, purity, phasing, starts, hexamer score, motif accumulation, endiness, approximate homopolymer, intensity decay, penultimate chastity, signal overlap with background (SOWS), and/or shifted purity G adjustment.

24. The neural network-based quality scorer of clause 22, wherein the quality predictor values include peak height, peak width, peak location, relative peak locations, peak height ration, peak spacing ration, and/or peak correspondence.

Clauses Set 5

1. A computer-implemented method of determining image regions indicative of analytes on a tile of a flow cell, the method comprising:

accessing a series of image sets generated during a sequencing run, each image set in the series generated during a respective sequencing cycle of the sequencing run, each image in the series depicting the analytes and their surrounding background, and each image in the series having a plurality of subpixels;

obtaining, from a base caller, a base call classifying each of the subpixels, thereby producing a base call sequence for each of the subpixels across a plurality of sequencing cycles of the sequencing run;

determining a plurality of disjointed regions of contiguous subpixels which share a substantially matching base call sequence; and generating an analyte map identifying the determined disjointed regions.

2. The computer-implemented method of clause 1, further including:

training a classifier based upon the determined plurality of disjointed regions of contiguous subpixels, the classifier being a neural network-based template generator for processing input image data to generate a decay map, a ternary map, or a binary map, representing one or more properties of each of a plurality of analytes represented in the input image data for base calling by a neural network-based base caller, preferably in order to increase the level of throughput in high-throughput nucleic acid sequencing technologies.

3. The computer-implemented method of any of clauses 1-2, further including:

generating the analyte map by identifying as background those subpixels that do not belong to any of the disjointed regions.

4. The computer-implemented method of any of clauses 1-3, wherein the analyte map identifies analyte boundary portions between two contiguous subpixels whose base call sequences do not substantially match.

5. The computer-implemented method of any of clauses 1-4, wherein the determining the plurality of disjointed regions of contiguous subpixels further includes:

identifying origin subpixels at preliminary center coordinates of the analytes determined by the base caller; and breadth-first searching for substantially matching base call sequences by beginning with the origin subpixels and continuing with successively contiguous non-origin subpixels.

6. The computer-implemented method of any of clauses 1-5, further including:

determining hyperlocated center coordinates of the analytes by calculating centers of mass of the disjointed regions of the analyte map as an average of coordinates of respective contiguous subpixels forming the disjointed regions; and storing the hyperlocated center coordinates of the analytes in the memory for use as ground truth for training the classifier.

7. The computer-implemented method of clause 6, further including:

identifying centers of mass subpixels in the disjointed regions of the analyte map at the hyperlocated center coordinates of the analytes;

upsampling the analyte map using interpolation and storing the upsampled analyte map in the memory for use as ground truth for training the classifier; and in the upsampled analyte map, assigning a value to each contiguous subpixel in the disjointed regions based on a decay factor that is proportional to distance of a contiguous subpixel from a center of mass subpixel in a disjointed region to which the contiguous subpixel belongs.

8. The computer-implemented method of clause 7, the method more preferably further including:

generating the decay map from the upsampled analyte map that expresses the contiguous subpixels in the disjointed regions and the subpixels identified as the background based on their assigned values; and storing the decay map in the memory for use as ground truth for training the classifier.

9. The computer-implemented method of clause 8, the method even more preferably further including:

in the upsampled analyte map, categorizing, on the analyte-by-analyte basis, the contiguous subpixels in the disjointed regions as analyte interior subpixels belonging to a same analyte, the centers of mass subpixels as analyte center subpixels, subpixels containing the analyte boundary portions as boundary subpixels, and the subpixels identified as the background as background subpixels; and storing the categorizations in the memory for use as ground truth for training the classifier.

10. The computer-implemented method of any of clauses 1-9, further including:

storing, on the analyte-by-analyte basis, coordinates of the analyte interior subpixels, the analyte center subpixels, the boundary subpixels, and the background subpixels in the memory for use as ground truth for training the classifier;

downscaling the coordinates by a factor used to upsample the analyte map; and storing, on the analyte-by-analyte basis, the downscaled coordinates in the memory for use as ground truth for training the classifier.

11. The computer-implemented method of any of clauses 1-10, further including:

in a binary ground truth data generated from the upsampled analyte map, using color coding to label the analyte center subpixels as belonging to an analyte center class and all other subpixels are belonging to a non-center class; and storing the binary ground truth data in the memory for use as ground truth for training the classifier.

12. The computer-implemented method of any of clauses 1-11, further including:

in a ternary ground truth data generated from the upsampled analyte map, using color coding to label the background subpixels as belonging to a background class, the analyte center subpixels as belonging to an analyte center class, and the analyte interior subpixels as belonging to an analyte interior class; and storing the ternary ground truth data in the memory for use as ground truth for training the classifier.

13. The computer-implemented method of any of clauses 1-12, further including:
  generating analyte maps for a plurality of tiles of the flow cell;
  storing the analyte maps in memory and determining spatial distribution of analytes in the tiles based on the analyte maps, including their shapes and sizes;
  in the upsampled analyte maps of the analytes in the tiles, categorizing, on an analyte-by-analyte basis, subpixels as analyte interior subpixels belonging to a same analyte, analyte center subpixels, boundary subpixels, and background subpixels;
  storing the categorizations in the memory for use as ground truth for training the classifier;
  storing, on the analyte-by-analyte basis across the tiles, coordinates of the analyte interior subpixels, the analyte center subpixels, the boundary subpixels, and the background subpixels in the memory for use as ground truth for training the classifier;
  downscaling the coordinates by the factor used to upsample the analyte map; and
  storing, on the analyte-by-analyte basis across the tiles, the downscaled coordinates in the memory for use as ground truth for training the classifier.
14. The computer-implemented method of any of clauses 1-13, wherein the base call sequences are substantially matching when a predetermined portion of base calls match on an ordinal position-wise basis.
15. The computer-implemented method of any of clauses 1-14, wherein the determining the plurality of disjointed regions of contiguous subpixels which share a substantially matching base call sequence is based upon a predetermined minimum number of subpixels for a disjointed region.
16. The computer-implemented method of any of clauses 1-15, wherein the flow cell has at least one patterned surface with an array of wells that occupy the analytes, further including:
  based on the determined shapes and sizes of the analytes, determining
    which ones of the wells are substantially occupied by at least one analyte,
    which ones of the wells are minimally occupied, and
    which ones of the wells are co-occupied by multiple analytes.
17. A computer-implemented method of determining metadata about analytes on a tile of a flow cell, the method comprising:
  accessing a set of images of the tile captured during a sequencing run and preliminary center coordinates of the analytes determined by a base caller;
  for each image set, obtaining, from a base caller, a base call classifying, as one of four bases,
    origin subpixels that contain the preliminary center coordinates and
    a predetermined neighborhood of contiguous subpixels that are successively contiguous to respective ones of the origin subpixels,
    thereby producing a base call sequence for each of the origin subpixels and for each of the predetermined neighborhood of contiguous subpixels;
  generating an analyte map that identifies the analytes as disjointed regions of contiguous subpixels that
    are successively contiguous to at least some of the respective ones of the origin subpixels and
    share a substantially matching base call sequence of the one of four bases with the at least some of the respective ones of the origin subpixels; and
  storing the analyte map in memory and determining the shapes and the sizes of the analytes based on the disjointed regions in the analyte map.
18. A computer-implemented method of generating training data for neural network-based template generation and base calling, the method comprising:
  accessing a multitude of images of a flow cell captured over a plurality of cycles of a sequencing run, the flow cell having a plurality of tiles and, in the multitude of images, each of the tiles having a sequence of image sets generated over the plurality of cycles, and each image in the sequence of image sets depicting intensity emissions of analytes and their surrounding background on a particular one of the tiles at a particular one the cycles;
  constructing a training set having a plurality of training examples, each training example corresponding to a particular one of the tiles and including image data from at least some image sets in the sequence of image sets of the particular one of the tiles; and
  generating at least one ground truth data representation for each of the training examples, the ground truth data representation identifying at least one property of analytes on the particular one of the tiles whose intensity emissions are depicted by the image data and being determined at least in part using the method of any of clauses 1-17.
19. The computer-implemented method of clause 18, wherein the at least one property of analytes is selected from the group consisting of: spatial distribution of analytes on the tile; analyte shape; analyte size; analyte boundary; and center of contiguous regions including a single analyte.
20. The computer-implemented method of any of clauses 18-19, wherein the image data includes images in each of the at least some image sets in the sequence of image sets of the particular one of the tiles.
21. The computer-implemented method of any of clauses 18-20, wherein the image data includes at least one image patch from each of the images.
22. The computer-implemented method of any of clauses 18-21, wherein the image data includes an upsampled representation of the image patch.
23. The computer-implemented method of any of clauses 18-22, wherein multiple training examples correspond to a same particular one of the tiles and respectively include as image data different image patches from each image in each of at least some image sets in a sequence of image sets of the same particular one of the tiles, and
  wherein at least some of the different image patches overlap with each other.
24. The computer-implemented method of any of clauses 18-23, wherein the ground truth data representation identifies the analytes as disjoint regions of adjoining subpixels, the centers of the analytes as centers of mass subpixels within respective ones of the disjoint regions, and their surrounding background as subpixels that do not belong to any of the disjoint regions.
25. The computer-implemented method of any of clauses 18-24, further including:
  storing, in memory, the training examples in the training set and associated ground truth data representations as the training data for the neural network-based template generation and base calling.
26. A computer-implemented method, including:
  accessing sequencing images of analytes produced by a sequencer;
  generating training data from the sequencing images; and
  using the training data for training a neural network to generate metadata about the analytes.

27. A computer-implemented method, including:
    accessing sequencing images of analytes produced by a sequencer;
    generating training data from the sequencing images; and
    using the training data for training a neural network to base call the analytes.

28. A computer-implemented method of determining image regions indicative of analytes on a tile of a flow cell, the method comprising:
    accessing a series of image sets generated during a sequencing run, each image set in the series generated during a respective sequencing cycle of the sequencing run, each image in the series depicting the analytes and their surrounding background, and each image in the series having a plurality of subpixels;
    obtaining, from a base caller, a base call classifying each of the subpixels, thereby producing a base call sequence for each of the subpixels across a plurality of sequencing cycles of the sequencing run; and
    determining a plurality of disjointed regions of contiguous subpixels which share a substantially matching base call sequence.

Clauses Set 6

1. A computer-implemented method of generating ground truth training data to train a neural network-based template generator for cluster metadata determination task, the method comprising:
    accessing a series of image sets generated during a sequencing run, each image set in the series generated during a respective sequencing cycle of the sequencing run, each image in the series depicting clusters and their surrounding background, each image in the series having pixels in a pixel domain, and each of the pixels is divided into a plurality of subpixels in a subpixel domain;
    obtaining, from a base caller, a base call classifying each of the subpixels as one of four bases (A, C, T, and G), thereby producing a base call sequence for each of the subpixels across a plurality of sequencing cycles of the sequencing run;
    generating a cluster map that identifies the clusters as disjointed regions of contiguous subpixels which share a substantially matching base call sequence;
    determining cluster metadata based on the disjointed regions in the cluster map,
        wherein the cluster metadata includes cluster centers, cluster shapes, cluster sizes, cluster background, and/or cluster boundaries; and
    using the cluster metadata to generate ground truth training data for training a neural network-based template generator for cluster metadata determination task,
        wherein the ground truth training data comprises a decay map, a ternary map, or a binary map,
        wherein the neural network-based template generator is trained to produce the decay map, the ternary map, or the binary map as output based on the ground truth training data, and
        wherein, upon execution of the cluster metadata determination task during inference, the cluster metadata is in turn determined from the decay map, the ternary map, or the binary map that are produced as the output by the trained neural network-based template generator.

2. The computer-implemented method of clause 1, further including:
    using the cluster metadata derived from the decay map, the ternary map, or the binary map produced as the output by the neural network-based template generator for base calling by a neural network-based base caller, in order to increase throughput in high-throughput nucleic acid sequencing technologies.

3. The computer-implemented method of clause 1, further including:
    generating the cluster map by identifying as background those subpixels that do not belong to any of the disjointed regions.

4. The computer-implemented method of clause 1, wherein the cluster map identifies cluster boundary portions between two contiguous subpixels whose base call sequences do not substantially match.

5. The computer-implemented method of clause 1, wherein the cluster map is generated based on:
    identifying origin subpixels at preliminary center coordinates of the clusters determined by the base caller; and
    breadth-first searching for substantially matching base call sequences by beginning with the origin subpixels and continuing with successively contiguous non-origin subpixels.

6. The computer-implemented method of clause 1, further including:
    determining hyperlocated center coordinates of the clusters by calculating centers of mass of the disjointed regions of the cluster map as an average of coordinates of respective contiguous subpixels forming the disjointed regions; and
    storing the hyperlocated center coordinates of the clusters in the memory for use as the ground truth training data for training the neural network-based template generator.

7. The computer-implemented method of clause 6, further including:
    identifying centers of mass subpixels in the disjointed regions of the cluster map at the hyperlocated center coordinates of the clusters;
    upsampling the cluster map using interpolation and storing the upsampled cluster map in the memory for use as the ground truth training data for training the neural network-based template generator; and
    in the upsampled cluster map, assigning a value to each contiguous subpixel in the disjointed regions based on a decay factor that is proportional to distance of a contiguous subpixel from a center of mass subpixel in a disjointed region to which the contiguous subpixel belongs.

8. The computer-implemented method of clause 7, further including:
    generating the decay map from the upsampled cluster map that expresses the contiguous subpixels in the disjointed regions and the subpixels identified as the background based on their assigned values; and
    storing the decay map in the memory for use as the ground truth training data for training the neural network-based template generator.

9. The computer-implemented method of clause 8, further including:
    in the upsampled cluster map, categorizing, on the cluster-by-cluster basis, the contiguous subpixels in the disjointed regions as cluster interior subpixels belonging to a same cluster, the centers of mass subpixels as cluster center subpixels, subpixels containing the cluster boundary portions as boundary subpixels, and the subpixels identified as the background as background subpixels; and
    storing the categorizations in the memory for use as the ground truth training data for training the neural network-based template generator.

10. The computer-implemented method of clause 9, further including:

storing, on the cluster-by-cluster basis, coordinates of the cluster interior subpixels, the cluster center subpixels, the boundary subpixels, and the background subpixels in the memory for use as the ground truth training data for training the neural network-based template generator;

downscaling the coordinates by a factor used to upsample the cluster map; and storing, on the cluster-by-cluster basis, the downscaled coordinates in the memory for use as the ground truth training data for training the neural network-based template generator.

11. The computer-implemented method of clause 10, further including:

generating cluster maps for a plurality of tiles of the flow cell;

storing the cluster maps in memory and determining the cluster metadata of clusters in the tiles based on the cluster maps, including the cluster centers, the cluster shapes, the cluster sizes, the cluster background, and/or the cluster boundaries;

in the upsampled cluster maps of the clusters in the tiles, categorizing, on a cluster-by-cluster basis, subpixels as cluster interior subpixels belonging to a same cluster, cluster center subpixels, boundary subpixels, and background subpixels;

storing the categorizations in the memory for use as the ground truth training data for training the neural network-based template generator;

storing, on the cluster-by-cluster basis across the tiles, coordinates of the cluster interior subpixels, the cluster center subpixels, the boundary subpixels, and the background subpixels in the memory for use as the ground truth training data for training the neural network-based template generator;

downscaling the coordinates by the factor used to upsample the cluster map; and storing, on the cluster-by-cluster basis across the tiles, the downscaled coordinates in the memory for use as the ground truth training data for training the neural network-based template generator.

12. The computer-implemented method of clause 11, wherein the base call sequences are substantially matching when a predetermined portion of base calls match on an ordinal position-wise basis.

13. The computer-implemented method of clause 1, wherein the cluster map is generated based upon a predetermined minimum number of subpixels for a disjointed region.

14. The computer-implemented method of clause 1, wherein the flow cell has at least one patterned surface with an array of wells that occupy the clusters, further including:

based on the determined shapes and sizes of the clusters, determining which ones of the wells are substantially occupied by at least one cluster, which ones of the wells are minimally occupied, and which ones of the wells are co-occupied by multiple clusters.

15. A computer-implemented method of determining metadata about clusters on a tile of a flow cell, the method comprising:

accessing a set of images of the tile captured during a sequencing run and preliminary center coordinates of the clusters determined by a base caller;

for each image set, obtaining, from a base caller, a base call classifying, as one of four bases, origin subpixels that contain the preliminary center coordinates and a predetermined neighborhood of contiguous subpixels that are successively contiguous to respective ones of the origin subpixels, thereby producing a base call sequence for each of the origin subpixels and for each of the predetermined neighborhood of contiguous subpixels;

generating a cluster map that identifies the clusters as disjointed regions of contiguous subpixels that are successively contiguous to at least some of the respective ones of the origin subpixels and share a substantially matching base call sequence of the one of four bases with the at least some of the respective ones of the origin subpixels; and storing the cluster map in memory and determining the shapes and the sizes of the clusters based on the disjointed regions in the cluster map.

16. A computer-implemented method of generating training data for neural network-based template generation and base calling, the method comprising:

accessing a multitude of images of a flow cell captured over a plurality of cycles of a sequencing run, the flow cell having a plurality of tiles and, in the multitude of images, each of the tiles having a sequence of image sets generated over the plurality of cycles, and each image in the sequence of image sets depicting intensity emissions of clusters and their surrounding background on a particular one of the tiles at a particular one the cycles;

constructing a training set having a plurality of training examples, each training example corresponding to a particular one of the tiles and including image data from at least some image sets in the sequence of image sets of the particular one of the tiles; and generating at least one ground truth data representation for each of the training examples, the ground truth data representation identifying at least one property of analytes on the particular one of the tiles whose intensity emissions are depicted by the image data.

17. The computer-implemented method of clause 16, wherein the at least one property of clusters is selected from the group consisting of: spatial distribution of clusters on the tile; cluster shape; cluster size; cluster boundary; and center of contiguous regions including a single cluster.

18. The computer-implemented method of clause 16, wherein the image data includes images in each of the at least some image sets in the sequence of image sets of the particular one of the tiles.

19. The computer-implemented method of clause 18, wherein the image data includes at least one image patch from each of the images.

20. The computer-implemented method of clause 19, wherein the image data includes an upsampled representation of the image patch.

21. The computer-implemented method of clause 16, wherein multiple training examples correspond to a same particular one of the tiles and respectively include as image data different image patches from each image in each of at least some image sets in a sequence of image sets of the same particular one of the tiles, and wherein at least some of the different image patches overlap with each other.

22. The computer-implemented method of clause 16, wherein the ground truth data representation identifies the clusters as disjoint regions of adjoining subpixels, the centers of the clusters as centers of mass subpixels within respective ones of the disjoint regions, and their surrounding background as subpixels that do not belong to any of the disjoint regions.

23. The computer-implemented method of clause 16, further including:

storing, in memory, the training examples in the training set and associated ground truth data representations as the training data for the neural network-based template generation and base calling.

24. A computer-implemented method, including:

accessing sequencing images of clusters produced by a sequencer;

generating training data from the sequencing images; and using the training data for training a neural network to generate metadata about the clusters.

25. A computer-implemented method, including:

accessing sequencing images of clusters produced by a sequencer;

generating training data from the sequencing images; and using the training data for training a neural network to base call the clusters.

26. A computer-implemented method of determining image regions indicative of analytes on a tile of a flow cell, the method comprising:

accessing a series of image sets generated during a sequencing run, each image set in the series generated during a respective sequencing cycle of the sequencing run, each image in the series depicting the analytes and their surrounding background, and each image in the series having a plurality of subpixels;

obtaining, from a base caller, a base call classifying each of the subpixels, thereby producing a base call sequence for each of the subpixels across a plurality of sequencing cycles of the sequencing run;

determining a plurality of disjointed regions of contiguous subpixels which share a substantially matching base call sequence; and generating a cluster map identifying the determined disjointed regions.

Clauses Set 7

1. A neural network-implemented method of determining analyte data from image data generated based upon one or more analytes, the method including:

receiving input image data, the input image data derived from a sequence of images, wherein each image in the sequence of images represents an imaged region and depicts intensity emissions indicative of the one or more analytes and a surrounding background of the intensity emissions at a respective one of a plurality of sequencing cycles of a sequencing run, and wherein the input image data comprises image patches extracted from each image in the sequence of images;

processing the input image data through a neural network to generate an alternative representation of the input image data; and processing the alternative representation through an output layer to generate an output indicating properties of respective portions of the imaged region.

2. The neural network-implemented method of clause 1, wherein the properties include whether a portion represents background or analyte, and whether a portion represents a center of a plurality of contiguous image portions each representing a same analyte.

3. The neural network-implemented method of clause 1, wherein the output identifies the one or more analytes, whose intensity emissions are depicted by the input image data, as disjoint regions of adjoining units, centers of the one or more analytes as center units at centers of mass of the respective ones of the disjoint regions, and the surrounding background of the intensity emissions as background units not belonging to any of the disjoint regions.

4. The neural network-implemented method of clause 3, wherein the adjoining units in the respective ones of the disjoint regions have intensity values weighted according to distance of an adjoining unit from a center unit in a disjoint region to which the adjoining unit belongs.

5. The neural network-implemented method of any of clauses 1-4, wherein the output is a binary map which classifies each portion as analyte or background.

6. The neural network-implemented method of any of clauses 1-5, wherein the output is a ternary map which classifies each portion as analyte, background, or center.

7. The neural network-implemented method of any of clauses 1-6, further including:

applying a peak locator to the output to find peak intensities in the output;

determining location coordinates of the centers of the analytes based on the peak intensities;

downscaling the location coordinates by an upsampling factor used to prepare the input image data; and storing the downscaled location coordinates in memory for use in base calling the analytes.

8. The neural network-implemented method of any of clauses 1-7, further including:

categorizing the adjoining units in the respective ones of the disjoint regions as analyte interior units belonging to a same analyte; and storing the categorization and downscaled location coordinates of the analyte interior units in the memory on an analyte-by-analyte basis for use in base calling the analytes.

9. The neural network-implemented method of any of clauses 1-8, further including:

obtaining training data for training the neural network, wherein the training data includes a plurality of training examples and corresponding ground truth data, wherein each training example includes image data from a sequence of image sets, wherein each image in the sequence of image sets represents a tile of a flow cell and depicts intensity emissions of analytes on the tile and their surrounding background captured for a particular image channel at a particular one of a plurality of sequencing cycles of a sequencing run performed on the flow cell, and wherein each ground truth data identifies properties of respective portions of the training examples; and using a gradient descent training technique to train the neural network and generating outputs for the training examples that progressively match the ground truth data, including iteratively optimizing a loss function that minimizes error between the outputs and the ground truth data, and updating parameters of the neural network based on the error.

10. The neural network-implemented method of any of clauses 1-9, wherein the properties comprise identifying whether a unit is a center or a non-center.

11. The neural network-implemented method of clause 9, further including:
    upon error convergence after a final iteration, storing the updated parameters of the neural network in memory to be applied to further neural network-based template generation and base calling.

12. The neural network-implemented method of any of clauses 9-11, wherein, in the ground truth data, the adjoining units in the respective ones of the disjoint regions have intensity values weighted according to distance of an adjoining unit from a center unit in a disjoint region to which the adjoining unit belongs.

13. The neural network-implemented method of any of clauses 9-11, wherein, in the ground truth data, the center units have highest intensity values within the respective ones of the disjoint regions.

14. The neural network-implemented method of any of clauses 9-13, wherein the loss function is mean squared error and the error is minimized on a unit-basis between the normalized intensity values of corresponding units in the outputs and the ground truth data.

15. The neural network-implemented method of any of clauses 9-14, wherein, in the training data, multiple training examples respectively include as image data different image patches from each image in a sequence of image sets of a same tile, and
    wherein at least some of the different image patches overlap with each other.

16. The neural network-implemented method of any of clauses 9-15, wherein, in the ground truth data,
    units classified as analyte centers are all assigned a same first predetermined class score, and
    units classified as non-centers are all assigned a same second predetermined class score.

17. The neural network-implemented method of any of clauses 9-16, wherein the loss function is custom-weighted binary cross-entropy loss and the error is minimized on a unit-basis between the prediction scores and the class scores of corresponding units in the outputs and the ground truth data.

18. The neural network-implemented method of any of clauses 9-17, wherein, in the ground truth data,
    units classified as background are all assigned a same first predetermined class score,
    units classified as analyte centers are all assigned a same second predetermined class score, and
    units classified as analyte interior are all assigned a same third predetermined class score.

19. The neural network-implemented method of any of clauses 1-18, further including:
    thresholding output values of the units and classifying a first subset of the units as background units depicting the surrounding background;
    locating peaks in the output values of the units and classifying a second subset of the units as center units containing centers of the analytes; and
    applying a segmenter to the output values of the units and determining shapes of the analytes as non-overlapping regions of contiguous units separated by the background units and centered at the center units, wherein the segmenter begins with the center units and determines, for each center unit, a group of successively contiguous units that depict a same analyte whose center is contained in the center unit.

20. The neural network-implemented method of any of clauses 1-19, wherein the non-overlapping regions have irregular contours and the units are units, further including:
    determining analyte intensity of a given analyte by:
    identifying units that contribute to the analyte intensity of the given analyte based on a corresponding non-overlapping region of contiguous units that identifies a shape of the given analyte;
    locating the identified units in one or more optical, pixel resolution images generated for one or more image channels at a current sequencing cycle;
    in each of the images, interpolating intensities of the identified units, combining the interpolated intensities, and normalizing the combined interpolated intensities to produce a per-image analyte intensity for the given analyte in each of the images; and
    combining the per-image analyte intensity for each of the images to determine the analyte intensity of the given analyte at the current sequencing cycle.

21. The neural network-implemented method of any of clauses 1-20, wherein the non-overlapping regions have irregular contours and the units are units, further including:
    determining analyte intensity of a given analyte by:
    identifying units that contribute to the analyte intensity of the given analyte based on a corresponding non-overlapping region of contiguous units that identifies a shape of the given analyte;
    locating the identified units in one or more unit resolution images upsampled from corresponding optical, pixel resolution images generated for one or more image channels at a current sequencing cycle;
    in each of the upsampled images, combining intensities of the identified units and normalizing the combined intensities to produce a per-image analyte intensity for the given analyte in each of the upsampled images; and
    combining the per-image analyte intensity for each of the upsampled images to determine the analyte intensity of the given analyte at the current sequencing cycle.

22. The neural network-implemented method of any of clauses 1-21, wherein the normalizing is based on a normalization factor, and
    wherein the normalization factor is a number of the identified units.

23. The neural network-implemented method of any of clauses 1-22, further including:
    base calling the given analyte based on the analyte intensity at the current sequencing cycle.

24. A neural network-implemented method of determining metadata about analytes on a flow cell, the method including:
    accessing image data that depicts intensity emissions of the analytes;
    processing the image data through one or more layers of a neural network and generating an alternative representation of the image data; and
    processing the alternative representation through an output layer and generating an output that identifies at least one of shapes and sizes of the analytes and/or centers of the analytes.

25. The neural network-implemented method of clause 24, wherein the image data further depicts intensity emissions of surrounding background of the analytes, further including:
    the output identifying spatial distribution of the analytes on the flow cell, including the surrounding background and boundaries between the analytes.

26. A computer-implemented method, including:
    processing image data through a neural network and generating an alternative representation of the image data, wherein the image data depicts intensity emissions of analytes; and processing the alternative representation through an output layer and generating an output that identifies metadata about the analytes, including at least one of spatial distribution of the analytes, shapes of the analytes, centers of the analytes, and/or boundaries between the analytes.

27. A neural network-implemented method of determining cluster metadata from image data generated based upon one or more clusters, the method including:

receiving input image data, the input image data derived from a sequence of images,
  wherein each image in the sequence of images represents an imaged region and depicts intensity emissions of the one or more clusters and their surrounding background at a respective one of a plurality of sequencing cycles of a sequencing run, and
  wherein the input image data comprises image patches extracted from each image in the sequence of images;

processing the input image data through a neural network to generate an alternative representation of the input image data, wherein the neural network is trained for cluster metadata determination task, including determining cluster background, cluster centers, and cluster shapes;

processing the alternative representation through an output layer to generate an output indicating properties of respective portions of the imaged region;

thresholding output values of the output and classifying a first subset of the respective portions of the imaged region as background portions depicting the surrounding background;

locating peaks in the output values of the output and classifying a second subset of the respective portions of the imaged region as center portions containing centers of the clusters; and applying a segmenter to the output values of the output and determining shapes of the clusters as non-overlapping regions of contiguous portions of the imaged region separated by the background portions and centered at the center portions.

What is claimed is:

1. A computer-implemented method of end-to-end sequencing, including template generation and base calling, comprising:
  accessing first image data and second image data that contain pixels in an optical, pixel resolution,
    wherein the first image data comprises images of clusters and their surrounding background captured by a sequencing system for initial ones of sequencing cycles of a sequencing run, and
    wherein the second image data comprises images of the clusters and their surrounding background captured by the sequencing system for the sequencing cycles of the sequencing run;
  processing the first image data through a neural network-based template generator, and producing a cluster map that identifies cluster metadata,
    wherein the cluster metadata includes cluster centers, cluster shapes, cluster sizes, cluster background, and/or cluster boundaries, and
    wherein the neural network-based template generator is trained on a task of mapping the images of the clusters to the cluster metadata;
  encoding the cluster metadata in a template image in an upsampled, subpixel resolution,
    wherein subpixels of the template and the pixels of the images of the clusters represent a same image area;
  modifying intensity values of the pixels of the second image data based on the template image, and producing an intensity modified version of the second image data with an intensity distribution that accounts for the cluster metadata; and
  processing the intensity modified version of the second image data through a neural network-based base caller, and producing base calls for one or more of the clusters at one or more sequencing cycles of the sequencing run, wherein the neural network-based base caller is trained on a task of mapping the images of the clusters to the base calls.

2. The computer-implemented method of claim 1, further including:
  supplementing the second image data with the template image; and
  processing the second image data, supplemented with the template image, through the neural network-based base caller, and producing base calls for one or more of the clusters at one or more sequencing cycles of the sequencing run.

3. The computer-implemented method of claim 1, wherein each subpixel in the template image is identified as either background subpixel, cluster center subpixel, or cluster interior subpixel.

4. The computer-implemented method of claim 3, wherein modifying intensity values of the pixels of the second image data comprises:
  calculating an area weighting factor for one or more pixels in the second image data based on how many subpixels in the template image that correspond to a pixel in the images of the second image data contain parts of one or more of the clusters; and
  modifying intensities of the pixels based on the area weighting factor.

5. The computer-implemented method of claim 4, wherein modifying intensity values of the pixels of the second image data comprises:
  upsampling the images of clusters and their surrounding background to the upsampled, subpixel resolution to produce upsampled images, and assigning a background intensity to those subpixels in the upsampled images that correspond to background subpixels in the template image and assigning cluster intensities to those subpixels in the upsampled images that correspond to cluster center subpixels and cluster interior subpixels in the template image.

6. The computer-implemented method of claim 5, wherein the background intensity has a zero value.

7. The computer-implemented method of claim 6, wherein the cluster intensities are determined by interpolating intensities of the pixels in the optical, pixel resolution.

8. The computer-implemented method of claim 7, wherein modifying intensity values of the pixels of the second image data comprises:
  upsampling the images of clusters and their surrounding background to the upsampled, subpixel resolution to produce upsampled images, and distributing an entire intensity of a pixel in the optical, pixel domain among only those constituent subpixels of the pixel in the upsampled images that correspond to the cluster center subpixels and the cluster interior subpixels in the template image.

9. A computer-implemented base calling method, comprising: using a first neural network to determine a template image about clusters, wherein the template image identifies at least one property selected from the group consisting of: spatial distribution of the clusters, cluster shape, centers of the clusters and cluster boundary; and using a second neural network to base call the clusters based on the template image.

10. The computer-implemented method of claim 9, wherein the template image comprises modified intensity values to identify at least one of the properties selected from the group consisting of: spatial distribution of the clusters, cluster shape, centers of the clusters and cluster boundary; and processing the modified intensity values through the second neural network to base call the clusters.

11. The computer-implemented method of claim 10, further comprising:

evaluating the template image in an upsampled subpixel domain for at least one particular cluster to identify a pixel that contains part of the at least one particular cluster and adjoining pixels to the pixel that also contain part of the at least one particular cluster;

calculating an area weighting factor for each pixel based on how many subpixels in each of the identified pixels contain parts of the at least one particular cluster; and modifying a pixel intensity value of the identified pixel and the adjoining pixels for processing based on the area weighting factor for a respective pixel.

12. The computer-implemented method of claim 11, wherein evaluating the template image further comprises:

processing one or more initial image sets respectively generated at one or more initial sequencing cycles of a plurality of sequencing cycles through the first neural network to produce the template image to identify the centers, shapes, and boundaries of the clusters at the upsampled, subpixel resolution; wherein each image set comprises one or more images, each of the images depicting intensity emissions of the clusters and their surrounding background in a respective one of one or more imaging channels captured at the optical, pixel resolution.

13. The computer-implemented method of claim 12, wherein evaluating the template image further comprises:

evaluating the cluster shape and boundaries of the at least one particular cluster to identify at least one pixel that contains part of the at least one particular cluster and adjoining pixels to the pixel that also contain part of the at least one particular cluster; and wherein the method further comprises storing the area weighting factor in the template image; and generating a modified version of each of the images with pixels having modified pixel intensity values;

processing modified versions of the images through the second neural network to generate an alternative representation of the modified versions; and base calling the at least one particular cluster using the alternative representation.

14. The computer-implemented method of claim 13, wherein the base calling further comprises:

accessing one or more images at the optical, pixel resolution in each of a current image set generated at a current one of the plurality of sequencing cycles, of a one or more preceding image sets respectively generated at one or more of the plurality of sequencing cycles preceding the current one of the plurality of sequencing cycles, and of a one or more succeeding image sets respectively generated at one or more of the plurality of sequencing cycles succeeding the current one of the plurality of sequencing cycles;

for pixels in each of the images, modifying a pixel intensity value based on the area weighting factor in the template image for a respective pixel;

generating a modified version of each of the images with pixels having modified pixel intensity values;

for the at least one particular cluster, extracting an image patch from each modified version such that each image patch has an array of pixels, and contains in its center pixel a center of the particular cluster identified in the template image;

convolving image patches extracted from modified versions of the images through a convolutional neural network of the second neural network to generate a convolved representation of the image patches;

processing the convolved representation through an output layer to produce, for the center pixel, likelihoods of a base incorporated in the at least one particular cluster at the current one of the plurality of sequencing cycles being A, C, T, and G; and classifying the base as A, C, T, or G based on the likelihoods.

15. The computer-implemented method of claim 14, further comprising:

prior to modifying the pixel intensity values, aligning each of the images captured at the optical, pixel resolution with the template image using cycle-specific and imaging channel-specific transformations.

16. The computer-implemented method of claim 9, further comprising:

evaluating the template image in an upsampled subpixel domain to identify subpixels that contain parts of any cluster; and assigning a background intensity to subpixels identified in the template image as not contributing to any cluster.

17. The computer-implemented method of claim 16, wherein evaluating the template image in an upsampled subpixel domain further comprises:

calculating how many subpixels in at least one pixel contain parts of any cluster and calculating a per-subpixel area weighting factor for the subpixels in the at least one pixel.

18. The computer-implemented method of claim 17, wherein the method comprises:

processing one or more initial image sets respectively generated at one or more initial sequencing cycles of a plurality of sequencing cycles through the first neural network to produce the template image at the upsampled, subpixel resolution, wherein each image set comprises one or more images, each of the images depicting intensity emissions of the clusters and their surrounding background in a respective one of one or more imaging channels captured at the optical, pixel resolution and wherein the template image classifies subpixels into classes including cluster center, background, and cluster interior;

upsampling each of the images captured at the optical, pixel resolution into a subpixel domain and assigning a background intensity to subpixels of each of the images identified in the template image as not contributing to any cluster;

processing the upsampled images through the second neural network to generate an alternative representation of the upsampled images; and base calling a plurality of the clusters using the alternative representation.

19. The computer-implemented method of claim 18, wherein upsampling each of the images further comprises:
- distributing intensity of a particular pixel among first subpixels of the particular pixel identified in the template image as contributing to any cluster by applying the per-subpixel area weighting factor and assigning a background intensity to second subpixels of the particular pixel identified in the template as not contributing to any cluster.

20. The computer-implemented method of claim 19, wherein the prior to upsampling the method comprises:
- accessing one or more images at the optical, pixel resolution in each
  - of a current image set generated at a current one of the plurality of sequencing cycles,
  - of a one or more preceding image sets respectively generated at one or more of the plurality of sequencing cycles preceding the current one of the plurality of sequencing cycles, and
  - of a one or more succeeding image sets respectively generated at one or more of the plurality of sequencing cycles succeeding the current one of the plurality of sequencing cycles; and after upsampling the method comprises:
- extracting an image patch from each upsampled image such that each image patch has an array of subpixels;
- convolving image patches extracted from the upsampled images through the convolutional neural network of the second neural network to generate a convolved representation of the image patches;
- processing the convolved representation through an output layer to produce, for each subpixel in the array, likelihoods of a base incorporated at the current one of the plurality of sequencing cycles being A, C, T, and G;
- classifying the base as A, C, T, or G based on the likelihoods; and
- base calling each one of the plurality of the clusters based on a base classification assigned to a respective subpixel containing a center of a corresponding cluster.

21. The computer-implemented method of claim 20, further comprising:
- prior to the upsampling, aligning each of the images captured at the optical, pixel resolution with the template image using cycle-specific and imaging channel-specific transformations.

22. A sequencing system, comprising:
- a receptacle coupled to a biosensor system, the biosensor system configured to comprise an array of light detectors, the biosensor system comprising a biosensor, and the biosensor comprising reaction sites configured to contain clusters;
- an illumination system configured to direct excitation light toward the biosensor and illuminate the clusters in the reaction sites, wherein at least some of the clusters provide emission signals when illuminated; and
- a system controller coupled to the receptacle and comprising an analysis module, the analysis module configured to:
  - generate a template image that reduces positional uncertainty by identifying at least one property selected from the group consisting of: spatial distribution of the clusters, cluster shape, centers of the clusters and cluster boundary;
  - obtain image data from the light detectors at each of a plurality of sequencing cycles, wherein the image data is derived from the emission signals detected by the light detectors; and
  - process the image data for each of the plurality of sequencing cycles based on the template image through a neural network and produce a base call for at least some of the clusters at each of the plurality of sequencing cycles.

* * * * *

UNITED STATES PATENT AND TRADEMARK OFFICE
CERTIFICATE OF CORRECTION

| | |
|---|---|
| PATENT NO. | : 11,436,429 B2 |
| APPLICATION NO. | : 16/826168 |
| DATED | : September 6, 2022 |
| INVENTOR(S) | : Kishore Jaganathan et al. |

It is certified that error appears in the above-identified patent and that said Letters Patent is hereby corrected as shown below:

On the Title Page

Under item (30) (Foreign Application Priority Data section) insert:
--Jun. 14, 2019 (NL) ............................ 2023310
Jun. 14, 2019 (NL) ............................ 2023311
Jun. 14, 2019 (NL) ............................ 2023312
Jun. 14, 2019 (NL) ............................ 2023316--

Signed and Sealed this
Twentieth Day of December, 2022

Katherine Kelly Vidal
*Director of the United States Patent and Trademark Office*